United States Patent
Lucas et al.

(10) Patent No.: US 10,968,181 B2
(45) Date of Patent: Apr. 6, 2021

(54) NRF2 ACTIVATOR

(71) Applicant: BIOGEN MA INC., Cambridge, MA (US)

(72) Inventors: Brian Stuart Lucas, Arlington, MA (US); Edward Yin-Shiang Lin, Ashland, MA (US); Andrew George Capacci, Cambridge, MA (US); Zhili Xin, Lexington, MA (US); Istvan Enyedy, Milton, MA (US); TeYu Chen, Charlestown, MA (US); John H. Jones, Framingham, MA (US); Kurt D. van Vloten, Bellingham, MA (US)

(73) Assignee: BIOGEN MA INC., Cambridge, MA (US)

( * ) Notice: Subject to any disclaimer, the term of this patent is extended or adjusted under 35 U.S.C. 154(b) by 0 days.

(21) Appl. No.: 16/473,667

(22) PCT Filed: Dec. 27, 2017

(86) PCT No.: PCT/US2017/068455
§ 371 (c)(1),
(2) Date: Jun. 26, 2019

(87) PCT Pub. No.: WO2018/125880
PCT Pub. Date: Jul. 5, 2018

(65) Prior Publication Data
US 2019/0345112 A1 Nov. 14, 2019

Related U.S. Application Data

(60) Provisional application No. 62/439,289, filed on Dec. 27, 2016.

(51) Int. Cl.
| | |
|---|---|
| *C07D 311/76* | (2006.01) |
| *C07D 217/04* | (2006.01) |
| *C07D 217/08* | (2006.01) |
| *C07D 223/16* | (2006.01) |
| *C07D 498/14* | (2006.01) |
| *A61K 31/352* | (2006.01) |
| *A61K 31/47* | (2006.01) |
| *C07D 217/20* | (2006.01) |
| *C07D 217/22* | (2006.01) |
| *C07D 223/14* | (2006.01) |
| *C07D 311/74* | (2006.01) |
| *C07D 401/04* | (2006.01) |
| *C07D 401/06* | (2006.01) |
| *C07D 405/04* | (2006.01) |
| *C07D 405/06* | (2006.01) |
| *C07D 413/06* | (2006.01) |
| *C07D 498/04* | (2006.01) |

(52) U.S. Cl.
CPC ........ *C07D 217/04* (2013.01); *C07D 217/08* (2013.01); *C07D 217/20* (2013.01); *C07D 217/22* (2013.01); *C07D 223/14* (2013.01); *C07D 311/74* (2013.01); *C07D 401/04* (2013.01); *C07D 401/06* (2013.01); *C07D 405/04* (2013.01); *C07D 405/06* (2013.01); *C07D 413/06* (2013.01); *C07D 498/04* (2013.01)

(58) Field of Classification Search
CPC .. C07D 311/76; C07D 217/04; C07D 217/08; C07D 223/16; C07D 498/14; A61K 31/352; A61K 31/47
See application file for complete search history.

(56) References Cited

FOREIGN PATENT DOCUMENTS

| | | | |
|---|---|---|---|
| JP | 2008110962 A | | 5/2008 |
| WO | 2011/156889 A1 | | 12/2011 |
| WO | 2012/116362 A2 | | 8/2012 |
| WO | 2016/065264 A1 | | 4/2016 |
| WO | 2016/203400 A1 | | 12/2016 |

OTHER PUBLICATIONS

International Search Report and Written Opinion for Application No. PCT/US2017/068455, dated Apr. 3, 2018, 9 pages.

*Primary Examiner* — Bruck Kifle
(74) *Attorney, Agent, or Firm* — McCarter & English, LLP; Steven G. Davis; Xin Zhang

(57) ABSTRACT

Provided are compounds of Formula I, or pharmaceutically acceptable salts thereof, and methods for their use and production.

24 Claims, 19 Drawing Sheets

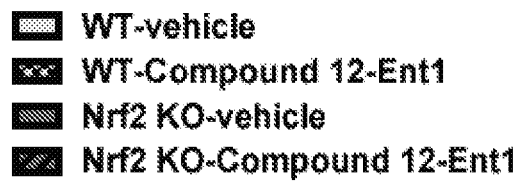
Figure 4A
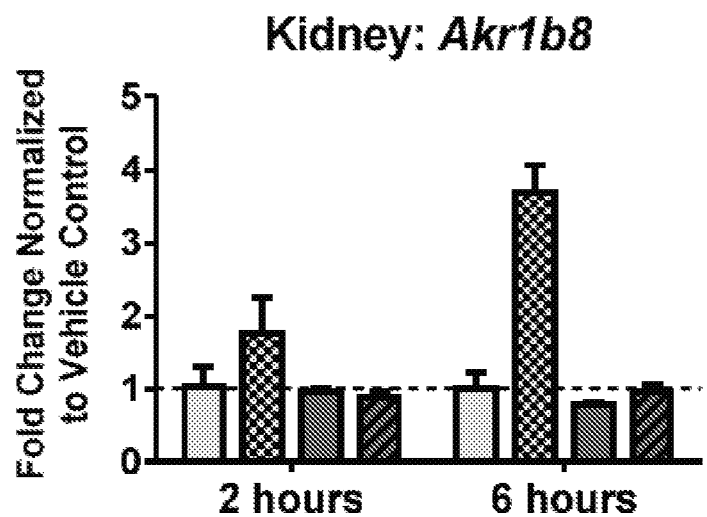
Figure 4B
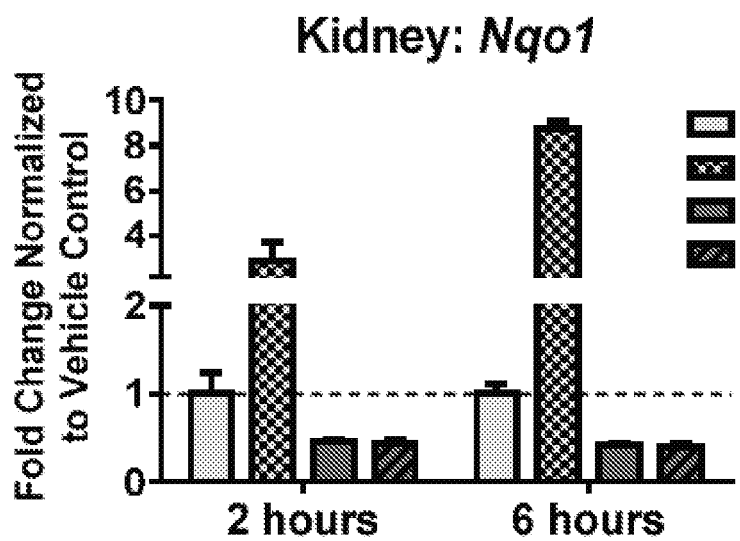

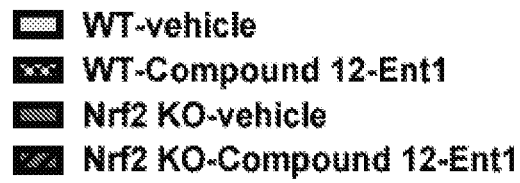
Figure 4C
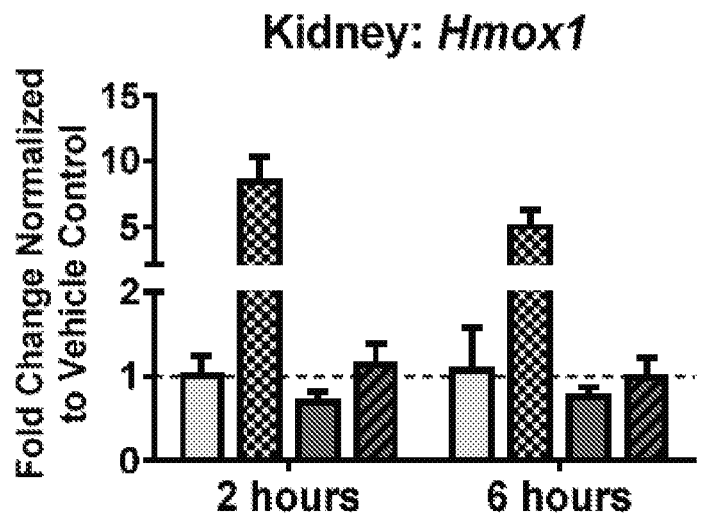
Figure 4D
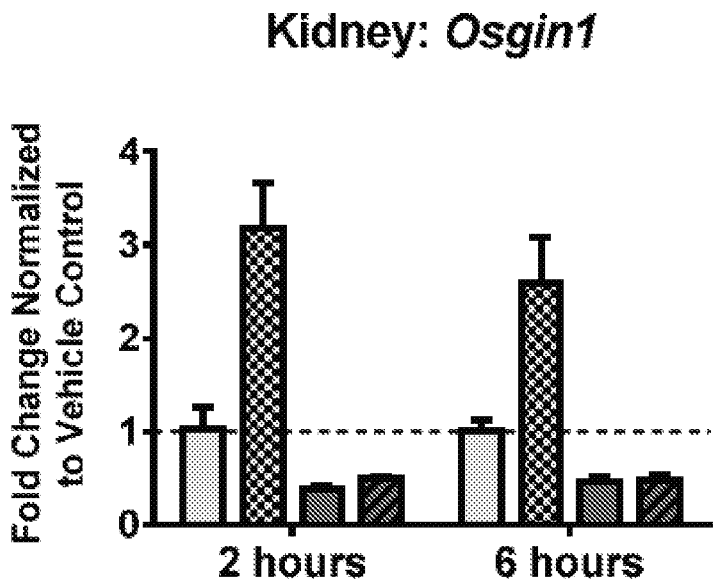

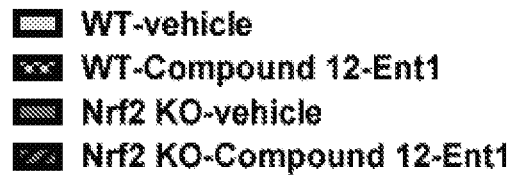
Figure 5C
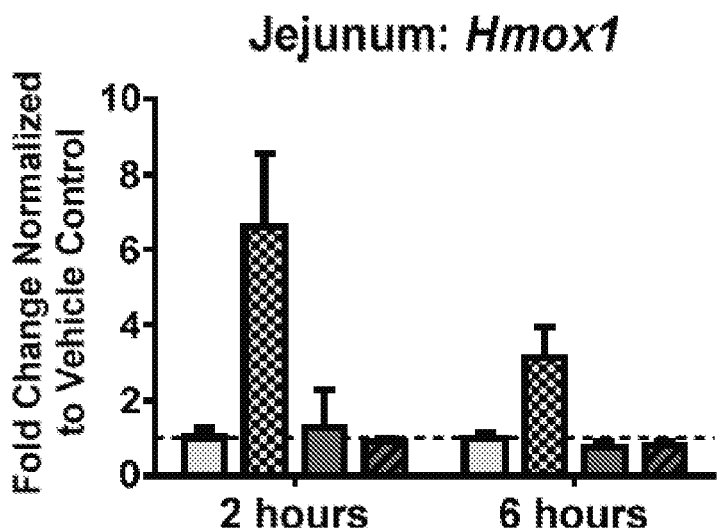
Figure 5D
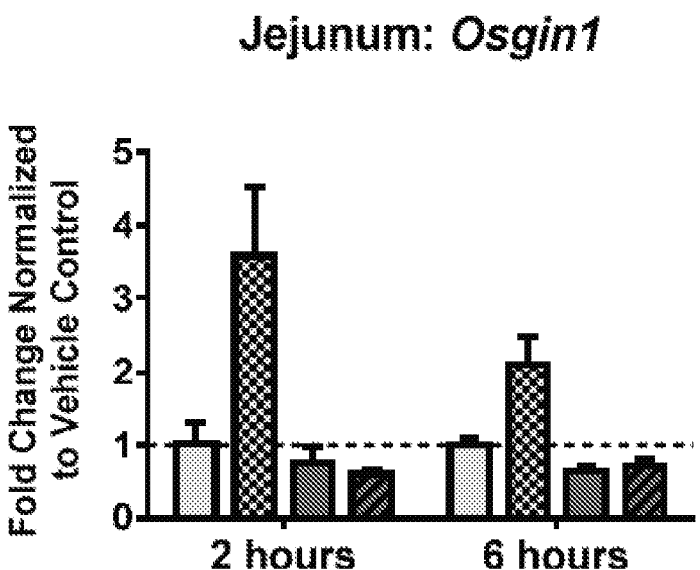

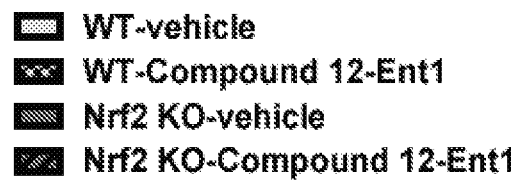
Figure 6A
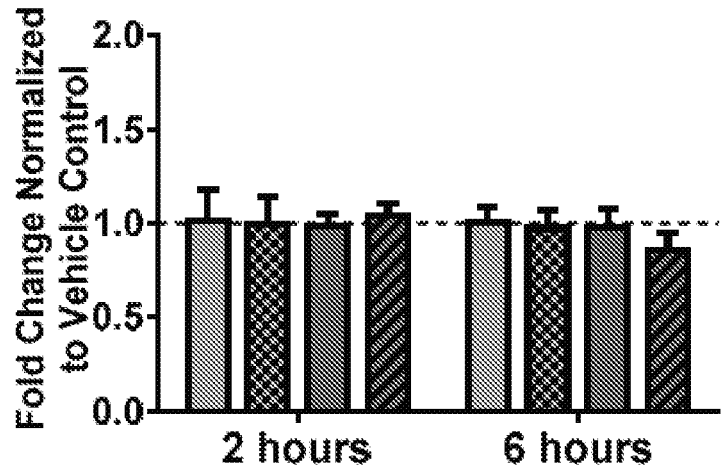
Figure 6B
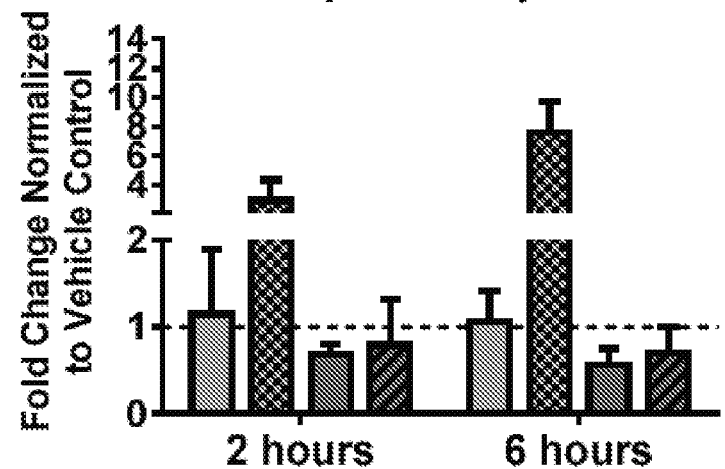

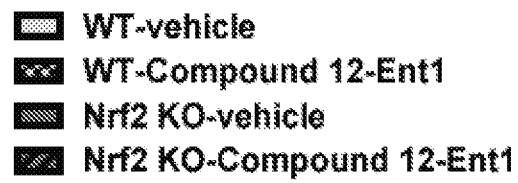
Figure 6C
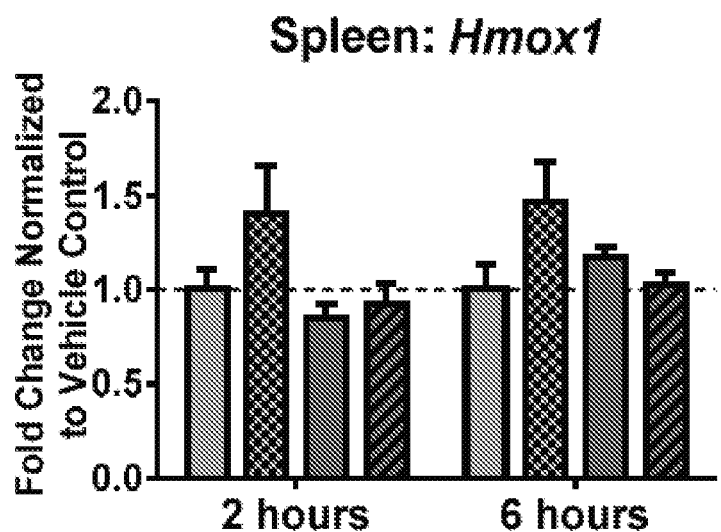
Figure 6D
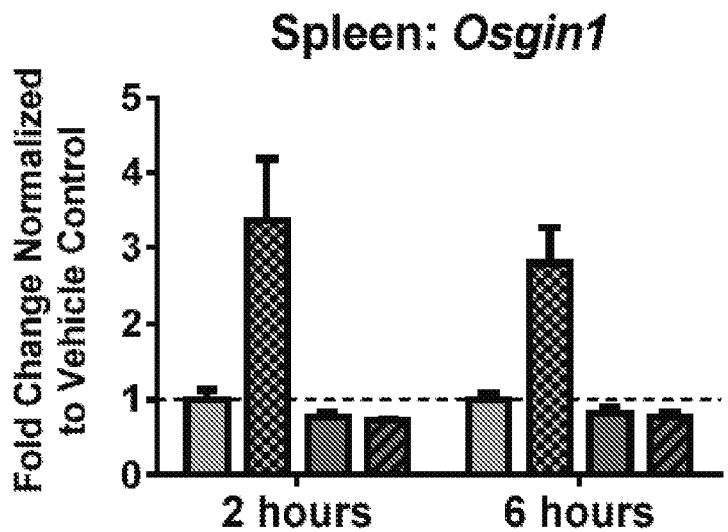

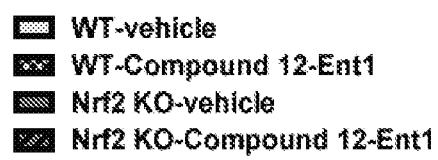
Figure 7A
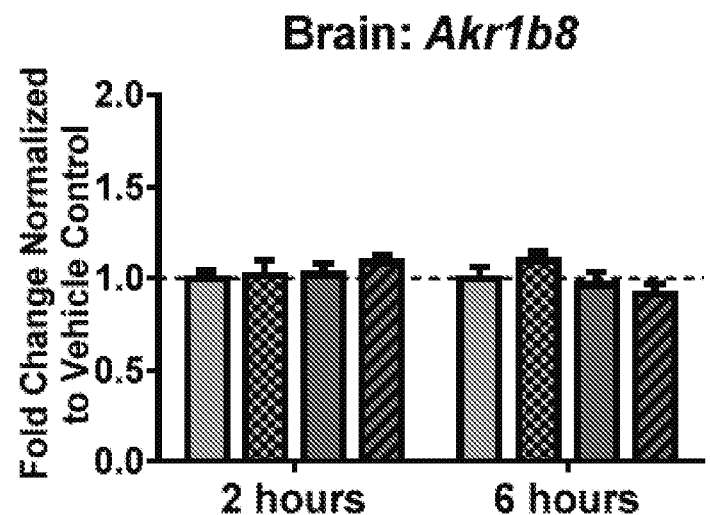
Figure 7B
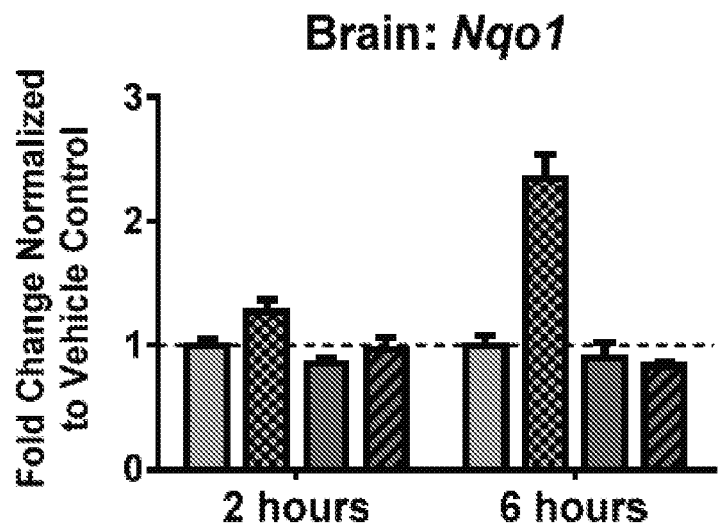

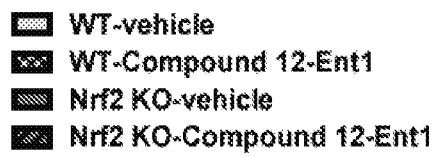
Figure 7C
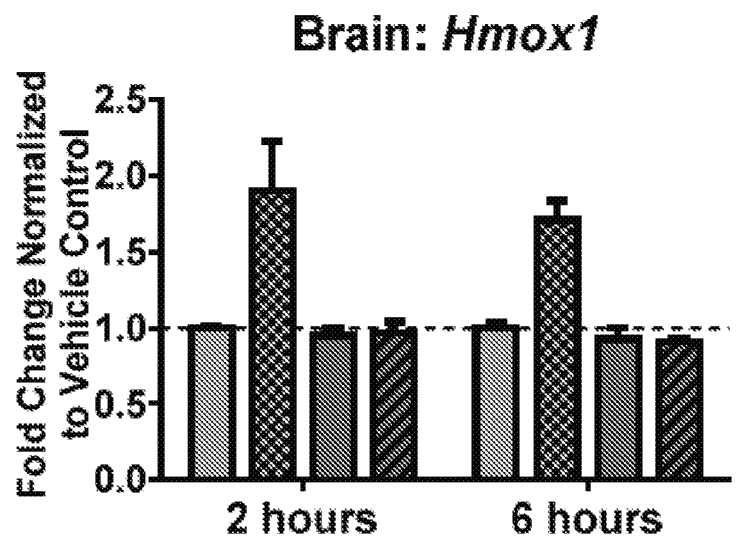
Figure 7D
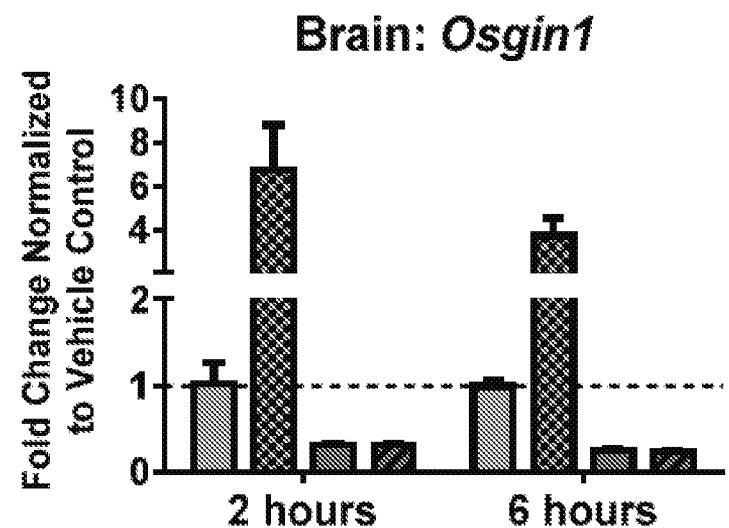

NRF2 ACTIVATOR

RELATED APPLICATION INFORMATION

This application is a 35 U.S.C. § 371 national stage filing of International Application No. PCT/US2017/068455, filed Dec. 27, 2017, which claims priority to U.S. Provisional Application No. 62/439,289, filed Dec. 27, 2016. The contents of each of the foregoing applications are incorporated herein by reference.

Nuclear factor erythroid 2 (NF-E2)-related factor 2 (Nrf2) belongs to the Cap 'N' Collar (CNC) family of transcription factors and contains a conserved basic leucine zipper (bZIP) structure. The main function of Nrf2 is to activate the cellular antioxidant response by inducing the production of proteins that are able to combat the harmful effects of oxidative stress.

Activation of the Nrf2 pathway to treat diseases caused by oxidative stress, such as a neurodegenerative disease, inflammation and/or an inflammatory disease, an autoimmune disease, an ischemic fibrotic disease, a cancer, premature aging, a cardiovascular disease, a liver disease, a hemoglobinopathy and a metabolic disorder, is being studied.

Moreover, Nrf2 activation has been shown to upregulates fetal hemoglobin which can ameliorates symptoms of hemoglobinopathy such as sickle cell disease and thalassemia (e.g. beta-thalassemia).

Therefore, a need exists for Nrf2 activators to treat these diseases.

SUMMARY

A first embodiment of the invention is a compound of Formula I:

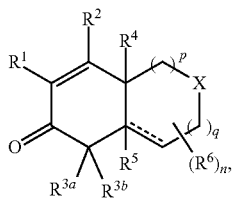

or a pharmaceutically acceptable salt thereof, wherein
$R^1$ is —CN, —C(O)$R^a$, $CH_3S(O)_2$— or $C_{1-8}$alkyl substituted with one or more fluorine atoms;
$R^a$ is H, $C_{1-12}$alkyl, $C_{2-12}$alkenyl, $C_{2-12}$alkynyl, a 3 to 12-membered carbocyclyl, a 3 to 12-membered heterocyclyl, —OR$^{11}$, —SR$^{14}$, —N(R$^{12}$)$_2$, —NR$^{13}$OR$^{13}$, —NR$^{13}$S(O)$_2$R$^{13}$, —NR$^{13}$C(O)R$^{13}$, —N(R$^{13}$)N(R$^{13}$)$_2$, —N(R$^{13}$)C(O)OR$^{13}$ or —N(R$^{13}$)C(O)N(R$^{13}$)$_2$, wherein the $C_{1-12}$alkyl, $C_{2-12}$alkenyl, $C_{2-12}$alkynyl, 3 to 12-membered carbocyclyl, and 3 to 12-membered heterocyclyl are each optionally substituted with one or more R$^{21}$;
$R^2$ is H, halo, —NO$_2$, —CN, —N$_3$, $C_{1-12}$alkyl, $C_{2-12}$alkenyl, $C_{2-12}$alkynyl, a 3 to 12-membered carbocyclyl, a 3 to 12-membered heterocyclyl, —C(O)R$^{13}$, —C(S)R$^{13}$, —C(O)OR$^{13}$, —C(S)SR$^{13}$, —C(O)SR$^{13}$, —C(S)OR$^{13}$, —SC(O)R$^{13}$, —OC(S)R$^{13}$, —SC(S)R$^{13}$, —C(O)N(R$^{13}$)$_2$, —OR$^{11}$, —SR$^{14}$, —N(R$^{12}$)$_2$, —N(R$^{13}$)OR$^{13}$, —N(R$^{13}$)S(O)$_2$R$^{13}$, —N(R$^{13}$)C(O)R$^{13}$, —N(R$^{13}$)N(R$^{13}$)$_2$, —N(R$^{13}$)C(O)OR$^{13}$, —N(R$^{13}$)C(O)N(R$^{13}$)$_2$, —S(O)$_2$R$^{13}$, —S(O)R$^{13}$, —S(O)N(R$^{13}$)$_2$, —S(O)$_2$N(R$^{13}$)$_2$, —N$^+$(R$^{13}$)$_3$, —S$^+$(R$^{13}$)$_2$ or —Si(R$^{13}$)$_3$, wherein the $C_{1-12}$alkyl, $C_{2-12}$alkenyl, $C_{2-12}$alkynyl, 3 to 12-membered carbocyclyl and 3 to 12-membered heterocyclyl are each optionally substituted with one or more R$^{21}$;
$R^{3a}$ is H, $C_{1-12}$alkyl, $C_{2-12}$alkenyl, $C_{2-12}$alkynyl, a 3 to 12-membered carbocyclyl, a 3 to 12-membered heterocyclyl, —C(O)R$^{13}$, —C(O)OR$^{13}$, —C(O)N(R$^{13}$)$_2$, —OR$^{11}$, —N(R$^{12}$)$_2$, —N(R$^{13}$)OR$^{13}$, —N(R$^{13}$)S(O)$_2$R$^{13}$, —N(R$^{13}$)C(O)R$^{13}$, —N(R$^{13}$)N(R$^{13}$)$_2$, —N(R$^{13}$)C(O)OR$^{13}$, —N(R$^{13}$)C(O)N(R$^{13}$)$_2$, —S(O)R$^{13}$, —S(O)N(R$^{13}$)$_2$ or —S(O)$_2$N(R$^{13}$)$_2$, wherein the $C_{1-12}$alkyl, $C_{2-12}$alkenyl, $C_{2-12}$alkynyl, 3 to 12-membered carbocyclyl and 3 to 12-membered heterocyclyl are each optionally substituted with one or more R$^{21}$; and
$R^{3b}$ is $C_{1-12}$alkyl, $C_{2-12}$alkenyl, $C_{2-12}$alkynyl, a 3 to 12-membered carbocyclyl, a 3 to 12-membered heterocyclyl, —C(O)R$^{13}$, —C(O)OR$^{13}$, —C(O)N(R$^{13}$)$_2$, —OR$^{11}$, —N(R$^{12}$)$_2$, —N(R$^{13}$)OR$^{13}$, —N(R$^{13}$)S(O)$_2$R$^{13}$, —N(R$^{13}$)C(O)OR$^{13}$, —N(R$^{13}$)N(R$^{13}$)$_2$, —N(R$^{13}$)C(O)OR, —N(R$^{13}$)C(O)N(R$^{13}$)$_2$, —S(O)R$^{13}$, —S(O)N(R$^{13}$)$_2$ or —S(O)$_2$N(R$^{13}$)$_2$, wherein the $C_{1-12}$alkyl, $C_{2-12}$alkenyl, $C_{2-12}$alkynyl, 3 to 12-membered carbocyclyl and 3 to 12-membered heterocyclyl are each optionally substituted with one or more R$^{21}$; or
$R^{3a}$ and $R^{3b}$ are taken together and are $C_{2-12}$alkylene, $C_{2-12}$alkenylene or $C_{2-12}$alkynylene; wherein the $C_{2-12}$alkylene, $C_{2-12}$alkenylene, $C_{2-12}$alkynylene and 3-6-membered carbocyclyl are each optionally substituted with one or more R$^{21}$;
$R^4$ is H, halo, —NO$_2$, —CN, —N$_3$, $C_{1-12}$alkyl, $C_{2-12}$alkenyl, $C_{2-12}$alkynyl, a 3 to 12-membered carbocyclyl, a 3 to 12-membered heterocyclyl, —C(O)R$^{13}$, —C(S)R$^{13}$, —C(O)OR$^{13}$, —C(S)SR$^{13}$, —C(O)SR$^{13}$, —C(S)OR$^{13}$, —SC(O)R$^{13}$, —OC(S)R$^{13}$, —SC(S)R$^{13}$, —C(O)N(R$^{13}$)$_2$, —OR$^{11}$, —SR$^{14}$, —N(R$^{12}$)$_2$, —N(R$^{13}$)OR$^{13}$, —N(R$^{13}$)S(O)$_2$R$^{13}$, —N(R$^{13}$)C(O)OR$^{13}$, —N(R$^{13}$)N(R$^{13}$)$_2$, —N(R$^{13}$)C(O)OR$^{13}$, —N(R$^{13}$)C(O)N(R$^{13}$)$_2$, —S(O)$_2$R$^{13}$, —S(O)R$^{13}$, —S(O)N(R$^{13}$)$_2$, —S(O)$_2$N(R$^{13}$)$_2$, —N$^+$(R$^{13}$)$_3$, —S$^+$(R$^{13}$)$_2$ or —Si(R$^{13}$)$_3$, wherein the $C_{1-12}$alkyl, $C_{2-12}$alkenyl, $C_{2-12}$alkynyl, 3 to 12-membered carbocyclyl and 3 to 12-membered heterocyclyl are each optionally substituted with one or more R$^{21}$;
" ----- " is either a single bond or a double bond, wherein when " ----- " is a double bond, then $R^5$ is absent; and when " ----- " is a single bond, then
$R^5$ is H, halo, —NO$_2$, —CN, —N$_3$, $C_{1-12}$alkyl, $C_{2-12}$alkenyl, $C_{2-12}$alkynyl, a 3 to 12-membered carbocyclyl, a 3 to 12-membered heterocyclyl, —C(O)R$^{13}$, —C(S)R$^{13}$, —C(O)OR$^{13}$, —C(S)SR$^{13}$, —C(O)SR$^{13}$, —C(S)OR$^{13}$, —SC(O)R$^{13}$, —OC(S)R$^{13}$, —SC(S)R$^{13}$, —C(O)N(R$^{13}$)$_2$, —OR$^{11}$, —SR$^{14}$, —N(R$^{12}$)$_2$, —N(R$^{13}$)OR$^{13}$, —N(R$^{13}$)S(O)$_2$R$^{13}$, —N(R$^{13}$)C(O)OR$^{13}$, —N(R$^{13}$)N(R$^{13}$)$_2$, —N(R$^{13}$)C(O)OR$^{13}$, —N(R$^{13}$)C(O)N(R$^{13}$)$_2$, —S(O)$_2$R$^{13}$, —S(O)R$^{13}$, —S(O)N(R$^{13}$)$_2$, —S(O)$_2$N(R$^{13}$)$_2$, —N$^+$(R$^{13}$)$_3$, —S$^+$(R$^{13}$)$_2$ or —Si(R$^{13}$)$_3$, wherein the $C_{1-12}$alkyl, $C_{2-12}$alkenyl, $C_{2-12}$alkynyl, 3 to 12-membered carbocyclyl and 3 to 12-membered heterocyclyl are each optionally substituted with one or more R$^{21}$; or
$R^5$ and $R^{3b}$ are taken together with the carbons to which they each are attached form a 3-6-membered carbocyclyl, wherein the 3-6-membered carbocyclyl is optionally substituted with one or more R$^{21}$;
$R^6$, in each occurrence, is independently halo, —NO$_2$, —CN, —N$_3$, $C_{1-12}$alkyl, $C_{2-12}$alkenyl, $C_{2-12}$alkynyl, a 3 to 12-membered carbocyclyl, a 3 to 12-membered heterocyclyl, —C(O)R$^{13}$, —C(S)R$^{13}$, —C(O)OR$^{13}$, —C(S)SR$^{13}$, —C(O)SR$^{13}$, —C(S)OR$^{13}$, —SC(O)R$^{13}$, —OC(S)

3

R$^{13}$, —SC(S)R$^{13}$, —C(O)N(R$^{13}$)$_2$, —OR$^{11}$, —SR$^{14}$, —N(R$^{12}$)$_2$, —N(R$^{13}$)OR$^{13}$, —N(R$^{13}$)S(O)$_2$R$^{13}$, —N(R$^{13}$)C(O)R$^{13}$, —N(R$^{13}$)N(R$^{13}$)$_2$, —N(R$^{13}$)C(O)OR$^{13}$, —N(R$^{13}$)C(O)N(R$^{13}$)$_2$, —S(O)$_2$R$^{13}$, —S(O)R$^{13}$, —S(O)N(R$^{13}$)$_2$, —S(O)$_2$N(R$^{13}$)$_2$, —N$^+$(R$^{13}$)$_3$, —S$^+$(R$^{13}$)$_2$ or —Si(R$^{13}$)$_3$; or two R$^6$ attached to the same ring carbon to form an oxo, =NR$^{14}$ or C$_{1-12}$alkylidene, wherein the C$_{1-12}$alkyl, C$_{2-12}$alkenyl, C$_{2-12}$alkynyl, 3 to 12-membered carbocyclyl, 3 to 12-membered heterocyclyl and C$_{1-12}$alkylidene are each optionally substituted with one or more R$^{21}$;

X is NR$^b$ or O;

R$^b$ is H, C$_{1-12}$alkyl, C$_{2-12}$alkenyl, C$_{2-12}$alkynyl, a 3 to 12-membered carbocyclyl, a 3 to 12-membered heterocyclyl, —C(O)R$^c$, —C(O)OR$^c$, —C(O)NR$^c$R$^c$, —S(O)$_2$R$^c$, —S(O)$_2$OR$^c$ or —S(O)$_2$NR$^c$R$^c$, wherein the C$_{1-12}$alkyl, C$_{2-12}$alkenyl, C$_{2-12}$alkynyl, 3 to 12-membered carbocyclyl and 3 to 12-membered heterocyclyl are each optionally substituted with one or more R$^{21}$;

R$^c$, in each occurrence, is independently selected from H, C$_{1-12}$alkyl, C$_{2-12}$alkenyl, C$_{2-12}$alkynyl, a 3 to 12-membered carbocyclyl and a 3 to 12-membered heterocyclyl, wherein the C$_{1-12}$alkyl, C$_{2-12}$alkenyl, C$_{2-12}$alkynyl, 3 to 12-membered carbocyclyl and 3 to 12-membered heterocyclyl are each optionally substituted with one or more R$^{21}$;

R$^{11}$, in each occurrence, is independently selected from H, C$_{1-12}$alkyl, C$_{2-12}$alkenyl, C$_{2-12}$alkynyl, a 3 to 12-membered carbocyclyl, a 3 to 12-membered heterocyclyl, C$_{1-12}$acyl and —Si(R$^{13}$)$_3$, wherein the C$_{1-12}$alkyl, C$_{2-12}$alkenyl, C$_{2-12}$alkynyl, 3 to 12-membered carbocyclyl, 3 to 12-membered heterocyclyl, and C$_{1-12}$acyl are each optionally substituted with one or more R$^{21}$;

R$^{12}$, in each occurrence, is independently selected from H, C$_{1-12}$alkyl, C$_{1-12}$alkoxy, C$_{2-12}$alkenyl, C$_{2-12}$alkynyl, a 3 to 12-membered carbocyclyl, a 3 to 12-membered heterocyclyl and —Si(R$^{13}$)$_3$, wherein the C$_{1-12}$alkyl, C$_{1-12}$alkoxy, C$_{2-12}$alkenyl, C$_{2-12}$alkynyl, 3 to 12-membered carbocyclyl and 3 to 12-membered heterocyclyl are each optionally substituted with one or more R$^{21}$;

R$^{13}$, in each occurrence, is independently selected from H, C$_{1-12}$alkyl, C$_{2-12}$alkenyl, C$_{2-12}$alkynyl, a 3 to 12-membered carbocyclyl, and a 3 to 12-membered heterocyclyl, wherein the C$_{1-12}$alkyl, C$_{2-12}$alkenyl, C$_{2-12}$alkynyl, 3 to 12-membered carbocyclyl and 3 to 12-membered heterocyclyl are optionally substituted with one or more R$^{21}$;

R$^{14}$, in each occurrence, is independently selected from H, C$_{1-12}$alkyl, C$_{2-12}$alkenyl, C$_{2-12}$alkynyl, a 3 to 12-membered carbocyclyl, a 3 to 12-membered heterocyclyl and C$_{1-12}$acyl, wherein the C$_{1-12}$alkyl, C$_{2-12}$alkenyl, C$_{2-12}$alkynyl, 3 to 12-membered carbocyclyl, 3 to 12-membered heterocyclyl and C$_{1-12}$acyl are each optionally substituted with one or more R$^{21}$;

R$^{21}$, in each occurrence, is independently selected from halo, —OH, —S(O)$_2$R$^{16}$, C$_{1-12}$alkyl, C$_{2-12}$alkenyl, C$_{2-12}$alkynyl, C$_{1-12}$alkoxy, a 3 to 12-membered carbocyclyl and a 3 to 12-membered heterocyclyl, wherein the C$_{1-12}$alkyl, C$_{2-12}$alkenyl, C$_{2-12}$alkynyl, C$_{1-12}$alkoxy, 3 to 12-membered carbocyclyl and 3 to 12-membered heterocyclyl are each optionally substituted with 1 to 3 groups selected from halo, —OH, C$_{1-4}$alkyl and C$_{1-4}$alkoxy;

R$^{16}$, in each occurrence, is independently selected from H or C$_{1-12}$alkyl;

n is 0 or an integer from 1 to 8;

p is 0, 1 or 2; and q is 1, 2 or 3, provided that the sum of p and q is not 4 or 5.

4

An alternative first embodiment of the invention is a compound of Formula I:

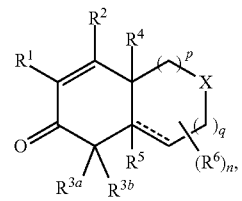

or a pharmaceutically acceptable salt thereof, wherein

R$^1$ is —CN, —C(O)R$^a$ or C$_{1-8}$alkyl substituted with one or more fluorine atoms;

R$^a$ is H, C$_{1-12}$alkyl, C$_{2-12}$alkenyl, C$_{2-12}$alkynyl, a 3 to 12-membered carbocyclyl, a 3 to 12-membered heterocyclyl, —OR$^{11}$, —SR$^{14}$, —N(R$^{12}$)$_2$, —NR$^{13}$OR$^{13}$, —NR$^{13}$S(O)$_2$R$^{13}$, —NR$^{13}$C(O)R$^{13}$, —N(R$^{13}$)N(R$^{13}$)$_2$, —N(R$^{13}$)C(O)OR$^{13}$ or —N(R$^{13}$)C(O)N(R$^{13}$)$_2$, wherein the C$_{1-12}$alkyl, C$_{2-12}$alkenyl, C$_{2-12}$alkynyl, 3 to 12-membered carbocyclyl, and 3 to 12-membered heterocyclyl are each optionally substituted with one or more R$^{21}$;

R$^2$ is H, halo, —NO$_2$, —CN, —N$_3$, C$_{1-12}$alkyl, C$_{2-12}$alkenyl, C$_{2-12}$alkynyl, a 3 to 12-membered carbocyclyl, a 3 to 12-membered heterocyclyl, —C(O)R$^{13}$, —C(S)R$^{13}$, —C(O)OR$^{13}$, —C(S)SR$^{13}$, —C(O)SR$^{13}$, —C(S)OR$^{13}$, —SC(O)R$^{13}$, —OC(S)R$^{13}$, —SC(S)R$^{13}$, —C(O)N(R$^{13}$)$_2$, —OR$^{11}$, —SR$^{14}$, —N(R$^{12}$)$_2$, —N(R$^{13}$)OR$^{13}$, —N(R$^{13}$)S(O)$_2$R$^{13}$, —N(R$^{13}$)C(O)R$^{13}$, —N(R$^{13}$)N(R$^{13}$)$_2$, —N(R$^{13}$)C(O)OR$^{13}$, —N(R$^{13}$)C(O)N(R$^{13}$)$_2$, —S(O)$_2$R$^{13}$, —S(O)R$^{13}$, —S(O)N(R$^{13}$)$_2$, —S(O)$_2$N(R$^{13}$)$_2$, —N$^+$(R$^{13}$)$_3$, —S$^+$(R$^{13}$)$_2$ or —Si(R$^{13}$)$_3$, wherein the C$_{1-12}$alkyl, C$_{2-12}$alkenyl, C$_{2-12}$alkynyl, 3 to 12-membered carbocyclyl and 3 to 12-membered heterocyclyl are each optionally substituted with one or more R$^{21}$;

R$^{3a}$ is H, C$_{1-12}$alkyl, C$_{2-12}$alkenyl, C$_{2-12}$alkynyl, a 3 to 12-membered carbocyclyl, a 3 to 12-membered heterocyclyl, —C(O)R$^{13}$, —C(O)OR$^{13}$, —C(O)N(R$^{13}$)$_2$, —OR$^{11}$, —N(R$^{12}$)$_2$, —N(R$^{13}$)OR$^{13}$, —N(R$^{13}$)S(O)$_2$R$^{13}$, —N(R$^{13}$)C(O)OR$^{13}$, —N(R$^{13}$)N(R$^{13}$)$_2$, —N(R$^{13}$)C(O)OR$^{13}$, —N(R$^{13}$)C(O)N(R$^{13}$)$_2$, —S(O)R$^{13}$, —S(O)N(R$^{13}$)$_2$ or —S(O)$_2$N(R$^{13}$)$_2$, wherein the C$_{1-12}$alkyl, C$_{2-12}$alkenyl, C$_{2-12}$alkynyl, 3 to 12-membered carbocyclyl and 3 to 12-membered heterocyclyl are each optionally substituted with one or more R$^{21}$; and R$^{3b}$ is C$_{1-12}$alkyl, C$_{2-12}$alkenyl, C$_{2-12}$alkynyl, a 3 to 12-membered carbocyclyl, a 3 to 12-membered heterocyclyl, —C(O)R$^{13}$, —C(O)OR$^{13}$, —C(O)N(R$^{13}$)$_2$, —OR$^{11}$, —N(R$^{12}$)$_2$, —N(R$^{13}$)OR$^{13}$, —N(R$^{13}$)S(O)$_2$R$^{13}$, —N(R$^{13}$)C(O)R$^{13}$, —N(R$^{13}$)N(R$^{13}$)$_2$, —N(R$^{13}$)C(O)OR$^{13}$, —N(R$^{13}$)C(O)N(R$^{13}$)$_2$, —S(O)R$^{13}$, —S(O)N(R$^{13}$)$_2$ or —S(O)$_2$N(R$^{13}$)$_2$, wherein the C$_{1-12}$alkyl, C$_{2-12}$alkenyl, C$_{2-12}$alkynyl, 3 to 12-membered carbocyclyl and 3 to 12-membered heterocyclyl are each optionally substituted with one or more R$^{21}$; or R$^{3a}$ and R$^{3b}$ are taken together and are C$_{2-12}$alkylene, C$_{2-12}$alkenylene or C$_{2-12}$alkynylene;

R$^4$ is H, halo, —NO$_2$, —CN, —N$_3$, C$_{1-12}$alkyl, C$_{2-12}$alkenyl, C$_{2-12}$alkynyl, a 3 to 12-membered carbocyclyl, a 3 to 12-membered heterocyclyl, —C(O)R$^{13}$, —C(S)R$^{13}$, —C(O)OR$^{13}$, —C(S)SR$^{13}$, —C(O)SR$^{13}$, —C(S)OR$^{13}$, —SC(O)R$^{13}$, —OC(S)R$^{13}$, —SC(S)R$^{13}$, —C(O)N(R$^{13}$)$_2$, —OR$^{11}$, —SR$^{14}$, —N(R$^{12}$)$_2$, —N(R$^{13}$)OR$^{13}$, —N(R$^{13}$)S(O)$_2$R$^{13}$, —N(R$^{13}$)C(O)R$^{13}$, —N(R$^{13}$)N(R$^{13}$)$_2$, —N(R$^{13}$)C(O)OR$^{13}$, —N(R$^{13}$)C(O)N(R$^{13}$)$_2$, —S(O)$_2$R$^{13}$, —S(O)

$R^{13}$, —S(O)N($R^{13}$)$_2$, —S(O)$_2$N($R^{13}$)$_2$, —N$^+$($R^{13}$)$_3$, —S$^+$($R^{13}$)$_2$ or —Si($R^{13}$)$_3$, wherein the $C_{1-12}$alkyl, $C_{2-12}$alkenyl, $C_{2-12}$alkynyl, 3 to 12-membered carbocyclyl and 3 to 12-membered heterocyclyl are each optionally substituted with one or more $R^{21}$;

" ----- " is either a single bond or a double bond, wherein when " ----- " is a double bond, then $R^5$ is absent; and when " ----- " is a single bond, then $R^5$ is H, halo, —NO$_2$, —CN, —N$_3$, $C_{1-12}$alkyl, $C_{2-12}$alkenyl, $C_{2-12}$alkynyl, a 3 to 12-membered carbocyclyl, a 3 to 12-membered heterocyclyl, —C(O)$R^{13}$, —C(S)$R^{13}$, —C(O)O$R^{13}$, —C(S)S$R^{13}$, —C(O)S$R^{13}$, —C(S)O$R^{13}$, —SC(O)$R^{13}$, —OC(S)$R^{13}$, —SC(S)$R^{13}$, —C(O)N($R^{13}$)$_2$, —O$R^{11}$, —S$R^{14}$, —N($R^{12}$)$_2$, —N($R^{13}$)O$R^{13}$, —N($R^{13}$)S(O)$_2$$R^{13}$, —N($R^{13}$)C(O)$R^{13}$, —N($R^{13}$)N($R^{13}$)$_2$, —N($R^{13}$)C(O)O$R^{13}$, —N($R^{13}$)C(O)N($R^{13}$)$_2$, —S(O)$_2$$R^{13}$, —S(O)$R^{13}$, —S(O)N($R^{13}$)$_2$, —S(O)$_2$N($R^{13}$)$_2$, —N$^+$($R^{13}$)$_3$, —S$^+$($R^{13}$)$_2$ or —Si($R^{13}$)$_3$, wherein the $C_{1-12}$alkyl, $C_{2-12}$alkenyl, $C_{2-12}$alkynyl, 3 to 12-membered carbocyclyl and 3 to 12-membered heterocyclyl are each optionally substituted with one or more $R^{21}$;

$R^6$, in each occurrence, is independently halo, —NO$_2$, —CN, —N$_3$, $C_{1-12}$alkyl, $C_{2-12}$alkenyl, $C_{2-12}$alkynyl, a 3 to 12-membered carbocyclyl, a 3 to 12-membered heterocyclyl, —C(O)$R^{13}$, —C(S)$R^{13}$, —C(O)O$R^{13}$, —C(S)S$R^{13}$, —C(O)S$R^{13}$, —C(S)O$R^{13}$, —SC(O)$R^{13}$, —OC(S)$R^{13}$, —SC(S)$R^{13}$, —C(O)N($R^{13}$)$_2$, —O$R^{11}$, —S$R^{14}$, —N($R^{12}$)$_2$, —N($R^{13}$)O$R^{13}$, —N($R^{13}$)S(O)$_2$$R^{13}$, —N($R^{13}$)C(O)$R^{13}$, —N($R^{13}$)N($R^{13}$)$_2$, —N($R^{13}$)C(O)O$R^{13}$, —N($R^{13}$)C(O)N($R^{13}$)$_2$, —S(O)$_2$$R^{13}$, —S(O)$R^{13}$, —S(O)N($R^{13}$)$_2$, —S(O)$_2$N($R^{13}$)$_2$, —N$^+$($R^{13}$)$_3$, —S$^+$($R^{13}$)$_2$ or —Si($R^{13}$)$_3$; or two $R^6$ attached to the same ring carbon to form an oxo, =N$R^{14}$ or $C_{1-12}$alkylidene, wherein the $C_{1-12}$alkyl, $C_{2-12}$alkenyl, $C_{2-12}$alkynyl, 3 to 12-membered carbocyclyl, 3 to 12-membered heterocyclyl and $C_{1-12}$alkylidene are each optionally substituted with one or more $R^{21}$;

X is N$R^b$ or O;

$R^b$ is H, $C_{1-12}$alkyl, $C_{2-12}$alkenyl, $C_{2-12}$alkynyl, a 3 to 12-membered carbocyclyl, a 3 to 12-membered heterocyclyl, —C(O)$R^c$, —C(O)O$R^c$, —C(O)N$R^c$$R^c$, —S(O)$_2$$R^c$, —S(O)$_2$O$R^c$ or —S(O)$_2$N$R^c$$R^c$, wherein the $C_{1-12}$alkyl, $C_{2-12}$alkenyl, $C_{2-12}$alkynyl, 3 to 12-membered carbocyclyl and 3 to 12-membered heterocyclyl are each optionally substituted with one or more $R^{21}$;

$R^c$, in each occurrence, is independently selected from H, $C_{1-12}$alkyl, $C_{2-12}$alkenyl, $C_{2-12}$alkynyl, a 3 to 12-membered carbocyclyl and a 3 to 12-membered heterocyclyl, wherein the $C_{1-12}$alkyl, $C_{2-12}$alkenyl, $C_{2-12}$alkynyl, 3 to 12-membered carbocyclyl and 3 to 12-membered heterocyclyl are each optionally substituted with one or more $R^{21}$;

$R^{11}$, in each occurrence, is independently selected from H, $C_{1-12}$alkyl, $C_{2-12}$alkenyl, $C_{2-12}$alkynyl, a 3 to 12-membered carbocyclyl, a 3 to 12-membered heterocyclyl, $C_{1-12}$acyl and —Si($R^{13}$)$_3$, wherein the $C_{1-12}$alkyl, $C_{2-12}$alkenyl, $C_{2-12}$alkynyl, 3 to 12-membered carbocyclyl, 3 to 12-membered heterocyclyl, and $C_{1-12}$acyl are each optionally substituted with one or more $R^{21}$;

$R^{12}$, in each occurrence, is independently selected from H, $C_{1-12}$alkyl, $C_{1-12}$alkoxy, $C_{2-12}$alkenyl, $C_{2-12}$alkynyl, a 3 to 12-membered carbocyclyl, a 3 to 12-membered heterocyclyl and —Si($R^{13}$)$_3$, wherein the $C_{1-12}$alkyl, $C_{1-12}$alkoxy, $C_{2-12}$alkenyl, $C_{2-12}$alkynyl, 3 to 12-membered carbocyclyl and 3 to 12-membered heterocyclyl are each optionally substituted with one or more $R^{21}$;

$R^{13}$, in each occurrence, is independently selected from H, $C_{1-12}$alkyl, $C_{2-12}$alkenyl, $C_{2-12}$alkynyl, a 3 to 12-membered carbocyclyl, and a 3 to 12-membered heterocyclyl, wherein the $C_{1-12}$alkyl, $C_{2-12}$alkenyl, $C_{2-12}$alkynyl, 3 to 12-membered carbocyclyl and 3 to 12-membered heterocyclyl are optionally substituted with one or more $R^{21}$;

$R^{14}$, in each occurrence, is independently selected from H, $C_{1-12}$alkyl, $C_{2-12}$alkenyl, $C_{2-12}$alkynyl, a 3 to 12-membered carbocyclyl, a 3 to 12-membered heterocyclyl and $C_{1-12}$ acyl, wherein the $C_{1-12}$alkyl, $C_{2-12}$alkenyl, $C_{2-12}$alkynyl, 3 to 12-membered carbocyclyl, 3 to 12-membered heterocyclyl and $C_{1-12}$acyl are each optionally substituted with one or more $R^{21}$;

$R^{21}$, in each occurrence, is independently selected from halo, —OH, $C_{1-12}$alkyl, $C_{2-12}$alkenyl, $C_{2-12}$alkynyl, $C_{1-12}$alkoxy, a 3 to 12-membered carbocyclyl and a 3 to 12-membered heterocyclyl, wherein the $C_{1-12}$alkyl, $C_{2-12}$alkenyl, $C_{2-12}$alkynyl, $C_{1-12}$alkoxy, 3 to 12-membered carbocyclyl and 3 to 12-membered heterocyclyl are each optionally substituted with 1 to 3 groups selected from halo, —OH and $C_{1-4}$alkoxy;

n is 0 or an integer from 1 to 8;

p is 1 or 2; and q is 1 or 2, provided that the sum of p and q is not 4.

Also provided is a pharmaceutical composition comprising at least one compound described herein, or a pharmaceutically acceptable salt thereof, and at least one pharmaceutically acceptable excipient.

Also provided is a method for activating Nrf2 in a subject in need thereof, the method comprising administering to the subject a therapeutically effective amount of a compound described herein, or a pharmaceutically acceptable salt thereof, thereby activating Nrf2 in the subject.

Also provided is a method for treating a disease caused by oxidative stress in a subject in need thereof, the method comprising administering to the subject a therapeutically effective amount of a compound according to any one of described herein, or a pharmaceutically acceptable salt thereof, thereby treating the disease in the subject.

Also provided is a method for treating a neurodegenerative disease, inflammation and/or an inflammatory disease, an autoimmune disease, an ischemic fibrotic disease, a cancer, premature aging, a cardiovascular disease, a liver disease, a hemoglobinopathy or a metabolic disorder in a subject in need thereof, the method comprising administering to the subject a therapeutically effective amount of a compound according to any one of described herein, or a pharmaceutically acceptable salt thereof, thereby treating the neurodegenerative diseases, inflammation and/or inflammatory disease, autoimmune disease, ischemic fibrotic disease, cancer, premature aging, cardiovascular disease, liver disease, hemoglobinopathy or metabolic disorder in the subject.

Other features or advantages will be apparent from the following detailed description of several embodiments, and also from the appended claims.

BRIEF DESCRIPTION OF THE DRAWINGS

FIGS. 4A to 4D show the expression of Akr1b8 (FIG. 4A), Nqo1 (FIG. 4B), Hmox1 (FIG. 4C) and Osgin1 (FIG. 4D) in kidney, isolated from mice with the wild-type Nrf2 or Nrf2−/−, at 2 hours and 6 hours after being treated with Compound 12-Ent1 (25 mg/kg) or a vehicle.

FIGS. 5A to 5D show the expression of Akr1b8 (FIG. 5A), Nqo1 (FIG. 5B), Hmox1 (FIG. 5C) and Osgin1 (FIG. 5D) in Jejunum, isolated from mice with the wild-type Nrf2 or Nrf2−/−, at 2 hours and 6 hours after being treated with Compound 12-Ent1 (25 mg/kg) or a vehicle.

FIGS. 6A to 6D show the expression of Akr1b8 (FIG. 6A), Nqo1 (FIG. 6B), Hmox1 (FIG. 6C) and Osgin1 (FIG. 6D) in spleen, isolated from mice with the wild-type Nrf2 or Nrf2−/−, at 2 hours and 6 hours after being treated with Compound 12-Ent1 (25 mg/kg) or a vehicle.

FIGS. 7A to 7D show the expression of Akr1b8 (FIG. 7A), Nqo1 (FIG. 7B), Hmox1 (FIG. 7C) and Osgin1 (FIG. 7D) in brain, isolated from mice with the wild-type Nrf2 or Nrf2−/−, at 2 hours and 6 hours after being treated with Compound 12-Ent1 (25 mg/kg) or a vehicle.

DETAILED DESCRIPTION

Figure 1A:
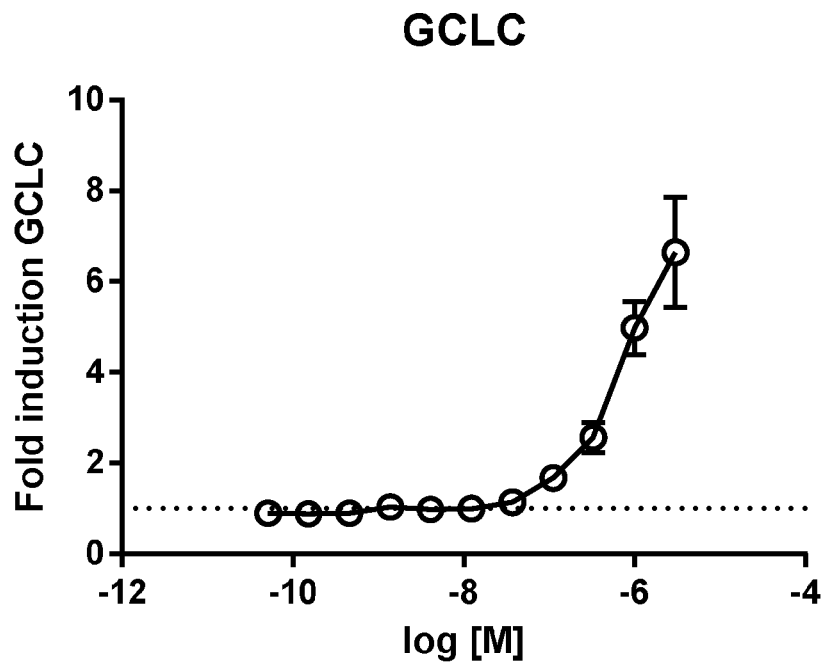
FIGS. 1A to 1D show transcription of GCLC (FIG. 1A), HMOX1 (FIG. 1B), OSGIN1 (FIG. 1C) and NQO1 (FIG. 1D) in human astrocytes treated with increasing concentrations of Compound 12-Ent1 for 20 hours. The x-axis represents log (molar concentrations of compound 12-Ent1). Values shown are mean±S.E.M. n=4-5 experiments.
Figure 1B:
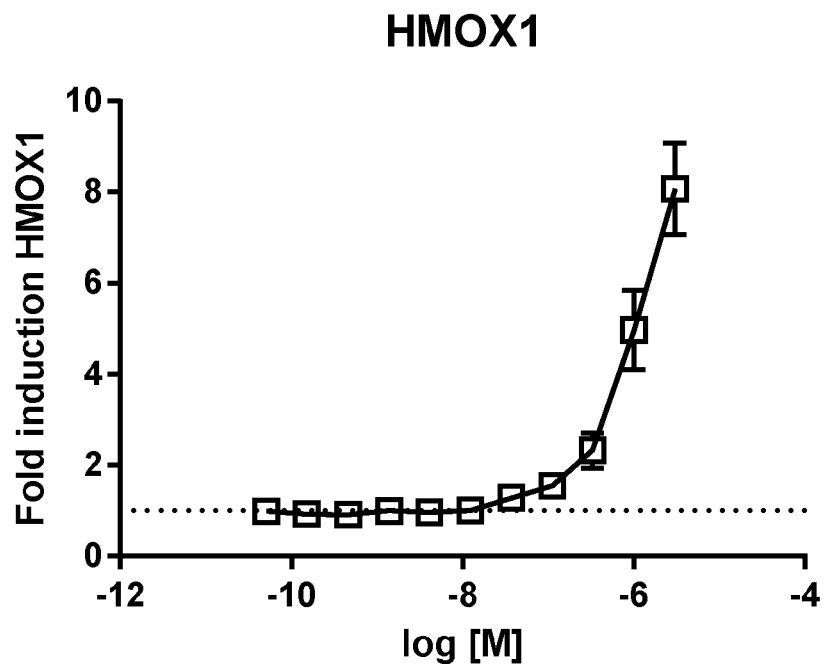
Figure 1C:
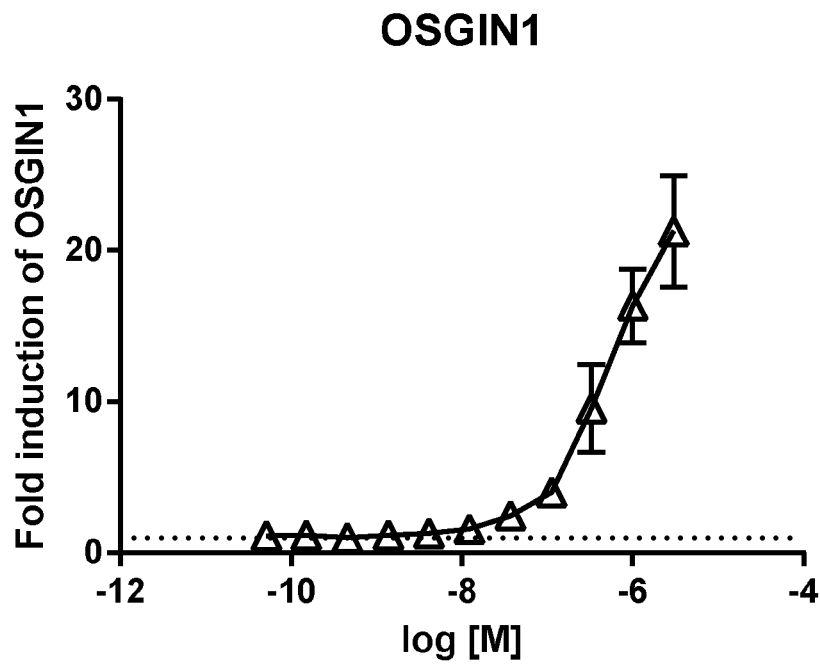
Figure 1D:
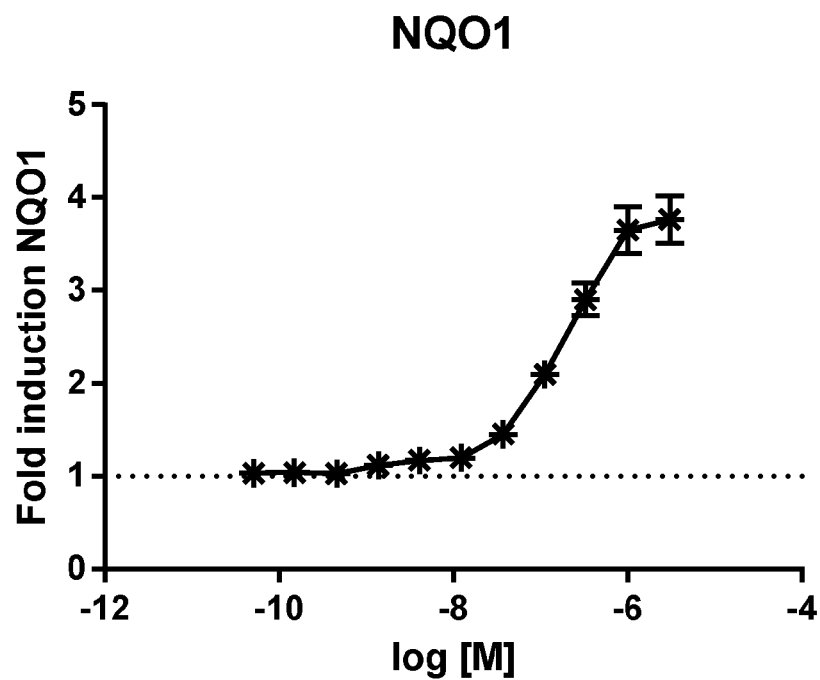

The compounds or pharmaceutically acceptable salts thereof as described herein can be Nrf2 activators.

In a second embodiment of the invention, the compound is represented by formula I, or a pharmaceutically acceptable salt thereof, wherein $R^a$ is H, $C_{1-4}$alkyl (which is optionally substituted with 1 to 4 halo groups), —SH, —$OR^{11}$, —$N(R^{12})_2$, —$NR^{13}OR^{13}$, —$NR^{13}S(O)_2R^{13}$, —$NR^{13}C(O)R^{13}$, —$N(R^{13})N(R^{13})_2$, —$N(R^{13})C(O)OR^{13}$ or —$N(R^{13})C(O)N(R^{13})_2$, wherein $R^1$ to $R^{13}$ in each occurrence, are independently H or $C_{1-6}$alkyl optionally substituted with 1 to 3 groups selected from halo, —OH, $C_{1-4}$alkoxy, a 6 to 12-membered aryl and a 5 to 12-membered heteroaryl; and wherein the values of the other variables are as defined for the first or alternative first embodiment. Preferably, $R^a$ is H, $C_{1-4}$alkyl (which is optionally substituted with 1 to 4 halo groups), —$OR^1$ or —$N(R^{12})_2$, wherein $R^1$ and $R^{12}$, in each occurrence, are independently H or $C_{1-4}$alkyl optionally substituted with 1 to 3 groups selected from halo, —OH or $C_{1-4}$alkoxy. More preferably, $R^a$ is H or $C_{1-4}$alkyl.

In a third embodiment of the invention, the compound is represented by Formula II:

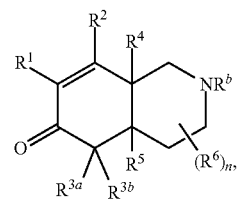

or a pharmaceutically acceptable salt thereof, wherein the values of the variables are as defined for the first, alternative first and/or second embodiments.

In a fourth embodiment of the invention, the compound is represented by Formula II(A):

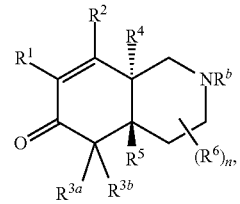

or a pharmaceutically acceptable salt thereof, wherein the values of the variables are as defined for the first, alternative first and/or second embodiments.

In a fifth embodiment of the invention, the compound is represented by Formula II(B):

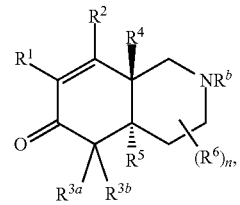

or a pharmaceutically acceptable salt thereof, wherein the values of the variables are as defined for the first, alternative first and/or second embodiments.

In a sixth embodiment of the invention, the compound is represented by Formula III:

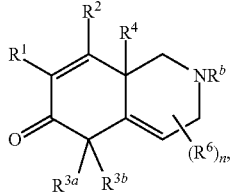

or a pharmaceutically acceptable salt thereof, wherein the values of the variables are as defined for the first, alternative first and/or second embodiments.

In a seventh embodiment of the invention, the compound is represented by Formula III(A):

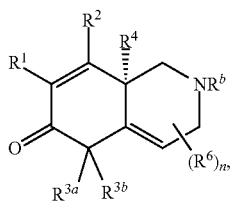

or a pharmaceutically acceptable salt thereof, wherein the values of the variables are as defined for the first, alternative first and/or second embodiments.

In an eighth embodiment of the invention, the compound is represented by Formula III(B):

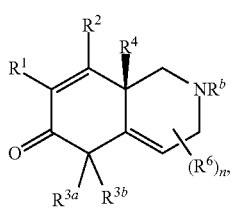

or a pharmaceutically acceptable salt thereof, wherein the values of the variables are as defined for the first, alternative first and/or second embodiments.

In a ninth embodiment of the invention, the compound is represented by the following formula:

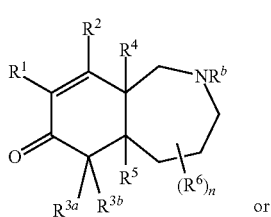

IV or

V

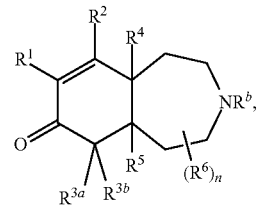

or a pharmaceutically acceptable salt thereof, wherein the values of the variables are as defined for the first, alternative first and/or second embodiments.

In a tenth embodiment of the invention, the compound is represented by the following formula:

IV(A)

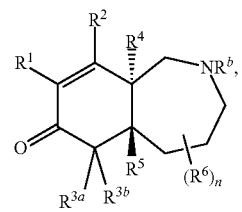

IV(B)

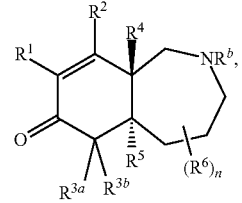

V(A)

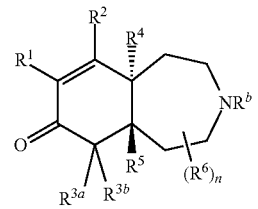

or

V(B)

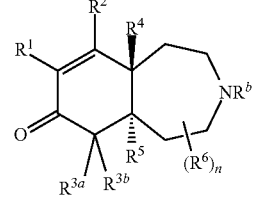

or a pharmaceutically acceptable salt thereof, wherein the values of the variables are as defined for the first, alternative first and/or second embodiments.

In an eleventh embodiment of the invention, the compound is represented by formula I, II, II(A), II(B), III, III(A), III(B), IV, IV(A), IV(B), V, V(A) or V(B), or a pharmaceutically acceptable salt thereof, wherein $R^b$ is H, $C_{1-12}$alkyl, a 6 to 12-membered aryl, a 3-12-membered heterocyclyl, —C(O)$R^c$, —C(O)O$R^c$, —C(O)N$R^c R^c$, —S(O)$_2 R^c$, —S(O)$_2$O$R^c$ or —S(O)$_2$N$R^c R^c$, wherein $R^c$ is H, $C_{1-6}$alkyl, a 3 to 8-membered cycloalkyl, a 3 to 8-membered heterocyclyl or a 6 to 12-membered aryl, wherein the alkyl, cycloalkyl, heterocyclyl and aryl, in each occurrence, in $R^b$ or $R^c$ are optionally substituted with 1 to 3 groups selected from halo, —OH, $C_{1-4}$alkoxy, a 6 to 12-membered aryl and a 5 to 12-membered heteroaryl wherein the heterocyclyl and heteroaryl each comprise 1 to 3 heteroatoms, wherein the heteroatoms are selected from the group consisting of N, S and O; and wherein the values of the other variables are as defined for the first, alternative first and/or second embodiments.

In a twelfth embodiment of the invention, the compound is represented by formula I, II, II(A), II(B), III, III(A), III(B), IV, IV(A), IV(B), V, V(A) or V(B), or a pharmaceutically acceptable salt thereof, wherein $R^b$ is H, $C_{1-6}$alkyl, phenyl, oxetanyl, pyrrolyl, pyrazolyl, imidazolyl, pyridinyl, pyridazinyl, pyrazinyl or pyrimidyl, wherein the $C_{1-6}$alkyl is optionally substituted with 1 to 3 halo, phenyl, pyrrolyl, pyrazolyl, imidazolyl, pyridinyl, pyridazinyl, pyrazinyl or pyrimidyl; and wherein the values of the other variables are as defined for the first, alternative first and/or second embodiments.

In a thirteenth embodiment of the invention, the compound is represented by formula I, II, II(A), II(B), III, III(A), III(B), IV, IV(A), IV(B), V, V(A) or V(B), or a pharmaceutically acceptable salt thereof, wherein $R^b$ is —C(O)$R^c$, —S(O)$_2R^c$ or —C(O)NR$^c$R$^c$; and $R^c$, in each occurrence, is independently H, $C_{1-6}$alkyl, cyclopropyl, cyclobutyl, cyclopentyl, cyclohexyl, phenyl, oxetanyl, pyrrolyl, pyrazolyl, imidazolyl, pyridinyl, pyridazinyl, pyrazinyl or pyrimidyl, wherein the cyclopropyl, cyclobutyl, cyclopentyl, cyclohexyl, phenyl, benzyl, oxetanyl, pyrrolyl, pyrazolyl, imidazolyl, pyridinyl, pyridazinyl, pyrazinyl or pyrimidyl is optionally substituted by 1 to 3 $C_{1-4}$alkyl groups; and the $C_{1-6}$alkyl is substituted with halo, phenyl or $C_{1-4}$alkoxy; and wherein the values of the other variables are as defined for the first, alternative first and/or second embodiments.

In a fourteenth embodiment of the invention, the compound is represented by Formula VI:

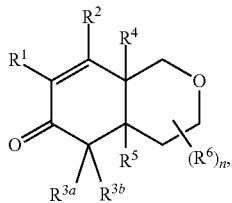

or a pharmaceutically acceptable salt thereof, wherein the values of the variables are as defined for the first, alternative first and/or second embodiments.

In a fifteenth embodiment, the compound is represented by Formula

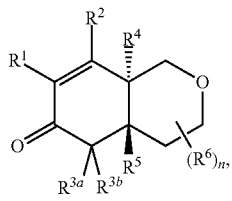

or a pharmaceutically acceptable salt thereof, wherein the values of the variables are as defined for the first, alternative first and/or second embodiments.

In a sixteenth embodiment of the invention, the compound is represented by Formula VI(B):

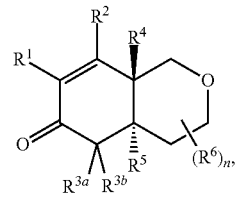

or a pharmaceutically acceptable salt thereof, wherein the values of the variables are as defined for the first, alternative first and/or second embodiments.

In a seventeenth embodiment of the invention, the compound is represented by Formula VII:

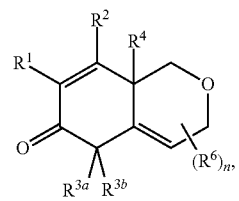

or a pharmaceutically acceptable salt thereof, wherein the values of the variables are as defined for the first, alternative first and/or second embodiments.

In an eighteenth embodiment of the invention, the compound is represented by Formula VII(A):

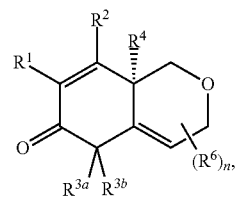

or a pharmaceutically acceptable salt thereof, wherein the values of the variables are as defined for the first, alternative first and/or second embodiments.

In a nineteenth embodiment of the invention, the compound is represented by Formula VII(B):

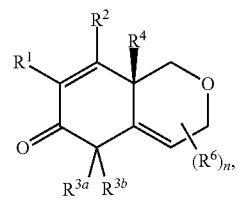

or a pharmaceutically acceptable salt thereof, wherein the values of the variables are as defined for the first, alternative first and/or second embodiments.

In a twentieth embodiment of the invention, the compound is represented by formula I, II, II(A), II(B), III, III(A), III(B), IV, IV(A), IV(B), V, V(A), V(B), VI, VI(A), VI(B), VII, VII(A) or VII(B), or a pharmaceutically acceptable salt thereof, wherein $R^1$ is —CN, —CF$_3$ or —C(O)R$^a$; and wherein the values of the other variables are as defined for the first, alternative first, second, eleventh, twelfth and/or thirteenth embodiments.

In a twenty-first embodiment of the invention, the compound is represented by formula I, II, II(A), II(B), III, III(A), III(B), IV, IV(A), IV(B), V, V(A), V(B), VI, VI(A), VI(B), VII, VII(A) or VII(B), or a pharmaceutically acceptable salt thereof, wherein $R^1$ is —CN; and wherein the values of the other variables are as defined for the first, alternative first, eleventh, twelfth and/or thirteenth embodiments.

In a twenty-second embodiment of the invention, the compound is represented by formula I, II, II(A), II(B), III, III(A), III(B), IV, IV(A), IV(B), V, V(A), V(B), VI, VI(A), VI(B), VII, VII(A) or VII(B), or a pharmaceutically acceptable salt thereof, wherein $R^1$ is —CF$_3$; and wherein the values of the other variables are as defined for the first, alternative first, eleventh, twelfth and/or thirteenth embodiments.

In a twenty-third embodiment of the invention, the compound is represented by formula I, II, II(A), II(B), III, III(A), III(B), IV, IV(A), IV(B), V, V(A), V(B), VI, VI(A), VI(B), VII, VII(A) or VII(B), or a pharmaceutically acceptable salt thereof, wherein $R^1$ is —C(O)R$^a$; and wherein the values of the other variables are as defined for the first, alternative first, second, eleventh, twelfth and/or thirteenth embodiments.

In a twenty-fourth embodiment of the invention, the compound is represented by formula I, II, II(A), II(B), III, III(A), III(B), IV, IV(A), IV(B), V, V(A), V(B), VI, VI(A), VI(B), VII, VII(A) or VII(B), or a pharmaceutically acceptable salt thereof, wherein $R^2$ is H, —OH, halo, C$_{1-12}$alkyl or C$_{1-12}$alkoxy, wherein the alkyl and alkoxy are each optionally substituted with 1 to 3 groups selected from halo, —OH, C$_{1-4}$alkoxy, a 6 to 12-membered aryl and a 5 to 12-membered heteroaryl; and wherein the values of the other variables are as defined for the first, alternative first, second, eleventh, twelfth, thirteenth, twentieth, twenty-first, twenty-second and/or twenty-third embodiments.

In a twenty-fifth embodiment of the invention, the compound is represented by formula I, II, II(A), II(B), III, III(A), III(B), IV, IV(A), IV(B), V, V(A), V(B), VI, VI(A), VI(B), VII, VII(A) or VII(B), or a pharmaceutically acceptable salt thereof, wherein $R^2$ is H or C$_{1-4}$alkyl; and wherein the values of the other variables are as defined for the first, alternative first, second, eleventh, twelfth, thirteenth, twentieth, twenty-first, twenty-second and/or twenty-third embodiments.

In a twenty-sixth embodiment of the invention, the compound is represented by formula I, II, II(A), II(B), III, III(A), III(B), IV, IV(A), IV(B), V, V(A), V(B), VI, VI(A), VI(B), VII, VII(A) or VII(B), or a pharmaceutically acceptable salt thereof, wherein $R^2$ is H; and wherein the values of the other variables are as defined for the first, alternative first, second, eleventh, twelfth, thirteenth, twentieth, twenty-first, twenty-second and/or twenty-third embodiments.

In a twenty-seventh embodiment of the invention, the compound is represented by formula I, II, II(A), II(B), III, III(A), III(B), IV, IV(A), IV(B), V, V(A), V(B), VI, VI(A), VI(B), VII, VII(A) or VII(B), or a pharmaceutically acceptable salt thereof, wherein $R^{3a}$ is H; and $R^{3b}$ is C$_{1-12}$alkyl, C$_{2-12}$alkenyl, C$_{2-12}$alkynyl, a 6 to 12-membered aryl, a 5 to 12-membered heteroaryl, —C(O)R$^{13}$, —OR$^{11}$, —N(R$^{12}$)$_2$ or —N(R$^{13}$)C(O)R$^{13}$, wherein R$^{11}$, in each occurrence, is independently H, C$_{1-12}$alkyl, C$_{1-12}$acyl, a 6 to 12-membered aryl or a 5 to 12-membered heteroaryl; and R$^{12}$ and R$^{13}$, in each occurrence, are independently H, C$_{1-12}$alkyl, a 6 to 12-membered aryl or a 5 to 12-membered heteroaryl, wherein the alkyl, alkenyl, alkynyl, aryl, heteroaryl and acyl, in each occurrence, in R$^{11}$, R$^{12}$ and R$^{13}$ are optionally substituted with 1 to 3 groups selected from halo, —OH, C$_{1-4}$alkoxy, a 6 to 12-membered aryl and a 5 to 12-membered heteroaryl; and wherein the values of the other variables are as defined for the first, alternative first, second, eleventh, twelfth, thirteenth, twentieth, twenty-first, twenty-second, twenty-third, twenty-fourth, twenty-fifth and/or twenty-sixth embodiments. In particular, $R^{3a}$ is H; and $R^{3b}$ is C$_{1-12}$alkyl, C$_{2-12}$alkenyl, C$_{2-12}$alkynyl, —C(O)R$^{13}$, —OR$^1$, —N(R$^{12}$)$_2$ or —N(R$^{13}$)C(O)R$^{13}$; wherein R$^{11}$ to R$^{13}$ are each independently H or C$_{1-4}$alkyl.

In a twenty-eighth embodiment of the invention, the compound is represented by formula I, II, II(A), II(B), III, III(A), III(B), IV, IV(A), IV(B), V, V(A), V(B), VI, VI(A), VI(B), VII, VII(A) or VII(B), or a pharmaceutically acceptable salt thereof, wherein $R^{3a}$ is C$_{1-12}$alkyl, C$_{2-12}$alkenyl, C$_{2-12}$alkynyl, a 3 to 12-membered carbocyclyl, a 3 to 12-membered heterocyclyl, —C(O)R$^{13}$, —C(O)OR$^{13}$, —C(O)N(R$^{13}$)$_2$, —OR$^{11}$, —N(R$^{12}$)$_2$, —N(R$^{13}$)OR$^{13}$, —N(R$^{13}$)S(O)$_2$R$^{13}$, —N(R$^{13}$)C(O)R$^{13}$, —N(R$^{13}$)N(R$^{13}$)$_2$, —N(R$^{13}$)C(O)OR$^{13}$, —N(R$^{13}$)C(O)N(R$^{13}$)$_2$, —S(O)R$^{13}$, —S(O)N(R$^{13}$)$_2$ or —S(O)$_2$N(R$^{13}$)$_2$, wherein the C$_{1-12}$alkyl, C$_{2-12}$alkenyl, C$_{2-12}$alkynyl, 3 to 12-membered carbocyclyl and 3 to 12-membered heterocyclyl are each optionally substituted with one or more R$^{21}$; and wherein the values of the other variables are as defined for the first, alternative first, second, eleventh, twelfth, thirteenth, twentieth, twenty-first, twenty-second, twenty-third, twenty-fourth, twenty-fifth and/or twenty-sixth embodiments.

In a twenty-ninth embodiment of the invention, the compound is represented by formula I, II, II(A), II(B), III, III(A), III(B), IV, IV(A), IV(B), V, V(A), V(B), VI, VI(A), VI(B), VII, VII(A) or VII(B), or a pharmaceutically acceptable salt thereof, wherein $R^{3a}$ and $R^{3b}$ are each independently C$_{1-12}$alkyl, C$_{2-12}$alkenyl, C$_{2-12}$alkynyl, —C(O)R$^{13}$, —OR$^{11}$, —N(R$^{12}$)$_2$ or —N(R$^{13}$)C(O)R$^{13}$; and R$^{11}$ to R$^{13}$ are each independently H or C$_{1-4}$alkyl; and wherein the values of the other variables are as defined for the first, alternative first, second, eleventh, twelfth, thirteenth, twentieth, twenty-first, twenty-second, twenty-third, twenty-fourth, twenty-fifth and/or twenty-sixth embodiments.

In a thirtieth embodiment of the invention, the compound is represented by formula I, II, II(A), II(B), III, III(A), III(B), IV, IV(A), IV(B), V, V(A), V(B), VI, VI(A), VI(B), VII, VII(A) or VII(B), or a pharmaceutically acceptable salt thereof, wherein $R^{3a}$ and $R^{3b}$ are each independently C$_{1-12}$alkyl; and wherein the values of the other variables are as defined for the first, alternative first, second, eleventh, twelfth, thirteenth, twentieth, twenty-first, twenty-second, twenty-third, twenty-fourth, twenty-fifth and/or twenty-sixth embodiments.

In a thirty-first embodiment of the invention, the compound is represented by formula I, II, II(A), II(B), III, III(A), III(B), IV, IV(A), IV(B), V, V(A), V(B), VI, VI(A), VI(B), VII, VII(A) or VII(B), or a pharmaceutically acceptable salt thereof, wherein $R^{3a}$ and $R^{3b}$ are each independently C$_{1-4}$alkyl; and wherein the values of the other variables are as defined for the first, alternative first, second, eleventh, twelfth, thirteenth, twentieth, twenty-first, twenty-second, twenty-third, twenty-fourth, twenty-fifth and/or twenty-sixth embodiments.

In a thirty-second embodiment of the invention, the compound is represented by formula I, II, II(A), II(B), III, III(A), III(B), IV, IV(A), IV(B), V, V(A), V(B), VI, VI(A), VI(B), VII, VII(A) or VII(B), or a pharmaceutically acceptable salt thereof, wherein $R^{3a}$ and $R^{3b}$ are each methyl; and wherein the values of the other variables are as defined for the first, alternative first, second, eleventh, twelfth, thirteenth, twentieth, twenty-first, twenty-second, twenty-third, twenty-fourth, twenty-fifth and/or twenty-sixth embodiments.

In a thirty-third embodiment of the invention, the compound is represented by formula I, II, II(A), II(B), III, III(A), III(B), IV, IV(A), IV(B), V, V(A), V(B), VI, VI(A), VI(B), VII, VII(A) or VII(B), or a pharmaceutically acceptable salt thereof, $R^{3a}$ and $R^{3b}$ are taken together and are $C_{2-12}$alkylene, $C_{2-12}$alkenylene or $C_{2-12}$alkynylene; and wherein the values of the other variables are as defined for the first, alternative first, second, eleventh, twelfth, thirteenth, twentieth, twenty-first, twenty-second, twenty-third, twenty-fourth, twenty-fifth and/or twenty-sixth embodiments.

In a thirty-fourth embodiment of the invention, the compound is represented by formula I, II, II(A), II(B), III, III(A), III(B), IV, IV(A), IV(B), V, V(A), V(B), VI, VI(A), VI(B), VII, VII(A) or VII(B), or a pharmaceutically acceptable salt thereof, wherein $R^{3a}$ and $R^{3b}$ are taken together and are $C_{2-5}$alkylene; and wherein the values of the other variables are as defined for the first, alternative first, second, eleventh, twelfth, thirteenth, twentieth, twenty-first, twenty-second, twenty-third, twenty-fourth, twenty-fifth and/or twenty-sixth embodiments. In a particular aspect, the $C_{2-5}$alkylene is selected from the group consisting of —CH$_2$CH$_2$—, —CH$_2$CH$_2$CH$_2$—, —CH$_2$CH(CH$_3$)—, —CH$_2$CH$_2$CH$_2$CH$_2$—, —CH$_2$CH(CH$_3$)CH$_2$—, —CH$_2$CH$_2$CH(CH$_3$)—, —CH$_2$C(CH$_3$)$_2$—, —CH$_2$CH$_2$CH$_2$CH$_2$CH$_2$—, —CH$_2$CH$_2$CH(CH$_3$)CH$_2$—, —CH$_2$CH$_2$CH$_2$CH(CH$_3$)—, —CH$_2$CH$_2$C(CH$_3$)$_2$—, —CH$_2$C(CH$_3$)$_2$CH$_2$— and —CH(CH$_3$)C(CH$_3$)$_2$—.

In a thirty-fifth embodiment of the invention, the compound is represented by formula I, II, II(A), II(B), III, III(A), III(B), IV, IV(A), IV(B), V, V(A), V(B), VI, VI(A), VI(B), VII, VII(A) or VII(B), or a pharmaceutically acceptable salt thereof, wherein $R^4$ is H, —OH, halo, $C_{1-12}$alkyl, $C_{1-12}$alkoxy or 6 to 12-membered aryl, wherein the alkyl, alkoxy and aryl are each optionally substituted with 1 to 3 groups selected from halo, —OH, $C_{1-4}$alkoxy, a 6 to 12-membered aryl and a 5 to 12-membered heteroaryl; and wherein the values of the other variables are as defined for the first, alternative first, second, eleventh, twelfth, thirteenth, twentieth, twenty-first, twenty-second, twenty-third, twenty-fourth, twenty-fifth, twenty-sixth, twenty-seven, twenty-eight, twenty-nine, thirtieth, thirty-first, thirty-second, thirty-third and/or thirty-fourth embodiments.

In a thirty-sixth embodiment of the invention, the compound is represented by formula I, II, II(A), II(B), III, III(A), III(B), IV, IV(A), IV(B), V, V(A), V(B), VI, VI(A), VI(B), VII, VII(A) or VII(B), or a pharmaceutically acceptable salt thereof, wherein $R^4$ is $C_{1-6}$alkyl or phenyl; and wherein the values of the other variables are as defined for the first, alternative first, second, eleventh, twelfth, thirteenth, twentieth, twenty-first, twenty-second, twenty-third, twenty-fourth, twenty-fifth, twenty-sixth, twenty-seven, twenty-eight, twenty-nine, thirtieth, thirty-first, thirty-second, thirty-third and/or thirty-fourth embodiments.

In a thirty-seventh embodiment of the invention, the compound is represented by formula I, II, II(A), II(B), III, III(A), III(B), IV, IV(A), IV(B), V, V(A), V(B), VI, VI(A), VI(B), VII, VII(A) or VII(B), or a pharmaceutically acceptable salt thereof, wherein $R^4$ is $C_{1-4}$alkyl or phenyl; and wherein the values of the other variables are as defined for the first, alternative first, second, eleventh, twelfth, thirteenth, twentieth, twenty-first, twenty-second, twenty-third, twenty-fourth, twenty-fifth, twenty-sixth, twenty-seven, twenty-eight, twenty-nine, thirtieth, thirty-first, thirty-second, thirty-third and/or thirty-fourth embodiments.

In a thirty-eighth embodiment of the invention, the compound is represented by formula I, II, II(A), II(B), IV, IV(A), IV(B), V, V(A), V(B), VI, VI(A) or VI(B), or a pharmaceutically acceptable salt thereof, wherein $R^5$ is H, —OH, halo, $C_{1-12}$alkyl or $C_{1-12}$alkoxy, wherein the alkyl and alkoxy are each optionally substituted with 1 to 3 groups selected from halo, —OH, $C_{1-4}$alkoxy, a 6 to 12-membered aryl and a 5 to 12-membered heteroaryl; and wherein the values of the other variables are as defined for the first, alternative first, second, eleventh, twelfth, thirteenth, twentieth, twenty-first, twenty-second, twenty-third, twenty-fourth, twenty-fifth, twenty-sixth, twenty-seven, twenty-eight, twenty-nine, thirtieth, thirty-first, thirty-second, thirty-third, thirty-fourth, thirty-fifth, thirty-sixth and/or thirty-seventh embodiments.

In a thirty-ninth embodiment of the invention, the compound is represented by formula I, II, II(A), II(B), IV, IV(A), IV(B), V, V(A), V(B), VI, VI(A) or VI(B), or a pharmaceutically acceptable salt thereof, wherein $R^5$ is H or $C_{1-6}$alkyl; and wherein the values of the other variables are as defined for the first, alternative first, second, eleventh, twelfth, thirteenth, twentieth, twenty-first, twenty-second, twenty-third, twenty-fourth, twenty-fifth, twenty-sixth, twenty-seven, twenty-eight, twenty-nine, thirtieth, thirty-first, thirty-second, thirty-third, thirty-fourth, thirty-fifth, thirty-sixth and/or thirty-seventh embodiments.

In a fortieth embodiment of the invention, the compound is represented by formula I, II, II(A), II(B), IV, IV(A), IV(B), V, V(A), V(B), VI, VI(A) or VI(B), or a pharmaceutically acceptable salt thereof, wherein $R^5$ is H; and wherein the values of the other variables are as defined for the first, alternative first, second, eleventh, twelfth, thirteenth, twentieth, twenty-first, twenty-second, twenty-third, twenty-fourth, twenty-fifth, twenty-sixth, twenty-seven, twenty-eight, twenty-nine, thirtieth, thirty-first, thirty-second, thirty-third, thirty-fourth, thirty-fifth, thirty-sixth and/or thirty-seventh embodiments.

In a forty-first embodiment of the invention, the compound is represented by formula I, II, II(A), II(B), III, III(A), III(B), IV, IV(A), IV(B), V, V(A), V(B), VI, VI(A), VI(B), VII, VII(A) or VII(B), or a pharmaceutically acceptable salt thereof, wherein $R^6$ is —OH, halo, $C_{1-12}$alkyl or $C_{1-12}$alkoxy, wherein the alkyl and alkoxy are each optionally substituted with 1 to 3 groups selected from halo, —OH, $C_{1-4}$alkoxy, a 6 to 12-membered aryl and a 5 to 12-membered heteroaryl; and wherein the values of the other variables are as defined for the first, alternative first, second, eleventh, twelfth, thirteenth, twentieth, twenty-first, twenty-second, twenty-third, twenty-fourth, twenty-fifth, twenty-sixth, twenty-seven, twenty-eight, twenty-nine, thirtieth, thirty-first, thirty-second, thirty-third, thirty-fourth, thirty-fifth, thirty-sixth, thirty-seventh, thirty-eighth, thirty-ninth and/or fortieth embodiments. In a particular embodiment, $R^6$ is methyl.

In a forty-second embodiment of the invention, the compound is represented by formula I, II, II(A), II(B), III, III(A), III(B), IV, IV(A), IV(B), V, V(A), V(B), VI, VI(A), VI(B), VII, VII(A) or VII(B), or a pharmaceutically acceptable salt thereof, wherein n is 1 or 2; and wherein the values of the other variables are as defined for the first, alternative first, second, eleventh, twelfth, thirteenth, twentieth, twenty-first, twenty-second, twenty-third, twenty-fourth, twenty-fifth, twenty-sixth, twenty-seven, twenty-eight, twenty-nine, thirtieth, thirty-first, thirty-second, thirty-third, thirty-fourth, thirty-fifth, thirty-sixth, thirty-seventh, thirty-eighth, thirty-ninth, fortieth and/or forty-first embodiments.

In a forty-third embodiment of the invention, the compound is represented by formula I, II, II(A), II(B), III, III(A), III(B), IV, IV(A), IV(B), V, V(A), V(B), VI, VI(A), VI(B), VII, VII(A) or VII(B), or a pharmaceutically acceptable salt thereof, wherein n is 2; and two $R^6$ are attached to the same ring carbon to form an oxo, $=NR^{14}$ or $C_{1-12}$alkylidene; and wherein the values of the other variables are as defined for the first, alternative first, second, eleventh, twelfth, thirteenth, twentieth, twenty-first, twenty-second, twenty-third, twenty-fourth, twenty-fifth, twenty-sixth, twenty-seven, twenty-eight, twenty-nine, thirtieth, thirty-first, thirty-second, thirty-third, thirty-fourth, thirty-fifth, thirty-sixth, thirty-seventh, thirty-eighth, thirty-ninth and/or fortieth embodiments.

In a forty-fourth embodiment of the invention, the compound is represented by Formula VIII(A):

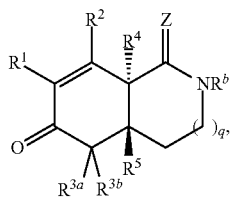

or a pharmaceutically acceptable salt thereof, wherein Z is O, $NR^{22}$ or $C(R^{22})_2$, wherein $R^{22}$ in each occurrence, is independently H or a $C_{1-4}$alkyl optionally substituted with 1 to 3 groups selected from halo, —OH and $C_{1-4}$alkoxy; and wherein the values of the other variables are as defined for the first, alternative first, second, eleventh, twelfth, thirteenth, twentieth, twenty-first, twenty-second, twenty-third, twenty-fourth, twenty-fifth, twenty-sixth, twenty-seven, twenty-eight, twenty-nine, thirtieth, thirty-first, thirty-second, thirty-third, thirty-fourth, thirty-fifth, thirty-sixth, thirty-seventh, thirty-eighth, thirty-ninth and/or fortieth embodiments.

In a forty-fifth embodiment of the invention, the compound is represented by Formula VIII(B):

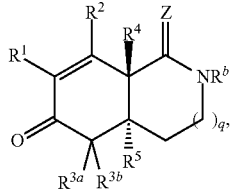

or a pharmaceutically acceptable salt thereof, wherein Z is O, $NR^{22}$ or $C(R^{22})_2$, wherein $R^{22}$, in each occurrence, is independently H or a $C_{1-4}$alkyl optionally substituted with 1 to 3 groups selected from halo, —OH and $C_{1-4}$alkoxy; and wherein the values of the other variables are as defined for the first, alternative first, second, eleventh, twelfth, thirteenth, twentieth, twenty-first, twenty-second, twenty-third, twenty-fourth, twenty-fifth, twenty-sixth, twenty-seven, twenty-eight, twenty-nine, thirtieth, thirty-first, thirty-second, thirty-third, thirty-fourth, thirty-fifth, thirty-sixth, thirty-seventh, thirty-eighth, thirty-ninth and/or fortieth embodiments.

In a forty-sixth embodiment of the invention, the compound is represented by the following formula:

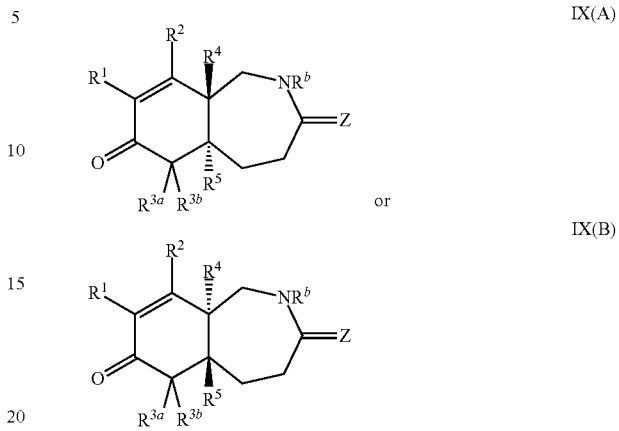

or a pharmaceutically acceptable salt thereof, wherein Z is O, $NR^{22}$ or $C(R^{22})_2$, wherein $R^{22}$, in each occurrence, is independently H or a $C_{1-4}$alkyl optionally substituted with 1 to 3 groups selected from halo, —OH and $C_{1-4}$alkoxy; and wherein the values of the other variables are as defined for the first, alternative first, second, eleventh, twelfth, thirteenth, twentieth, twenty-first, twenty-second, twenty-third, twenty-fourth, twenty-fifth, twenty-sixth, twenty-seven, twenty-eight, twenty-nine, thirtieth, thirty-first, thirty-second, thirty-third, thirty-fourth, thirty-fifth, thirty-sixth, thirty-seventh, thirty-eighth, thirty-ninth and/or fortieth embodiments.

In a forty-seventh embodiment of the invention, the compound is represented by the following formula:

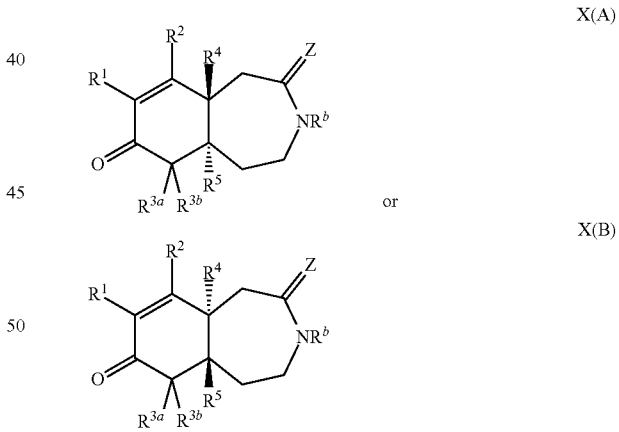

or a pharmaceutically acceptable salt thereof, wherein Z is O, $NR^{22}$ or $C(R^{22})_2$, wherein $R^{22}$ in each occurrence, is independently H or a $C_{1-4}$alkyl optionally substituted with 1 to 3 groups selected from halo, —OH and $C_{1-4}$alkoxy; and wherein the values of the other variables are as defined for the first, alternative first, second, eleventh, twelfth, thirteenth, twentieth, twenty-first, twenty-second, twenty-third, twenty-fourth, twenty-fifth, twenty-sixth, twenty-seven, twenty-eight, twenty-nine, thirtieth, thirty-first, thirty-second, thirty-third, thirty-fourth, thirty-fifth, thirty-sixth, thirty-seventh, thirty-eighth, thirty-ninth and/or fortieth embodiments.

In a forty-eighth embodiment of the invention, the compound is represented by formula VIII(A), VIII(B), IX(A), IX(B), X(A) or X(B), or a pharmaceutically acceptable salt thereof, wherein Z is O; and wherein the values of the other variables are as defined for the first, alternative first, second, eleventh, twelfth, thirteenth, twentieth, twenty-first, twenty-second, twenty-third, twenty-fourth, twenty-fifth, twenty-sixth, twenty-seven, twenty-eight, twenty-nine, thirtieth, thirty-first, thirty-second, thirty-third, thirty-fourth, thirty-fifth, thirty-sixth, thirty-seventh, thirty-eighth, thirty-ninth and/or fortieth embodiments.

In a forty-ninth embodiment of the invention, the compound is represented by formula I, II, II(A), II(B), III, III(A), III(B), IV, IV(A), IV(B), V, V(A), V(B), VI, VI(A), VI(B), VII, VII(A) or VII(B), or a pharmaceutically acceptable salt thereof, wherein n is 0; and wherein the values of the other variables are as defined for the first, alternative first, second, eleventh, twelfth, thirteenth, twentieth, twenty-first, twenty-second, twenty-third, twenty-fourth, twenty-fifth, twenty-sixth, twenty-seven, twenty-eight, twenty-nine, thirtieth, thirty-first, thirty-second, thirty-third, thirty-fourth, thirty-fifth, thirty-sixth, thirty-seventh, thirty-eighth, thirty-ninth and/or fortieth embodiments.

In a fiftieth embodiment of the invention, the compound is represented by formula I, II, II(A), II(B), IV, IV(A), IV(B), V, V(A), V(B), VI, VI(A) or VI(B), or a pharmaceutically acceptable salt thereof, wherein $R^1$ is —CN, —$CF_3$ or —C(O)$R^a$; $R^2$ is H, —OH, halo, $C_{1-12}$alkyl or $C_{1-12}$alkoxy, wherein the alkyl and alkoxy are each optionally substituted with 1 to 3 groups selected from halo, —OH, $C_{1-4}$alkoxy, a 6 to 12-membered aryl and a 5 to 12-membered heteroaryl; $R^{3a}$ is H, $C_{1-12}$alkyl, $C_{2-12}$alkenyl, $C_{2-12}$alkynyl, —C(O)$R^{13}$, —$OR^{11}$, —N($R^{12}$)$_2$ or —N($R^{13}$)C(O)$R^{13}$; and $R^{3b}$ is $C_{1-12}$alkyl, $C_{2-12}$alkenyl, $C_{2-12}$alkynyl, —C(O)$R^{13}$, —$OR^{11}$, —N($R^{12}$)$_2$ or —N($R^{13}$)C(O)$R^{13}$, wherein $R^1$ to $R^{13}$ are each independently H or $C_{1-4}$alkyl; or $R^{3a}$ and $R^{3b}$ taken together with the carbon, to which they are both attached to, form a $C_{3-6}$ membered non-aromatic ring; $R^4$ is H, —OH, halo, $C_{1-12}$alkyl, $C_{1-12}$alkoxy or 6 to 12-membered aryl, wherein the alkyl, alkoxy and aryl are each optionally substituted with 1 to 3 groups selected from halo, —OH, $C_{1-4}$alkoxy, a 6 to 12-membered aryl and a 5 to 12-membered heteroaryl; "------" is a single bond; $R^5$ is H, —OH, halo, $C_{1-12}$alkyl or $C_{1-12}$alkoxy, wherein the alkyl and alkoxy are each optionally substituted with 1 to 3 groups selected from halo, —OH, $C_{1-4}$alkoxy, a 6 to 12-membered aryl and a 5 to 12-membered heteroaryl; $R^b$ is H, $C_{1-12}$alkyl, a 6 to 12-membered aryl, a 3-12-membered heterocyclyl, —C(O)$R^c$, —C(O)O$R^c$, —C(O)N$R^cR^c$, —S(O)$_2R^c$, —S(O)$_2$O$R^c$ or —S(O)$_2$N$R^cR^c$, wherein $R^c$, in each occurrence, is independently H, $C_{1-6}$alkyl, a 3 to 8-membered cycloalkyl, a 3 to 8-membered heterocyclyl or a 6 to 12-membered aryl, wherein the alkyl, cycloalkyl, heterocyclyl and aryl, in each occurrence, in $R^b$ or $R^c$ are optionally substituted with 1 to 3 groups selected from halo, —OH, $C_{1-4}$alkoxy, a 6 to 12-membered aryl and a 5 to 12-membered heteroaryl, wherein the heterocyclyl comprises 1 to 3 heteroatoms, wherein the heteroatoms are selected from the group consisting of N, S and O; and n is 0 or 2, wherein, when n is 2, two $R^6$ are attached to the same ring carbon to form an oxo, =$NR^{14}$ or $C_{1-12}$alkylidene; and wherein the values of the other variables are as defined for the first or alternative first embodiment. Alternatively, the compound is represented by formula I, II, II(A), II(B), IV, IV(A), IV(B), V, V(A), V(B), VI, VI(A) or VI(B), or a pharmaceutically acceptable salt thereof, wherein $R^1$ is —CN or —$CF_3$; $R^2$ is H or $C_{1-4}$alkyl; $R^{3a}$ is H or $C_{1-6}$alkyl and $R^{3b}$ is $C_{1-6}$alkyl; or $R^{3a}$ and $R^{3b}$ taken together with the carbon, to which they are both attached to, form a $C_{3-6}$ membered non-aromatic ring; $R^4$ is $C_{1-6}$alkyl or phenyl; "------" is a single bond; $R^5$ is H or $C_{1-6}$alkyl; $R^b$ is H, $C_{1-6}$alkyl, phenyl, oxetanyl, pyrrolyl, pyrazolyl, imidazolyl, pyridinyl, pyridazinyl, pyrazinyl or pyrimidyl, wherein the $C_{1-6}$alkyl is optionally substituted with 1 to 3 halo, phenyl, pyrrolyl, pyrazolyl, imidazolyl, pyridinyl, pyridazinyl, pyrazinyl or pyrimidyl; and n is 0 or 2, wherein, when n is 2, two $R^6$ are attached to the same ring carbon to form an oxo; and wherein the values of the other variables are as defined for the first or alternative first embodiment. In another alternative, the compound is represented by formula I, II, II(A), II(B), IV, IV(A), IV(B), V, V(A), V(B), VI, VI(A) or VI(B), or a pharmaceutically acceptable salt thereof, wherein $R^1$ is —CN or —$CF_3$; $R^2$ is H or $C_{1-4}$alkyl; $R^{3a}$ is H or $C_{1-6}$alkyl and $R^{3b}$ is $C_{1-6}$alkyl, or $R^{3a}$ and $R^{3b}$ taken together with the carbon, to which they are both attached to, form a $C_{3-6}$ membered non-aromatic ring; $R^4$ is $C_{1-6}$alkyl; "------" is a single bond; $R^5$ is H or $C_{1-6}$alkyl; $R^b$ is —C(O)$R^c$, —S(O)$_2R^c$ or —C(O)N$R^cR^c$, wherein $R^c$, in each occurrence, is independently H, $C_{1-6}$alkyl, cyclopropyl, cyclobutyl, cyclopentyl, cyclohexyl, phenyl, oxetanyl, pyrrolyl, pyrazolyl, imidazolyl, pyridinyl, pyridazinyl, pyrazinyl or pyrimidyl, wherein the cyclopropyl, cyclobutyl, cyclopentyl, cyclohexyl, phenyl, benzyl, oxetanyl, pyrrolyl, pyrazolyl, imidazolyl, pyridinyl, pyridazinyl, pyrazinyl or pyrimidyl is optionally substituted by 1 to 3 $C_{1-4}$alkyl groups; and the $C_{1-6}$alkyl is substituted with halo, phenyl or $C_{1-4}$alkoxy; and n is 0 or 2, wherein, when n is 2, two $R^6$ are attached to the same ring carbon to form an oxo; and wherein the values of the other variables are as defined for the first or alternative first embodiment. In a further alternative, the compound is represented by formula I, II, II(A) or II(B), or a pharmaceutically acceptable salt thereof, wherein $R^1$ is —CN; $R^2$ is H; $R^{3a}$ is H or $C_{1-4}$alkyl and $R^{3b}$ is $C_{1-4}$alkyl, or $R^{3a}$ and $R^{3b}$ taken together with the carbon, to which they are both attached to, form a $C_{3-6}$ membered non-aromatic ring; $R^4$ is $C_{1-4}$alkyl or phenyl; "------" is a single bond; $R^5$ is H; X is $NR^b$, wherein $R^b$ is H, $C_{1-4}$alkyl, phenyl, benzyl, oxetanyl, pyrrolyl, pyrazolyl, imidazolyl, pyridinyl, pyridazinyl, pyrazinyl, pyrimidyl, —C(O)$R^c$, —C(O)NH$R^c$ or —S(O)$_2R^c$; wherein the $C_{1-4}$alkyl, phenyl, benzyl, pyrrolyl, pyrazolyl, imidazolyl, pyridinyl, pyridazinyl, pyrazinyl or pyrimidyl are optionally substituted with 1 or 2 $C_{1-4}$alkyl groups or 1 to 4 halo; and $R^c$ is H, $C_{1-6}$alkyl, cyclopropyl, cyclobutyl, cyclopentyl, cyclohexyl, phenyl, benzyl, oxetanyl, pyrrolyl, pyrazolyl, imidazolyl, pyridinyl, pyridazinyl, pyrazinyl or pyrimidyl; wherein the cyclopropyl, cyclobutyl, cyclopentyl, cyclohexyl, phenyl, benzyl, oxetanyl, pyrrolyl, pyrazolyl, imidazolyl, pyridinyl, pyridazinyl, pyrazinyl or pyrimidyl is optionally substituted by 1 to 3 $C_{1-4}$alkyl groups; and the $C_{1-6}$alkyl is substituted with phenyl or $C_{1-4}$alkoxy; n is 0 or 2, wherein, when n is 2, two $R^6$ are attached to the same ring carbon to form an oxo; p and q are each 1; and wherein the values of the other variables are as defined for the first or alternative first embodiment.

In a fifty-first embodiment of the invention, the compound is represented by formula I, III, III(A), III(B), VII, VII(A) or VII(B), or a pharmaceutically acceptable salt thereof, wherein $R^1$ is —CN, —$CF_3$ or —C(O)$R^a$; $R^2$ is H, —OH, halo, $C_{1-12}$alkyl or $C_{1-12}$alkoxy, wherein the alkyl and alkoxy are each optionally substituted with 1 to 3 groups selected from halo, —OH, $C_{1-4}$alkoxy, a 6 to 12-membered aryl and a 5 to 12-membered heteroaryl; $R^{3a}$ is H, $C_{1-12}$alkyl, $C_{2-12}$alkenyl, $C_{2-12}$alkynyl, —C(O)$R^{13}$, —$OR^{11}$, —N($R^{12}$)$_2$ or —N($R^{13}$)C(O)$R^{13}$; and $R^{3b}$ is $C_{1-12}$alkyl, $C_{2-12}$alkenyl, $C_{2-12}$alkynyl, —C(O)$R^{13}$, —O$R^{11}$, —N($R^{12}$)$_2$ or —N($R^{13}$)C(O)$R^{13}$, wherein $R^1$ to $R^{13}$ are each independently H or $C_{1-4}$alkyl; or $R^{3a}$ and $R^{3b}$ taken together with the carbon, to which they are both attached to, form a $C_{3-8}$ membered non-aromatic ring; $R^4$ is H, —OH, halo, $C_{1-12}$alkyl, $C_{1-12}$alkoxy or 6 to 12-membered aryl, wherein the alkyl, alkoxy and aryl are each optionally substituted with 1 to 3 groups selected from halo, —OH, $C_{1-4}$alkoxy, a 6 to 12-membered aryl and a 5 to 12-membered heteroaryl; "======" is a double bond; $R^b$ is H, $C_{1-12}$alkyl, a 6 to 12-membered aryl, a 3-12-membered heterocycly, —C(O)$R^c$, —C(O)O$R^c$, —C(O)N$R^cR^c$, —S(O)$_2R^c$, —S(O)$_2$O$R^c$ or —S(O)$_2$N$R^cR^c$, wherein $R^c$, in each occurrence, is independently H, $C_{1-6}$alkyl, a 3 to 8-membered cycloalkyl, a 3 to 8-membered heterocyclyl or a 6 to 12-membered aryl, wherein the alkyl, cycloalkyl, heterocyclyl and aryl, in each occurrence, in $R^b$ or $R^c$ are optionally substituted with 1 to 3 groups selected from halo, —OH, $C_{1-4}$alkoxy, a 6 to 12-membered aryl and a 5 to 12-membered heteroaryl, wherein the heterocyclyl and heteroaryl each comprise 1 to 3 heteroatoms, wherein the heteroatoms are selected from the group consisting of N, S and O; and n is 0; and wherein the values of the other variables are as defined for the first or alternative first embodiment. Alternatively, the compound is represented by formula I, III, III(A), III(B), VII, VII(A) or VII(B), or a pharmaceutically acceptable salt thereof, wherein $R^1$ is —CN or —CF$_3$; $R^2$ is H or $C_{1-4}$alkyl; $R^{3a}$ is $C_{1-6}$alkyl and $R^{3b}$ is $C_{1-6}$alkyl, or $R^{3a}$ and $R^{3b}$ taken together with the carbon, to which they are both attached to, form a $C_{3-6}$ membered non-aromatic ring; $R^4$ is $C_{1-6}$alkyl; "======" is a double bond; $R^b$ is H, $C_{1-6}$alkyl, phenyl, oxetanyl, pyrrolyl, pyrazolyl, imidazolyl, pyridinyl, pyridazinyl, pyrazinyl or pyrimidyl, wherein the alkyl is optionally substituted with 1 to 3 halo, phenyl, pyrrolyl, pyrazolyl, imidazolyl, pyridinyl, pyridazinyl, pyrazinyl or pyrimidyl; and n is 0; and wherein the values of the other variables are as defined for the first or alternative first embodiment. In another alternative, the compound is represented by formula I, III, III(A), III(B), VII, VII(A) or VII(B), or a pharmaceutically acceptable salt thereof, wherein $R^1$ is —CN or —CF$_3$; $R^2$ is H or $C_{1-4}$alkyl; $R^{3a}$ is $C_{1-6}$alkyl and $R^{3b}$ is $C_{1-6}$alkyl, or $R^{3a}$ and $R^{3b}$ taken together with the carbon, to which they are both attached to, form a $C_{3-6}$ membered non-aromatic ring; $R^4$ is $C_{1-6}$alkyl; "======" is a double bond; $R^b$ is —C(O)$R^c$, —S(O)$_2R^c$ or —C(O)N$R^cR^c$; wherein $R^c$, in each occurrence, is independently H, $C_{1-6}$alkyl, cyclopropyl, cyclobutyl, cyclopentyl, cyclohexyl, phenyl, oxetanyl, pyrrolyl, pyrazolyl, imidazolyl, pyridinyl, pyridazinyl, pyrazinyl or pyrimidyl, wherein the cyclopropyl, cyclobutyl, cyclopentyl, cyclohexyl, phenyl, benzyl, oxetanyl, pyrrolyl, pyrazolyl, imidazolyl, pyridinyl, pyridazinyl, pyrazinyl or pyrimidyl is optionally substituted by 1 to 3 $C_{1-4}$alkyl groups; and the $C_{1-6}$alkyl is substituted with halo, phenyl or $C_{1-4}$alkoxy; and n is 0; and wherein the values of the other variables are as defined for the first or alternative first embodiment. In a further alternative, the compound is represented by formula I, III, III(A) or III(B), or a pharmaceutically acceptable salt thereof, wherein $R^1$ is —CN; $R^2$ is H; $R^{3a}$ is $C_{1-4}$alkyl and $R^{3b}$ is $C_{1-4}$alkyl, or $R^{3a}$ and $R^{3b}$ taken together with the carbon, to which they are both attached to, form a $C_{3-6}$ membered non-aromatic ring; $R^4$ is $C_{1-4}$alkyl; "======" is a double bond; X is N$R^b$, wherein $R^b$ is $C_{1-4}$alkyl, pyridazinyl, pyrazinyl, pyrimidyl or —C(O)$R^c$, wherein $R^c$ is $C_{1-6}$alkyl; n is 0; and p and q are each 1; and wherein the values of the other variables are as defined for the first or alternative first embodiment.

In a fifty-second embodiment of the invention, the compound is selected from the group consisting of:
(4aR,5R,8aS)-5-methyl-1,6-dioxo-8a-phenyl-2-(3-pyridylmethyl)-3,4,4a,5-tetrahydroisoquinoline-7-carbonitrile;
(4aS,5S,8aR)-5-methyl-1,6-dioxo-8a-phenyl-2-(3-pyridylmethyl)-3,4,4a,5-tetrahydroisoquinoline-7-carbonitrile;
(4aR,5R,8aR)-2-(2-hydroxyethyl)-5-methyl-1,6-dioxo-8a-phenyl-3,4,4a,5-tetrahydroisoquinoline-7-carbonitrile;
(4aS,5S,8aS)-2-(2-hydroxyethyl)-5-methyl-1,6-dioxo-8a-phenyl-3,4,4a,5-tetrahydroisoquinoline-7-carbonitrile;
(4aS,5R,8aR)-5-methyl-1,6-dioxo-8a-phenyl-2-(2-pyridylmethyl)-3,4,4a,5-tetrahydroisoquinoline-7-carbonitrile;
(4aR,5S,8aS)-5-methyl-1,6-dioxo-8a-phenyl-2-(2-pyridylmethyl)-3,4,4a,5-tetrahydroisoquinoline-7-carbonitrile;
(4aR,5R,8aS)-2-cyclobutyl-5-methyl-1,6-dioxo-8a-phenyl-3,4,4a,5-tetrahydroisoquinoline-7-carbonitrile;
(4aS,5S,8aR)-2-cyclobutyl-5-methyl-1,6-dioxo-8a-phenyl-3,4,4a,5-tetrahydroisoquinoline-7-carbonitrile;
(4aR,5R,8aR)-5-methyl-2-[(1-methylpyrazol-4-yl)methyl]-1,6-dioxo-8a-phenyl-3,4,4a,5-tetrahydroisoquinoline-7-carbonitrile;
(4aS,5S,8aS)-5-methyl-2-[(1-methylpyrazol-4-yl)methyl]-1,6-dioxo-8a-phenyl-3,4,4a,5-tetrahydroisoquinoline-7-carbonitrile;
(4aR,5R,8aS)-2-[(3-methoxyphenyl)methyl]-5-methyl-1,6-dioxo-8a-phenyl-3,4,4a,5-tetrahydroisoquinoline-7-carbonitrile;
(4aS,5S,8aR)-2-[(3-methoxyphenyl)methyl]-5-methyl-1,6-dioxo-8a-phenyl-3,4,4a,5-tetrahydroisoquinoline-7-carbonitrile;
(4aS,5S,8aR)-2-[(3-fluorophenyl)methyl]-5-methyl-1,6-dioxo-8a-phenyl-3,4,4a,5-tetrahydroisoquinoline-7-carbonitrile;
(4aR,5R,8aS)-2-[(3-fluorophenyl)methyl]-5-methyl-1,6-dioxo-8a-phenyl-3,4,4a,5-tetrahydroisoquinoline-7-carbonitrile;
(4aS,5S,8aR)-2-[(4-methoxyphenyl)methyl]-5-methyl-1,6-dioxo-8a-phenyl-3,4,4a,5-tetrahydroisoquinoline-7-carbonitrile;
(4aR,5R,8aS)-2-[(4-methoxyphenyl)methyl]-5-methyl-1,6-dioxo-8a-phenyl-3,4,4a,5-tetrahydroisoquinoline-7-carbonitrile;
(4aS,5S,8aS)-2-isopropyl-5-methyl-1,6-dioxo-8a-phenyl-3,4,4a,5-tetrahydroisoquinoline-7-carbonitrile;
(4aR,5R,8aR)-2-isopropyl-5-methyl-1,6-dioxo-8a-phenyl-3,4,4a,5-tetrahydroisoquinoline-7-carbonitrile;
(4aS,5S,8aR)-2-(cyclopropylmethyl)-5-methyl-1,6-dioxo-8a-phenyl-3,4,4a,5-tetrahydroisoquinoline-7-carbonitrile;
(4aR,5R,8aS)-2-(cyclopropylmethyl)-5-methyl-1,6-dioxo-8a-phenyl-3,4,4a,5-tetrahydroisoquinoline-7-carbonitrile;
(4aS,5S,8aR)-2-[(4-fluorophenyl)methyl]-5-methyl-1,6-dioxo-8a-phenyl-3,4,4a,5-tetrahydroisoquinoline-7-carbonitrile;
(4aR,5R,8aS)-2-[(4-fluorophenyl)methyl]-5-methyl-1,6-dioxo-8a-phenyl-3,4,4a,5-tetrahydroisoquinoline-7-carbonitrile;
(4aS,5S,8aR)-2-(2,2-difluoroethyl)-5-methyl-1,6-dioxo-8a-phenyl-3,4,4a,5-tetrahydroisoquinoline-7-carbonitrile;
(4aR,5R,8aS)-2-(2,2-difluoroethyl)-5-methyl-1,6-dioxo-8a-phenyl-3,4,4a,5-tetrahydroisoquinoline-7-carbonitrile;
(4aS,5S,8aR)-2-[(2-fluorophenyl)methyl]-5-methyl-1,6-dioxo-8a-phenyl-3,4,4a,5-tetrahydroisoquinoline-7-carbonitrile;
(4aR,5R,8aS)-2-[(2-fluorophenyl)methyl]-5-methyl-1,6-dioxo-8a-phenyl-3,4,4a,5-tetrahydroisoquinoline-7-carbonitrile;

(4aS,8aR)-2-(2-methoxyethyl)-5,5-dimethyl-1,6-dioxo-8a-phenyl-4,4a-dihydro-3H-isoquinoline-7-carbonitrile;
(4aR,8aR)-2-(2-methoxyethyl)-5,5-dimethyl-1,6-dioxo-8a-phenyl-4,4a-dihydro-3H-isoquinoline-7-carbonitrile;
(4aS,5S,8aR)-2-(2-methoxyethyl)-5-methyl-1,6-dioxo-8a-phenyl-3,4,4a,5-tetrahydroisoquinoline-7-carbonitrile;
(4aR,5R,8aS)-2-(2-methoxyethyl)-5-methyl-1,6-dioxo-8a-phenyl-3,4,4a,5-tetrahydroisoquinoline-7-carbonitrile;
(4aS,8aS)-2,5,5-trimethyl-1,6-dioxo-8a-phenyl-4,4a-dihydro-3H-isoquinoline-7-carbonitrile;
(4aR,8aR)-2,5,5-trimethyl-1,6-dioxo-8a-phenyl-4,4a-dihydro-3H-isoquino line-7-carbonitrile;
(4aR,8aR)-5,5,8a-trimethyl-2-(2-methylpyrimidin-4-yl)-6-oxo-1,3,4,4a-tetrahydroisoquino line-7-carbonitrile;
(5aR,9aS)-3-acetyl-5a,9,9-trimethyl-8-oxo-2,4,5,9a-tetrahydro-1H-3-benzazepine-7-carbonitrile;
(4aR,8aR)-5,5,8a-trimethyl-2-(6-methylpyrimidin-4-yl)-6-oxo-1,3,4,4a-tetrahydroisoquinoline-7-carbonitrile hydrochloride;
(5aS,9aR)-2-(2,2-difluoroethyl)-6,6,9a-trimethyl-7-oxo-3,4,5,5a-tetrahydro-1H-2-benzazepine-8-carbonitrile;
(4aS,8aR)-5,5,8a-trimethyl-2-(2-methylpyrimidin-5-yl)-6-oxo-1,3,4,4a-tetrahydroisoquino line-7-carbonitrile;
(4aS,8aR)-5,5,8a-trimethyl-6-oxo-2-(2,2,2-trifluoroacetyl)-1,3,4,4a-tetrahydroisoquino line-7-carbonitrile;
(8aR)-2-ethyl-5,5-dimethyl-1,6-dioxo-8a-phenyl-3H-isoquinoline-7-carbonitrile;
(8aS)-2-ethyl-5,5-dimethyl-1,6-dioxo-8a-phenyl-3H-isoquinoline-7-carbonitrile;
(4aR,8aS)-2-ethyl-5,5-dimethyl-1,6-dioxo-8a-phenyl-4,4a-dihydro-3H-isoquino line-7-carbonitrile;
(4aS,8aR)-2-ethyl-5,5-dimethyl-1,6-dioxo-8a-phenyl-4,4a-dihydro-3H-isoquino line-7-carbonitrile;
(4aR,5S,8aR)-2-acetyl-5-ethyl-5,8a-dimethyl-6-oxo-1,3,4,4a-tetrahydroisoquinoline-7-carbonitrile;
(5R,8aR)-2-acetyl-5-benzyl-5,8a-dimethyl-6-oxo-1,3-dihydroisoquinoline-7-carbonitrile;
(5S,8aR)-2-acetyl-5-benzyl-5,8a-dimethyl-6-oxo-1,3-dihydroisoquinoline-7-carbonitrile;
(5R,8aR)-2-acetyl-5-ethyl-5,8a-dimethyl-6-oxo-1,3-dihydroisoquinoline-7-carbonitrile;
(5S,8aR)-2-acetyl-5-ethyl-5,8a-dimethyl-6-oxo-1,3-dihydroisoquinoline-7-carbonitrile;
(4aS,5R,8aR)-2,5-dimethyl-1,6-dioxo-8a-phenyl-3,4,4a,5-tetrahydroisoquinoline-7-carbonitrile;
(4aR,5S,8aS)-2,5-dimethyl-1,6-dioxo-8a-phenyl-3,4,4a,5-tetrahydroisoquinoline-7-carbonitrile;
(8aR)-2,5,5-trimethyl-1,6-dioxo-8a-phenyl-3H-isoquinoline-7-carbonitrile;
(8aS)-2,5,5-trimethyl-1,6-dioxo-8a-phenyl-3H-isoquinoline-7-carbonitrile;
(4aS,5R,8aR)-2-ethyl-5-methyl-1,6-dioxo-8a-phenyl-3,4,4a,5-tetrahydroisoquinoline-7-carbonitrile;
(4aR,5S,8aS)-2-ethyl-5-methyl-1,6-dioxo-8a-phenyl-3,4,4a,5-tetrahydroisoquinoline-7-carbonitrile;
(4aS,8aR)-2-[(2S)-2-fluoropropanoyl]-5,5,8a-trimethyl-6-oxo-1,3,4,4a-tetrahydroisoquino line-7-carbonitrile;
(4aS,8aR)-2-[(2R)-2-fluoropropanoyl]-5,5,8a-trimethyl-6-oxo-1,3,4,4a-tetrahydroisoquino line-7-carbonitrile;
(4aS,8aR)-2-(2,2-difluoroethyl)-5,5-dimethyl-6-oxo-8a-phenyl-1,3,4,4a-tetrahydroisoquinoline-7-carbonitrile;
(4aR,8aS)-2-(2,2-difluoroethyl)-5,5-dimethyl-6-oxo-8a-phenyl-1,3,4,4a-tetrahydroisoquinoline-7-carbonitrile;
methyl (4aS,8aR)-7-cyano-5,5,8a-trimethyl-6-oxo-1,3,4,4a-tetrahydroisoquinoline-2-carboxylate;
(4aS,8aR)-2-acetyl-5,5,8a-trimethyl-6-oxo-1,3,4,4a-tetrahydroisoquinoline-7-carbonitrile;
tert-butyl (4aR,8aR)-7-cyano-5,5,8a-trimethyl-6-oxo-1,3,4,4a-tetrahydroisoquinoline-2-carboxylate;
(4aS,8aR)-2-acetyl-5,5-dimethyl-6-oxo-8a-phenyl-1,3,4,4a-tetrahydroisoquinoline-7-carbonitrile;
(4aR,8aS)-2-acetyl-5,5-dimethyl-6-oxo-8a-phenyl-1,3,4,4a-tetrahydroisoquinoline-7-carbonitrile;
(4aR,5R,8aS)-5-methyl-1,6-dioxo-8a-phenyl-3,4,4a,5-tetrahydro-2H-isoquinoline-7-carbonitrile;
(4aS,5S,8aR)-5-methyl-1,6-dioxo-8a-phenyl-3,4,4a,5-tetrahydro-2H-isoquinoline-7-carbonitrile;
(4aS,8aR)-5,5,8a-trimethyl-6-oxo-2-pyrazin-2-yl-1,3,4,4a-tetrahydroisoquino line-7-carbonitrile;
(4aS,8aR)-2-(2,2-difluoroethyl)-8a-ethyl-5,5-dimethyl-6-oxo-1,3,4,4a-tetrahydroisoquinoline-7-carbonitrile;
(4aR,8aS)-2-(2,2-difluoroethyl)-8a-ethyl-5,5-dimethyl-6-oxo-1,3,4,4a-tetrahydroisoquinoline-7-carbonitrile;
(4aS,8aR)-8a-ethyl-5,5-dimethyl-6-oxo-2-pyrimidin-2-yl-1,3,4,4a-tetrahydroisoquino line-7-carbonitrile;
(4aR,8aS)-8a-ethyl-5,5-dimethyl-6-oxo-2-pyrimidin-2-yl-1,3,4,4a-tetrahydroisoquino line-7-carbonitrile;
(4aS,8aR)-2-acetyl-8a-ethyl-5,5-dimethyl-6-oxo-1,3,4,4a-tetrahydroisoquinoline-7-carbonitrile;
(4aR,8aS)-2-acetyl-8a-ethyl-5,5-dimethyl-6-oxo-1,3,4,4a-tetrahydroisoquino line-7-carbonitrile;
(4aR,8aR)-2-(2-methoxyethyl)-5,5,8a-trimethyl-6-oxo-1,3,4,4a-tetrahydroisoquino line-7-carbonitrile;
(4aR,8aR)-5,5,8a-trimethyl-2-(2-methylsulfonylethyl)-6-oxo-1,3,4,4a-tetrahydroisoquino line-7-carbonitrile;
(5aS,9aR)-2-acetyl-6,6,9a-trimethyl-7-oxo-3,4,5,5a-tetrahydro-1H-2-benzazepine-8-carbonitrile;
(5aS,9aR)-6,6,9a-trimethyl-3,7-dioxo-2,4,5,5a-tetrahydro-1H-2-benzazepine-8-carbonitrile;
(5aR,9aS)-5a,9,9-trimethyl-4,8-dioxo-2,3,5,9a-tetrahydro-1H-3-benzazepine-7-carbonitrile;
(5aS,9aS)-1,6,6,9a-tetramethyl-2,7-dioxo-3,4,5,5a-tetrahydro-1-benzazepine-8-carbonitrile;
(5aS,9aS)-6,6,9a-trimethyl-2,7-dioxo-3,4,5,5a-tetrahydro-1H-1-benzazepine-8-carbonitrile;
(3R,4aS,8aR)-2-acetyl-3,5,5,8a-tetramethyl-6-oxo-1,3,4,4a-tetrahydroisoquinoline-7-carbonitrile;
(3S,4aR,8aS)-2-acetyl-3,5,5,8a-tetramethyl-6-oxo-1,3,4,4a-tetrahydroisoquinoline-7-carbonitrile;
(4aR,8aS)-2,5,5,8a-tetramethyl-3,6-dioxo-4,4a-dihydro-1H-isoquinoline-7-carbonitrile;
(4aS,8aR)-2,5,5,8a-tetramethyl-3,6-dioxo-4,4a-dihydro-1H-isoquinoline-7-carbonitrile;
(4aR,8aS)-5,5,8a-trimethyl-3,6-dioxo-1,2,4,4a-tetrahydroisoquinoline-7-carbonitrile;
(4aS,8aR)-5,5,8a-trimethyl-3,6-dioxo-1,2,4,4a-tetrahydroisoquinoline-7-carbonitrile;
(4aR,7aR,8aR)-3-ethyl-7a-methyl-4,7-dioxo-4a-phenyl-2,8-dihydro-1H-cyclopropa[e]isoquinoline-6-carbonitrile;
(4aS,7aS,8aS)-3-ethyl-7a-methyl-4,7-dioxo-4a-phenyl-2,8-dihydro-1H-cyclopropa[e]isoquinoline-6-carbonitrile;
(4aR,8aR)-2-ethyl-5,5-dimethyl-8a-phenyl-7-(trifluoromethyl)-4,4a-dihydro-3H-isoquinoline-1,6-dione;
(4aS,8aS)-2-ethyl-5,5-dimethyl-8a-phenyl-7-(trifluoromethyl)-4,4a-dihydro-3H-isoquinoline-1,6-dione;
(4aS,8aR)-2-acetyl-5,5,8a-trimethyl-7-(trifluoromethyl)-1,3,4,4a-tetrahydroisoquinolin-6-one;
(4aR,8aS)-2-acetyl-5,5,8a-trimethyl-6-oxo-1,3,4,4a-tetrahydroisoquinoline-7-carboxamide;
(4aS,8aR)-2-acetyl-5,5,8a-trimethyl-6-oxo-1,3,4,4a-tetrahydroisoquinoline-7-carboxamide;
(8aR)-8a-(4-fluorophenyl)-2,5,5-trimethyl-1,6-dioxo-3H-isoquinoline-7-carbonitrile;

(8aS)-8a-(4-fluorophenyl)-2,5,5-trimethyl-1,6-dioxo-3H-isoquinoline-7-carbonitrile;
(8aR)-8a-(4-chlorophenyl)-2,5,5-trimethyl-1,6-dioxo-3H-isoquinoline-7-carbonitrile;
(8aR)-8a-(4-chlorophenyl)-2,5,5-trimethyl-1,6-dioxo-3H-isoquinoline-7-carbonitrile;
(8aS)-8a-(3-fluorophenyl)-2,5,5-trimethyl-1,6-dioxo-3H-isoquinoline-7-carbonitrile;
(8aR)-8a-(3-fluorophenyl)-2,5,5-trimethyl-1,6-dioxo-3H-isoquinoline-7-carbonitrile;
(8aR)-8a-(4-methoxyphenyl)-2,5,5-trimethyl-1,6-dioxo-3H-isoquinoline-7-carbonitrile;
(8aR)-8a-(4-methoxyphenyl)-2,5,5-trimethyl-1,6-dioxo-3H-isoquinoline-7-carbonitrile;
(8aR)-8a-benzyl-2,5,5-trimethyl-1,6-dioxo-3H-isoquinoline-7-carbonitrile;
(8aS)-8a-benzyl-2,5,5-trimethyl-1,6-dioxo-3H-isoquinoline-7-carbonitrile;
(4aS,8aS)-2-acetyl-5,5,8a-trimethyl-7-methylsulfonyl-1,3,4,4a-tetrahydroisoquinolin-6-one;
(8aS)-5,5-dimethyl-2-(1-methylpyrazol-3-yl)-1,6-dioxo-8a-phenyl-3H-isoquinoline-7-carbonitrile;
(8aR)-5,5-dimethyl-2-(1-methylpyrazol-3-yl)-1,6-dioxo-8a-phenyl-3H-isoquinoline-7-carbonitrile;
(8aS)-5,5-dimethyl-2-(1-methylpyrazol-4-yl)-1,6-dioxo-8a-phenyl-3H-isoquinoline-7-carbonitrile;
(8aR)-5,5-dimethyl-2-(1-methylpyrazol-4-yl)-1,6-dioxo-8a-phenyl-3H-isoquinoline-7-carbonitrile;
(8aS)-5,5-dimethyl-2-(2-methylpyrazol-3-yl)-1,6-dioxo-8a-phenyl-3H-isoquinoline-7-carbonitrile;
(8aR)-5,5-dimethyl-2-(2-methylpyrazol-3-yl)-1,6-dioxo-8a-phenyl-3H-isoquinoline-7-carbonitrile;
(8aS)-5,5-dimethyl-2-(1-methylimidazol-2-yl)-1,6-dioxo-8a-phenyl-3H-isoquinoline-7-carbonitrile;
(8aR)-5,5-dimethyl-2-(1-methylimidazol-2-yl)-1,6-dioxo-8a-phenyl-3H-isoquinoline-7-carbonitrile;
(8aS)-5,5-dimethyl-2-(6-methylpyrimidin-4-yl)-1,6-dioxo-8a-phenyl-3H-isoquinoline-7-carbonitrile;
(8aR)-5,5-dimethyl-2-(6-methylpyrimidin-4-yl)-1,6-dioxo-8a-phenyl-3H-isoquinoline-7-carbonitrile;
(8aS)-5,5-dimethyl-2-(2-methylpyrimidin-4-yl)-1,6-dioxo-8a-phenyl-3H-isoquinoline-7-carbonitrile;
(8aR)-5,5-dimethyl-2-(2-methylpyrimidin-4-yl)-1,6-dioxo-8a-phenyl-3H-isoquinoline-7-carbonitrile;
(8aS)-5,5-dimethyl-1,6-dioxo-8a-phenyl-2-pyridazin-4-yl-3H-isoquinoline-7-carbonitrile;
(8aR)-5,5-dimethyl-1,6-dioxo-8a-phenyl-2-pyridazin-4-yl-3H-isoquinoline-7-carbonitrile;
(8aS)-5,5-dimethyl-1,6-dioxo-8a-phenyl-2-pyrimidin-5-yl-3H-isoquinoline-7-carbonitrile;
(8aR)-5,5-dimethyl-1,6-dioxo-8a-phenyl-2-pyrimidin-5-yl-3H-isoquinoline-7-carbonitrile;
(8aS)-5,5-dimethyl-1,6-dioxo-8a-phenyl-2-pyridazin-3-yl-3H-isoquinoline-7-carbonitrile;
(8aR)-5,5-dimethyl-1,6-dioxo-8a-phenyl-2-pyridazin-3-yl-3H-isoquinoline-7-carbonitrile;
(8aS)-5,5-dimethyl-1,6-dioxo-8a-phenyl-2-pyrazin-2-yl-3H-isoquinoline-7-carbonitrile;
(8aR)-5,5-dimethyl-1,6-dioxo-8a-phenyl-2-pyrazin-2-yl-3H-isoquinoline-7-carbonitrile;
(8aS)-5,5-dimethyl-1,6-dioxo-8a-phenyl-2-pyrimidin-4-yl-3H-isoquinoline-7-carbonitrile;
(8aR)-5,5-dimethyl-1,6-dioxo-8a-phenyl-2-pyrimidin-4-yl-3H-isoquinoline-7-carbonitrile;
(8aS)-5,5-dimethyl-1,6-dioxo-8a-phenyl-2-(2-pyridyl)-3H-isoquinoline-7-carbonitrile;
(8aR)-5,5-dimethyl-1,6-dioxo-8a-phenyl-2-(2-pyridyl)-3H-isoquinoline-7-carbonitrile;
(8aS)-5,5-dimethyl-1,6-dioxo-8a-phenyl-2-(3-pyridyl)-3H-isoquinoline-7-carbonitrile;
(8aR)-5,5-dimethyl-1,6-dioxo-8a-phenyl-2-(3-pyridyl)-3H-isoquinoline-7-carbonitrile;
(8aS)-5,5-dimethyl-1,6-dioxo-8a-phenyl-2-(4-pyridyl)-3H-isoquinoline-7-carbonitrile;
(8aR)-5,5-dimethyl-1,6-dioxo-8a-phenyl-2-(4-pyridyl)-3H-isoquinoline-7-carbonitrile;
(8aS)-5,5-dimethyl-1,6-dioxo-8a-phenyl-2-pyrimidin-2-yl-3H-isoquinoline-7-carbonitrile;
(8aR)-5,5-dimethyl-1,6-dioxo-8a-phenyl-2-pyrimidin-2-yl-3H-isoquinoline-7-carbonitrile;
(4aS,5S,8aR)-2-(4-methoxyphenyl)-5-methyl-1,6-dioxo-8a-phenyl-3,4,4a,5-tetrahydroisoquinoline-7-carbonitrile;
(4aR,5R,8aS)-2-(4-methoxyphenyl)-5-methyl-1,6-dioxo-8a-phenyl-3,4,4a,5-tetrahydroisoquinoline-7-carbonitrile;
(4aS,5S,8aR)-2-(4-fluorophenyl)-5-methyl-1,6-dioxo-8a-phenyl-3,4,4a,5-tetrahydroisoquinoline-7-carbonitrile;
(4aR,5R,8aS)-2-(4-fluorophenyl)-5-methyl-1,6-dioxo-8a-phenyl-3,4,4a,5-tetrahydroisoquinoline-7-carbonitrile;
(4aS,5S,8aR)-5-methyl-1,6-dioxo-8a-phenyl-2-pyrimidin-4-yl-3,4,4a,5-tetrahydroisoquinoline-7-carbonitrile;
(4aR,5R,8aS)-5-methyl-1,6-dioxo-8a-phenyl-2-pyrimidin-4-yl-3,4,4a,5-tetrahydroisoquinoline-7-carbonitrile;
(4aS,5R,8aR)-5-methyl-1,6-dioxo-2,8a-diphenyl-3,4,4a,5-tetrahydroisoquinoline-7-carbonitrile;
(4aR,5S,8aS)-5-methyl-1,6-dioxo-2,8a-diphenyl-3,4,4a,5-tetrahydroisoquinoline-7-carbonitrile;
(4aR,5R,8aS)-2-ethyl-5,8a-dimethyl-1,6-dioxo-3,4,4a,5-tetrahydroisoquinoline-7-carbonitrile;
(4aS,5S,8aR)-2-ethyl-5,8a-dimethyl-1,6-dioxo-3,4,4a,5-tetrahydroisoquinoline-7-carbonitrile;
(4aR,5R,8aS)-2,5,8a-trimethyl-1,6-dioxo-3,4,4a,5-tetrahydroisoquinoline-7-carbonitrile;
(4aS,5S,8aR)-2,5,8a-trimethyl-1,6-dioxo-3,4,4a,5-tetrahydroisoquinoline-7-carbonitrile;
(4aR,8aR)-2-isopropyl-5,5,8a-trimethyl-1,6-dioxo-4,4a-dihydro-3H-isoquinoline-7-carbonitrile;
(4aS,8aS)-2-isopropyl-5,5,8a-trimethyl-1,6-dioxo-4,4a-dihydro-3H-isoquinoline-7-carbonitrile;
(4aS,8aS)-2,5,5,8a-tetramethyl-1,6-dioxo-4,4a-dihydro-3H-isoquinoline-7-carbonitrile;
(4aR,8aR)-2,5,5,8a-tetramethyl-1,6-dioxo-4,4a-dihydro-3H-isoquinoline-7-carbonitrile;
(8aR)-2-ethyl-5,5,8a-trimethyl-1,6-dioxo-3H-isoquinoline-7-carbonitrile;
(8aS)-2-ethyl-5,5,8a-trimethyl-1,6-dioxo-3H-isoquinoline-7-carbonitrile;
(8aR)-2-cyclobutyl-5,5-dimethyl-1,6-dioxo-8a-phenyl-3H-isoquinoline-7-carbonitrile;
(8aS)-2-cyclobutyl-5,5-dimethyl-1,6-dioxo-8a-phenyl-3H-isoquinoline-7-carbonitrile;
(8aR)-5,5-dimethyl-1,6-dioxo-8a-phenyl-2-(3-pyridylmethyl)-3H-isoquinoline-7-carbonitrile;
(8aS)-5,5-dimethyl-1,6-dioxo-8a-phenyl-2-(3-pyridylmethyl)-3H-isoquinoline-7-carbonitrile;
(8aR)-2-cyclopropyl-5,5-dimethyl-1,6-dioxo-8a-phenyl-3H-isoquinoline-7-carbonitrile;
(8aS)-2-cyclopropyl-5,5-dimethyl-1,6-dioxo-8a-phenyl-3H-isoquinoline-7-carbonitrile;
(8aR)-2-isopropyl-5,5-dimethyl-1,6-dioxo-8a-phenyl-3H-isoquinoline-7-carbonitrile;
(8aS)-2-isopropyl-5,5-dimethyl-1,6-dioxo-8a-phenyl-3H-isoquinoline-7-carbonitrile;

(8aR)-2-cyclopentyl-5,5-dimethyl-1,6-dioxo-8a-phenyl-3H-isoquinoline-7-carbonitrile;
(8aS)-2-cyclopentyl-5,5-dimethyl-1,6-dioxo-8a-phenyl-3H-isoquinoline-7-carbonitrile;
(8aR)-2-isobutyl-5,5-dimethyl-1,6-dioxo-8a-phenyl-3H-isoquinoline-7-carbonitrile;
(8aS)-2-isobutyl-5,5-dimethyl-1,6-dioxo-8a-phenyl-3H-isoquinoline-7-carbonitrile;
(8aR)-2-benzyl-5,5-dimethyl-1,6-dioxo-8a-phenyl-3H-isoquinoline-7-carbonitrile;
(8aS)-2-benzyl-5,5-dimethyl-1,6-dioxo-8a-phenyl-3H-isoquinoline-7-carbonitrile;
(8aR)-2-(2-methoxyethyl)-5,5-dimethyl-1,6-dioxo-8a-phenyl-3H-isoquinoline-7-carbonitrile;
(8aS)-2-(2-methoxyethyl)-5,5-dimethyl-1,6-dioxo-8a-phenyl-3H-isoquinoline-7-carbonitrile;
(8aR)-2-(cyclopropylmethyl)-5,5-dimethyl-1,6-dioxo-8a-phenyl-3H-isoquinoline-7-carbonitrile;
(8aS)-2-(cyclopropylmethyl)-5,5-dimethyl-1,6-dioxo-8a-phenyl-3H-isoquinoline-7-carbonitrile;
(4aR,5R,8aS)-2-benzyl-5,8a-dimethyl-1,6-dioxo-3,4,4a,5-tetrahydroisoquinoline-7-carbonitrile;
(4aS,5S,8aR)-2-benzyl-5,8a-dimethyl-1,6-dioxo-3,4,4a,5-tetrahydroisoquinoline-7-carbonitrile;
(8aR)-2,5,5,8a-tetramethyl-1,6-dioxo-3H-isoquinoline-7-carbonitrile;
(8aS)-2,5,5,8a-tetramethyl-1,6-dioxo-3H-isoquinoline-7-carbonitrile;
(4aR,5R,8aS)-5-methyl-2-[(2-methyl-4-pyridyl)methyl]-1,6-dioxo-8a-phenyl-3,4,4a,5-tetrahydroisoquinoline-7-carbonitrile;
(4aS,5S,8aR)-5-methyl-2-[(2-methyl-4-pyridyl)methyl]-1,6-dioxo-8a-phenyl-3,4,4a,5-tetrahydroisoquinoline-7-carbonitrile;
(4aR,5R,8aS)-5-methyl-2-[(5-methylisoxazol-3-yl)methyl]-1,6-dioxo-8a-phenyl-3,4,4a,5-tetrahydroisoquinoline-7-carbonitrile;
(4aS,5S,8aR)-5-methyl-2-[(5-methylisoxazol-3-yl)methyl]-1,6-dioxo-8a-phenyl-3,4,4a,5-tetrahydroisoquinoline-7-carbonitrile;
(4aR,5R,8aS)-5-methyl-1,6-dioxo-8a-phenyl-2-(4-pyridylmethyl)-3,4,4a,5-tetrahydroisoquino line-7-carbonitrile;
(4aS,5S,8aR)-5-methyl-1,6-dioxo-8a-phenyl-2-(4-pyridylmethyl)-3,4,4a,5-tetrahydroisoquinoline-7-carbonitrile;
(5aS,9aR)-5a,9,9-trimethyl-4,8-dioxo-2,3,4,5,5a,8,9,9a-octahydro-1H-benzo[d]azepine-7-carbonitrile;
(5aR,9aS)-6,6,9a-trimethyl-3,7-dioxo-2,3,4,5,5a,6,7,9a-octahydro-1H-benzo[c]azepine-8-carbonitrile;
(5aR,9aS)-2-acetyl-6,6,9a-trimethyl-7-oxo-2,3,4,5,5a,6,7,9a-octahydro-1H-benzo[c]azepine-8-carbonitrile;
(4aS,8aR)-2-(2-fluoroethyl)-5,5,8a-trimethyl-6-oxo-1,3,4,4a-tetrahydroisoquinoline-7-carbonitrile;
(8aR)-2,5,5,8a-tetramethyl-6-oxo-1,3-dihydroisoquinoline-7-carbonitrile hydrochloride;
(8aS)-2,5,5,8a-tetramethyl-6-oxo-1,3-dihydroisoquinoline-7-carbonitrile hydrochloride;
(4aS,8aR)-5,5,8a-trimethyl-2-(oxetan-3-yl)-6-oxo-1,3,4,4a-tetrahydroisoquinoline-7-carbonitrile;
(4aR,8aS)-5,5,8a-trimethyl-2-(oxetan-3-yl)-6-oxo-1,3,4,4a-tetrahydroisoquinoline-7-carbonitrile
(8aR)-5,5,8a-trimethyl-6-oxo-2-pyrimidin-2-yl-1,3-dihydroisoquinoline-7-carbonitrile hydrochloride;
(8aS)-5,5,8a-trimethyl-6-oxo-2-pyrimidin-2-yl-1,3-dihydroisoquinoline-7-carbonitrile hydrochloride;
(4aR,5R,8aS)-2-benzyl-5-methyl-1,6-dioxo-8a-phenyl-3,4,4a,5-tetrahydroisoquinoline-7-carbonitrile;
(4aS,5S,8aR)-2-benzyl-5-methyl-1,6-dioxo-8a-phenyl-3,4,4a,5-tetrahydroisoquinoline-7-carbonitrile;
(8aR)-2-(2,2-dimethylpropanoyl)-5,5,8a-trimethyl-6-oxo-1,3-dihydroisoquino line-7-carbonitrile;
(8aS)-2-(2,2-dimethylpropanoyl)-5,5,8a-trimethyl-6-oxo-1,3-dihydroisoquinoline-7-carbonitrile;
(4aS,8aR)-2-formyl-5,5,8a-trimethyl-6-oxo-1,3,4,4a-tetrahydroisoquinoline-7-carbonitrile;
(4aR,8aS)-2-formyl-5,5,8a-trimethyl-6-oxo-1,3,4,4a-tetrahydroisoquinoline-7-carbonitrile;
(4aS,8aR)-2-(2,2-difluoroethyl)-5,5,8a-trimethyl-6-oxo-1,3,4,4a-tetrahydroisoquinoline-7-carbonitrile;
(4aR,8aS)-2-(2,2-difluoroethyl)-5,5,8a-trimethyl-6-oxo-1,3,4,4a-tetrahydroisoquinoline-7-carbonitrile;
(4aS,8aR)-7-cyano-N,5,5,8a-tetramethyl-6-oxo-1,3,4,4a-tetrahydroisoquinoline-2-carboxamide;
(4aR,8aS)-7-cyano-N,5,5,8a-tetramethyl-6-oxo-1,3,4,4a-tetrahydroisoquinoline-2-carboxamide;
(4aS,8aR)-5,5,8a-trimethyl-6-oxo-2-(2,2,2-trifluoroethyl)-1,3,4,4a-tetrahydroisoquino line-7-carbonitrile;
(4aR,8aS)-5,5,8a-trimethyl-6-oxo-2-(2,2,2-trifluoroethyl)-1,3,4,4a-tetrahydroisoquino line-7-carbonitrile;
(4aS,8aR)-5,5,8a-trimethyl-6-oxo-2-pyrimidin-2-yl-1,3,4,4a-tetrahydroisoquino line-7-carbonitrile;
(4aR,8aS)-5,5,8a-trimethyl-6-oxo-2-pyrimidin-2-yl-1,3,4,4a-tetrahydroisoquinoline-7-carbonitrile;
(4aS,8aR)-2-(2,2-dimethylpropanoyl)-5,5,8a-trimethyl-6-oxo-1,3,4,4a-tetrahydroisoquinoline-7-carbonitrile;
(4aR,8aS)-2-(2,2-dimethylpropanoyl)-5,5,8a-trimethyl-6-oxo-1,3,4,4a-tetrahydroisoquinoline-7-carbonitrile;
(4aS,8aR)-5,5,8a-trimethyl-2-(2-methylpropanoyl)-6-oxo-1,3,4,4a-tetrahydroisoquino line-7-carbonitrile;
(4aR,8aS)-5,5,8a-trimethyl-2-(2-methylpropanoyl)-6-oxo-1,3,4,4a-tetrahydroisoquino line-7-carbonitrile;
(4aS,8aR)-5,5,8a-trimethyl-6-oxo-2-propanoyl-1,3,4,4a-tetrahydroisoquino line-7-carbonitrile;
(4aR,8aS)-5,5,8a-trimethyl-6-oxo-2-propanoyl-1,3,4,4a-tetrahydroisoquino line-7-carbonitrile;
(4aS,5S,8aR)-2-acetyl-5,8a-dimethyl-6-oxo-3,4,4a,5-tetrahydro-1H-isoquinoline-7-carbonitrile;
(4aR,5R,8aS)-2-acetyl-5,8a-dimethyl-6-oxo-3,4,4a,5-tetrahydro-1H-isoquino line-7-carbonitrile;
(8aR)-2-acetyl-5,5,8a-trimethyl-6-oxo-1,3-dihydroisoquinoline-7-carbonitrile;
(8aS)-2-acetyl-5,5,8a-trimethyl-6-oxo-1,3-dihydroisoquinoline-7-carbonitrile;
(4aR,8aS)-5,5,8a-trimethyl-2-(1-methylpyrazole-4-carbonyl)-6-oxo-1,3,4,4a-tetrahydroisoquino line-7-carbonitrile;
(4aS,8aR)-5,5,8a-trimethyl-2-(1-methylpyrazole-4-carbonyl)-6-oxo-1,3,4,4a-tetrahydroisoquino line-7-carbonitrile;
(4aR,8aS)-5,5,8a-trimethyl-6-oxo-2-(pyrimidine-5-carbonyl)-1,3,4,4a-tetrahydroisoquinoline-7-carbonitrile;
(4aS,8aR)-5,5,8a-trimethyl-6-oxo-2-(pyrimidine-5-carbonyl)-1,3,4,4a-tetrahydroisoquino line-7-carbonitrile;
(4aR,8aS)-5,5,8a-trimethyl-6-oxo-2-(pyridine-3-carbonyl)-1,3,4,4a-tetrahydroisoquino line-7-carbonitrile;
(4aS,8aR)-5,5,8a-trimethyl-6-oxo-2-(pyridine-3-carbonyl)-1,3,4,4a-tetrahydroisoquino line-7-carbonitrile;
(4aR,8aS)-2-(2-methoxyacetyl)-5,5,8a-trimethyl-6-oxo-1,3,4,4a-tetrahydroisoquinoline-7-carbonitrile;
(4aS,8aR)-2-(2-methoxyacetyl)-5,5,8a-trimethyl-6-oxo-1,3,4,4a-tetrahydroisoquinoline-7-carbonitrile;
(4aR,8aS)-5,5,8a-trimethyl-2-(oxetane-3-carbonyl)-6-oxo-1,3,4,4a-tetrahydroisoquino line-7-carbonitrile;

(4aS,8aR)-5,5,8a-trimethyl-2-(oxetane-3-carbonyl)-6-oxo-1,3,4,4a-tetrahydroisoquinoline-7-carbonitrile;
(4aR,8aS)-2-(cyclopropanecarbonyl)-5,5,8a-trimethyl-6-oxo-1,3,4,4a-tetrahydroisoquino line-7-carbonitrile;
(4aS,8aR)-2-(cyclopropanecarbonyl)-5,5,8a-trimethyl-6-oxo-1,3,4,4a-tetrahydroisoquino line-7-carbonitrile;
(4aS,8aR)-2-butanoyl-5,5,8a-trimethyl-6-oxo-1,3,4,4a-tetrahydroisoquinoline-7-carbonitrile;
(4aR,8aS)-2-butanoyl-5,5,8a-trimethyl-6-oxo-1,3,4,4a-tetrahydroisoquinoline-7-carbonitrile;
(4aS,8aR)-2-(cyclohexanecarbonyl)-5,5,8a-trimethyl-6-oxo-1,3,4,4a-tetrahydroisoquinoline-7-carbonitrile;
(4aR,8aS)-2-(cyclohexanecarbonyl)-5,5,8a-trimethyl-6-oxo-1,3,4,4a-tetrahydroisoquinoline-7-carbonitrile;
(4aS,8aR)-2-benzyl-5,5,8a-trimethyl-6-oxo-1,3,4,4a-tetrahydroisoquinoline-7-carbonitrile;
(4aR,8aS)-2-benzyl-5,5,8a-trimethyl-6-oxo-1,3,4,4a-tetrahydroisoquinoline-7-carbonitrile;
(4aS,8aR)-2-(benzenesulfonyl)-5,5,8a-trimethyl-6-oxo-1,3,4,4a-tetrahydroisoquinoline-7-carbonitrile;
(4aR,8aS)-2-(benzenesulfonyl)-5,5,8a-trimethyl-6-oxo-1,3,4,4a-tetrahydroisoquinoline-7-carbonitrile;
(4aS,8aR)-5,5,8a-trimethyl-2-methylsulfonyl-6-oxo-1,3,4,4a-tetrahydroisoquino line-7-carbonitrile;
(4aR,8aS)-5,5,8a-trimethyl-2-methylsulfonyl-6-oxo-1,3,4,4a-tetrahydroisoquino line-7-carbonitrile;
(4aS,8aR)-2-benzoyl-5,5,8a-trimethyl-6-oxo-1,3,4,4a-tetrahydroisoquinoline-7-carbonitrile;
(4aR,8aS)-2-benzoyl-5,5,8a-trimethyl-6-oxo-1,3,4,4a-tetrahydroisoquinoline-7-carbonitrile;
(4aS,8aR)-2,5,5,8a-tetramethyl-6-oxo-1,3,4,4a-tetrahydroisoquinoline-7-carbonitrile;
(4aR,8aS)-2,5,5,8a-tetramethyl-6-oxo-1,3,4,4a-tetrahydroisoquinoline-7-carbonitrile;
(4aS,8aR)-5,5,8a-trimethyl-6-oxo-2,3,4,4a-tetrahydro-1H-isoquinoline-7-carbonitrile hydrochloride;
(4aR,8aS)-5,5,8a-trimethyl-6-oxo-2,3,4,4a-tetrahydro-1H-isoquinoline-7-carbonitrile hydrochloride;
(4aR,8aS)-2-acetyl-5,5,8a-trimethyl-6-oxo-1,3,4,4a-tetrahydroisoquinoline-7-carbonitrile;
(4aS,8aR)-2-acetyl-5,5,8a-trimethyl-6-oxo-1,3,4,4a-tetrahydroisoquinoline-7-carbonitrile;
(8aS)-5,5,8a-trimethyl-6-oxo-1,3-dihydroisochromene-7-carbonitrile;
(8aS)-5,5,8a-trimethyl-6-oxo-1,3,4,4a-tetrahydroisochromene-7-carbonitrile,
and pharmaceutically acceptable salts thereof.

In a fifty-third embodiment of the invention, the compound is represented by Formula XI:

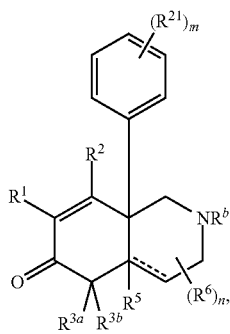

or a pharmaceutically acceptable salt thereof, wherein the values of the variables are as defined for the first, alternative first and/or second embodiments.

In a fifty-fourth embodiment of the invention, the compound is represented by formula XI, or a pharmaceutically acceptable salt thereof, wherein $R^b$ is H, $C_{1-6}$alkyl, 3 to 6 membered cycloalkyl, —C(O)$R^c$, phenyl or a monocyclic heteroaryl, wherein the alkyl and cycloalkyl is optionally substituted with one or more halo, hydroxyl, $C_{1-4}$alkoxy, 3 to 6 membered cycloalkyl, phenyl, or monocyclic heteroaryl; and wherein the cycloalkyl, phenyl and monocyclic heteroaryl, in each occurrence, are optionally substituted with one or more groups selected from halo, $C_{1-4}$alkyl and $C_{1-4}$alkoxy; and wherein the values of the other variables are as defined for the first, alternative first and/or second embodiments.

In a fifty-fifth embodiment of the invention, the compound is represented by formula XI, or a pharmaceutically acceptable salt thereof, wherein $R^1$ is —CN or —CF$_3$; $R^2$ is H or $C_{1-4}$alkyl; $R^{3a}$ is H or $C_{1-4}$alkyl; $R^{3b}$ is $C_{1-4}$alkyl; $R^5$ is H, or $R^5$ and $R^{3b}$ are taken together with the carbons to which they each are attached to form 3 to 6 membered cycloalkyl; $R^b$ is H, $C_{1-4}$alkyl, 3 to 6 membered cycloalkyl, —C(O)$R^c$, phenyl, or a monocyclic heteroaryl, wherein the cycloalkyl, phenyl and monocyclic heteroaryl, as values of $R^b$, each are optionally substituted with 1 to 3 groups selected from halo, $C_{1-4}$alkoxy, $C_{1-4}$haloalkoxy, $C_{1-4}$alkyl or $C_{1-4}$haloalkyl, wherein the alkyl, as a value of $R^b$, is optionally substituted with 1 to 3 halo, hydroxyl, $C_{1-4}$alkoxy, 3 to 6 membered cycloalkyl, phenyl, or monocyclic heteroaryl, wherein the cycloalkyl, phenyl and monocyclic heteroaryl as substituents of $R^b$ each are optionally substituted with 1 to 3 groups selected from halo, $C_{1-4}$alkoxy or $C_{1-4}$alkyl; and wherein the monocyclic heteroaryl as a value of $R^b$ or a substituent of $R^b$, in each occurrence, is selected from the group consisting of pyrazolyl, imidazolyl, pyridinyl, pyridazinyl, pyrazinyl and pyrimidyl; $R^c$ is H or $C_{1-4}$alkyl; $R^{21}$ is halo, $C_{1-4}$alkoxy, $C_{1-4}$haloalkoxy, $C_{1-4}$alkyl or $C_{1-4}$haloalkyl; m is 0, 1 or 2; and n is 0 or 2, if n is 2, two $R^6$ attached to the same ring carbon taken together form an oxo.

In a fifty-sixth embodiment of the invention, the compound is represented by formula XI, or a pharmaceutically acceptable salt thereof, wherein $R^2$ is H; $R^{3a}$ is H or methyl; $R^{3b}$ is methyl; $R^5$ is H or $R^5$ and $R^{3b}$ are taken together with the carbons to which they each are attached to form cyclopropyl; $R^b$ is H, acetyl, methyl (optionally substituted with cyclopropyl, phenyl, fluoro-substituted phenyl, methoxy-substituted phenyl, methyl-substituted pyrazolyl, pyridinyl, methyl-substituted pyridinyl, methyl-substituted isoxazole, pyrimidyl or methyl-substituted pyrimidyl), ethyl (optionally substituted with a hydroxyl, a methoxy or two fluoro), isopropyl, isobutyl, cyclopropyl, cyclobutyl, cyclopentyl, phenyl (optionally substituted with fluoro or methoxy), pyrazolyl (optionally substituted with methyl), imidazolyl, pyridinyl, pyridazinyl, pyrazinyl or pyrimidyl; $R^{21}$ is fluoro, chloro or methoxy; and m is 0 or 1; and wherein the values of the other variables are as defined for the first, alternative first, second, fifty-fourth and/or fifty-fifth embodiment.

In a fifty-seventh embodiment of the invention, the compound is represented by formula XI, or a pharmaceutically acceptable salt thereof, wherein $R^1$ is —CF$_3$; and wherein the values of the other variables are as defined for the first, alternative first, second, fifty-fourth, fifty-fifth, and/or fifty-sixth embodiments.

In a fifty-eighth embodiment of the invention, the compound is represented by formula XI, or a pharmaceutically acceptable salt thereof, wherein $R^1$ is —CN; and wherein the values of the other variables are as defined for the first, alternative first, second, fifty-fourth, fifty-fifth, and/or fifty-sixth embodiments.

In a fifty-ninth embodiment of the invention, the compound is represented by formula XII:

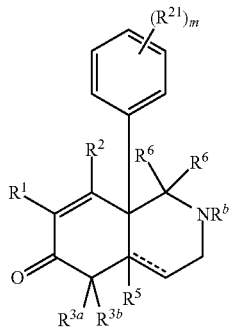

or a pharmaceutically acceptable salt thereof, wherein each $R^6$ is H or both $R^6$ taken together are an oxo; and wherein the values of the variables are as defined for the first, alternative first, second, fifty-fourth, fifty-fifth, fifty-sixth, fifty-seventh, and/or fifty-eighth embodiments.

In a sixtieth embodiment of the invention, the compound is represented by formula XIII,

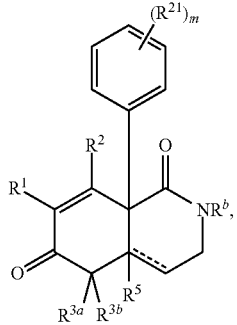

or a pharmaceutically acceptable salt thereof, wherein the values of the variables are as defined for the first, alternative first, second, fifty-fourth, fifty-fifth, fifty-sixth, fifty-seventh, and/or fifty-eighth embodiments.

In a sixty-first embodiment of the invention, the compound is represented by one of the following formulae:

XIV(A)

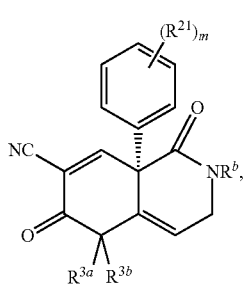

XIV(B)

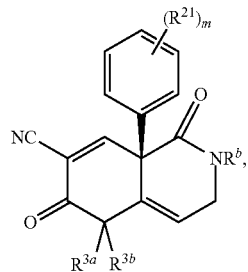

XV(A)

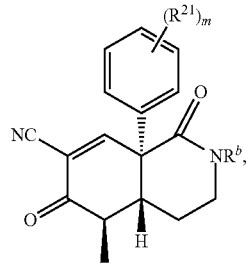

XV(B)

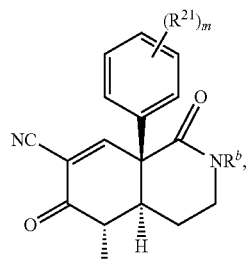

or a pharmaceutically acceptable salt thereof, wherein the values of the variables are as defined for the first, alternative first, second, fifty-fourth, fifty-fifth, fifty-sixth, fifty-seventh, and/or fifty-eighth embodiments.

In a sixty-second embodiment of the invention, the compound is represented by one of the following formulae:

XVI(A)

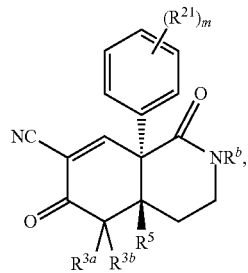

XVI(B)

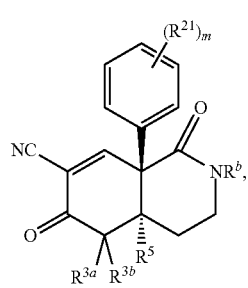

XVII(A)

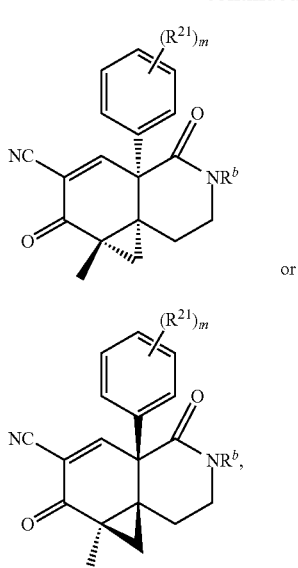

or

XVII(B)

or a pharmaceutically acceptable salt thereof, wherein the values of the variables are as defined for the first, alternative first, second, fifty-fourth, fifty-fifth, fifty-sixth, fifty-seventh, and/or fifty-eighth embodiments.

In one embodiment, the compound represented by Formula XI, XII, XIII, XV(A), XV(B), XVI(A) or XVI(B) is not (4aR,5R,8aR)-2-benzyl-5-methyl-1,6-dioxo-8a-phenyl-3,4,4a,5-tetrahydroisoquinoline-7-carbonitrile or (4aS,5S,8aS)-2-benzyl-5-methyl-1,6-dioxo-8a-phenyl-3,4,4a,5-tetrahydroisoquinoline-7-carbonitrile.

As used herein, the term "alkyl" refers to a fully saturated branched or unbranched hydrocarbon moiety. Unless otherwise specified, the alkyl comprises 1 to 12 carbon atoms, preferably 1 to 8 carbon atoms, more preferably 1 to 6 carbon atoms or most preferably 1 to 4 carbon atoms. Representative examples of alkyl include, but are not limited to, methyl, ethyl, n-propyl, iso-propyl, n-butyl, sec-butyl, iso-butyl, tert-butyl, n-pentyl, isopentyl, neopentyl and n-hexyl.

As used herein, the term "alkylene" refers to a non-aromatic divalent group, wherein the alkylene group is attached with two a-bonds, with two saturated carbon atoms as the points of attachment. An alkylene is a linear or branched acyclic structure with no carbon-carbon double or triple bonds, and no atoms other than carbon and hydrogen. The groups, —CH$_2$— (methylene), —CH$_2$CH$_2$—, —CH$_2$C(CH$_3$)$_2$CH$_2$— and —CH$_2$CH$_2$CH$_2$—, are non-limiting examples of alkylene groups.

As used herein, the term "alkenyl" refers to an unsaturated hydrocarbon group which may be linear or branched and has at least one carbon-carbon double bond. Alkenyl groups with 2-12 carbon atoms or 2-6 carbon atoms are preferred. The alkenyl group may contain 1, 2 or 3 carbon-carbon double bonds, or more. Preferably, alkenyl groups contain one or two double bonds, most preferably one double bond. Examples of alkenyl groups include ethenyl, n-propenyl, isopropenyl, n-but-2-enyl, n-hex-3-enyl and the like.

As used herein, the term "alkenylene" refers to a non-aromatic divalent group, wherein the alkenylene group is attached with two a-bonds, with two carbon atoms as points of attachment. An alkenylene is linear or branched acyclic structure havingat least one nonaromatic carbon-carbon double bond with no carbon-carbon triple bonds and no atoms other than carbon and hydrogen. The groups, —CH═CH—, —CH═C(CH$_3$)CH$_2$— and —CH═CHCH$_2$—, are non-limiting examples of alkenylene groups.

As used herein, the term "alkynyl" refers to an unsaturated hydrocarbon group which is linear or branched and has at least one carbon-carbon triple bond. Alkynyl groups with 2-12 carbon atoms or 2-6 carbon atoms can be preferred. The alkynyl group may contain 1, 2 or 3 carbon-carbon triple bonds, or more. Preferably, alkynyl groups contain one or two triple bonds, most preferably one triple bond. Examples of alkynyl groups include ethynyl, n-propynyl, n-but-2-ynyl, n-hex-3-ynyl and the like.

As used herein, the term "alkynylene" refers to a non-aromatic divalent group, wherein the alkynylene group is attached with two a-bonds, with two carbon atoms as points of attachment. An alkynylene is a linear or branched acyclic structure having at least one carbon-carbon triple bond with no atoms other than carbon and hydrogen. The groups, —C≡C—, —C≡CCH$_2$— and —C≡CCH(CH$_3$)—, are non-limiting examples of alkynylene groups.

As used herein, the term "alkylidene" refers to the divalent group ═CRR', wherein the alkylidene group is attached with one σ-bond and one π-bond, in which R and R' are independently hydrogen, alkyl, or R and R' are taken together to represent alkylene. Non-limiting examples of alkylidene groups include: ═CH$_2$, ═CH(CH$_2$CH$_3$) and ═C(CH$_3$)$_2$.

As used herein, the term "acyl" refers to a monovalent group with a carbon atom of a carbonyl group as the point of attachment, further having a linear or branched, cyclo, cyclic or acyclic structure, further having no additional atoms that are not carbon or hydrogen, beyond the oxygen atom of the carbonyl group. The groups, —CHO, —C(O)CH$_3$ (acetyl, Ac), —C(O)CH$_2$CH$_3$, —C(O)CH$_2$CH$_2$CH$_3$, —C(O)CH(CH$_3$)$_2$, —C(O)CH(CH$_2$)$_2$, —C(O)C$_6$H$_5$, —C(O)C$_6$H$_4$CH$_3$, —C(O)C$_6$H$_4$CH$_2$CH$_3$, —COC$_6$H$_3$(CH$_3$)$_2$ and —C(O)CH$_2$C$_6$H$_5$, are non-limiting examples of acyl groups. The term "acyl" therefore encompasses, but is not limited to, groups sometimes referred to as "alkyl carbonyl" and "aryl carbonyl" groups.

As used herein, the term "alkoxy" refers to the group —OR, in which R is a C$_{1-12}$alkyl, as that term is defined above. Non-limiting examples of alkoxy groups include: —OCH$_3$, —OCH$_2$CH$_3$, —OCH$_2$CH$_2$CH$_3$, —OCH(CH$_3$)$_2$, —OCH(CH$_2$)$_2$, —O-cyclopropyl, —O-cyclobutyl, —O—cyclopentyl and —O-cyclohexyl.

The number of carbon atoms in a group is specified herein by the prefix "C$_{x-xx}$", wherein x and xx are integers. For example, "C$_{1-4}$alkyl" is an alkyl group which has from 1 to 4 carbon atoms.

As used herein, the term "halogen" or "halo" may be fluoro, chloro, bromo or iodo.

As used herein, the term "heterocyclyl" refers to a saturated or unsaturated, monocyclic or bicyclic (e.g., bridged, fused or spiro ring systems) ring system which has from 3- to 12-ring members, or in particular 3- to 6-ring members or 5- to 7-ring members, at least one of which is a heteroatom, and up to 4 (e.g., 1, 2, 3 or 4) of which may be heteroatoms, wherein the heteroatoms are independently selected from O, S and N, and wherein C can be oxidized (e.g., C(O)), N can be oxidized (e.g., N(O)) or quaternized, and S can be optionally oxidized to sulfoxide and sulfone. Unsaturated heterocyclic rings include heteroaryl rings and heterocyclic rings that is not aromatic. As used herein, the term "heteroaryl" refers to an aromatic 5 to 12 membered monocyclic or bicyclic ring system, having 1 to 4 heteroatoms independently selected from O, S and N, and wherein N can be oxidized (e.g., N(O)) or quaternized, and S can be optionally oxidized to sulfoxide and sulfone. In one embodiment, a heterocyclyl is a 3- to 7-membered saturated monocyclic or a 3- to 6-membered saturated monocyclic or a 5- to 7-membered saturated monocyclic ring. In one embodiment, an non-aromatic heterocyclyl is a 3- to 7-membered unsaturated monocyclic or a 3- to 6-membered unsaturated monocyclic or a 5- to 7-membered unsaturated monocyclic ring. In another embodiment, a heterocyclyl is a 6 or -7-membered bicyclic ring. The heterocyclyl group can be attached at a heteroatom or a carbon atom. Examples of heterocyclyls include aziridinyl, oxiranyl, thiiranyl, oxaziridinyl, dioxiranyl, azetidinyl, oxetanyl, thietanyl, pyrrolidinyl, tetrahydrofuranyl, thiolanyl, imidazolidinyl, pyrazolidinyl, oxazolidinyl, isoxazolidinyl, thiazolidinyl, isothiazolidinyl, dioxolanyl, dithiolanyl, oxathiolanyl, piperidinyl, tetrahydropyranyl, thianyl, piperazinyl, morpholinyl, thiomorpholinyl, dioxanyl, dithianyl, trioxanyl, trithianyl, azepanyl, oxepanyl, thiepanyl, dihydrofuranyl, imidazolinyl, dihydropyranyl, and heteroaryl rings including azirinyl, oxirenyl, thiirenyl, diazirinyl, azetyl, oxetyl, thietyl, pyrrolyl, furanyl, thiophenyl (or thienyl), imidazolyl, pyrazolyl, oxazolyl, isoxazolyl, thiazolyl, isothiazolyl, furazanyl, oxadiazolyl, thiadiazolyl, dithiazolyl, triazolyl, tetrazolyl, pyridyl pyranyl, thiopyranyl, pyrazinyl, pyrimidyl, pyridazinyl, oxazinyl, thiazinyl, dioxinyl, dithiinyl, oxathianyl, triazinyl, tetrazinyl, azepinyl, oxepinyl, thiepinyl, diazepinyl, thiazepinyl, 1-oxo-pyridyl, hydantoinyl, pyrrolidinonyl, pyrrolidinyl, tetrahydropyrimidinyl, tetrahydropyrindinyl, tetrahydrothiophenyl, tetrahydrothiopyranyl, thienyl, valerolactamyl, and the like. Examples of bicyclic heterocyclic ring systems include azaindolyl, benzimidazolyl, benzo[1,3]dioxolyl, benzo[1,4]dioxinyl, benzofuryl, benzoisoxazolyl, benzoisothiazolyl, benzothiadiazolyl, benzothiazolyl, benzothienyl, benzotriazolyl, benzoxadiazolyl, benzoxazolyl, cyclopentaimidazolyl, cyclopentatriazolyl, imidazo[1,2-a]pyridyl, indazolyl, indolizinyl, indolyl, isoquinolinyl, oxazolopyridinyl, purinyl, pyrazolo[3,4]pyrimidinyl, pyridopyazinyl, pyridopyrimidinyl, pyrrolo[2,3]pyrimidinyl, pyrrolopyrazolyl, pyrroloimidazolyl, pyrrolotriazolyl, quinazolinyl, quinolinyl, tetrahydroindolyl, thiazolopyridinyl, 3-azabicyclo[3.1.0]hexanyl, 3-azabicyclo[3.1.1]heptanyl, 2-azaspiro[3.3]heptanyl, 2-oxa-6-azaspiro[3.3]heptanyl and 5-azaspiro[2.3]hexanyl.

As used herein, the term "carbocyclyl" refers to saturated, partially unsaturated, or aromatic monocyclic or bicyclic hydrocarbon groups of 3-12 carbon atoms, 3-6 carbon atoms or 5-7 carbon atoms. The term "carbocyclyl" encompasses cycloalkyl groups and aromatic groups. The term "cycloalkyl" refers to completely saturated monocyclic or bicyclic or spiro hydrocarbon groups of 3-12 carbon atoms, 3-6 carbon atoms or 5-7 carbon atoms. "Aromatic group or "aryl" refers to an aromatic 6-12 membered monocyclic or bicyclic ring system. Exemplary monocyclic carbocyclyl groups include, but are not limited to, cyclopropyl, cyclobutyl, cyclopentyl, cyclohexyl, cycloheptyl, cyclopropenyl, cyclobutenyl, cyclopenentyl, cyclohexenyl, cycloheptenyl, cyclobutadienyl, cyclopentadienyl, cyclohexadienyl, cycloheptadienyl, phenyl and cycloheptatrienyl. Exemplary bicyclic carbocyclyl groups include bicyclo[2.1.1]hexyl, bicyclo[2.2.1]heptyl, bicyclo[2.2.1]heptenyl, tricyclo[2.2.1.0$^{2,6}$]heptanyl, 6,6-dimethylbicyclo[3.1.1]heptyl, 2,6,6-trimethylbicyclo[3.1.1]heptyl, spiro[2.2]pentanyl and spiro[3.3]heptanyl.

The term "bridged ring system," as used herein, is a ring system that has a carbocyclyl or heterocyclyl ring wherein two non-adjacent atoms of the ring are connected (bridged) by one or more (preferably from one to three) atoms selected from C, N, O or S. A bridged ring system may have from 6-7 ring members.

The term "fused ring system," as used herein, is a ring system that has a carbocyclyl or heterocyclyl ring wherein two adjacent atoms of the ring are connected (bridged) by one or more (preferably from one to three) atoms selected from C, N, O or S. A fused ring system may have from 4-10 ring members.

The term "spiro ring system," as used herein, is a ring system that has two rings each of which are independently selected from a carbocyclyl or a heterocyclyl, wherein the two ring structures having one ring atom in common. Spiro ring systems have from 5 to 7 ring members.

In cases where a compound provided herein is sufficiently basic or acidic to form stable nontoxic acid or base salts, preparation and administration of the compounds as pharmaceutically acceptable salts may be appropriate. Examples of pharmaceutically acceptable salts are organic acid addition salts formed with acids which form a physiological acceptable anion, for example, tosylate, methanesulfonate, acetate, citrate, malonate, tartarate, succinate, benzoate, ascorbate, a-ketoglutarate or a-glycerophosphate. Inorganic salts may also be formed, including hydrochloride, sulfate, nitrate, bicarbonate and carbonate salts.

Pharmaceutically acceptable salts may be obtained using standard procedures well known in the art, for example by reacting a sufficiently basic compound such as an amine with a suitable acid affording a physiologically acceptable anion. Alkali metal (for example, sodium, potassium or lithium) or alkaline earth metal (for example calcium) salts of carboxylic acids can also be made.

Pharmaceutically-acceptable base addition salts can be prepared from inorganic and organic bases. Salts from inorganic bases can include, but are not limited to, sodium, potassium, lithium, ammonium, calcium and magnesium salts. Salts derived from organic bases can include, but are not limited to, salts of primary, secondary or tertiary amines, such as alkyl amines, dialkyl amines, trialkyl amines, substituted alkyl amines, di(substituted alkyl) amines, tri(substituted alkyl) amines, alkenyl amines, dialkenyl amines, trialkenyl amines, substituted alkenyl amines, di(substituted alkenyl) amines, tri(substituted alkenyl) amines, cycloalkyl amines, di(cycloalkyl) amines, tri(cycloalkyl) amines, substituted cycloalkyl amines, disubstituted cycloalkyl amine, trisubstituted cycloalkyl amines, cycloalkenyl amines, di(cycloalkenyl) amines, tri(cycloalkenyl) amines, substituted cycloalkenyl amines, disubstituted cycloalkenyl amine, trisubstituted cycloalkenyl amines, aryl amines, diaryl amines, triaryl amines, heteroaryl amines, diheteroaryl amines, triheteroaryl amines, heterocycloalkyl amines, diheterocycloalkyl amines, triheterocycloalkyl amines or mixed di- and tri-amines where at least two of the substituents on the amine can be different and can be alkyl, substituted alkyl, alkenyl, substituted alkenyl, cycloalkyl, substituted cycloalkyl, cycloalkenyl, substituted cycloalkenyl, aryl, heteroaryl, heterocycloalkyl and the like. Also included are amines where the two or three substituents, together with the amino nitrogen, form a heterocycloalkyl and heteroaryl group. Non-limiting examples of amines can include, isopropylamine, trimethyl amine, diethyl amine, tri(iso-propyl) amine, tri(n-propyl) amine, ethanolamine, 2-dimethylaminoethanol, tromethamine, lysine, arginine, histidine, caffeine, procaine, hydrabamine, choline, betaine, ethylenediamine, glucosamine, N-alkylglucamines, theobromine, purines, piperazine, piperidine, morpholine, N-ethylpiperidine and the like. Other carboxylic acid derivatives can be useful, for example, carboxylic acid amides, including carboxamides, lower alkyl carboxamides or dialkyl carboxamides and the like.

The disclosed compounds, or pharmaceutically acceptable salts thereof, can contain one or more asymmetric centers in the molecule. In accordance with the present disclosure any structure that does not designate the stereochemistry is to be understood as embracing all the various stereoisomers (e.g., diastereomers and enantiomers) in pure or substantially pure form, as well as mixtures thereof (such as a racemic mixture, or an enantiomerically enriched mixture). It is well known in the art how to prepare such optically active forms (for example, resolution of the racemic form by recrystallization techniques, synthesis from optically-active starting materials, by chiral synthesis or chromatographic separation using a chiral stationary phase). The disclosed compounds may exist in tautomeric forms and mixtures and separate individual tautomers are contemplated. In addition, some compounds may exhibit polymorphism.

When a particular steroisomer (e.g., enantiomer, diasteromer, etc.) of a compound used in the disclosed methods is depicted by name or structure, the stereochemical purity of the compounds is at least 20%, 30%, 40%, 50%, 60%, 70%, 80%, 90%, 95%, 97%, 99%, 99.5% or 99.9%. "Sterero-chemical purity" means the weight percent of the desired stereoisomer relative to the combined weight of all stereoisomers.

In one embodiment, any position occupied by hydrogen is meant to include enrichment by deuterium above the natural abundance of deuterium as well. For example, one or more hydrogen atoms are replaced with deuterium at an abundance that is at least 3340 times greater than the natural abundance of deuterium, which is 0.015% (i.e., at least 50.1% incorporation of deuterium), at least 3500 (52.5% deuterium incorporation at each designated deuterium atom), at least 4000 (60% deuterium incorporation), at least 4500 (67.5% deuterium incorporation), at least 5000 (75% deuterium), at least 5500 (82.5% deuterium incorporation), at least 6000 (90% deuterium incorporation), at least 6333.3 (95% deuterium incorporation), at least 6466.7 (97% deuterium incorporation), at least 6600 (99% deuterium incorporation), or at least 6633.3 (99.5% deuterium incorporation). In one embodiment, hydrogen is present at all positions at its natural abundance. The compounds or pharmaceutically acceptable salts thereof as described herein, may exist in tautomeric forms and mixtures and separate individual tautomers are contemplated.

Another embodiment is a pharmaceutical composition comprising at least one compound described herein, or a pharmaceutically acceptable salt thereof, and at least one pharmaceutically acceptable carrier.

The compounds provided herein can be useful to activate the NRF2 pathway in a cell. In one embodiment, the method comprises contacting a cell with an effective amount of a compound provided herein, or a pharmaceutically acceptable salt thereof. In one embodiment, the cell is contacted in vitro or in vivo. In one embodiment, contacting the cell includes administering the compound to a subject.

One embodiment of the invention includes a method for activating Nrf2 in a subject in need thereof, the method comprising administering to the subject a therapeutically effective amount of a compound described herein, or a pharmaceutically acceptable salt thereof, thereby activating Nrf2 in the subject.

One embodiment of the invention includes a method for inhibiting a KEAP1 protein in a cell, the method comprising contacting a cell with an effective amount of a compound provided herein, or a pharmaceutically acceptable salt thereof, thereby inhibiting a KEAP1 protein in the cell.

One embodiment of the invention includes a method for increasing a cell's ability to resist a stress, the method comprising administering to the subject a therapeutically effective amount of a compound described herein, or a pharmaceutically acceptable salt thereof, thereby increasing the cell's ability to resist the stress. The stress is selected from the group consisting of heat shock, oxidative stress, osmotic stress, DNA damage, inadequate salt level, inadequate nitrogen level and inadequate nutrient level.

One embodiment of the invention includes a method for mimiking the effect of nutrient restriction on the cell, the method comprising administering to the subject a therapeutically effective amount of a compound described herein, or a pharmaceutically acceptable salt thereof, thereby mimiking the effect of the nutrient restriction on the cell.

One embodiment of the invention includes a method for promoting survival of a eukaryotic cell (e.g., a mammalian cell) or increasing the lifespan of the cell, the method comprising administering to the subject a therapeutically effective amount of a compound provided herein, or a pharmaceutically acceptable salt thereof, thereby promoting survival of the eukaryotic cell or increasing the lifespan of the cell.

One embodiment of the invention includes a method for treating a disease associated with cell death in a subject in need thereof, the method comprising administering to the subject a therapeutically effective amount of a compound described herein, or a pharmaceutically acceptable salt thereof, thereby treating the disease associated with cell death in the subject.

One embodiment of the invention includes a method for treating a disease caused by oxidative stress in a subject in need thereof, the method comprising administering to the subject a therapeutically effective amount of a compound provided herein, or a pharmaceutically acceptable salt thereof, thereby treating the disease caused by oxidative stress in the subject.

One embodiment of the invention includes a method for treating a disorder in a subject in need thereof, wherein the disorder is selected from the group consisting of a neurodegenerative disease, inflammation/an inflammatory disease, an autoimmune disease, an ischemic fibrotic disease, a cancer, premature aging, a cardiovascular disease, a liver disease, a hemoglobinopathy, thalassemia (e.g. beta-thalassemia) and a metabolic disorder, the method comprising administering to the subject a therapeutically effective amount of a compound provided herein, or a pharmaceutically acceptable salt thereof, thereby treating the disorder in the subject. Hemoglobinopathy includes sickle cell disease (SCD). In one embodiment, the disorder is sickle cell disease or thalassemia (e.g. beta-thalassemia). More specifically, the disorder is sickle cell disease.

In one embodiment, the neurodegenerative disease can be selected from the group consisting of Alzheimer's disease (AD), Parkinson's disease (PD), Huntington disease (HD) and other CAG-triplet repeat (or polyglutamine) diseases, amyotrophic lateral sclerosis (ALS; Lou Gehrig's disease), diffuse Lewy body disease, chorea-acanthocytosis, primary lateral sclerosis, multiple sclerosis (MS), frontotemporal dementia, Friedreich's ataxia and epilepsy (repression of microglia activation). More preferably, the neurodegenerative disease is Parkinson disease or amyotrophic lateral sclerosis.

In one embodiment, the inflammatory disease can be selected from the group consisting of chronic cholecystitis, aortic valve stenosis, restenosis, a skin disease, a pulmonary diseases and a disease of the airway, inflammatory uveitis, atherosclerosis, arthritis, conjunctivitis, pancreatitis, a chronic kidney disease (CDK), an inflammatory condition associated with diabetes, an ischemia, a transplant rejection, a CD14 mediated sepsis, a non-CD14 mediated sepsis, Behcet's syndrome, ankylosing spondylitis, sarcoidosis and gout. In some embodiments, the skin disease is selected from the group consisting of rash, contact dermatitis and atopic dermatitis. In one embodiment, the pulmonary disease and disease of the airway is selected from the group consisting of Adult Respiratory Disease Syndrome (ARDS), Chronic Obstructive Pulmonary Disease (COPD), pulmonary fibrosis, an interstitial lung disease, asthma, chronic cough, allergic rhinitis, bronchiectasis and bronchitis. In one embodiment, the inflammatory condition associated with diabetes is selected from a diabetic retinopathy, a diabetic cardiomyopathy and a diabetes-induced aortic damage.

In one embodiment, the autoimmune disease is selected from the group consisting of psoriasis, inflammatory bowel disease, rheumatoid arthritis, systemic lupus erythematosus, multiple sclerosis, type 1 diabetes, systemic sclerosis and Sjogren's syndrome. In one embodiment, the inflammatory bowel disease is Crohn's disease or ulcerative colitis. In one embodiment, the autoimmune disease is type 1 diabetes. Alternatively, the autoimmune disease is multiple sclerosis.

In one embodiment, the ischemic fibrotic disease is selected from the group consisting of stroke, acute lung injury, acute kidney injury, ischemic cardiac injury, acute liver injury and ischemic skeletal muscle injury.

In one embodiment, the cancer is selected from the group consisting of prostate cancer, bladder cancer, ovarian cancer, breast cancer (e.g., breast cancer with mutated BRCA1), head and neck cancer, chronic lymphocytic leukemia, thymus cancer, hepatocellular carcinoma, colorectal cancer, colon cancer, skin cancer, pancreatic cancer, leukemia, lung cancer, glioblastoma, cervical cancer, lymphoma, Waldenstrim's macroglobulinemia and multiple myeloma.

In one embodiment, the cardiovascular disease can be selected from the group consisting of pulmonary arterial hypertension, systemic hypertension, coronary artery disease, peripheral artery disease and atherosclerosis.

In one embodiment, the liver disease can be selected from the group consisting of non-alcoholic steatohepititis (NASH), alcoholic liver disease, primary biliary cirrhosis and primary sclerosing cholangitis.

In one embodiment, the hemoglobinopathy is a condition that involves a mutation in human beta-globin or an expression control sequence thereof, such as sickle cell disease (SCD) or beta-thalassemia. SCD typically arises from a mutation substituting thymine for adenine in the sixth codon of the beta-chain gene of hemoglobin (i.e., GAG to GTG of the HBB gene). This mutation causes glutamate to valine substitution in position 6 of the Hb beta chain. The resulting Hb, referred to as HbS, has the physical properties of forming polymers under deoxy conditions. SCD is typically an autosomal recessive disorder. Beta-Thalassemias are a group of inherited blood disorders caused by a variety of mutational mechanisms that result in a reduction or absence of synthesis of P-globin and leading to accumulation of aggregates of unpaired, insoluble c-chains that cause ineffective erythropoiesis, accelerated red cell destruction, and severe anemia. Subjects with beta-thalassemia exhibit variable phenotypes ranging from severe anemia to clinically asymptomatic individuals. The genetic mutations present in β thalassemias are diverse, and can be caused by a number of different mutations. The mutations can involve a single base substitution or deletions or inserts within, near or upstream of the β globin gene. For example, mutations occur in the promoter regions preceding the beta-globin genes or cause production of abnormal splice variants.

Examples of thalassemias include thalassemia minor, thalassemia intermedia, and thalassemia major.

Thalassemia minor refers to thalassemia where only one of beta-globin alleles bears a mutation. Individuals typically suffer from microcytic anemia. Detection usually involves lower than normal MCV value (<80 fL) plus an increase in fraction of Hemoglobin A2 (>3.5%) and a decrease in fraction of Hemoglobin A (<97.5%). Genotypes can be β+/β or β−0/β.

Thalassemia intermedia refers to a thalassemia intermediate between the major and minor forms. Affected individuals can often manage a normal life but may need occasional transfusions, e.g., at times of illness or pregnancy, depending on the severity of their anemia. Genotypes can be β+/β+ or β−0/β.

Thalassemia major refers to a thalassemia where both beta-globin alleles have thalassemia mutations. This is a severe microcytic, hypochromic anemia. If left untreated, it causes anemia, splenomegaly, and severe bone deformities and typically leads to death before age 20. Treatment consists of periodic blood transfusion; splenectomy if splenomegaly is present, and treatment of transfusion-caused iron overload. Cure is possible by bone marrow transplantation. Cooley's anemia is named after Thomas Benton Cooley. Genotypes include β+/β−0 or β−0/β−0 or β+/β+.

Although carriers of sickle cell trait do not suffer from SCD, individuals with one copy of HbS and one copy of a gene that codes for another abnormal variant of hemoglobin, such as HbC or Hb beta-thalassemia, have a less severe form of the disease. For example, another specific defect in beta-globin causes another structural variant, hemoglobin C (HbC). Hemoglobin C (abbreviated as Hb C or HbC) is an abnormal hemoglobin in which substitution of a glutamic acid residue with a lysine residue at the 6th position of the P-globin chain has occurred. A subject that is a double heterozygote for HbS and HbC (HbSC disease) is typically characterized by symptoms of moderate clinical severity.

Another common structural variant of beta-globin is hemoglobin E or hemoglobin E (HbE). HbE is an abnormal hemoglobin in which substitution of a glutamic acid residue with a lysine residue at the 26th position of the β-globin chain has occurred. A subject that is a double heterozygote for HbS and HbE has HbS/HbE syndrome, which usually causes a phenotype similar to HbS/b+ thalassemia, discussed below.

Some mutations in the beta-globin gene can cause other structural variations of hemoglobin or can cause a deficiency in the amount of β-globin being produced. These types of mutations are referred to as beta-thalassemia mutations.

The absence of beta-globin is referred to as beta-zero (β−0) thalassemia. A subject that is a double heterozygote for HbS and β−0 thalassemia (i.e., HbS/β−0 thalassemia) can suffer symptoms clinically indistinguishable from sickle cell anemia.

A reduced amount of beta-globin is referred to as β-plus (β+) thalassemia. A subject that is a double heterozygote for HbS and β+ thalassemia (i.e., HbS/β+ thalassemia) can have mild-to-moderate severity of clinical symptoms with variability among different ethnicities.

Rare combinations of HbS with other abnormal hemoglobins include HbD Los Angeles, G-Philadelphia, HbO Arab, and others.

Nrf2 upregulates fetal hemoglobin which alleviates some of the symptoms of these disorders. Therefore, in some embodiments, the disclosed compositions are used to treated SCD or thalassemia (e.g. beta-thalassemia).

In some embodiments, the disclosed compositions and methods are used to treating a subject with an HbS/β-0 genotype, an HbS/β+ genotype, an HBSC genotype, an HbS/HbE genotype, an HbD Los Angeles genotype, a G-Philadelphia genotype, or an abHbO Arab genotype.

In some embodiments, the compositions disclosed herein are administered to a subject in an effective amount to treat one or more symptoms of sickle cell disease, a thalassemia (e.g. beta-thalassemia), or a related disorder. In subjects with sickle cell disease, or a related disorder, physiological changes in RBCs can result in a disease with the following signs: (1) hemolytic anemia; (2) vaso-occlusive crisis; and (3) multiple organ damage from microinfarcts, including heart, skeleton, spleen, and central nervous system. Thalassemia can include symptoms such as anemia, fatigue and weakness, pale skin or jaundice (yellowing of the skin), protruding abdomen with enlarged spleen and liver, dark urine, abnormal facial bones and poor growth, and poor appetite.

Retinopathy due to SCD can also be treated by administering an effective amount of a compound according to any one of described herein. Sickle retinopathy occurs when the retinal blood vessels get occluded by sickle red blood cells and the retina becomes ischemic, angiogenic factors are made in retina. In sickle cell disease, this occurs mostly in the peripheral retina, which does not obscure vision at first. Eventually, the entire peripheral retina of the sickle cell patient becomes occluded and many neovascular formations occur. Administration of a compound according to any one of described herein can reduce or inhibit the formation of occlusions in the peripheral retina of a sickle cell patient.

In one embodiment, the metabolic disorder is diabetes, obesity, metabolic syndrome or hypertension. In particular, the diabetes is type 1 diabetes, type 2 diabetes or gestational diabetes.

As used herein, the term "subject" and "patient" may be used interchangeably, and means a mammal in need of treatment, e.g., companion animals (e.g., dogs, cats and the like), farm animals (e.g., cows, pigs, horses, sheep, goats and the like) and laboratory animals (e.g., rats, mice, guinea pigs and the like). Typically, the subject is a human in need of treatment.

As used herein, the term "treating" or "treatment" refers to obtaining desired pharmacological and/or physiological effect. The effect can be therapeutic, which includes achieving, partially or substantially, one or more of the following results: partially or totally reducing the extent of the disease, disorder or syndrome; ameliorating or improving a clinical symptom or indicator associated with the disorder; and delaying, inhibiting or decreasing the likelihood of the progression of the disease, disorder or syndrome.

The dose of a compound provided herein, or a pharmaceutically acceptable salt thereof, administered to a subject can be 10 μg-5,000 mg; 10 μg to 1 mg; 1 to 500 mg; or 500 to 5,000 mg.

Administering a compound described herein, or a pharmaceutically acceptable salt thereof, to a mammal comprises any suitable delivery method. Administering a compound described herein, or a pharmaceutically acceptable salt thereof, to a mammal includes administering a compound described herein, or a pharmaceutically acceptable salt thereof, topically, enterally, parenterally, transdermally, transmucosally, via inhalation, intracisternally, epidurally, intravaginally, intravenously, intramuscularly, subcutaneously, intradermally and intravitreally to the mammal. Administering a compound described herein, or a pharmaceutically acceptable salt thereof, to a mammal also includes administering topically, enterally, parenterally, transdermally, transmucosally, via inhalation, intracisternally, epidurally, intravaginally, intravenously, intramuscularly, subcutaneously, intradermally and intravitreally to a mammal a compound that metabolizes within or on a surface of the body of the mammal to a compound described herein, or a pharmaceutically acceptable salt thereof.

Thus, a compound or pharmaceutically acceptable salt thereof as described herein, may be systemically administered, e.g., orally, in combination with a pharmaceutically acceptable vehicle such as an inert diluent or an assimilable edible carrier. They may be enclosed in hard or soft shell gelatin capsules, may be compressed into tablets, or may be incorporated directly with the food of the patient's diet. For oral therapeutic administration, the compound or pharmaceutically acceptable salt thereof as described herein may be combined with one or more excipients and used in the form of ingestible tablets, buccal tablets, troches, capsules, elixirs, suspensions, syrups or wafers and the like. Such compositions and preparations should contain at least about 0.1% of active compound. The percentage of the compositions and preparations may, of course, be varied and may conveniently be between about 2 to about 60% of the weight of a given unit dosage form. The amount of active compound in such therapeutically useful compositions can be such that an effective dosage level will be obtained.

The tablets, troches, pills, capsules and the like can include the following: binders such as gum tragacanth, acacia, corn starch and gelatin; excipients such as dicalcium phosphate; a disintegrating agent such as corn starch, potato starch, alginic acid and the like; a lubricant such as magnesium stearate; a sweetening agent such as sucrose, fructose, lactose and aspartame; and a flavoring agent.

The active compound may also be administered intravenously or intraperitoneally by infusion or injection. Solutions of the active compound or its salts can be prepared in water, optionally mixed with a nontoxic surfactant.

Exemplary pharmaceutical dosage forms for injection or infusion can include sterile aqueous solutions or dispersions and sterile powders comprising the active ingredient which are adapted for the extemporaneous preparation of sterile injectable or infusible solutions or dispersions. In all cases, the ultimate dosage form should be sterile, fluid and stable under the conditions of manufacture and storage.

Sterile injectable solutions can be prepared by incorporating the active compound in the required amount in the appropriate solvent with various of the other ingredients enumerated above, as required, followed by filter sterilization. In the case of sterile powders for the preparation of sterile injectable solutions, the preferred methods of preparation can be vacuum drying and the freeze drying techniques, which can yield a powder of the active ingredient plus any additional desired ingredient present in the previously sterile-filtered solutions.

Exemplary solid carriers can include finely divided solids such as talc, clay, microcrystalline cellulose, silica, alumina and the like. Useful liquid carriers include water, alcohols, glycols and water-alcohol/glycol blends, in which the compounds or pharmaceutically acceptable salts thereof as described herein can be dissolved or dispersed at effective levels, optionally with the aid of non-toxic surfactants.

Useful dosages of a compound or pharmaceutically acceptable salt thereof as described herein can be determined by comparing their in vitro activity and in vivo activity in animal models. Methods for the extrapolation of effective dosages in mice and other animals, to humans are known to the art; for example, see U.S. Pat. No. 4,938,949, which is incorporated by reference in its entirety.

The amount of a compound or pharmaceutically acceptable salt thereof as described herein, required for use in treatment can vary not only with the particular salt selected but also with the route of administration, the nature of the condition being treated and the age and condition of the patient and can be ultimately at the discretion of the attendant physician or clinician. In general, however, a dose can be in the range of from about 0.1 to about 10 mg/kg of body weight per day.

The a compound or pharmaceutically acceptable salt thereof as described herein can be conveniently administered in unit dosage form; for example, containing 0.01 to 10 mg or 0.05 to 1 mg, of active ingredient per unit dosage form. In some embodiments, a dose of 5 mg/kg or less can be suitable.

The desired dose may conveniently be presented in a single dose or as divided doses administered at appropriate intervals.

The disclosed method can include a kit comprising a compound or pharmaceutically acceptable salt thereof as described herein and instructional material which can describe administering a compound or pharmaceutically acceptable salt thereof as described herein or a composition comprising a compound or pharmaceutically acceptable salt thereof as described herein to a cell or a subject. This should be construed to include other embodiments of kits that are known to those skilled in the art, such as a kit comprising a (such as sterile) solvent for dissolving or suspending a compound or pharmaceutically acceptable salt thereof as described herein or composition prior to administering a compound or pharmaceutically acceptable salt thereof as described herein or composition to a cell or a subject. In some embodiments, the subject can be a human.

EXAMPLE

The terms "Ent1" and Ent2" do not infer structural assignment as to one enantiomer or the other. The absolute configuration of final compounds was only determined in certain instances as described below:

Key:
A: Absolute configuration determined by x-ray crystallography and/or circular dichroism
B: Absolute configuration assigned by comparison to a class A compound or derived from a common intermediate in the synthesis of a class A compound
C: Absolute configuration assigned based on literature precedent
D: Absolute configuration unknown

| Compound | Stereochemical Determination |
|---|---|
| 12-Ent1 | A |
| 12-Ent2 | A, B |
| 12-JEnt1 | D |
| 12-JEnt2 | D |
| 13-Ent1 | D |
| 13-Ent2 | D |
| 14-Ent1 | D |
| 14-Ent2 | D |
| 15-Ent1 | D |
| 15-Ent2 | D |
| 16-Ent1 | D |
| 16-Ent2 | D |
| 17-Ent1 | D |
| 17-Ent2 | D |
| 18-Ent1 | D |
| 18-Ent2 | D |
| 19-Ent1 | D |
| 19-Ent2 | D |
| 20-Ent1 | D |
| 20-Ent2 | D |
| 21-Ent1 | D |
| 21-Ent2 | D |
| 22-Ent1 | D |
| 22-Ent2 | D |
| 23-Ent1 | D |
| 23-Ent2 | D |
| 24-Ent1 | D |
| 24-Ent2 | D |
| 25-Ent1 | D |
| 25-Ent2 | D |
| 26-Ent1 | D |
| 26-Ent2 | D |
| 27-Ent1 | D |
| 27-Ent2 | D |
| 28-Ent1 | D |
| 28-Ent2 | D |
| 29-Ent1 | D |
| 29-Ent2 | D |
| 30-Ent1 | D |
| 30-Ent2 | D |
| 31-Ent1 | D |
| 31-Ent2 | D |
| 32-Ent1 | D |
| 32-Ent2 | D |
| 33-Ent1 | D |
| 33-Ent2 | D |
| 34-Ent1 | D |
| 34-Ent2 | D |
| 35-Ent1 | D |
| 35-Ent2 | D |
| 36-Ent1 | D |
| 36-Ent2 | D |
| 37-Ent1 | D |
| 37-Ent2 | D |
| 38-Ent1 | D |
| 38-Ent2 | D |
| 39-Ent1 | B |
| 46-Ent1 | D |
| 46-Ent2 | D |
| 47-Ent1 | B |
| 48-Ent1 | D |
| 48-Ent2 | D |
| 49-Ent1 | D |
| 50-Ent1 | D |
| 51-Ent1 | C |
| 51-Ent2 | C |
| 52-Ent1 | C |
| 52-Ent2 | C |
| 53-Ent1 | C |
| 53-Ent2 | C |
| 54 | B |
| 55 | B |
| 56-Ent1 | D |
| 56-Ent2 | D |
| 57-Ent1 | D |
| 57-Ent2 | D |
| 58-Ent1 | D |
| 58-Ent2 | D |
| 59 | B |
| 60-Ent1 | D |

-continued

| Compound | Stereochemical Determination |
|---|---|
| 60-Ent2 | D |
| 61-Ent1 | D |
| 61-Ent2 | D |
| 62-Ent1 | B |
| 63 | B |
| 64 | B |
| 65-Ent1 | D |
| 65-Ent2 | D |
| 66 | D |
| 67 | D |
| 69-Ent1 | D |
| 69-Ent2 | D |
| 70-Ent1 | A |
| 70-Ent2 | B |
| 71-Ent1 | C |
| 71-Ent2 | C |
| 72-Ent1 | B |
| 73-Ent1 | B |
| 74-Ent1 | B |
| 75-Ent1 | B |
| 76-Ent1 | B |
| 77-Ent1 | D |
| 77-Ent2 | D |
| 78-Ent1 | D |
| 78-Ent2 | D |
| 79 | B |
| 80 | B |
| 81-Ent1 | C |
| 82-Ent1 | C |
| 83-Ent1 | B |
| 84-Ent1 | D |
| 84-Ent2 | D |
| 85-Ent1 | D |
| 85-Ent2 | D |
| 86-Ent1 | D |
| 86-Ent2 | D |
| 87-Ent1 | D |
| 87-Ent2 | D |
| 88-Ent1 | D |
| 88-Ent2 | D |
| 89-Ent1 | D |
| 89-Ent2 | D |
| 90-Ent1 | D |
| 90-Ent2 | D |
| 91-Ent1 | D |
| 91-Ent2 | D |
| 92-Ent1 | D |
| 92-Ent2 | D |
| 93-Ent1 | D |
| 93-Ent2 | D |
| 94-Ent1 | D |
| 94-Ent2 | D |
| 95-Ent1 | D |
| 95-Ent2 | D |
| 96-Ent1 | D |
| 96-Ent2 | D |
| 97-Ent1 | D |
| 97-Ent2 | D |
| 98-Ent1 | D |
| 98-Ent2 | D |
| 99-Ent1 | D |
| 99-Ent2 | D |
| 100-Ent1 | D |
| 100-Ent2 | D |
| 101-Ent1 | D |
| 101-Ent2 | D |
| 102-Ent1 | D |
| 102-Ent2 | D |
| 103-Ent1 | D |
| 103-Ent2 | D |
| 104-Ent1 | D |
| 105-Ent1 | D |
| 105-Ent2 | D |
| 106-Ent1 | D |
| 106-Ent2 | D |
| 107-Ent1 | D |

-continued

| Compound | Stereochemical Determination |
|---|---|
| 107-Ent2 | D |
| 108-Ent1 | D |
| 108-Ent2 | D |
| 109-Ent1 | D |
| 109-Ent2 | D |
| 110-Ent1 | D |
| 110-Ent2 | D |
| 111-Ent1 | D |
| 111-Ent2 | D |
| 112-Ent1 | D |
| 112-Ent2 | D |
| 113-Ent1 | D |
| 113-Ent2 | D |
| 114-Ent1 | D |
| 114-Ent2 | D |
| 115-Ent1 | D |
| 115-Ent2 | D |
| 116-Ent1 | D |
| 116-Ent2 | D |
| 117-Ent1 | D |
| 117-Ent2 | D |
| 118-Ent1 | D |
| 118-Ent2 | D |
| 120-Ent1 | D |
| 120-Ent2 | D |
| 121-Ent1 | D |
| 121-Ent2 | D |
| 122-Ent1 | D |
| 122-Ent2 | D |
| 123-Ent1 | D |
| 123-Ent2 | D |
| 124-Ent1 | D |
| 124-Ent2 | D |
| 125-Ent1 | D |
| 125-Ent2 | D |
| 126-Ent1 | D |
| 126-Ent2 | D |
| 127-Ent1 | D |
| 127-Ent2 | D |
| 128-Ent1 | D |
| 128-Ent2 | D |
| 129-Ent1 | D |
| 129-Ent2 | D |
| 130-Ent1 | D |
| 130-Ent2 | D |
| 131-Ent1 | D |
| 131-Ent2 | D |
| 132-Ent1 | D |
| 132-Ent2 | D |
| 133-Ent1 | D |
| 133-Ent2 | D |
| 134-Ent1 | D |
| 134-Ent2 | D |
| 135-Ent1 | D |
| 135-Ent2 | D |
| 136-Ent1 | D |
| 136-Ent2 | D |
| 137-Ent1 | D |
| 137-Ent2 | D |
| 138-Ent1 | D |
| 138-Ent2 | D |
| 149 | B |
| 150-Ent1 | D |
| 150-Ent2 | D |
| 151-Ent1 | D |
| 151-Ent2 | D |
| 152-Ent1 | D |
| 152-Ent2 | D |
| 153-Ent1 | D |
| 153-Ent2 | D |
| 154-Ent1 | D |
| 154-Ent2 | D |
| 155-Ent1 | B |
| 155-Ent2 | B |
| 156 | B |
| 159 | D |

| Compound | Stereochemical Determination |
|---|---|
| 161-Ent1 | D |
| 161-Ent2 | D |
| 163-Ent1 | D |
| 163-Ent2 | D |
| 164-Ent1 | D |
| 164-Ent2 | D |
| 165-Ent1 | D |
| 165-Ent2 | D |
| 166 | C |
| 167 | C |
| 168-Ent1 | B |

Example 1. Synthesis of Compounds 12-Ent1 and 12-Ent2

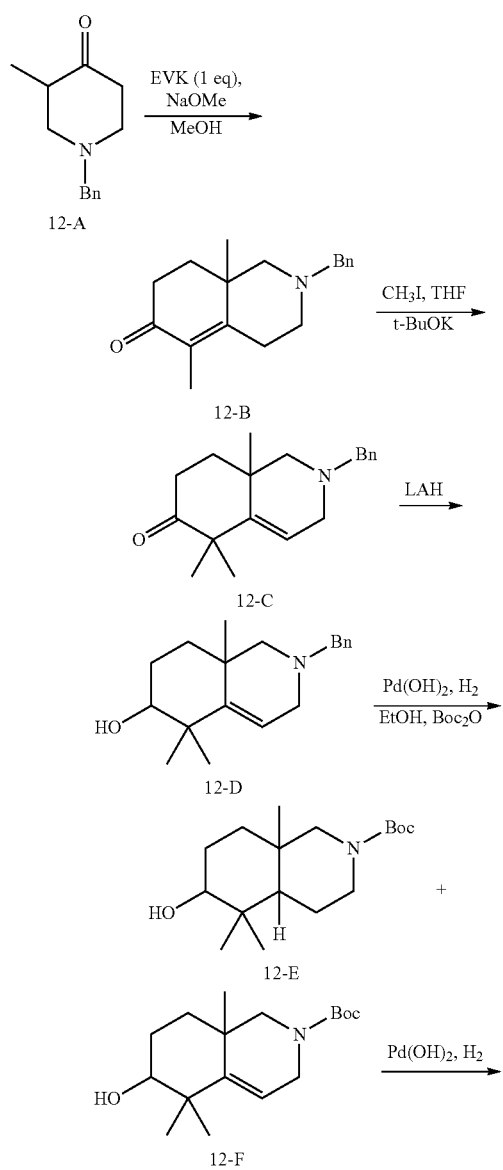

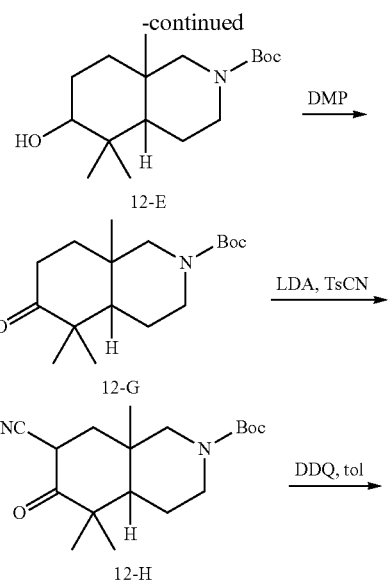

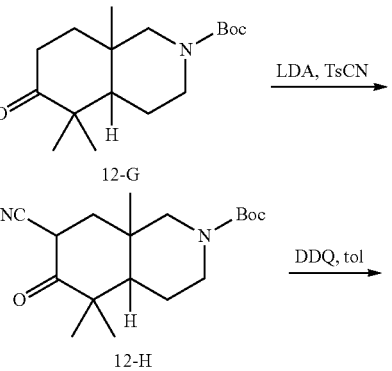

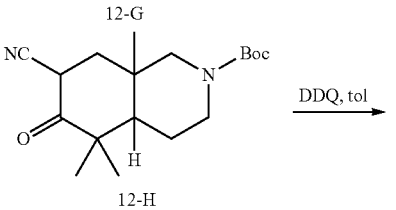


Preparation of Compound 12-B

Compound 12-A (20 g, 98 mmol, 1.0 eq.) in 200 mL of MeOH was added at −5° C. to a solution of MeONa which was made by 2.5 g of Na (1.1 eq.) in 100 mL of MeOH. After 1 hour at −5° C., compound Ethyl vinyl ketone (14.8 mL, 147.6 mmol, 1.5 eq.) in 50 mL of MeOH was added dropwise and the reaction mixture was stirred for 4 hours at −5° C. TLC (PE/EA=5/1) showed the starting material was remained and new spot was detected. The mixture was poured into 50 mL of water, concentrated and the residue was extracted with EA (50 mL×3), the organic layer was dried over anhydrous Na$_2$SO$_4$, filtered and concentrated, the residue was purified by chromatography (PE/EA=30/1) on silica gel to give 12 g of compound 12-B (yield ~63.5%) as a yellow oil.

$^1$H NMR: (400 MHz, CDCl$_3$) δ: 7.35-7.23 (m, 5H), 3.56 (d, J=13.2 Hz, 1H), 3.39 (d, J=13.6 Hz, 1H), 3.04-3.00 (m, 1H), 2.61-2.40 (m, 6H), 2.05-1.98 (m, 1H), 1.78-1.73 (m, 4H), 1.57-1.51 (m, 1H), 1.34 (s, 3H).

Preparation of Compound 12-C

A solution of t-BuOK (22.3 mL, 22.3 mmol, 1.5 eq, 1 M in THF) was added dropwise to a solution of compound 12-B (4 g, 14.9 mmol, 1.0 eq.) in 30 mL of THF at 0° C. After 0.5 hour, MeI (1.4 mL, 22.3 mmol, 1.5 eq.) in 10 mL of THF was added dropwise to the mixture. The mixture was stirred at 20° C. for 1.5 hour. The mixture was concentrated and the residue was purified by Prep-HPLC (TFA) to give 1.8 g of impure compound 12-C which contained the known byproduct. An 100 mg aliquot of impure 12-C was purified by Prep-TLC (PE/EA=8/1) for characterization purposes.

LCMS: (M+H: 284.2)

$^1$H NMR: (400 MHz, CDCl$_3$) δ: 7.35-7.22 (m, 5H), 5.50 (s, 1H), 3.68 (d, J=12.8 Hz, 1H), 3.46-3.34 (m, 1H), 2.78-2.74 (m, 1H), 2.52-2.47 (m, 3H), 1.97 (d, J=8.0 Hz, 1H), 1.76-1.68 (m, 1H), 1.58-1.50 (m, 2H), 1.22 (d, J=9.6 Hz, 6H), 1.15 (s, 3H).

Preparation of Compound 12-D

Lithium Aluminum Hydride (161 mg, 4.2 mmol, 1.2 eq.) was added in portions to compound 12-C (1 g, 3.5 mmol, 1.0 eq.) in THF (20 mL) at 0° C., then the mixture was stirred at 20-23° C. for 2 hours. TLC (PE/EA=8/1) showed the starting material was consumed completely. The reaction was quenched by addition of 0.161 mL of water, 0.161 mL of aqueous NaOH (15%) and 0.483 mL of water in turn to the reaction mixture. The reaction mixture was filtered and the filter cake was washed with ethyl acetate. The filtrate was concentrated to give 940 mg of compound 12-D (crude) as a yellow oil which was used directly in next step without further purification.

LCMS: (M+H: 285.9)

Preparation of Compounds 12-E and 12-F

Pd(OH)$_2$/C (200 mg, 20%, dry) was added to a mixture of compound 12-D (940 mg, 3.3 mmol, 1.0 eq.) and Boc$_2$O (863 mg, 3.96 mmol, 1.2 eq.) in EtOH (30 mL) at 20-23° C., then the mixture was stirred at 20-23° C. under H$_2$ balloon (~15 psi) for 18 hours. TLC (PE/EA=5/1) showed the starting material was consumed completely. Filtered and the filtrate was concentrated, the residue was purified by chromatography (PE/EA=10/1) on silica gel to give a mixture of compounds 12-E and 12-F (~750 mg).

LCMS: (M−56+H: 242.0, 240.0)

Preparation of Compound 12-E

Pd(OH)$_2$/C (200 mg, 20%, dry) was added to a mixture of compound 12-E and 12-F (750 mg mixture) in EtOH (30 mL), then the mixture was stirred at 22~24° C. under H$_2$ balloon (~15 psi) for 3 days. The mixture was filtered and concentrated to give compound 12-E (640 mg, yield ~85%) as a slightly yellow oil which was used directly in next step without further purification.

LCMS: (M−56+H: 242.0)

Preparation of Compound 12-G

Dess-Martin reagent (1.1 g, 2.589 mmol, 1.2 eq.) was added in portions to compound 12-E (640 mg, 2.15 mmol, 1.0 eq.) in 20 mL of DCM at 26-28° C., then the mixture was stirred at this temperature for 1 hour. TLC (PE/EA=5/1) showed the starting material was consumed completely. The reaction was quenched by NaHCO$_3$ (aq), extracted with DCM (10 mL×3), dried over anhydrous Na$_2$SO$_4$, filtered and concentrated. The residue was purified by chromatography (PE/EA=10/1) on silica gel to give about 600 mg of compound 12-G (yield 94%) as a white solid.

LCMS: (M−100+H: 195.9)

$^1$H NMR: (400 MHz, CDCl$_3$) δ: 4.34-4.21 (m, 1H), 3.88-3.71 (m, 1H), 2.68-2.64 (m, 2H), 2.37-2.27 (m, 2H), 1.63-1.42 (m, 14H), 1.28-0.84 (m, 9H).

Preparation of Compound 12-H

LDA (0.37 mL, 0.74 mmol, 2 M in THF, 1.1 eq.) was added dropwise to a solution of compound 12-G (200 mg, 0.68 mmol, 1.0 eq.) in 10 mL of THF at −70° C., after 1 hour at this temperature, TsCN (135 mg, 0.74 mmol, 1.1 eq.) in 1 mL of THF was added to the mixture at −70° C., and the mixture was stirred at −70° C. for another 1 hour. TLC (PE/EA=3/1) showed the starting material remained and a new spot was detected. The reaction was quenched with 2 mL of NH$_4$Cl, 10 mL of water was added, and the mixture was extracted with EA (10 mL×3). The organic layer was dried over anhydrous Na$_2$SO$_4$, filtered and concentrated, the residue was purified by prep-TLC (PE/EA=3/1) to give about 60 mg of compound 12-H (yield ~28%) as a white solid.

LCMS: (M−56+42: 306.1)

Preparation of Compound 12-I

A mixture of compound 12-H (60 mg, 0.19 mmol, 1.0 eq.) and DDQ (64 mg, 0.28 mmol, 1.5 eq.) in 3 mL of toluene was stirred at reflux for 2 hours. The mixture was filtered and the filtrate was concentrated. The residue was purified by prep-TLC (PE/EA=3/1) to give about 25 mg of 12-I (yield ~41.7%).

$^1$H NMR: (400 MHz, CDCl$_3$) δ: 7.37 (s, 1H), 4.36-3.88 (m, 2H), 2.61-2.49 (m, 2H), 1.79-1.75 (m, 1H), 1.64-1.42 (m, 2H), 1.40 (s, 9H), 1.15 (d, J=4.0 Hz, 6H), 1.03 (s, 3H).

Preparation of Compound 12-J

Compound 12-I (200 mg, 0.63 mmol, 1.0 eq) in DCM/TFA (2/0.4 mL) was stirred at ~22° C. for 3 hours. TLC (PE/EA=3/1) showed the starting material was consumed completely. The solvent was removed and the residue was used directly in next step without further purification (~350 mg crude).

Preparation of Compounds 12-Ent1 and 12-Ent2

Triethylamine (0.53 mL, 3.78 mmol, 6.0 eq) was added to crude compound 12-J (191 mg in theory, 350 mg crude, 0.63 mmol, 1.0 eq) in 2 mL of DCM, then acetyl chloride (65 uL, 0.945 mmol, 1.5 eq.) was added in one portion. The mixture was stirred at 22° C. for 1 hour under N$_2$. TLC (EA) showed the starting material was consumed completely, the mixture was purified by prep-TLC (EA) and separated by SFC (Column: AD 250 mm×30 mm, 5 um; Condition: Neu-ETOH; Begin B: 25%; Flow Rate: 70 mL/min) to give 12-Ent1 (40 mg, Rt=3.416 min) and 12-Ent2 (39.3 mg, Rt=4.095 min) as white solids. The absolute stereochemistry was not assigned.

Data for 12-Ent1:
  HPLC: (Purity: 98.13%)
  LCMS: (M+H: 261.0)
  SFC: (ee: 100%)
  $^1$H NMR: (400 MHz, CDCl$_3$) δ: 7.38 (d, J=17.2 Hz, 1H), 4.84 (d, J=13.6 Hz, 0.37H), 4.56 (d, J=12.8 Hz, 0.68H), 3.99-3.95 (m, 0.69H), 3.56 (d, J=12.8 Hz, 0.41H), 3.04-2.95 (m, 1H), 2.37-2.34 (m, 1H), 2.10-2.06 (m, 3H), 1.88-1.84 (m, 1H), 1.63-1.59 (m, 2H), 1.19-1.14 (m, 6H), 1.04 (s, 3H).

Data for 12-Ent2:
  HPLC: (Purity: 96.86%)
  LCMS: (M+H: 261.1)
  SFC: (ee: 99.5%)
  $^1$H NMR: (400 MHz, CDCl$_3$) δ: 7.38 (d, J=17.6 Hz, 1H), 4.84 (d, J=13.2 Hz, 0.51H), 4.56 (d, J=12.8 Hz, 0.85H), 3.97 (d, J=13.2 Hz, 0.80H), 3.56 (d, J=12.8 Hz, 0.61H), 3.05-2.94 (m, 1H), 2.37-2.10 (m, 1H), 2.07 (d, J=8.4 Hz, 3H), 1.87-1.85 (m, 1H), 1.67-1.56 (m, 2H), 1.19-1.14 (m, 6H), 1.04 (s, 3H).

Determination of Absolute Stereochemistry of 12-Ent1:

The absolute stereochemistry was determined by a Vibrational Circular Dichroism study performed by Biotools, Inc. (Jupiter, Fla.). The absolute stereochemistry of 12-Ent1 was also determined by Single Crystal X-Ray Diffraction performed by Crystallographic Resources, Inc. (Dewitt Mich.).

Based on the agreement of both methods, 12-Ent1 was determined to be as shown below:

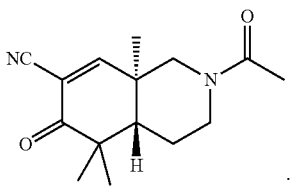 [SMILES: CC(=O)N1CC[C@@H]2C(C)(C)C(=O)C(C#N)=C[C@@]2(C)C1]

Preparation of Compounds 12-JEnt1 and 12-JEnt2

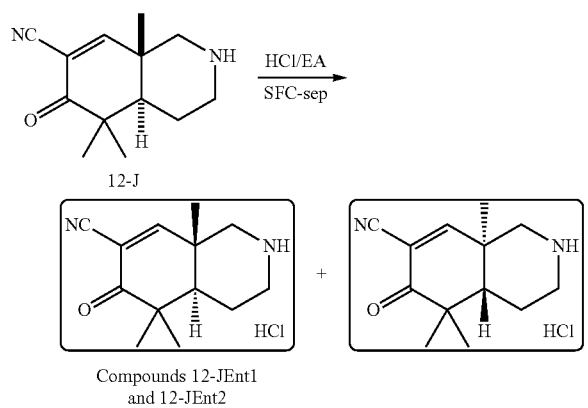

Racemic compound 12-J was separated by SFC (Column: C2 250 mm×30 mm, 10 um; Condition: Base-MeOH; Begin B: 45%; FlowRate: 80 mL/min) to give 12-JEnt1 (51.9 mg, Rt=6.15 min) and 44.9 mg of 12-JEnt2 (44.9 mg, Rt=7.78 min) as yellow solids. The absolute stereochemistry was not determined.

Data for 12-JEnt1
HPLC: (Purity: 97.78%)
LCMS: (M+1: 219.1)
SFC: (99.63%)
$^1$H NMR: (400 MHz, MeOD-$d_4$) δ: 7.75 (s, 1H), 3.44 (d, J=39.2 Hz, 1H), 3.35 (d, J=6.4 Hz, 1H), 3.08-3.02 (m, 2H), 2.25-2.21 (m, 1H), 1.97-1.92 (m, 2H), 1.44 (s, 3H), 1.24 (s, 3H), 1.13 (s, 3H).

Data for 12-JEnt2:
HPLC: (Purity: 94.56%)
LCMS: (M+1: 219.1)
SFC: (98.87%)
$^1$H NMR: (400 MHz, MeOD-$d_4$) δ: 7.75 (s, 1H), 3.53-3.47 (m, 1H), 3.36 (d, J=11.2 Hz, 1H), 3.05 (d, J=10.0 Hz, 2H), 2.23 (d, J=8.4 Hz, 1H), 1.92 (s, 2H), 1.43 (s, 3H), 1.22 (s, 3H), 1.11 (s, 3H).

As an alternative to racemic synthesis, enantioselective synthesis can be used to afford enantioenriched intermediates of scheme 12.

Synthesis of Enantio-Enriched Intermediate 12-G

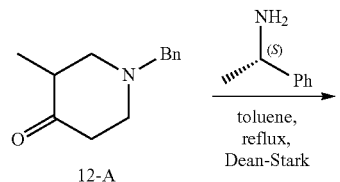

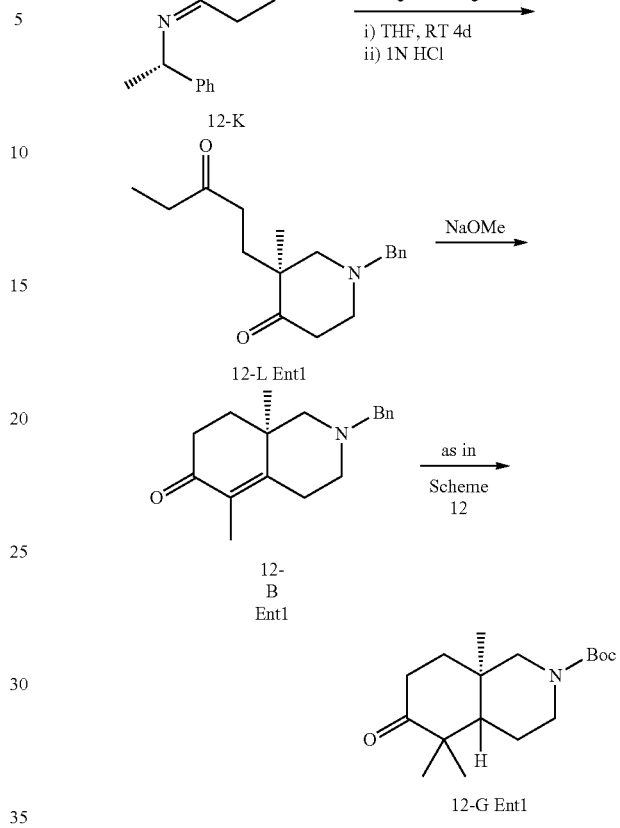

Enantio-enriched intermediate 12-G can be obtained as follows:

Preparation of Compound 12-K

To a solution of compound 12-A (100 g, 0.49 mol, 1.0 eq) in toluene (1 L) was added (S)-1-phenylethanamine (72 g, 0.59 mol, 1.2 eq) at 18° C. in one portion and fitted with a Dean-Stark. The reaction mixture was heated to reflux for 20 h, cooled to room temperature and concentrated under reduced pressure to supply crude compound 12-K (175 g), which was used for next step without further purification.

Preparation of Compound 12-L Ent1

To a solution of compound 12-K (175 g, 0.57 mol, 1.0 eq) in 1.5 L of anhydrous THF was added EVK (58 g, 0.69 mol, 1.2 eq). After addition the mixture was stirred at room temperature for 4 days under nitrogen. The solvents were removed. 1 N HCl (50 mL) was added to the residue oil. The mixture was diluted with water (100 mL), extracted with EA (200 mL×3). The combined organic layers was washed with brine (200 mL), dried over anhydrous $Na_2SO_4$, filtered and concentrated under reduced pressure to supply crude compound 12-L-Ent1 (205 g), which was used for next step without further purification.

Preparation of Compound 12-B Ent1

The reactions were performed in two batches, and the work-up was combined together To a 2 L three-neck round bottom flask containing 600 mL of methanol in an ice/water bath was added sodium (8.05 g, 1.0 eq) piecewise. Compound 12-L Ent1 (100 g, 0.35 mol, 1.0 eq) was added as a solution in 500 mL of methanol. The reaction was heated to 55° C. for 5 h. TLC (PE/EA=5:1)

showed compound 12-L Ent1 was consumed completely. The mixture was acidified to make pH=7-9 in ice-bath and concentrated to give the residue, for which was diluted into water (400 ml) and extracted with EA (300 mL×3). The combined organic layer was washed with brine (300 mL), dried over anhydrous $Na_2SO_4$, filtered and concentrated to give the crude product, which purified by column chromatography on silica gel (PE/EA=50:1-30:1-5:1) to supply compound 12-B Ent1 (83 g, 80% yield) as pale-yellow oil. (note: twice purification). Enantiopurity was assessed at this stage using chiral SFC. The ee was found to be 86.3%: Column: Chiralcel OJ-3 150×4.6 mm I.D., 3 um Mobile phase: A: $CO_2$; B: ethanol (0.05% DEA) Gradient: from 5% to 40% of B in 5 min and hold 40% for 2.5 min, then 5% of B for 2.5 min Flowrate: 2.5 mL/min Column temp.: 35° C. Rt for 12-B Ent1 is 2.79 min. Rt for 12-B Ent2 is 2.54 min under these conditions.

$^1$HNMR: (400 MHz, $CDCl_3$) δ: 7.34-7.24 (m, 5H), 3.55-3.49 (m, 1H), 3.34 (d, J=13.3 Hz, 1H), 3.07-2.86 (m, 2H), 2.69-2.29 (m, 7H), 1.67 (s, 3H), 1.52-1.46 (m, 1H), 1.29 (s, 3H).

Compound 12-G-Ent1 can be obtained from 12-B Ent1 by following the same sequence used for the racemate described in Scheme 12. Scheme 12 intermediates enriched in the opposite enantiomer can be obtained as above by starting with (R)-1-phenylethanamine.

Example 2. Synthesis of Compounds 13-Ent1 and 13-Ent2

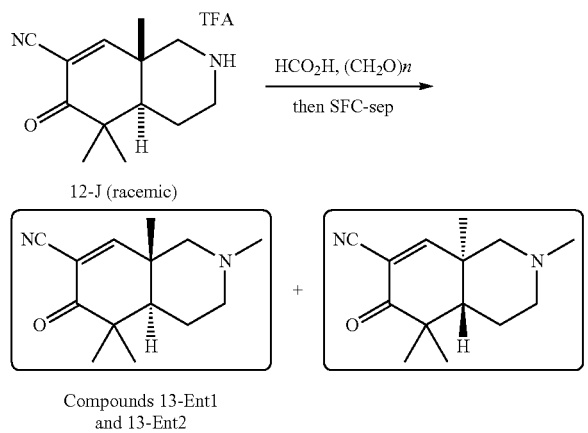

Compounds 13-Ent1 and 13-Ent2

A mixture of compound racemic 12-J (480 mg crude, 1.45 mmol, 1.0 eq), and $(CH_2O)_n$ (217 mg, 7.25 mmol, 5.0 eq.) in $HCO_2H$ (5 mL) was stirred at 90° C. for 1.5 hour. LCMS showed the starting material was consumed completely. The solvent was removed in vacuum and then adjusted to a pH of 9-10 with $NaHCO_3$ (sat). The aqueous phase was extracted with DCM (10 mL×4) and the combined organic layer was dried over anhydrous $Na_2SO_4$, filtered and concentrated. The residue was purified by prep-TLC (EA) to give about 120 mg of racemic compound which was separated by SFC (Column: C2 250 mm×30 mm, 10 um; Condition: Base-ETOH; Begin B: 15%; FlowRate: 60 ml/min) to give of 13-Ent1 (36.9 mg, Rt=3.42 min) and of 13-Ent2 (19.9 mg, Rt=3.75 min) as yellow solids. The absolute stereochemistry was not defined.

Data for 13-Ent1:
HPLC: (Purity: 98.24%)
LCMS: (M+1: 233.1)
SFC: (ee: 99.76%)
$^1$H NMR: (400 MHz, MeOD-$d_4$) δ: 7.69 (s, 1H), 3.06 (d, J=10.4 Hz, 1H), 2.79 (d, J=10.8 Hz, 1H), 2.31 (s, 3H), 2.04 (d, J=12.4 Hz, 2H), 2.06-2.00 (m, 2H), 1.85-1.65 (m, 1H), 1.36 (s, 3H), 1.19 (s, 3H), 1.09 (s, 3H).
$^1$H NMR: (400 MHz, $CDCl_3$) δ: 7.38 (s, 1H), 3.07 (d, J=9.6 Hz, 1H), 2.66 (d, J=10.0 Hz, 1H), 2.29 (s, 3H), 1.96 (d, J=10.8 Hz, 2H), 1.79 (dd, J=2.4, 12.0 Hz, 1H), 1.66-1.57 (m, 2H), 1.36 (s, 3H), 1.19 (s, 3H), 1.09 (s, 3H).

Data for 13-Ent2:
HPLC: (Purity: 96.37%)
LCMS: (M+1: 233.1)
SFC: (ee: 99.1%)
$^1$H NMR: (400 MHz, $CDCl_3$) δ: 7.39 (s, 1H), 3.03 (d, J=9.2 Hz, 1H), 2.61 (d, J=10.4 Hz, 1H), 2.27 (s, 3H), 1.92 (d, J=3.2 Hz, 2H), 1.91-1.71 (m, 1H), 1.66-1.59 (m, 2H), 1.37 (s, 3H), 1.21 (s, 3H), 1.11 (s, 3H).
$^1$H NMR: (400 MHz, MeOD-$d_4$) δ: 7.69 (s, 1H), 3.05 (d, J=10.8 Hz, 1H), 2.77 (d, J=10.8 Hz, 1H), 2.29 (s, 3H), 1.98 (d, J=10.8 Hz, 2H), 1.83-1.80 (m, 2H), 1.78-1.64 (m, 1H), 1.36 (s, 3H), 1.19 (s, 3H), 1.09 (s, 3H).

Example 3. Synthesis of Compounds 14-Ent1 and 14-Ent2

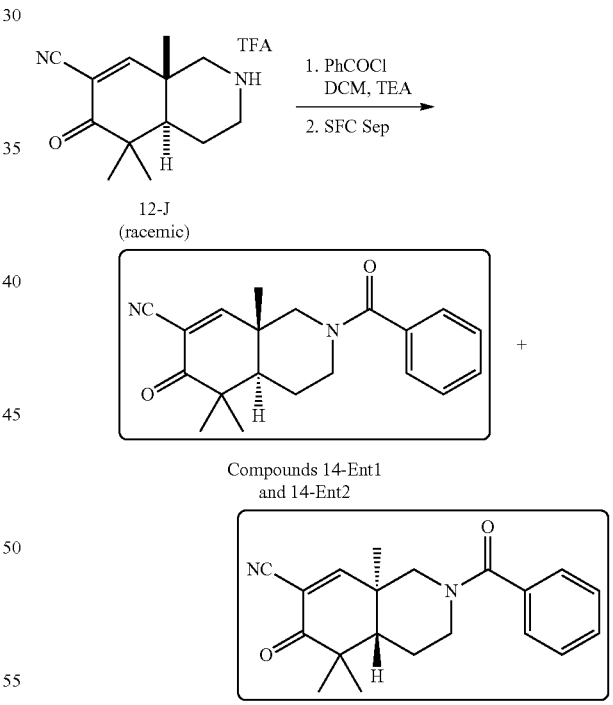

Compounds 14-Ent1 and 14-Ent2

To a solution of Compound 12-J (racemic, 500 mg crude of about 40% purity, 0.91 mmol, 1.0 eq) and TEA (458 mg, 4.58 mmol, 5.0 eq), in DCM (5 mL) was added benzoyl chloride (192 mg, 1.37 mmol, 1.5 eq) at 25° C. for 1.5 h. The reaction mixture was stirred at 25° C. for 2 hours. TLC (PE:EA=2:1) showed the starting materials were consumed completely. The mixture was quenched with saturated $NaHCO_3$ (30 mL) and extracted with DCM (20 mL×2). The combined organic phase was dried over sodium sulfate, and filtered. The filtrate was concentrated in vacuo to give the residue, which was purified by prep-HPLC (acid, Phenomenex Synergi C18 150×30 mm×4 um, water (0.05% HCl)-ACN as mobile phase, from 41-61%, Flow Rate: 25 mL/min) to give racemic product (120 mg, yield: 41%) as a white solid. Further separation by SFC (column: AD (250 mm×30 mm, 5 um), condition: Base-EtOH) to give enantiomers 14-Ent1 (Rt=3.576 min, 56.7 mg) and 14-Ent2 (Rt=4.337 min, 55.3 mg), both as white solid. The absolute stereochemistry was not determined.

Data for 14-Ent1

$^1$H-NMR: (400 MHz, CHLOROFORM-d) δ: 7.55-7.30 (m, 6H), 5.12-4.62 (m, 1H), 4.08-3.52 (m, 1H), 3.12-2.52 (m, 2H), 1.94 (d, J=12.5 Hz, 1H), 1.72 (br. s., 1H), 1.58 (br. s., 3H), 1.32 (br. s., 1H), 1.21 (br. s., 3H), 1.09 (s, 3H).

HPLC: (Purity: 96.82%).
SFC: (ee 98.65%).
LCMS: (M+H: 323.0).

Data for 14-Ent2

$^1$HNMR: (400 MHz, CDCl3) δ: 7.59-7.30 (m, 6H) 5.16-4.64 (m, 1H) 4.06-3.52 (m, 1H), 3.14-2.55 (m, 2H), 1.95 (d, J=12.1 Hz, 1H) 1.72 (br. s., 1H) 1.59 (br. s., 3H) 1.32 (br. s., 1H) 1.21 (br. s., 3H) 1.09 (s, 3H)

HPLC: (Purity: 94.81%).
SFC: (ee: 99%).
LCMS: (M+H: 323.0).

Example 4. Synthesis of Compounds 15-Ent1 and 15-Ent2

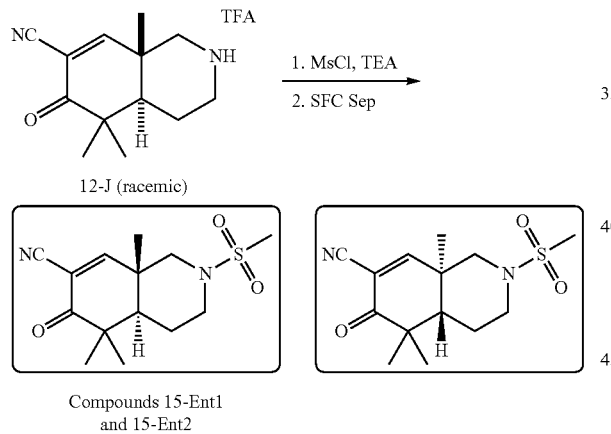

Compounds 15-Ent1 and 15-Ent2

To a solution of Compound 12-J (500 mg racemic crude with about 40% purity, 0.91 mmol, 1.0 eq) and TEA (458 mg, 4.58 mmol, 5.0 eq), in DCM (5 mL) was added methanesulfonyl chloride (156 mg, 1.37 mmol, 1.5 eq) at 25° C. for 1.5 h. The reaction mixture was stirred at 25° C. for 2 hours. TLC (PE:EA=1:2) showed the starting materials were consumed completely. The mixture was quenched with saturated aqueous NaHCO$_3$ (30 mL) and extracted with DCM (20 mL×2). The combined organic phase was dried over sodium sulfate, and filtered. The filtrate was concentrated in vacuo to give the residue, which was purified by prep-TLC (PE:EA=1:3) to give racemic product (120 mg, yield; 45%) as a white solid. Further separation by SFC (column: AD (250 mm×30 mm, 5 um), condition: Base-EtOH) to give enantiomer 15-Ent1 (19224-130-1, Rt=3.764 min, 21.7 mg) and 15-Ent2 (19224-130-2, Rt=4.591 min, 21.5 mg) both as white solid. The absolute stereochemistry was not assigned.

Data for 15-Ent1

$^1$H NMR (400 MHz, CHLOROFORM-d) δ: 7.39 (s, 1H) 4.07-4.02 (m, 1H), 3.65 (d, J=11.4 Hz, 1H), 2.82 (s, 3H), 2.70 (td, J=11.5, 2.74 Hz, 1H), 2.60 (d, J=10.9 Hz, 1H), 1.92-1.73 (m, 3H), 1.39 (s, 3H), 1.24 (s, 3H), 1.13 (s, 3H).

HPLC: (Purity: 99.24%).
SFC: (ee 98.02%).
LCMS: (M+H: 297.2).

Data for 15-Ent2

$^1$HNMR: (400 MHz, CDCl$_3$) δ: 7.39 (s, 1H), 4.04-4.01 (m, 1H), 3.65 (d, J=11.4 Hz, 1H), 2.82 (s, 3H), 2.70 (td, J=11.5, 2.74 Hz, 1H), 2.60 (d, J=11.4 Hz, 1H), 1.90-1.72 (m, 3H), 1.39 (s, 3H), 1.24 (s, 3H), 1.13 (s, 3H).

HPLC: (Purity: 97.43%).
SFC: (ee: 96.82%).
LCMS: (M+H: 297.1).

Example 5. Synthesis of Compounds 16-Ent1 and 16-Ent2

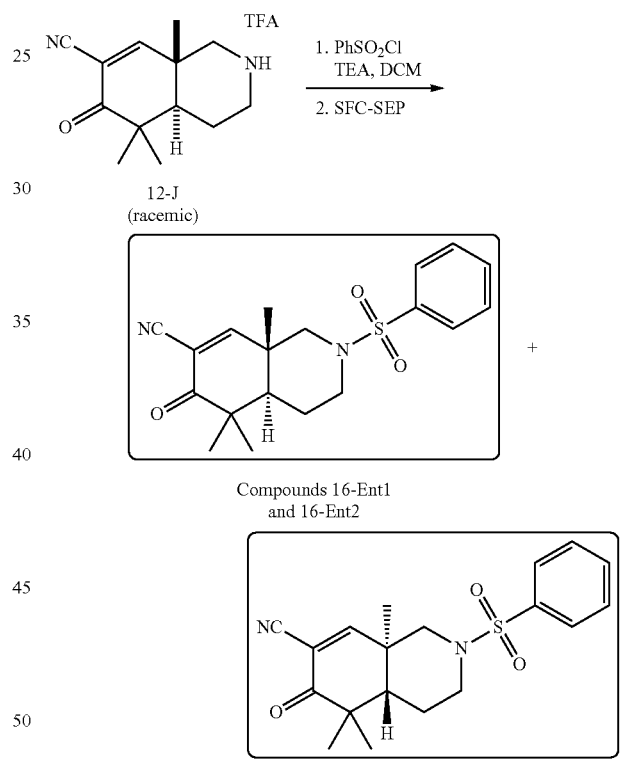

Compounds 16-Ent1 and 16-Ent2

To a solution of 12-J (racemic, 500 mg crude, about 40% purity, 0.91 mmol, 1.0 eq) and TEA (458 mg, 4.58 mmol, 5.0 eq) in DCM (5 mL) was added benzenesulfonyl chloride (241 mg, 1.37 mmol, 1.5 eq) at 0° C. The reaction mixture was stirred at 25° C. for 2 hours. TLC (PE:EA=1:2) showed the starting materials were consumed completely. The mixture was quenched with saturated aqueous NaHCO$_3$ (30 mL) and extracted with DCM (20 mL×2). The combined organic phase was dried over sodium sulfate, and filtered. The filtrate was concentrated in vacuo to give the residue, which was purified by prep-TLC (PE:EA=1:1) to give product (180 mg, racemate, yield; 55%) as a white solid. Further separation by SFC (column: AD (250 mm×30 mm, 5 um), condition: Base-EtOH) to give enantiomer 16-Ent1 (Rt=4.425 min, 84.8 mg) and 16-Ent2 (Rt=7.961 min, 43.1 mg), both as white solids. The absolute stereochemistry was not determined.

Data for 16-Ent1

$^1$H NMR: (400 MHz, CHLOROFORM-d) δ: 7.75 (d, J=7.4 Hz, 2H), 7.65-7.56 (m, 1H), 7.55-7.50 (m, 2H), 7.37 (s, 1H), 4.10-4.00 (m, 1H), 3.65 (d, J=10.9 Hz, 1H), 2.26 (td, J=11.7, 3.13 Hz, 1H), 2.17 (d, J=10.9 Hz, 1H), 1.91-1.85 (m, 1H), 1.68 (d, J=11.4 Hz, 2H), 1.43 (s, 3H), 1.16 (s, 3H), 1.11 (s, 3H).

HPLC: (Purity: 95.59%).
SFC: (ee: 100%).
LCMS: (M+H: 359.1).

Data for 16-Ent2

$^1$H NMR: (400 MHz, CHLOROFORM-d) δ 7.76 (d, J=7.4 Hz, 2H), 7.65-7.56 (m, 1H), 7.55-7.50 (m, 2H), 7.37 (s, 1H), 4.07-4.01 (m, 1H), 3.65 (d, J=10.9 Hz, 1H), 2.26 (d, J=3.13 Hz, 1H), 2.17 (d, J=10.9 Hz, 1H), 1.91-1.85 (m, 1H), 1.73-1.61 (m, 2H), 1.43 (s, 3H), 1.17 (s, 3H) 1.11 (s, 3H).

HPLC: (Purity: 97.01%).
SFC: (ee: 99.78%).
LCMS: (M+H: 359.1).

Example 6. Synthesis of Compounds 17-Ent1 and 17-Ent2

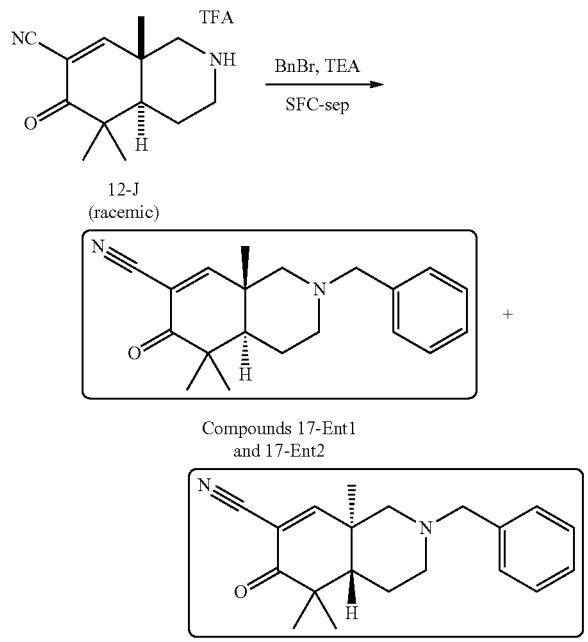

To a solution of compound 12-J (racemate, 500 mg, crude about 40% purity, 0.91 mmol, 1.0 eq) and TEA (458 mg, 4.58 mmol, 5.0 eq) in DCM (5 mL) was added (bromomethyl)benzene (186 mg, 1.01 mmol, 1.2 eq) at 25° C. The reaction mixture was stirred at 25° C. for 18 hours. LCMS showed the starting materials were consumed completely. The mixture was quenched with water (15 mL) and extracted with DCM (10 mL×3). The combined organic phase was dried over sodium sulfate, and filtered. The filtrate was concentrated in vacuo to give the residue, which was purified by prep-HPLC (Phenomenex Gemini C18 250×21.2 mm×5 um, water with 10 mM of NH$_4$HCO$_3$-ACN as mobile phase, from 53-83%, Flow Rate 25 ml/min) to give product (racemic, 100 mg, yield; 35%) as colorless oil. Further separation by SFC (column: OJ 250 mm×30 mm, 5 um, condition: Base-EtOH) to give the two enantiomers 17-Ent1 (Rt=2.907 min, 29.4 mg) and 17-Ent2 (Rt=3.433 min, 35.4 mg) both as colorless oils.

Data for 17-Ent1

$^1$H NMR: (400 MHz, CHLOROFORM-d) δ 7.35-7.23 (m, 6H), 3.59 (d, J=13.3 Hz, 1H), 3.38 (d, J=13.3 Hz, 1H), 3.06 (d, J=10.9 Hz, 1H), 2.57 (d, J=10.1 Hz, 1H), 2.06-1.99 (m, 1H), 1.87 (d, J=10.6 Hz, 1H), 1.76-1.67 (m, 1H), 1.68-1.63 (m, 1H) 1.55 (dd, J=12.5, 2.4 Hz, 1H), 1.33 (s, 3H), 1.17 (s, 3H), 1.08 (s, 3H).

HPLC: (Purity: 100%).
SFC: (ee: 99.5%).
LCMS: 19224-138-1C (M+H: 308.9).

Data for 17-Ent2

$^1$HNMR: (400 MHz, CDCl$_3$) δ: 7.35-7.23 (m, 6H), 3.59 (d, J=13.3 Hz, 1H), 3.38 (d, J=13.3 Hz, 1H), 3.06 (d, J=10.9 Hz, 1H), 2.53 (d, J=10.1 Hz, 1H), 2.06-1.99 (m, 1H), 1.80 (d, J=10.6 Hz, 1H), 1.76-167 (m, 1H), 1.68-1.63 (m, 1H) 1.56 (dd, J=12.5, 2.4 Hz, 1H), 1.28 (s, 3H), 1.12 (s, 3H), 1.04 (s, 3H).

HPLC: (Purity: 100%).
SFC: (ee: 99.64%).
LCMS: (M+H: 309.0).

Example 7. Synthesis of Compounds 18-Ent1 and 18-Ent2

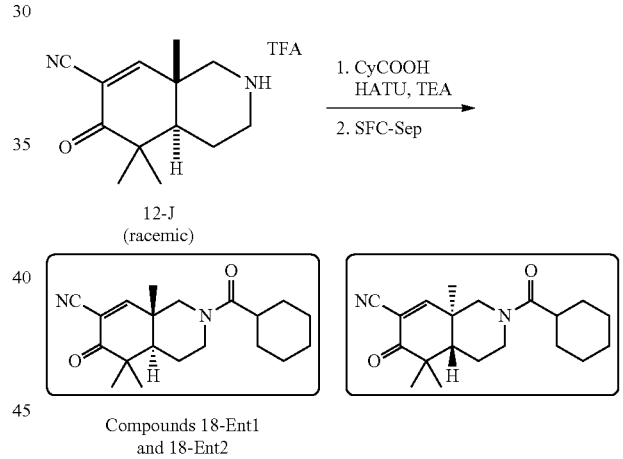

A solution of TEA (458 mg, 4.58 mmol, 5.0 eq), HATU (522 mg, 1.37 mmol, 1.5 eq) and cyclohexanecarboxylic acid (176 mg, 1.37 mmol, 1.5 eq) in DCM (5 mL) was stirred at 25° C. for 1.5 h. Compound 12-J (racemic, 500 mg crude about 40% purity, 0.91 mmol, 1.0 eq) in DCM (2 mL) was added to above the mixture dropwise at 25° C. The reaction mixture was stirred at 25° C. for 18 hours. TLC (PE:EA=2:1) showed the starting materials were consumed completely. The mixture was quenched with Saturated NaHCO$_3$ (30 mL) and extracted with DCM (20 mL×2). The combined organic phase was dried over sodium sulfate, and filtered. The filtrate was concentrated in vacuo to give the residue, which was purified by prep-TLC (PE:EA=1:1) to give racemic product (100 mg, yield: 32%) as a white solid. Further separation by SFC (column: AD 250 mm×30 mm, 5 um, condition: Base-EtOH) to give enantiomers 18-Ent1 (Rt=4.347 min, 18.2 mg) and 18-Ent2 (19224-138-2, Rt=4.983 min, 17.2 mg), both were white solids. The absolute stereochemistry was not defined.

Data for 18-Ent1
  $^1$H-NMR: (400 MHz, CHLOROFORM-d) δ: 7.49 (s, 1H), 4.96-4.57 (m, 1H), 4.25-4.21 (m, 1H), 3.08-2.97 (m, 1H), 2.59-2.38 (m, 2H), 1.98-1.74 (m, 5H). 1.62-1.51 (m, 5H), 1.35-1.23 (m, 7H), 1.18 (s, 2H), 1.11 (s, 3H).
  HPLC: (Purity: 100%).
  SFC: (ee: 96.08%).
  LCMS: (M+H: 329.1).
Data for 18-Ent2
  $^1$HNMR: (400 MHz, CDCl$_3$) δ: 7.49 (s, 1H), 4.98-4.51 (m, 1H), 4.29-4.20 (m, 1H), 3.08-2.97 (m, 1H), 2.59-2.38 (m, 2H), 1.97-1.74 (m, 5H). 1.62-1.49 (m, 5H), 1.35-1.23 (m, 7H), 1.18 (s, 2H), 1.11 (s, 3H).
  HPLC: (Purity: 94.14%).
  SFC: (ee: 98.32%).
  LCMS: (M+H: 329.1).

Example 8. Synthesis of Compounds 19-Ent1 and 19-Ent2

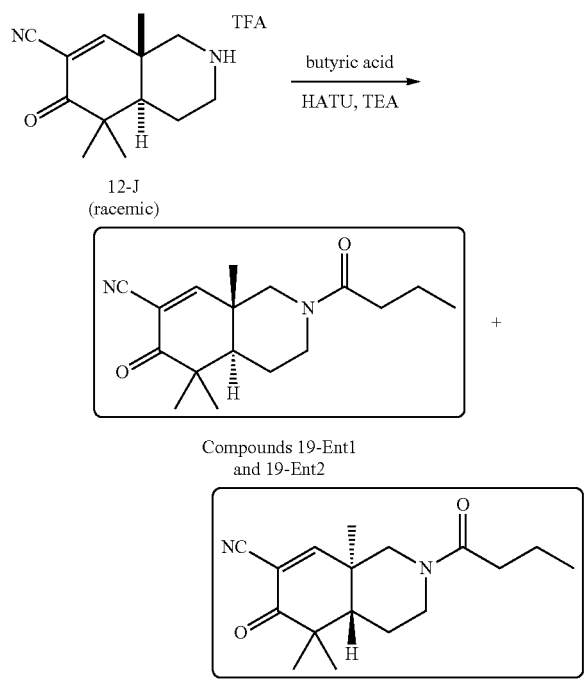

Data for 19-Ent1:
  $^1$H NMR (400 MHz, CDCl$_3$) δ: 7.51-7.45 (m, 1H), 4.65 (d, J=12.5 Hz, 1H), 4.13-3.53 (m, 1H), 3.15-2.93 (m, 1H), 2.50-2.24 (m, 3H), 1.95-1.85 (m, 1H), 1.77-1.65 (m, 4H), 1.24 (br. s., 4H), 1.20 (s, 2H), 1.11 (s, 3H), 1.05-0.88 (s, 3H).
  HPLC: (Purity: 100%).
  SFC: (ee: 100%).
  LCMS: (M+H: 289).
Data for 19-Ent2:
  $^1$HNMR: (400 MHz, CDCl$_3$) δ: 7.51-7.45 (m, 1H), 4.66 (d, J=12.5 Hz, 1H), 4.13-3.51 (m, 1H), 3.12-2.90 (m, 1H), 2.50-2.24 (m, 3H), 1.95-1.85 (m, 1H), 1.77-1.65 (m, 4H), 1.25 (br. s., 4H), 1.20 (s, 2H), 1.11 (s, 3H), 1.05-0.88 (s, 3H).
  HPLC: (Purity: 100%).
  SFC: (ee: 99.8%).
  LCMS: (M+H: 289).

Example 9. Synthesis of Compounds 20-Ent1 and 20-Ent2

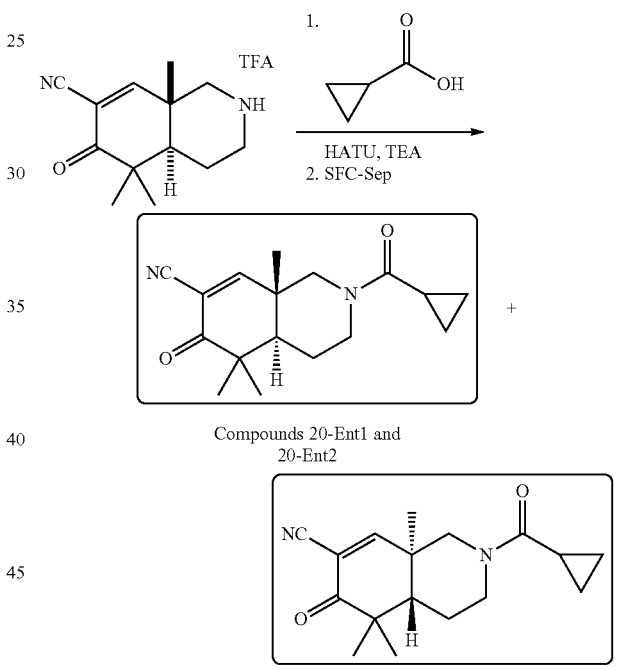

A solution of TEA (458 mg, 4.58 mmol, 5.0 eq), HATU (522 mg, 1.37 mmol, 1.5 eq) and butyric acid (120 mg, 1.37 mmol, 1.5 eq) in DCM (5 mL) was stirred at 25° C. for 1.5 h. Compound 12-J (500 mg crude, racemic, about 40% purity, 0.91 mmol, 1.0 eq) in DCM (2 mL) was added to the above mixture dropwise at 25° C. The reaction mixture was stirred at 25° C. for 18 hours. TLC (PE:EA=2:1) showed the starting materials were consumed completely. The mixture was quenched with Saturated NaHCO$_3$ (30 mL) and extracted with DCM (20 mL×2). The combined organic phase was dried over sodium sulfate, and filtered. The filtrate was concentrated in vacuo to give the residue, which was purified by prep-TLC (PE:EA=1:1) to give racemic product (200 mg, yield; 60%) as a white solid. Further separation by SFC (column: AD (250 mm×30 mm, 5 um), condition: Base-EtOH) to give enantiomer 19-Ent1 (Rt=3.621 min, 81.7 mg) and 19-Ent2 (Rt=4.392 min, 96.8 mg), both are white solid. The absolute stereochemistry was not determined.

A mixture of cyclopropanecarboxylic acid (203 mg, 2.35 mmol, 1.2 eq.), HATU (1.1 g, 2.94 mmol, 1.5 eq.) and TEA (595 mg, 5.88 mmol, 3.0 eq.) in DCM (5 mL) was stirred at 20° C. for 1 h. Then compound 12-J (500 mg, 1.96 mmol, 1.0 eq) was added. The mixture was stirred at 20° C. for 16 h. LCMS showed the reaction was complete. The mixture was combined with batch 19243-114-1 and worked up together. The mixture was purified by prep-TLC (PE/EA=1/1) to give the product (200 mg, racemate, 44.0% yield) as a white solid.

The enantiomers were separated by SFC (Mobile phase: Supercritical CO2/EtOH (0.1% NH$_3$.H$_2$O); Column: Chiralpak OD (250 mm×30 mm, 10 um); Detection wavelength: 220 nm) to give 20-Ent1 (Rt=4.306 min, 76.3 mg, 38.15% yield) as a white solid and 20-Ent2 (Rt=6.013 min, 63.3 mg, 31.65% yield) as white solids. The absolute stereochemistry for both enantiomers was not determined.

Data for 20-Ent1:
  LCMS: (M+H: 287.2)
  HPLC: (96.08% purity)
  SFC: (ee %: 100%)
  ¹HNMR: (400 MHz, CDCl₃) δ: 7.48 (s., 1H), 4.89 (br. s, 1H), 4.62 (br. s, 1H), 4.46 (br. s, 1H), 4.05 (br. s, 1H), 3.10 (br. s, 1H), 2.57-2.43 (m, 1H), 2.01-1.93 (m, 1H), 1.73-1.66 (m, 1H), 1.34-1.16 (m, 6H), 1.11 (s, 3H), 1.00 (s., 2H), 0.82 (s., 2H).
Data for 20-Ent2:
  LCMS: (M+H: 287.1)
  HPLC: (99.48% purity)
  SFC: (ee %: 100%)
  ¹HNMR: (400 MHz, CDCl₃) δ: 7.48 (s., 1H), 4.89 (br. s, 1H), 4.62 (br. s, 1H), 4.47 (br. s, 1H), 4.05 (br. s, 1H), 3.10 (br. s, 1H), 2.58-2.42 (m, 1H), 2.00-1.92 (m, 1H), 1.80 (s., 1H), 1.30-1.16 (m, 6H), 1.11 (s, 3H), 1.00 (s., 2H), 0.82 (s., 2H).

Example 10. Synthesis of Compounds 21-Ent1 and 21-Ent2

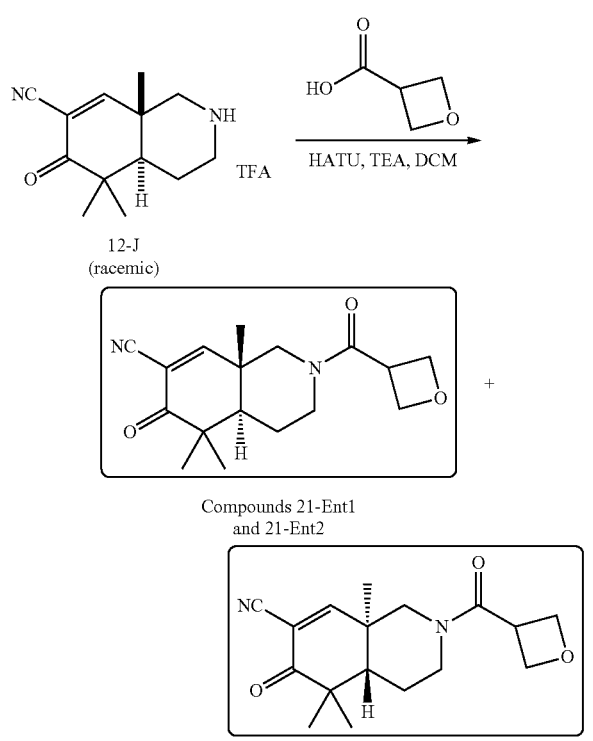

A mixture of oxetane-3-carboxylic acid (78 mg, 0.76 mmol, 1.2 eq.); HATU (395 g, 0.95 mmol, 1.5 eq.) and TEA (191 mg, 1.89 mmol, 3.0 eq.) in DCM (5 mL) was stirred at 20° C. for 1 h. Then compound 12-J (200 mg racemate, 0.63 mmol, 1.0 eq) was added. The mixture was stirred at 20° C. for 16 h. LCMS showed the reaction was complete. The mixture was purified by prep-TLC (EtOAc) to give the racemic product (60 mg, 31.3% yield) as yellow oil which was further separated by SFC (Mobile phase: Supercritical CO₂/MeOH with 0.1% NH3.H2O; Column: Chiralpak OD (250 mm*30 mm, 10 um); Detection wavelength: 220 nm) to give single enantiomer 21-Ent1 (Rt=5.034 min, 8.0 mg, 13.3% yield) as a white solid and single enantiomer 21-Ent2 (Rt=5.754 min, 7.6 mg, 12.7% yield) as a white solid. The absolute stereochemistry for both enantiomers was not determined.

Data for 21-Ent1
  LCMS: (M+H: 303.2)
  HPLC: (98.95% purity)
  SFC: (ee %: 99.64%)
  ¹HNMR: (400 MHz, MeOD) δ: 7.81 (s, 0.58H), 7.73 (s, 0.34H), 4.88-4.72 (m, 4H), 4.53 (d, J=12.6 Hz, 0.74H), 4.36-4.26 (m, 1H), 3.63 (d, J=11.8 Hz, 0.77H), 3.43 (d, J=12.0 Hz, 0.44H), 3.09-2.93 (m, 1H), 2.60 (d, J=12.8 Hz, 1H), 2.12-2.03 (m, 1H), 1.77-1.63 (m, 2H), 1.25-1.19 (m, 5H), 1.17 (s, 1H), 1.09 (s, 3H).
Data for 21-Ent2
  LCMS: (M+H: 303.2)
  HPLC: (98.32% purity)
  SFC: (ee %: 100%)
  ¹HNMR: (400 MHz, MeOD) δ: 7.81 (s, 0.6H), 7.73 (s, 0.35H), 4.88-4.72 (m, 4H), 4.53 (d, J=12.6 Hz, 0.7H), 4.32-4.22 (m, 1H), 3.63 (d, J=13.6 Hz, 0.75H), 3.43 (d, J=13.0 Hz, 0.48H), 3.08-2.95 (m, 1H), 2.60 (d, J=12.6 Hz, 1H), 2.13-2.02 (m, 1H), 1.78-1.63 (m, 2H), 1.24-1.19 (m, 5H), 1.17 (s, 1H), 1.09 (s, 3H).

Example 11. Synthesis of Compounds 22-Ent1 and 22-Ent2

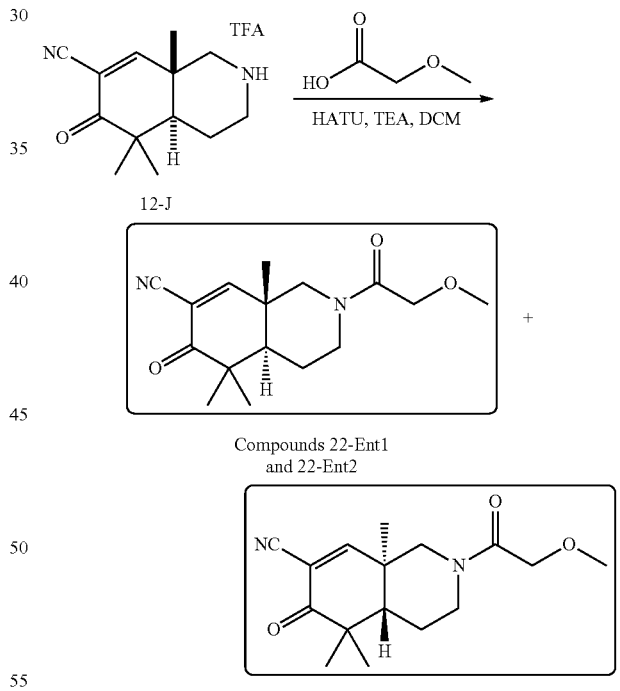

A mixture of 2-methoxyacetic acid (137 mg, 1.52 mmol, 1.2 eq.); HATU (724 g, 1.91 mmol, 1.5 eq.) and TEA (386 mg, 3.81 mmol, 3.0 eq.) in DCM (5 mL) was stirred at 30° C. for 1 h. Then compound 12-J (400 mg racemate, 1.27 mmol, 1.0 eq) was added. The mixture was stirred at 30° C. for 16 h. LCMS showed the reaction was complete. The mixture was purified by prep-TLC (EtOAc) to give racemic product (200 mg, 54.2% yield) as a brown solid. The obtained product was separated by SFC (Mobile phase: Supercritical CO₂/EtOH with 0.1% NH3.H2O; Column: Chiralpak OD (250 mm*30 mm, 5 um); Detection wavelength: 220 nm) to give single enantiomer 22-Ent1 (Rt=4.001 min, 38.3 mg, 19.2% yield) as a white solid and single enantiomer 22-Ent2 (Rt=4.631 min, 35.1 mg, 19.2% yield) as a white solid. The absolute stereochemistry for both enantiomers was not determined.

Data for 22-Ent1:
MS: (M+H: 291.17)
HPLC: (93.64% purity)
SFC: (ee %: 96.35%)
$^1$HNMR: (400 MHz, CDCl$_3$, T=40° C.) δ: 7.48-7.38 (m, 1H), 4.83 (br. s., 0.45H), 4.58 (d, J=12.0 Hz, 0.82H), 4.30-4.02 (m, 3H), 3.86 (d, J=9.4 Hz, 0.44H), 3.45 (s, 3H), 3.07-2.91 (m, 1H), 2.61-2.44 (m, 1H), 1.94 (d, J=11.0 Hz, 1H), 1.80-1.64 (m, 2H), 1.31-1.19 (m, 6H), 1.12 (s, 3H).

Data for 22-Ent2:
MS: (M+H: 291.17)
HPLC: (93.40% purity) SFC: (ee %: 97.73%)
$^1$HNMR: (400 MHz, CDCl$_3$) δ: 7.50-7.41 (m, 1H), 4.83 (d, J=12.8 Hz, 0.43H), 4.57 (d, J=12.6 Hz, 0.8H), 4.29-4.19 (m, 0.8H), 4.17-4.04 (m, 2H), 3.83 (d, J=12.6 Hz, 0.47H), 3.51-3.36 (m, 3H), 3.07-2.93 (m, 1H), 2.60-2.44 (m, 1H), 1.98-1.89 (m, 1H), 1.82-1.66 (m, 2H), 1.31-1.17 (m, 6H), 1.11 (s, 3H).

Example 12. Synthesis of Compounds 23-Ent1 and 23-Ent2 was separated by SFC (Mobile phase: Superaritical CO$_2$/MeOH with 0.1% NH3.H2O; Column: Chiralpak OD (250 mm*30 mm, 5 um); Detection wavelength: 220 nm) to give single enantiomer 23-Ent1 (Rt=4.928 min, 70.4 mg, 30.6% yield) as a white solid and single enantiomer 23-Ent2 (Rt=7.154 min, 63.5 mg, 27.6% yield) as a white solid.

Data for 23-Ent1
MS: (M+H: 324.16)
HPLC: (98.83% purity)
SFC: (ee %: 99.76%)
$^1$HNMR: (400 MHz, DMSO_d$_6$, T=80° C.) δ: 8.66 (d, J=5.0 Hz, 1H), 8.62 (s, 1H), 7.98 (br. s., 1H), 7.83 (d, J=7.8 Hz, 1H), 7.48 (dd, J=4.8, 7.8 Hz, 1H), 4.03 (br. s, 2H), 3.12 (m, 1H), 3.05-2.96 (m, 1H), 2.11 (dd, J=2.8, 12.6 Hz, 1H), 1.83-1.65 (m, 1H), 1.60 (d, J=14.8 Hz, 1H), 1.23-1.12 (m, 6H), 1.04 (s, 3H).

Data for 23-Ent2:
MS: (M+H: 324.16)
HPLC: (98.39% purity)
SFC: (ee %: 100%)
$^1$HNMR: (400 MHz, DMSO_d$_6$) δ: 8.66-8.58 (m, 2H), 8.17 (s., 0.5H), 7.96-7.74 (m, 1.5H), 7.50 (dd, J=5.2, 7.4 Hz, 1H), 4.74-4.52 (m, 1H), 3.71-3.49 (m, 1H), 3.18-3.03 (m, 1H), 2.80-2.62 (m, 1H), 2.11 (m, 1H), 1.85-1.59 (m, 1.6H), 1.51 (d, J=11.6 Hz, 0.75H), 1.33-0.72 (m, 9H).

Example 13. Synthesis of Compounds 24-Ent1 and 24-Ent2

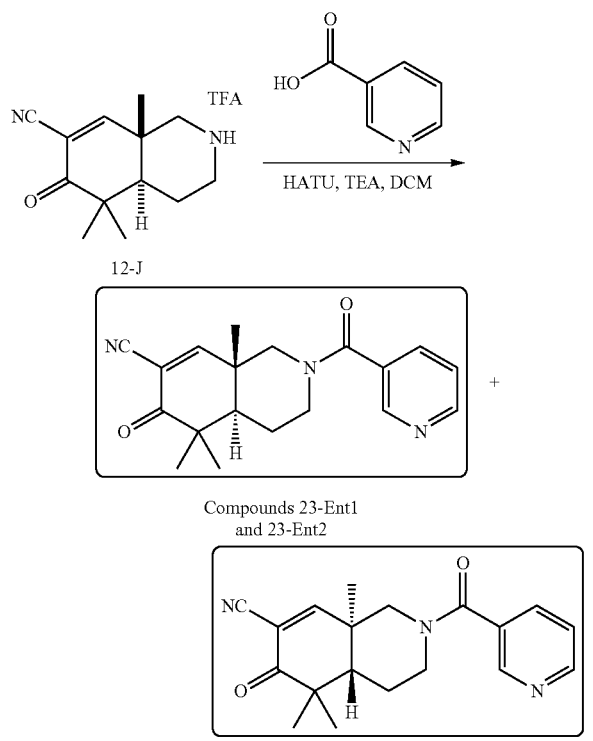

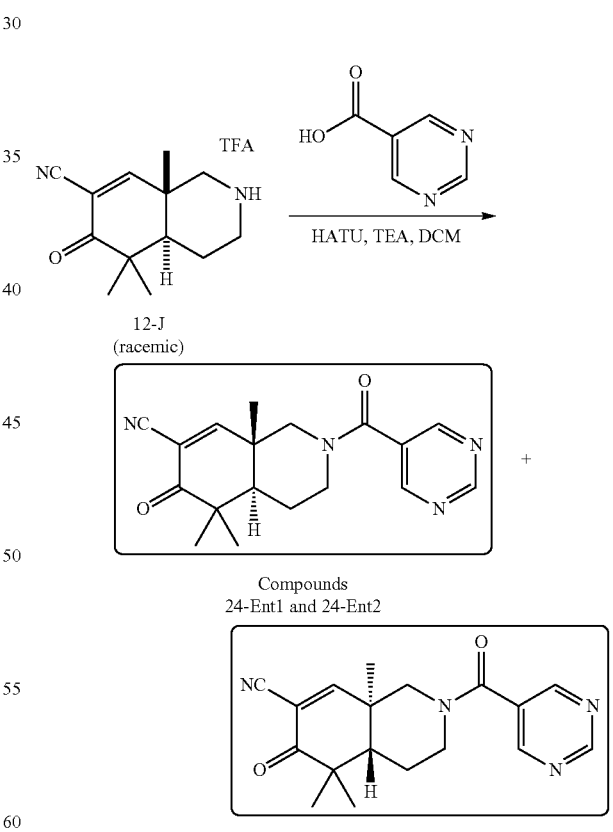

A mixture of nicotinic acid (187 mg, 1.52 mmol, 1.2 eq.); HATU (724 g, 1.91 mmol, 1.5 eq.) and TEA (386 mg, 3.81 mmol, 3.0 eq.) in DCM (5 mL) was stirred at 30° C. for 1 h.

Then compound 12-J (400 mg racemate, 1.27 mmol, 1.0 eq) was added. The mixture was stirred at 30° C. for 16 h. LCMS showed the reaction was complete. The mixture was purified by prep-TLC (EtOAc) to give the racemic product (230 mg, 60% yield) as a yellow solid. The obtained product A mixture of pyrimidine-5-carboxylic acid (189 mg, 1.52 mmol, 1.2 eq.); HATU (724 g, 1.91 mmol, 1.5 eq.) and TEA (386 mg, 3.81 mmol, 3.0 eq.) in DCM (5 mL) was stirred at 30° C. for 1 h. Then compound 12-J (400 mg, 1.27 mmol, 1.0 eq) was added. The mixture was stirred at 30° C. for 16 h. LCMS showed the reaction was complete. The mixture was purified by prep-TLC (EtOAc) to give the crude product (200 mg, crude). It was re-purified by prep-HPLC (Mobile phase A: water with 0.225% formic acid, Mobile phase B: acetonitrile; Column: Phenomenex Synergi C18 100*21.2 mm*4 um, Detection wavelength: 220 nm) to give the racemic product (100 mg, 24.3% yield) as a white solid. The obtained product was separated by SFC (Mobile phase: Superaritical $CO_2$/EtOH with 0.1% NH3.H2O; Column: Chiralpak OD (250 mm*30 mm, 5 um); Detection wavelength: 220 nm) to give single enantiomer 24-Ent1 (Rt=5.350 min, 34.7 mg, 34.7% yield) as a white solid and single enantiomer 24-Ent2 (Rt=7.285 min, 25.9 mg, 25.9% yield) as a light yellow solid.

Data for 24-Ent1:
LCMS: (M+H: 325.2)
HPLC: (94.84% purity)
SFC: (ee %: 98.71%)
$^1$HNMR: (400 MHz, DMSO_$d_6$) δ: 9.29 (s, 1H), 8.99-8.80 (m, 2H), 8.17 (s., 0.53H), 7.88 (s., 0.36H), 4.74-4.46 (m, 1H), 3.71-3.68 (m, 1H), 3.38-3.12 (m, 1H), 2.80-2.71 (m, 1H), 2.19-2.04 (m, 1H), 1.84-1.49 (m, 2H), 1.29-0.84 (m, 9H).

Data for 24-Ent2:
LCMS: (M+H: 325.2)
HPLC: (100% purity)
SFC: (ee %: 100%)
$^1$HNMR: (400 MHz, DMSO_$d_6$) δ: 9.25 (s., 1H), 8.94-8.77 (m, 2H), 8.13 (s., 0.62H), 7.84 (s., 0.35H), 4.69-4.50 (m, 1H), 3.67-3.52 (m, 1H), 3.17-3.01 (m, 1H), 2.80-2.66 (m, 1H), 2.19-2.04 (m, 1H), 1.84-1.49 (m, 2H), 1.29-0.84 (m, 9H).

Example 14. Synthesis of Compounds 25-Ent1 and 25-Ent2

1-methyl-1H-pyrazole-4-carboxylic Acid

A mixture of 1-methyl-1H-pyrazole-4-carboxylic acid (192 mg, 1.52 mmol, 1.2 eq.); HATU (724 g, 1.91 mmol, 1.5 eq.) and TEA (385 mg, 3.81 mmol, 3.0 eq.) in DCM (5 mL) was stirred at 30° C. for 1 h. Then compound 12-J (400 mg racemate, 1.27 mmol, 1.0 eq) was added. The mixture was stirred at 30° C. for 16 h. LCMS showed the reaction was complete. The mixture was purified by prep-HPLC (Mobile phase A: water with 0.225% formic acid, Mobile phase B: acetonitrile; Column: Phenomenex Synergi C18 100*21.2 mm*4 um, Detection wavelength: 220 nm) to give the racemic product (200 mg, 48.3% yield) as a yellow solid. The obtained product was separated by SFC (Mobile phase: Supercritical $CO_2$/EtOH with 0.1% NH3.H2O; Column: Chiralpak OD (250 mm*30 mm, 5 um); Detection wavelength: 220 nm) to give single enantiomer 25-Ent1 (Rt=3.976 min, 59.0 mg, 29.5% yield) as a white solid and single enantiomer 25-Ent2 (Rt=5.133 min, 50 mg, 25.0% yield) as a white solid. The absolute stereochemistry for both enantiomers was not determined.

Data for 25-Ent1:
LCMS: (M+H: 327.2)
HPLC: (95.04% purity)
SFC: (ee %: 99.23%)
$^1$HNMR: (400 MHz, DMSO-$d_6$) δ: 8.15-8.02 (m, 2H), 7.68 (s, 1H), 4.50-4.19 (m, 2H), 3.86 (s, 3H), 2.97 (br. s., 2H), 2.09 (d, J=14.6 Hz, 1H), 1.70 (br. s., 1H), 1.58 (d, J=12.8 Hz, 1H), 1.18-1.05 (m, 6H), 1.00 (s, 3H).

Data for 25-Ent2:
LCMS: (M+H: 327.2)
HPLC: (95.45% purity)
SFC: (ee %: 100%)
$^1$HNMR: (400 MHz, DMSO_$d_6$) δ: 8.15-8.00 (m, 2H), 7.68 (s, 1H), 4.48-4.22 (m, 2H), 3.86 (s, 3H), 2.96 (br. s., 2H), 2.09 (d, J=14.8 Hz, 1H), 1.77-1.66 (m, 1H), 1.58 (d, J=12.4 Hz, 1H), 1.18-1.05 (m, 6H), 1.00 (s, 3H).

Example 15. Synthesis of Compounds 26-Ent and 26-Ent2

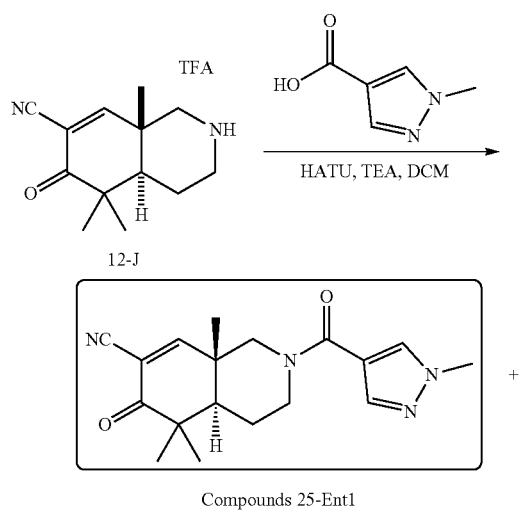

Compounds 25-Ent1
and 25-Ent2

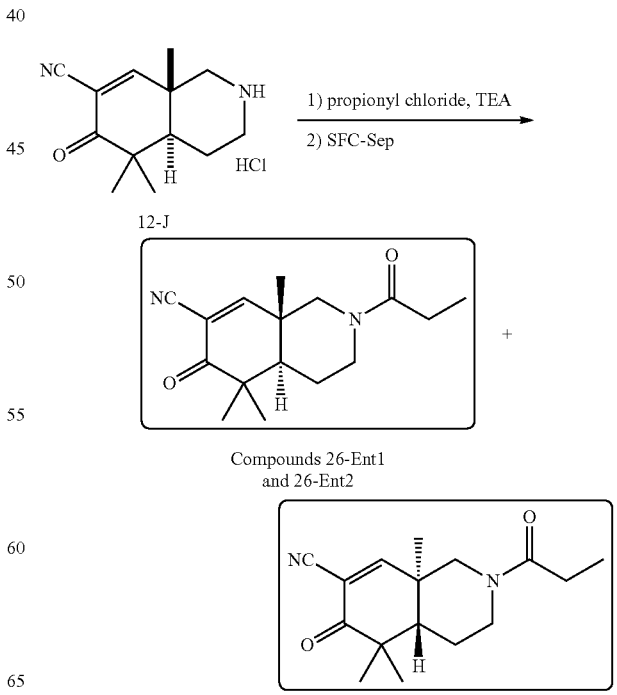

Compounds 26-Ent1
and 26-Ent2

To a solution of compound 12-J (racemic) (160 mg, 0.63 mmol, 1.0 eq.) and TEA (255 mg, 2.52 mmol, 4.0 eq) in DCM (2 mL) was added propionyl chloride (88 mg, 0.95 mmol, 1.5 eq.) dropwise. The mixture was stirred at 10° C. for 30 min. LCMS showed the reaction was complete. The mixture was purified by prep-TLC (EtOAc) to give the racemate (80 mg, 47.1% yield) as brown gum. The compound was separated by SFC (Mobile phase: Supercritical $CO_2$/EtOH; Column: Chiralpak AD (250 mm*30 mm, 5 um); Detection wavelength: 220 nm) to give 26-Ent1 (Rt=3.548 min, 35.7 mg, 44.6% yield) as a white solid and 26-Ent2 (Rt=4.420 min, 33.1 mg, 41.4% yield) as a white solid. The absolute stereochemistry was not determined.

Data for 26-Ent1:
HPLC: (Purity: 100.0%)
LCMS: (M+H: 275.1)
SFC: (ee: 99.28%)
$^1$H NMR: (400 MHz, $CDCl_3$) δ=7.51-7.41 (m, 1H), 4.94 (m, 0.4H), 4.65 (m, 0.8H), 4.09 (m, 0.7H), 3.68 (m, 0.4H), 3.08-2.95 (m, 1H), 2.52-2.33 (m, 3H), 1.97-1.88 (m, 1H), 1.79-1.65 (m, 2H), 1.32-1.15 (m, 9H), 1.11 (s, 3H).

Data for 26-Ent2:
HPLC: (Purity: 100.00%)
LCMS: (M+H: 275.2)
SFC: (ee: 100%)
$^1$H NMR: (400 MHz, $CDCl_3$) δ=7.51-7.41 (m, 1H), 4.94 (m, 0.4H), 4.65 (m, 0.8H), 4.09 (m, 0.7H), 3.68 (m, 0.4H), 3.08-2.95 (m, 1H), 2.52-2.33 (m, 3H), 1.97-1.88 (m, 1H), 1.79-1.65 (m, 2H), 1.32-1.15 (m, 9H), 1.11 (s, 3H).

Example 16. Synthesis of Compound 27-Ent1 and 27-Ent2

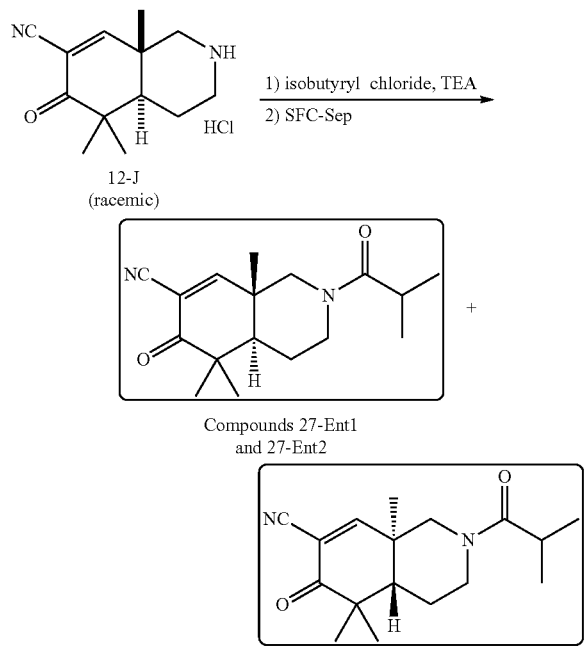

To a solution of compound 12-J (160 mg, 0.63 mmol, 1.0 eq.) and TEA (255 mg, 2.52 mmol, 4.0 eq) in DCM (2 mL) was added isobutyryl chloride (101 mg, 0.95 mmol, 1.5 eq.) dropwise. The mixture was stirred at 10° C. for 30 min. LCMS showed the reaction was complete. The mixture was purified by prep-TLC (EtOAc) to give the racemate (90 mg, 48.1% yield) as brown gum. It was separated by SFC (Mobile phase: Superaritical $CO_2$/EtOH; Column: Chiralpak AD (250 mm*30 mm, 5 um); Detection wavelength: 220 nm) to give 27-Ent1 (Rt=3.587 min, 35.2 mg, 39.1% yield) as a white solid and 27-Ent2 (Rt=4.469 min, 38.5 mg, 42.8% yield) as a white solid. The absolute stereochemistry was not determined.

Data for 27-Ent1:
HPLC: (Purity: 99.02%)
LCMS: (M+H: 289.2)
SFC: (ee: 99.10%)
$^1$H NMR: (400 MHz, $CDCl_3$) δ=7.52-7.41 (m, 1H), 4.93 (br., 0.4H), 4.67 (m, 0.8H), 4.17 (m, 0.8H), 3.77 (br. s, 0.4H), 3.10-2.97 (m, 1H), 2.92-2.74 (m, 1H), 2.52-2.37 (m, 1H), 1.99-1.89 (m, 1H), 1.78-1.65 (m, 2H), 1.32-1.05 (m, 15H).

Data for 27-Ent2:
HPLC: (Purity: 98.75%)
LCMS: (M+H: 289.2)
SFC: (ee: 99.44%)
$^1$H NMR: (400 MHz, $CDCl_3$) δ=7.52-7.41 (m, 1H), 4.93 (br., 0.4H), 4.67 (m, 0.8H), 4.17 (m, 0.8H), 3.77 (br. s, 0.4H), 3.10-2.97 (m, 1H), 2.92-2.74 (m, 1H), 2.52-2.37 (m, 1H), 1.99-1.89 (m, 1H), 1.78-1.65 (m, 2H), 1.32-1.05 (m, 15H).

Example 17. Synthesis of Compounds 28-Ent and 28-Ent2

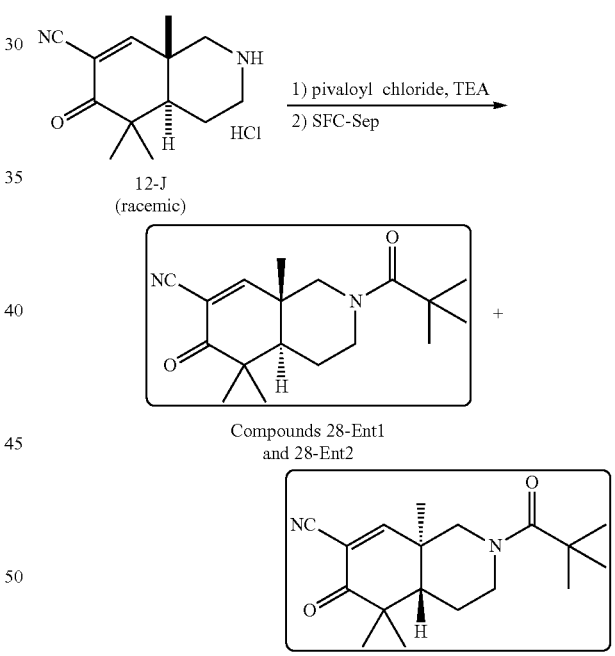

To a solution of compound 12-J (85 mg, 0.41 mmol, 1.0 eq.) and TEA (205 mg, 1.64 mmol, 4.0 eq) in DCM (2 mL) was added pivaloyl chloride (74 mg, 0.61 mmol, 1.5 eq.) dropwise. The mixture was stirred at 10° C. for 30 min. LCMS showed the reaction was complete. The mixture was purified by prep-TLC (PE/EtOAc=1/1) to give the racemate (70 mg, 69.3% yield) as a white solid. It was separated by SFC (Mobile phase: Supercritical $CO_2$/EtOH; Column: Chiralpak AD (250 mm*30 mm, 5 um); Detection wavelength: 220 nm) to give 28-Ent1 (Rt=3.148 min, 14.7 mg, 21.0% yield) as a white solid and 28-Ent2 (Rt=3.898 min, 13.3 mg, 19.0% yield) as a white solid. The stereochemistry was not defined.

Data for 28-Ent1:
 HPLC: (Purity: 100.0%)
 MS: (M+H: 303.2088)
 SFC: (ee: 98.54%)
 $^1$H NMR: (400 MHz, CDCl$_3$) δ=7.49 (s, 1H), 4.65-4.62 (m, 1H), 4.53-4.48 (m, 1H), 3.04-2.95 (m, 1H), 2.46 (m, 1H), 1.94 (m, 1H), 1.78-1.64 (m, 2H), 1.33 (s, 9H), 1.24 (s, 3H), 1.21 (s, 3H), 1.12 (s, 3H).
Data for 28-Ent2:
 HPLC: (Purity: 97.48%)
 MS: (M+H: 303.2087)
 SFC: (ee: 99.78%)
 $^1$H NMR: (400 MHz, CDCl$_3$) δ=7.49 (s, 1H), 4.65-4.62 (m, 1H), 4.53-4.48 (m, 1H), 3.04-2.95 (m, 1H), 2.46 (m, 1H), 1.94 (m, 1H), 1.78-1.64 (m, 2H), 1.33 (s, 9H), 1.24 (s, 3H), 1.21 (s, 3H), 1.12 (s, 3H).

Example 18. Synthesis of Compounds 29-Ent1 and 29-Ent2

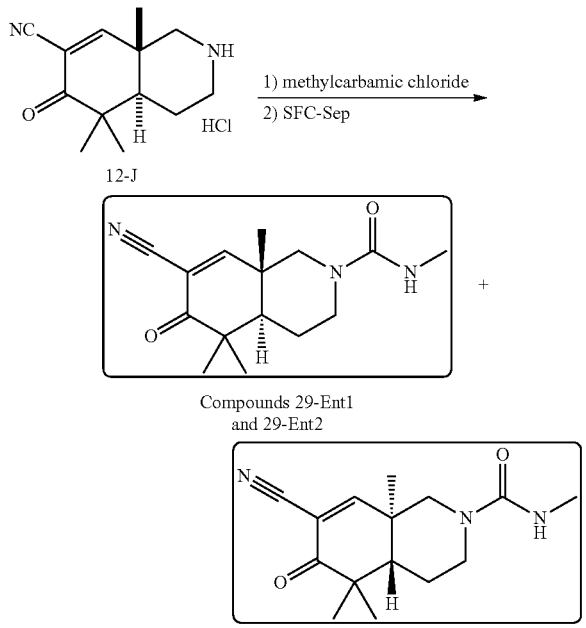

To a of solution of 12-J (100 mg, 0.39 mmol, 1.0 eq.) in DCM (2 mL) was added TEA (120 mg, 1.17 mmol, 3.0 eq.) and methylcarbarnic (59 mg, 0.59 mmol, 1.5 eq.). The mixture was stirred at 20° C. for 30 min. LCMS showed the reaction was complete. The mixture was purified by prep-TLC (EtOAc) to give the racemate (50 mg, 46.3% yield) as yellow oil. It was separated by SFC (Mobile phase: Superaritical CO$_2$/MeOH; Column: Chiralpak AD (250 mm*30 mm, 5 um); Detection wavelength: 220 nm) to give 29-Ent1 (Rt=3.773 min, 20.4 mg, 40.8% yield) as a white solid and 29-Ent2 (Rt=5.624 min, 22.1 mg, 44.2% yield) as a white solid. The absolute stereochemistry was not determined.
Data for 29-Ent1:
 HPLC: (Purity: 100.0%)
 LCMS: (M+H: 276.2)
 SFC: (ee: 100%)
 $^1$H NMR: (400 MHz, CDCl$_3$) δ=7.45 (s, 1H), 4.47 (br. s., 1H), 4.10-4.06 (m, 1H), 4.02-3.94 (m, 1H), 2.90-2.81 (m, 4H), 2.63-2.59 (m, 1H), 1.88-1.82 (m, 1H), 1.80-1.71 (m, 1H), 1.65-1.61 (m, 1H), 1.27 (s, 3H), 1.24 (s, 3H), 1.11 (s, 3H).

Data for 29-Ent2:
 HPLC: (Purity: 100.0%)
 LCMS: (M+H: 276.1)
 SFC: (ee: 100%)
 $^1$H NMR: (400 MHz, CDCl$_3$) δ=7.45 (s, 1H), 4.47 (br. s., 1H), 4.10-4.06 (m, 1H), 4.02-3.94 (m, 1H), 2.90-2.81 (m, 4H), 2.63-2.59 (m, 1H), 1.88-1.82 (m, 1H), 1.80-1.71 (m, 1H), 1.65-1.61 (m, 1H), 1.27 (s, 3H), 1.24 (s, 3H), 1.11 (s, 3H).

Example 19. Synthesis of Compounds 30-Ent1 and 30-Ent2

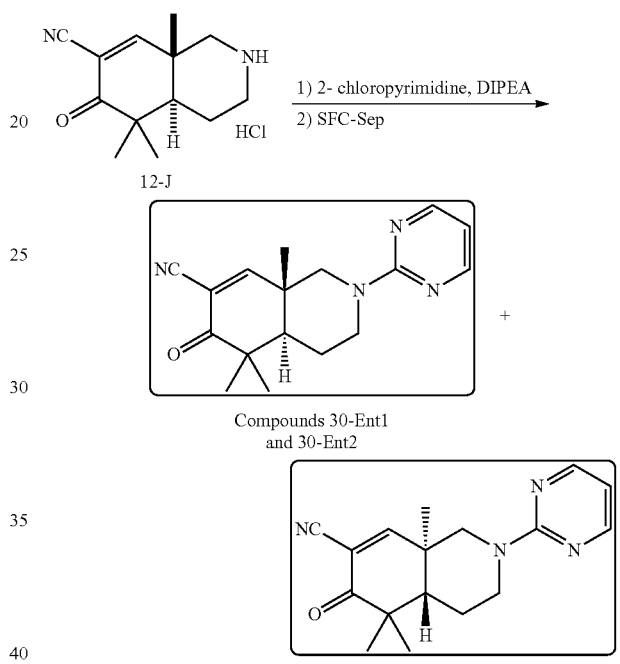

A mixture of compound 12-J (145 mg, 0.59 mmol, 1.0 eq.), 2-chloropyrimidine (102 mg, 0.89 mmol, 1.5 eq) and DIPEA (304 mg, 2.36 mmol, 4.0 eq.) in THF (5 mL) was stirred at 70° C. for 16 h. LCMS showed the reaction was complete. The mixture was purified by prep-TLC (PE/EtOAc=2/1) to give the racemate (50 mg, 29.6% yield) as a white solid. It was separated by SFC (Mobile phase: Supercritical CO$_2$/EtOH; Column: Chiralpak AD (250 mm*30 mm, 5 um); Detection wavelength: 220 nm) to give 30-Ent1 (Rt=3.791 min, 6.0 mg, 12.0% yield) as a white solid and 30-Ent2 (Rt=5.451 min, 7.0 mg, 14.0% yield) as a white solid. The absolute stereochemistry was not determined.
Data for 30-Ent1:
 HPLC: (Purity: 100.0%)
 LCMS: (M+H: 297.0)
 SFC: (ee: 99.62%)
 $^1$H NMR: (400 MHz, CDCl$_3$) δ=8.32 (d, J=4.8 Hz, 2H), 7.53 (s, 1H), 6.53 (t, J=4.8 Hz, 1H), 5.09-5.05 (dd, J=4.4 Hz, J=2 Hz, 1H), 4.85 (d, J=12.4 Hz, 1H), 2.87-2.71 (m, 2H), 1.98 (m, 1H), 1.84-1.68 (m, 2H), 1.27 (s, 3H), 1.24 (s, 3H), 1.12 (s, 3H).
Data for 30-Ent2:
 HPLC: (Purity: 97.70%)
 LCMS: (M+H: 296.9)
 SFC: (ee: 99.78%)

¹H NMR: (400 MHz, CDCl₃) δ=8.32 (d, J=4.8 Hz, 2H), 7.53 (s, 1H), 6.53 (t, J=4.8 Hz, 1H), 5.09-5.05 (dd, J=4.4 Hz, J=2 Hz, 1H), 4.85 (d, J=12.4 Hz, 1H), 2.87-2.71 (m, 2H), 1.98 (m, 1H), 1.84-1.68 (m, 2H), 1.27 (s, 3H), 1.24 (s, 3H), 1.12 (s, 3H).

Example 20. Synthesis of Compounds 31-Ent and 31-Ent2

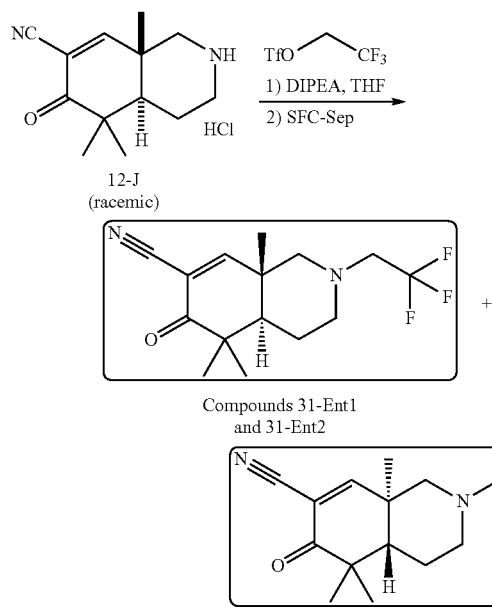

A mixture of compound 12-J (200 mg, 0.68 mmol, 1.0 eq.), 2,2,2-trifluoroethyl trifluoromethanesulfonate (310 mg, 1.36 mmol, 2.0 eq), and DIPEA (260 mg, 2.04 mmol, 3.0 eq.) in THF (3 mL) was stirred at 75° C. for 2 h. LCMS showed the reaction was complete. The mixture was purified by prep-TLC (PE/EtOAc=4/1) to give the racemate (80 mg, 33.9% yield) as a yellow oil. The racemic product was separated by SFC (Mobile phase: Supercritical CO₂/MeOH; Column: Chiralpak AD (250 mm*30 mm, 5 um); Detection wavelength: 220 nm) to give 31-Ent1 (Rt=1.843 min, 24.9 mg, 31.1% yield) as a white solid and 31-Ent2 (Rt=2.322 min, 23.3 mg, 29.1% yield) as a white solid. The absolute stereochemistry was not determined.

Data for 31-Ent1:
HPLC: (Purity: 100.0%)
LCMS: (M+H: 301.1)
SFC: (ee: 99.28%)
¹H NMR: (400 MHz, CDCl₃) δ=7.36 (s, 1H), 3.14 (m., 1H), 3.02 (m., 2H), 2.72 (m, 1H), 2.50-2.38 (m, 2H), 1.86-1.76 (m, 1H), 1.71-1.64 (m, 1H), 1.60 (m, 1H), 1.37 (s, 3H), 1.21 (s, 3H), 1.11 (s, 3H).

Data for 31-Ent2:
HPLC: (Purity: 100.0%)
LCMS: (M+H: 300.7)
SFC: (ee: 99.75%)
¹H NMR: (400 MHz, CDCl₃) δ=7.36 (s, 1H), 3.14 (m., 1H), 3.02 (m., 2H), 2.72 (m, 1H), 2.50-2.38 (m, 2H), 1.86-1.76 (m, 1H), 1.71-1.64 (m, 1H), 1.60 (m, 1H), 1.37 (s, 3H), 1.21 (s, 3H), 1.11 (s, 3H).

Example 21. Synthesis of Compounds 32-Ent and 32-Ent2

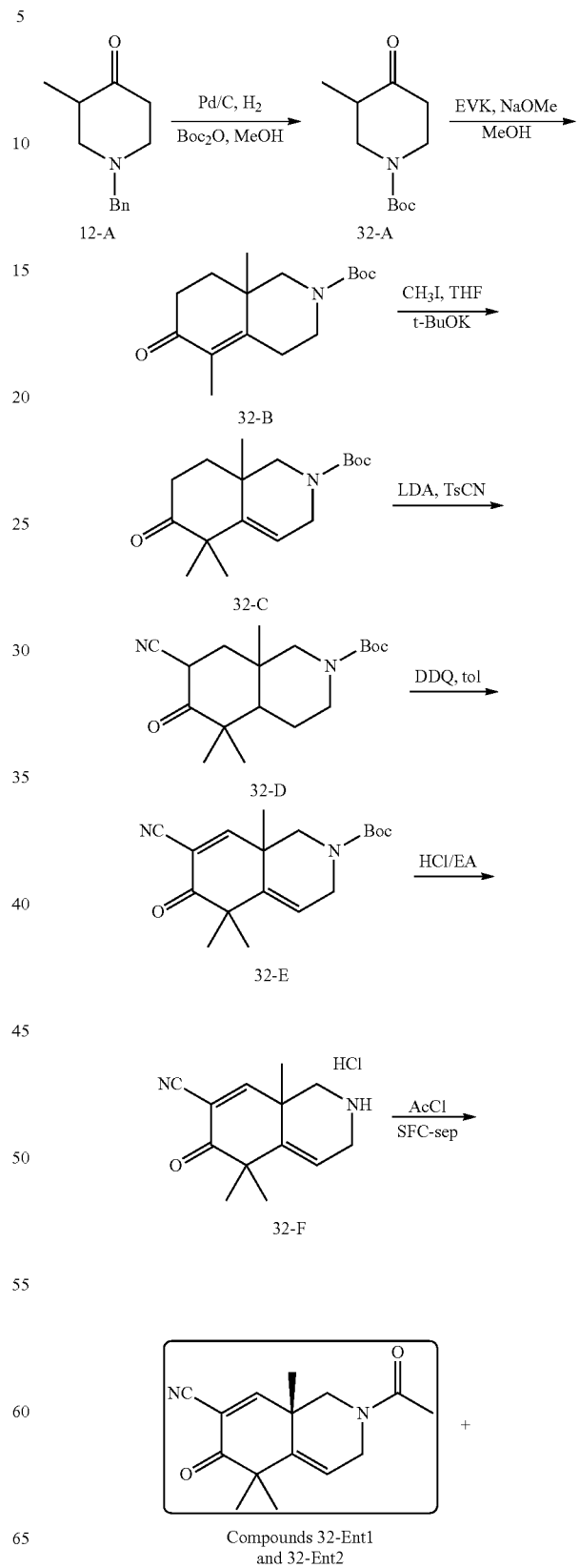

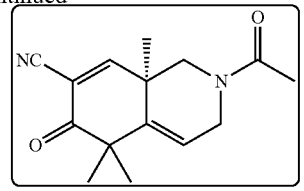

Preparation of Compound 32-A

A mixture of compound 12-A (80 g, 0.39 mol, 1 eq.) and Pd(OH)$_2$/C (4 g) in ethanol (800 mL) was stirred under 45 psi of H$_2$ at 40° C. for 20 hours. TLC (PE/EtOAc=5:1) indicated completion. The suspension was filtered through a pad of celite and washed with EA (400 mL×2), the filtrate was concentrated under reduced pressure to give a crude product of compound 32-A (80 g, crude) as colorless gum.

$^1$H NMR: (400 MHz, CHLOROFORM-d) δ: 4.20-4.13 (m, 1H), 3.33-3.14 (m, 1H), 2.56-2.35 (m, 3H), 2.02 (s, 2H), 1.47 (s, 9H), 1.02 (d, J=6.6 Hz, 3H).

Preparation of Compound 32-B

Na (8.6 g, 0.375 mol, 1.0 eq) was added to MeOH (800 mL) in many portions at 25° C. and stirred until Na was disappeared and then was added compound 32-A (80 g, 37.5 mmol), EVK (31.55 g, 0.375 mol, 1.0 eq) was added to the above solution at 0° C. dropwise over 5 mins under N$_2$ atmosphere. The reaction mixture was stirred at 25° C. for 18 hours. TLC (PE/EA=5:1) showed the starting materials were consumed completely. The mixture was quenched with saturated NH$_4$Cl (800 mL) and extracted with EA (800 mL×2). The combined organic phase was dried over sodium sulfate, and filtered. The filtrate was concentrated in vacuo to give the residue, which was purified by prep-HPLC (base, (Phenomenex Gemini C18 250*21.2 mm*5 um, water (10 mM NH4HCO$_3$)-ACN as mobile phase, from 53-83%, Flow Rate (ml/min): 25) to give compound 32-B (30 g, yield; 42%) as a white solid.

$^1$H NMR: (400 MHz, CHLOROFORM-d) δ: 4.03-3.73 (m, 1H), 3.01-2.59 (m, 3H), 2.55-2.36 (m, 3H), 1.75 (s, 3H), 1.48 (s, 9H), 1.22 (s, 3H).

Preparation of Compound 32-C

Potassium tert-butoxide (108 mL, 108 mmol, 1.0 eq) was added to the solution of compound 32-B (30 g, 108 mmol, 1.0 eq.) in THF (anhydrous, 400 mL) dropwise at 0-5° C. The resulting brown solution was stirred at 15° C. for 2 hrs. Methyl iodide (17.1 g, 108 mmol, 1.0 eq.) was added to the solution at 0° C. via syringe. The yellow suspension was stirred at 10~15° C. for 18 hrs. TLC (PE/EtOAc=5:1) indicated completion. Sat. NH$_4$Cl (300 mL) was added, the solvent THF was removed under reduced pressure. The residue was extracted with EtOAc (300 mL×2). The combined organic layers were washed with water (200 mL×2), brine (100 mL×2), dried over Na$_2$SO$_4$, filtered and concentrated. The residue was purified by column chromatography on silica gel (PE/EtOAc=30:1) to give compound 32-C (21 g, 66.7%) as a white solid.

$^1$H NMR: (400 MHz, CHLOROFORM-d) δ: 5.64-5.42 (m, 1H). 4.40-4.14 (m, 1H), 3.96-3.48 (m, 2H), 2.44-2.79 (m, 3H), 1.76 (br. s., 2H), 1.47 (s, 9H), 1.25 (s, 6H), 1.08 (s, 3H).

Preparation of Compound 32-D

To a yellow suspension of compound 32-C (1.9 g, 6.48 mmol, 1.0 eq.) in anhydrous THF (50 mL) was added LDA (2 M in THF/heptane, 6.48 mL, 12.9 mmol, 2.0 eq.) dropwise via syringe at −78° C. The yellow suspension was stirred at −78° C. for 1 h before TsCN (2.35 g, 12.9 mmol, 2.0 eq.) in anhydrous THF (10 mL) was added via syringe. The resulting yellow mixture was stirred at 12° C. for another 18 hrs. TLC (EtOAc/PE=3:1) indicated completion. The reaction mixture was quenched with Sat. NH$_4$Cl (50 mL). After separation, the solvent was removed under reduced pressure then water layer was extracted with EA (30 mL×2). The combined organic layers were dried over anhydrous sodium sulfate. Filtered and concentrated to give compound 32-D (2.4 g, crude) as a white solid, which was used for next step without further purification.

Preparation of Compound 32-E

To a yellow solution of compound 32-D (2.2 g crude, 6.9 mmol, 1.0 eq.) in toluene (20 mL) was added DDQ (1.57 g, 6.9 mmol, 1.2 eq.) in one portion. The resulting dark mixture was heated to 120° C. for 2 hours. TLC (EtOAc/PE=3:1) indicated completion. The crude product was purified by column chromatography (EA/PE=10:1-5:1) to give compound 32-E (700 mg 36.2%) as a yellow solid.

1H NMR: (400 MHz, CHLOROFORM-d) δ: 7.23 (s, 1H), 5.74-5.55 (m, 1H), 4.50-4.21 (m, 1H), 4.06-3.57 (m, 2H), 2.74-2.53 (m, 1H), 1.46 (s, 9H), 1.41 (s, 3H), 1.32 (d, J=6.3 Hz, 6H).

Preparation of Compound 32-F

To a solution of compound 32-E (200 mg, 0.63 mmol, 1.0 eq) in EA (5 mL) was added EA/HCl (5 mL) at 12° C. The reaction mixture was stirred at 12° C. for 2 hours. TLC (PE/EA=2:1) showed the starting materials were consumed completely. The solvent was removed to give the crude compound 32-F (220 mg, crude), which was used for next step without further purification.

Preparation of Compounds 32-Ent and 32-Ent2

To a solution of compound 32-F (220 mg, 1.0 mmol, 1.0 eq) and TEA (404 mg, 4.0 mmol, 4.0 eq), in DCM (5 mL) was added acetyl chloride (117 mg, 1.5 mmol, 1.5 eq) at 25° C. for 1 h. The reaction mixture was stirred at 12° C. for 10 hours. TLC (PE/EA=2:1) showed the starting material was consumed completely. The mixture was quenched with saturated NaHCO$_3$ (30 mL) and extracted with DCM (20 mL×2). The combined organic phase was dried over sodium sulfate, and filtered. The filtrate was concentrated in vacuo to give the residue, which was purified by prep-HPLC (Phenomenex Synergi C18 150*30 mm*4 um, water (0.05% HCl)-ACN as mobile phase, from 41-61%, Flow Rate (ml/min): 25)) to give racemic product (100 mg, yield; 41%) as a white solid. Further separation by SFC (column: AD (250 mm*30 mm, 5 um), condition: Base-EtOH) to give enantiomer 32-Ent1 (19254-60-1, Rt=6.937 min, 20.1 mg) and 32-Ent2 (19254-60-2, Rt=7.718 min, 25.2 mg) both as white solid.

Data for 32-Ent1

$^1$H NMR: (400 MHz, METHANOL-d$_4$) δ: 7.67 (d, J=7.8 Hz, 1H), 5.78 (dt, J=18.6, 3.0 Hz, 1H), 4.55-4.49 (m, 1H), 4.34-4.29 (m, 0.6H), 4.06-3.90 (m, 1H), 3.65-3.59 (m, 0.5H), 3.03 (d, J=12.9 Hz, 0.5H), 2.52 (d, J=12.5 Hz, 0.6H), 2.17 (d, J=7.4 Hz, 3H), 1.46-1.39 (m, 3H), 1.34 (d, J=1.6 Hz, 6H).

HPLC: (Purity: 100%).

SFC: (ee: 100%).

LCMS: (M+H: 258.9).

Data for 32-Ent2

$^1$H NMR (400 MHz, METHANOL-d$_4$) δ: 7.67 (d, J=7.8 Hz, 1H), 5.78 (dt, J=18.6, 3.0 Hz, 1H), 4.55-4.49 (m, 1H), 4.34-4.29 (m, 0.6H), 4.06-3.90 (m, 1H), 3.65-3.59 (m, 0.5H), 3.03 (d, J=12.9 Hz, 0.5H), 2.52 (d, J=12.5 Hz, 0.6H), 2.17 (d, J=7.4 Hz, 3H), 1.46-1.39 (m, 3H), 1.34 (d, J=1.6 Hz, 6H).

HPLC: (Purity: 100%).

SFC: (ee: 99.85%).

LCMS: (M+H: 259.3).

Example 22. Synthesis of Compounds 33-Ent and 33-Ent2

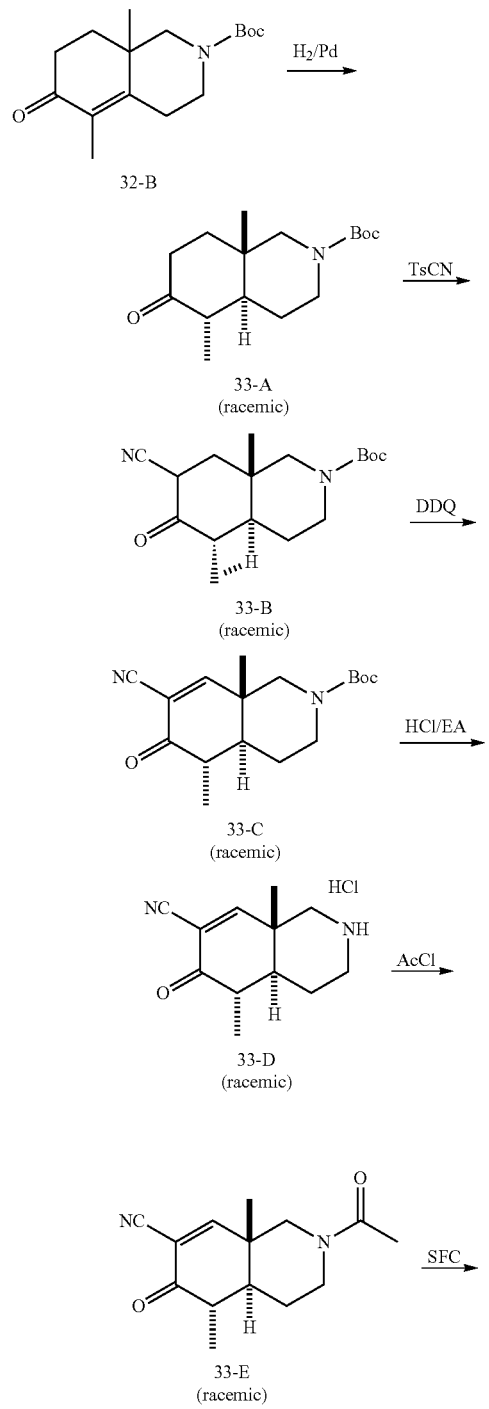

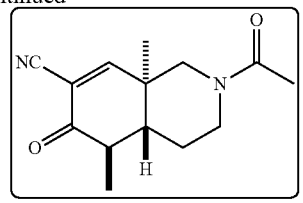

Compounds 33-Ent1 and 33-Ent2

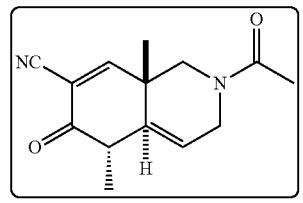

Preparation of Compound 33-A

To a solution of compound 32-B (1.9 g, 6.8 mmol, 1.0 eq.) in EtOH (50 mL) was added Pd/C (0.2 g, 10%). The mixture was degassed with $H_2$ for 3 times and then stirred at 10° C. for 16 h under $H_2$ atmosphere (15 psi). TLC (PE/EA=3/1) showed the reaction was complete. The mixture was filtered and the filtrate was concentrated to give compound 33-A (1.9 g, crude) as a colorless gum.

$^1$HNMR: (400 MHz, DMSO-$d_6$) δ=4.11 (br. s., 1H), 3.85-3.52 (m, 2H), 2.76-2.54 (m, 2H), 2.37-2.09 (m, 3H), 1.61-1.46 (m, 2H), 1.40 (m, 9H), 1.29-1.15 (m, 2H), 1.06-0.80 (m, 6H).

Preparation of Compound 33-B

To a solution of compound 33-A (1.9 g, 6.75 mmol, 1.0 eq.) in THF (50 mL) was added LDA (7.3 g, 13.50 mmol, 2.0 eq, 2M) dropwise at −78° C. The mixture was stirred at −78° C. for 1 h. Then a solution of TsCN (2.45 g, 13.50 mmol, 2.0 eq) in THF (10 mL) was added dropwise −78° C. The mixture was stirred at 10° C. for 16 h. TLC (PE/EA=3/1) showed the reaction was complete. The reaction mixture was quenched with $NH_4Cl$ aq. (50 mL) and extracted with EtOAc (50 mL×3). The combined organic layer was dried over $Na_2SO_4$, filtered and concentrated to give compound 33-B (2.0 g, crude) as yellow oil.

Preparation of Compound 33-C

A mixture of compound 33-B (2.0 g, 6.3 mmol, 1.0 eq.) and DDQ (2.8 g, 12.5 mmol, 2.0 eq.) in toluene (30 mL) was stirred at 120° C. for 1 h. TLC (PE/EA=3/1) showed the reaction was complete. The mixture was filtered and the filtrate was concentrated to give the crude product. It was purified by chromatography column (PE/EA=10/1) to give compound 33-C (440 mg, 22.0% yield) as a brown solid.

$^1$HNMR: (400 MHz, ACETONE-$d_6$) δ=7.79 (s, 1H), 4.34-4.10 (m, 2H), 2.83 (s, 1H), 2.68 (br. s., 1H), 2.57-2.42 (m, 1H), 1.91 (dt, J=3.6, 12.8 Hz, 1H), 1.67 (d, J=12.6 Hz, 1H), 1.51 (d, J=13.8 Hz, 1H), 1.44 (s, 9H), 1.19 (s., 3H), 1.11 (d, J=6.8 Hz, 3H). NOE experiments were used to confirm the relative stereochemistry.

Preparation of Compound 33-D

To a solution of compound 33-C (90 mg, 0.3 mmol, 1.0 eq.) in EtOAc (1 mL) was added HCl/EtOAc (5 mL). The mixture was stirred at 20° C. for 1 h. TLC (PE/EtOAc=3/1) showed the reaction was complete. The mixture was concentrated to give compound 33-D (71 mg, crude) as a yellow solid.

Preparation of Compounds 33-Ent and 33-Ent2

To a solution of compound 33-D (71 mg, 0.3 mmol, 1.0 eq.) and TEA (121 mg, 1.2 mmol, 4.0 eq.) in DCM (2 mL) was added acetyl chloride (28 mg, 0.35 mmol, 1.2 eq.) dropwise. The mixture was stirred at 10° C. for 30 min. TLC (EtOAc) showed the reaction was complete. The mixture was purified by prep-TLC (EtOAc) to give racemic product (50 mg, 69.4% yield) as a white solid. The racemic product was separated by SFC (Mobile phase: Supercritical $CO_2$/ EtOH; Column: Chiralpak AD (250 mm*30 mm, 5 um); Detection wavelength: 220 nm) to give 33-Ent1 (Rt=3.911 min, 10.0 mg, 20.0% yield) as a white solid and single enantiomer 33-Ent2 (Rt=4.554 min, 9.2 mg, 18.4% yield) as a light yellow solid. The absolute configuration of each enantiomer was not established.

Data for 33-Ent1
 LCMS: (M+H: 247.1)
 HPLC: (100% purity)
 SFC: (ee %: 98.22%)
 $^1$HNMR: (400 MHz, Acetone) δ: 7.81 (d, J=7.6 Hz, 1H), 4.73-4.61 (m, 1H), 4.09-3.97 (m, 1H), 3.14-3.05 (m, 1H), 2.85 (m, 3H), 2.58-2.45 (m, 2H), 1.99-1.87 (m, 1H), 1.73-1.63 (m, 1H), 1.52-1.39 (m, 1H), 1.32-1.21 (m, 2H), 1.19-1.07 (m, 4H).

Data for 33-Ent2:
 LCMS: (M+H: 247.1)
 HPLC: (100% purity)
 SFC: (ee: 98.38%)
 $^1$HNMR: (400 MHz, Acetone) δ 7.81 (d, J=7.6 Hz, 1H), 4.73-4.61 (m, 1H), 4.09-3.97 (m, 1H), 3.14-3.05 (m, 1H), 2.85 (m, 3H), 2.58-2.45 (m, 2H), 1.99-1.87 (m, 1H), 1.73-1.63 (m, 1H), 1.52-1.39 (m, 1H), 1.32-1.21 (m, 2H), 1.19-1.07 (m, 4H).

Example 23. Synthesis of Compounds 34-Ent1 and 34-Ent2

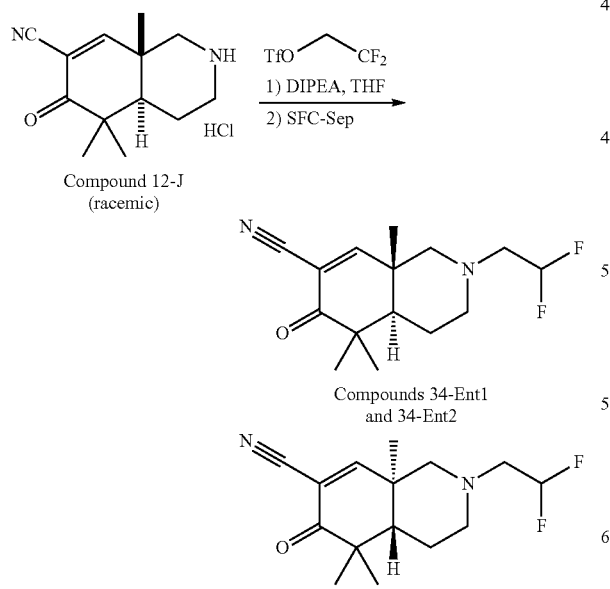

A mixture of compound 12-J (200 mg, 0.68 mmol, 1.0 eq.), 2,2-difluoro-2,λ$^3$-ethyl trifluoromethanesulfonate (300 mg, 1.36 mmol, 2.0 eq) and DIPEA (260 mg, 2.04 mmol, 3.0 eq.) in THF (2 mL) was stirred at 75° C. for 2 h. LCMS showed the reaction was complete. The mixture was purified by prep-TLC (PE/EtOAc=4/1) to give the racemate (120 mg, 54.05% yield) as yellow oil. It was separated by SFC (Mobile phase: Supercritical $CO_2$/MeOH; Column: Chiralpak AD (250 mm*30 mm, 5 um); Detection wavelength: 220 nm) to give 34-Ent1 as the first eluting enantiomer (Rt=2.426 min, 41.0 mg, 34.17% yield) as an off-white solid and 34-Ent2 as the second eluting enantiomer (Rt=2.729 min, 41.0 mg, 34.17% yield) as an off-white solid. The absolute stereochemistry was not determined.

Data for 34-Ent1:
 HPLC: (Purity: 95.98%)
 LCMS: (M+H: 282.6)
 SFC: (ee: 98.713%)
 $^1$H NMR: (400 MHz, CDCl$_3$)$_{δ=7.37}$ (s, 1H), 6.02-5.67 (m, 1H), 3.14-3.08 (m, 1H), 2.81-2.68 (m, 3H), 2.33-2.20 (m, 2H), 1.85-1.73 (m, 1H), 1.70-1.57 (m, 2H), 1.37 (s, 3H), 1.21 (s, 3H), 1.11 (s, 3H).

Data for 34-Ent2:
 HPLC: (Purity: 96.067%)
 LCMS: (M+H: 282.9)
 SFC: (ee: 99.382%)
 $^1$H NMR: (400 MHz, CDCl$_3$) δ=7.37 (s, 1H), 6.02-5.69 (m, 1H), 3.14-3.08 (m, 1H), 2.81-2.68 (m, 3H), 2.33-2.21 (m, 2H), 1.83-1.74 (m, 1H), 1.70-1.59 (m, 2H), 1.37 (s, 3H), 1.21 (s, 3H), 1.11 (s, 3H).

Example 24. Synthesis of Compounds 35-Ent1 and 35-Ent2

To a solution of Compound 12-J (180 mg, racemate, 0.70 mmol, 1.0 eq) and TBD-1 (104 mg, 1.4 mmol, 2.0 eq) in tol (3 mL) was added ethyl formate (218 mg, 2.79 mmol, 1.5 eq) at 25° C. The reaction mixture was stirred at 25° C. for 18 hours. TLC (PE/EA=1:20) showed the starting materials were consumed completely. The mixture was concentrated in vacuo to give the residue, which was purified by prep-TLC (PE/EA=1:20) to give product (100 mg, yield: 58%) as a white solid. Further separation by SFC (column: AD (250 mm*30 mm, 5 um), condition: Base-EtOH) afforded 35-Ent1 as the first eluting enantiomer (Rt=3.807, 4.061 min, 44.5 mg) and 35-Ent2 as the second eluting enantiomer (Rt=4.960 min, 46.3 mg) both as white solid. The absolute stereochemistry was not determined.

Data for 35-Ent1:
$^1$H NMR (400 MHz, CDCl$_3$): δ: 8.14-7.90 (m, 1H), 7.46-7.28 (m, 1H), 4.64-4.25 (m, 1H), 3.81-3.24 (m, 1H), 3.12-2.95 (m, 1H), 2.44-2.59 (m, 1H), 1.93 (dd, J=9.2, 6.2 Hz, 1H) 1.70-1.57 (m, 2H), 1.20-1.15 (m, 6H), 1.04 (d, J=2.2 Hz, 3H).
HPLC: (Purity: 96.32%).
SFC: (ee: 98.1%).
LCMS: (M+H: 247.1).

Data for 35-Ent2:
$^1$H NMR (400 MHz, CDCl$_3$): δ: 8.13-7.91 (m, 1H), 7.46-7.29 (m, 1H), 4.66-4.22 (m, 1H), 3.84-3.21 (m, 1H), 3.16-2.95 (m, 1H), 2.61-2.41 (m, 1H), 1.99-1.87 (m, 1H), 1.71-1.59 (m, 2H), 1.20-1.14 (m, 6H), 1.04 (d, J=2.2 Hz, 3H).
HPLC: (Purity: 99.69%).
SFC: (ee: 99.6%).
LCMS: (M+H: 247.1).

Example 25. Synthesis of Compounds 36-Ent1 and 36-Ent2

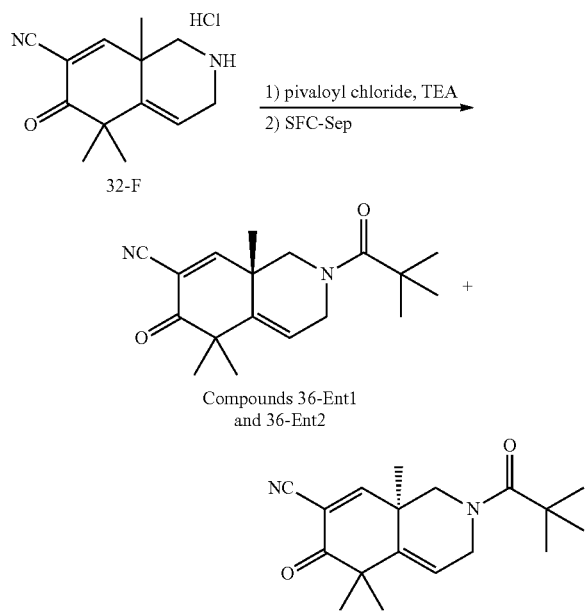

To a solution of compound 32-F (120 mg, 0.47 mmol, 1.0 eq.) and TEA (190 mg, 1.88 mmol, 4.0 eq) in DCM (5 mL) was added pivaloyl chloride (115 mg, 0.94 mmol, 2.0 eq.) dropwise. The mixture was stirred at 15° C. for 1 h. LCMS showed the reaction was complete. The mixture was purified by prep-TLC (PE/EtOAc=2/1) to give the racemate (70 mg, 50.0% yield) as a white solid. It was separated by SFC (Mobile phase: Supercritical CO$_2$/EtOH; Column: Chiralpak (S, S) Whelk-01 250×30 mm I.D., 10 um) to give 36-Ent1 (Rt=5.004 min, 26.0 mg, 37.14% yield) as a white solid and 36-Ent2 (Rt=3.903 min, 20.1 mg, 28.71% yield) as a white solid. The absolute stereochemistry was not determined.

Data for 36-Ent1:
HPLC: (Purity: 100.0%)
MS: M+H: 301.1904)
SFC: (ee: 99.074%)
$^1$H NMR: (400 MHz, CDCl$_3$) δ: 7.35 (s, 1H), 5.68 (t, J=3.2 Hz, 1H), 4.61-4.53 (m, 2H), 3.96-3.90 (m, 1H), 2.63-2.59 (m, 1H), 1.44 (s, 3H), 1.39 (s, 3H), 1.37 (s, sH), 1.34 (s, 9H).

Data for 36-Ent2:
HPLC: (Purity: 96.52%)
MS: (M+H: 301.1892)
SFC: (ee: 100%)
$^1$H NMR: (400 MHz, CDCl$_3$) δ: 7.35 (s, 1H), 5.68 (t, J=3.2 Hz, 1H), 4.61-4.53 (m, 2H), 3.96-3.90 (m, 1H), 2.63-2.59 (m, 1H), 1.44 (s, 3H), 1.39 (s, 3H), 1.37 (s, sH), 1.34 (s, 9H).

Example 26. Synthesis of Compounds 37-Ent and 37-Ent2

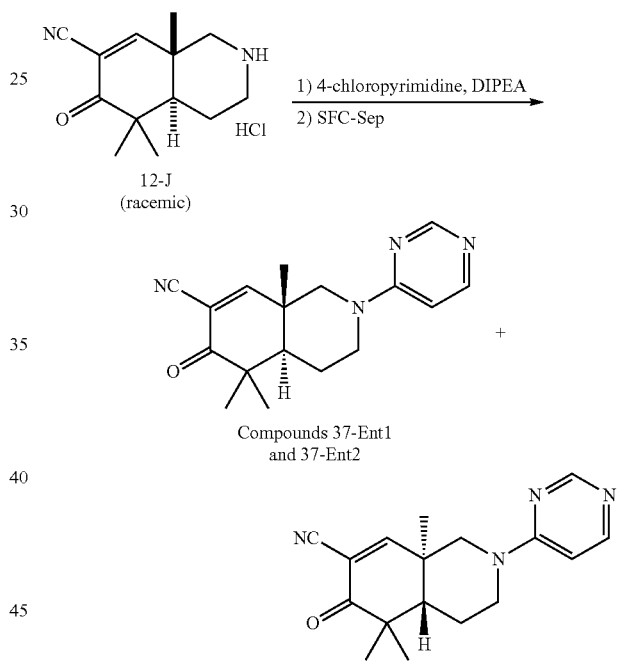

A mixture of compound 12-J (200 mg, 0.79 mmol, 1.0 eq.), 4-chloropyrimidine (178 mg, 1.58 mmol, 2.0 eq) and DIPEA (1 g, 7.9 mmol, 10.0 eq.) in THF (10 mL) was heated to reflux for 5 h. LCMS showed the target product was obtained. The mixture was purified by P-TLC (EA/MeOH=9:1) to give the final product (100 mg, 42.9%). It was separated by SFC (Mobile phase: Supercritical CO$_2$/EtOH; Column: Chiralpak AD (250 mm*30 mm, 5 um); Detection wavelength: 220 nm) to give 37-Ent1 (~40 mg, Rt=4.609 min) and 37-Ent2 (~30 mg, Rt=5.561 min). The compounds were further purified by prep-HPLC (Mobile phase A: 0.225% Formic acid in water, Mobile phase B: acetonitrile; Column: Phenomenex Synergi C18 150*30 mm*4 um, Detection wavelength: 220 nm) to give 37-Ent1 (9.2 mg, 7.8% yield) as a white solid and 37-Ent2 (11.1 mg, 9.5% yield) as colorless gum.

Data for 37-Ent1:
$^1$H NMR: (400 MHz, CDCl$_3$) δ: 8.60 (s, 1H), 8.25 (d, J=6.5 Hz, 1H), 7.52 (s, 1H), 6.57 (d, J=6.5 Hz, 1H), 4.65 (m, 1H), 4.48 (m, 1H), 2.94-2.86 (m, 1H), 2.72 (d, J=12.5 Hz, 1H), 2.03-1.98 (m, 1H), 1.83-1.70 (m, 2H), 1.27 (s, 3H), 1.23 (s, 3H), 1.12 (s, 3H).
HPLC: (Purity: 100.0%).
MS: (M+H: 297.1).
SFC: (ee: 97.9%)

Data for 37-Ent2:
$^1$H NMR: (400 MHz, CDCl$_3$) δ: 8.61 (s, 1H), 8.25 (d, J=6.0 Hz, 1H), 7.52 (s, 1H), 6.57 (d, J=6.5 Hz, 1H), 4.65 (m, 1H), 4.49 (m, 1H), 2.94-2.86 (m, 1H), 2.72 (d, J=12.5 Hz, 1H), 2.03-1.98 (m, 1H), 1.83-1.70 (m, 2H), 1.27 (s, 3H), 1.23 (s, 3H), 1.12 (s, 3H)
HPLC: (Purity: 100.0%).
SFC: (ee: 99.06%)
MS: (M+H: 297.2).

Example 27. Synthesis of Compound 38-Ent1 and 38-Ent2

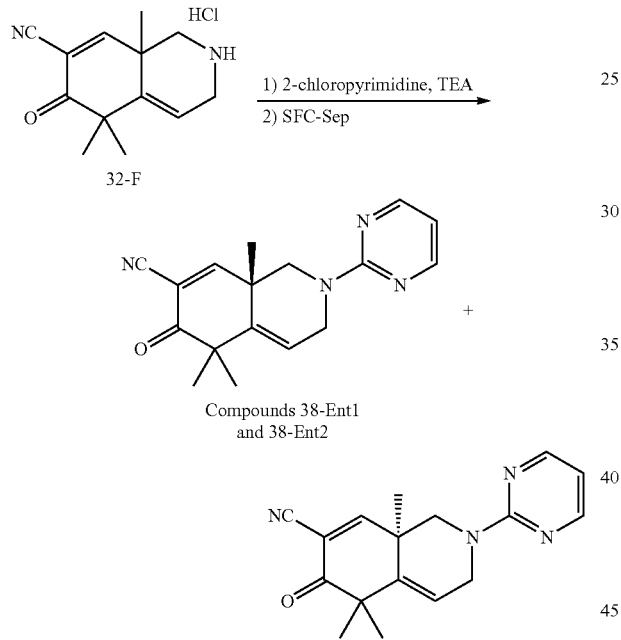

To a solution of compound 32-F (120 mg, 0.47 mmol, 1.0 eq.) and TEA (190 mg, 1.88 mmol, 4.0 eq) in THF (5 mL) was added 2-chloropyrimidine (107.1 mg, 0.94 mmol, 2.0 eq.) dropwise. The mixture was stirred at 75° C. for 2 h. LCMS showed the reaction was completed. The mixture was purified by prep-TLC (PE/EtOAc=2/1) to give the racemate (50 mg, 36.0% yield) as a white solid. It was separated by SFC (Column: OJ 250×30 mm I.D., 5 um, Mobile phase: A: Supercritical CO$_2$, B: ETOH, A:B=70:30 at 60 ml/min, Column Temp: 38° C., Nozzle Pressure: 100 Bar, Nozzle Temp: 60° C., Evaporator Temp: 20° C., Trimmer Temp: 25° C., Wavelength: 220 nm) to give 38-Ent1 (8 mg, Rt=3.580 min) and 38-Ent2 (4.8 mg, Rt=4.535 min) both as white solid.

The two isomers are further purified by prep-HPLC (Phenomenex Synergi C18 150*30 mm*4 um water (HCl, 0.05%)-ACN as mobile phase, from 26-46%, Flow Rate (ml/min): 25) to give 38-Ent1 (4.8 mg) and 38-Ent2 (2.6 mg) both as white solid.

Data for 38-Ent1:
HPLC: (Purity: 98.77%)
LCMS: (M+H: 295.1)
SFC: (ee: 99.01%)
$^1$H NMR: (400 MHz, MeOD) δ: 8.59 (d, J=4.7 Hz, 2H), 7.75 (s, 1H), 6.97 (t, J=5.1 Hz, 1H), 5.93 (t, J=3.1 Hz, 1H), 4.92 (d, J=12.5 Hz, 1H), 4.52 (dd, J=18.4, 2.7 Hz, 1H), 4.02 (dd, J=18.4 3.52 Hz, 1H), 2.98 (d, J=12.5 Hz, 1H), 1.48 (s, 3H), 1.41 (s, 3H), 1.38 (s, 3H).

Data for 38-Ent2:
HPLC: (Purity: 100%)
LCMS: (M+H: 295.1)
SFC: (ee: 99.48%)
$^1$H NMR: (400 MHz, MeOD) δ: 8.59 (d, J=4.7 Hz, 2H), 7.75 (s, 1H), 6.97 (t, J=5.1 Hz, 1H), 5.93 (t, J=3.1 Hz, 1H), 4.92 (d, J=12.5 Hz, 1H), 4.52 (dd, J=18.4, 2.7 Hz, 1H), 4.02 (dd, J=18.4, 3.5 Hz, 1H), 2.98 (d, J=12.5 Hz, 1H), 1.48 (s, 3H), 1.41 (s, 3H), 1.38 (s, 3H).

Example 28. Synthesis of Compound 39-Ent1

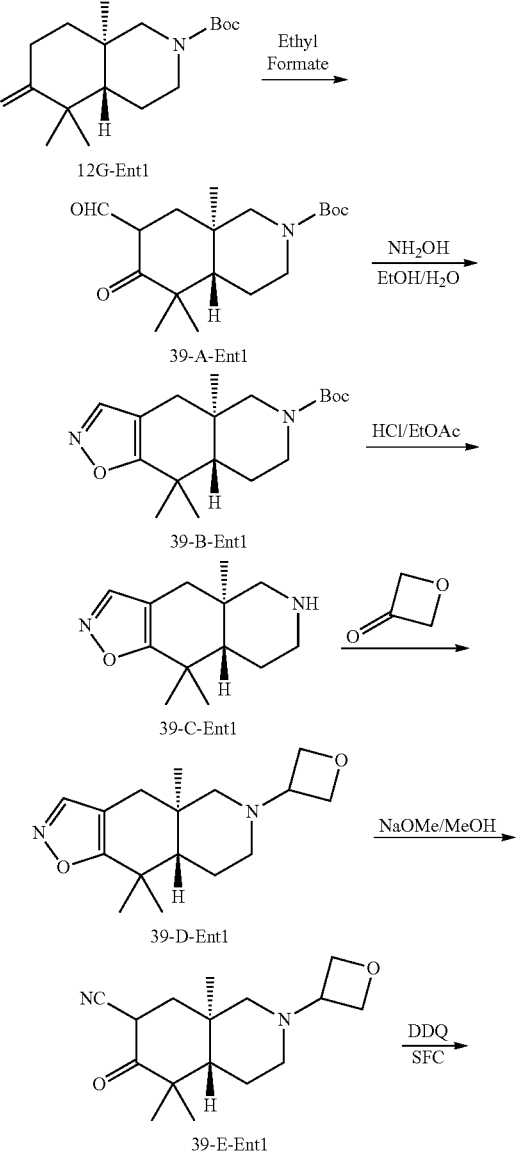

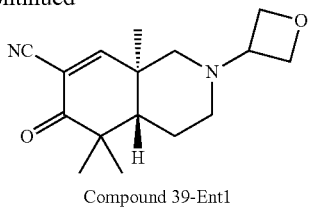

Compound 39-Ent1

Preparation of Compound 39-A Ent1

To a solution of compound 12-G Ent1 (10 g, 0.034 mol, 1.0 eq) in Ethyl formate (50.3 g, 0.68 mol, 20.0 eq) was added NaOMe/MeOH (21 mL, 116 mmol, 3.4 eq, 5.4 M in MeOH) at 0-5° C. The mixture was stirred at 28° C. under $N_2$ atmosphere for 18 hours. LCMS showed compound 12-G Ent1 was consumed completely. The reaction mixture was quenched by water (50 mL), extracted with EtOAc (50 mL×2). The combined organic layer was washed with brine (50 mL×1), dried over anhydrous $Na_2SO_4$, filtered, concentrated under reduced pressure to supply crude compound 39-A Ent1 (18.0 g) as pale-yellow solid, which was used for next step without further purification.

LCMS: (M−56: 268.4)

Preparation of Compound 39-B Ent1

To a solution of compound 39-A Ent1 (18 g, 58 mmol, 1.0 eq) in 20 mL of EtOH/$H_2O$ (V=5:1) was added hydrochloride hydroxylamine (5.12 g, 70 mmol, 1.0 eq) at 28° C. After addition the mixture was stirred at 55° C. for 18 h. TLC (PE/EA=3:1) showed compound 39-A Ent1 was consumed completely. The mixture was concentrated under reduced pressure to about 10 mL, diluted with water (100 mL), adjusted pH to 8 by adding saturated aqueous $NaHCO_3$, and extracted with EtOAc (50 mL×3). The combined organic layer was washed with brine (30 mL×2), dried over anhydrous $Na_2SO_4$, filtered, and concentrated to give the crude, which was purified by column chromatography on silica gel (PE/EA=15:1-5:1) to supply compound 39-B Ent1 (4.2 g) as colorless oil.

Preparation of Compound 39-C Ent1

A mixture of compound 39-B Ent1 (500 mg, 0.63 mmol, 1.0 eq) in HC/EA (10 mL) was stirred at 28° C. for 3 hours. TLC (PE/EA=3:1) showed the starting materials were consumed completely. The solvent was removed to give the crude compound 39-C Ent1 (600 mg), which was used for next step without further purification.

Preparation of Compound 39-D Ent1

A solution of compound 39-C Ent1 (600 mg, crude), oxetan-3-one (1.96 mg, 27.2 mmol) and TEA (1.09 g, 0.72 mmol) in THF (10 mL) was stirred at 28° C. for 30 min and then $NaBH(OAc)_3$ (2.3 g, 10.8 mmol) was added. The mixture solution was stirred at 28° C. for additional 18 hours. LCMS showed the starting materials were consumed completely. The reaction solution was poured into water (50 mL) and extracted with EA (50 mL×2). The combined organic layers were dried over anhydrous sodium sulfate, filtered and concentrated to give crude 39-D Ent1 (400 mg), which was used for next step without further purification.

LCMS: (M+H: 277.1)

Preparation of Compound 39-E Ent1:

To a solution of compound 39-D Ent1 (400 mg, crude) in MeOH (3 mL) was added MeONa/MeOH (3.61 mL, 7.22 mmol, 2M) at 25° C. The reaction mixture was stirred at 25° C. for 18 hours. TLC (PE/EA=3:1) showed the starting materials were consumed completely. The mixture was acidified with HCl (1M) to pH=7-9 and concentrated to remove MeOH. Then the mixture was diluted into water (15 mL) extracted with EA (30 mL×2). The combined organic layers were dried over anhydrous sodium sulfate, filtered and concentrated to give crude 39-E Ent1 (308 mg), which was used for next step without further purification.

Preparation of Compound 39-Ent

To a yellow solution of compound 39-E Ent1 (308 mg, 1.11 mmol, 1.0 eq.) in toluene (10 mL) was added DDQ (252 mg, 1.11 mmol, 1.0 eq.) in one portion. The mixture was heated to 85° C. for 2 hours. TLC (PE/EA=2:1) showed the starting materials were consumed completely. The crude product was purified by prep-TLC (EA/PE=3:1-2:1-1:1) to give the product (100 mg), for which was further separation by SFC (column: AD (250 mm×30 mm, 5 um), condition: Neu-MeOH) to give compound 39-Ent1 (Rt=3.603 min, 52.6 mg) as colorless oil.

Data for 39-Ent1:

HPLC: (Purity: 99.49%)

MS: (M+H: 275.16)

SFC: (ee: 100%)

$^1$H NMR: (400 MHz, CHLOROFORM-d) δ: 7.29 (s, 1H), 4.65-4.46 (m, 4H), 3.42 (quin, J=6.4 Hz, 1H), 2.84 (br d, J=9.2 Hz, 1H), 2.39 (dd, J=1.4, 10.4 Hz, 1H), 1.82-1.69 (m, 3H), 1.65-1.54 (m, 2H), 1.32 (s, 3H), 1.14 (s, 3H), 1.05 (s, 3H)

Example 29. Synthesis of Compound 39-Ent2

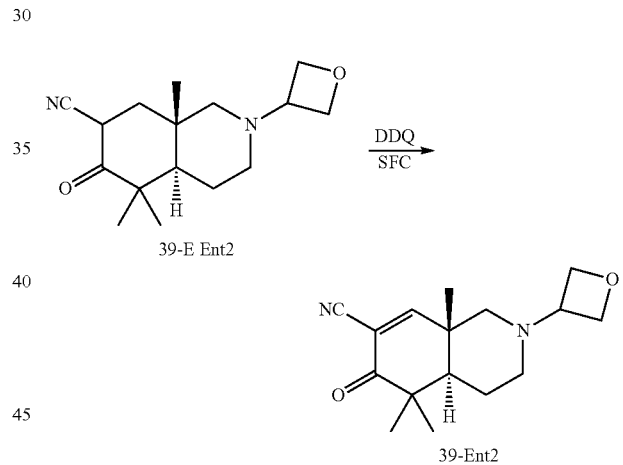

To a yellow solution of compound 39-E Ent2 (110 mg, 0.39 mmol, 1.0 eq., prepared in a manner analogous to that described for 39-E Ent1, described previously, except that the starting material is 12-G Ent2) in toluene (2 mL) was added DDQ (90.5 mg, 0.39 mmol, 1.0 eq.) in one portion. The mixture was heated to 80° C. for 2 hours. TLC (PE/EA=3:1) showed the starting materials were consumed completely. The crude product was purified by prep-TLC (EA/PE=3:1-2:1) to give compound (30 mg). Further separation by SFC (column: AD (250 mm*30 mm, 5 um), condition: Neu-MeOH) to give 39-Ent2 (Rt=3.847 min, 14.4 mg) as colorless oil.

Data for 39-Ent2:

HPLC: (Purity: 99.67%)

LCMS: (M+H: 275.1)

SFC: (ee: 99.62%)

$^1$H NMR: (400 MHz, CHLOROFORM-d) δ: 7.37 (s, 1H), 4.67-4.51 (m, 4H), 3.51-3.45 (m, 1H), 2.90 (d, J=9.4 Hz,

1H), 2.45 (dd, J=10.2, 1.2 Hz, 1H), 1.86-1.72 (m, 3H), 1.68-1.61 (m, 2H), 1.39 (s, 3H), 1.19 (s, 3H), 1.11 (s, 3H).

Example 30. Synthesis of Compounds 46-Ent and 46-Ent2

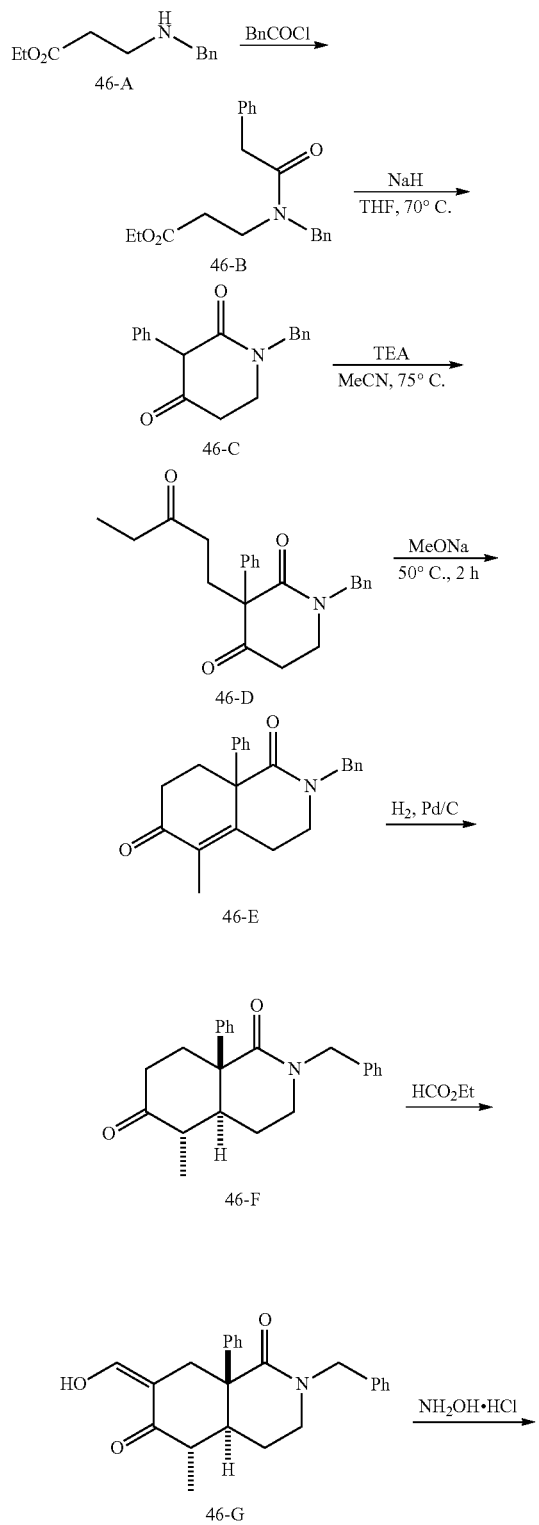

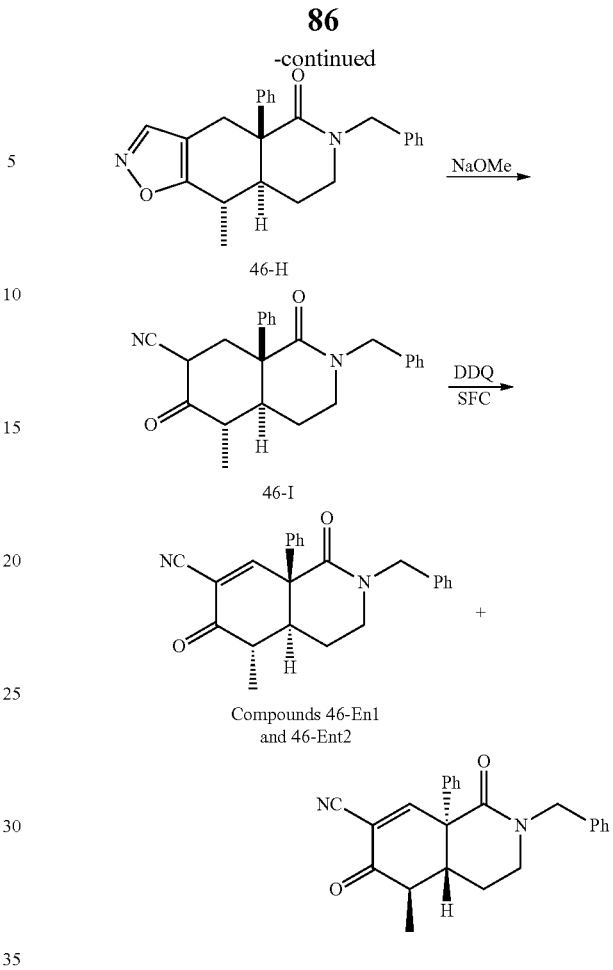

Preparation of Compound 46-B

To a solution of compound 46-A (ethyl 3-(benzylamino)propanoate, 20 g, 96.6 mol, 1.0 eq) and TEA (11.7 g, 115.9 mol, 1.2 eq) in DCM (200 mL) was added 2-phenylacetyl chloride (14.9 g, 96.6 mol, 3 eq) dropwise. The mixture was stirred at 28° C. for 18 hours. TLC (PE:EA=1:1) showed a little starting material still remained ($R_f$=0.2) and a new spot was detected ($R_f$=0.8). The mixture was poured into Sat. NaHCO$_3$ (50 mL) and extracted with DCM (50 mL×3). The combined organic phase was dried over Na$_2$SO$_4$, filtered and concentrated to give the residue, which was purified by column chromatography (eluting with PE:EA=50:1-5:1) and further purified by column chromatography (eluting with PE) to give compound 46-B (27 g, 80%) as colorless oil.

$^1$H NMR (400 MHz, CHLOROFORM-d) δ: 7.36-7.25 (m, 8H), 7.09 (d, J=7.1 Hz, 2H), 4.65-4.47 (m, 3H), 4.19-4.10 (m, 4H), 3.84 (s, 1H), 2.02 (s, 2H), 1.22-1.19 (m, 3H).

Preparation of Compound 46-C

To a solution of compound 46-B (18 g, 55.6 mol, 1.0 eq) in THF (100 mL) was added NaH (2.8 g, 71.9 mol, 1.3 eq) in many portions at 0° C. The mixture was stirred at reflux for 18 hours. TLC (PE:EA=1:1) showed the starting material was consumed completely. The mixture was poured into Sat. NH$_4$Cl (50 mL) and extracted with EA (50 mL×3). The combined organic phase was dried over Na$_2$SO$_4$, filtered and concentrated to give the residue, which was purified by column chromatography (eluting with PE:EA=30:1-5:1) and further purified by column chromatography (eluting with PE) to give compound 46-C (6 g, 25%) as a white solid.

Preparation of Compound 46-D

To a solution of compound 46-C (2 g, 7.16 mol, 1.0 eq) and TEA (2 g, 7.16 mol, 1.0 eq) in MeCN (100 mL) was added EVK (818 mg, 8.6 mol, 1.2 eq) dropwise at 0° C. The mixture was stirred at reflux for 18 hours. TLC (PE:EA=8:1) showed the starting material was consumed completely. The mixture was poured into water (50 mL) and extracted with EA (50 mL×3). The combined organic phase was dried over Na$_2$SO$_4$, filtered and concentrated to give compound 46-D (2.8 g, crude), which was used for next step without further purification.

Preparation of Compound 46-E

To a solution of compound 46-D (2.8 g, 7.7 mol, 1.0 eq) in MeOH (20 mL) was added MeONa/MeOH (3.85 mL, 7.7 mol, 2M, 1.2 eq) dropwise at 0° C. The mixture was stirred at reflux for 18 hours. TLC (PE:EA=8:1) showed the starting material was consumed completely. The mixture was poured into Sat.NH$_4$Cl (50 mL) and extracted with EA (50 mL×3). The combined organic phase was dried over Na$_2$SO$_4$, filtered and concentrated to give the residue, which was purified by column chromatography (eluting with PE:EA=30:1-5:1) and further purified by column chromatography (eluting with PE) to give compound 46-E (1.1 g, 60%) as a white solid.

$^1$H NMR (400 MHz, CHLOROFORM-d) δ: 7.34-7.24 (m, 8H), 7.14-7.09 (m, 2H), 4.62 (d, J=1.1 Hz, 2H), 3.08-3.00 (m, 1H), 2.88 (m, 1H), 2.71-2.56 (m, 3H), 2.54-2.45 (m, 1H), 2.36 (J=16.8, 3.6 Hz, 1H), 2.15-2.05 (m, 1H), 1.88 (s, 3H).

Preparation of Compound 46-F

The reactions were set in two batches in parallel.

A mixture of compound 46-E (1.1 g, 3.17 mol, 1.0 eq.) and Pd/C (200 mg) in ethanol (20 mL) was stirred under 15 psi of H$_2$ at 27° C. for 18 hours. TLC (PE/EtOAc=2:1) indicated completion. The suspension was filtered through a pad of celite and washed with EA (200 mL×2), the filtrate was concentrated under reduce pressure to give a crude product of compound 46-F (900 mg, crude), for which was purified by Prep-HPLC to give compound 46-F (300 mg, 27.3%) as a white solid.

$^1$H NMR (400 MHz, CHLOROFORM-d) δ: 7.78-7.65 (m, 2H), 7.37-7.21 (m, 6H), 7.13-7.04 (m, 2H), 4.47-4.43 (m, 2H), 3.20-3.00 (m, 2H), 2.94-2.82 (m, 1H), 2.79-2.68 (m, 1H), 2.37-2.27 (m, 3H), 2.18-2.08 (m, 2H), 2.04-1.93 (m, 1H), 1.12 (d, J=6.4 Hz, 3H).

Preparation of Compound 46-G

To a solution of compound 46-F (140 mg, 0.4 mmol, 1.0 eq) in Ethyl formate (2 mL) was added NaOMe (0.25 mL, 1.36 mmol, 3.4 eq, 5.4 M in MeOH) at 0-5° C. The mixture was stirred at 23° C. under N$_2$ atmosphere for 1 h and turned to a suspension. LCMS (19207-12-1A) showed the reaction completion. The reaction mixture was diluted with toluene (10 mL), quenched with aq.HCl(1M) until pH=7 and extracted with EtOAc (25 mL×3). The combined organic phase was dried over anhydrous Na$_2$SO$_4$, filtered, concentrated under reduced pressure to supply crude compound 46-G (130 mg, crude) as a yellow gum, which was used directly in the next step without purification.

MS: (M+H 376.6)

Preparation of Compound 46-H

To a solution of compound 46-G (130 mg, 0.34 mmol, 1.0 eq) in EtOH/H$_2$O (V=10:1, 3 mL) was added hydrochloride hydroxylamine (24.2 mg, 0.34 mmol, 1.0 eq). The mixture was stirred at 50° C. for 18 hours. LCMS showed the reaction was completed. The mixture was concentrated under reduced pressure to give the residue, which was diluted with water (20 mL). The mixture was extracted with EtOAc (25 mL×3). The combined organic layer was dried over anhydrous Na$_2$SO$_4$, filtered, and concentrated under reduced pressure to give compound 46-H (105 mg, crude) as a yellow gum, which was used directly in the next step without purification.

MS: (M+H 373.3)

Preparation of Compound 46-I

To a solution of compound 46-H (105 mg, 0.28 mmol, 1.0 eq) in MeOH (2 mL) was added NaOMe/MeOH (0.56 mL, 1.12 mmol, 4.0 eq, 2M). The mixture was stirred at 25° C. for 18 hours. TLC (PE/EA=3:1) showed the reaction was completed. The mixture was acidified with HCl (M) to make pH=7-9, which was diluted with water (20 mL) and extracted with EtOAc (20 mL×2). The combined organic phase was dried over anhydrous Na$_2$SO$_4$, filtered, and concentrated under reduced pressure to give compound 46-I (110 mg, crude), which was used directly in the next step without purification.

Preparation of Compounds 46-Ent and 46-Ent2

To a solution of compound 46-I (110 mg, 0.48 mmol, 1 eq) in toluene (3 mL) was added DDQ (109.9 mg, 0.48 mmol, 1 eq). The mixture was stirred at 80° C. for 3 hours and turned to a suspension. The mixture was concentrated in vacuo to give the residue, which was purified by Pre-HPLC (PE/EA=3:1) to give racemic product (45 mg).

Further separation by SFC (column: AD (250 mm×30 mm, 10 um), condition: Neu-MeOH) to give enantiomer 46-Ent1 (Rt=3.670 min, 15.4 mg) and 46-Ent2 (Rt=6.337 min, 21.4 mg), both as oils.

Data for 46-Ent1

$^1$H NMR (400 MHz, CHLOROFORM-d) δ: 8.46 (s, 1H), 7.40-7.30 (m, 8H), 7.09-7.03 (m, 2H), 4.89-4.81 (m, 1H), 4.55 (d, J=14.1 Hz, 1H), 3.57-3.37 (m, 2H), 2.41-2.32 (m, 2H), 1.80-1.77 (m, 1H), 1.65-1.58 (m, 1H), 1.08 (br d, J=6.3 Hz, 3H).

HPLC: (Purity: 94.06%).

SFC: (ee 100%).

LCMS: (M+H: 371.1).

Data for 46-Ent2

$^1$H NMR (400 MHz, CHLOROFORM-d) δ: 8.46 (s, 1H) 7.40-7.29 (m, 8H), 7.09-7.03 (m, 2H), 4.89-4.80 (m, 1H), 4.55 (d, J=14.1 Hz, 1H), 3.57-3.38 (m, 2H), 2.42-2.31 (m, 2H), 1.80-1.77 (m, 1H), 1.65-1.57 (m, 1H), 1.08 (br d, J=6.3 Hz, 3H).

HPLC: (Purity: 98.14%).

SFC: (ee 100%).

LCMS: (M+H: 371.1).

Example 31. Synthesis of Compound 47-Ent1

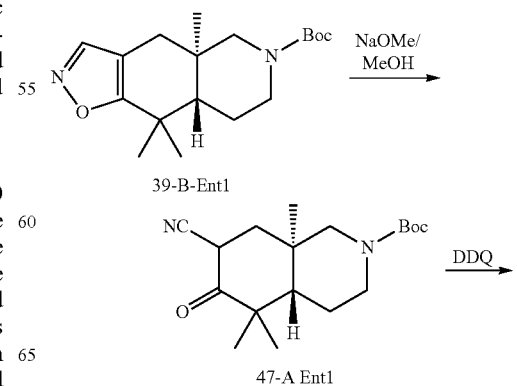

-continued

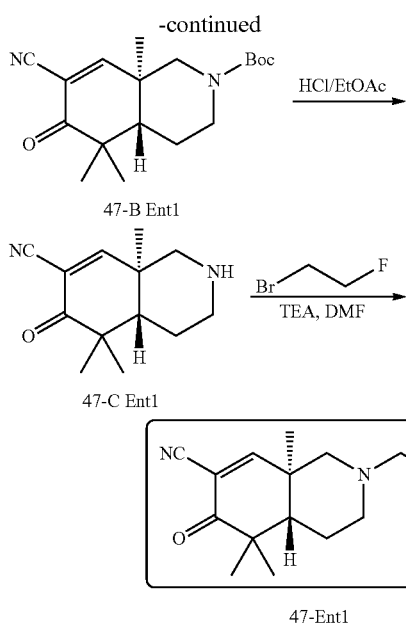

47-B Ent1

47-C Ent1

47-Ent1

Preparation of Compound 47-A Ent1

The starting material 39-B-Ent1 (600 mg) was recrystallized (20 mL, PE/EtOAc=10/1) from crude compound 38-B-Ent1 (2 g, ee value=−87%).

To a solution of compound 39-B-Ent1 (600 mg, 1.8 mmol, 1.0) in MeOH (3 mL) was added MeONa/MeOH (3.75 mL, 7.5 mmol, 2M) at 27° C. The reaction mixture was stirred at 27° C. for 18 hours. TLC (PE/EA=3:1) showed the starting materials were consumed completely. The mixture was acidified with HCl (M) to make pH=7-9 and concentrated to remove MeOH. The mixture was diluted into water (50 mL) and extracted with EA (30 mL×2). The combined organic layers were dried over anhydrous sodium sulfate, filtered and concentrated to give crude 47-A Ent1 (620 mg) as yellow oil, which was used for next step without further purification.

Preparation of Compound 47-B Ent1

To a yellow solution of compound 47-A Ent1 (620 mg, 2.32 mmol, 1.0 eq.) in toluene (3 mL) was added DDQ (527 mg, 2.32 mmol, 1.0 eq.) in one portion. The mixture was heated to reflux for 2 hours. TLC (PE/EA=3:1) showed the starting materials were consumed completely. The crude product was purified by prep-TLC (EA/PE=20:1-5:1) to give compound 47-B Ent1 (320 mg) as a white solid.

$^1$H NMR (400 MHz, CHLOROFORM-d) δ: 7.42 (s, 1H), 4.54-3.83 (m, 2H), 2.82-2.46 (m, 2H), 1.81 (dd, J=2.7, 12.3 Hz, 1H), 1.74-1.61 (m, 2H), 1.45 (s, 9H), 1.20 (d, J=3.3 Hz, 6H), 1.08 (s, 3H)

Preparation of Compound 47-C Ent1

To a solution of compound 47-B Ent1 (150 mg, 0.47 mmol, 1.0 eq) in EA (15 mL) was added HCl/EA (3 mL) at 25° C. The reaction mixture was stirred at 25° C. for 2 hours. TLC (PE/EA=2:1) showed the starting materials were consumed completely. The solvent was removed to give the crude compound 47-C Ent1 (130 mg, crude) as a white solid, which was used for next step without further purification.

Preparation of Compound 47-Ent1

To a solution of compound 47-C Ent1 (130 mg, 0.59 mmol) and TEA (95.2 mg, 0.94 mmol) in DMF (3 mL) was added 1-bromo-2-fluoroethane (118 mg, 0.94 mmol) dropwise. The mixture was stirred at 110° C. for 1 h. TLC (PE/EA=3:1) showed the reaction was complete. The mixture was purified by prep-TLC (PE/EtOAc=2/1) to give 47-Ent1 (Rt=2.694 mins, 39.8 mg) as colorless oil.

Data for 47-Ent1
  HPLC: (Purity: 98.83%)
  LCMS: (M+H: 265.1)
  SFC: (ee: 96.3%)
  $^1$H NMR: (400 MHz, CHLOROFORM-d) δ: 7.37 (s, 1H), 4.67-4.38 (m, 2H), 3.08 (br d, J=9.8 Hz, 1H), 2.84-2.59 (m, 3H), 2.24-2.03 (m, 2H), 1.65 (br d, J=10.6 Hz, 2H), 1.56 (br d, J=12.5 Hz, 1H), 1.34 (br s, 3H), 1.18 (br s, 3H), 1.08 (br s, 3H).

Example 32. Synthesis of Compounds 48-Ent1 and 48-Ent2

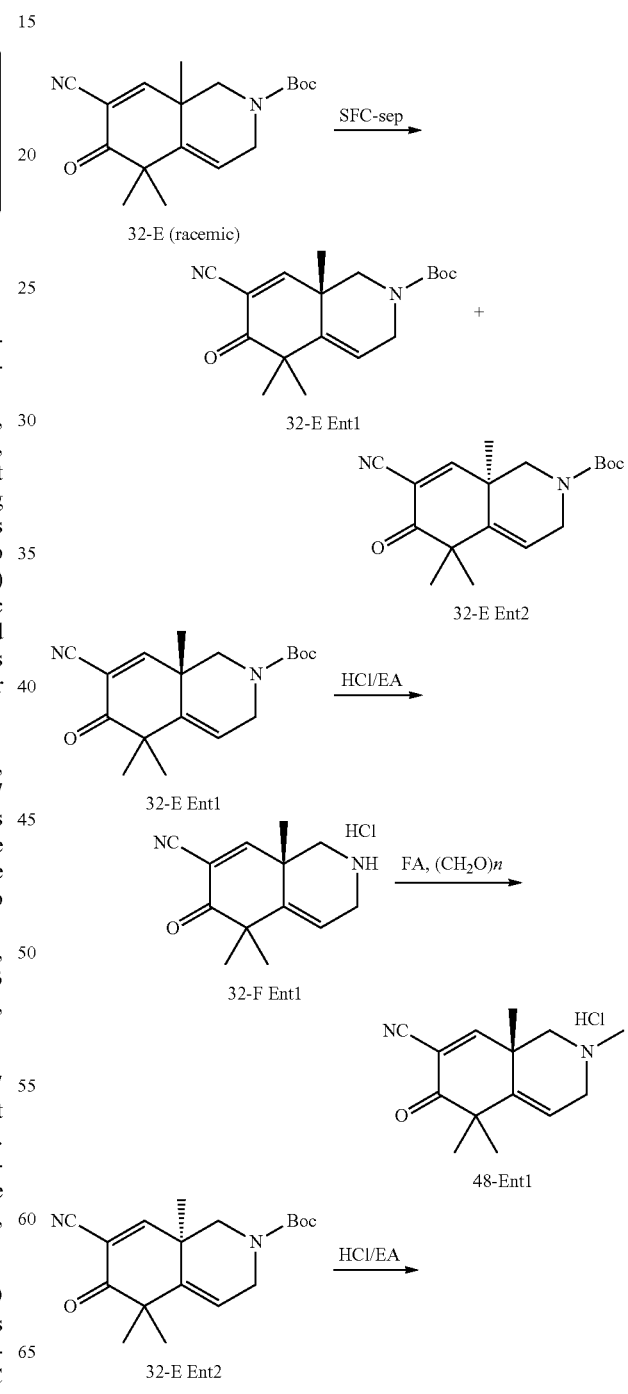

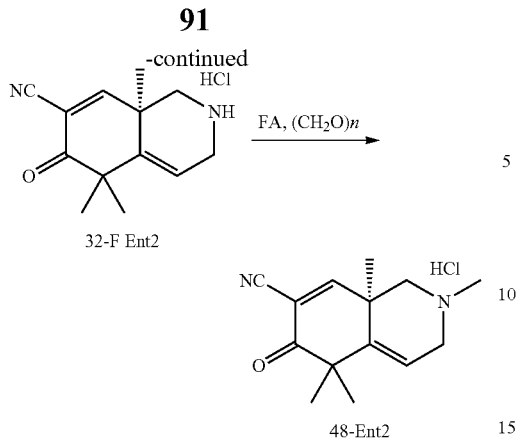

32-F Ent2 → 48-Ent2

Preparation of Compounds 32-E Ent1 and Ent2

Racemic compound 32-E (3.0 g, 9.5 mmol, 1 eq) was separated by SFC (Mobile phase: Superaritical Neutral: CO$_2$/EtOH; Column: 150 mm×4.6 mm, 3 um; Detection wavelength: 220 nm) to give 32-E Ent1 (Rt=3.781 min, 830 mg, 27.7% yield) as a white solid and 32-E Ent2 (Rt=5.448 min, 680 mg, 22.7% yield) as a white solid. The absolute stereochemistry of each enantiomer depicted in the above scheme was assigned arbitrarily and was not determined.

Data for 32-E Ent1:
HPLC: (Purity: 85.25%)
SFC: (ee: 100%)
$^1$H NMR: (400 MHz, CDCl$_3$) δ=7.31 (s, 1H), 5.75-5.58 (m, 1H), 4.52-4.23 (m, 1H), 4.16-3.90 (m, 1H), 3.78-3.62 (m, 1H), 2.78-2.56 (m, 1H), 1.50 (s, 9H), 1.45 (s, 3H), 1.36 (d, J=6.1 Hz, 6H).

Data for 32-E-Ent2:
HPLC: (Purity: 96.62%)
SFC: (ee: 100%)
$^1$H NMR: (400 MHz, CD3CN) δ=7.31 (s, 1H), 5.75-5.58 (m, 1H), 4.52-4.23 (m, 1H), 4.16-3.90 (m, 1H), 3.78-3.62 (m, 1H), 2.78-2.56 (m, 1H), 1.50 (s, 9H), 1.45 (s, 3H), 1.36 (d, J=6.1 Hz, 6H)

Preparation of Compound 32-F Ent1

To a solution of compound 32-E Ent1 (830 mg, 2.6 mmol, 1.0 eq) in EtOAc (10 mL) was added HCl/EA (1.4 mL) at 25° C. The reaction mixture was stirred at 25° C. for 3 hours. TLC (PE/EA=3:1) showed the starting materials were consumed completely. The solvent was removed to give the crude compound 32F Ent1 (650 mg, crude), which was used for the next step without further purification.

Preparation of Compound 48 Ent1

To a solution of compound 32-F Ent1 (250 mg, 0.99 mmol, 1.0 eq) and (CH$_2$O)n (148.5 mg, 4.95 mmol, 5.0 eq) in HCOOH (4 mL) was stirred at 90° C. for 2 h. TLC showed that the starting material was consumed and a new spot was detected (Rf=0.5). The reaction mixture was poured into Sat. NaHCO$_3$ to keep the pH=7 and extracted with EtOAc (30 mL×3). The combined organic layer was dried over Na$_2$SO$_4$, filtrated and concentrated to get the residue, which was purified by prep-TLC (EtOAc) to give the 19203-84-1 (150 mg, crude) and further purified by preparation of HPLC (column: Phenomenex Synergi C18 150*30 mm*4 um; Mobile phase: from 0% to 14% water (0.05% HCl)-ACN) to give 48-Ent1 (60 mg, 26.4% yield) as white solid. The absolute stereochemistry was not determined.

Data for 48-Ent1
HPLC: (Purity: 99.41%)
MS: (M+H: 231.1424)
Chiral SFC: (ee: 79.952%)
$^1$H NMR: (400 MHz, D$_2$O) δ=7.68 (s, 1H), 5.75 (s, 1H), 4.10-3.97 (m, 1H), 3.69-3.50 (m, 2H), 3.15 (br d, J=12.1 Hz, 1H), 2.97 (s, 3H), 1.63 (s, 3H), 1.34 (br d, J=8.6 Hz, 6H)

Compound 48-Ent2 can be made in an analogous manner to that described for 48-Ent1, starting with 32-E Ent2.

Data for 48-Ent2
HPLC: (Purity: 96.64%)
MS: (M+H: 231.14)
Chiral SFC: (ee 95.37%)
$^1$H NMR: (400 MHz, D$_2$O) δ=7.68 (s, 1H), 5.75 (s, 1H), 4.09-3.98 (m, 1H), 3.71-3.50 (m, 1H), 3.70-3.50 (m, 1H), 3.20-3.10 (m, 1H), 3.01-2.95 (m, 3H), 2.98 (s, 3H), 1.34 (br d, J=8.4 Hz, 6H)

Example 33. Synthesis of Compound 49-Ent1

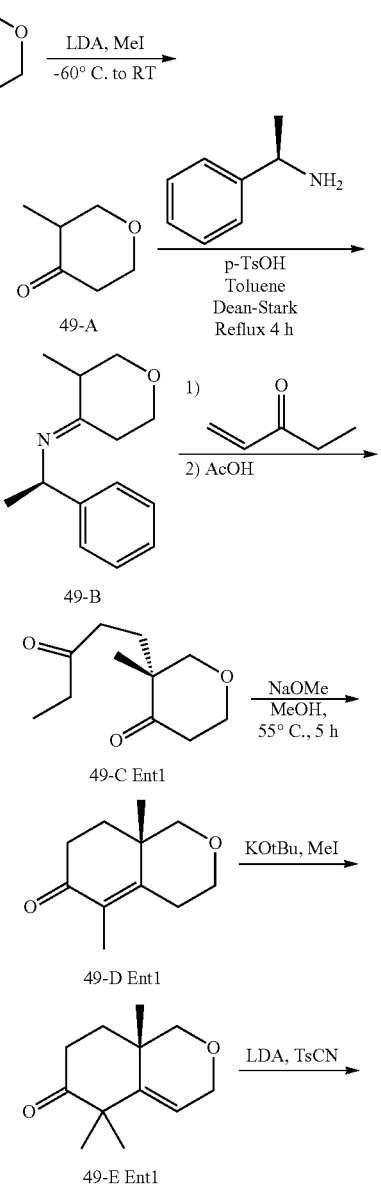

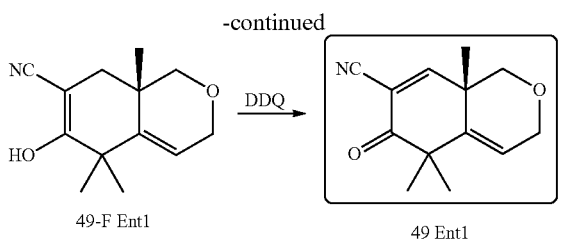

Preparation of Compound 49-A

The reaction was set in two batches in parallel and work-up was combined.

To a stirred solution of LDA (2 M in THF, 600 mL, 1.2 mol, 1.2 eq) in THF (200 mL) was added a solution of tetrahydro-4H-pyran-4-one (100 g, 1.0 mol, 1.0 eq.) and HMPA (175 mL) in THF (600 mL) dropwise at −70° C. under $N_2$, and the reaction mixture was stirred at −70° C. for 1 h. Then Methyl iodide (695.44 g, 4.9 mol, 4.9 eq) in THF (200 mL) was added to the above reaction mixture at −70° C., and the reaction mixture was stirred at 25° C. for 16 h. TLC (PE/EA=4:1) showed the starting material was remained with the desired spot detected. The reaction mixture was quenched by saturated ammonium chloride solution (50 mL). EtOAc (100 mL) and $H_2O$ (200 mL) were added. The two phases were separated, and the aqueous phase was extracted with EtOAc (200 mL×10). The combined organic phase was dried over anhydrous $Na_2SO_4$, filtered and concentrated to give a crude product, which was purified together with batch 19225-129-1 by column chromatography (PE/EA=50:1 to 20:1) to give compound 49-A as colorless oil (10 g, pure) and 56 g of crude compound 49-A.

$^1$H-NMR: (400 MHz, $CDCl_3$) δ: 4.22-4.11 (m, 2H), 3.69-3.67 (m, 1H), 3.29 (t, J=10.8 Hz, 1H), 2.66-2.62 (m, 2H), 2.38-2.35 (m, 1H), 0.96 (d, J=10.8 Hz, 1H).

Preparation of Compound 49-B

To a solution of compound 49-A (10 g, 87.7 mmol, 1.0 eq) in PhMe (150 mL) was added (R)-1-phenylethan-1-amine (10.6 g, 87.7 mmol, 1.0 eq) and TsOH (151 mg, 0.88 mmol, 0.01 eq) at 25° C. The reaction mixture was stirred at 140° C. with a Dean-Stark apparatus for 5 h. Then the reaction mixture was cooled to room temperature, concentrated in vacuo. PhMe (20 mL) was added, the formed solid was filtered off, and the filtrate was concentrated under reduced pressure to supply the crude compound 49-B, which was used for next step directly.

Preparation of Compound 49-C Ent1

A mixture of compound 49-B (20.5 g, 94.5 mmol, 1.0 eq) and ethyl vinyl ketone (15.9 g, 189 mmol, 2.0 eq.) in 150 mL of anhydrous THF was stirred at 25° C. for 3 day. After that a solution of 20% aqueous acetic acid (20 mL) was added below 20° C. and the mixture was stirred at 25° C. for 3 h. The solvent were removed under reduced pressure. 1 N HCl (80 mL) was added to the residue oil, followed by EtOAc (80 mL). TLC (PE/EA=4:1) showed a new spot was detected. The two phases were separated, and the aqueous phase was extracted with EtOAc (40 mL×3). The combined organic layers were dried over anhydrous $Na_2SO_4$. Filtered, the filtrate was concentrated under reduced pressure and the residue was purified by column chromatography on silica gel (PE/EA=40:2-10:1) to supply compound 49-C Ent1 (12 g, crude) as yellow oil, which was used for the next step.

Preparation of Compound 49-D Ent1

To a solution of compound 49-C Ent1 (2.5 g, 12.6 mmol, 1.0 eq.) in MeOH (18.9 mL) was added MeONa (2M, 18.9 mL, 37.8 mmol, 3.0 eq.) at 0° C., and the reaction mixture was heated to 55° C. for 16 h. TLC (PE/EA=4:1) showed compound 49-C Ent1 was consumed completely. The solvent was removed in vacuo to give a residue. EtOAc (30 mL) and $H_2O$ (20 mL) were added, and the two phase were separated. The aqueous layer was separated and extracted with EtOAc (20 mL×3). The combined organic phase was dried over anhydrous $Na_2SO_4$. Filtered and concentrated, the residue was purified by column chromatography on silica gel (PE/EA=20:1-4:1) to supply compound 49-D Ent1 (1.7 g, 74.9%) as yellow oil.

$^1$H-NMR: (400 MHz, $CDCl_3$) δ: 4.16-4.13 (m, 1H), 3.59 (d, J=11.2 Hz, 1H), 3.42-3.35 (m, 1H), 3.13 (d, J=11.2 Hz, 1H), 2.52-2.45 (m, 4H), 1.76 (s, 3H), 1.60-1.56 (m, 2H), 1.34 (s, 3H).

Preparation of Compound 49-E Ent1

To a solution of compound 49-D Ent1 (1.7 g, 9.4 mmol, 1.0 eq.) in THF (40 mL) was added t-BuOK (1M in THF, 14.1 mL, 14.1 mmol, 1.5 eq.) dropwise at 0° C. under $N_2$, and the reaction mixture was stirred at 25° C. for 1 h. Then MeI (2.0 g, 14.1 mmol, 1.5 eq.) in THF (10 mL) was added to the above reaction mixture at 0° C. After addition, the reaction mixture was stirred at 25° C. for another 1 h. TLC (PE:EA=4:1) showed the starting material was consumed. Saturated $NH_4Cl$ (5 mL) was added to quench the reaction, followed by EtOAc (10 mL) and $H_2O$ (10 mL). The two phases were separated, and the aqueous phase was extracted with EtOAc (10 mL×3). The combined organic phase was dried over $Na_2SO_4$, filtered, concentrated to give a crude product, which was purified by column chromatography (PE:EA=20:1 to 5:1) to give compound 49-E Ent1 as yellow oil (1.1 g, 60.1%).

$^1$HNMR: (400 MHz, $CDCl_3$) δ: 5.55 (s, 1H), 4.26-4.21 (m, 2H), 3.55 (d, J=10.4 Hz, 1H), 3.29 (d, J=10.4 Hz, 1H), 2.61-2.50 (m, 2H), 1.70-1.62 (m, 2H), 1.28 (s, 3H), 1.26 (s, 3H), 1.23 (s, 3H).

Preparation of Compound 49-F Ent1

To a solution of compound 49-E Ent1 (350 mg, 1.8 mmol, 1.0 eq.) in THF (8 mL) was added LDA (1.08 mL, 2.16 mmol, 1.2 eq.) at −78° C. under $N_2$. The reaction mixture was stirred at −78° C. for 1 h. Then TsCN (391 mg, 2.16 mmol, 1.2 eq.) in THF (2 mL) was added dropwise to the above reaction mixture at −78° C., and the reaction mixture was stirred at this temperature for 1.5 h. TLC (PE:EA=4:1) showed the starting material was consumed. Saturated $NH_4Cl$ (5 mL) was added to quench the reaction, followed by $H_2O$ (5 mL). The two phases were separated, and the aqueous phase was extracted with EtOAc (10 mL×2). The combined organic phase was dried over $Na_2SO_4$, filtered, concentrated to give a crude product, which was purified by column chromatography (PE/EA=20:1 to 4:1) to give a crude product compound 49-F Ent1 (0.2 g, 50.6%), which was used for the next step.

Preparation of Compound 49-Ent

A reaction mixture of compound 49-F Ent1 (200 mg, 0.91 mmol, 1.0 eq.) and DDQ (247 mg, 1.09 mol, 1.2 eq.) in PhMe (10 mL) was stirred under reflux for 1.5 h. TLC (PE/EA=3:1) showed the starting material was consumed with new spot detected. The solvent was concentrated to give a crude product, which was purified together with batch 19225-144-1 by prep-TLC (PE/EA=2:1) to give 49-Ent1 (157.6 mg, 79.6%) as white solid. The enantiomeric excess was not definitively determined.

¹H-NMR: (400 MHz, CDCl₃) δ: 7.20 (s, 1H), 5.68 (s, 1H), 4.37 (dd, J=17.2, 2.6 Hz, 2H), 3.67 (d, J=10.4 Hz, 1H), 3.29 (d, J=10.4 Hz, 1H), 1.60 (s, 3H), 1.38 (s, 3H), 1.36 (s, 3H).

HPLC: (95.16%)

MS: (M+H: 218.1)

Example 34. Synthesis of Compound 50-Ent1

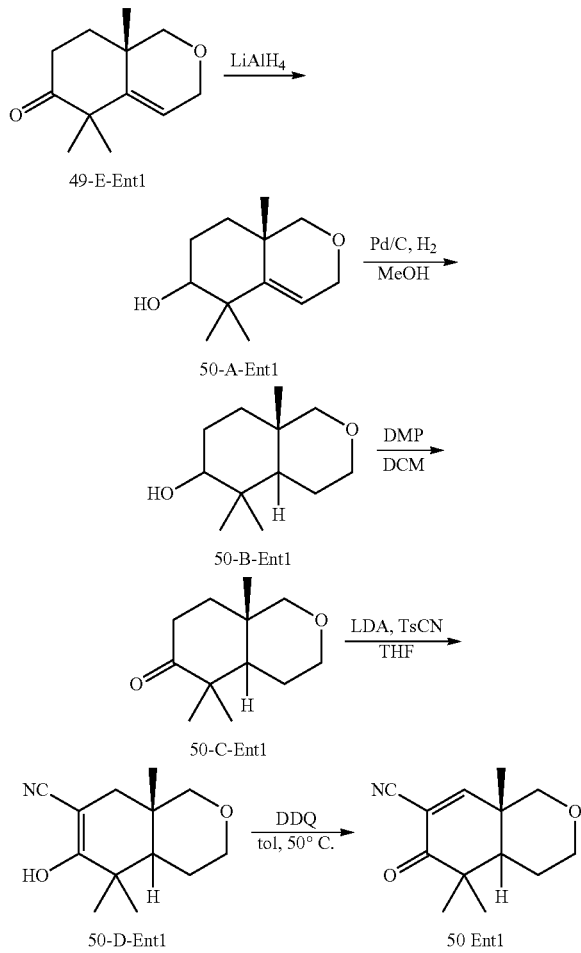

Preparation of Compound 50-A-Ent1

To a solution of compound 49-E-Ent1 (1.5 g, 7.73 mmol, 1.0 eq.) in THF (30 mL) was added LiAlH₄ (0.35 g, 9.27 mmol, 1.2 eq.) at 0° C. The mixture was stirred at this temperature for 1 h. TLC (PE/EA=4/1) showed the reaction was complete. The reaction was quenched with H₂O (0.35 mL) showly at 0° C., then, aq. NaOH (15%, 0.35 mL) and H₂O (1.05 mL) were added. The mixture was dried over Na₂SO₄, filtered and the filtrate was concentrated to give the crude compound 50-A-Ent1 (1.46 g, 96.6% yield) which was used for the next step without further purification as white solid.

¹HNMR: (400 MHz, CDCl₃) δ: 5.49 (s., 1H), 4.20 (s., 2H), 3.44 (d, J=10.4 Hz, 1H), 3.12 (d, J=10.4 Hz, 1H), 1.88-1.69 (m, 2H), 1.37-1.36 (m, 1H), 1.27 (s, 3H), 1.27-1.20 (m, 1H), 1.14 (s, 3H), 1.09 (s, 3H).

Preparation of Compound 50-B-Ent1

To a solution of compound 50-A-Ent1 (1.46 g, 7.45 mmol, 1.0 eq.) in MeOH (20 mL) was added Pd/C (10%, 0.3 g, 20% w/w) under N₂, the solution was degassed and purged with H₂ for 3 times. The mixture was stirred under H₂ (50 Psi) at 50° C. for 16 h. TLC showed the reaction was complete. The mixture was filtered and the filtrate was concentrated to give the crude compound 50-B-Ent1 (1.3 g, 89% yield) as oil which was used for the next step without further purification.

Preparation of Compound 50-C-Ent1

To a mixture of Compound 50-B-Ent1 (1.3 g, 6.56 mmol, 1.0 eq.) in DCM (20 mL) was added DMP (3.3 g, 7.87 mmol, 1.2 eq.), the mixture was stirred at 12° C. for 3 h. TLC (PE:EA=3:1) showed the reaction was complete. The mixture was filtered and the filtrate was washed with aq. NaHCO₃ (20 mL), the combined organic layer was concentrated to give the crude product which was purified by column chromatography on silica gel (PE:EA=20:1 to 5:1) to give compound 50-C-Ent1 (1.2 g, 93.7%) as oil.

Preparation of Compound 50-D-Ent1

To a solution of compound 50-C-Ent1 (1.2 g, 6.12 mmol, 1.0 eq.) in THF (15 mL) was added LDA (2M in hexane, 6.12 mL, 12.24 mmol, 2.0 eq.) at −78° C., the mixture was stirred at this temperature for 1.5 h, then, TsCN (2.2 g, 12.24 mmol, 2.0 eq.) in THF (5 mL) was added, the mixture was stirred at 12° C. for 16 h. TLC (PE/EA=3/1) showed the reaction was complete. The mixture was quenched with sat. NH₄Cl (30 mL) and extracted with EA (10 mL×3), the combined organic layers was dried over Na₂SO₄, filtered and the filtrate was concentrated to give crude product, which was purified by column chromatography on silica gel (PE:EA=20:1 to 10:1) to give compound 50-D-Ent1 (0.6 g, 44.4%) as solid.

Preparation of Compound 50-Ent1

To a solution of compound 50-D-Ent1 (300 mg, 1.35 mmol, 1.0 eq.) in toluene (50 mL) was added DDQ (0.6 g, 2.7 mmol, 2.0 eq.), the mixture was stirred at 50° C. for 16 h. TLC (PE:EA=3:1) showed the reaction was complete. The mixture was concentrated in vacuum. The residue was purified by column chromatography (PE/EA=15/1) to give the product which was further purified by prep-HPLC (Mobile phase A: 0.225% formic acid in water, Mobile phase B: acetonitrile; Column: Agela ASB 150*25 mm*5 um, Detection wavelength: 220 nm) to give compound 50-Ent1 (38 mg, 12.7% yield) as a light yellow solid. A single isomer of product was obtained. 2-D NMR NOESY studies were inconclusive in determining the relative stereochemistry of the ring fusion in this product.

HPLC: (Purity: 100%).

LCMS: (M+H: 220.1).

¹HNMR: (400 MHz, CDCl₃) δ: 7.33 (s, 1H), 3.98-3.88 (m, 1H), 3.75 (d, J=11.6 Hz, 1H), 3.36-3.35 (m, 1H), 3.24 (d, J=12.0 Hz, 1H), 1.84-1.83 (m, 1H), 1.75-1.67 (m, 1H), 1.34 (s, 3H), 1.34-1.33 (m, 1H), 1.30 (s, 3H), 1.17 (s, 3H).

Example 35. Synthesis of Compound 51-Ent1 and 51-Ent2

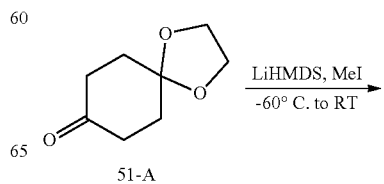

51-A

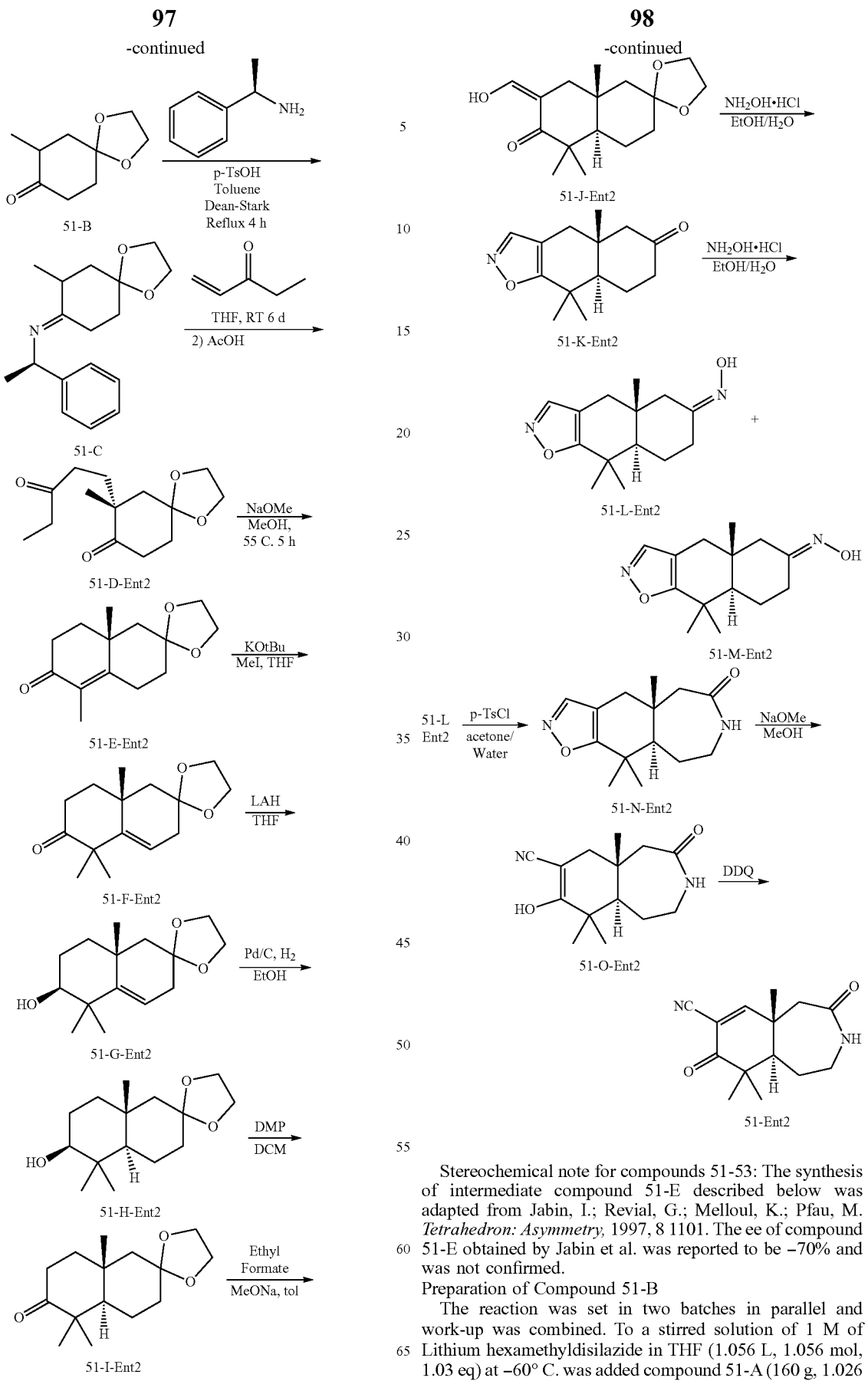

Stereochemical note for compounds 51-53: The synthesis of intermediate compound 51-E described below was adapted from Jabin, I.; Revial, G.; Melloul, K.; Pfau, M. *Tetrahedron: Asymmetry*, 1997, 8 1101. The ee of compound 51-E obtained by Jabin et al. was reported to be −70% and was not confirmed.

Preparation of Compound 51-B

The reaction was set in two batches in parallel and work-up was combined. To a stirred solution of 1 M of Lithium hexamethyldisilazide in THF (1.056 L, 1.056 mol, 1.03 eq) at −60° C. was added compound 51-A (160 g, 1.026 mol, 1 eq) in DMF (600 mL) slowly using an addition funnel and keeping the temperature below −60° C. The reaction mixture was allowed to stir below −60° C. for 1.5 h, and then treated with Methyl iodide (142 g, 1.00 mol, 0.99 eq) dropwise. Warmed to room temperature and stirred for 20 h. TLC (PE/EA=3:1) showed a little compound 51-A remained. The reaction mixture was quenched by half-saturated ammonium chloride solution (1.5 L) below 20° C. Extracted with MTBE (1 L×6). The combined organic phase was concentrated under reduced pressure to about 2 L, washed with brine (500 mL×3). The brine layer was extracted with MTBE (500 mL×3). The combined organic layer was dried over anhydrous $Na_2SO_4$, filtered and concentrated. The residue was azeotroped with heptane 4 times (300 mL×4). The resultant oil was slurried with heptanes (~800 mL) until it dissolved at room temperature, and then cooled to −10° C. with vigorous stirring. The reaction oiled out but eventually crystallized. The pale-yellow solid was filtered and rinsed with heptanes (300 mL×3) to supply compound 51-B (260 g, 74.5% yield) as pale-yellow solid.

$^1$H-NMR: (400 MHz, $CDCl_3$) δ: 4.14-3.92 (m, 4H), 2.81-2.58 (m, 2H), 2.44-2.31 (m, 1H), 2.16-1.89 (m, 3H), 1.78-1.67 (m, 1H), 1.03 (d, J=6.7 Hz, 3H)

Preparation of Compound 51-C

To 2 L of round bottom flask containing compound 51-B (50 g, 0.294 mol, 1.0 eq), (R)-1-phenylethan-1-amine (35.2 g, 0.291 mol, 1.0 eq) and TsOH (0.505 g, 2.94 mmol, 0.01 eq) in 600 mL of anhydrous toluene was fitted with a Dean-Stark and heated to reflux for 20 h. The reaction was cooled to room temperature, concentrated to about 300 mL, the formed solid was filtered off, the filtrate was concentrated under reduced pressure to supply crude compound 51-C which was used for next step directly.

Preparation of Compound 51-D Ent2

To the solution of compound 51-C (80.29 g, 0.294 mol, 1.0 eq) in 100 mL of anhydrous THF was added ethyl vinyl ketone (39.04 g, 0.441 mol, 1.5 eq). After addition the mixture was stirred at room temperature for 6 days under nitrogen. After that 120 mL of a solution of 20% aqueous acetic acid was added below 20° C. and the mixture was stirred at 25° C. for 3 h. The solvents were removed under reduced pressure. 1 N HCl (40 mL) was added to the residue oil. The mixture was diluted with water (100 mL), extracted with MTBE (200 mL×4), the combined organic layers was washed with brine (200 mL×2), dried over anhydrous $Na_2SO_4$. Filtered, the filtrate was concentrated under reduced pressure and the residue was purified by column chromatography on silica gel (PE/EA=30:1-20:1-10:1) to supply compound 51-D Ent2 (44 g, 59% yield) as yellow oil and 10 g of impure compound 51-D Ent2 as yellow oil.

$^1$H-NMR: (400 MHz, $CDCl_3$) δ: 3.98 (d, J=2.0 Hz, 4H), 2.65-2.46 (m, 2H), 2.45-2.32 (m, 3H), 2.28-2.17 (m, 1H), 2.14-2.06 (m, 1H), 2.01-1.90 (m, 3H), 1.85-1.69 (m, 2H), 1.10 (s, 3H), 1.03 (t, J=7.3 Hz, 3H).

Preparation of Compound 51-E Ent2

To a 2 L three-neck round bottom flask containing 600 mL of methanol in an ice/water bath was added Sodium (11.95 g, 0.52 mol, 3.0 eq) piecewise. Compound 51-D Ent2 (44 g, 0.173 mol, 1.0 eq) was added as a solution in 600 mL of methanol. The reaction mixture was heated to 55° C. for 5 h. TLC (PE/EA=3:1) showed compound 51-D Ent2 was consumed completely. The solvent was removed in vacuo. The residue was slurried in 1.0 L of MTBE and 160 mL of water. 1N HCl was added to pH of ~4 in ice-bath. The aqueous layer was separated and extracted with MTBE (300 mL×2). The organic phase was washed with brine (300 mL×3) and dried over anhydrous $Na_2SO_4$. Filtered and concentrated, the residue was purified by column chromatography on silica gel (PE/EA=50:1-30:1-15:1) to supply compound 51-E Ent2 (33 g, 80% yield) as pale-yellow oil.

$^1$H-NMR: (400 MHz, $CDCl_3$) δ: 4.07-3.98 (m, 2H), 3.97-3.89 (m, 2H), 2.75 (td, J=3.7, 15.0 Hz, 1H), 2.61-2.34 (m, 3H), 1.97-1.89 (m, 1H), 1.88-1.70 (m, 6H), 1.68-1.62 (m, 2H), 1.35 (s, 3H).

Preparation of Compound 51-F Ent2

Potassium tert-butoxide (18.16 g, 162 mmol, 1.5 eq) was added to the solution of compound 51-E Ent2 (25.5 g, 108 mmol, 1 eq) in 900 mL of THF by portionwise at 0-5° C., then the mixture was stirred at 25° C. for 1.5 h. Methyl iodide (34.88 g, 246 mmol, 2.3 eq) was added to the mixture at 0° C. by dropwise, and then stirred at 20-25° C. for 18 h. TLC (PE:EA=4:1) showed compound 51-E Ent2 was remained and the desired product was observed. 50 mL of saturated $NH_4Cl$ was added to the mixture and the mixture was extracted with EtOAc (200 mL×3). The organic layers were combined and washed with 100 mL of brine, dried over anhydrous $Na_2SO_4$, filtered and concentrated. The residue was purified by column chromatography on silica gel (PE/acetone=200:1) to give compound 51-F Ent2 (12 g, 52% yield) as yellow oil.

Preparation of Compound 51-G Ent2

To the suspension of LAH (7.459 g, 38.2 mmol, 1.2 eq) in 150 mL of anhydrous THF was added compound 51-F Ent2 (8.0 g, 32 mmol, 1.0 eq) in 20 mL of anhydrous THF by dropwise. After addition the mixture was stirred at 25° C. for 1.5 h. TLC (PE:EA=3:1) showed compound 51-F Ent2 was consumed completely. 1.45 mL of water was added slowly (caution: gas evolution), then 1.45 mL of 15% aqueous NaOH and 4.5 mL of water were added in turn. The mixture was diluted with EA (300 mL) and stirred with anhydrous $Na_2SO_4$ (20 g) for 30 min, filtered through a pad of celite. The filter cake was washed with EA (500 mL×2). The combined filtrate was concentrated under reduced pressure to supply crude compound 51-G Ent2 (8.0 g) as pale-yellow oil.

$^1$H-NMR: (400 MHz, $CDCl_3$) δ: 5.52 (t, J=3.7 Hz, 1H), 4.05-3.85 (m, 4H), 3.27 (d, J=8.2 Hz, 1H), 2.47-2.36 (m, 1H), 2.34-2.24 (m, 1H), 1.89-1.76 (m, 1H), 1.74-1.62 (m, 3H), 1.60-1.51 (m, 2H), 1.47 (br. s., 1H), 1.29 (s, 3H), 1.17 (s, 3H), 1.07 (s, 3H).

Preparation of Compound 51-H Ent2

To a solution of compound 51-G Ent2 (8 g, 31.7 mmol, 1.0 eq) in 80 mL of EtOH was added $Pd(OH)_2$/C (2.0 g) under $N_2$ atmosphere. The suspension was degassed under vacuum and purged with $H_2$ for several times. The mixture was stirred under $H_2$ (15 psi) at 20° C. for 24 hours. TLC (PE/EA=3:1, $KMnO_4$) showed compound 51-G Ent2 was consumed completely. The suspension was filtered through a pad of Celite and the pad was washed with EtOAc (300 mL×2). The combined filtrate was concentrated under reduced pressure to give crude compound 51-H Ent2 (10 g) as colorless oil. The crude compound 51-H Ent2 was slurried with MTBE/heptanes (6 mL/10 mL) and cooled to −10° C. The crystalline material formed was collected and dried under vacuum to supply compound 51-H Ent2 (4.0 g pure) as white solid.

$^1$H-NMR: (400 MHz, $CDCl_3$) δ: 3.97-3.94 (m, 2H), 3.90-3.86 (m, 2H), 3.28-3.22 (m, 1H), 1.88-1.67 (m, 1H), 1.64-1.53 (m, 2H), 1.52-1.49 (m, 4H), 1.32-1.28 (m, 2H), 1.21-1.09 (m, 1H), 1.04 (s, 3H), 1.01 (s, 3H), 0.9-0.8 (m, 1H), 0.79 (s, 3H).

Preparation of Compound 51-I Ent2

To a solution of compound 51-H Ent2 (2.0 g, 7.87 mmol, 1.0 eq) in 50 mL of DCM was added Dess-Marin Periodinane (DMP) (4.0 g, 9.45 mmol, 1.2 eq) in ice-bath. The mixture was stirred at 0-5° C. under N₂ atmosphere for 1.5 h. TLC (PE/EA=3:1) showed compound 51-H Ent2 was consumed completely. The mixture was diluted with DCM (50 mL), adjusted pH to 8 by adding saturated aqueous NaHCO₃. The mixture was filtered through a pad of celite, concentrated. The residue was stirred in EtOAc (100 mL) and filtered, concentrated, purified by column chromatography on silica gel (PE/EA=50:1-40:1-30:1) to supply compound 51-I Ent2 (1.4 g, 72.4% yield) as a colorless solid.

¹H-NMR: (400 MHz, CDCl₃) δ: 4.06-3.81 (m, 4H), 2.69-2.68 (m, 1H), 2.38-2.36 (m, 1H), 1.94-1.84 (m, 1H), 1.74-1.46 (m, 6H), 1.43-1.34 (m, 2H), 1.21 (s, 3H), 1.11 (s, 3H), 1.04 (s, 3H).

Preparation of Compound 51-J Ent2

To a solution of compound 51-I Ent2 (4.5 g, 17.85 mmol, 1.0 eq) in 28 mL of Ethyl formate (26.39 g, 357 mmol, 20.0 eq) was added NaOMe (11.23 mL, 60.69 mmol, 3.4 eq, 5.4 M in MeOH) at 0-5° C. The mixture was stirred at 23° C. under N₂ atmosphere for 30 min, slurried with toluene (30 mL) for 4 h. TLC (PE/EA=6:1) showed compound 51-I Ent2 was consumed completely. The reaction was quenched by addition of water (150 mL), adjusted pH to 5 by adding AcOH, extracted with EtOAc (50 mL×3). The combined organic layer was washed with brine (30 mL×2), dried over anhydrous Na₂SO₄, filtered, concentrated under reduced pressure to supply crude compound 51-J Ent2 (5.0 g) as pale-yellow solid.

Preparation of Compound 51-K Ent2

To a solution of compound 51-J Ent2 (5.0 g, 17.8 mmol, 1.0 eq) in 200 mL of EtOH/H₂O (V:V=10:1) was added hydrochloride hydroxylamine (1.23 g, 17.8 mmol, 1.0 eq) in 20 mL of EtOH/H2O (V:V=10:1) by dropwise. After addition the mixture was stirred at 50° C. for 18 h. TLC (PE/EA=2:1) showed compound 51-J Ent2 was consumed completely. The mixture was concentrated under reduced pressure to about 10 mL, diluted with water (100 mL), adjusted pH to 7 by adding saturated aqueous NaHCO₃. Extracted with EtOAc (50 mL×3). The combined organic layer was washed with brine (30 mL×2), dried over anhydrous Na₂SO₄, filtered, and concentrated under reduced pressure, the residue was slurried with MTBE (10 mL), filtered. The filter cake was collected to supply compound 51-K Ent2 (2.1 g, 51% yield) as white solid and a second crop of 1.0 g of impure compound 51-K Ent2 as yellow solid.

¹HNMR: (400 MHz, CDCl₃) δ: 8.03 (s, 1H), 2.53-2.20 (m, 6H), 2.16-2.06 (m, 1H), 2.05-1.97 (m, 1H), 1.93-1.77 (m, 1H), 1.42 (s, 3H), 1.24 (s, 3H), 0.92 (s, 3H).

Preparation of Compounds 51-L Ent2 and 51-M Ent2

Compound 51-K Ent2 (2.30 g, 9.86 mmol) and Hydroxylamine hydrochloride (822.21 mg, 11.83 mmol, 492.34 uL) were combined in 30 mL of ethanol and heated to 50° C. After 2 h, the reaction was concentrated to dryness and deposited on 10 g silica gel. The reaction was purified by silica gel chromatography using a 25-35% gradient of ethyl acetate in heptane to afford two white crystalline solids. The first eluting isomer was assigned the structure of compound 51-L Ent2 (900.00 mg, 3.62 mmol, 36.76% yield) The second eluting isomer was assigned the structure of compound 51-M Ent2 (1.10 g, 4.43 mmol, 44.93% yield). The configuration of the oximes so assigned was confirmed by subsequent Beckmann rearrangement to form compound 51-N Ent2 (below).

Data for 51-L Ent2:

¹H NMR (400 MHz, CHLOROFORM-d) δ ppm 8.06 (s, 1H) 6.79 (s, 1H) 3.34 (dd, J=13.4, 2.4 Hz, 1H) 2.52-2.59 (m, 1H) 2.41 (d, J=2.0 Hz, 2H) 2.15 (td, J=13.5, 5.1 Hz, 1H) 1.93-2.00 (m, 1H) 1.62-1.80 (m, 3H) 1.57 (s, 1H) 1.38 (s, 3H) 1.23 (s, 3H) 0.92 (s, 3H).

Data for 51-M Ent2:

¹H NMR (400 MHz, CHLOROFORM-d) δ ppm 8.03-8.06 (m, 1H) 7.26 (s, 1H) 3.54 (ddt, J=14.2, 4.4, 2.1, 2.1 Hz, 1H) 2.33-2.41 (m, 2H) 2.25 (dd, J=13.4, 2.1 Hz, 1H) 2.10 (d, J=13.6 Hz, 1H) 1.93 (ddt, J=13.0, 5.5, 2.7, 2.7 Hz, 1H) 1.54-1.80 (m, 4H) 1.38-1.40 (m, 3H) 1.20-1.24 (m, 3H) 0.90 (s, 3H)

Preparation of Compound 51-N Ent2

Compound 51-L Ent2 was dissolved in 30 mL acetone and treated with 9 mL sat. NaHCO₃ and 3 mL water. To this mixture was added Tosyl chloride (682.53 mg, 3.58 mmol) in 10 mL acetone. The reaction was heated to reflux for 3 h, then cooled to RT and stirred overnight. LC/MS indicates reaction was incomplete. To the reaction was added an additional charge of 500 mg of Ts-Cl and the reaction was again heated at reflux for 3 h. The reaction was allowed to cool and stir overnight. The reaction was concentrated to remove acetone and redissolved in ethyl acetate. The layers were separated and the organic phase was washed with sat. NaHCO₃ and brine, dried over MgSO₄, filtered, and concentrated. The reaction was purified on a 24 g silica gel column eluted with a gradient of 35-70% acetone in heptane to afford compound 51-N Ent2 (360.00 mg, 1.45 mmol, 80.99% yield).

Data for 51-N Ent2:

¹H NMR (400 MHz, DMSO-d₆) δ ppm 8.34 (s, 1H) 7.60 (br s, 1H) 3.04-3.21 (m, 2H) 2.74 (d, J=13.1 Hz, 1H) 2.14-2.38 (m, 2H) 1.84-2.00 (m, 2H) 1.74 (dd, J=12.3, 3.0 Hz, 1H) 1.37-1.53 (m, 1H) 1.19-1.27 (m, 5H) 1.13 (s, 3H) 0.84 (s, 3H)

Preparation of Compound 51-0 Ent2

Compound 51-N Ent2 (26 mg, 0.10 mmol) was dissolved in 1 mL of methanol and treated with 5.4 M of Sodium methoxide in methanol(0.06 mL, 0.3 mmol). The reaction was monitored for disappearance of starting material. Upon completion, the reaction was concentrated to dryness and diluted with ethyl acetate and water. The pH was adjusted to 3 with 1N HCl and the organic phase was separated, dried over MgSO₄, filtered, and concentrated.

¹H NMR (400 MHz, DMSO-d6) δ ppm 9.88 (s, 1H) 7.56 (br s, 1H) 2.95-3.16 (m, 2H) 2.57 (d, J=13.1 Hz, 1H) 2.16 (d, J=15.3 Hz, 1H) 1.71-1.87 (m, 3H) 1.54 (dd, J=12.2, 2.6 Hz, 1H) 1.27-1.44 (m, 1H) 1.11 (s, 3H) 0.97 (s, 3H) 0.90 (s, 3H).

Preparation of Compound 51-Ent2

Compound 51-0 Ent2 (31 mg, 0.12 mmol) in 3 mL benzene was treated with Dichlorodicyanoquinone (DDQ) (34 mg, 0.15 mmol) and heated to reflux for 3 h. The reaction was cooled to RT and filtered and rinsed with benzene. The filtrate was concentrated and purified by silica gel column chromatography using 2.5% methanol in dichloromethane using a 4 g silica gel cartridge.

Data for 51-Ent2:

¹H NMR (400 MHz, CHLOROFORM-d) δ ppm 1.05 (s, 14H) 1.20 (s, 3H) 1.30 (s, 3H) 1.69-1.98 (m, 3H) 2.42 (dd, J=13.93, 1.63 Hz, 1H) 2.72 (d, J=13.80 Hz, 1H) 3.11-3.42 (m, 2H) 6.12 (br. s., 1H) 7.29 (s, 1H).

HPLC Purity: 95%

LC/MS (M+H)=247.

Preparation of Compound 51-Ent1

Compound 51-Ent1 was prepared in a manner analogous to that described above for 51-Ent2 using (S)-1-phenylethan-1-amine in place of (R)-1-phenylethan-1-amine.

¹H NMR: (400 MHz, CD₃CN) δ: 7.62 (s, 1H), 6.35 (br, 1H), 3.18-3.24 (m, 2H), 2.80 (d, J=14.0 Hz, 1H), 2.35 (dd,

J=2.0, 14.0 Hz, 1H), 2.11 (dd, J=2.0, 12.0 Hz, 1H), 1.87-1.92 (m, 1H), 1.69-1.79 (m, 1H), 1.28 (s, 3H), 1.21 (s, 3H), 1.08 (s, 3H)

HPLC: (Purity: 97.76%)
SFC: (ee: 99.74%)
LCMS: (M+H: 247.1)

Example 36. Synthesis of Compound 52-Ent1 and 52-Ent2

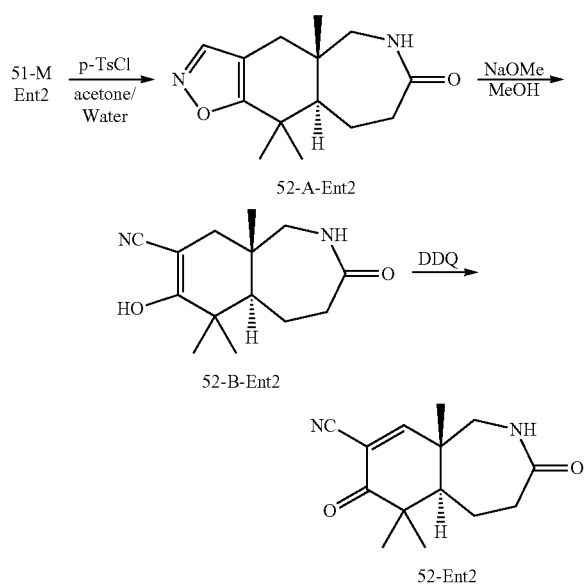

Preparation of Compound 52-A Ent2

Compound 51-M Ent2 (511.00 mg, 2.06 mmol) was dissolved in 30 mL of acetone and treated with 9 mL of sat. NaHCO₃ solution and 3 mL of water. The reaction was treated with p-Tosyl chloride (785.48 mg, 4.12 mmol) in 4 mL of acetone and heated to 60° C. for 3 h. The reaction was allowed to cool and stir overnight. The reaction was concentrated to remove acetone and redissolved in ethyl acetate. The layers were separated and the organic phase was washed with sat. NaHCO₃ solution and brine, dried over MgSO₄, filtered, and concentrated. Purification on a 24 g silica gel column eluted with 35-60% acetone in heptane afforded compound 52-A Ent2 (330.00 mg, 1.33 mmol, 64.51% yield) as a white solid.

Data for 52-A Ent2: ¹H NMR (400 MHz, DMSO-d6) δ ppm 8.35 (s, 1H) 7.48 (br s, 1H) 3.23 (br d, J=12.8 Hz, 1H) 2.53-2.69 (m, 1H) 2.02-2.30 (m, 3H) 1.85 (br dd, J=14.2, 8.2 Hz, 1H) 1.64 (br d, J=11.8 Hz, 1H) 1.41 (q, J=12.6 Hz, 1H) 1.26 (s, 3H) 1.10 (s, 3H) 0.76 (s, 3H).

Preparation of Compound 52-B Ent2:

To a solution of compound 52-A Ent2 in 5 mL methanol was added 5.4 M of Sodium methoxide in methanol(0.29 mL, 1.6 mmol). After 3 h, the reaction was concentrated and partitioned between water and ethyl acetate. 1N HCl was used to adjust pH to 3. The organic phase was separated and washed with brine, dried over MgSO₄, filtered and concentrated. LC/MS and NMR show incomplete conversion to product (~90% conversion). The intermediate was carried on crude to the next step.

LC/MS (M+H)=249.

Preparation of Compound 52-Ent2

Compound 52-B Ent2 (120 mg, 0.48 mmol) in 10 mL benzene (insoluble) was treated with Dichlorodicyanoquinone (DDQ, 0.115 g, 0.507 mmol) and heated to reflux for 4 hours. The reaction was cooled to RT, filtered, and rinsed with benzene. The crude material was purified twice using silica gel chromatography using heptanes/acetone as the eluent to afford a product containing ~7% of an impurity. Further purification by SFC afforded 98% pure 52-Ent2.

¹H NMR (400 MHz, DMSO-d6) δ ppm 8.01 (s, 1H) 7.60 (br s, 1H) 3.40 (br s, 5H) 3.29 (dd, J=14.7, 4.9 Hz, 1H) 2.97 (dd, J=14.7, 7.7 Hz, 1H) 2.36-2.47 (m, 1H) 2.25 (br dd, J=13.9, 7.4 Hz, 1H) 2.03 (dd, J=11.8, 2.0 Hz, 1H) 1.69-1.83 (m, 1H) 1.41-1.60 (m, 1H) 1.15 (s, 3H) 1.06 (s, 3H) 0.97 (s, 3H).

HPLC Purity: 98%
LC/MS (M+H)=247.

Preparation of Compound 52-Ent1

Compound 52-Ent1 was prepared in a manner analogous to that described above for 52-Ent2 using (S)-1-phenylethan-1-amine in place of (R)-1-phenylethan-1-amine.

Example 37. Synthesis of Compound 53-Ent2

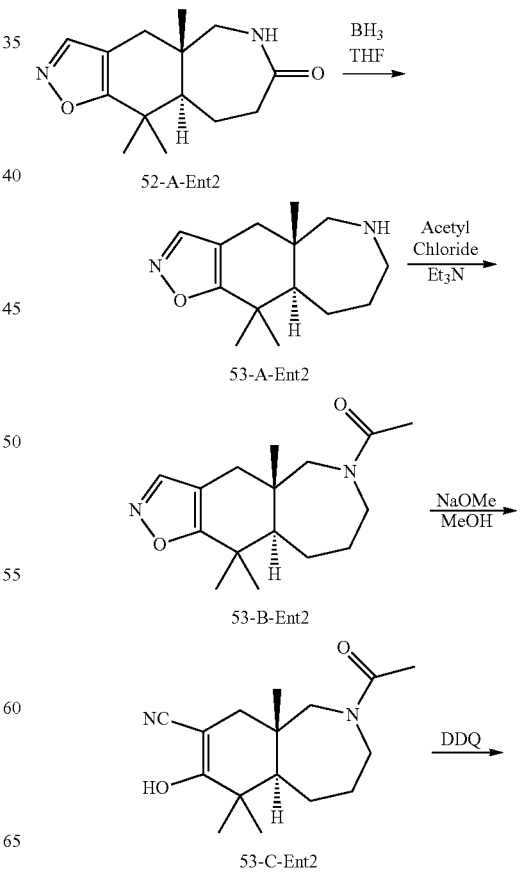

-continued

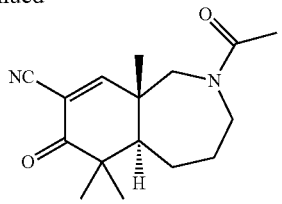

53-Ent2

Preparation of Compound 53-A Ent2:

Compound 52-A Ent2 (100.00 mg, 402.71 umol) in 4 mL of anhydrous THF was treated with borane; tetrahydrofuran (1 M, 1.61 mL) overnight. The reaction was quenched by the slow addition of 1 mL of 1N HCL and allowed to stir for 3 h. The reaction was quenched with sat $Na_2CO_3$ until pH of 12. Extracted with ethyl acetate and washed with brine. The reaction was dried over $MgSO_4$, filtered, and concentrated. The product was purified by an acid/base extraction as follows: The crude material as partioned between 1N HCl and ethyl ether. The ethyl ether layer ("neutral organic) was discarded. The pH of the HCl layer was adjusted to 12 using 1N NaOH and then extracted with dichloromethane. The dichloromethane layer was dried over $MgSO_4$, filtered, and concentrated to afford 53-A Ent2 (51.00 mg, 217.63 umol, 54.04% yield).

Data for 53-A Ent2:

$^1$H NMR (400 MHz, CHLOROFORM-d) δ ppm 8.03 (s, 1H) 3.23 (dd, J=11.4, 5.6 Hz, 1H) 2.81 (d, J=14.1 Hz, 1H) 2.65 (td, J=12.2, 4.5 Hz, 1H) 2.44-2.57 (m, 2H) 2.00 (d, J=14.8 Hz, 1H) 1.79-1.93 (m, 2H) 1.70 (br dd, J=13.2, 5.9 Hz, 1H) 1.35-1.55 (m, 3H) 1.33 (s, 3H) 1.23 (s, 3H) 0.83 (d, J=0.8 Hz, 3H).

Preparation of Compound 53-B Ent2:

Compound 53-A Ent2 (51.00 mg, 217.63 umol) in 3 mL of anhydrous DCM was treated with triethylamine (66.07 mg, 652.90 umol, 90.51 uL) and Acetyl chloride (25.63 mg, 326.45 umol, 23.30 uL). After 10 min, the reaction was quenched by addition of sat. $NaHCO_3$ solution and diluted with ethyl acetate. The layers were separated layers and the organic phase was washed with brine. The organic phase was dried over $MgSO_4$, filtered, and concentrated to afford crude 53-B Ent2 (60.00 mg, 217.10 umol, 99% yield).

LC/MS (M+H)=277.

Preparation of Compound 53-C Ent2

To a solution of 53-B Ent2 (60.00 mg, 217.10 umol) in 3 mL of methanol was added sodium methoxide (375.29 mg, 1.74 mmol, 25% purity) The reaction was allowed to stir for 3 days and formed a single peak of the desired mass by LC/MS. The reaction was concentrated and partioned between ethyl acetate and water. The aqueous phase was adjusted to a pH of 3 using 1 N HCl and the organic phase was separated and washed with brine, dried over $MgSO_4$, filtered, and concentrated to afford crude 53-C Ent2. LC/MS (M+H)=277.

Preparation of Compound 53-Ent2

Compound 53-C Ent2 (80.00 mg, 289.47 umol) was dissolved in 6 mL of anhydrous benzene, treated with DDQ (72.28 mg, 318.41 umol), and heated to reflux for 4 h. The reaction was cooled to RT and filtered. The filtrate was concentrated and deposited on 400 mg of silica gel and purified twice using 30% acetone in heptane to afford a white solid, 42 mg of 53-Ent2. The compound is a single peak by TLC and HPLC analysis but appears to be a ~4:1 mixture of atropisomers by $^1$H-NMR.

Data for 53-Ent2:

$^1$H-NMR. (d6-DMSO): δ ppm 8.12 (s, 0.8H), 8.05 (s, 0.2H), 3.72 (d, J=14.8 Hz, 0.2H), 3.58 (series of m, 1.8H), 3.40-3.15 (series of m, 2H), 2.09 (m, 0.2H), 2.04 (s, 0.6H), 2.02 (s, 2.4H), 1.90-1.65 (series of m, 2H), 1.51 (m, 2H), 1.14 (s, 1.2H), 1.13 (s, 2.4H), 1.10 (s, 2.4H), 0.99 (m, 3H).

LC/MS (M+H): 275.

HPLC Purity: 99%

Example 38. Synthesis of Compound 54

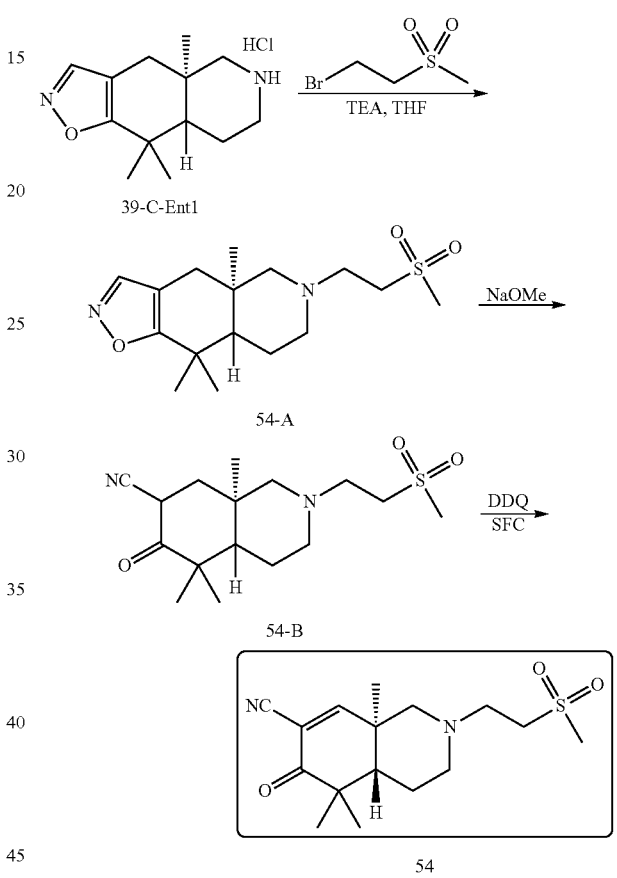

Preparation of Compound 54-A:

To a solution of compound 39-C-Ent1 (300 mg, 1.36 mmol, 1.0 eq.), and TEA (274 mg, 2.72 mmol, 2 eq) in THF (10 mL) was added 1-bromo-2-(methylsulfonyl)ethane (507 mg, 2.72 mmol, 2 eq). The mixture was stirred at 70° C. for 16 hours. The mixture turned to a black-brown solution. LCMS showed the reaction was completed. Most of the starting material was almost consumed and the desired product was detected. The mixture was concentrated in vacuo to give compound 54-A (400 mg, crude), which was used in the next step without purification.

LCMS: (M+H=327.1)

Preparation of Compound 54-B:

To a solution of compound 54-A (400 mg, 1.22 mmol, 1 eq) in MeOH (5 mL) was added a solution of NaOMe in MeOH (1.83 mL, 3.66 mmol, 3 eq, 2M). The mixture was stirred at 28° C. for 16 hours. The mixture turned to clear. TLC (PE:EA=5:1) showed the reaction worked. Most of the starting material was almost consumed and a new spot was detected. The mixture was diluted with water (25 mL) and extracted with EtOAc (25 mL×3). The combined organic phase was dried over Na2SO4, and filtered. The filtrate was concentrated in vacuo to give compound 54-B (300 mg, crude), which was used directly in the next step without purification.

Preparation of Compound 54:

To a solution of compound 54-B (300 mg, 0.92 mmol, 1 eq) in toluene (5 mL) was added DDQ (208 mg, 0.92 mmol, 1 eq). The mixture was stirred at 50° C. for 3 hours. The mixture turned to a black-brown suspension. TLC (PE: EA=5:1) showed the reaction worked. Most of the starting material was almost consumed but no obvious new spot was detected, and no desired product was detected in LCMS. The mixture was warmed to 110° C. and stirred at 110° C. for 16 hours. TLC (PE:EA=5:1) showed a new spot was detected. The mixture was poured into water (20 mL) and extracted with EtOAc (25 mL×3). The combined organic phase was washed with aq. NaHCO$_3$ (50 mL×3). The organic phase was dried over Na$_2$SO$_4$ and filtered. The filtrate was concentrated in vacuo to give the residue, which was purified by pre-TLC (PE:EA=3:1) to give 54 (160 mg, crude) which was further separated by SFC (C2 250 mm*30 mm, 10 um, condition: 0.1% NH$_3$H$_2$O MEOH) to give 54 (19209-72-1, 19.4 mg, Rt=6.20 min) as a white solid.

Spectra for Compound 54

$^1$H NMR (400 MHz, CDCl$_3$) δ 7.35 (s, 1H), 3.16-3.05 (m, 3H), 2.98 (s, 3H), 2.91-2.86 (m, 2H), 2.67-2.54 (m, 1H), 2.15-1.98 (m, 2H), 1.74-1.63 (m, 3H), 1.32 (s, 3H), 1.19 (s, 3H), 1.08 (s, 3H)

SFC: (ee: 98.60%)

HPLC: (Purity: 96.55%)

LCMS: (M+H 325.1)

Example 39: Synthesis of Compound 55

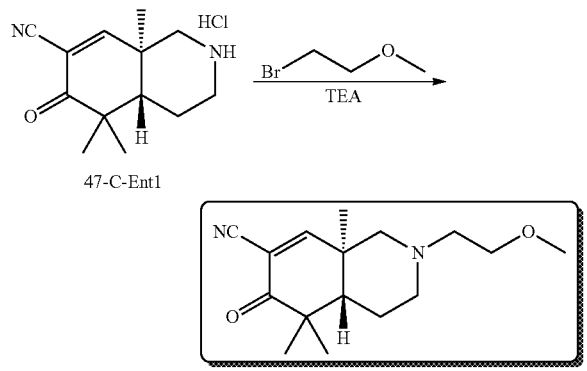

To a solution of compound 47-C-Ent1 (80 mg, 0.37 mmol, 1.0 eq.) and 1-bromo-2-methoxyethane (61 mg, 0.44 mmol, 1.2 eq.) in DMF (2 mL) was added TEA (112 mg, 1.11 mmol, 3.0 eq) dropwise. The mixture was stirred at 110° C. for 2 h. TLC (PE/EtOAc=1/1, Rf=0.5) showed compound 47-C-Ent1 was consumed completely. The mixture was purified by prep-TLC (PE/EtOAc=1/1) to give a racemic compound, which was separated by SFC (Condition: 0.1% NH$_3$H2O ETOH; Column: OJ (250 mm*30 mm, 5 um); Detection wavelength: 220 nm) to obtain 55 (28.8 mg) as a yellow oil.

Spectra of 55:

HPLC: (Purity: 97.91%)

MS: (M+H: 277.2)

SFC: (ee: 99.12%)

$^1$H NMR: (400 MHz, CDC$_3$) δ: 7.37 (s, 1H), 3.50-3.46 (m, 2H), 3.33 (s, 3H), 3.06 (d, J=6.8 Hz, 1H), 2.69 (d, J=10.4 Hz, 1H), 2.60-2.59 (m, 1H), 2.53-2.51 (m, 1H), 2.05-1.96 (m, 2H), 1.80-1.69 (m, 1H), 1.64-1.61 (m, 1H), 1.33 (s, 3H), 1.17 (s, 3H), 1.08 (s, 3H).

Example 40: Synthesis of Compounds 56-Ent and 56-Ent2

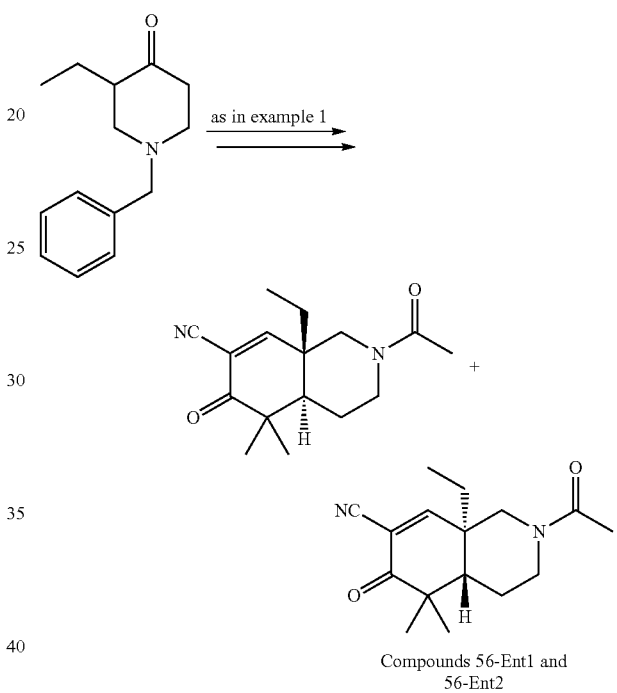

Compounds 56-Ent1 and 56-Ent2

Compounds 56-Ent1 and 56-Ent2 were made in a manner analagous to compounds 12-Ent1 and 12-Ent2 (example 1), starting from 1-benzyl-3-ethylpiperidin-4-one. The racemic mixture was separated by SFC (Mobile phase: 0.1% NH$_3$.H$_2$O/MeOH; Column: Chiralpak AD (250 mm*30 mm, 5 um); FlowRate: 60 mL/min) to give 56-Ent1 as the first eluting enantiomer (34.1 mg, Rt=3.415 min) as a light yellow solid and 56-Ent2 as the second eluting enantiomer. (28.3 mg, Rt=4.149 min) as a light yellow solid. The absolute stereochemistry was not determined.

Data for 56-Ent1:

HPLC: (Purity: 97.69%)

LCMS: (M+H: 275.2)

SFC: (Rt=3.024, ee: 99.05%)

$^1$H NMR: (400 MHz, DMSO) δ=8.22-8.05 (m, 1H), 4.79-4.52 (m, 1H), 4.08-3.88 (m, 1H), 3.01-2.82 (m, 1H), 2.43-2.26 (m, 1H), 2.07-2.01 (m, 4H), 1.76-1.49 (m, 3H), 1.40-1.27 (m, 1H), 1.13 (s, 3H), 1.05 (s, 3H), 0.91-0.82 (m, 3H)

1H NMR (T=80° C.): (400 MHz, DMSO) δ=8.04 (s, 1H), 4.75 (s, 1H), 3.95 (s, 1H), 2.67-2.66 (m, 1H), 2.33-2.32 (m, 1H), 2.04-2.01 (m, 4H), 1.79-1.77 (m, 2H), 1.76-1.74 (m, 1H), 1.15 (s, 1H), 1.08 (s, 3H), 0.91-0.87 (m, 3H)

Spectra for 56-Ent2:
 HPLC: (Purity: 97.24%)
 LCMS: (M+H: 275.1)
 SFC: (Rt=4.486, ee: 95.84%)
 $^1$H NMR: (400 MHz, DMSO) δ=8.21-8.04 (m, 1H), 4.80-4.51 (m, 1H), 4.08-3.87 (m, 1H), 3.01-2.83 (m, 1H), 2.36-2.27 (m, 1H), 2.10-2.00 (m, 4H), 1.86-1.58 (m, 2H), 1.53 (br d, J=10.2 Hz, 1H), 1.34 (br dd, J=6.8, 13.9 Hz, 1H), 1.13 (s, 3H), 1.05 (s, 3H), 0.92-0.79 (m, 3H)
 $^1$H NMR (T=80° C.): (400 MHz, DMSO) δ=8.06 (br s, 1H), 5.10-4.53 (m, 1H), 3.99 (br s, 1H), 2.68 (s, 1H), 2.34 (br s, 1H), 2.07-2.02 (m, 4H), 1.89-1.62 (m, 2H), 1.57 (br d, J=11.5 Hz, 1H), 1.40 (br d, J=11.5 Hz, 1H), 1.17 (s, 3H), 1.10 (s, 3H), 0.94-0.88 (t, J=7.5 Hz, 3H)

Synthesis of 57-Ent1 and 57-Ent2:

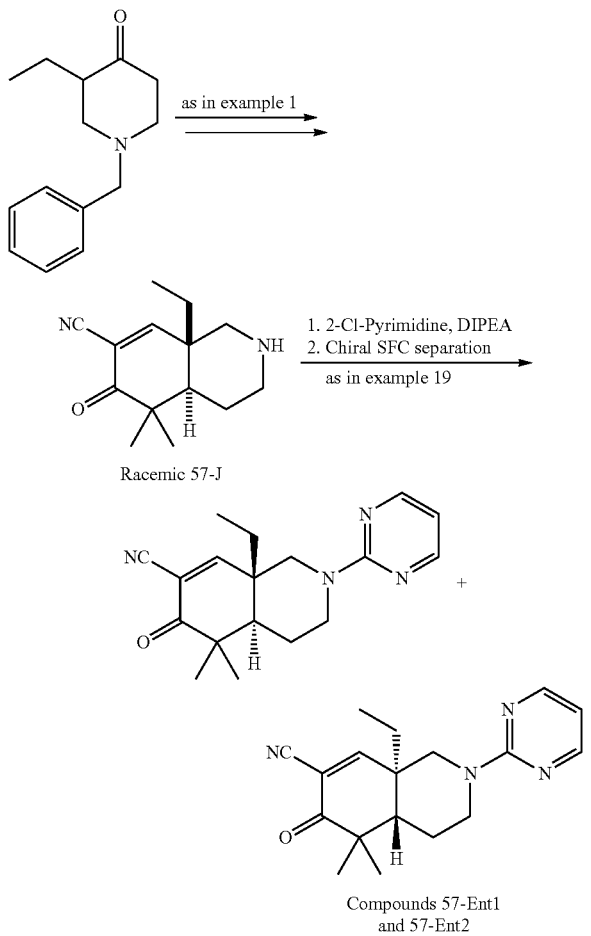

Compounds 57-Ent1 and 57-Ent2

Racemic compound 57-J was obtained in a manner analogous to that described for intermediate 12-J (example 1), starting from 1-benzyl-3-ethylpiperidin-4-one. Compounds 57-Ent1 and 57-Ent2 were synthesized in a manner analogous to that described for Compounds 30-Ent1 and 30Ent2 (example 19), using 57-J instead of 12-J. Compounds 57-Ent1 and 57-Ent2 were separated by chiral SFC (Mobile phase: Neu-MeOH; Column: Chiralpak OD (250 mm*30 mm, 5 um); FlowRate: 60 mL/min) to give the first eluting enantiomer called 57-Ent1 (22.0 mg, Rt=3.091 min) as a light yellow solid and the second eluting enantiomer called 57-Ent2 (23.2 mg, Rt=4.998 min) as a light yellow solid. The absolute stereochemistry was not determined.

Spectra for 57-Ent1:
 HPLC: (Purity: 95.28%)
 LCMS: (M+H: 311.2)
 SFC: (Rt=3.091, ee: 100%)
 $^1$H NMR: (400 MHz, CDCl3) δ=8.33 (d, J=4.7 Hz, 2H), 7.63 (s, 1H), 6.54 (t, J=4.7 Hz, 1H), 5.19 (dd, J=1.8, 13.1 Hz, 1H), 5.07-4.98 (m, 1H), 2.79 (dt, J=3.5, 12.7 Hz, 1H), 2.57 (d, J=11.7 Hz, 1H), 2.04-1.95 (m, 1H), 2.04-1.94 (m, 1H), 1.87-1.76 (m, 1H), 1.67 (br d, J=13.3 Hz, 1H), 1.58 (s, 6H), 1.51-1.42 (m, 1H), 1.26 (s, 3H), 1.19 (s, 3H), 0.97 (t, J=7.6 Hz, 3H)

Spectra for 57-Ent2:
 HPLC: (Purity: 96.60%)
 LCMS: (M+H: 311.2)
 SFC: (Rt=4.998, ee: 100%)
 $^1$H NMR: (400 MHz, CDCl3) δ=8.33 (d, J=4.7 Hz, 2H), 7.64 (s, 1H), 6.54 (t, J=4.7 Hz, 1H), 5.20 (dd, J=2.0, 12.9 Hz, 1H), 5.06-4.98 (m, 1H), 2.79 (dt, J=3.3, 12.8 Hz, 1H), 2.57 (d, J=12.9 Hz, 1H), 2.02-1.94 (m, 2H), 1.81 (dq, J=4.3, 12.7 Hz, 1H), 1.67 (br d, J=13.3 Hz, 1H), 1.56 (s, 6H), 1.51-1.43 (m, 1H), 1.26 (s, 3H), 1.19 (s, 3H), 0.97 (t, J=7.4 Hz, 3H)

Example 41: Synthesis of Compounds 58-Ent1 and 58-Ent2

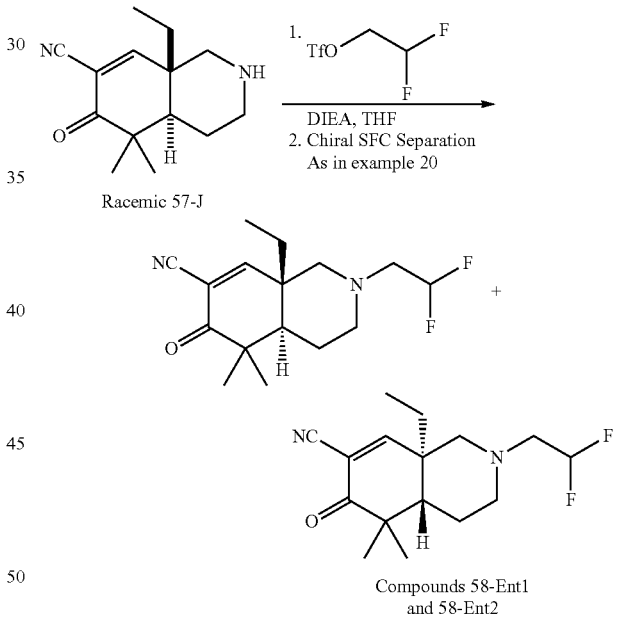

Compounds 58-Ent1 and 58-Ent2

Compounds 58-Ent1 and 58-Ent2 were synthesized in a manner analogous to that described for Compounds 31-Ent1 and 31Ent2 (example 20), using 57-J instead of 12-J. Chiral separation was performed by SFC (Mobile phase: Neu-MeOH; Column: Chiralpak AD (250 mm*30 mm, 5 um); FlowRate: 60 mL/min) to give the first eluting enantiomer called 58-Ent1 (23.9 mg, Rt=1.966 min) as a light yellow solid and the second eluting enantiomer called 58-Ent2 (38.4 mg, Rt=2.629 min) as a light yellow solid. The absolute stereochemistry was not determined.

Spectra for 58-Ent1:
 HPLC: (Purity: 99.74%)
 LCMS: (M+H: 297.1)
 SFC: (Rt=1.966, ee: 100%)

¹H NMR: (400 MHz, CDCl₃) δ=7.49 (s, 1H), 6.06-5.68 (m, 1H), 3.18-3.08 (m, 2H), 2.85-2.72 (m, 2H), 2.45-2.35 (m, 1H), 2.29 (dt, J=2.8, 11.5 Hz, 1H), 2.01 (br d, J=11.0 Hz, 1H), 1.86 (dq, J=4.3, 12.6 Hz, 1H), 1.56 (br dd, J=2.6, 13.0 Hz, 1H), 1.48-1.37 (m, 1H), 1.26 (br s, 1H), 1.18 (d, J=12.3 Hz, 6H), 0.91 (t, J=7.5 Hz, 3H)

Spectra for 58-Ent2:
  HPLC: (Purity: 99.74%)
  LCMS: (M+H: 311.2)
  SFC: (Rt=2.629, ee: 99.90%)
  ¹H NMR: (400 MHz, CDCl₃) δ=7.49 (s, 1H), 6.05-5.69 (m, 1H), 3.18-3.05 (m, 2H), 2.85-2.70 (m, 2H), 2.45-2.34 (m, 1H), 2.29 (dt, J=3.1, 11.6 Hz, 1H), 2.01 (d, J=11.0 Hz, 1H), 1.73-1.66 (m, 1H), 1.56 (br dd, J=2.4, 13.0 Hz, 1H), 1.42 (qd, J=6.9, 13.6 Hz, 1H), 1.26 (br s, 1H), 1.18 (d, J=12.6 Hz, 6H), 0.91 (t, J=7.5 Hz, 3H)

Example 42: Synthesis of Compound 59

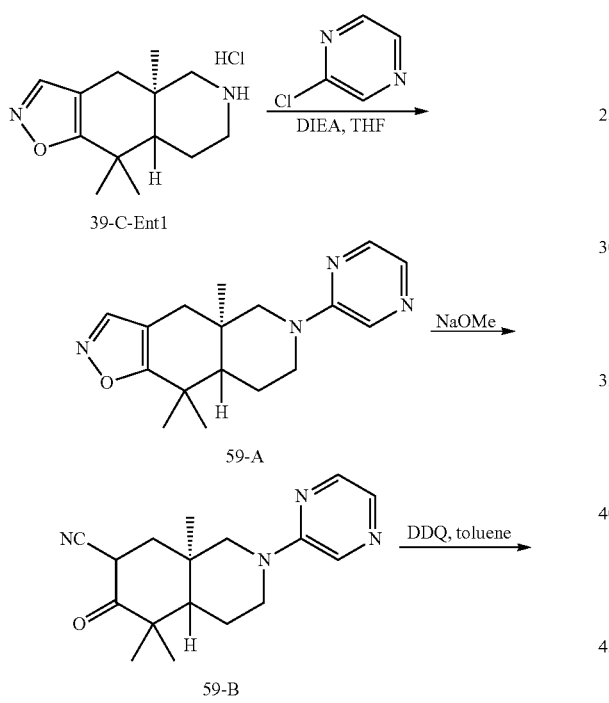

To a solution of compound 39-C-Ent1 (200 mg, 0.91 mmol, 1.0 eq) in 5 mL of DMF was added TEA (276 mg, 2.73 mmol, 3.0 eq) and 2-chloropyrazine (312 mg, 2.73 mmol, 3.0 eq). After addition, the mixture was stirred at 120° C. for 18 h. TLC (DCM:MeOH=10:1) indicated completion. The mixture was diluted with water (20 mL), extracted with EtOAc (15 mL×3). The combined organic layer was dried over anhydrous Na₂SO₄, filtered, concentrated and purified by prep-TLC (PE:EA=1:2) to supply compound 59-A (200 mg, mixture of cis- and trans-isomer) as yellow gum.

To a solution of compound 59-A (200 mg, 0.67 mmol, 1.0 eq) in 6 mL of anhydrous methanol was added NaOMe (1.34 mL, 2.68 mmol, 4.0 eq, 2 M in methanol). The mixture was stirred at 26° C.-30° C. for 18 h. TLC (PE/EA=1:2) showed no new spot was observed. NaOMe (1.34 mL, 2.68 mmol, 4.0 eq, 2 M in methanol) was added and the mixture was stirred at 26° C.-30° C. for 18 h. TLC (PE/EA=1:2) showed only one spot was observed. The mixture was concentrated; the residue was diluted with water (15 mL), adjusted pH to 7 by adding 1N HCl aq. and extracted with EtOAc (10 mL×3). The combined organic layer was dried over anhydrous Na₂SO₄, filtered, concentrated under reduced pressure to supply crude compound 59-B (130 mg) as pale-yellow gum.

To a solution of compound 59-B (100 mg, 0.34 mmol, 1.0 eq) in 4 mL/2 mL of toluene/MeCN was added DDQ (91 mg, 0.4 mmol, 1.2 eq). The mixture was stirred at 100° C. for 1 h. TLC (PE:EA=1:1) showed only one spot was observed. The mixture was concentrated under reduced pressure and purified by prep-TLC (PE:EA=2:3) for twice to supply compound 59 (25 mg), which was re-purified by SFC (column: AD 250 mm*30 mm, 5 um, condition: 0.1% NH₃.H₂O-EtOH) to give 59 (Rt=6.30 min, 3.5 mg, 3.5% yield) as pale-yellow gum.

¹HNMR: (400 MHz, CDCl₃) δ: 8.11 (s, 1H), 8.08-8.02 (m, 1H), 7.89 (d, J=2.4 Hz, 1H), 7.40 (d, J=1.5 Hz, 1H), 4.19-4.11 (m, 1H), 3.93-3.85 (m, 1H), 3.28 (m, 1H), 3.21-3.09 (m, 1H), 2.05-1.96 (m, 1H), 1.94-1.86 (m, 1H), 1.50-1.45 (m, 1H), 1.47 (s, 3H), 1.40 (s, 3H), 1.24 (s, 3H).

SFC: (Rt: 6.300 min, ee: 99.687%)
HPLC: (Purity: 100%)
LCMS: (M+H: 297.1)

Example 43: Preparation of Compounds 60-Ent1 and 60-Ent2

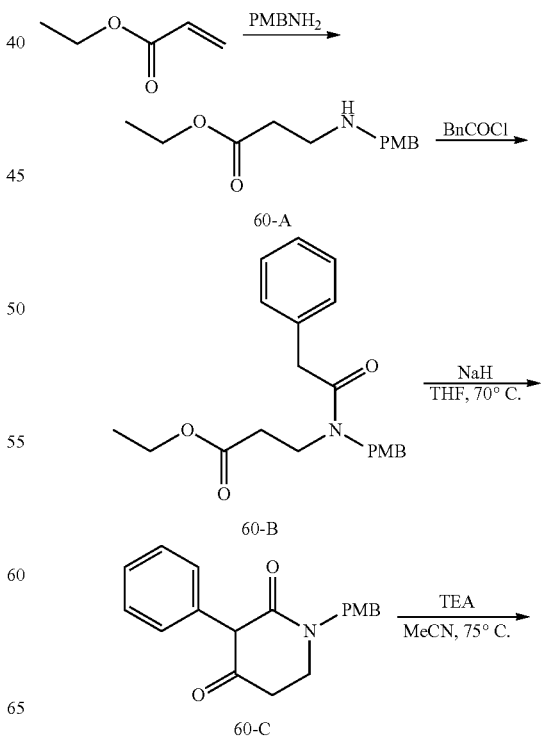

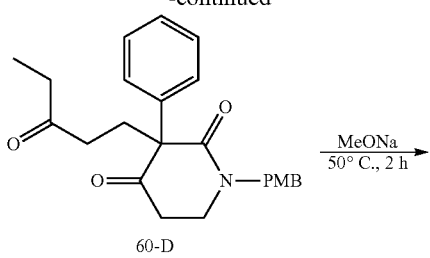

60-D

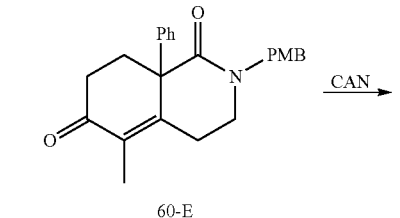

60-E

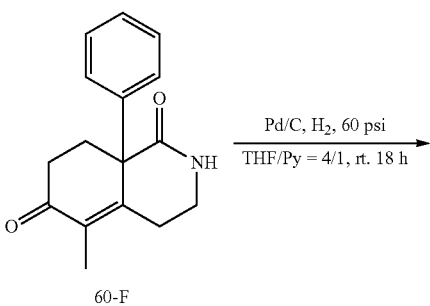

60-F

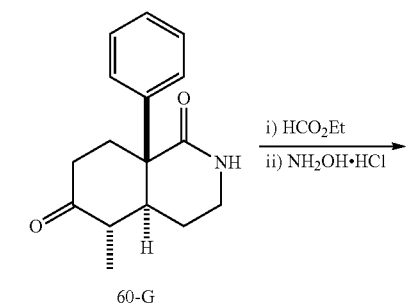

60-G

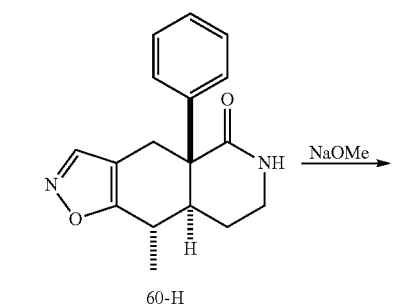

60-H

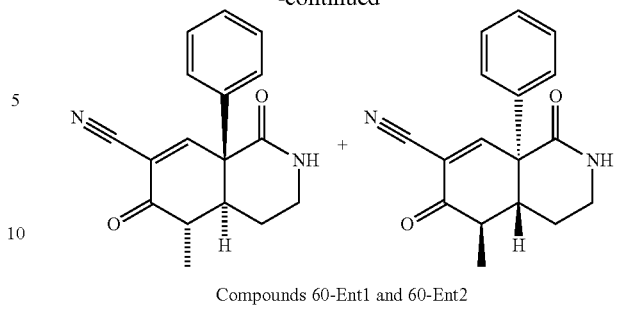

60-I

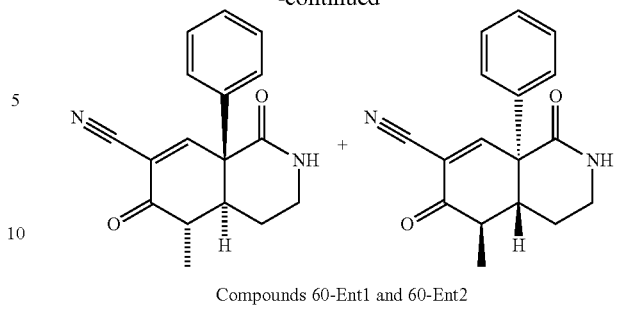

Compounds 60-Ent1 and 60-Ent2

Preparation of compound 60-A

To a solution of compound PMBNH$_2$ (50 g, 36.5 mmol, 1.0 eq) in EtOH (500 mL) was added compound methyl acrylate (36.5 g, 36.5 mmol, 1.0 eq) drop-wise. The reaction mixture was stirred at 15° C. for 16 hours. TLC (PE/EA=2:1) showed PMBNH$_2$ was consumed completely. The solvent was removed to give the crude compound 60-A (75 g, crude) as a yellow oil, which was used for the next step without further purification.

$^1$H NMR: (400 MHz, CDCl$_3$) δ=7.23 (d, J=8.6 Hz, 2H), 6.84 (d, J=8.6 Hz, 2H), 4.14 (q, J=7.0 Hz, 2H), 3.80 (s, 3H), 3.74-3.65 (m, 3H), 2.88 (t, J=6.6 Hz, 2H), 2.52 (t, J=6.5 Hz, 2H), 1.30-1.20 (m, 4H).

Preparation of Compound 60-B

To a solution of compound 60-A (20 g, 84 mmol, 1.0 eq) in acetone (200 mL) and H$_2$O (20 mL) was added K$_2$CO$_3$ (12 g, 84 mmol, 1.0 eq) and followed by BnCOCl (16 g, 84 mmol, 1.0 eq). The suspension solution was stirred at 28° C. for 3 hours. TLC (PE/EA=3:1) showed that the compound 60-A was consumed completely. The reaction mixture was diluted with 1 N HCl (200 mL) and extracted with EtOAc (200 mL×3). The combined organic layer was washed with brine (200 m L×2), dried over Na$_2$SO$_4$, filtered and concentrated to give compound 60-B (30 g, yield equivalent) as a yellow oil.

$^1$H NMR: (400 MHz, CDCl$_3$) δ=7.37-7.30 (m, 3H), 7.28-7.22 (m, 2H), 7.21-7.12 (m, 1H), 7.03 (d, J=8.8 Hz, 1H), 6.91-6.82 (m, 2H), 4.61-4.48 (m, 2H), 4.16-4.07 (m, 2H), 3.84-3.80 (m, 3H), 3.76-3.73 (m, 1H), 3.66-3.54 (m, 2H), 2.63 (t, J=7.0 Hz, 1H), 1.29-1.19 (m, 4H).

Preparation of Compound 60-C

To a solution of compound 60-B (30 g, 85 mmol, 1.0 eq) in THF (300 mL) was added NaH (3.4 g, 10.2 mmol, 1.2 eq) in portions at 25° C. The suspension was stirred at 70° C. for 16 h. TLC (PE/EA=3:1) showed the compound 60-B was consumed completely. The reaction mixture was diluted with H$_2$O (300 mL), adjusted pH=4 by 1N HCl and extracted with EtOAc (400 mL×2). The combined organic layer was washed with brine, dried over Na$_2$SO$_4$, filtered and concentrated to give compound 60-C (30 g, crude) as a yellow solid, which was used for the next step without further purification.

$^1$H NMR: (400 MHz, CDCl$_3$) δ=7.33-7.21 (m, 4H), 7.17-7.02 (m, 3H), 6.85-6.75 (m, 2H), 4.63 (d, J=2.3 Hz, 1H), 4.50-4.40 (m, 2H), 3.74 (d, J=5.5 Hz, 3H), 3.57-3.43 (m, 2H), 2.58-2.48 (m, 2H)

Preparation of Compound 60-D

To a solution of compound 60-C (30 g, 97.1 mmol, 1.0 eq) and TEA (11.8 g, 116.5 mmol, 1.2 eq) in MeCN (300 mL) was added EVK (9.7 g, 116.5 mmol, 1.2 eq). The reaction mixture was stirred at 75° C. for 16 hours. TLC (PE/EA=3:1) showed the compound 60-C was consumed completely.

The solvent was removed to give the crude compound 60-D (32 g, crude) as a yellow oil, which was used for next step without further purification.

LCMS: (M+H: 394.3)

Preparation of Compound 60-E

To a 1 L three-neck round bottom flask containing 460 mL of methanol in an ice/water bath was added Sodium (1.9 g, 81.4 mmol, 1.0 eq) piecewise. Compound 60-D (32 g, 81.4 mmol, 1.0 eq) was added as a solution in 50 mL of methanol. The reaction mixture was stirred at 50° C. for 2 h. TLC (PE/EtOAc=3:1) showed the compound 60-D was consumed completely. The reaction mixture was diluted with H$_2$O (500 mL), adjusted pH=4 by 1N HCl and extracted with EtOAc (300 mL×2). The combined organic layer was washed with brine, dried over Na$_2$SO$_4$, filtered and concentrated to obtained the residue, which was purified by column chromatography on silica gel (PE/EtOAc=10:1) to give compound 60-E (9.6 g, 32.0%) as a yellow solid.

$^1$H NMR: (400 MHz, CDCl$_3$) δ=7.35-7.25 (m, 5H), 7.10-7.02 (m, 2H), 6.83-6.74 (m, 2H), 4.58-4.48 (m, 2H), 3.76 (s, 3H), 3.04-2.95 (m, 1H), 2.82 (ddd, J=6.0, 9.5, 13.1 Hz, 1H), 2.68-2.58 (m, 3H), 2.57-2.41 (m, 1H), 2.50-2.41 (m, 1H), 2.34 (td, J=3.5, 17.1 Hz, 1H), 2.13-2.05 (m, 1H), 2.07 (dd, J=2.2, 4.7 Hz, 1H), 1.86 (s, 3H)

Preparation of Compound 60-F

To a solution of compound 60-E (4.9 g, 13.1 mmol, 1.0 eq) in MeCN/H$_2$O (100 mL, V=2:1) was added CAN (21.44 g, 39.2 mmol, 3.0 eq) at 0° C. in one portion. The mixture was stirred at 30-35° C. for 3 hours. TLC (PE:EA=1:2) showed the reaction was completed. Most of the starting material was consumed and a new spot was detected. The mixture was extracted with EtOAc (50 mL×2). The combined organic phase was dried over Na$_2$SO$_4$, filtered and concentrated to give crude, which was purified by column chromatography on silica gel (PE/EA=2:1-EA, 100%) to give compound 60-F (2.4 g, 72%) as a yellow solid.

$^1$H NMR (400 MHz, METHANOL-d4) δ: 7.39-7.29 (m, 5H), 3.19-3.10 (m, 1H), 2.87-2.71 (m, 3H), 2.47-2.33 (m, 2H), 2.30-2.20 (m, 1H), 2.06-2.00 (m, 1H), 1.89 (s, 3H).

Preparation of Compound 60-G

A mixture of compound 60-F (2 g, 3.92 mol, 1.0 eq.) and Pd(OH)$_2$/C (200 mg) in Py/THF (40 mL) was stirred under 50 psi of H$_2$ at 32° C. for 30 hours. LCMS indicated completion. The suspension was filtered through a pad of celite and washed with EA (30 mL×2), the filtrate was concentrated under reduce pressure to give a crude product, which was purified prep-HPLC (base) to give desired product 60-G (1.52 g, yield: 47%) as off-yellow solid.

$^1$H NMR (400 MHz, METHANOL-d$_4$) δ: 7.62 (br d, J=7.5 Hz, 2H), 7.40-7.28 (m, 3H), 3.27-3.22 (m, 1H), 3.11 (td, J=6.5, 13.0 Hz, 1H), 2.77-2.57 (m, 2H), 2.36-2.14 (m, 4H), 1.11 (d, J=6.6 Hz, 3H).

Preparation of Compound 60-H

To a solution of compound 60-G (300 mg, 1.17 mmol, 1 eq) in ethyl formate (1.74 g, 23.5 mmol, 20 eq) was added a solution of NaOMe/MeOH (0.74 mL, 3.99 mmol, 3.4 eq, 5.4M) at 0° C. dropwise. The mixture was stirred at 32-35° C. for 5 hours. LCMS (19207-134-1A) showed the reaction was completed. Most of the starting material was almost consumed. The mixture was poured into water (20 mL) and acidified to male PH=6-8. The mixture was extracted with EtOAc (25 mL×3). The combined organic phase was dried over Na$_2$SO$_4$, and filtered. The filtrate was concentrated in vacuo to give 320 mg of crude formylation product, which was used directly in the next step without purification.

To a solution of crude formylation product (320 mg, 1.12 mmol, 1 eq) in EtOH (20 mL) and water (2 mL) was added hydrochloride hydroxylamine (93 mg, 1.34 mmol, 1.2 eq). The mixture was stirred at reflux for 18 hours. The mixture turned to clear. LCMS showed the reaction was completed. Most of the starting material was almost consumed. The mixture was concentrated in vacuo to give the residue, which was treated with water (20 mL) and extracted with EtOAc (25 mL×3). The combined organic phase was dried over Na$_2$SO$_4$, and filtered. The filtrate was concentrated in vacuo to give the residue, which was purified by prep-HPLC (base) to give compound 60-H (150 mg, yield: 47%) as a white solid.

$^1$H NMR (400 MHz, METHANOL-d$_4$) δ: 8.35 (s, 1H), 7.27-7.14 (m, 5H), 3.61-3.54 (m, 1H), 3.45 (dt, J=6.0, 12.3 Hz, 1H), 3.34 (br s, 1H), 2.96 (dd, J=2.0, 16.8 Hz, 1H), 2.20-2.07 (m, 2H), 2.04-1.94 (m, 1H), 1.88-1.74 (m, 1H), 1.31 (br d, J=6.4 Hz, 3H).

Preparation of Compound 60-I

To a solution of compound 60-H (120 mg, 0.42 mmol, 1 eq) in MeOH (2 mL) was added a solution of NaOMe/MeOH (0.85 mL, 1.7 mmol, 4.0 eq, 2M). The mixture was stirred at 30° C. for 18 hours. TLC (PE:EA=1:1) showed most of the starting material was almost consumed and a new spot was detected. The mixture was poured into water (20 mL) and acidified with (2M) to male PH=6-8. The mixture was extracted with EtOAc (25 mL×3). The combined organic phase was dried over Na$_2$SO$_4$ and filtered. The filtrate was concentrated in vacuo to give compound 60-I (110 mg, crude) as colorless oil, which was used directly in the next step without purification.

Preparation of Compounds 60-Ent1 and 60-Ent2

To a solution of compound 60-I (110 mg, 0.39 mmol, 1 eq) in toluene (3 mL) was added DDQ (88.5 mg, 0.39 mmol, 1.0 eq). The mixture was stirred at 85° C. for 1 hour. The mixture turned to a suspension. TLC (PE:EA=1:3) showed most of the starting material was almost consumed and a new spot was detected. The mixture was concentrated in vacuo to give the residue, which was purified by column chromatography on silica gel (PE/EA=1:1) to give product (70 mg, yield: 63%) as a racemic mixture. The racemic mixture was further separated by SFC (column: OJ (250 mm*30 mm, 5 um) condition: 0.1% NH$_3$.H$_2$O-ETOH) to give 60-Ent1 (19207-143-1, 22.2 mg, yield: 31.2% Rt=4.078 min) and 60-Ent2 (19207-143-2, 17.6 mg, yield: 31.2%, Rt=6.090 min). Both are pale white solids.

Spectra for 60-Ent1

$^1$H NMR (400 MHz, METHANOL-d$_4$) δ: 8.26 (s, 1H), 7.49-7.28 (m, 5H), 3.61-3.43 (m, 2H), 2.67-2.52 (m, 1H), 2.40 (qd, J=6.6, 13.0 Hz, 1H), 1.87 (br dd, J=6.7, 14.1 Hz, 1H), 1.67-1.51 (m, 1H), 1.11 (d, J=6.7 Hz, 3H).

SFC: (Rt: 4.001 min, ee: 96.7%)

HPLC: (Purity: 98.43%)

LCMS: (M+H=281.1)

Spectra for 60-Ent2

$^1$H NMR (400 MHz, METHANOL-d$_4$) δ: 8.26 (s, 1H), 7.49-7.28 (m, 5H), 3.61-3.43 (m, 2H), 2.67-2.52 (m, 1H), 2.40 (qd, J=6.6, 13.0 Hz, 1H), 1.87 (br dd, J=6.7, 14.1 Hz, 1H), 1.67-1.51 (m, 1H), 1.11 (d, J=6.7 Hz, 3H).

SFC: (Rt: 6.042 min, ee: 96.9%)

HPLC: (Purity: 97.21%)

LCMS: (M+H=281.1)

Example 44: Preparation of Compounds 61-Ent1 and 61-Ent2

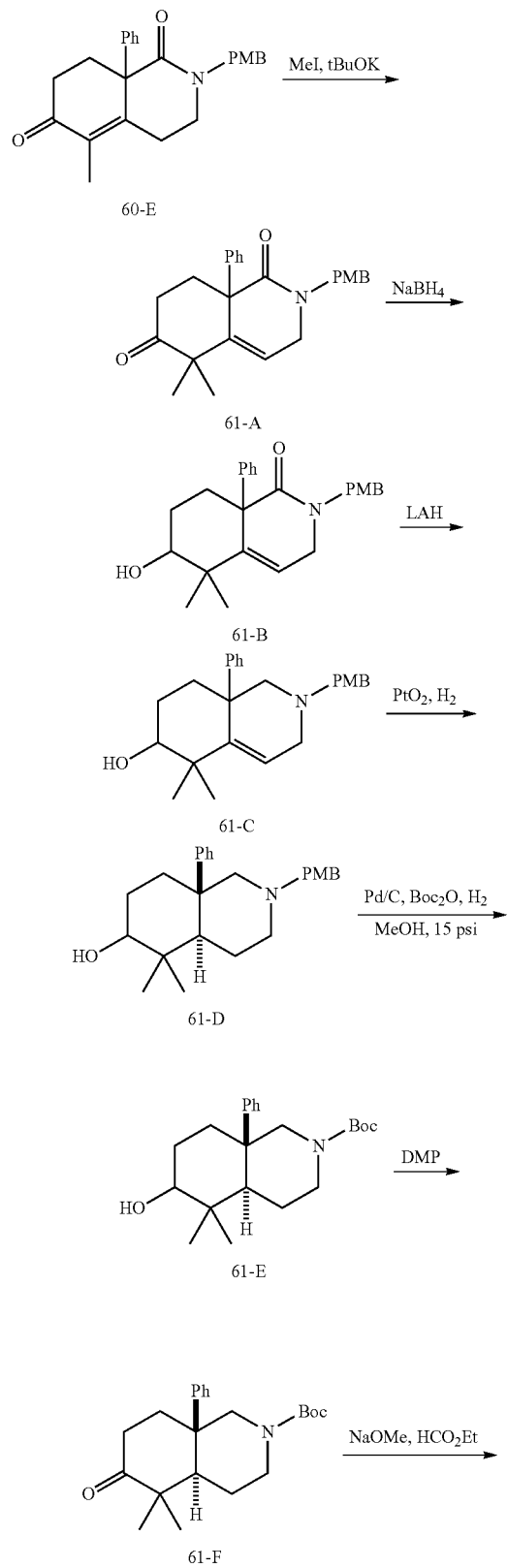
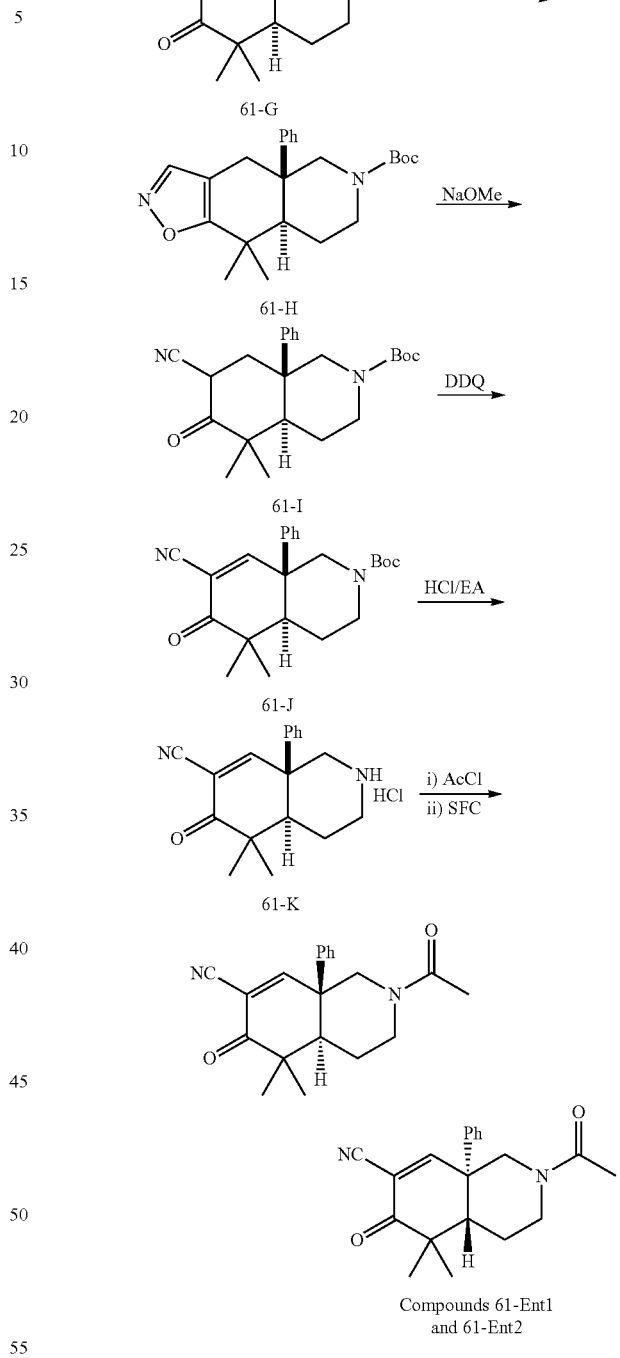

Compounds 61-Ent1 and 61-Ent2

Preparation of Compound 61-A:

MeI (756 mg, 5.33 mmol, 2.0 eq) was added to a solution of Potassium tert-Butoxide (598 mg, 5.33 mmol, 2.0 eq), compound 60-E (1.0 g, 2.67 mmol, 1.0 eq) in THF 20 mL by portionwise at 0-5° C., then the mixture was stirred at 25° C. for 4 hours. TLC (PE:EtOAc=3:1) showed compound 60-E was consumed completely. The mixture was poured into water 40 mL, extracted with EtOAc (40 mL). The organic layer was washed with brine 40 mL, dried over anhydrous $Na_2SO_4$, filtered and concentrated. The residue was purified by column chromatography on silica gel (PE: EtOAc from 100:1 to 3:1) to give compound 61-A (380 mg, 36.9% yield) as colorless oil.

$^1$HNMR: (400 MHz, CDCl$_3$) δ: 7.40-7.38 (m, 2H), 7.33-7.27 (m, 3H), 6.82 (d, J=8.4 Hz, 2H), 6.70 (d, J=8.8 Hz, 2H), 6.14 (t, J=2.8 Hz, 1H), 4.61 (d, J=14.8 Hz, 1H), 4.32 (d, J=14.8 Hz, 1H), 3.76 (s, 3H), 3.62 (d, J=4.0 Hz, 2H), 3.08-3.03 (m, 1H), 2.76-2.71 (m, 1H), 2.43-2.38 (m, 2H), 1.36 (s, 3H), 1.22 (s, 2H).

Preparation of Compound 61-B

NaBH$_4$ (349 mg, 9.26 mmol, 2.0 eq) was added to a solution of compound 61-A (1.8 g, 4.63 mol, 1.0 eq) in MeOH 20 mL at 0° C., stirred at 25° C. for 14 hours. TLC (PE:EtOAc=1:1) showed compound 61-A was consumed completely. The reaction was quenched with water 10 mL, extracted with EtOAc (100 mL). The organic layer was washed with brine 50 mL, dried over anhydrous Na$_2$SO$_4$, filtered and concentrated to get compound 61-B (1.9 g, 96.5% yield) as a yellow solid.

$^1$HNMR: (400 MHz, CDCl$_3$) δ: 7.39-7.37 (m, 2H), 7.32-7.24 (m, 3H), 6.98 (d, J=8.4 Hz, 2H), 6.77 (d, J=8.8 Hz, 2H), 5.95-5.94 (m, 1H), 4.62 (d, J=14.4 Hz, 1H), 4.30 (d, J=14.4 Hz, 1H), 3.98-3.79 (m, 3H), 3.77 (s, 3H), 3.79-3.31 (m, 2H), 1.92-1.75 (m, 2H), 1.31-1.29 (m, 1H), 1.20 (s, 3H), 0.42 (s, 3H).

Preparation of Compound 61-C

LAH (348 mg, 9.20 mmol, 2.0 eq) was added to solution of compound 61-B (1.8 g, 4.60 mmol, 1.0 eq) in anhydrous THF 20 mL at 0° C. The mixture was stirred at 25° C. for 14 hours. TLC (PE:EtOAc=1:2) showed compound 61-B was consumed completely. The reaction was quenched with 0.4 mL of water, followed by 0.4 mL of 15% aqueous NaOH and 1.2 mL of water, filtered, and the filtrate was concentrated under reduced pressure to supply compound 61-C (1.93 g, 100% yield) as colorless oil, which was used to next step directly.

Preparation of Compound 61-D

PtO$_2$ (50 mg) was added to a solution of compound 61-C (650 mg, 1.72 mmol, 1.0 eq) in MeOH 20 mL under Ar, stirred under H$_2$ (15 psi) at 25° C. for 24 hours. LCMS (19214-126-1A) showed compound 61-C was consumed completely. The mixture was filtered, and the filtrate was concentrated to give compound 61-D (300 mg, 45.9% yield) as colorless oil.

LCMS: (M+H: 380.3).

Preparation of Compound 61-E

Pd/C (50 mg) was added to a solution of compound 61-D (300 mg, 0.79 mmol, 1.0 eq), Boc$_2$O (207 mg, 0.95 mmol, 1.2 eq) in MeOH 10 mL under Ar, stirred under H$_2$ (15 psi) at 25° C. for 14 hours. LCMS (19214-128-1B) showed compound 5 was consumed completely. The mixture was filtered, and the filtrate was concentrated to give compound 61-E (200 mg, 100% yield) as yellow oil, which was used to next step directly.

LCMS: (M−56: 304.1).

Preparation of Compound 61-F

DMP (283 mg, 0.669 mmol, 1.2 eq) was added to a solution of compound 61-E (200 mg, 0.557 mmol, 1.0 eq) in CH$_2$Cl$_2$ 8 mL at 0° C., stirred at 25° C. for 14 hours. LCMS (19214-148-1A) showed compound 61-E was consumed completely. The mixture was diluted water 50 mL, extracted with EtOAc (30 mL×3), washed with brine 50 mL, and dried over anhydrous Na$_2$SO$_4$, filtered, and the filtrate was concentrated to get compound 61-F (180 mg, 90.5% yield) as pale-yellow oil.

LCMS: (M−56: 302.2).

Preparation of Compound 61-G

NaOMe (0.3 mL, 1.51 mmol, 5.4 M in MeOH) was added to a solution of compound 61-F (180 mg, 0.504 mmol, 1.0 eq) in HCOOEt 4 mL, stirred at 25° C. for 2 hours. LCMS (19214-150-1A) showed compound 61-F was consumed completely. The mixture was diluted with water 10 mL, adjusted to pH=5 with HOAc, extracted with EtOAc (20 mL×2), washed with brine 20 mL, and dried over anhydrous Na$_2$SO$_4$, filtered, and the filtrate was concentrated to get compound 61-G (150 mg, 77.3% yield) as yellow oil.

LCMS: (M−56: 330.1).

Preparation of Compound 61-H

Hydrochloride hydroxylamine (37.7 mg, 0.584 mmol, 1.0 eq) was added to a solution of compound 61-G (150 mg, 0.39 mmol, 1.0 eq) in 5 mL of EtOH/H$_2$O (V:V=10:1), the reaction mixture was stirred at 50° C. for 14 hours. LCMS (19214-151-1A) showed compound 61-G was consumed completely. The mixture was diluted with water (20 mL), adjusted pH to 7 by adding saturated aqueous NaHCO$_3$, extracted with EtOAc (20 mL). The organic layer was washed with brine (15 mL), dried over anhydrous Na$_2$SO$_4$, filtered, and concentrated to get compound 61-H (130 mg, 87.8% yield) as yellow oil.

LCMS: (M−56: 327.1).

Preparation of Compound 61-I

NaOMe/MeOH (0.3 mL, 5.0 eq, 1.70 mmol, 5.4M) was added to a solution of compound 61-H (130 mg, 0.34 mmol, 1.0 eq) in MeOH (5 mL), the reaction mixture was stirred at 50° C. for 14 hours. LCMS (19334-1-1A) showed compound 61-H was consumed completely. The mixture was adjusted to pH=7 with 1N HCl and extracted with EtOAc (20 mL). The organic layer was washed with brine (20 mL), dried over anhydrous Na$_2$SO$_4$, filtered, and concentrated to get compound 61-I (110 mg, 84.6% yield) as a white solid.

LCMS: (M-Boc: 282.9).

Preparation of Compound 61-J

A mixture of compound 61-I (160 mg, 0.42 mmol, 1.0 eq) in MeOH 5 mL was added DDQ (142 mg, 0.63 mmol, 1.5 eq), and the mixture was stirred at 110° C. for 14 hours. TLC (PE/EtOAc=3/1, Rf=0.6) showed compound 61-I was consumed completely. The mixture was concentrated, and the residue was purified by pre-TLC PE/EtOAc=3:1 to get compound 61-J (90 mg, 56.6% yield) as a yellow solid.

$^1$HNMR: (400 MHz, CDCl$_3$) δ: 7.57 (s, 1H), 7.31-7.29 (m, 5H), 4.64-4.35 (m, 2H), 3.01-2.90 (m, 2H), 2.16-2.12 (m, 1H), 2.03-1.99 (m, 1H), 1.62-1.60 (m, 1H), 1.38-1.36 (m, 9H), 1.19 (s, 3H), 0.50 (s, 3H).

Preparation of Compound 61-K

HCl/EtOAc (1 mL, 4M) was added to a solution of compound 61-J (90 mg, 0.24 mmol, 1.0 eq) in EtOAc (1 mL), and the mixture was stirred at 25° C. for 1 hour. LCMS (19334-11-1A) showed compound 61-J was consumed completely. The mixture was concentrated to get compound 61-K (74 mg, 98.9% yield) as a yellow solid, which was used to next step directly.

LCMS: (M+H: 281.1).

Preparation of Compounds 61-Ent1 and 61-Ent2

A solution of AcCl (25.6 mg, 1.5 eq, 0.33 mmol) in CH$_2$Cl$_2$ 1 mL was added to a solution of compound 61-K (69 mg, 0.22 mmol, 1.0 eq), TEA (44 mg, 2.0 eq, 0.44 mmol) in CH$_2$Cl$_2$ 3 mL at 0° C. The mixture was stirred at 25° C. under N$_2$ atmosphere for 1 hour. LCMS (19334-13-1A) showed compound 61-K was consumed completely. The mixture was concentrated, and the residue was purified by pre-TLC (PE/EtOAc=1:2) to get a racemate, which further purified by SFC (column: AD (250 mm*30 mm, 10 um), condition: 0.1% NH₃H₂O ETOH) to give 61-Ent1 (12.5 mg, 33.3% yield) and 61-Ent2 (12.5 mg, 33.3% yield) as a white solid.

Spectra for 61-Ent1:
¹HNMR: (400 MHz, Methanol-d₄) δ: 8.11-7.97 (m, 1H), 7.35-7.32 (m, 5H), 5.00-4.83 (m, 1H), 4.36-4.08 (m, 1H), 3.42-3.33 (m, 1H), 2.90-2.84 (m, 1H), 2.48-2.44 (m, 1H), 2.40 (s, 1H), 2.26-2.18 (m, 1H), 1.73-1.72 (m, 3H), 1.19 (s, 3H), 0.45 (d, J=6.4 Hz, 3H).
HPLC: (Purity: 99.37%)
SFC: (ee: 100%)
LCMS: (M+H: 323.2)

Spectra for 61-Ent2:
¹HNMR: (400 MHz, Methanol-d₄) δ: 8.11-7.96 (m, 1H), 7.35-7.31 (m, 5H), 4.99-4.83 (m, 1H), 4.36-4.08 (m, 1H), 3.42-3.38 (m, 1H), 2.90-2.85 (m, 1H), 2.47-2.44 (m, 1H), 2.39 (s, 1H), 2.26-2.17 (m, 1H), 1.78-1.72 (m, 3H), 1.19 (s, 3H), 0.45 (d, J=6.4 Hz, 3H).
HPLC: (Purity: 100%)
SFC: (ee: 100%)
LCMS: (M+H: 323.2).

Example 45: Preparation of Compound 62-Ent1

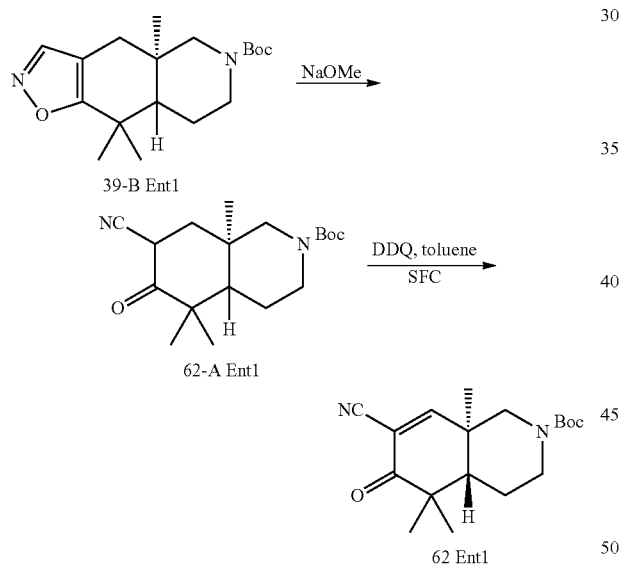

Preparation of Compound 62-A Ent1
To MeOH (16 mL) was added a solid of Na (717 mg, 31.21 mmol, 5 eq) in many portions at 25° C. and stirring until Na was disappeared. Then compound 39-B Ent1 (2 g, 6.24 mmol, 1.0 eq) was added. The reaction mixture was stirred at 30° C. for 12 hours. TLC (PE/EA=3:1) showed the starting materials were consumed completely. The mixture was quenched by Sat. NH₄Cl (20 mL) and extracted with EtOAc (20 mL×3). The combined organic layer was washed with brine (50 mL), dried over anhydrous Na₂SO₄, filtered, concentrated under reduced pressure to supply crude compound 62-A Ent1 (2 g) as yellow oil.

Preparation of Compound 62 Ent1
To a solution of compound 62-A Ent1 (2 g, 6.24 mmol, 1.0 eq) in Tol. (30 mL) was added DDQ (1.7 g, 7.49 mmol, 1.2 eq) slowly. The mixture was stirred at 50° C. for 2 h. TLC (PE/EA=3:1) showed compound 10 was consumed completely. The mixture was diluted with water (50 mL), and extracted with EtOAc (50 mL×3). The combined organic layer dried over anhydrous Na₂SO₄, filtered, and concentrated under reduced pressure. The residue was purified by column chromatography (PE/EtOAc=100:1-5:1) to give crude compound 62 Ent1 (1.2 g, 60% yield) as a light yellow solid. LCMS: (M−99: 219.1) The crude compound 62 Ent1 (900 mg) was purified by SFC (Condition: Neu-MeOH; Column: AD (250 mm*30 mm, 10 um); FlowRate: 50 mL/min) to give 450 mg as a white solid. An 80 mg portion of this material was further purified by SFC (Condition: Neu-MeOH; Column: AD (250 mm*30 mm, 10 um); FlowRate: 50 mL/min) to give pure 62 Ent1 (37 mg, Rt=3.737 min) as a white solid.

Data for 62-Ent1
HPLC: (Purity: 98.81%)
LCMS: M-Boc: 219.1)
SFC: (Rt=3.737, ee: 100%)
¹H NMR: (400 MHz, CDCl₃) δ=7.44 (s, 1H), 4.59-4.21 (m, 1H), 4.20-3.88 (m, 1H), 4.20-3.88 (m, 1H), 2.68 (s, 2H), 1.84 (m, 1H), 1.70 (m, 1H), 1.63-1.59 (m, 1H), 1.48 (s, 9H), 1.23 (d, J=3.1 Hz, 6H), 1.10 (s, 3H)

Example 46: Preparation of Compound 63

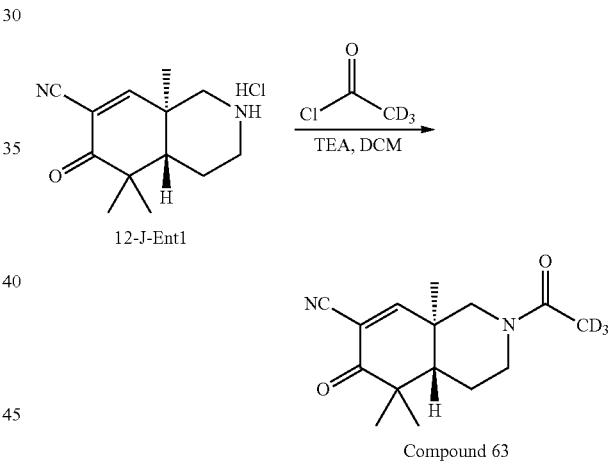

A mixture of compound 12-J-Ent1 (100 mg, 0.39 mmol, 1.0 eq.) and TEA (159 mg, 1.57 mmol, 4.0 eq.) in DCM (5 mL) was added acetyl-d₃ chloride (64 mg, 0.78 mmol, 2.0 eq) dropwise at 0° C. The mixture was stirred at 10° C. for 0.5 h. LCMS showed that the starting material was consumed completely and the desired product was observed. The mixture was concentrated in vacuo and purified by prep-HPLC (Column: Phenomenex Synergi C18 150*30 mm*4 um, Condition: water (0.225% FA)-ACN; FlowRate: 25 mL/min) to give 63 (85 mg) as a white solid. The crude 63 was separated by SFC (Mobile phase: 0.1% NH₃.H₂O-EtOH; Column: Chiralpak OD (250 mm*30 mm, 5 um); FlowRate: 60 mL/min) to give 63 (36.0 mg, Rt=4.16 min, yield: 35.5%) as a white solid.

LCMS: (M+H: 264.1, crude)
SFC: (Rt=3.86 min; crude)
¹H NMR: (400 MHz, CDCl₃) δ=7.42-7.47 (m, 1H), 4.61-4.93 (m, 1H), 3.61-4.05 (m, 1H), 3.05-3.12 (m, 1H), 2.11-2.44 (m, 1H), 1.91-1.95 (m, 1H), 1.78-1.64 (m, 2H), 1.27-1.20 (m, 6H), 1.11 (s, 3H).
HPLC: (Purity: 99.63%)
LCMS: (M+H: 264.1)
SFC: (Rt=4.16, ee: 98.9%)

Example 47: Preparation of Compound 64

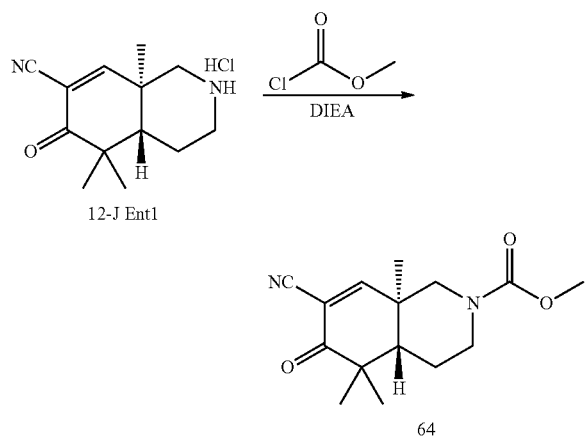

To a mixture of compound 12-J-Ent1 (100 mg, 0.39 mmol, 1.0 eq.) and TEA (159 mg, 1.57 mmol, 4.0 eq.) in DCM (5 mL) was added methylchloroformate (130 mg, 1.14 mmol, 2.0 eq). The mixture was stirred at 10° C. for 0.5 h. LCMS showed that the starting material was consumed completely and the desired product was observed. The mixture was concentrated in vacuo and purified by prep-HPLC (Column: Phenomenex Synergi C18 150*30 mm*4 um, Condition: water (0.225% FA)-ACN; FlowRate: 25 mL/min) to give 64 (120 mg, enantio-enriched) as a white solid. The enantio-enriched 64 was separated by SFC (Mobile phase: Neu-EtOH; Column: Chiralpak AD (250 mm*30 mm, 10 um); FlowRate: 50 mL/min) to give 64 (28.0 mg, Rt=2.89 min, yield: 28%) as a white solid.

1H NMR: (400 MHz, CDCl3) δ=7.42 (s, br, 1H), 4.34-4.46 (m, 1H), 3.92-4.14 (m, 1H), 3.74 (s, 3H), 2.60-2.75 (m, 2H), 1.90-1.81 (m, 1H), 1.71-1.74 (m, 1H), 1.62-1.65 (m, 1H), 1.28-1.22 (m, 6H), 1.11 (s, 3H).
HPLC: (Purity: 95.35%).
LCMS: (M+H: 227.1).
SFC: (Rt=2.89, Purity: 97.36%).

Example 48: Synthesis of Compounds 65-Ent1 and 65-Ent2

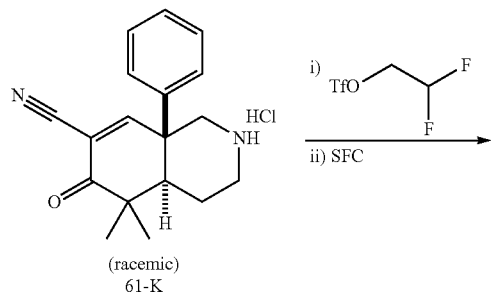

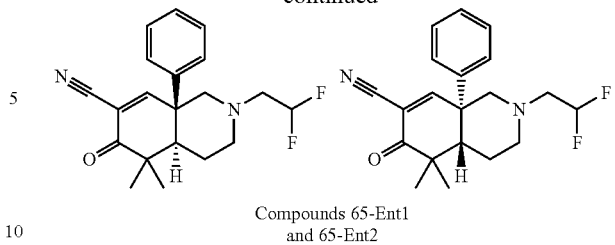

Compounds 65-Ent1 and 65-Ent2

A mixture of racemic compound 61-K (110 mg, 0.35 mmol, 1.0 eq), 2,2-difluoroethyl trifluoromethanesulfonate (111.4 mg, 1.5 eq, 0.52 mmol), DIEA (135 mg, 1.05 mmol, 3.0 eq) in THF 3 mL, was stirred at 80° C. for 2 hours. LCMS) showed compound 61-K was consumed completely. The mixture was concentrated, and the residue was purified by prep-TLC (PE:EtOAc=3:1) to get a mixture, further purified by SFC (column: AD (250 mm*30 mm, 5 um), condition: 0.1% NH3H2O/ETOH) to give 65-Ent1 (27 mg, 45.0% yield) and 65-Ent2 (21 mg, 35.0% yield) as a white solid. The absolute configuration was not determined.

Spectra for 65-Ent1
1HNMR: (400 MHz, CDCl3) δ: 7.85-7.82 (m, 2H), 7.42 (s, 1H), 7.31-7.29 (m, 3H), 6.06-5.76 (m, 1H), 3.36 (d, J=10.0 Hz, 1H), 3.18 (d, J=6.4 Hz, 1H), 2.89-2.81 (m, 2H), 2.58 (d, J=6.8 Hz, 1H), 2.48-2.46 (m, 1H), 1.96-1.94 (m, 2H), 1.15 (s, 3H), 0.46 (s, 3H).
HPLC: (Purity: 98.86%)
SFC: (Rt: 2.995 min, ee: 100%)
LCMS: (M+H: 345.2)

Spectra for 65-Ent2
1HNMR: (400 MHz, CDCl3) δ: 7.85-7.82 (m, 2H), 7.42 (s, 1H), 7.32-7.29 (m, 3H), 6.08-5.78 (m, 1H), 3.36 (d, J=10.0 Hz, 1H), 3.18 (d, J=6.4 Hz, 1H), 2.89-2.81 (m, 2H), 2.58 (d, J=6.8 Hz, 1H), 2.48-2.47 (m, 1H), 1.96-1.94 (m, 2H), 1.15 (s, 3H), 0.46 (s, 3H).
HPLC: (Purity: 100%)
SFC: (Rt: 3.509 min, ee: 98.55%)
LCMS: (M+H: 345.2).

Example 49: Preparation of Compounds 66 and 67

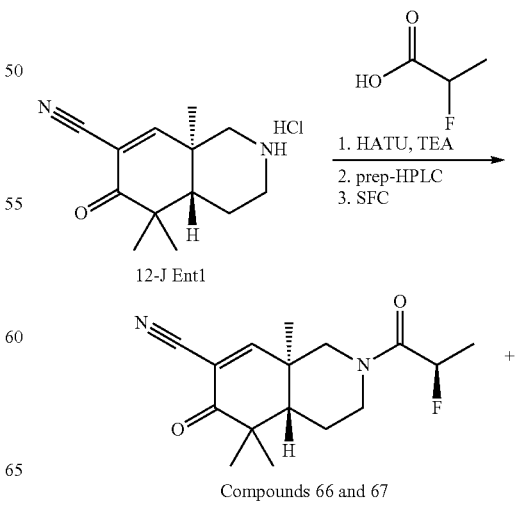

Compounds 66 and 67

-continued

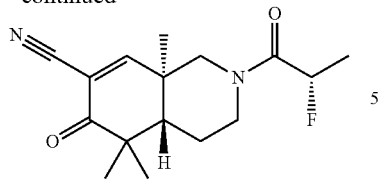

A mixture of compound 12-J Ent1 (200 mg, 0.785 mmol, 1.0 eq.), 2-fluoropropanoic acid (72 mg, 0.785 mmol, 1.0 eq.) and DIEA (202 mg, 1.570 mmol, 2.0 eq.) and HATU (298 mg, 0.785 mmol, 1.0 eq.) in CH$_3$CN (4 mL) was stirred at 20° C. for 16 h. LCMS showed that the starting material was consumed completely and the desired product was observed. The mixture was added Sat. NH$_4$Cl (15 mL). The residue was extracted with EtOAc (15 mL×3). The combined organic layers were washed with brine (15 mL), dried over Na$_2$SO$_4$, filtered and concentrated. The residue was purified by prep-HPLC (Column: Phenomenex Synergi C18 150*30 mm*4 um, Condition: water (0.225% FA)-ACN; FlowRate: 25 mL/min) to give the crude diasteromers 66 (79 mg, 34.2% yield) and compound 67 (86 mg, 37.3% yield). Both isomers are yellow solid.

The crude compounds were further purified by SFC as follows:

The crude compound 66 (79 mg) was separated by SFC (Mobile phase: Neu-EtOH; Column: IC (250 mm*30 mm, 10 um); FlowRate: 60 mL/min) to give 66 (34.8 mg, Rt=7.26 min, 44% yield) as a yellow solid. The absolute configuration of the fluorine-bearing carbon was not established.
Spectra for 66:
$^1$H NMR: (400 MHz, CDCl$_3$) δ=7.50-7.40 (m, 1H), 5.44-5.15 (m, 1H), 4.91-4.50 (m, 1H), 4.35-3.86 (m, 1H), 3.17-2.92 (m, 1H), 2.65-2.43 (m, 1H), 2.06-1.89 (m, 1H), 1.75-1.65 (m, 2H), 1.59-1.56 (m, 3H), 1.29-1.20 (m, 6H), 1.12 (s, 3H)
HPLC: (Purity: 99.04%)
LCMS: (M+H: 293.2)
SFC: (Rt=7.26 min, ee: 99.03%)

The crude compound 67 (86 mg) was separated by SFC (Mobile phase: Neu-EtOH; Column: IC (250 mm*30 mm, 10 um); FlowRate: 60 mL/min) to give 67 (46.1 mg, Rt=6.013 min, 53.6% yield) as a yellow solid. The absolute configuration of the fluorine-bearing carbon was not established.
Spectra for 67:
$^1$H NMR: (400 MHz, CDCl$_3$) δ=7.54-7.43 (m, 1H), 5.50-5.18 (m, 1H), 4.89-4.55 (m, 1H), 4.32-3.99 (m, 1H), 3.15-2.94 (m, 1H), 2.73-2.47 (m, 1H), 2.04-1.93 (m, 1H), 1.91-1.69 (m, 2H), 1.67-1.59 (m, 3H), 1.32-1.23 (m, 6H), 1.14 (s, 3H)
HPLC: (Purity: 99.38%)
LCMS: (M+H: 293.2)
SFC: (Rt=6.013, ee: 100%)

Example 50: Preparation of Compounds 69-Ent and 69-Ent2

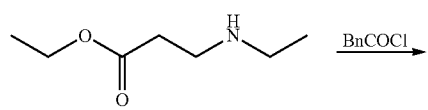

-continued

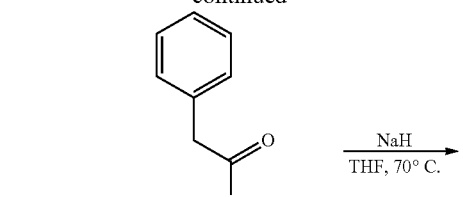

69-A

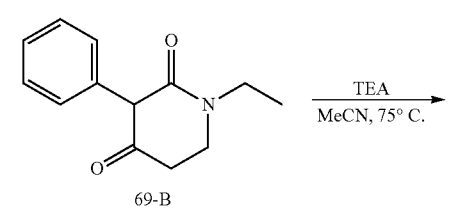

69-B

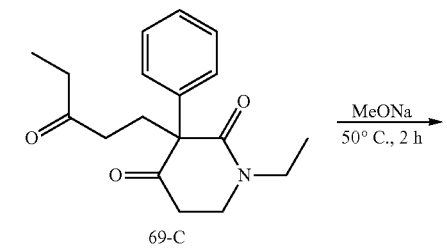

69-C

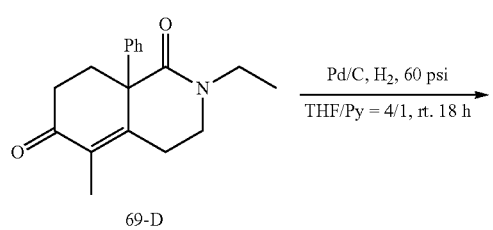

69-D

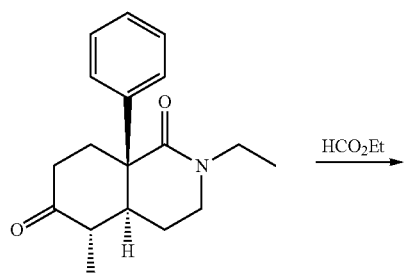

69-E

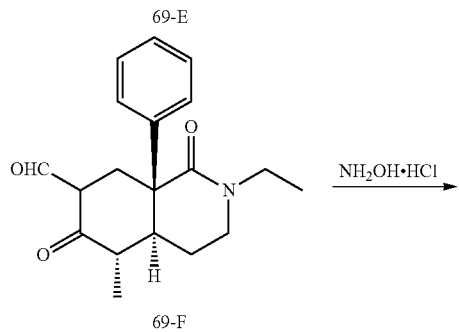

69-F

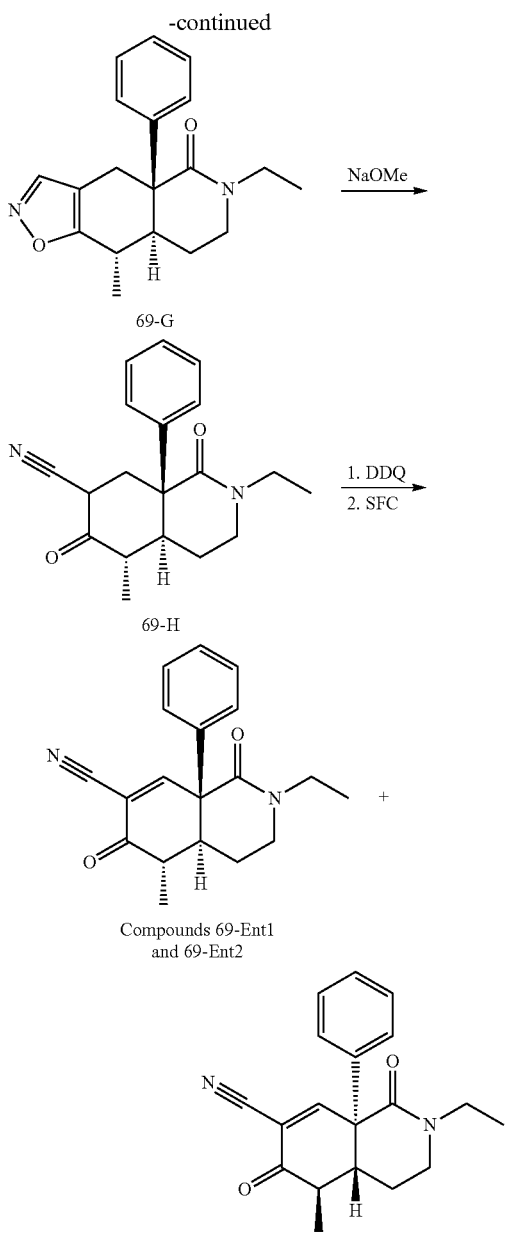

69-G

69-H

Compounds 69-Ent1 and 69-Ent2

Preparation of Compound 69-A

To a mixture of ethyl 3-(ethylamino)propanoate (15 g, 100 mmol, 1.0 eq) and BnCOCl (18 g, 120 mmol, 1.2 eq) in acetone/H$_2$O (300 mL, V=10:1) was added K$_2$CO$_3$ (16.6 g, 120 mmol, 1.2 eq) at 0° C. in one portion. The suspension solution was stirred at 12-18° C. for 5 hours. TLC (PE/EA=1:1) showed that the ethyl 3-(ethylamino)propanoate was consumed completely. The reaction mixture was poured in to water (150 mL) and extracted with EtOAc (100 mL×2). The combined organic layers were dried over Na$_2$SO$_4$, filtered and concentrated to give compound 69-A (32 g, yield equivalent) as yellow oil, which was used for next step without further purification.

$^1$H NMR: (400 MHz, CDCl$_3$) δ: 7.37-7.10 (m, 5H), 4.19-4.03 (m, 2H), 3.78-3.66 (m, 2H), 3.65-3.53 (m, 2H), 3.42-3.27 (m, 2H), 2.62 (t, J=7.0 Hz, 1H), 2.49-2.35 (m, 1H), 1.29-1.19 (m, 3H), 1.13-1.04 (m, 3H).

Preparation of Compound 69-B

To a solution of compound 69-A (32 g, 120 mmol, 1.0 eq) in THF (300 mL) was added NaH (5.8 g, 150 mmol, 1.2 eq) in many portions at 45° C. The suspension was stirred at 75° C. for 16 hs. TLC (PE/EA=1:1) showed the compound 69-A was consumed completely and a new spot was detected. The reaction mixture was quenched with H$_2$O (150 mL), adjusted pH=4 by 1N HCl and extracted with EtOAc (100 mL×2). The combined organic layer was washed with brine, dried over Na$_2$SO$_4$, filtered and concentrated to give compound 69-B (22 g, crude) as a yellow solid, which was used for the next step without further purification.

$^1$H NMR: (400 MHz, CDCl$_3$) δ: 7.52-7.10 (m, 5H), 3.76-3.46 (m, 3H), 3.40-3.17 (m, 1H), 2.82-2.15 (m, 2H), 2.11-2.00 (m, 1H), 1.29-1.23 (m, 5H).

Preparation of Compound 69-C

To a solution of compound 69-B (22 g, 100 mmol, 1.0 eq) and TEA (20.2 g, 200 mmol, 2.0 eq) in MeCN (200 mL) was added EVK (8.5 g, 100 mmol, 1.2 eq). The reaction mixture was stirred at 75° C. for 18 hours. TLC (PE/EA=1:1) showed the compound 69-B was consumed completely and a new spot was detected. The solvent was removed to give the crude compound 69-C (25 g, crude) as yellow oil, which was used for next step without further purification.

LCMS: (M+H: 302.1)

Preparation of Compound 69-D

To a solution of compound 69-C (22 g, crude) in methanol (50 mL) MeOH/MeONa (150 mL, 1M) at 0° C. The reaction mixture was stirred at 55° C. for 18 hs. LCMS (19336-83-1A) showed the compound 69-C was consumed completely. The reaction mixture was acidified with 1N HCl to make pH=7-9 and concentrated to remove MeOH. The crude was diluted into water (80 mL) and extracted with EtOAc (80 mL×2). The combined organic layer was washed with brine, dried over Na$_2$SO$_4$, filtered and concentrated to obtained the residue, which was purified by column chromatography on silica gel (PE/EtOAc=10:1-5:1) to give compound 69-D (6 g, 30.0%) as a yellow solid.

LCMS: (M+H: 284.1)

$^1$H NMR: (400 MHz, CDCl$_3$) δ: 7.40-7.20 (m, 5H), 3.69-3.53 (m, 1H), 3.36-3.24 (m, 1H), 3.11-3.01 (m, 1H), 2.99-2.90 (m, 1H), 2.86-2.66 (m, 2H), 2.59-2.48 (m, 1H), 2.44-2.26 (m, 2H), 2.13-2.02 (m, 1H), 1.89 (s, 3H), 1.02 (t, J=7.0 Hz, 2H), 1.10-0.96 (m, 1H).

Preparation of Compound 69-E

A mixture of compound 69-D (4 g, 14.1 mol, 1.0 eq.) and Pd/C (400 mg) in Py/THF (40 mL, V=4:1) was stirred under 40-50 psi of H$_2$ at 7-15° C. for 18 hours. TLC (PE/EA=1:1) showed the compound 69-D was consumed completely. The suspension was filtered through a pad of celite and concentrated to give the crude. The crude was diluted into EA (100 mL), washed with HCl (1M, 100×2), dried over Na$_2$SO$_4$, filtered and concentrated to give desired product 69-E (3.2 g, yield: 80%) as a yellow solid.

$^1$HNMR (400 MHz, CHLOROFORM-d) δ: 7.64-7.53 (m, 2H), 7.37-7.27 (m, 3H), 3.51-3.42 (m, 1H), 3.30-3.22 (m, 1H), 3.21-3.10 (m, 2H), 2.86 (qd, J=6.4, 12.2 Hz, 1H), 2.69-2.64 (m, 1H), 2.37-2.31 (m, 1H), 2.30-2.17 (m, 3H), 2.13-2.04 (m, 2H), 1.15 (d, J=6.5 Hz, 3H), 1.02 (t, J=7.2 Hz, 3H).

Preparation of Compound 69-F

To a solution of compound 69-E (1.2 g, 4.21 mmol, 1.0 eq) in ethyl formate (6.2 g, 84.2 mmol, 20 eq) was added a solution of NaOMe/MeOH (3.11 mmoL, 16.8 mL, 3.4 eq, 5.4M) at 0° C. dropwise. The mixture was stirred at 17° C. for 18 hours. LCMS (19336-88-1A) showed the reaction was completed. Most of the starting material was almost consumed. The mixture was poured into water (50 mL) and acidified to male PH=3-4. The mixture was extracted with EtOAc (50 mL×2). The combined organic phase was dried over Na₂SO₄, and filtered. The filtrate was concentrated in vacuo to give compound 69-F (1.5 g, crude), which was used directly in the next step without purification.

LCMS: (M+H: 314.1)

Preparation of Compound 69-G

To a solution of compound 69-F (1.5 mg, 4.79 mmol, 1 eq) in EtOH/H₂O (20 mL, V=5:1) was added hydrochloride hydroxylamine (330 mg, 4.79 mmol, 1.0 eq). The mixture was stirred at 55° C. for 3 hours. LCMS showed the reaction was completed. The mixture was concentrated in vacuo to give the residue, which was treated with saturated NaHCO₃ (50 mL) and extracted with EtOAc (30 mL×2). The combined organic phase was dried over Na₂SO₄, and filtered. The filtrate was concentrated in vacuo to give the residue, which was purified by column chromatography on silica gel (PE/EA=10:1-5:1-1:1) to give compound 69-G (800 mg, yield: 75%) as a yellow solid.

LCMS: (M+H: 311.1)

¹H NMR (400 MHz, CHLOROFORM-d) δ: 8.20 (s, 1H), 7.25-7.00 (m, 5H), 3.71-3.62 (m, 1H), 3.61-3.53 (m, 1H), 3.52-3.35 (m, 3H), 2.98 (dd, J=2.6, 17.0 Hz, 1H), 2.35-2.23 (m, 1H), 2.16 (s, 1H), 2.05-1.91 (m, 2H), 1.89-1.79 (m, 1H), 1.33 (d, J=6.8 Hz, 3H), 1.25 (t, J=7.2 Hz, 3H).

Preparation of Compound 69-H

To a solution of compound 69-G (800 mg, 2.57 mmol, 1.0 eq) in MeOH (5 mL) was added a solution of NaOMe/MeOH (5 mL, 2M). The mixture was stirred at 8-15° C. for 18 hours. TLC (PE:EA=1:1) showed most of the starting material was almost consumed and a new spot was detected. The mixture was poured into water (30 mL) and acidified with HCl (1M) to make PH=4-5. The mixture was extracted with EtOAc (30 mL×2). The combined organic phase was dried over Na₂SO₄ and filtered. The filtrate was concentrated in vacuo to give compound 69-H (820 mg, crude) as colorless oil, which was used directly in the next step without purification.

Preparation of Compounds 69-Ent and 69-Ent2

To a solution of crude racemic compound 69-H (820 mg, 2.6 mmol, 1.0 eq) in toluene (10 mL) was added DDQ (590 mg, 2.6 mmol, 1.0 eq). The mixture was stirred at 85° C. for 2 hours. TLC (PE:EA=1:2) showed most of the starting material was consumed and a new spot was detected. The mixture was concentrated in vacuo to give the residue, which was purified by column chromatography on silica gel (PE/EA=10:1-5:1-1:1) to give oxidized product (300 mg, yield: 79.3%) as a racemic mixture. The racemic mixture was further separated by SFC (column: OJ (AD (250 mm*30 mm, 10 um)) condition: Neu-ETOH) to give 69-Ent1 (88 mg, yield: 29.3% Rt=4.029 min) and 69-Ent2 (77 mg, yield: 25.6%, Rt=5.739 min). Both as pale white solids. The absolute configuration was not determined.

Spectra for 69-Ent1

¹H NMR (400 MHz, CHLOROFORM-d₄) δ: 8.45 (s, 1H), 7.32-7.44 (m, 3H), 7.13 (dd, J=1.5, 8.0 Hz, 2H), 3.46-3.74 (m, 4H), 2.46-2.35 (m, 2H), 1.89 (br dd, J=7.0, 14.0 Hz, 1H), 1.75-1.61 (m, 1H), 1.29 (t, J=7.0 Hz, 3H), 1.15 (d, J=6.0 Hz, 3H).

SFC: (ee: 100%)
HPLC: (Purity: 96.64%)
LCMS: (M+H=309.0)

Spectra for 69-Ent2

¹H NMR (400 MHz, METHANOL-d₄) δ: 8.45 (s, 1H), 7.33-7.44 (m, 3H), 7.13 (dd, J=1.5, 8.0 Hz, 2H), 3.43-3.74 (m, 4H), 2.33-2.49 (m, 2H), 1.89 (br dd, J=7.0, 14.0 Hz, 1H), 1.74-1.61 (m, 1H), 1.29 (t, J=7.0 Hz, 3H), 1.15 (d, J=6.0 Hz, 3H).

SFC: (ee: 100%)
HPLC: (Purity: 100%)
LCMS: (M+H=309.0)

Example 51: Preparation of Compound 53-Ent

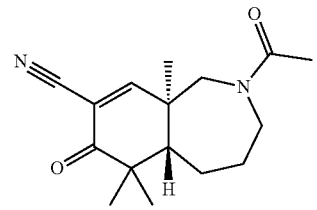 [SMILES: CC(=O)N1CCC[C@@H]2C(C)(C)C(=O)C(C#N)=C[C@@]2(C)C1]

Compound 53-Ent1 can be obtained in a manner analogous to that described for Compound 53-Ent2 by using (S)-1-phenylethan-1-amine in place of (R)-1-phenylethan-1-amine in the conversion of 51-B to 51-C. 1HNMR: (400 MHz, Methanol-d₄) δ: 7.96 (s, 1H), 3.74-3.78 (m, 1H), 3.57-3.58 (m, 2H), 3.38-3.39 (m, 1H), 2.16 (s, 3H), 2.10-2.12 (m, 1H), 1.95-1.88 (m, 2H), 1.64-1.66 (m, 2H), 1.20-1.25 (m, 6H), 1.10-1.08 (m, 3H).

HPLC: (Purity: 97.98%)
SFC: (Column: Chiralcel OD-3 150×4.6 mm I.D., 3 um Mobile phase: A: CO₂ B: ethanol (0.05% DEA) Gradient: from 5% to 40% of B in 5 min and hold 40% for 2.5 min, then 5% of B for 2.5 min Flow rate: 2.5 mL/min Column temp.: 35° C. (ee: 96.4%)
LCMS: (M+H: 275.1)

Example 52: Preparation of Compound 70

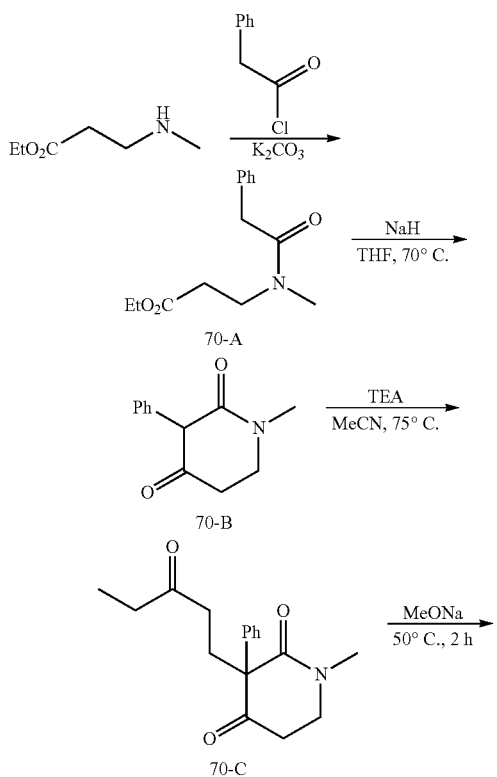

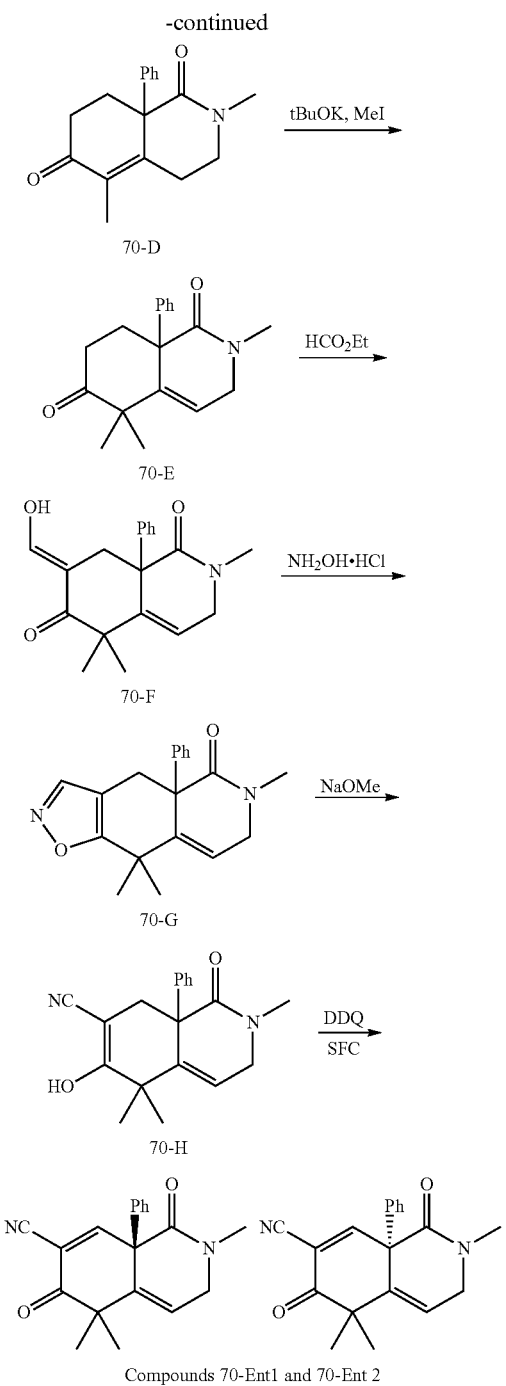

a yellow oil which was used next step without further purification.

LCMS: (M+H: 250.1).

Preparation of Compound 70-B

To a solution of compound 70-A (9 g, 36.1 mmol, 1.0 eq.) in THF (anhydrous, 100 mL) was added NaH (1.04 g, 43.3 mmol, 1.2 eq.). The mixture was stirred at 70° C. for 12 hours. LCMS showed that the starting material was consumed completely and the desired product was detected. The mixture was poured into water (100 mL) and adjusted pH to 3-4 by adding 1M HCl aq. The mixture was extracted with EtOAc (100 mL×4). The combined organic phase was dried over sodium sulfate, and filtered. The filtrate was concentrated in vacuo to give the compound 70-B (9.5 g, crude) as a yellow oil which was used next step without further purification.

LCMS: (M+H: 204.1).

Preparation of Compound 70-C

To a solution of compound 70-B (9 g, 44.3 mmol, 1.0 eq.) in MeCN (90 mL) was TEA (8.9 g, 8.86 mmol, 2.0 eq.) and EVK (4.4 g, 53.1 mmol, 1.2 eq.). The mixture was stirred at 75° C. for 18 hours. TLC (PE/EA=1:1) showed the starting materials were consumed completely and a new spot was observed. The mixture concentrated in vacuo to give compound 70-C (8.5 g, crude) as a yellow oil which was used next step without further purification.

LCMS: (M+H: 288.1).

Preparation of Compound 70-D

Na (768 mg, 33.4 mmol, 1.2 eq.) was added to a stirred MeOH (160 mL) in many portions at 20° C. and until Na was disappeared. Then compound 70-C (8 g, 27.8 mmol, 1.0 eq.) was added. The reaction mixture was stirred at 25° C. for 16 hours. TLC (PE/EA=1:1) showed the starting materials were consumed completely and a new spot was observed. The mixture quenched by Sat. NH$_4$Cl (160 mL) and extracted with EtOAc (300 mL×3). The combined organic layer was dried over anhydrous Na$_2$SO$_4$, filtered, concentrated under reduced pressure to give the residue, which was purified by column chromatography (PE/EtOAc=100:1 to 10:1) to give compound 70-D (3.6 g, 48% yield) as a white solid.

LCMS: (M+H: 270.1).

$^1$H NMR: (400 MHz, CDCl$_3$) δ 7.28-7.34 (m, 3H), 7.22-7.27 (m, 2H), 3.01-3.11 (m, 2H), 2.98 (s, 3H), 2.79-2.90 (m, 1H), 2.62-2.71 (m, 1H), 2.49 (dd, J=4.03, 14.67 Hz, 1H), 2.38-2.44 (m, 1H), 2.27-2.34 (m, 1H), 2.03-2.10 (m, 1H), 1.88 (t, J=1.28 Hz, 3H).

Preparation of Compound 70-E

To a solution of compound 70-D (1.5 g, 5.57 mmol, 1.0 eq.) in THF (anhydrous, 30 mL) was added potassium ter-butoxide (6.68 mL, 6.68 mmol, 1.2 eq. 1 M in THF) slowly at 0° C. The resulting brown solution was stirred at 15° C. for 0.5 hour. Methyl iodine (790 mg, 5.57 mmol, 1.0 eq.) was added to the solution at 0° C. via syringe. The suspension was stirred at 15° C. for 16 hours. LCMS showed that the starting material was consumed completely and the desired product was detected. The mixture was added Sat. NH$_4$Cl (50 mL). The residue was extracted with EtOAc (50 mL×3). The combined organic layers were washed with brine (100 mL), dried over Na$_2$SO$_4$, filtered and concentrated to give compound 70-E (1.3 g, 86.6% yield) as a yellow solid.

LCMS: (M+H: 284.1).

$^1$H NMR: (400 MHz, CDCl$_3$) δ 7.37-7.48 (m, 2H), 7.28-7.35 (m, 2H), 7.21-7.26 (m, 1H), 6.09-6.22 (m, 1H), 3.84-3.95 (m, 1H), 3.70-3.78 (m, 1H), 2.90-2.94 (m, 3H),

To a solution of ethyl 3-(methylamino)propanoate (14 g, 107 mmol, 1 eq.) in acetone (140 mL) and H$_2$O (14 mL) was added K$_2$CO$_3$ (22.1 g, 160 mmol, 1.5 eq.). Then 2-phenylacetyl chloride (19.8 g, 128 mmol, 1.2 eq.) was added dropwise. The mixture was stirred at 16° C. for 2 hours. TLC (PE/EA=1:1) showed that the starting material was consumed completely and a new spot was observed. The mixture was poured into water (150 mL) and extracted with EtOAc (205 mL×3). The combined organic phase was dried over sodium sulfate, and filtered. The filtrate was concentrated in vacuo to give the compound 70-A (21 g, crude) as 2.71-2.82 (m, 1H), 2.27-2.51 (m, 2H), 1.58 (s, 1H), 1.33-1.40 (m, 3H), 1.19-1.26 (m, 3H)

Preparation of Compound 70-F

Na (0.36 g, 15.6 mmol, 3.4 eq.) was added to a stirred of MeOH (15 mL) in many portions at 25° C. and until Na was disappeared and then was added compound 70-E (1.3 g, 4.59 mmol, 1.0 eq.) in HCOOEt (20 mL) was added the above solution at 0° C. dropwise over 5 min under $N_2$. The reaction mixture was stirred at 20° C. for 12 hours. LCMS showed that the starting material was consumed completely and the desired product was detected. The mixture was quenched by water (50 mL), adjusted pH to 5 by adding AcOH, extracted with EtOAc (50 mL×3). The combined organic layer was washed with brine (100 mL×2), dried over anhydrous $Na_2SO_4$, filtered, concentrated under reduced pressure to supply compound 70-F (1.4 g, crude) as yellow oil.

LCMS: (M+H: 312.1)

Preparation of Compound 70-G

To a solution of compound 70-F (1.4 g, 4.49 mmol, 1.0 eq.) in EtOH (15 mL) and $H_2O$ (3 mL) was added hydrochloride hydroxylamine (312 mg, 4.49 mmol, 1.0 eq.). After addition the mixture was stirred at 50° C. for 16 h. TLC (PE/EA=1:1) showed the starting materials were consumed completely and a new spot was observed. The mixture was diluted with $NaHCO_3$ (20 mL), and extracted with EtOAc (30 mL×3). The combined organic layer dried over anhydrous $Na_2SO_4$, filtered, and concentrated under reduced pressure, the residue was purified by column chromatography (PE/EtOAc=20:1 to 5:1) to give compound 70-G (1.3 g, 92.8% yield) as a yellow solid.

LCMS: (M+H: 309.1)

$^1$H NMR: (400 MHz, $CDCl_3$) δ 8.19 (s, 1H), 7.11-7.26 (m, 5H), 6.09 (dd, J=2.6, 4.0 Hz, 1H), 4.29 (dd, J=2.6, 18.2 Hz, 1H), 4.09 (dd, J=4.2, 18.2 Hz, 1H), 3.91 (d, J=16.6 Hz, 1H), 3.01-3.07 (m, 3H), 2.81 (d, J=16.4 Hz, 1H), 1.46-1.53 (m, 3H), 0.88-0.92 (m, 3H)

Preparation of Compound 70-H

Na (485 mg, 21.07 mmol, 5.0 eq.) was added to a stirred of MeOH (11 mL) in many portions at 25° C. and until Na was disappeared. Then compound 70-G (1.3 g, 4.21 mmol, 1.0 eq.) was added. The reaction mixture was stirred at 20° C. for 12 hours. TLC (PE/EA=1:1) showed the starting materials were consumed completely and a new spot was observed. The mixture quenched by Sat. $NH_4Cl$ (20 mL) and extracted with EtOAc (30 mL×3). The combined organic layer was washed with brine (150 mL), dried over anhydrous $Na_2SO_4$, filtered, concentrated under reduced pressure to supply compound 70-H (1.2 g, crude) as yellow oil.

LCMS: (M+H: 309.1).

Preparation of Compounds 70-Ent1 and 70-Ent2

To a solution of compound 70-H (1.2 g, 3.89 mmol, 1.0 eq.) in Tol. (20 mL) was added DDQ (1.14 g, 4.67 mmol, 1.2 eq.) slowly. The mixture was stirred at 50° C. for 2 hours. LCMS showed that the starting material was consumed completely and the desired product was detected. The mixture was diluted with water (30 mL), and extracted with EtOAc (30 mL×3). The combined organic layers was dried over anhydrous $Na_2SO_4$, filtered, and concentrated under reduced pressure. The residue was purified by column chromatography (PE/EtOAc=20:1 to 3:1) to give crude racemic product (200 mg) as a colorless oil. The residue was further purified by prep-SFC (Column: AD (250 mm*30 mm; 10 um); Condition: Neu-EtOH; FlowRate: 80%) to give the 70-Ent1 (59 mg, 4.9% yield) as white solid and 70-Ent2 (78 mg, 6.5% yield) as white solid.

Spectra for 70-Ent1

$^1$H NMR: (400 MHz, $CDCl_3$) δ 8.83 (s, 1H), 7.29-7.42 (m, 5H), 6.18 (dd, J=1.8, 5.0 Hz, 1H), 4.23 (dd, J=1.8, 18.40 Hz, 1H), 3.95 (dd, J=5.2, 18.2 Hz, 1H), 2.97 (s, 3H), 1.44 (s, 3H), 0.85 (s, 3H)

HPLC: (Purity: 100%)

SFC: (Rt=3.019, ee: 100%)

LCMS: (M+H: 307.1)

Spectra for 70-Ent2:

$^1$H NMR: (400 MHz, $CDCl_3$) δ 8.83 (s, 1H), 7.28-7.44 (m, 5H), 6.18 (dd, J=1.8 5.0 Hz, 1H), 4.23 (dd, J=1.8, 18.4 Hz, 1H), 3.95 (dd, J=5.2, 18.2 Hz, 1H), 2.97 (s, 3H), 1.44 (s, 3H), 0.85 (s, 3H)

HPLC: (Purity: 98.80%)

SFC: (Rt=4.463, ee: 100%)

LCMS: (M+H: 307.1)

Example 53: Preparation of Compounds 71-Ent1 and 71-Ent2

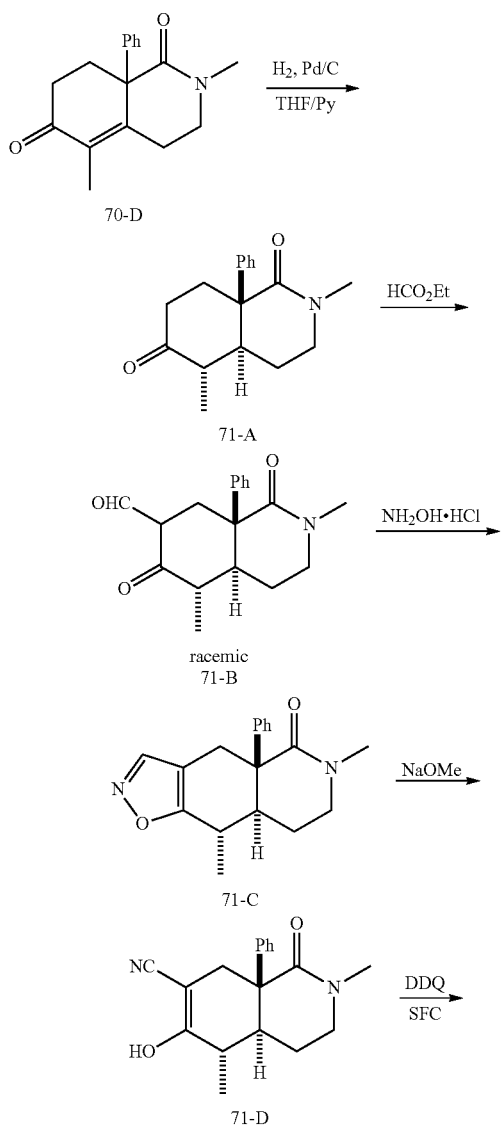

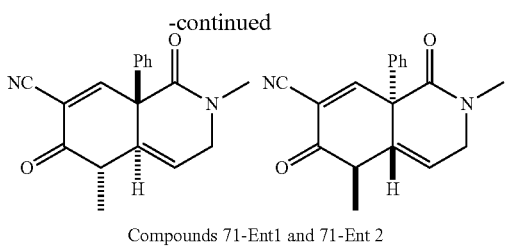

Compounds 71-Ent1 and 71-Ent 2

Preparation of Compound 71-A
Pd/C (100 mg) was added to a solution of compound 70-D (1.0 g, 3.71 mmol, 1.0 eq) in pyridine 4 mL and MeOH 20 mL under argon, and the mixture was stirred under $H_2$ (45 psi) at 20° C. for 14 hours. TLC (PE:EtOAc=1:1, Rf=0.5) showed compound 70-D was consumed completely. The mixture was filtered, and the filtrate was concentrated to give compound 71-A (1.0 g, 100% in yield) as yellow oil. 10
$^1$HNMR: (400 MHz, CDCl$_3$) δ: 7.63 (d, Jd=7.6 Hz, 2H), 7.34-7.36 (m, 2H), 7.29-7.31 (m, 1H), 3.24-3.27 (m, 2H), 2.93 (s, 3H), 2.76-2.68 (m, 2H), 2.35-2.36 (m, 1H), 2.23-2.26 (m, 2H), 2.11-2.14 (m, 3H), 1.16 (d, J=6.8 Hz, 3H).
Preparation of Compound 71-B
NaOMe (2 mL, 11.5 mmol, 5.4 M in MeOH) was added to a solution of compound 71-A (1.0 g, 3.69 mmol, 1.0 eq) in HCOOEt 10 mL, and the mixture was stirred at 25° C. for 2 hours. TLC (PE:EtOAc=1:1, Rf=0.2) showed compound 71-A was consumed completely. The mixture was diluted with water 10 mL, adjusted pH=5 with HOAc, extracted with EtOAc (40 mL). The organic layer was washed with brine 20 mL, and dried over anhydrous Na$_2$SO$_4$, filtered, and the filtrate was concentrated to get compound 71-B (700 mg, 67.6% yield) as yellow solid, which was used to next step directly.
Preparation of Compound 71-C
Hydrochloride hydroxylamine (178 mg, 2.57 mmol, 1.1 eq) was added to a solution of compound 71-B (700 mg, 2.34 mmol, 1.0 eq) in 10 mL of EtOH/H2O (V:V=10:1), and the mixture was stirred at 50° C. for 14 hours. LCMS (19334-118-1A) showed compound 71-B was consumed completely. The mixture was diluted with water (20 mL), extracted with EtOAc (40 mL). The organic layer was washed with brine (20 mL), dried over anhydrous Na$_2$SO$_4$, filtered, and concentrated to get compound 71-C (500 mg, 83.8% yield) as yellow oil.
LCMS: (M+H: 297.1).
$^1$HNMR: (400 MHz, CDCl$_3$) δ: 8.22 (s, 1H), 7.20-7.27 (m, 3H), 7.03-7.05 (m, 2H), 3.55-3.56 (m, 2H), 3.41 (d, J=17.2 Hz, 1H), 3.11 (s, 3H), 2.98-3.02 (m, 1H), 2.30-2.31 (m, 1H), 2.01-2.04 (m, 2H), 1.86-1.96 (m, 1H), 1.34 (d, J=6.8 Hz, 3H).
Preparation of Compound 71-D
NaOMe/MeOH (1.3 mL, 5.0 eq, 6.76 mmol, 5.4M) was added to a solution of compound 71-C (400 mg, 1.35 mmol, 1.0 eq) in MeOH 5 mL, and the mixture was stirred at 50° C. for 2 hours. LCMS (19334-119-1A) showed compound 71-C was consumed completely. The mixture was adjusted to pH=7 with 1N HCl extracted with EtOAc (20 mL). The organic layer was washed with brine (20 mL), dried over anhydrous Na$_2$SO$_4$, filtered, and concentrated to get compound 71-D (110 mg, 84.6% yield) as a yellow solid.
LCMS: (M+H: 297.1).
$^1$HNMR: (400 MHz, CDCl$_3$) δ: 7.67 (d, J=8.0 Hz, 1H), 7.20-7.30 (m, 6H), 3.47-3.51 (m, 2H), 3.11-3.20 (m, 2H), 3.05 (s, 3H), 2.76-2.82 (m, 1H), 1.87-1.95 (m, 4H), 1.24-1.27 (m, 2H), 1.13-1.18 (m, 3H).

Preparation of Compounds 71-Ent1 and 71-Ent2
DDQ (402 mg, 1.77 mmol, 1.5 eq) was added to a solution of compound 71-D (350 mg, 1.18 mmol, 1.0 eq) in toluene 10 mL, and the mixture was stirred at 110° C. for 1 hour. TLC (PE:EtOAc=1:1, Rf=0.6) showed compound 71-D was consumed completely. The mixture was concentrated, and the residue was purified by pre-TLC PE/EtOAc=1:1 to get a racemic compound, which was further separated by SFC (column: AD (250 mm*30 mm, 10 um), condition: 0.1% NH$_3$H$_2$O ETOH) to give 71-Ent1 (70 mg, 20.2% in yield) and 71-Ent2 (70 mg, 20.2% in yield) as a white solid.
Spectra of 71-Ent1
$^1$HNMR: (400 MHz, CDCl$_3$) δ: 8.45 (s, 1H), 7.35-7.43 (m, 3H), 7.10-7.13 (m, 2H), 3.54-3.62 (m, 2H), 3.15 (s, 3H), 2.42-2.46 (m, 2H), 1.86-1.90 (m, 1H), 1.67-1.72 (m, 1H), 1.15 (d, J=6.0 Hz, 3H).
HPLC: (Purity: 100%)
SFC: (Column: Chiralcel OD-3 150×4.6 mm I.D., 3 um Mobile phase: A: CO2 B: ethanol (0.05% DEA) Gradient: from 5% to 40% of B in 5 min and hold 40% for 2.5 min, then 5% of B for 2.5 min Flow rate: 2.5 mL/min Column temp.: 35° C. (ee: 99.78%)
LCMS: (M+H: 295.1).
Spectra of 71-Ent2
$^1$HNMR: (400 MHz, CDCl$_3$) δ: 8.46 (s, 1H), 7.35-7.43 (m, 3H), 7.10-7.13 (m, 2H), 3.52-3.59 (m, 2H), 3.15 (s, 3H), 2.42-2.44 (m, 2H), 1.86-1.91 (m, 1H), 1.67-1.72 (m, 1H), 1.15 (d, J=6.0 Hz, 3H).
HPLC: (Purity: 99.45%).
SFC: (Column: Chiralcel OD-3 150×4.6 mm I.D., 3 um Mobile phase: A: CO2 B: ethanol (0.05% DEA) Gradient: from 5% to 40% of B in 5 min and hold 40% for 2.5 min, then 5% of B for 2.5 min Flow rate: 2.5 mL/min Column temp.: 35° C. (ee: 98.72%).
LCMS: (M+H: 295.1).

Example 54. Synthesis of Compound 72 Ent1

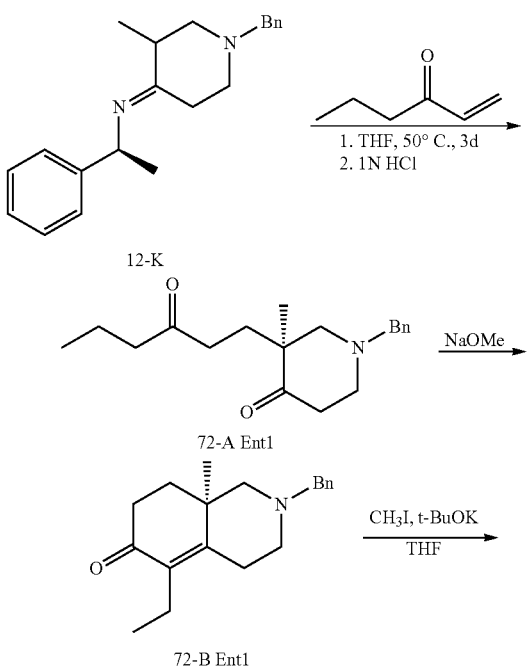

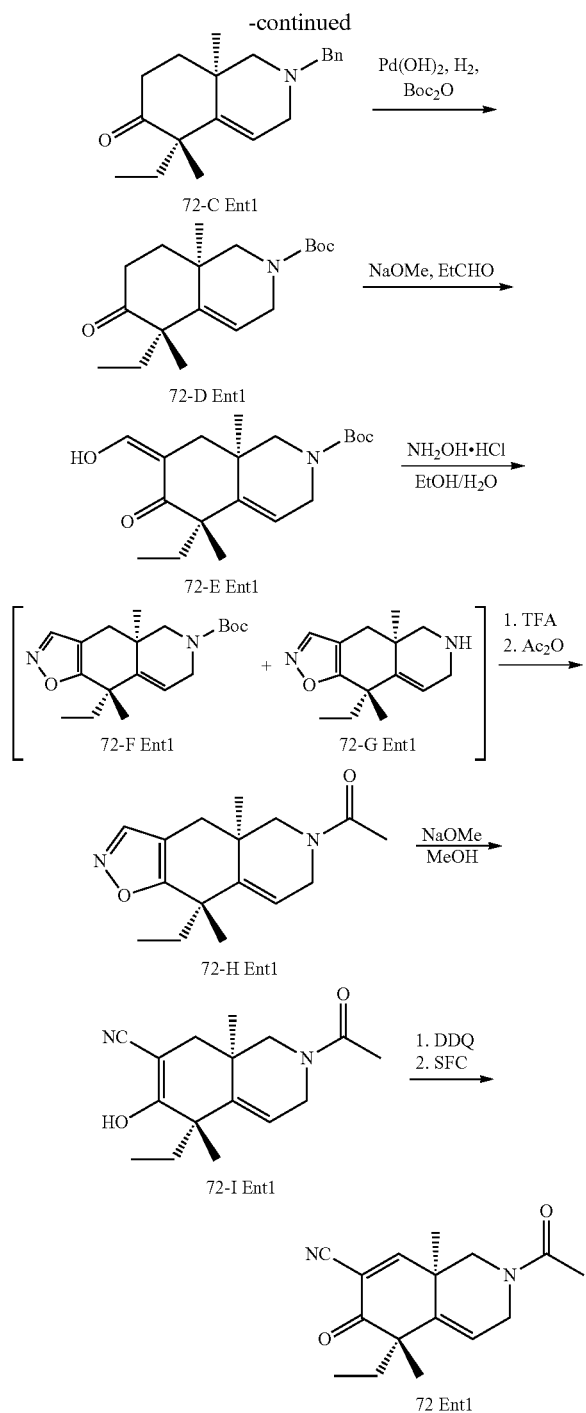

LCMS (M+H 302.2)

1H NMR (400 MHz, CDCl$_3$) δ: 7.40-7.28 (m, 5H), 3.63-3.56 (m, 1H), 3.55-3.48 (m, 1H), 2.95-2.87 (m, 1H), 2.70-2.58 (m, 2H), 2.58-2.48 (m, 1H), 2.43-2.28 (m, 4H), 2.28-2.16 (m, 3H), 1.80-1.66 (m, 1H), 1.66-1.56 (m, 2H), 1.00 (s, 3H), 0.91 (t, J=7.4 Hz, 3H)

Preparation of 72-B Ent1

To a solution of 72-A Ent1 (5.59 g, 18.6 mmol) in methanol (20.6 mL) was added sodium methoxide (4.5 M in methanol, 13.2 mL, 59.4 mmol). The mixture was stirred at 50° C. overnight, diluted with water and extracted with ethyl acetate. The organic layer was washed with brine, dried (MgSO4), and concentrated. The crude material was purified by silica gel chromatography with ethyl acetate in heptanes (0-30%) as eluent. Mixed fractions were repurified (same method) and combined to afford 72-B Ent1 (4.36 g, 82.9% yield).

LCMS (M+H 284.2)

1H NMR (400 MHz, CDCl$_3$) δ: 7.40-7.28 (m, 5H), 3.62-3.55 (m, 1H), 3.42 (d, J=13.3 Hz, 1H), 3.09-3.02 (m, 1H), 2.68-2.44 (m, 4H), 2.43-2.23 (m, 3H), 2.08-1.99 (m, 1H), 1.83-1.69 (m, 2H), 1.60-1.53 (m, 1H), 1.38 (s, 3H), 0.89 (t, J=7.5 Hz, 3H)

Preparation of 72-C Ent1

72-B Ent1 (2.06 g, 7.27 mmol) was azeotroped with toluene then taken up in THF (65.0 mL). The reaction was cooled by a room temperature water bath and to the reaction was added t-BuOK (929.8 mg, 8.29 mmol) portionwise. After 1.5 h of stirring, methyl iodide (511 uL, 8.21 mmol) was added dropwise. After 1 d of stirring, the reaction was diluted with saturated sodium bicarbonate, extracted with ethyl acetate, washed with saturated sodium chloride, dried over sodium sulfate, filtered and evaporated. Purification by silica gel chromatography using 0-30% ethyl acetate in heptanes as eluent afforded 72-C Ent1 (1.02 g, 47.2% yield). Single diastereomer by 1H NMR. Structure confirmed by NMR (nOe).

LCMS (M+H 298.2)

1H NMR (400 MHz, CDCl$_3$) δ=7.40-7.28 (m, 5H), 5.45 (dd, J=2.3, 4.3 Hz, 1H), 3.70 (d, J=13.3 Hz, 1H), 3.48 (d, J=13.3 Hz, 1H), 3.38 (dd, J=4.3, 16.6 Hz, 1H), 2.78 (dd, J=2.0, 16.6 Hz, 1H), 2.62-2.49 (m, 2H), 2.47-2.39 (m, 1H), 2.01-1.90 (m, 2H), 1.76-1.66 (m, 1H), 1.57-1.49 (m, 1H), 1.45 (dd, J=7.3, 13.6 Hz, 1H), 1.18 (d, J=3.0 Hz, 6H), 0.76 (t, J=7.4 Hz, 3H).

Preparation of 72-D Ent1

72-C Ent1 (323.0 mg, 1.09 mmol) was dissolved in methanol (10.0 mL) along with Boc$_2$O (284.4 mg, 1.30 mmol) and Pd(OH)$_2$/C (few milligrams). The vessel was evacuated then backfilled with hydrogen five times. The reaction was hydrogenated (balloon pressure) overnight. The reaction was filtered through Celite, washed with methanol and evaporated to give 72-D Ent1 (366.9 mg, 109.5% yield crude).

LCMS (M+H 308.3)

Preparation of 72-E Ent1

72-D Ent1 (366.9 mg, 1.19 mmol) was dissolved in ethyl formate (4.00 mL, 49.7 mmol). With stirring was added sodium methoxide (4.37 M in methanol, 1.09 mL, 4.76 mmol) slowly and the reaction was stirred at room temperature overnight. The reaction was diluted with water and acetic acid (273 uL, 4.77 mmol) was added. The mixture was extracted with ethyl acetate, washed with saturated sodium chloride solution, dried over sodium sulfate, filtered and Preparation of Compound 72-A Ent1

12-K (9.35 g, 30.5 mmol) was dissolved in THF (62.3 mL); then hex-1-en-3-one (3.59 g, 36.6 mmol) and hydroquinone (67.2 mg, 610 umol) were added. The mixture was stirred at 50° C., sheltered from light for 3 days. Reaction was diluted with 1 N HCl (2 eq). After stirring for 30 min, the reaction was made basic by adding 10 N NaOH (4 eq). After stirring 10 min, the reaction was extracted with ethyl acetate. The organic layer was washed with brine, dried (Na$_2$SO$_4$), and concentrated. The crude material was chromatographed on silica gel with 0-30% ethyl acetate in heptanes as eluent to give 72-A Ent1 (5.59 g, 60.8% yield).

evaporated to give 72-E Ent1 (431.2 mg, 108.0% yield crude).

LCMS (M+H 336.3)

Preparation of 72-F Ent1+72-G Ent1

To a solution of 72-E Ent1 (313.2 mg, 933.7 umol) in ethyl alcohol (8.9 mL) and water (0.44 mL) was added hydroxylamine hydrochloride (648.8 mg, 9.34 mmol). The solution was stirred under reflux for 1.5 h. The solvent was removed under vacuum to provide a solid. The solid was then dissolved in saturated aqueous potassium carbonate and ethyl acetate. The layers were then separated and the organic layer was washed with saturated sodium chloride, dried over sodium sulfate, filtered, and concentrated to give a mixture (232.8 mg) of 72-F Ent1 and 72-G Ent1.

LCMS (M+H 333.2, 233.1)

Preparation of 72-H Ent1

A mixture of 72-F Ent1 and 72-G Ent1 (232.8 mg) was dissolved in DCM (4.0 mL) and TFA (4.0 mL) was added. The reaction was stirred for 1.5 h then evaporated to dryness. After azeotroping with DCM, the residue was taken up in DCM (8.0 mL) and acetic anhydride (141.8 uL, 1.50 mmol) was added. With stirring was added diisopropylethylamine (524 uL, 3.00 mmol). After 3 h stirring at RT, reaction was diluted with ethyl acetate, washed with dilute sodium bicarbonate, washed with saturated sodium chloride, dried over sodium sulfate, filtered, evaporated. Purification by silica gel chromatography using 0-20% methanol in methylene chloride as eluent gave 72-H Ent1 (214.9 mg, 83.9% from 72-E Ent1) LCMS (M+H 275.1)

Preparation of 72-I Ent1

To a solution of 72-H Ent1 (214.9 mg, 783.3 umol) in methanol (10.0 mL) under nitrogen was added sodium methoxide (25% in methanol, 895.5 uL, 3.92 mmol) at room temperature. The mixture was stirred at 50° C. for 1 h. The reaction then was diluted with water and 1 eq 1N HCl (relative to NaOMe) was added. Volatiles were evaporated under reduced pressure. The solution was extracted with ethyl acetate, washed with saturated sodium chloride, dried over sodium sulfate then filtered and concentrated to give 72-I Ent1 (199.7 mg, 92.9% yield crude).

LCMS (M+H 275.1)

Preparation of 72 Ent1

72-I Ent1 (199.7 mg, 727.9 umol) was dissolved in toluene (9.0 mL) and DDQ (247.8 mg, 1.09 mmol) was added. The mixture was heated to reflux for 60 minutes. Reaction was cooled, diluted with toluene, filtered. Sample was purified by preparative HPLC followed by SFC (Column: CHIRALPAK IG 30×250 mm, 5 um; Method: 30% Methanol in CO2 (flow rate: 100 mL/min), ABPR 120 bar, MBPR 40 psi) to give 72 Ent1 (16.2 mg, 8.2%).

Data for 72 Ent1:

HPLC (Purity: 100%)

LCMS (M+H 273.1)

SFC (ee: 100%)

$^1$H NMR (400 MHz, CD$_3$OD) δ: 7.67 (s, 0.5H), 7.65 (s, 0.5H), 5.77 (t, J=3.3 Hz, 1H), 5.72 (t, J=3.1 Hz, 0.5H), 4.60-4.52 (m, 1H), 4.37 (dd, J=3.0, 18.3 Hz, 0.5H), 4.03 (dd, J=3.5, 18.3 Hz, 0.5H), 3.92 (d, J=12.5 Hz, 0.5H), 3.65 (dd, J=3.5, 19.8 Hz, 0.5H), 3.03 (d, J=12.5 Hz, 0.5H), 2.52 (d, J=12.3 Hz, 0.5H), 2.19 (s, 1.5H), 2.18 (s, 1.5H), 1.84-1.74 (m, 1H), 1.61-1.51 (m, 1H), 1.42 (s, 1.5H), 1.36 (s, 1.5H), 1.28 (s, 3H), 0.87-0.77 (m, 3H). NMR consistent with 1:1 mixture of rotamers.

Example 55. Synthesis of Compound 73 Ent1

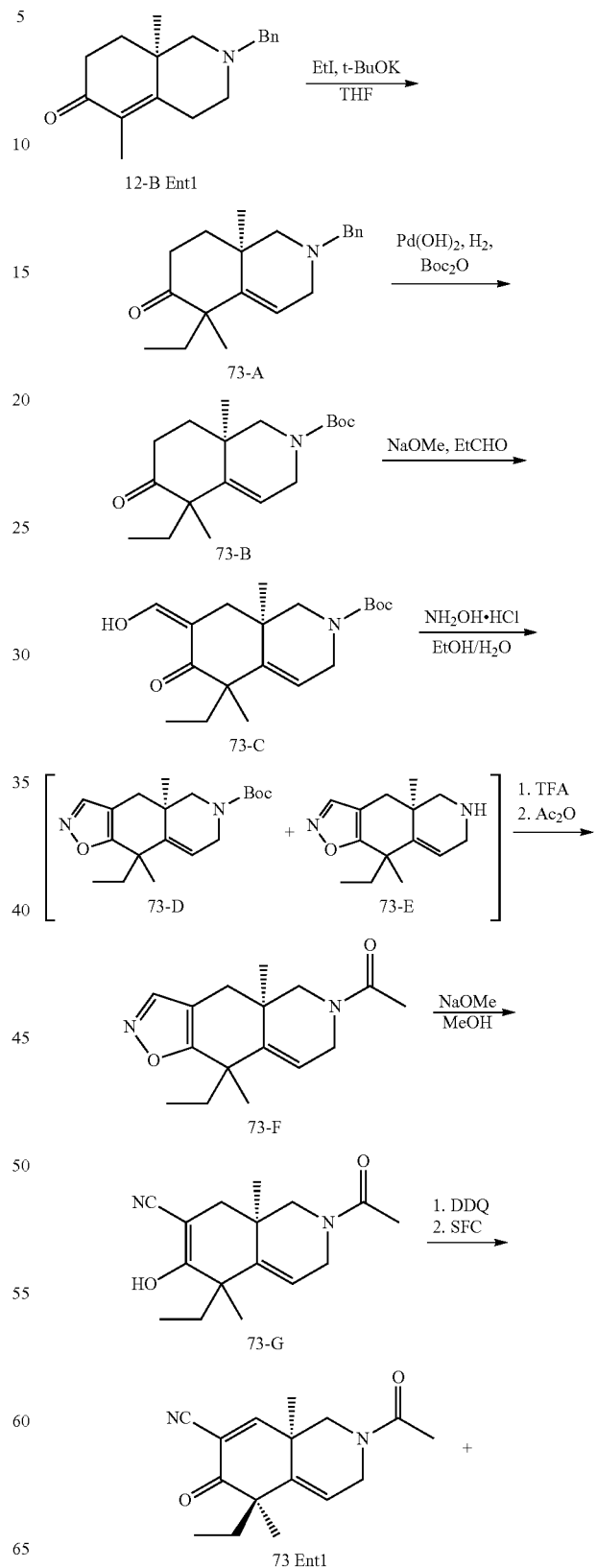

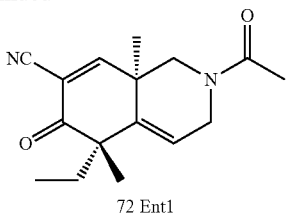

72 Ent1

Preparation of Compound 73-A

12-B Ent1 (122.3 mg, 0.40 mmol, hydrochloride salt) was first taken up in ethyl acetate and washed with 1N NaOH solution. Organics were washed with saturated sodium chloride, dried over sodium sulfate, filtered, evaporated. Sample azeotroped with toluene then taken up in THF (3.5 mL) and cooled in a room temperature water bath. To the reaction was added t-BuOK (1M in THF, 454.5 uL, 0.454 mmol). After stirring 1 h, iodoethane (36 uL, 0.45 mmol) was added. After stirring 1 d, the reaction was diluted with saturated sodium bicarbonate, extracted with ethyl acetate, washed with brine, dried over sodium sulfate, filtered, and concentrated. Purification by column chromatography using 0-30% ethyl acetate in heptanes as eluent afforded 73-A (22.5 mg, 18.9% yield). Approximately 5:3 mixture of diastereomers by 1H NMR, minor is 72-C Ent1.

LCMS (M+H 298.2)

1H NMR (400 MHz, CDCl$_3$) δ: 7.41-7.29 (m, 4H), 7.26-7.22 (m, 1H), 5.49-5.41 (m, 1H), 3.69 (d, J=13.3 Hz, 1H), 3.48 (d, J=13.3 Hz, 1H), 3.43-3.27 (m, 1H), 2.83-2.72 (m, 1H), 2.63-2.48 (m, 2H), 2.48-2.32 (m, 1H), 2.02-1.88 (m, 1H), 1.85-1.61 (m, 2H), 1.59-1.37 (m, 2H), 1.21-1.13 (m, 6H), 0.75 (dt, J=3.4, 7.3 Hz, 3H). Sample is a mixture of diastereomers by comparison with 72-C.

Preparation of Compound 73-B

73-A (410.5 mg, 1.38 mmol) was dissolved in methanol (12.7 mL) along with Boc$_2$O (361.4 mg, 1.66 mmol) and Pd(OH)$_2$/C (few mg). The vessel was evacuated then backfilled with hydrogen five times. The reaction was hydrogenated (balloon pressure) overnight. The reaction was filtered through Celite, washed with methanol and evaporated to give 73-B (457.8 mg, 107.9% yield crude).

LCMS (M+H—C4H8 252.1)

Preparation of Compound 73-C

To a solution of 73-B (457.8 mg, 1.49 mmol) in ethyl formate (5.0 mL, 62.2 mmol) at RT, sodium methoxide (4.37 M in methanol, 1.36 mL, 5.94 mmol) was added dropwise. The reaction mixture was stirred at RT overnight. Reaction was diluted with water, brought to pH 5 with AcOH, then extracted with ethyl acetate. The organics were washed with saturated sodium chloride, dried over sodium sulfate, filtered and evaporated to give 73-C (431.2 mg, 86.2%).

LCMS (M+Na 358.1)

Preparation of Compound 73-D and 73-E

To a solution of 73-C (431.2 mg, 1.29 mmol) in ethyl alcohol (12.2 mL) and water (612 uL) was added hydroxylamine hydrochloride (893.3 mg, 12.85 mmol). The solution was stirred under reflux for 2.5 hours. The solvent was removed under vacuum to provide a solid. The solid was then dissolved in saturated aqueous potassium carbonate and ethyl acetate. The layers were then separated and the organic layer was washed with saturated sodium chloride, dried over sodium sulfate, filtered, and concentrated to give a mixture of 73-D and 73-E (295.1 mg).

LCMS (M+H 333.2, 233.1)

Preparation of Compound 73-F

A mixture of 73-D and 73-E (295.1 mg) was dissolved in DCM (4.2 mL) and TFA (5.1 mL, 66.4 mmol) was added. The reaction was stirred for 1.5 h, at which point the reaction was evaporated to dryness then azeotroped with DCM. The residue was taken up in DCM (10.2 mL) and acetic anhydride (180.6 uL, 1.91 mmol) was added. With stirring was added diisopropylethylamine (665.4 uL, 3.81 mmol). After stirring for 1 h at RT, reaction was diluted with ethyl acetate, washed with dilute sodium bicarbonate, washed with saturated sodium chloride, dried over sodium sulfate, filtered, evaporated to give 73-F (335.3 mg, 94.6% yield from 73-C).

LCMS (M+H 275.2)

Preparation of Compound 73-G

To a solution of 73-F (335.3 mg, 1.22 mmol) in methanol (15.0 mL) under nitrogen was added sodium methoxide (25% in methanol, 1.40 mL, 6.11 mmol) at room temperature. The mixture was stirred at 50° C. for 1.5 hours. The reaction then was diluted with water and 1 eq 1N HCl (relative to NaOMe) was added. Volatiles were evaporated under reduced pressure. The solution was extracted with ethyl acetate, washed with saturated sodium chloride, dried over sodium sulfate then filtered and concentrated to give 73-G (314.3 mg, 93.9% yield).

LCMS (M+H 275.2).

Preparation of 73 Ent1

73-G (314.3 mg, 1.15 mmol) was dissolved in toluene (14.2 mL) and DDQ (390.1 mg, 1.72 mmol) was added. The mixture was heated at reflux for 60 minutes. Sample was cooled, diluted with toluene, filtered. Separation by preparative HPLC was followed by second (achiral) preparative HPLC (Column: Waters Sunfire PREP C18 OBD 50×100 mm, 5 um; Method: 95% water/5% ACN (initial conditions) to 40% water/60% ACN over 15 minutes in 0.1% TFA (flow rate: 80 mL/min) then SFC (Column: CHIRALPAK IG 30×250 mm, 5 um; Method: 25% Methanol in CO2 (flow rate: 100 mL/min), ABPR 120 bar, MBPR 40 psi) to give 73 Ent1 (E1, first eluting) (7.2 mg, 2.3% yield) and 72 Ent1 (E2, second eluting) (10.1 mg, 3.2% yield).

Data for 73 Ent1:
 HPLC (Purity: 97.5%)
 LCMS (M+H 273.1)
 SFC (ee: 100%)
 1H NMR (400 MHz, CD$_3$OD) δ: 7.76 (s, 0.5H), 7.73 (s, 0.5H), 5.77 (t, J=3.4 Hz, 0.5H), 5.72 (t, J=3.3 Hz, 0.5H), 4.60-4.49 (m, 1H), 4.33 (dd, J=3.1, 18.2 Hz, 0.5H), 4.08 (dd, J=3.3, 18.3 Hz, 0.5H), 3.95 (d, J=12.5 Hz, 0.5H), 3.70 (dd, J=3.3, 19.8 Hz, 0.5H), 3.20 (d, J=12.8 Hz, 0.5H), 2.68 (d, J=12.5 Hz, 0.5H), 2.19 (s, 1.5H), 2.18 (s, 1.5H), 2.06-1.84 (m, 2H), 1.41 (s, 1.5H), 1.35 (s, 1.5H), 1.34 (d, J=1.3 Hz, 3H), 0.75 (t, J=7.3 Hz, 3H). NMR consistent with 1:1 mixture of rotamers.

Example 56. Synthesis of Compound 74 Ent1

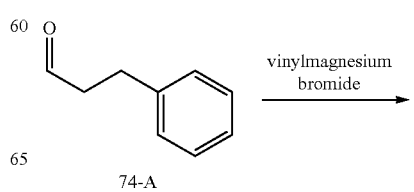

74-A

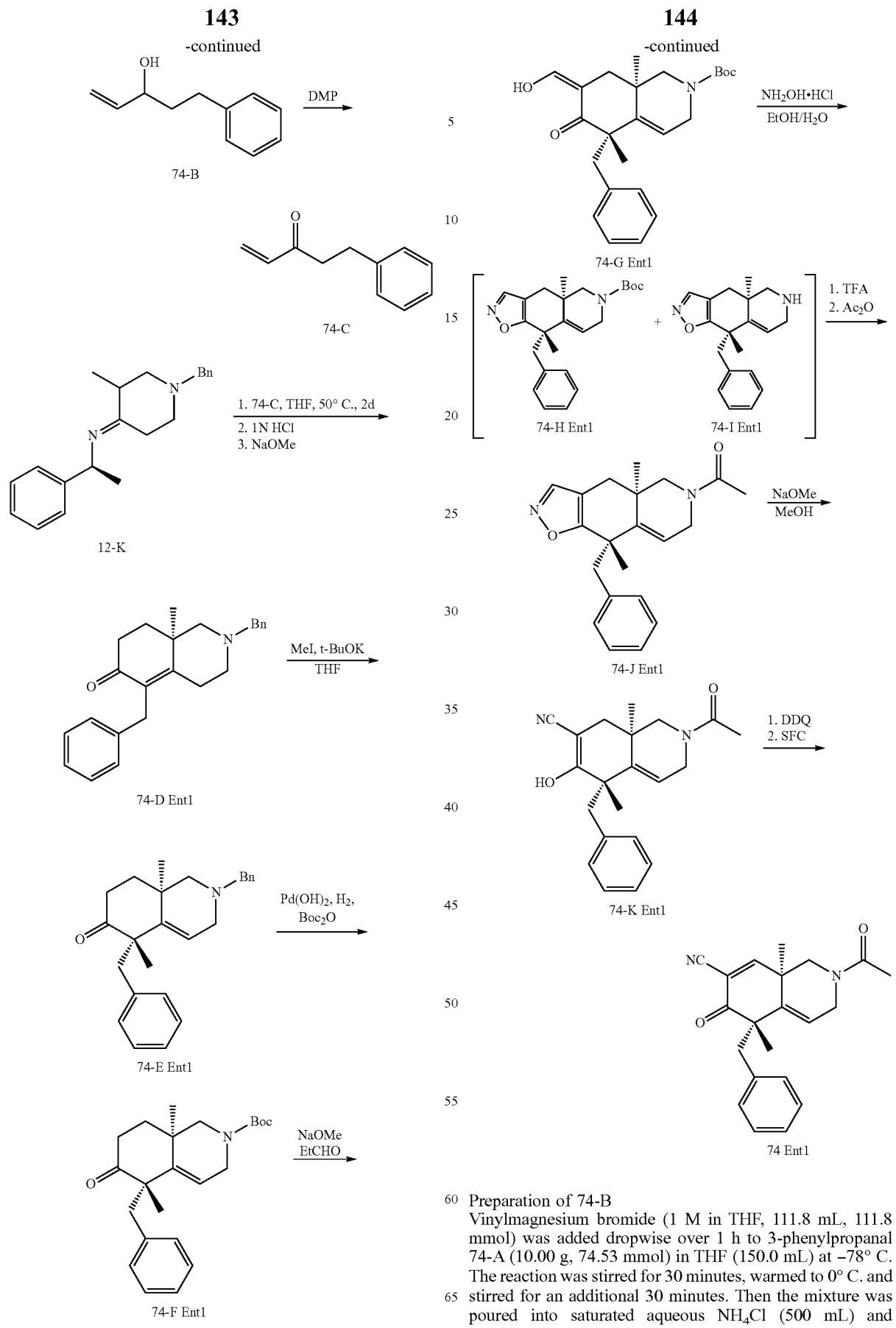
Preparation of 74-B
Vinylmagnesium bromide (1 M in THF, 111.8 mL, 111.8 mmol) was added dropwise over 1 h to 3-phenylpropanal 74-A (10.00 g, 74.53 mmol) in THF (150.0 mL) at −78° C. The reaction was stirred for 30 minutes, warmed to 0° C. and stirred for an additional 30 minutes. Then the mixture was poured into saturated aqueous NH$_4$Cl (500 mL) and extracted with Et$_2$O. The combined organic layers were washed with saturated aqueous NaCl, dried (MgSO4), and concentrated under reduced pressure to give 74-B (11.71 g, 96.9% yield) as a pale yellow oil.

1H NMR (400 MHz, CDCl$_3$) δ=7.33-7.28 (m, 2H), 7.25-7.16 (m, 3H), 5.92 (ddd, J=6.0, 10.5, 17.1 Hz, 1H), 5.26 (d, J=17.1 Hz, 1H), 5.15 (d, J=10.5 Hz, 1H), 4.15 (q, J=6.3 Hz, 1H), 2.79-2.66 (m, 2H), 1.91-1.83 (m, 2H), 1.73 (br s, 1H)

Preparation of 74-C

74-B (11.71 g, 72.2 mmol) was dissolved in DCM (300.0 mL). To this was added Dess-Martin periodinane (36.74 g, 86.6 mmol) portionwise. After 2 h stirring at RT, the reaction was diluted with ethyl acetate, washed with saturated sodium thiosulfate, washed with saturated sodium bicarbonate, washed with saturated sodium chloride, dried over sodium sulfate and evaporated. Sample taken up in ethyl acetate and washed twice with water, then once with saturated sodium chloride, dried over magnesium sulfate, filtered, evaporated. Sample taken up in 100 mL ether and filtered. Organics washed twice with water, dried over magnesium sulfate, filtered, evaporated. Sample was purified by silica gel column using 0-30% ethyl acetate in heptanes as eluent to give the product 74-C (3.93 g, 34.0% yield).

1H NMR (400 MHz, CDCl3) δ: 7.35-7.28 (m, 2H), 7.25-7.16 (m, 3H), 6.37 (dd, J=10.5, 17.8 Hz, 1H), 6.22 (d, J=17.1 Hz, 1H), 5.84 (dd, J=0.6, 10.4 Hz, 1H), 3.01-2.88 (m, 4H)

Preparation of 74-D Ent1

12-K (2.00 g, 6.53 mmol) was dissolved in THF (13.3 mL); then 74-C (1.20 g, 7.52 mmol) and hydroquinone (14.4 mg, 131 umol) were added. The mixture was stirred at 50° C., sheltered from light for 2 days. The reaction was diluted with 1 N HCl (2 eq), made basic by adding 10 N NaOH (4 eq), and extracted with ethyl acetate. The organic layer was washed with brine, dried (Na$_2$SO$_4$), and concentrated. The crude material was chromatographed on silica gel with ethyl acetate in heptanes (0-30%) as eluent. This material was dissolved in methanol (1.08 mL) and to this was added sodium methoxide (4.5 M in methanol, 691 uL, 3.11 mmol). The mixture was stirred at 50° C. overnight. The reaction was diluted with water and extracted with ethyl acetate. The organic layer was washed with brine, dried (Na$_2$SO$_4$), and concentrated. The crude material was purified by silica gel chromatography with 0-30% ethyl acetate in heptanes as eluent to afford 74-D Ent1 (195.0 mg, 8.6% yield).

LCMS (M+H 346.2)

1H NMR (400 MHz, CDCl$_3$) δ: 7.38-7.29 (m, 4H), 7.26-7.19 (m, 3H), 7.17-7.04 (m, 3H), 3.76-3.62 (m, 2H), 3.55 (d, J=13.2 Hz, 1H), 3.42 (d, J=13.2 Hz, 1H), 3.02-2.95 (m, 1H), 2.72-2.40 (m, 5H), 2.02-1.92 (m, 1H), 1.91-1.71 (m, 2H), 1.67-1.57 (m, 1H), 1.42 (s, 3H)

Preparation of 74-E Ent1

74-D Ent1 (195.0 mg, 564 umol) was azeotroped with toluene then dissolved in THF (5.0 mL). To this was added t-BuOK (76.0 mg, 677 umol). After stirring for 1 h, methyl iodide (39.4 uL, 632 umol) was added. After stirring 1 d, the reaction was diluted with saturated sodium bicarbonate, extracted with ethyl acetate, washed with saturated sodium chloride, dried over sodium sulfate, filtered and evaporated. Purification by silica gel chromatography using 0-30% ethyl acetate in heptanes as eluent afforded 74-E Ent1 (64.8 mg, 31.9% yield). 7.5:1 mixture of diastereomers by 1H NMR, minor is 75-A Ent1. Structure confirmed by NMR (nOe).

LCMS (M+H 360.2)

1H NMR (400 MHz, CDCl$_3$) δ: 7.39-7.28 (m, 5H), 7.27-7.01 (m, 5H), 5.33 (dd, J=2.5, 4.0 Hz, 1H), 3.67 (d, J=13.3 Hz, 1H), 3.48 (d, J=13.3 Hz, 1H), 3.33 (dd, J=4.0, 16.6 Hz, 1H), 3.26 (d, J=13.1 Hz, 1H), 2.81-2.73 (m, 2H), 2.55-2.48 (m, 2H), 2.44 (d, J=10.5 Hz, 1H), 1.97 (d, J=10.8 Hz, 1H), 1.72-1.62 (m, 1H), 1.51-1.41 (m, 1H), 1.22 (s, 3H), 0.76 (s, 3H)

Preparation of 74-F Ent1

74-E Ent1 (201.7 mg, 561 umol) was dissolved in methanol (5.4 mL) along with Boc$_2$O (146.9 mg, 673 umol) and Pd(OH)$_2$/C (few mg). The vessel was evacuated then backfilled with hydrogen five times. The reaction was hydrogenated (balloon pressure) overnight. Additional Boc$_2$O (52 mg, 238 umol) and catalyst (few mg) added and the hydrogenation continued (as above). After 4 h, the reaction was filtered through Celite, washed with methanol and evaporated to give 74-F Ent1 (259.1 mg, 125.0% yield crude).

LCMS (M+Na 392.2)

Preparation of 74-G Ent1

74-F Ent1 (259.1 mg, 701.2 umol) was dissolved in ethyl formate (1.81 mL, 22.44 mmol). To this was added sodium methoxide (4.37 M in methanol, 513.5 uL, 2.24 mmol) dropwise. After stirring overnight, the reaction was diluted with water and 1 eq AcOH (relative to NaOMe) was added. The reaction was extracted with ethyl acetate, washed with saturated sodium chloride, dried over sodium sulfate, filtered and evaporated to give 74-G Ent1 (159.0 mg, 57.0%).

LCMS (M+Na 420.2)

Preparation of 74-H Ent1 and 74-I Ent1

To a solution of 74-G Ent1 (159.0 mg, 400.0 umol) in ethyl alcohol (3.8 mL) and water (190 uL) was added hydroxylamine hydrochloride (278.0 mg, 4.00 mmol). The solution was stirred under reflux for 1.5 hours. The solvent was removed to provide a solid. The solid was then dissolved in saturated aqueous potassium carbonate and ethyl acetate. The layers were then separated and the organic layer was washed with saturated sodium chloride, dried over sodium sulfate, filtered, and concentrated to give a mixture of 74-H Ent1 and 74-I Ent1 (135.3 mg).

LCMS (M+H 395.2, 295.2)

Preparation of 74-J Ent1

A mixture of 74-H Ent1 and 74-I Ent1 (135.3 mg) was dissolved in DCM (3.5 mL) and TFA (3.5 mL) was added. The reaction was stirred for 1 h, at which point the reaction was evaporated to dryness, then azeotroped with DCM. The residue was taken up in DCM (6.0 mL) and acetic anhydride (65.2 uL, 689 umol) was added. With stirring was added diisopropylethylamine (240.8 uL, 1.38 mmol). After 1 h at RT, reaction was diluted with ethyl acetate, washed with dilute sodium bicarbonate, washed with saturated sodium chloride, dried over sodium sulfate, filtered, evaporated. Purification by silica gel chromatography using 0-20% methanol in methylene chloride as eluent gave 74-J Ent1 (109.7 mg, 81.5% from 74-G Ent1).

LCMS (M+H 337.2)

Preparation of 74-K Ent1

To a solution of 74-J Ent1 (109.7 mg, 326 umol) in methanol (5.0 mL) under nitrogen was added sodium methoxide (25% in methanol, 372.8 uL, 1.63 mmol) at room temperature. The mixture was stirred at 50° C. for 3 hours. The reaction then was diluted with water and 1 eq 1N HCl (relative to NaOMe) was added. The solution was extracted with ethyl acetate, washed with saturated sodium chloride, dried over sodium sulfate then filtered and concentrated to give 74-K Ent1 (104.7 mg, 95.4% yield crude)

LCMS (M+H 337.2)

Preparation of 74 Ent1

74-K Ent1 (104.7 mg, 311.2 umol) was dissolved in toluene (5.1 mL) and DDQ (101.0 mg, 445 umol) was added. The mixture was heated to reflux for 60 minutes. Reaction cooled to room temperature. The reaction was filtered and concentrated. The residue was then purified by preparative HPLC then separated by SFC (Column: CHIRALPAK IG 30×250 mm, 5 um; Co-solvent: 35% Methanol (w/o any modifier) in CO2 (flow rate: 100 mL/min), ABPR 120 bar, MBPR 40 psi) to give 74 Ent1 (13.5 mg, 13.0% yield).

Data for 74 Ent1:

HPLC (Purity: 100%)

LCMS (M+H 335.2)

SFC (ee: 100%)

1H NMR (400 MHz, CD$_3$OD) δ: 7.75 (s, 0.5H), 7.73 (s, 0.5H), 7.29-7.17 (m, 3H), 7.05-6.97 (m, 2H), 5.67 (t, J=3.4 Hz, 0.5H), 5.63 (t, J=3.3 Hz, 0.5H), 4.56 (d, J=12.3 Hz, 0.5H), 4.50 (dd, J=2.8, 19.8 Hz, 0.5H), 4.32 (dd, J=2.9, 18.4 Hz, 0.5H), 4.03 (dd, J=3.5, 18.3 Hz, 0.5H), 3.93 (d, J=12.5 Hz, 0.5H), 3.69-3.62 (m, 0.5H), 3.12-2.52 (m, 3H), 2.19 (d, J=1.5 Hz, 3H), 1.35 (s, 1.5H), 1.33 (s, 1.5H), 1.20 (d, J=3.0 Hz, 3H). NMR consistent with 1:1 mixture of rotamers.

Example 57. Synthesis of Compound 75 Ent1

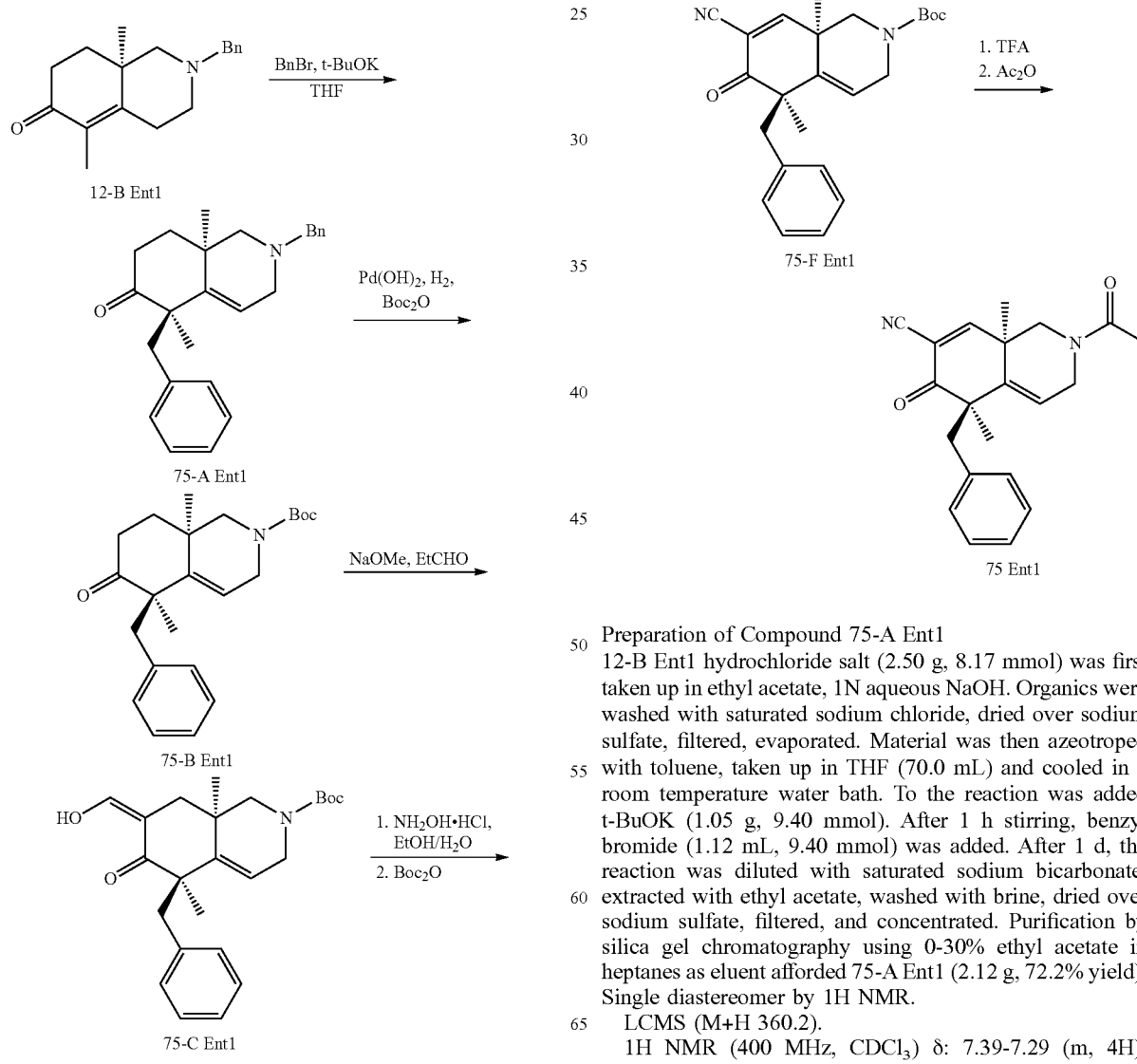
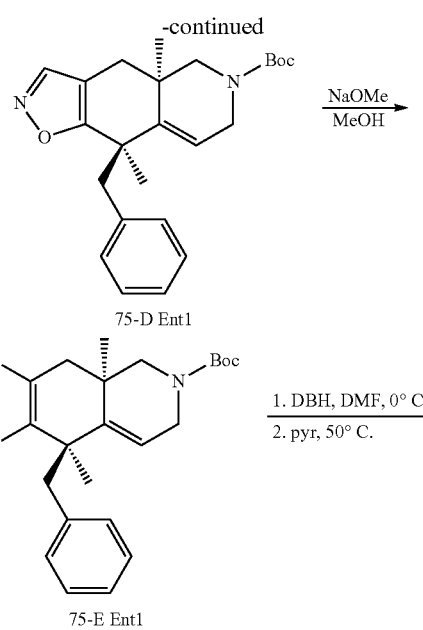

Preparation of Compound 75-A Ent1

12-B Ent1 hydrochloride salt (2.50 g, 8.17 mmol) was first taken up in ethyl acetate, 1N aqueous NaOH. Organics were washed with saturated sodium chloride, dried over sodium sulfate, filtered, evaporated. Material was then azeotroped with toluene, taken up in THF (70.0 mL) and cooled in a room temperature water bath. To the reaction was added t-BuOK (1.05 g, 9.40 mmol). After 1 h stirring, benzyl bromide (1.12 mL, 9.40 mmol) was added. After 1 d, the reaction was diluted with saturated sodium bicarbonate, extracted with ethyl acetate, washed with brine, dried over sodium sulfate, filtered, and concentrated. Purification by silica gel chromatography using 0-30% ethyl acetate in heptanes as eluent afforded 75-A Ent1 (2.12 g, 72.2% yield). Single diastereomer by 1H NMR.

LCMS (M+H 360.2).

1H NMR (400 MHz, CDCl$_3$) δ: 7.39-7.29 (m, 4H), 7.26-7.19 (m, 4H), 7.07-7.03 (m, 2H), 5.53 (dd, J=1.9, 4.4

Hz, 1H), 3.69 (d, J=13.1 Hz, 1H), 3.48 (d, J=13.1 Hz, 1H), 3.39 (dd, J=4.5, 16.3 Hz, 1H), 2.98-2.88 (m, 2H), 2.84 (dd, J=1.6, 16.4 Hz, 1H), 2.47-2.34 (m, 2H), 2.14-2.06 (m, 1H), 1.84 (d, J=10.8 Hz, 1H), 1.31 (s, 3H), 1.17-1.09 (m, 1H), 1.08 (s, 3H), 0.90-0.72 (m, 1H)

Preparation of Compound 75-B Ent1

75-A Ent1 (2.12 g, 5.90 mmol) was dissolved in methanol (50.0 mL) along with Boc$_2$O (1.87 g, 8.57 mmol) and Pd(OH)$_2$/C (few mg). The vessel was evacuated then backfilled with hydrogen five times. The reaction was hydrogenated (balloon pressure) overnight. The reaction was filtered through Celite, washed with methanol and evaporated. Residue was purified by silica gel chromatography using 0-30% ethyl acetate in heptanes as eluent to give 75-B Ent1 (1.52 g, 69.7% yield).

LCMS (M+Na 392.2)

1H NMR (400 MHz, CDCl3) δ: 7.25-7.19 (m, 3H), 7.05-6.99 (m, 2H), 5.55-5.36 (m, 1H), 4.48-4.21 (m, 1H), 3.88-3.61 (m, 2H), 3.03-2.95 (m, 1H), 2.93-2.82 (m, 1H), 2.55-2.37 (m, 2H), 2.31-2.15 (m, 1H), 1.60-1.49 (m, 2H), 1.48 (br s, 9H), 1.30 (s, 3H), 0.97 (s, 3H)

Preparation of Compound 75-C Ent1

To a solution of 75-B Ent1 (1.52 g, 4.11 mmol) in ethyl formate (13.8 mL, 171.7 mmol) at RT, sodium methoxide (4.37 M in methanol, 3.77 mL, 16.5 mmol) was added dropwise. The reaction mixture was stirred at RT for 3 d. Reaction was diluted with water, then acetic acid (941.1 uL, 16.45 mmol) was added. The mixture was then extracted with ethyl acetate. The organics were washed with saturated sodium chloride, dried over sodium sulfate, filtered and evaporated to give 75-C Ent1 (1.76 g, 107.7% yield)

LCMS (M+Na 420.2)

1H NMR (400 MHz, CDCl$_3$) δ: 14.81 (d, J=6.0 Hz, 1H), 7.85 (d, J=6.0 Hz, 1H), 7.20-7.12 (m, 3H), 7.00-6.94 (m, 2H), 5.74-5.59 (m, 1H), 4.54-4.27 (m, 1H), 3.86-3.62 (m, 2H), 3.07-2.92 (m, 2H), 2.46-2.27 (m, 1H), 1.58-1.39 (m, 14H), 0.98-0.80 (m, 3H)

Preparation of Compound 75-D Ent1

To a solution of 75-C Ent1 (1.76 g, 4.43 mmol) in ethyl alcohol (42.1 mL) and water (2.11 mL) was added hydroxylamine hydrochloride (3.08 g, 44.28 mmol). The solution was stirred under reflux for 2 hours. The solvent was removed to provide a solid. The solid was then dissolved in saturated aqueous potassium carbonate and ethyl acetate. The layers were then separated and the organic layer was washed with saturated sodium chloride, dried over sodium sulfate, filtered, and concentrated. Material was dissolved in DCM (51.6 mL). To this was added Boc$_2$O (1.21 g, 5.54 mmol) and then triethylamine (1.28 mL, 9.24 mmol) with stirring. After stirring overnight at room temperature, the reaction was diluted with water and extracted with ethyl acetate. The organics were washed with saturated sodium chloride, dried over sodium sulfate, filtered and evaporated. The residue was purified by silica gel chromatography using 0-30% ethyl acetate in heptanes as eluent to give the 75-D Ent1 (1.45 g, 83.1% yield).

LCMS (M+H 395.2).

1H NMR (400 MHz, CDCl$_3$) δ: 7.94 (s, 1H), 7.19-6.97 (m, 3H), 6.62-6.55 (m, 2H), 5.94-5.82 (m, 1H), 4.58-4.32 (m, 1H), 3.92-3.64 (m, 2H), 3.11 (s, 2H), 2.49-2.31 (m, 1H), 1.91-1.82 (m, 1H), 1.67-1.43 (m, 13H), 0.93 (s, 3H)

Preparation of Compound 75-E Ent1

To an ether (17.2 mL) solution of 75-D Ent1 (850.0 mg, 1.72 mmol, 80% purity) (previously azeotroped with ether) under nitrogen was added sodium methoxide (25% in methanol, 1.97 mL, 8.62 mmol) at room temperature. The mixture was stirred at this temperature for 2 hours then diluted with ether then washed with 1N HCl solution twice. The aqueous layers were combined and extracted with ether and the combined organic layers were washed with water then brine before being dried over sodium sulfate, then filtered and concentrated to give 75-E Ent1 (725.2 mg, 106.9% crude)

LCMS (M+Na 417.2).

Preparation of Compound 75-F Ent1

To a solution of 75-E Ent1 (150.3 mg, 381 umol) in DMF (3.31 mL) at 0° C., 1,3-dibromo-5,5-dimethyl-imidazolidine-2,4-dione (63.0 mg, 220 umol) was added, and the solution was stirred for 2 hours. Pyridine (1.69 mL, 21.0 mmol) was added, and the solution was heated at 50° C. overnight. After concentration in vacuo, the residue was purified on a silica gel column using 0-30% ethyl acetate in heptanes as eluent to give 75-F Ent1 (85.2 mg, 57.0% yield).

LCMS (M+H 393.2).

1H NMR (400 MHz, CDCl$_3$) δ: 7.25-7.14 (m, 3H), 6.99-6.90 (m, 3H), 5.90-5.74 (m, 1H), 4.53-4.28 (m, 1H), 4.02-3.68 (m, 2H), 3.25-3.01 (m, 2H), 2.72-2.50 (m, 1H), 1.53-1.43 (m, 12H), 1.25 (s, 3H)

Preparation of Compound 75 Ent1

75-F Ent1 (85.2 mg, 217 umol) was dissolved in DCM (1.50 mL). To this was added trifluoroacetic acid (1.50 mL) and the reaction was stirred at room temperature for 2 h. Volatiles were removed by evaporation, followed by azeotrope with dichloromethane (twice). Sample was dissolved in DCM (3.0 mL). To this was added acetic anhydride (31.0 uL, 328 umol) followed by diisopropylethylamine (113.7 uL, 651 umol) with stirring. After 1 h, reaction was evaporated to dryness and the residue was purified by preparative HPLC to give the 75 Ent1 (50.8 mg, 70.0% yield).

Data for 75 Ent1:

HPLC (Purity: 100%)

LCMS (M+H 335.1)

SFC (ee: 99.5% based on ee of 12-B Ent1)

1H NMR (400 MHz, CD$_3$OD) δ: 7.38 (s, 0.5H), 7.34 (s, 0.5H), 7.24-7.13 (m, 3H), 6.99-6.94 (m, 2H), 6.04 (t, J=3.3 Hz, 0.5H), 5.99 (t, J=3.3 Hz, 0.5H), 4.59 (dd, J=3.0, 19.8 Hz, 0.5H), 4.43 (d, J=12.5 Hz, 0.5H), 4.38 (dd, J=3.3, 18.3 Hz, 0.5H), 4.13 (dd, J=3.4, 18.4 Hz, 0.5H), 3.81 (d, J=12.8 Hz, 0.5H), 3.74 (dd, J=3.5, 19.8 Hz, 0.5H), 3.27-3.20 (m, 1H), 3.14 (dd, J=4.3, 13.3 Hz, 1H), 2.95 (d, J=12.8 Hz, 0.5H), 2.45 (d, J=12.3 Hz, 0.5H), 2.18 (s, 1.5H), 2.14 (s, 1.5H), 1.51 (d, J=1.8 Hz, 3H), 1.26 (s, 1.5H), 1.20 (s, 1.5H)

Example 58. Synthesis of Compound 76 Ent1

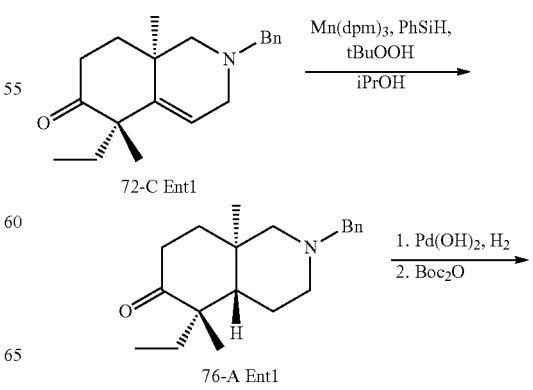

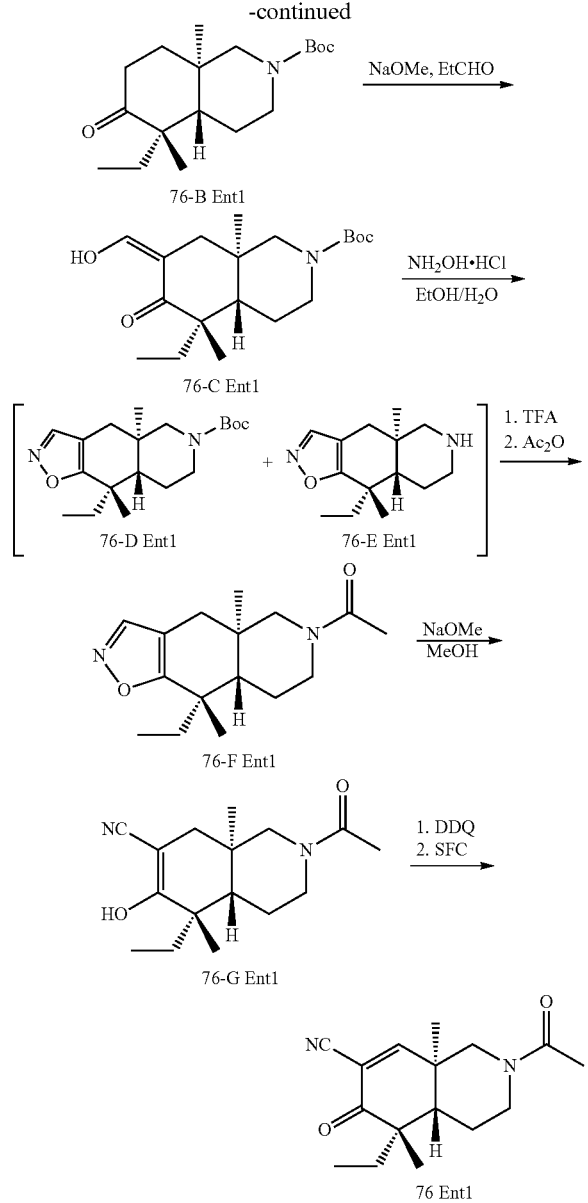

Preparation of Compound 76-A Ent1

To a reaction vial containing 72-C Ent1 (154.0 mg, 518 umol) was added anhydrous isopropanol (2.00 mL) and tris(2,2,6,6-tetramethyl-3,5-heptanedionato)manganese(III) (31.3 mg, 51.8 umol). The solution was degassed for 10 minutes by bubbling nitrogen through. Separately, phenylsilane (80.2 uL, 652 umol) and tert-butyl hydroperoxide (5.5 M in decane, 170.4 uL, 0.937 mmol) in isopropanol (1.00 mL) were degassed for 10 minutes in a similar manner. The second solution was added to the first via syringe slowly over 15 minutes. After 1 d, the solution was concentrated and purified on silica gel column using 0-30% ethyl acetate in heptanes as eluent to afford 76-A Ent1 (53.0 mg, 34.2% yield).
Diastereoselectivity not determined.
LCMS (M+H 300.2)
Preparation of Compound 76-B Ent1

76-A Ent1 (53.0 mg, 177 umol) was dissolved in methanol (5.0 mL). To this was added Pd(OH)$_2$/C (few mg). Reaction was evacuated, then backfilled with hydrogen three times. Reaction was hydrogenated under balloon pressure of hydrogen overnight. The reaction was filtered through Celite, which was then washed with methanol and evaporated. Residue was dissolved in DCM (2.00 mL) and to this was added Boc$_2$O (47.9 mg, 219 umol) and then triethylamine (50.1 uL, 361 umol). After stirring for 1.5 h, sample was diluted with water, extracted with ethyl acetate, washed with saturated sodium chloride, dried over sodium sulfate, filtered and evaporated. Residue was purified by silica gel chromatography to give 76-B Ent1 (87.2 mg, 159.2% crude).
LCMS (M+H 310.3)
Preparation of Compound 76-C Ent1

To a solution of 76-B Ent1 (42.0 mg, 136 umol) in ethyl formate (2.20 mL, 27.3 mmol) at RT, sodium methoxide (311 uL, 4.37 M, 1.36 mmol) was added dropwise. The reaction mixture was stirred at RT for 1 d then heated at 55° C. for 1 d. The reaction had dried out so sample was resuspended in toluene, diluted with water, brought to pH 5 with acetic acid, then extracted with ethyl acetate. The organics were washed with saturated sodium chloride, dried over sodium sulfate, filtered and evaporated to give 76-C Ent1 (41.5 mg, 90.6% yield crude).
LCMS (M+H 338.2)
Preparation of Compound 76-D Ent1+76-E Ent1

To a solution of 76-C Ent1 (41.5 mg, 123 umol) in ethyl alcohol (1.17 mL) and water (58.5 uL) was added hydroxylamine hydrochloride (85.5 mg, 1.23 mmol). The solution was stirred under reflux for 1.5 hours. The solvent was removed to provide a solid. The solid was then dissolved in saturated aqueous potassium carbonate and ethyl acetate. The layers were then separated and the organic layer was washed with saturated sodium chloride, dried over sodium sulfate, filtered, and concentrated to give a mixture of 76-D Ent1 and 76-E Ent1 (26.0 mg)
LCMS (M+H 335.1, 235.1)
Preparation of Compound 76-F Ent1

A mixture of 76-D Ent1 and 76-E Ent1 (26.0 mg) was dissolved in DCM (1.00 mL) and TFA (1.00 mL) was added. The reaction was stirred for 2 h, at which point the reaction was evaporated to dryness then azeotroped with DCM. The residue was taken up in DCM (2.00 mL) and acetic anhydride (11.0 uL, 117 umol) was added. With stirring was added diisopropylethylamine (40.7 uL, 233 umol). After 2 h at RT, reaction was diluted with ethyl acetate, washed with water, washed with saturated sodium chloride, dried over sodium sulfate, filtered, evaporated. Purification by silica gel chromatography using 0-100% ethyl acetate in heptanes as eluent gave 76-F Ent1 (17.4 mg, 51.1% from 76-C Ent1).
LCMS (M+H 277.2)
Preparation of Compound 76-G Ent1

To a solution of 76-F Ent1 (17.4 mg, 63.0 umol) in methanol (2.00 mL) under nitrogen was added sodium methoxide (25% in methanol, 72.0 uL, 314.80 umol) at room temperature. The mixture was stirred at 50° C. for 3 hours. The reaction then was diluted with water and 1 eq 1N HCl was added. The solution was extracted with ethyl acetate, washed with saturated sodium chloride, dried over sodium sulfate then filtered and concentrated to give 76-G Ent1 (17.0 mg, 97.7% yield crude)
LCMS (M+H 277.2)
Preparation of Compound 76 Ent1

76-G Ent1 (17.0 mg, 61.5 umol) was dissolved in toluene (1.00 mL) and DDQ (20.0 mg, 88.0 umol) was added. The mixture was heated to reflux for 4 h and the reaction cooled to room temperature. The reaction was filtered and concentrated. The residue was then purified by column chromatography using 0-20% methanol in methylene chloride as eluent. The compound was further purified by SFC (Column: CHIRALPAK OX-H 30×250 mm, 5 um; Co-solvent: 35% Methanol in $CO_2$ (flow rate: 100 mL/min), ABPR 120 bar, MBPR 40 psi) to give 76 Ent1 (6.6 mg, 39.0%).

Data for 76 Ent1:
HPLC (Purity: 99.6%)
LCMS (M+H 275.2)
SFC (ee: 100%)
1H NMR (400 MHz, $CD_3OD$) δ: 7.70 (s, 0.6H), 7.69 (s, 0.4H), 4.76 (td, J=2.2, 13.2 Hz, 0.4H), 4.52 (dd, J=1.8, 12.5 Hz, 0.6H), 4.11 (td, J=2.2, 13.4 Hz, 0.6H), 3.84 (dd, J=1.8, 13.1 Hz, 0.4H), 3.10 (dt, J=3.4, 13.0 Hz, 0.6H), 3.02 (d, J=13.1 Hz, 0.4H), 2.56 (dt, J=4.5, 12.4 Hz, 0.4H), 2.49 (br d, J=12.3 Hz, 0.6H), 2.17 (s, 1.8H), 2.13 (s, 1.2H), 2.12-1.44 (m, 5H), 1.30 (s, 1.2H), 1.25 (s, 1.8H), 1.18 (s, 3H), 0.83 (t, J=7.5 Hz, 3H). 1H NMR suggests 6:4 mixture of rotamers.

Example 59. Synthesis of Compounds 77-Ent1 and 77-Ent2

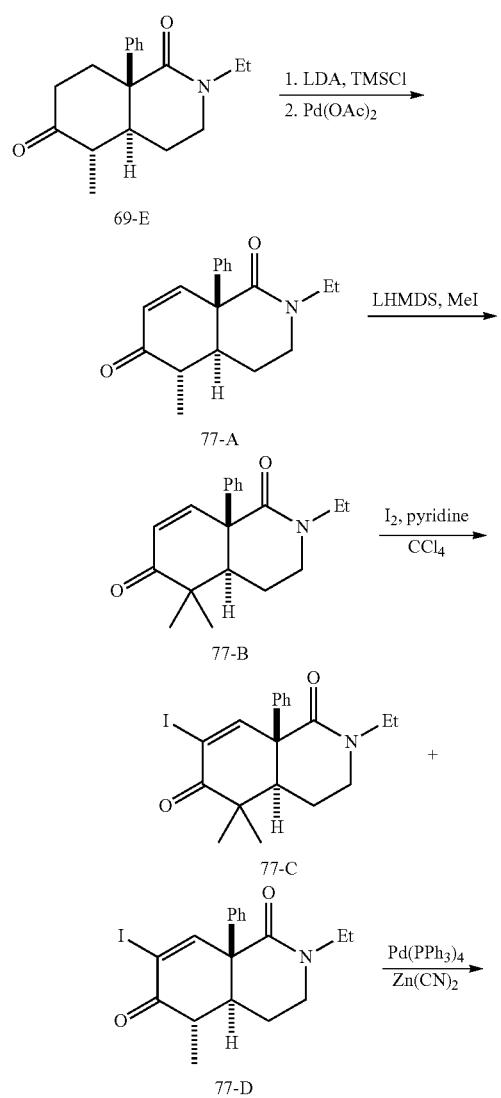

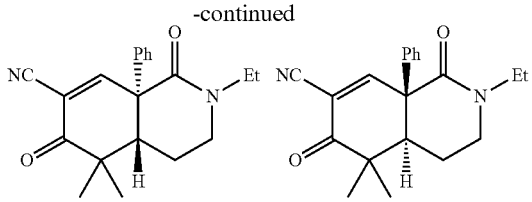

Compounds 77-Ent1 and 77-Ent2

Procedure for Preparation of Compound 77-A

A solution of LDA (0.44 M, 17.35 mL) under nitrogen at −78° C. was added to a solution of compound 69-E (1.98 g, 6.94 mmol) in THF (46.27 mL) under nitrogen at −78° C. After 30 minutes, trimethylsilyl chloride (979.88 mg, 9.02 mmol, 1.14 mL) was added rapidly to the solution via syringe. The cooling bath was then removed and the reaction was warmed to room temperature over 60 minutes. The solution was then partitioned between EtOAc (150 ml) and $NaHCO_3$ (150 ml). After separation of layers, the aqueous layer was extracted with EtOAc (2×150 ml) and the combined organic layers were washed with brine then dried over sodium sulfate, filtered, and concentrated. This material was then dissolved in acetonitrile (70 mL) and the mixture was evacuated and backfilled with nitrogen (3×). Palladium(II) acetate (1.87 g, 8.33 mmol) was then added in one portion and the flask was again evacuated and backfilled with nitrogen (3×). The mixture was then stirred at room temperature for 24 hours. The mixture was then filtered through celite which was then washed with EtOAc and the solution was concentrated. The residue was then purified by column chromatography (5-50% EtOAc/heptane) to provide compound 77-A (1.85 g, 6.53 mmol, 94% yield) as a brown solid which was used as is. A small sample (~150 mg) was purified by chromatography (5-50% EtOAc/heptane) then submitted to chiral SFC separation to obtain 77A-ent-1 (28.6 mg, Rt=2.73 min) and 77A-ent-2 (28.5 mg, Rt=3.33 min). SFC conditions: Column: CHIRALCEL IC 30×250 mm, 5 um; Method: 40% Methanol in $CO_2$ (flow rate: 100 mL/min), ABPR 120 bar, MBPR 40 psi.

Data for 77A-Ent-1
HPLC: (Purity: 97%)
LCMS: (M+H=284.1)
SFC: (ee: 100%)
$^1$HNMR (400 MHz, $CDCl_3$) δ ppm 7.71 (d, J=10.0 Hz, 1H), 7.39-7.28 (m, 3H), 7.26-7.22 (m, 2H), 6.33 (d, J=10.0 Hz, 1H), 3.77-3.64 (m, 1H), 3.63-3.41 (m, 3H), 2.42-2.26 (m, 2H), 1.86 (br d, J=4.8 Hz, 1H), 1.73-1.60 (m, 1H), 1.30 (t, J=7.2 Hz, 3H), 1.10 (d, J=6.3 Hz, 3H).

Data for 77A-Ent-2
HPLC: (Purity: 98%)
LCMS: (M+H=284.1)
SFC: (ee: 100%)
$^1$HNMR (400 MHz, $CDCl_3$) δ ppm 7.71 (d, J=10.0 Hz, 1H), 7.38-7.29 (m, 3H), 7.26-7.22 (m, 2H), 6.33 (d, J=10.0 Hz, 1H), 3.70 (dd, J=7.2, 13.4 Hz, 1H), 3.63-3.41 (m, 3H), 2.42-2.33 (m, 1H), 2.33-2.26 (m, 1H), 1.92-1.81 (m, 1H), 1.72-1.59 (m, 1H), 1.30 (t, J=7.2 Hz, 3H), 1.10 (d, J=6.5 Hz, 3H).

Procedure for Preparation of Compound 77-B

Compound 77-A (750.00 mg, 2.65 mmol) was dissolved in THF (26.50 mL) and cooled to −78° C. A solution of [bis(trimethylsilyl)amino]lithium (1 M, 26.47 mL) was then added and the mixture was stirred at −78° C. for 60 minutes then warmed to 0° C. and stirred for 60 minutes before cooling to −78° C. Methyl iodide (12.77 g, 89.99 mmol, 5.60 mL) was then added and the mixture was stirred at −78° C. then slowly warmed to room temperature and stirred overnight. The reaction was quenched with saturated aqueous ammonium chloride and diluted with EtOAc. The layers were separated and the aqueous layer was extracted with EtOAc. The combined organic layers were dried over sodium sulfate, filtered, and concentrated. The residue was purified by column chromatography (5-60% EtOAc/heptane) to provide 77-B (443.5 mg, 56% yield) as a brown solid containing a small amount of starting material. This material was used without further purification.

$^1$HNMR (500 MHz, CDCl$_3$) δ ppm 7.76 (d, J=10.4 Hz, 1H), 7.71 (d, J=10.4 Hz, 1H), 7.33-7.28 (m, 3H), 7.26-7.22 (m, 2H), 6.44 (d, J=10.4 Hz, 1H), 6.33 (d, J=10.4 Hz, 1H), 3.74-3.65 (m, 2H), 3.61-3.51 (m, 1H), 3.46-3.38 (m, 1H), 2.46 (dd, J=2.4, 13.4 Hz, 1H), 2.06-2.05 (m, 1H), 2.13-2.02 (m, 1H), 1.81 (ddd, J=2.4, 6.9, 13.9 Hz, 1H), 1.27 (t, J=7.3 Hz, 3H), 1.16-1.12 (m, 3H), 0.54 (s, 3H).

Procedure for Preparation of Compound 77-C

To a solution of compound 77-B (312.00 mg, 1.05 mmol) in pyridine (1.40 mL) and carbon tetrachloride (2.80 mL) was added iodine (798.84 mg, 3.15 mmol), and the solution was heated at 60° C. for 16 h. The reaction mixture was then cooled to room temperature and quenched with saturated aqueous sodium thiosulfate solution (25 mL), and extracted with DCM (2×50 mL). The combined organic extracts were washed with brine and dried with Na$_2$SO$_4$. The mixture was then concentrated and purified by column chromatography (5-50% EtOAc/heptanes) to provide compound 77-C (340.00 mg, 76.5% yield) as a yellow foam with a small amount of monomethylated material 77-D. The material was used in the next step without further purification.

$^1$HNMR (400 MHz, CDCl$_3$)$_6$ ppm 8.54 (s, 1H), 8.50 (s, 1H), 7.34-7.28 (m, 3H), 7.16 (dd, J=1.1, 7.2 Hz, 2H), 3.73-3.61 (m, 2H), 3.55 (dt, J=6.9, 12.2 Hz, 1H), 3.49-3.38 (m, 1H), 2.54 (dd, J=2.0, 13.3 Hz, 1H), 2.15-2.00 (m, 1H), 1.81 (br dd, J=7.4, 13.4 Hz, 1H), 1.27 (t, J=7.5 Hz, 3H), 1.17 (s, 3H), 0.57 (s, 3H).

Procedure for Preparation of Compounds 77-Ent and 77-Ent2

Compound 77-C (200.00 mg, 472.49 umol), Zinc cyanide (166.45 mg, 1.42 mmol), and tetrakis(triphenylphosphine) palladium(0) (109.20 mg, 94.50 umol) were taken up in DMF (6.75 mL). The vial was sparged with nitrogen for 10 minutes and the reaction was stirred at 80° C. for 40 minutes. The reaction mixture was then cooled to room temperature, diluted with ether, washed with water then dried with sodium sulfate, filtered, and concentrated. The material was then purified by column chromatography (5-50% EtOAc/Heptanes) to provide a white solid which was then separated by chiral SFC to provide 77-Ent1 (29.8 mg, Rt=3.09 min) and 77-Ent-2 (26.9 mg, Rt=4.90 min). Chiral SFC conditions: Column: CHIRALPAK IA 30×250 mm, 5 um. Method: 15% Methanol in CO$_2$ (flow rate: 100 mL/min), ABPR 120 bar, MBPR 40 psi.

Data for 77-ent-1
HPLC: (Purity: 98%)
LCMS: (M+H=323.1)
SFC: (ee: 100%)
$^1$HNMR (500 MHz, CDCl$_3$) δ ppm 8.52 (s, 1H), 7.36-7.33 (m, 2H), 7.29-7.26 (m, 1H), 7.14-7.11 (m, 2H), 3.74-3.64 (m, 2H), 3.56 (dt, J=6.7, 12.2 Hz, 1H), 3.44 (qd, J=7.3, 13.4 Hz, 1H), 2.46 (dd, J=2.1, 13.1 Hz, 1H), 2.10 (ddt, J=6.7, 11.6, 13.4 Hz, 1H), 1.85 (ddd, J=1.8, 6.7, 14.0 Hz, 1H), 1.28 (t, J=7.0 Hz, 3H), 1.21 (s, 3H), 0.60 (s, 3H).

Data for 77-ent-2
HPLC: (Purity: 99%)
LCMS: (M+H=323.1)
SFC: (ee: 100%)
$^1$HNMR (500 MHz, CDCl$_3$)$_6$ ppm 8.52 (s, 1H), 7.37-7.33 (m, 2H), 7.29-7.26 (m, 1H), 7.13 (dd, J=1.8, 7.9 Hz, 2H), 3.74-3.64 (m, 2H), 3.56 (dt, J=6.7, 12.2 Hz, 1H), 3.44 (qd, J=6.9, 14.7 Hz, 1H), 2.46 (dd, J=2.4, 13.4 Hz, 1H), 2.10 (ddt, J=7.3, 12.2, 14.0 Hz, 1H), 1.85 (ddd, J=2.1, 6.6, 13.9 Hz, 1H), 1.28 (t, J=7.0 Hz, 3H), 1.21 (s, 3H), 0.60 (s, 3H).

Example 60. Synthesis of Compounds 78-Ent1 and 78-Ent2

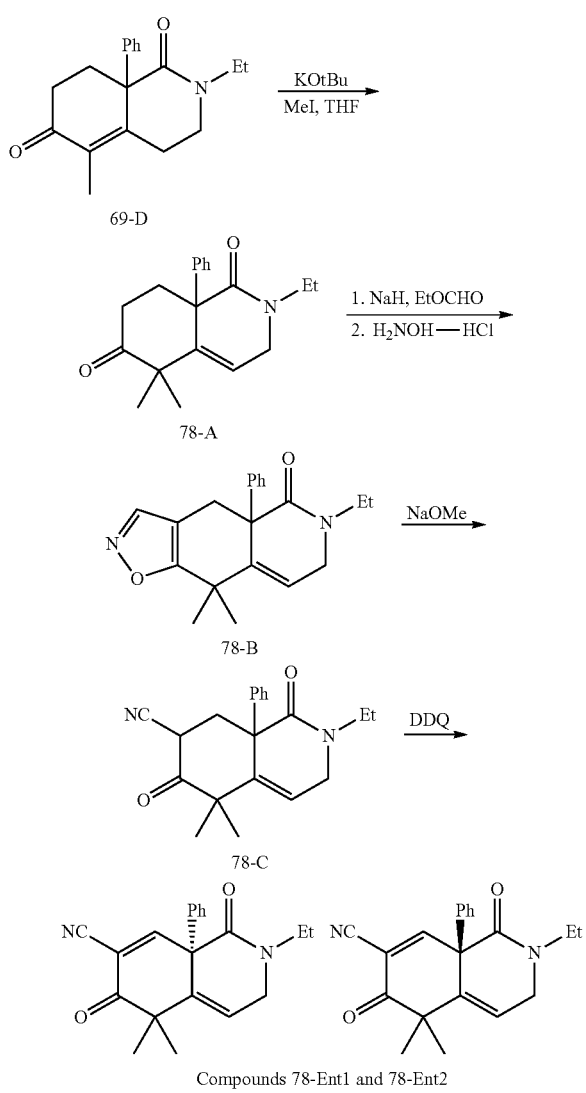

Compounds 78-Ent1 and 78-Ent2

Procedure for Preparation of Compound 78-A

To a solution of compound 69-D (100.00 mg, 352.90 umol) in THF (1.91 mL) was added potassium tert-butoxide (1 M in THF, 423.48 uL) slowly at 0° C. The resulting solution was stirred at 0° C. for 30 minutes. Iodomethane (50.09 mg, 352.90 umol, 22 uL) was then added and the suspension was slowly warmed to room temperature and stirred at this temperature overnight. The mixture was quenched by addition of saturated aqueous ammonium chloride and diluted with EtOAc. The layers were separated and the aqueous layer was extracted with EtOAc (3×). The combined organic layers were washed with brine then dried over sodium sulfate, filtered, and concentrated. The material was used in the next step without purification.

LCMS: (M+H=298.2)

Procedure for Preparation of Compound 78-B

Compound 78-A (105 mg, 353.07 umol) was dissolved in ethyl formate (523.11 mg, 7.06 mmol, 568.60 uL) and treated with sodium methoxide (5.4 M in methanol, 261.53 uL). After 30 minutes, a white solid formed and the mixture was diluted with toluene (5.00 mL) and stirred for an additional 3 hours. Water was then added followed by acetic acid to adjust the pH to ~5. Ethyl acetate was then added and the layers were separated. The organic phase was washed with brine then dried over sodium sulfate, filtered, and concentrated. This material was then dissolved in ethanol (3.34 mL) and water (166.83 uL) and hydroxylamine hydrochloride (243.45 mg, 3.50 mmol, 145.78 uL) was added. The solution was stirred at reflux for 1 hour. The solvent was then removed to provide a solid. The solid was then dissolved in saturated aqueous sodium bicarbonate and ethyl acetate. The layers were then separated and the organic layer was washed with water then dried over sodium sulfate, filtered, and concentrated. This material (78-B) was used in the next step without further purification.

LCMS: (M+H=323.1)

Procedure for Preparation of Compound 78-C

To a solution of compound 78-B (113.00 mg, 350.50 umol) in ether (3.51 mL) under nitrogen was added sodium methoxide (4.37 M, 400.46 uL) at room temperature. The mixture was stirred at this temperature for 2 hours then diluted with Ether then washed with 5% HCl solution (2×). The aqueous layers were combined and extracted with Ether (2×) and the combined organic layers were washed with water then brine before being dried over sodium sulfate then filtered and concentrated. A yellow foam (78-C) was obtained and was used in the next step without further purification.

LCMS: (M+H=323.1)

Procedure for Preparation of Compounds 78-Ent and 78-Ent2

Compound 78-C (113 mg, 350.50 umol) was dissolved in toluene (3.51 mL) and DDQ (87.52 mg, 385.55 umol) was added. The mixture was heated to 100° C. for 60 minutes then cooled to room temperature. The reaction was filtered and concentrated. The residue was then purified by column chromatography (5-60% EtOAc/Heptane, 12 g column). The product was isolated as an off-white solid and was then separated by SFC to provide 78-ent1 (17.3 mg, Rt=2.26 min) and 78-ent-2 (17.4 mg, Rt=2.89 min) as tan solids. Chiral SFC conditions: Column: CHIRALPAK IG 30×250 mm, 5 um. Method: 35% Methanol (w/o any modifier) in $CO_2$ (flow rate: 100 mL/min), ABPR 120 bar, MBPR 40 psi).

Data for 78-Ent1

HPLC: (Purity: 95%)
LCMS: (M+H=321.1)
SFC: (ee: 100%)

$^1$HNMR (500 MHz, $CDCl_3$) δ ppm 8.82 (s, 1H), 7.39-7.35 (m, 3H), 7.34-7.30 (m, 3H), 6.20 (dd, J=1.8, 5.5 Hz, 1H), 4.17 (dd, J=2.4, 18.3 Hz, 1H), 3.94 (dd, J=4.9, 18.3 Hz, 1H), 3.49-3.41 (m, 1H), 3.41-3.32 (m, 1H), 1.45 (s, 3H), 1.08 (t, J=7.3 Hz, 3H), 0.87 (s, 3H).

Data for 78-Ent2

HPLC: (Purity: 97%)
LCMS: (M+H=321.2)
SFC: (ee: 100%)

$^1$HNMR (500 MHz, $CDCl_3$)$_6$ ppm 8.82 (s, 1H), 7.39-7.35 (m, 3H), 7.34-7.31 (m, 2H), 6.20 (dd, J=2.1, 5.2 Hz, 1H), 4.17 (dd, J=1.8, 18.3 Hz, 1H), 3.94 (dd, J=5.5, 18.3 Hz, 1H), 3.49-3.40 (m, 1H), 3.40-3.33 (m, 1H), 1.45 (s, 3H), 1.08 (t, J=7.0 Hz, 3H), 0.87 (s, 3H).

Example 61: Synthesis of Compound 79

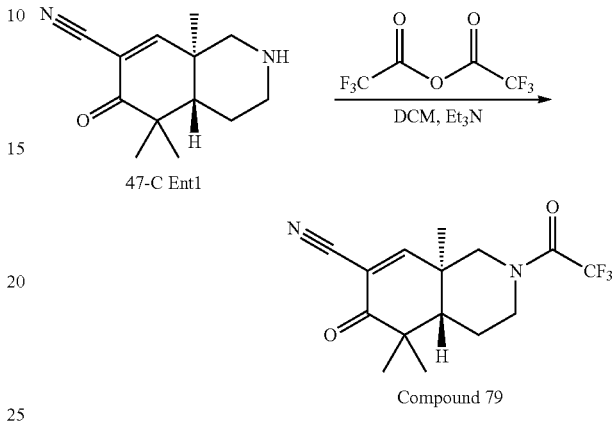

To a solution of compound 47-C Ent1 (124.00 mg, 568.05 umol) in DCM (2.89 g, 34.08 mmol, 2.18 mL) was added triethylamine (172.44 mg, 1.70 mmol, 236.22 uL). The reaction mixture was cooled to 0° C. and stirred while (2,2,2-trifluoroacetyl) 2,2,2-trifluoroacetate (131.24 mg, 624.86 umol, 86.91 uL) was added dropwise. The mixture was slowly warmed to room temperature and stirred for 2 hours. Added EtOAc then washed with $NaHCO_{3(aq)}$, H2O, and Brine. The organic layer was dried over sodium sulfate and solvent removed in vacuo. The residue was purified by reversed phase chromatography (C-18) to yield compound 79 (50.7 mg, 28% yld) as an off white solid powder.

LCMS: ESI-MS (M−H): 313

$^1$H NMR (500 MHz, CHLOROFORM-d) δ 7.41-7.50 (m, 1H), 4.79-4.85 (m, 0.34H), 4.53 (dd, J=1.83, 12.82 Hz, 0.69H), 4.22-4.28 (m, 0.68H), 3.81 (br d, J=13.43 Hz, 0.33H), 3.17 (ddd, J=3.66, 12.21, 14.04 Hz, 0.70H), 3.09 (d, J=13.43 Hz, 0.33H), 2.71-2.80 (m, 0.36H), 2.69 (d, J=12.21 Hz, 0.68H), 1.96-2.05 (m, 1H), 1.73-1.89 (m, 2H), 1.24-1.28 (m, 6H), 1.12-1.15 (m, 3H)

Example 62: Synthesis of Compound 80

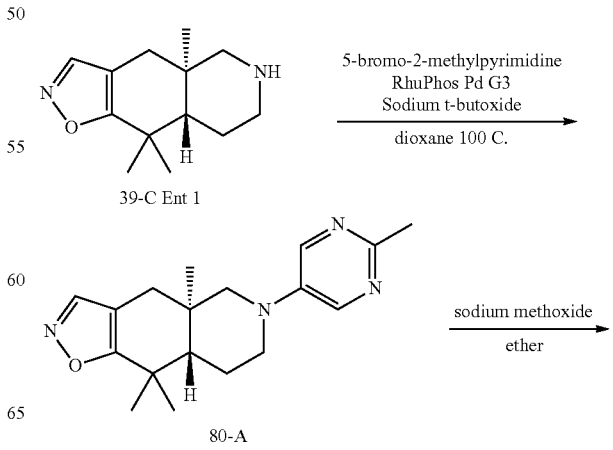

-continued

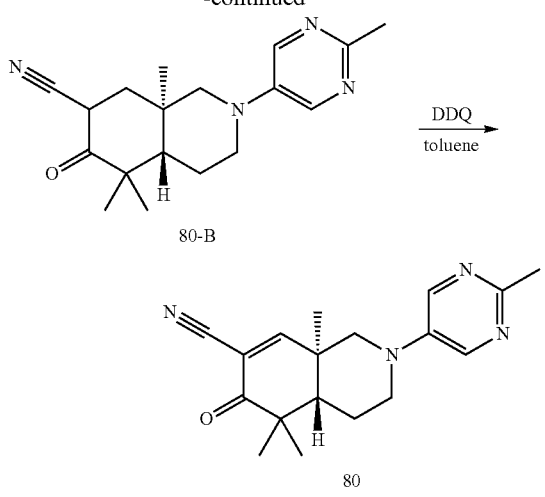

Step 1: Preparation of Compound 80-A

To a vial was added compound 39-C Ent 1 (180.31 mg, 818.45 umol), sodium tert-butoxide (163.86 mg, 1.71 mmol), RuPhos (31.83 mg, 68.20 umol), RuPhos Pd G3 (57.04 mg, 68.20 umol) and dioxane (1.42 mL). The reaction mixture was sparged with nitrogen for 15 minutes and 5-bromo-2-methyl-pyrimidine (118.00 mg, 682.04 umol) was added. The reaction was heated at 100° C. for 2 hours. Added EtOAc then washed with 1N HCL$_{(aq.)}$ and was extracted with EtOAc. The combined organic layers were dried over sodium sulfate, filtered and concentrated. The residue was purified by flash chromatography, gradient elution 0 to 100% EtOAc: Heptane to yield crude compound 80-A (63 mg) as a tan oil. Crude material carried forward.

LCMS: ESI-MS (M+H)$^+$: 313.1

Step 2: Preparation of Compound 80-B

To a solution of compound 80-A (63.00 mg, 201.66 umol) in ether (1.43 g, 19.32 mmol, 2.02 mL) was added sodium methoxide (4.37 M, 230.73 uL). The reaction mixture was stirred at room temperature for 2 hours. Added Ether then washed with 1N HCl$_{(Aq.)}$ solution and extracted with Ether. The combined organic layers were dried over sodium sulfate, filtered and concentrated. The residue (yellow oil) was carried forwards without further purification.

LCMS: ESI-MS (M+H)$^+$: 313.1.

Step 3: Preparation of Compound 80

To a solution of compound 80-B (63.00 mg, 201.66 umol) in Toluene (1.75 g, 19.01 mmol, 2.01 mL) was added DDQ (59.51 mg, 262.16 umol). The mixture was heated to reflux for 1.5 hours then cooled to room temperature. Added EtOAc then washed with NaHCO$_{3(Aq.)}$ and Brine. The organic layer was dried over sodium sulfate and solvent removed in vacuo. The residue was purified by reversed phase chromatography (C-18) to yield compound 80 (20.1 mg, 32% yld) as an off white powder.

LCMS: ESI-MS (M+H)$^+$: 311.1.

$^1$H NMR (400 MHz, CHLOROFORM-d) δ 8.64 (s, 2H), 7.51-7.55 (m, 1H), 3.94-4.03 (m, 1H), 3.57-3.65 (m, 1H), 2.89-3.00 (m, 1H), 2.81-2.89 (m, 1H), 2.80 (s, 3H), 1.90-2.00 (m, 2H), 1.82-1.89 (m, 1H), 1.40 (s, 3H), 1.28 (s, 4H), 1.16 (s, 3H)

Example 63: Synthesis of Compound 81-Ent1

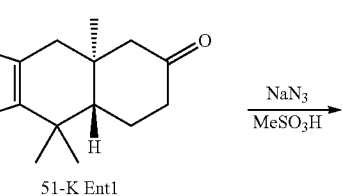

51-K Ent1

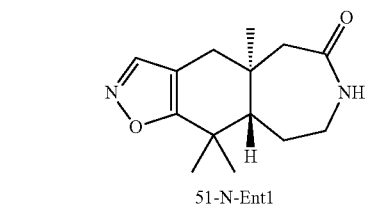

51-N-Ent1

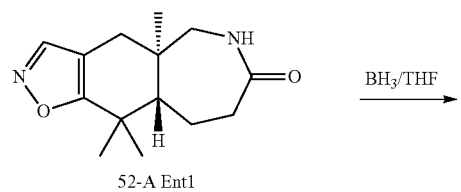

52-A Ent1

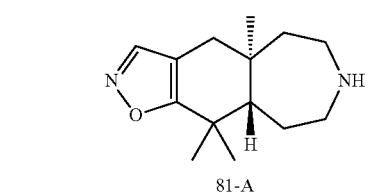

81-A

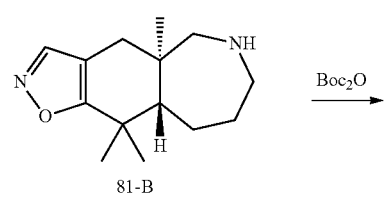

81-B

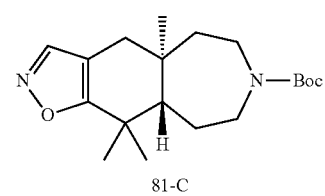

81-C

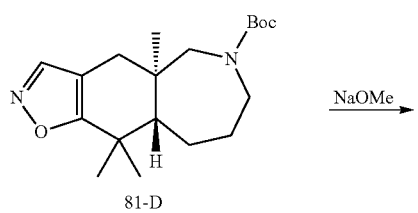

81-D

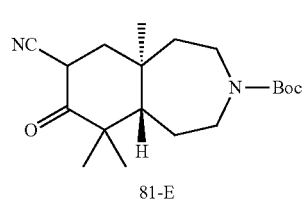

81-E

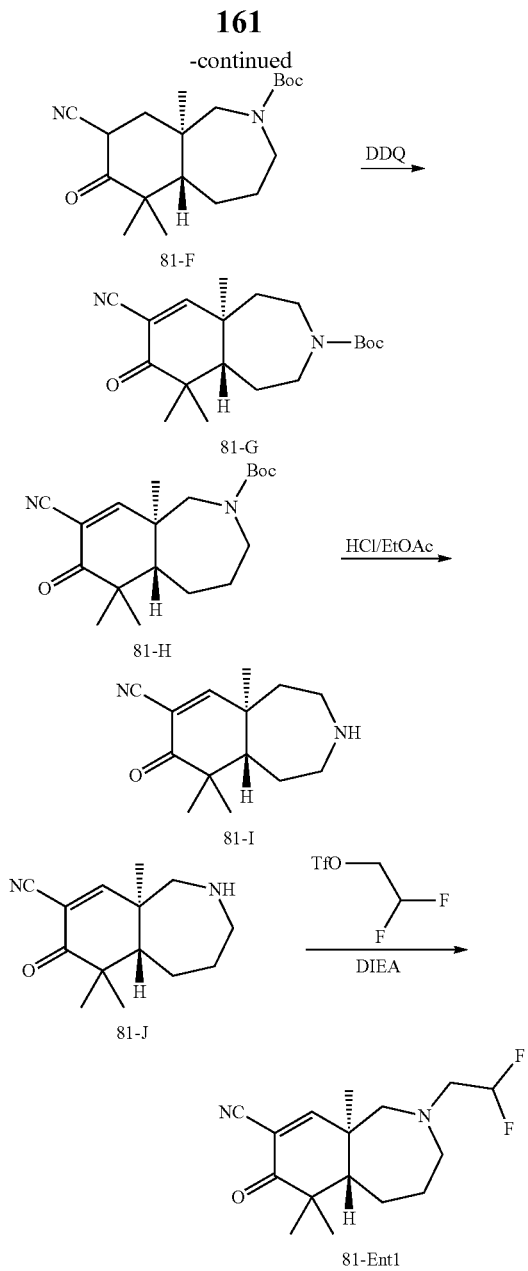

Preparation of Compounds 51-N-Ent1 and 52-A-Ent1

To a solution of 51-K Ent1 (obtained in a manner analogous to that described for 51-K-Ent2, using (S)-1-phenylethan-1-amine in place of (R)-1-phenylethan-1-amine in the transformation of 51-B to 51-C) (3.0 g, 12.85 mmol, 1.0 eq) in $CH_2Cl_2$ 100 mL was added $MeSO_3H$ (16.0 g, 167 mmol, 13.0 eq) and followed by $NaN_3$ (1.7 g, 25.7 mmol, 2.0 eq) at 0° C. The reaction mixture was allowed to stir at 20° C. for 14 hours. The reaction was detected on LCMS (19334-152-1A) showed that it was almost desired product. The reaction mixture was poured into saturated aqueous $NaHCO_3$ 150 mL, extracted with $CH_2Cl_2$ (150 mL×2). The organic phase was washed with brine (150 mL). The combined organic layers were dried over anhydrous $Na_2SO_4$, filtered and concentrated to give a mixture of compounds 51-N-Ent1 and 52-A-Ent1 (2.0 g, 62.7% yield) as yellow solid.

LCMS: (M+H: 249.1).

$^1$HNMR: (400 MHz, $CDCl_3$) δ: 8.21 (s, 1H), 8.05 (s, 1H), 7.48 (s, 1H), 3.36-3.46 (m, 3H), 3.27-3.29 (m, 1H), 2.72-2.76 (m, 2H), 2.35-2.39 (m, 1H), 2.32-2.35 (m, 1H), 2.18-2.25 (m, 1H), 2.14-2.16 (m, 1H), 11.74-1.75 (m, 1H), 1.63-1.64 (m, 1H), 1.35-1.37 (m, 3H), 1.21-1.23 (m, 3H), 0.95-1.04 (m, 3H).

Preparation of Compounds 81-A and 81-B $BH_3.Me_2S$ (2.2 mL, 10 M/L, 21.7 mmol, 3.0 eq) was added to a solution of compounds 51-N-Ent1 and 52-A-Ent1 (1.8 g, 7.25 mmol, 1.0 eq) in THF 50 mL at 20° C. The resulting mixture was stirred at 80° C. for 14 hours. TLC (PE/EtOAc=3/1, Rf=0.5) showed the starting material was consumed completely. The mixture was quenched with methanol 50 mL, concentrated to supply residue, which was purified by silica gel ($CH_2Cl_2$:MeOH from 20:1 to 5:1) to get a mixture of compounds 81-A and 81-B (150 mg, 27.8% yield) as yellow solid $^1$HNMR: (400 MHz, $CDCl_3$) δ: 8.01 (s, 1H), 3.22-3.26 (m, 1H), 2.80-2.84 (m, 1H), 2.64-2.70 (m, 1H), 2.52-2.54 (m, 2H), 2.50-2.51 (m, 1H), 1.99-2.03 (m, 1H), 1.80-1.82 (m, 1H), 1.43-1.46 (m, 1H), 1.32 (s, 3H), 1.22 (s, 3H), 0.83 (s, 3H).

Preparation of Compounds 81-C and 81-D

A solution of 81-A and 81-B (800 mg, 3.41 mmol, 1.0 eq) in MeOH 20 mL, $Boc_2O$ (893 mg, 4.10 mmol, 1.1 eq) was added, followed by DIEA (879 mg, 6.82 mmol, 2.0 eq). The resulting mixture was stirred at 20° C. for 14 hours. The mixture was concentrated to get compounds 81-C and 81-D (800 mg, 70.1% yield) as yellow solid.

LCMS: (M+H: 335.2).

$^1$HNMR: (400 MHz, $CDCl_3$) δ: 8.01 (d, J=2.8 Hz, 1H), 3.66-3.71 (m, 1H), 3.44-3.49 (m, 1H), 3.17-3.31 (m, 3H), 2.42-2.45 (m, 1H), 2.22-2.35 (m, 1H), 2.12-2.18 (m, 1H), 1.86-1.89 (m, 2H), 1.46-1.47 (m, 10H), 1.32 (s, 3H), 1.26 (s, 3H), 1.20 (s, 3H), 0.87 (s, 3H).

Preparation of Compounds 81-E and 81-F

NaOMe/MeOH (2.2 mL, 5.0 eq, 11.96 mmol, 5.4M) was added to a solution of compound 81-C and 81-D (800 mg, 2.39 mmol, 1.0 eq) in MeOH 10 mL, which was stirred at 25° C. for 14 hours. LCMS showed compounds 81-C and 81-D were consumed completely. The mixture was adjusted to pH=5 with 1N HCl, extracted with EtOAc (40 mL). The organic layer was washed with brine (20 mL), dried over anhydrous $Na_2SO_4$, filtered, and concentrated to get a mixture of compounds 81-E and 81-F (600 mg, 75.0% yield) as a white solid.

LCMS: (M−56: 279.1).

$^1$HNMR: (400 MHz, $CDCl_3$) δ: 3.97-4.00 (m, 1H), 3.88-3.89 (m, 1H), 3.67-3.70 (m, 1H), 3.44-3.48 (m, 2H), 3.17-3.21 (m, 3H), 2.84-2.97 (m, 1H), 2.34-2.38 (m, 1H), 1.47-1.49 (m, 18H), 1.18-1.19 (m, 6H), 1.12-1.14 (m, 3H), 0.87-1.90 (m, 3H).

Preparation of Compounds 81-G and 81-H

DDQ (509 mg, 2.24 mmol, 1.5 eq) was added to a solution of compounds 81-E and 81-F (500 mg, 1.50 mmol, 1.0 eq) in 10 mL toluene and stirred at 110° C. for 4 hours. TLC (PE/EtOAc=3/1, Rf=0.7) showed compounds 81-E and 81-F were consumed completely. The mixture was concentrated, and the residue was purified by pre-TLC PE/EtOAc=3:1 to get compounds 81-G and 81-H (400 mg, 80.5% yield) as a yellow solid.

$^1$HNMR: (400 MHz, $CDCl_3$) δ: 7.60 (d, J=6.4 Hz, 1H), 3.61-3.77 (m, 1H), 3.44-3.47 (m, 1H), 3.26-3.29 (m, 1H), 3.13-3.18 (m, 1H), 1.78-1.92 (m, 3H), 1.45-1.48 (m, 1H), 1.20-1.22 (m, 10H), 1.18-1.19 (m, 3H), 1.09-1.10 (m, 3H).

Preparation of Compounds 81-I and 81-J

HCl/EtOAc (4 mL, 4M) was added to a solution of compounds 81-G and 81-H (400 mg, 1.20 mmol, 1.0 eq) in EtOAc 4 mL at 0° C., the mixture was stirred at 20° C. for 14 hours. TLC (PE:EtOAc=3:1, Rf=0.1) showed compounds 81-G and 81-F were consumed completely. The mixture was concentrated to give compounds 81-I and 81-J (320 mg, 100% in yield) as yellow solids.

$^1$HNMR: (400 MHz, CDCl$_3$) δ: 10.34 (s, 1H), 9.49 (s, 1H), 7.44 (s, 1H), 3.30-3.39 (m, 3H), 3.07 (s, 1H), 2.00-2.26 (m, 5H), 1.54 (s, 3H), 1.28 (s, 3H), 1.14 (s, 3H).

Preparation of 81-Ent1

A mixture of 81-I and 81-J (20 mg, 0.074 mmol, 1.0 eq), 2,2-difluoroethyl trifluoro-methanesulfonate (31 mg, 0.149 mmol, 2.0 eq), DIEA (28 mg, 0.222 mmol, 3.0 eq) in THF 1 mL. The mixture was stirred at 20° C. for 1 hour. LCMS (19441-83-1A) showed compounds 81-I and 81-J were consumed completely. The mixture was concentrated, and the residue was purified by prep-TLC (PE/EtOAc=3/1) to get a residue, which was further purified by SFC (The first time: column: OJ (250 mm*30 mm, 5 um), condition: Neu-IPA; The second time: column: C$_2$ (250 mm*30 mm, 10 um), Neu-IPA; The third time: column: IC (250 mm*30 mm, 10 um), condition: Neu-IPA) to get 81-Ent1 (11 mg, 50.0% yield) as yellow solid.

$^1$HNMR: (400 MHz, CDCl$_3$) δ: 7.31 (s, 1H), 5.65-5.95 (m, 1H), 2.97-2.98 (m, 2H), 2.93-2.96 (m, 2H), 2.73 (d, J=13.6 Hz, 1H), 2.63 (d, J=13.6 Hz, 1H), 1.88-1.91 (m, 2H), 1.68-1.69 (m, 2H), 1.50 (s, 3H), 1.26 (s, 3H), 1.20 (s, 3H), 1.08 (s, 3H).

HPLC: (Purity: 100%)

SFC: (Column: Chiralcel OD-3 150×4.6 mm I.D., 3 um Mobile phase: A: CO$_2$ B: ethanol (0.05% DEA) Gradient: from 5% to 40% of B in 5 min and hold 40% for 2.5 min, then 5% of B for 2.5 min Flow rate: 2.5 mL/min Column temp.: 35° C., ee: 85.7%).

LCMS: (M+H: 297.1).

Example 64: Synthesis of Compound 82-Ent1

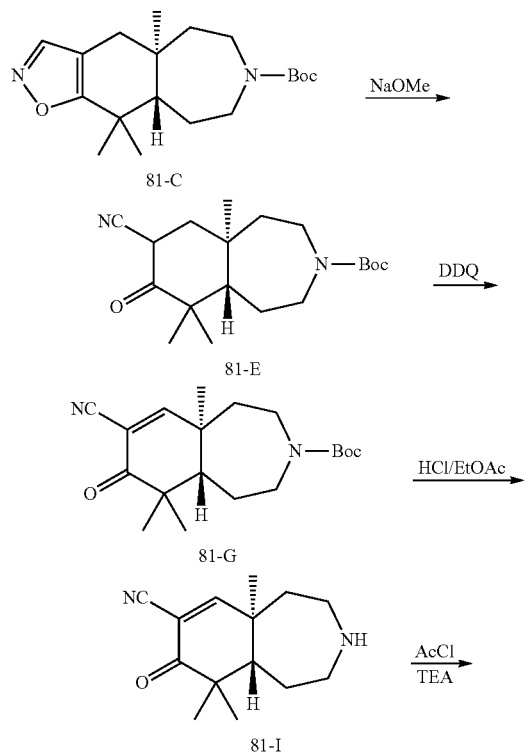

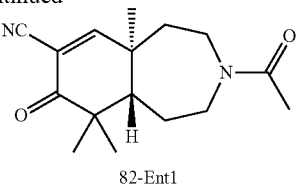

Compound 81-C can obtained from a mixture of 81-C and 81-D by purification using prep-HPLC separation (Mobile phase A: water (0.05% ammonia hydroxide v/v)-ACN, Mobile phase B: acetonitrile; Column: Waters Xbridge Prep OBD C18 100*19 mm*5 um, Detection wavelength: 220 nm) to get compound 81-C as yellow solid and 81-D.

LCMS: (M+H: 335.1).

Spectra for 81C $^1$HNMR: (400 MHz, CDCl$_3$) δ: 8.02 (d, J=3.6 Hz, 1H), 3.65-3.72 (m, 1H), 3.44-3.49 (m, 1H), 3.18-3.25 (m, 3H), 2.42-2.46 (m, 1H), 2.18-2.22 (m, 1H), 1.90-2.08 (m, 2H), 1.46-1.47 (m, 9H), 1.32 (s, 3H), 1.26 (s, 3H), 1.20 (s, 3H).

Spectra for 81-D $^1$HNMR: (400 MHz, CDCl$_3$) δ: 8.01 (s, 1H), 4.86-5.01 (m, 1H), 3.71-4.13 (m, 1H), 3.31-3.58 (m, 4H), 2.98-3.02 (m, 1H), 2.32-2.36 (m, 1H), 2.17-2.20 (m, 1H), 1.46-1.48 (m, 9H), 1.33 (s, 3H), 1.22 (s, 3H), 0.92 (s, 3H).

Preparation of Compound 81-E

NaOMe/MeOH (0.6 mL, 5.0 eq, 2.98 mmol, 5.4M) was added to a solution of compound 81-C (200 mg, 0.60 mmol, 1.0 eq) in MeOH 2 mL, which was stirred at 20° C. for 14 hours. LCMS showed compound 81-C was consumed completely. The mixture was poured into water 10 mL, adjusted to pH=7 with 1N HCl extracted with EtOAc (20 mL). The organic layer was washed with brine (10 mL), dried over anhydrous Na$_2$SO$_4$, filtered, and concentrated to get compound 81-E (150 mg, 75.0% yield) as a yellow oil.

$^1$HNMR: (400 MHz, CDCl$_3$) δ: 4.85-5.01 (m, 1H), 3.98-4.04 (m, 1H), 3.71-3.73 (m, 1H), 3.43-3.46 (m, 2H), 3.32-3.39 (m, 3H), 3.13-3.15 (m, 1H), 1.47 (s, 9H), 1.19-1.24 (m, 3H), 1.11-1.12 (m, 3H), 0.82-0.97 (m, 3H).

Preparation of Compound 81-G

DDQ (152 mg, 0.67 mmol, 1.5 eq) was added to a solution of compound 81-E (150 mg, 0.45 mmol, 1.0 eq) in toluene 3 mL, stirred at 110° C. for 1 hour. TLC (PE/EtOAc=3/1, Rf=0.6) showed compound 81-E was consumed completely. The mixture was concentrated, and the residue was purified by pre-TLC PE/EtOAc=3/1 to get compound 81-G (100 mg, 67.1% yield) as a yellow oil.

$^1$HNMR: (400 MHz, CDCl$_3$) δ: 7.26 (s, 1H), 3.64-3.85 (m, 1H), 3.38-3.49 (m, 2H), 3.16-3.22 (m, 1H), 1.93-1.94 (m, 1H), 1.76-1.78 (m, 1H), 1.59-1.62 (m, 3H), 1.44 (s, 9H), 1.26 (s, 3H), 1.21 (s, 3H), 1.07 (d, J=4.4 Hz, 3H).

Preparation of Compound 81-I

HCl/EtOAc (2 mL, 4M) was added to a solution of compound 81-G (100 mg, 0.30 mmol, 1.0 eq) in EtOAc 2 mL at 0° C., the mixture was stirred at 20° C. for 2 hours. TLC (PE/EtOAc=3/1, Rf=0.1) showed compound 81-G was consumed completely. The mixture was concentrated to give compound 81-I (70 mg, 86.7% in yield) as yellow solid.

$^1$HNMR: (400 MHz, CDCl$_3$) δ: 9.95 (s, 1H), 9.74 (s, 1H), 7.32 (s, 1H), 3.40-3.50 (m, 2H), 3.18-3.25 (m, 2H), 2.20 (br, s, 2H), 2.02 (br, s, 2H), 1.85 (br, s, 1H), 1.36 (s, 3H), 1.26-1.28 (m, 4H), 1.11 (s, 3H).

Preparation of Compound 81-Ent1

AcCl (25 mg, 0.32 mmol, 1.5 eq) was added to a solution of compound 81-I (70 mg, 0.21 mmol, 1.0 eq), DIEA (82 mg, 0.63 mmol, 3.0 eq) in CH$_2$Cl$_2$ 2 mL at 0° C., the mixture was stirred at 20° C. for 14 hours. LCMS showed compound 81-I was consumed completely. The mixture was concentrated, and the residue was purified by prep-TLC (CH$_2$Cl$_2$/MeOH=20/1) to 81-Ent1 (23 mg, 32.1% yield) as yellow solid.

$^1$HNMR: (400 MHz, Methanol-d$_4$) δ: 7.58 (d, J=2.8 Hz, 1H), 3.73-3.97 (m, 2H), 3.47-3.62 (m, 2H), 2.11 (d, J=9.2 Hz, 3H), 1.71-2.00 (m, 5H), 1.32 (d, J=9.6 Hz, 3H), 1.21 (d, J=14.0 Hz, 3H), 1.08 (d, J=4.0 Hz, 3H).

HPLC: (Purity: 99.05%)

SFC: (Column: Chiralpak AS-3 150×4.6 mm I.D., 3 um Mobile phase: A: CO2 B: ethanol (0.05% DEA) Gradient: from 5% to 40% of B in 5 min and hold 40% for 2.5 min, then 5% of B for 2.5 min, Flow rate: 2.5 mL/min Column temp.: 35° C. (ee: 96.6%)

LCMS: (M+H: 275.0).

Example 65: Synthesis of Compound 168-Ent1

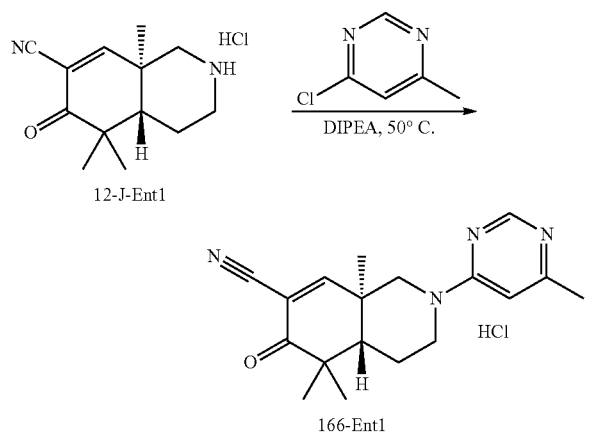

To a solution of 12-J-Ent1 (100 mg, 0.39 mmol, 1.0 eq.) and 4-chloro-6-methylpyrimidine (150 mg, 1.17 mmol, 3.0 eq) in dioxane (3 mL) was added DIPEA (150 mg, 1.17 mmol, 3.0 eq.) in one portion at 10-18° C. The reaction mixture was stirred stired at 130° C. for 2 hours. LCMS showed the target product was obtained. The mixture was concentrated to give the crude, which was purified by pre-HPLC (water (0.05% HCl)-ACN (Column: Phenomenex Synergi C18 150*30 mm*4 um, FlowRate ml/min: 25) to give 168-Ent1 (Rt=4.159 min, 41 mg, yield: 38.4% yield) as a yellow solid.

Spectra for 168-Ent1:

$^1$H NMR: (400 MHz, METHANOL-d4) δ: 8.16 (d, J=7.6 Hz, 1H), 7.74-7.98 (m, 1H), 6.98-7.27 (m, 1H), 5.21-5.51 (m, 1H), 4.26-4.54 (m, 1H), 3.26-3.32 (m, 1H), 2.96-3.05 (m, 1H), 2.62 (d, J=3.6 Hz, 3H), 2.31 (dd, J=4.33, 11.3 Hz, 1H), 1.79-2.00 (m, 2H), 1.28 (s, 3H), 1.24 (d, J=4.2 Hz, 3H), 1.13 (d, J=1.0 Hz, 3H).

HPLC: (Purity: 95.4%).

LCMS: (M+H: 311.0).

SFC condition: (Column: ChiralPak AD-3 150×4.6 mm I.D., 3 um, Mobile phase: A: CO$_2$ B: Ethanol (0.05% DEA), Gradient: from 5% to 40% of B in 5.5 min and hold 40% for 3 min, then 5% of B for 1.5 min, Flow rate: 2.5 mL/min Column temperature: 40° C., ee: 100%)

Example 66: Synthesis of Compound 83-Ent1

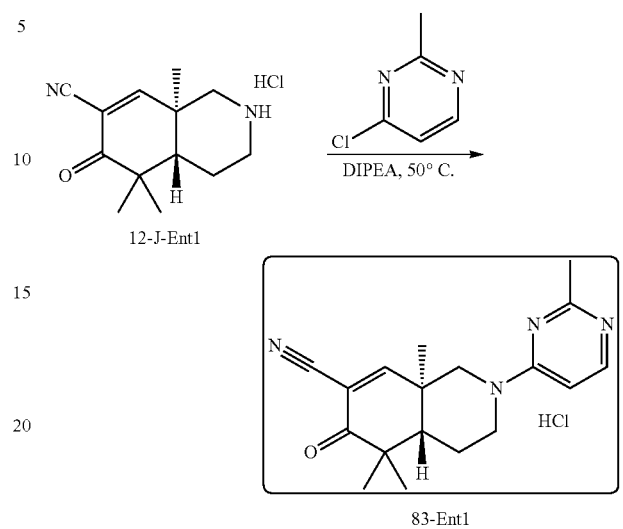

To a solution of 12-J-Ent1 (95 mg, 0.37 mmol, 1.0 eq.) and 4-chloro-2-methylpyrimidine (143 mg, 1.12 mmol, 3.0 eq) in dioxane (3 mL) was added DIPEA (145 mg, 1.12 mmol, 3.0 eq.) in one portion at 10-18° C. The reaction mixture was stirred at 130° C. for 2 hours.

LCMS showed the target product was obtained. The mixture was concentrated to give the crude, which was purified by pre-HPLC (water (0.05% HCl)-ACN (Column: Phenomenex Synergi C18 150*30 mm*4 um, FlowRate ml/min: 25) to give 83-Ent1 (Rt=3.986 min, 16 mg, yield: 15% yield) as a yellow solid.

Spectra for 83-Ent1

$^1$H NMR: (400 MHz, METHANOL-d$_4$) δ: 8.64 (d, J=11.00 Hz, 1H), 7.76-7.93 (m, 1H), 7.14 (d, J=9.0 Hz, 1H), 5.14-5.54 (m, 1H), 4.18-4.57 (m, 1H), 3.24-3.30 (m, 1H), 2.91-3.06 (m, 1H), 2.51 (s, 3H), 2.24-2.36 (m, 1H), 1.82-2.00 (m, 2H), 1.28 (s, 3H), 1.22-1.25 (m, 3H), 1.13 (s, 3H).

HPLC: (Purity: 97.5%).

LCMS: (M+H: 311.0).

SFC condition: (Column: ChiralCel OJ-H 150×4.6 mm I.D., 5 um, Mobile phase: A: CO$_2$ B: Ethanol (0.05% DEA), Gradient: from 5% to 40% of B in 5.5 min and hold 40% for 3 min, then 5% of B for 1.5 min, Flow rate: 2.5 mL/min Column temperature: 40° C., ee: 100%)

Example 67: Synthesis of Compounds 84-Ent1 and 84-Ent2

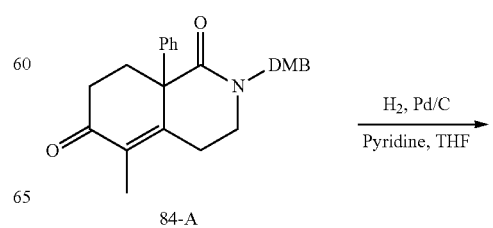

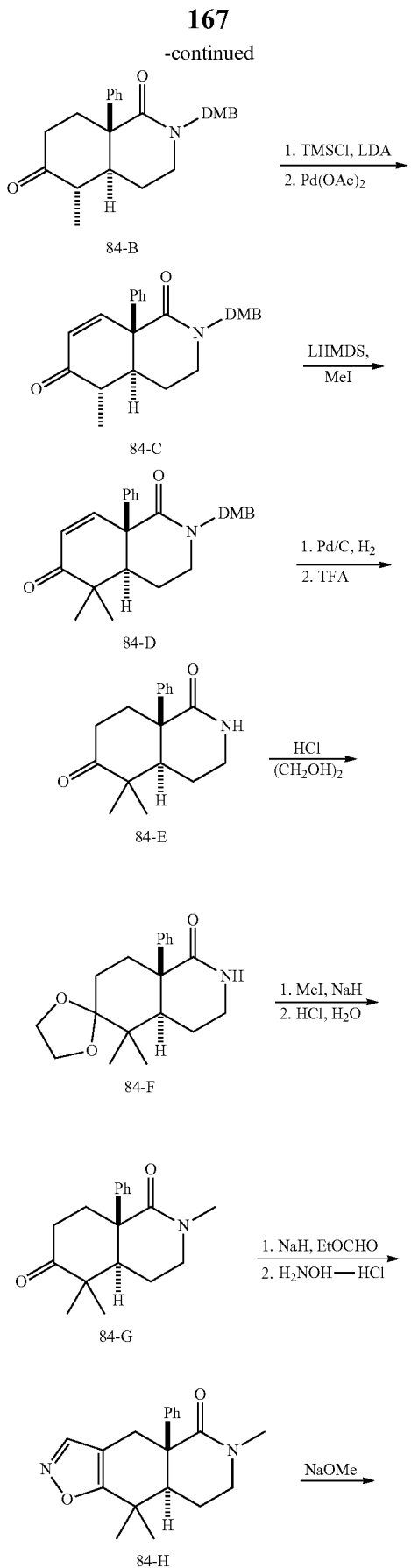

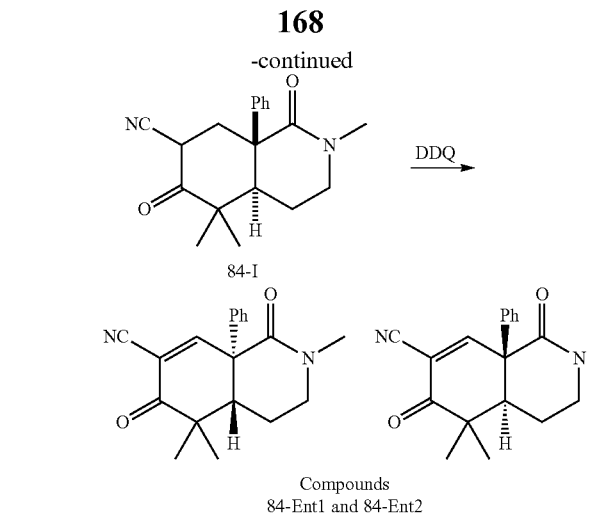

Compounds
84-Ent1 and 84-Ent2

Procedure for Preparation of Compound 84-B

Compound 84-A can be obtained in a manner analogous to that described for compound 60-E. To a solution of compound 84-A (20 g, 49.32 mmol, 1.0 eq., 80% purity) in a mixture solvent of pyridine/THF (480 mL, 1/5, v/v) was added 10% dry Pd/C (5.0 g) under $N_2$ protection. The suspension was degassed under vacuum and purged with $H_2$ several times. The resulting mixture was stirred under $H_2$ (50 psi) at 30° C. for 24 hours. LCMS showed that the starting material was consumed completely and the desired compound MS value was detected. Then the reaction mixture was filtered through a celite of pad and washed with EtOAc (800 mL). The filtrate was concentrated under reduced pressure. The residue was triturated by a mixture solvent of petroleum ether/EtOAc (200 mL, 6/1, v/v) and filtered to afford the compound 84-B (14 g, 87% yield) as a white solid, which was used directly for next step.

LCMS: (M+Na: 430.1).

$^1$H NMR: (400 MHz, CDCl$_3$) δ 7.62-7.61 (m, 2H), 7.35-7.32 (m, 2H), 7.28 (d, J=7.2 Hz, 1H), 6.98 (d, J=8.4 Hz, 1H), 6.41-6.37 (m, 2H), 4.57-4.44 (m, 2H), 3.78 (s, 3H), 3.42 (s, 3H), 3.21-3.04 (m, 2H), 2.91-2.83 (m, 1H), 2.77-2.2.71 (m, 1H), 2.37-2.24 (m, 3H), 2.16-2.05 (m, 2H), 1.99-1.91 (m, 1H), 1.13 (d, J=6.0 Hz, 3H).

Procedure for Preparation of Compound 84-C

A solution of LDA (0.44 M, 127 mL) under nitrogen at −78 C was added to a solution of 84-B (20.73 g, 50.87 mmol) in THF (127 mL) under nitrogen at −78 C via cannula. After 60 minutes, Trimethylsilyl chloride (7.18 g, 66.13 mmol, 8.35 mL) was added to the solution via syringe. The cooling bath was then removed and the reaction was warmed to room temperature over 2 hours. The solution was then partitioned between EtOAc (250 ml) and NaHCO3 (250 ml) solutions. After separation of layers, the aqueous layer was extracted with EtOAc (2×75 ml) and the combined organic layers were washed with brine then dried over sodium sulfate, filtered, and concentrated. This material was used in the next step without further purification. The residue was dissolved in acetonitrile (510 mL) and the mixture was evacuated and backfilled with nitrogen (3×). Palladium(II) acetate (13.70 g, 61.04 mmol) was then added in one portion and the flask was again evacuated and backfilled with nitrogen (3×). The mixture was then stirred at room temperature for 20 hours. The mixture was then filtered through celite and washed with EtOAc. The EtOAc solution was then concentrated. The resulting residue was purified by column chromatography (5-60% EtOAc/heptane) to provide 84-C (13.30 g, 32.80 mmol, 64.5% yield) as a white solid.

LCMS: (M+H: 406.3).

$^1$HNMR (400 MHz, CDCl$_3$) δ 7.76 (d, J=10.3 Hz, 1H), 7.34-7.31 (m, 1H), 7.30-7.27 (m, 3H), 7.24-7.19 (m, 2H), 6.54-6.47 (m, 2H), 6.34 (d, J=10.0 Hz, 1H), 4.95 (d, J=14.1 Hz, 1H), 4.52 (d, J=14.1 Hz, 1H), 3.86 (s, 3H), 3.84 (s, 3H), 3.57-3.47 (m, 1H), 3.40 (dt, J=7.0, 12.0 Hz, 1H), 2.42-2.22 (m, 2H), 1.83-1.72 (m, 1H), 1.62-1.49 (m, 1H), 1.07 (d, J=6.5 Hz, 3H).

Procedure for Preparation of Compound 84-D

Compound 84-C (3.10 g, 7.65 mmol) was dissolved in THF (41 mL) and cooled to −78° C. A solution of [bis (trimethylsilyl)amino]lithium (1.0 M, 14.92 mL) was then added and the mixture was stirred at −78° C. for 60 minutes then warmed to 0° C. and stirred for 60 minutes before cooling to −78° C. Methyl iodide (36.89 g, 259.93 mmol, 16.18 mL) was then added and the mixture was stirred at −78° C. for 1 hour then slowly warmed to room temperature and stirred overnight. The reaction was quenched with sat aq. ammonium chloride and diluted with EtOAc. The layers were separated and the aqueous layer was extracted with EtOAc. The combined organic layers were dried over sodium sulfate, filtered, and concentrated. The residue was purified by column chromatography (5-60% EtOAc/heptane) to provide 84-D as a brown solid (2.1 g, 65% yield).

$^1$HNMR (400 MHz, CDCl$_3$) δ ppm 7.82 (d, J=9.77 Hz, 1H), 7.29 (d, J=8.55 Hz, 1H), 7.26-7.19 (m, 5H), 6.53-6.47 (m, 2H), 6.44 (d, J=10.38 Hz, 1H), 4.97 (d, J=14.04 Hz, 1H), 4.45 (d, J=14.04 Hz, 1H), 3.85 (s, 3H), 3.84 (s, 3H), 3.63 (dd, J=12.82, 6.71 Hz, 1H), 3.43 (td, J=12.36, 7.02 Hz, 1H), 2.44 (dd, J=13.43, 2.44 Hz, 1H), 2.03-1.92 (m, 1H), 1.72 (ddd, J=13.58, 6.56, 2.44 Hz, 1H), 1.11 (s, 3H), 0.51 (s, 3H).

Procedure for Preparation of Compound 84-E

Compound 84-D (2.10 g, 5.01 mmol) was dissolved in ethanol (100 mL) and 10% palladium on carbon (533.16 mg, 501.00 umol) was added. The mixture was degassed with nitrogen then placed under a balloon of hydrogen. The mixture was stirred for 6 hours then flushed with nitrogen and filtered through celite and concentrated. This residue was then dissolved in TFA (28.54 g, 250.50 mmol, 19.2 mL). The mixture was heated to 50° C. for 4 hours. The mixture was then cooled to room temperature, concentrated and purified by column chromatography (10-65% of [1:1 EtOAc/EtOH mix]: heptane) to provide 84-E as an off-white solid (1.23 g, 90% yield).

$^1$HNMR (500 MHz, CDCl$_3$) δ ppm 7.34-7.27 (m, 4H), 7.26-7.21 (m, 1H), 6.01 (br s, 1H), 3.66 (br s, 1H), 3.55 (br s, 1H), 3.01-2.82 (m, 2H), 2.82-2.70 (m, 1H), 2.62-2.41 (m, 2H), 2.11 (d, J=6.71 Hz, 1H), 1.73 (d, J=12.82 Hz, 1H), 1.09 (s, 3H), 0.21 (s, 3H).

Procedure for Preparation of Compound 84-F

A mixture of compound 84-E (1.23 g, 4.53 mmol), PPTS (342 mg, 1.36 mmol), and Ethylene glycol (3.28 mL) in Toluene (16.4 mL) were heated to reflux for 16 hours with a Dean-Stark apparatus. The mixture was cooled to room temperature, diluted with EtOAc, and washed with NaHCO$_3$ (2×), brine (2×), and dried over sodium sulfate, filtered, and concentrated. The material was then purified by column chromatography (10-75% of [1:1 EtOAc/EtOH]: heptane) to provide 84-F as an off-white solid (793.00 mg, 56% yield).

$^1$HNMR (400 MHz, CDCl$_3$) δ ppm 7.67-7.61 (m, 2H), 7.33-7.28 (m, 2H), 7.25-7.20 (m, 1H), 5.47 (br s, 1H), 4.09-3.89 (m, 4H), 3.70-3.61 (m, 1H), 3.60-3.50 (m, 1H), 2.87 (dt, J=14.37, 3.48 Hz, 1H), 2.46-2.33 (m, 2H), 2.27-2.16 (m, 1H), 2.12-2.02 (m, 1H), 1.98-1.90 (m, 1H), 1.84 (dt, J=13.43, 3.33 Hz, 1H), 0.87 (s, 3H), 0.53 (s, 3H).

Procedure for Preparation of Compound 84-G

Sodium hydride (38.05 mg, 951.14 umol, 60% purity) was added to an oven dried vial under nitrogen and dissolved in THF (2.4 mL) then cooled to 0° C. Compound 84-F (150 mg, 475.57 umol) was added and the mixture was warmed to room temperature and stirred for 2 hours. Methyl iodide (128 mg, 903.58 umol, 56 uL) was then added and the mixture was stirred overnight. The reaction was then diluted with water, extracted with EtOAc (2×), and the combined organic layers were dried over sodium sulfate, filtered, and concentrated. The material was used in the next step without purification. The residue was dissolved in THF (0.79 mL) and treated with HCl (1 M, 394.62 uL) and allowed to stir overnight. The mixture was diluted with 20 mL brine and 60 mL EtOAc. The layers were separated and the aqueous layer was extracted with 20 mL EtOAc. The combined organic phases were washed with sat NaHCO$_3$ and brine then dried over MgSO4, filtered, and concentrated. A white crystalline solid (84-G) was obtained and was used in the next step without purification.

$^1$HNMR (500 MHz, CDCl$_3$) δ ppm 7.30-7.27 (m, 1H), 7.26 (s, 1H), 7.24-7.19 (m, 1H), 7.19-7.15 (m, 2H), 3.64-3.53 (m, 2H), 3.07 (s, 3H), 2.97-2.84 (m, 2H), 2.79-2.69 (m, 1H), 2.54-2.44 (m, 2H), 2.18-2.08 (m, 1H), 1.77-1.70 (m, 1H), 1.07 (s, 3H), 0.20 (s, 3H).

Procedure for Preparation of Compound 84-H

Compound 84-G (135.00 mg, 473.05 umol) was dissolved in ethyl formate (701 mg, 9.46 mmol, 761.83 uL) and treated with sodium methoxide (5.4 M, 350.41 uL). The mixture was diluted with Toluene (6.76 mL) and stirred overnight. Water was added followed by 1N HCl to adjust the pH to ~5. Ethyl acetate was then added and the layers were separated. The organic phase was washed with brine then dried over sodium sulfate, filtered, and concentrated. The material was then used in the next step without further purification. The residue was dissolved in ethanol (2.26 mL) and water (113 uL) and hydroxylamine hydrochloride (330 mg, 4.75 mmol) was added. The solution was stirred under reflux for 2 hours. The solvent was removed to provide a solid. The solid was then dissolved in sat. aq. sodium bicarbonate and ethyl acetate. The layers were then separated and the organic layer was washed with water then dried over sodium sulfate, filtered, and concentrated. This material (84-H) was then used in the next step without purification.

$^1$HNMR (400 MHz, CDCl$_3$)$_6$ ppm 8.25 (s, 1H), 7.21-7.16 (m, 3H), 7.11 (m, 2H), 3.72-3.64 (m, 1H), 3.60 (m, 2H), 3.10 (s, 3H), 2.90 (d, J=16.48 Hz, 1H), 2.28-2.17 (m, 2H), 1.94-1.83 (m, 1H), 1.35 (s, 3H), 0.49 (s, 3H).

Procedure for Preparation of Compound 84-I

To a solution of compound 84-H (147.60 mg, 475.53 umol) in ether (4.76 mL) under nitrogen was added sodium methoxide (4.37 M, 544.08 uL) at room temperature. The mixture was stirred at this temperature for 2 hours then diluted with Ether then washed with 5% HCl solution (2×). The aqueous layers were combined and extracted with Ether (2×) and the combined organic layers were washed with water then brine before being dried over sodium sulfate then filtered and concentrated. The faintly yellow foam (84-I) obtained appeared as an apparent mixture of Keto-Enol forms by 1H NMR and was used in the next step in the sequence without further purification. LCMS: (M+H: 311.2).

Procedure for Preparation of Compounds 84-Ent and 84-Ent2

Compound 84-I (147.60 mg, 475.53 umol) was dissolved in Toluene (4.76 mL) and DDQ (118.74 mg, 523.08 umol) was added. The mixture was heated to 100° C. for 60 minutes then cooled to room temperature. The reaction was then concentrated. The residue was then purified by column chromatography (5-60% EtOAc/Heptane, 12 g column). The product was isolated as a faint red solid (122 mg, 62.5% yield) which was then separated by chiral SFC (Column: CHIRALPAK IA 30×250 mm, 5 um; Method: 40% Methanol in CO₂ [flow rate: 100 mL/min], ABPR 120 bar, MBPR 40 psi) to provide 84-Ent1 (38.9 mg, Rt=1.45 min) and 84-Ent2 (40.2 mg, Rt=1.91 min) as off-white solids.

Data for 84-Ent-1

HPLC: (Purity: 100%)

LCMS: (M+H: 309.2)

SFC: (ee: 100%)

¹HNMR (500 MHz, CDCl₃)₆ ppm 8.52 (s, 1H), 7.39-7.33 (m, 3H), 7.13-7.10 (m, 2H), 3.69 (dd, J=12.21, 6.10 Hz, 1H), 3.58 (td, J=12.21, 6.71 Hz, 1H), 3.13 (s, 3H), 2.49 (dd, J=13.43, 2.44 Hz, 1H), 2.11 (tdd, J=13.43, 13.43, 11.60, 7.33 Hz, 1H), 1.84 (ddd, J=13.89, 6.56, 2.14 Hz, 1H), 1.21 (s, 3H), 0.60 (s, 3H).

Data for 84-Ent-2

HPLC: (Purity: 99%)

LCMS: (M+H: 309.2)

SFC: (ee: 100%)

¹HNMR (500 MHz, CDCl₃)₆ ppm 8.52 (s, 1H), 7.39-7.33 (m, 3H), 7.13-7.10 (m, 2H), 3.69 (dd, J=12.21, 6.10 Hz, 1H), 3.58 (td, J=12.21, 6.71 Hz, 1H), 3.13 (s, 3H), 2.49 (dd, J=13.43, 2.44 Hz, 1H), 2.11 (tdd, J=13.43, 13.43, 11.60, 7.33 Hz, 1H), 1.84 (ddd, J=13.89, 6.56, 2.14 Hz, 1H), 1.21 (s, 3H), 0.60 (s, 3H).

Example 68: Synthesis of Compounds 85-Ent1 and 85-Ent2

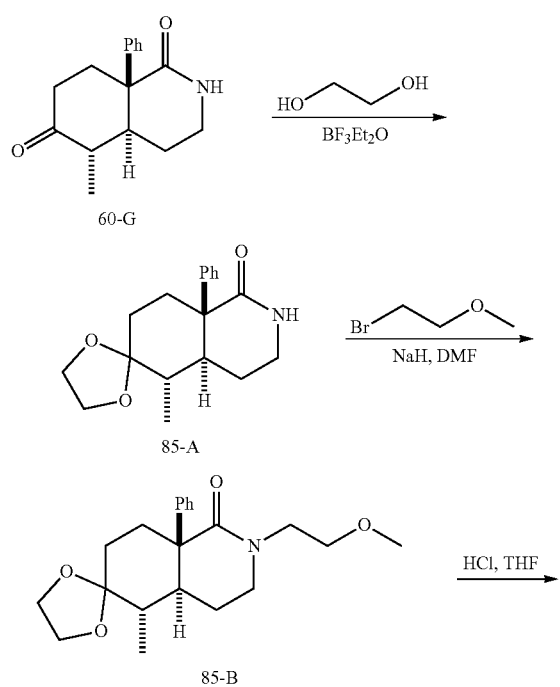

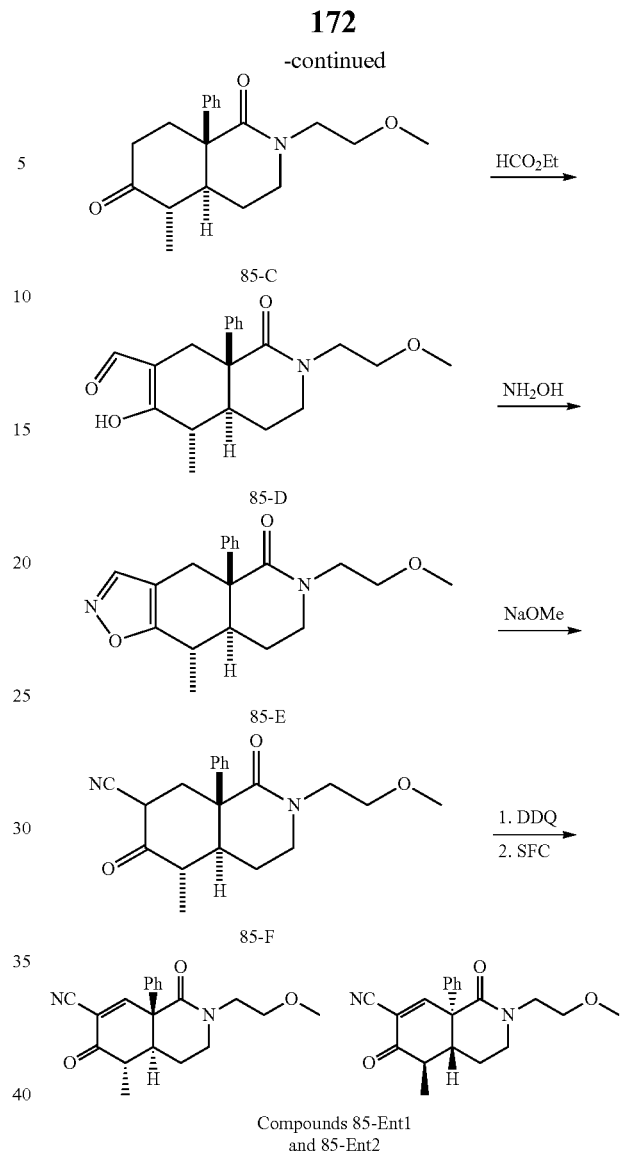

Compounds 85-Ent1 and 85-Ent2

Preparation of Compound 85-A

To a solution of compound 60-G (1.06 g, 4.12 mmol, 1 eq.) in THF (12 mL) was added ethylene glycol (5.1 g, 82.4 mmol, 20 eq.). Then BF₃/OEt₂ (292 mg, 2.06 mmol, 0.5 eq.) was added. The reaction mixture was stirred at 10-20° C. for 16 hours. LCMS showed that the starting material was consumed completely and the desired product was detected. The mixture was quenched by water (25 mL) and extracted with EtOAc (25 mL×3). The combined organic layer was dried over anhydrous Na₂SO₄, filtered, concentrated under reduced pressure to give the residue, which was purified by column chromatography (PE/EtOAc=10:1 to 1:1) to give compound 85-A (900 mg, 72% yield) as a yellow oil.

LCMS: (M+H: 302.1).

¹H NMR: (400 MHz, CDCl₃) δ 7.62 (d, J=7.50 Hz, 2H), 7.26-7.33 (m, 2H), 7.18-7.26 (m, 1H), 5.70 (br s, 1H), 3.95 (s, 2H), 3.74 (s, 2H), 3.17 (tt, J=4.38, 8.52 Hz, 1H), 2.88-3.02 (m, 1H), 2.48-2.64 (m, 1H), 2.24-2.32 (m, 1H), 2.11-2.17 (m, 3H), 1.91-2.02 (m, 1H), 1.61 (td, J=3.34, 13.62 Hz, 1H), 1.23-1.34 (m, 1H), 0.99 (d, J=6.62 Hz, 3H).

Preparation of Compound 85-B

To a solution of compound 85-A (700 mg, 2.33 mmol, 1.0 eq.) in DMF (10 mL) was added NaH (186 mg, 4.66 mmol, 2.0 eq.) at 0° C. and stirred at 15° C. for 0.5 hour. Then 1-bromo-2-methoxyethane (484 mg, 3.49 mmol, 1.5 eq.) was added. The mixture was stirred at 20° C. for 2 hours. LCMS showed that the starting material was consumed completely and the desired product was detected. The reaction mixture was diluted with EtOAc (50 mL). Then Sat. NaHCO$_3$ (50 mL) and extracted with EtOAc (50 mL×3). The combined organic layer was washed with brine (100 mL) and dried over anhydrous Na$_2$SO$_4$, filtered, concentrated under reduced pressure to give the residue, which was purified by column chromatography (PE/EtOAc=20:1 to 3:1) to give compound 85-B (850 mg, 88% yield) as a light yellow solid.

LCMS: (M+H: 360.1).

Preparation of Compound 85-C

To a solution of compound 85-B (800 mg, 1.90 mmol, 1.0 eq.) in THF (anhydrous, 20 mL) was added HCl (9 mL, 9.04 mmol, 5 eq., 1 M in water). The solution was stirred at 20° C. for 12 hours. LCMS showed that the starting material was consumed completely and the desired product was detected. The mixture was added Sat. NH$_4$HCO$_3$ (20 mL). The residue was extracted with EtOAc (20 mL×3). The combined organic layers were dried over Na$_2$SO$_4$, filtered and concentrated to give the crude compound 85-C, which was purified by column chromatography (PE/EtOAc=20:1 to 1:1) to give compound 85-C (310 mg, 44% yield) as a colorless oil.

LCMS: (M+CH$_3$CN: 346.1).

$^1$H NMR: (400 MHz, CDCl$_3$) δ 7.61 (d, J=7.02 Hz, 2H), 7.33-7.41 (m, 2H), 7.31 (d, J=7.02 Hz, 1H), 3.58-3.65 (m, 1H), 3.39-3.53 (m, 3H), 3.28-3.38 (m, 2H), 3.25 (s, 3H), 2.80-2.90 (m, 1H), 2.64-2.73 (m, 1H), 1.96-2.40 (m, 6H), 1.16 (d, J=6.58 Hz, 3H)

Preparation of Compound 85-D

Na (79 mg, 3.45 mmol, 3.5 eq.) was added to MeOH (3.5 mL) in many portions at 25° C. and stirring until Na was disappeared, and then a mixture of compound 85-C (310 mg, 0.98 mmol, 1.0 eq.) and HCOOEt (5 mL) were added to the above solution dropwise over 5 min under N$_2$. The reaction mixture was stirred at 20° C. for 12 hours. LCMS showed that the starting material was consumed completely and the desired product was detected. The mixture was added Sat. NH$_4$Cl (25 mL) and extracted with EtOAc (30 mL×3). The combined organic layer was washed with brine (30 mL×3), dried over anhydrous Na$_2$SO$_4$, filtered, concentrated under reduced pressure to supply compound 85-D (290 mg, 85% yield) as yellow oil.

LCMS: 19437-100-1C (M+H: 344.1).

Preparation of Compound 85-E

To a solution of compound 85-D (290 mg, 0.84 mmol, 1.0 eq.) in EtOH (5 mL) and H$_2$O (1 mL) was added hydrochloride hydroxylamine (64 mg, 0.93 mmol, 1.1 eq.). After addition the mixture was stirred at 50° C. for 16 h. LCMS showed that the starting material was consumed completely and the desired product was detected. The mixture was diluted with NaHCO$_3$ (20 mL), and extracted with EtOAc (30 mL×3). The combined organic layer dried over anhydrous Na$_2$SO$_4$, filtered, and concentrated under reduced pressure to give compound 85-E (200 mg, 69% yield) as yellow gum.

LCMS: (M+H: 341.1)

$^1$H NMR: (400 MHz, CDCl$_3$) δ 8.23 (s, 1H), 7.19-7.24 (m, 3H), 7.09-7.16 (m, 2H), 3.87-3.95 (m, 1H), 3.72-3.80 (m, 2H), 3.53-3.70 (m, 3H), 3.43 (s, 3H), 3.38-3.41 (m, 1H), 3.01 (dd, J=2.84, 16.88 Hz, 1H), 2.26 (br d, J=7.02 Hz, 1H), 1.84-1.96 (m, 2H), 1.32-1.37 (m, 3H).

Preparation of Compound 85-E

Na (68 mg, 2.94 mmol, 5 eq.) was added MeOH (1.5 mL) in many portions at 25° C. and stirring until Na was disappeared. Then compound 85-D (200 mg, 0.59 mmol, 1.0 eq.) was added. The reaction mixture was stirred at 20° C. for 16 hours. TLC (PE/EA=1:1) showed the starting materials were consumed completely and a new spot was observed. The mixture quenched by Sat. NH$_4$Cl (15 mL) and extracted with EtOAc (15 mL×3). The combined organic layer was washed with brine (20 mL×2), dried over anhydrous Na$_2$SO$_4$, filtered, concentrated under reduced pressure to supply compound 85-E (220 mg, crude) as yellow gum.

LCMS: (M+H: 341.1).

Preparation of Compounds 85-Ent and 85-Ent2

To a solution of compound 85-E (200 mg, 0.59 mmol, 1.0 eq.) in Tol. (3 mL) was added DDQ (170 mg, 0.71 mmol, 1.2 eq.) slowly. The mixture was stirred at 80° C. for 2 hours. LCMS showed that the starting material was consumed completely and the desired product was detected. The mixture was diluted with water (30 mL), and extracted with EtOAc (30 mL×3). The combined organic layers was dried over anhydrous Na$_2$SO$_4$, filtered, and concentrated under reduced pressure. The residue was purified by prep-HPLC (Column: Xtimate C18 150*25 mm*5 um; water (10 mM NH$_4$HCO$_3$)-ACN, FlowRate: 25 mL/min) to give the racemate product (89 mg) as a colorless oil. The racemate was further separated by prep-SFC (Column: AD (250 mm*30 mm; 10 um); Condition: Neu-EtOH; FlowRate: 60 mL/min) to give the enantiomer 85-Ent1 (42 mg, 21% yield) as light yellow solid and enantiomer 85-Ent2 (43 mg, 21.5% yield) as white solid.

Spectra for 85-Ent1:

$^1$H NMR: (400 MHz, CDCl$_3$) δ 8.45 (s, 1H), 7.34-7.44 (m, 3H), 7.19-7.24 (m, 2H), 3.93-3.98 (m, 1H), 3.74-3.82 (m, 2H), 3.56-3.71 (m, 2H), 3.45 (s, 3H), 3.37-3.43 (m, 1H), 2.35-2.47 (m, 2H), 1.86 (dd, J=7.20, 13.56 Hz, 1H), 1.64-1.76 (m, 1H), 1.15 (d, J=6.24 Hz, 3H)

HPLC: (Purity: 100%)

SFC: (Rt=3.999 min, ee: 100%)

LCMS: (M+H: 399.0)

Spectra for 85-Ent2:

$^1$H NMR: (400 MHz, CDCl$_3$) δ 8.45 (s, 1H), 7.34-7.44 (m, 3H), 7.19-7.24 (m, 2H), 3.93-3.98 (m, 1H), 3.74-3.82 (m, 2H), 3.56-3.71 (m, 2H), 3.45 (s, 3H), 3.37-3.43 (m, 1H), 2.35-2.47 (m, 2H), 1.86 (dd, J=7.20, 13.56 Hz, 1H), 1.64-1.76 (m, 1H), 1.15 (d, J=6.24 Hz, 3H)

HPLC: (Purity: 100%)

SFC: (Rt=5.583 min, ee: 99.94%)

LCMS: (M+H: 399.0)

Example 69: Synthesis of Compounds 86-Ent1 and 86-Ent2

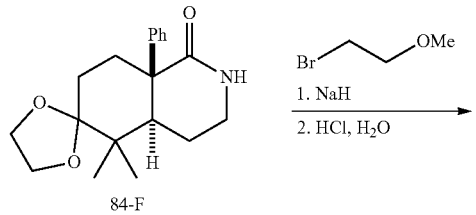

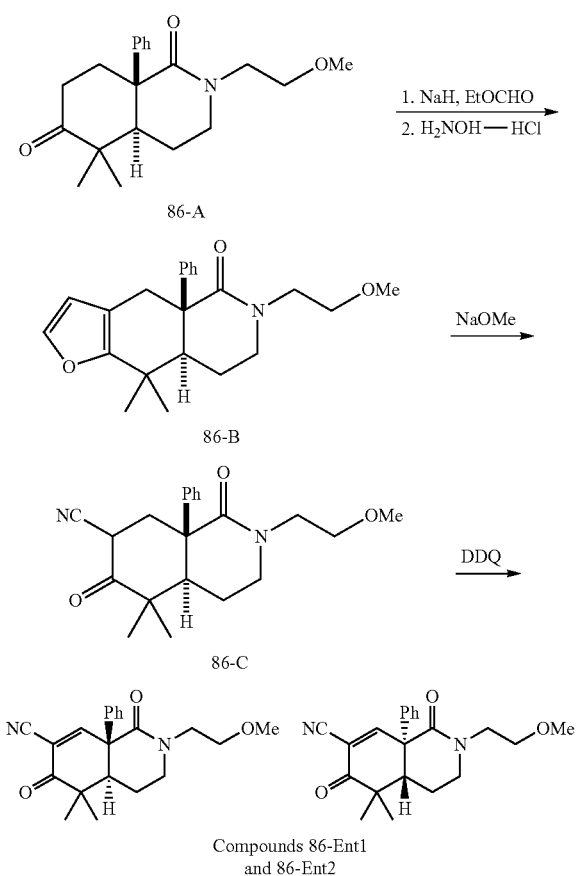

Procedure for Preparation of Compound AC-11

Sodium hydride (25.36 mg, 634.10 umol, 60% purity) was added to an oven dried vial under nitrogen and dissolved in THF (1.59 mL) then cooled to 0° C. Compound 84-F (100.00 mg, 317.05 umol) was added and the mixture was warmed to room temperature and stirred for 2 hours. 1-bromo-2-methoxy-ethane (83.73 mg, 602.40 umol, 56.57 uL) was then added and the mixture was stirred overnight. The mixture was then heated to 60° C. for 6 hours. Sodium iodide (95.05 mg, 634.10 umol) was added and the mixture was stirred at 60° C. overnight. The reaction was then cooled to room temperature, diluted with water, extracted with EtOAc, and the combined organic layers were dried over sodium sulfate, filtered, and concentrated. The residue was purified by flash chromatography (10-75% EtOAc/Heptanes, Rf-0.2 in 50% EtOAc/heptanes) to provide a 100 mg (84% yield) of a yellow oil which contained an inseparable, unidentified byproduct. This mixture was used in the next step without further purification. The residue (100.00 mg, 267.75 umol) was then dissolved in THF (1.34 mL) and treated with HCl (1 M, 669.37 uL) and allowed to stir overnight. Additional HCl (1 M, 669.37 uL) was added and the mixture was heated to 75° C. for 3 hrs. The mixture was then cooled to room temperature and diluted with 20 mL brine and 60 mL EtOAc. The layers were separated and the aqueous layer was extracted with 20 mL EtOAc. The combined organic phases were washed with sat NaHCO$_3$ and brine, dried over MgSO$_4$, filtered, and concentrated. A white solid was isolated (86-A) and was used without further purification.
LCMS: (M+H: 330.2)

Procedure for Preparation of Compound 86-B

Compound 86-A (88.00 mg, 267.13 umol) was dissolved in ethyl formate (395.78 mg, 5.34 mmol, 430.20 uL) and treated with sodium methoxide (5.4 M in methanol, 197.87 uL). The mixture was diluted with Toluene (3.82 mL) and stirred overnight. Water was then added followed by 1N HCl to adjust the pH to ~5. Ethyl acetate was then added and the layers were separated. The organic phase was washed with brine then dried over sodium sulfate, filtered, and concentrated to provide an oil. The material was then used in the next step without further purification. LCMS: (M+H: 358.2).

The oil previously obtained (95.50 mg, 267.18 umol) was dissolved in ethanol (1.27 mL) and water (63.61 uL) was added hydroxylamine hydrochloride (185.66 mg, 2.67 mmol). The solution was stirred at reflux for 2 hours. The solvent was then removed to provide a solid. The solid was then dissolved in saturated aqueous sodium bicarbonate and ethyl acetate. The layers were then separated and the organic layer was washed with water then dried over sodium sulfate, filtered, and concentrated. This material (86-B) was then used in the next step without purification.
LCMS: (M+H: 355.2)

Procedure for Preparation of Compound 86-C

To a solution of 86-B (94.70 mg, 267.18 umol) in ether (2.67 mL) under nitrogen was added sodium methoxide (4.37 M, 305.70 uL) at room temperature. The mixture was stirred at this temperature for 2 hours then diluted with Ether then washed with 5% HCl solution (2×). The aqueous layers were combined and extracted with Ether (2×) and the combined organic layers were washed with water then brine before being dried over sodium sulfate then filtered and concentrated. The faintly yellow foam (86-C) was used in the next step in the sequence without further purification.
LCMS: (M+H: 355.2)

Procedure for Preparation of Compounds 86-Ent and 86-Ent2

Compound 86-C (94.70 mg, 267.18 umol) was dissolved in toluene (2.67 mL) and DDQ (66.72 mg, 293.90 umol) was added. The mixture was heated to 100° C. for 90 minutes then cooled to room temperature. The reaction was filtered and concentrated. The residue was then purified by column chromatography (10-75% EtOAc/Heptane, 12 g column). The product was isolated as an oil which was then separated by SFC (Column: CHIRALPAK IG 30×250 mm, 5 um. Method: 40% Methanol in CO$_2$ [flow rate: 100 mL/min], ABPR 120 bar, MBPR 40 psi) to provide 86-Ent-1 (14.8 mg, Rt=2.49 min) and 86-Ent-2 (14.3 mg, Rt=4.09 min) as off-white solids.

Data for 86-Ent1
HPLC: (Purity: 98%)
LCMS: (M+H: 353.2)
SFC: (ee: 100%)
$^1$HNMR (500 MHz, CDCl$_3$) δ 8.52 (s, 1H), 7.39-7.33 (m, 3H), 7.23-7.19 (m, 2H), 3.99-3.87 (m, 2H), 3.78-3.69 (m, 1H), 3.68-3.59 (m, 2H), 3.46-3.41 (m, 3H), 3.35 (ddd, J=3.7, 7.9, 14.0 Hz, 1H), 2.49 (dd, J=2.1, 13.1 Hz, 1H), 2.12 (ddt, J=7.3, 12.2, 13.4 Hz, 1H), 1.79 (ddd, J=2.1, 6.7, 13.7 Hz, 1H), 1.20 (s, 3H), 0.59 (s, 3H).

Data for 86-Ent2
HPLC: (Purity: 98%)
LCMS: (M+H: 353.2)
SFC: (ee: 100%)
$^1$HNMR (500 MHz, CDCl$_3$) δ ppm 8.52 (s, 1H), 7.38-7.33 (m, 3H), 7.23-7.20 (m, 2H), 4.00-3.87 (m, 2H), 3.76-

3.70 (m, 1H), 3.68-3.59 (m, 2H), 3.46-3.41 (m, 3H), 3.35 (ddd, J=3.7, 7.9, 14.0 Hz, 1H), 2.49 (dd, J=2.4, 13.4 Hz, 1H), 2.12 (ddt, J=7.3, 12.2, 13.4 Hz, 1H), 1.79 (ddd, J=2.1, 6.6, 13.9 Hz, 1H), 1.20 (s, 3H), 0.59 (s, 3H).

Example 70: Synthesis of Compounds 87-Ent1 and 87-Ent2

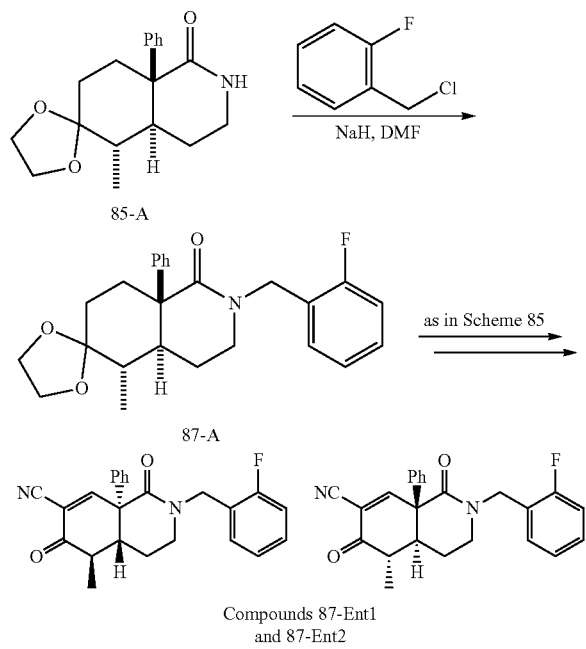

Compounds 87-Ent1 and 87-Ent2 can be made in a manner analogous to that described for 85-Ent1 and 85-Ent2.
Procedure for Synthesis of 87-A.
NaH (99 mg, 2.48 mmol, 2.0 eq) was added to a solution of compound 85-A (400 mg, 1.24 mmol, 1.0 eq) in DMF 10 mL at 0° C. The mixture was stirred at 0° C. for 1 hour. Subsequently, 2-fluorobenzylchloride (352 mg, 1.87 mmol, 1.5 eq) was added to the mixture. The resulting mixture was stirred at 20° C. for 14 hours. LCMS showed compound 85-A was consumed completely. The mixture was poured into water 50 mL, and filtered. The cake was dried to get compound 87-A (500 mg, 91.9% in yield) as yellow solid.
LCMS: (M+H: 410.1).
¹HNMR: (400 MHz, Methanol-d₄) δ: 7.56-7.58 (m, 2H), 7.30-7.32 (m, 2H), 7.25-7.27 (m, 2H), 7.01-7.04 (m, 3H), 4.64 (d, J=15.6 Hz, 1H), 4.50 (d, J=14.8 Hz, 1H), 3.93-3.97 (m, 4H), 3.17-3.19 (m, 1H), 2.97-2.99 (m, 1H), 2.53-2.57 (m, 1H), 2.16-2.19 (m, 3H), 2.05-2.15 (m, 2H), 1.62-1.66 (m, 1H), 1.21-1.25 (m, 1H), 0.97 (d, J=6.4 Hz, 3H), 0.86-0.88 (m, 1H).
Procedure for the Purification and Chiral Separation of 87-Ent1 and 87-Ent2:
The crude reaction mixture was purified by prep-TLC PE/EtOAc=2/1 to get a racemic compound, which was further purified by SFC (column: AD (250 mm*30 mm, 10 um), condition: Neu-MeOH) to give 87-Ent1 (67 mg, 42.1% in yield) and 87-Ent2 (67 mg, 42.1% in yield) as a white solid.
Spectra for 87-Ent1
¹HNMR: (400 MHz, CDCl₃) δ: 8.47 (s, 1H), 7.49-7.51 (m, 1H), 7.34-7.36 (m, 4H), 7.09-7.19 (m, 2H), 7.06-7.08 (m, 2H), 4.88 (d, J=14.4 Hz, 1H), 4.74 (d, J=14.0 Hz, 1H), 3.51-3.63 (m, 2H), 2.39-2.43 (m, 2H), 1.83-1.89 (m, 1H), 1.65-1.66 (m, 1H), 1.13 (d, J=6.4 Hz, 3H).
HPLC: (Purity: 100%)
SFC: (Column: Chiralpak AD-3 150×4.6 mm I.D., 3 um Mobile phase: A: CO₂ B: ethanol (0.05% DEA) Gradient: from 5% to 40% of B in 5 min and hold 40% for 2.5 min, then 5% of B for 2.5 min Flow rate: 2.5 mL/min Column temp.: 35° C. (ee: 99.82%)
LCMS: (M+H: 389.1).
Spectra for 87-Ent2
¹HNMR: (400 MHz, CDCl₃) δ: 8.47 (s, 1H), 7.49-7.51 (m, 1H), 7.35-7.36 (m, 4H), 7.12-7.19 (m, 2H), 7.08-7.09 (m, 2H), 4.88 (d, J=14.4 Hz, 1H), 4.74 (d, J=14.4 Hz, 1H), 3.51-3.63 (m, 2H), 2.39-2.43 (m, 2H), 1.84-1.89 (m, 1H), 1.63-1.65 (m, 1H), 1.13 (d, J=6.4 Hz, 3H).
HPLC: (Purity: 100%).
SFC: (Column: Chiralpak AD-3 150×4.6 mm I.D., 3 um Mobile phase: A: CO₂ B: ethanol (0.05% DEA) Gradient: from 5% to 40% of B in 5 min and hold 40% for 2.5 min, then 5% of B for 2.5 min Flow rate: 2.5 mL/min Column temp.: 35° C. (ee: 98.96%).
LCMS: (M+H: 389.0).

Example 71: Synthesis of Compounds 88-Ent1 and 88-Ent2

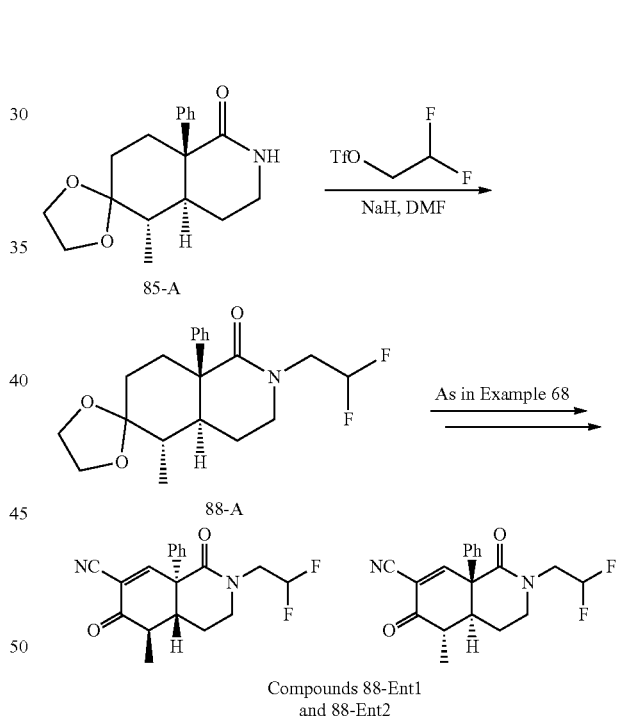

Compounds 88-Ent1 and 88-Ent2 can be made in a manner analogous to that described for 85-Ent1 and 85-Ent2.
Procedure for the Preparation of 88-A:
NaH (120 mg, 3.0 mmol, 2.0 eq) was added to a solution of compound 85-A (450 mg, 1.50 mmol, 1.0 eq) in DMF 10 mL at 0° C. The mixture was stirred at 0° C. for 1 hour. Subsequently, 2,2-difluoroethyl trifluoromethanesulfonate (480 mg, 2.3 mmol, 1.5 eq) was added to the mixture. The resulting mixture was stirred at 20° C. for 14 hours. LCMS showed compound 85-A was consumed completely. The mixture was poured into water 50 mL, and filtered. The cake was dried to get compound 88-A (480 mg, 72.0% in yield) as yellow solid.

¹HNMR: (400 MHz, Methanol-d₄) δ: 7.55-7.57 (m, 2H), 7.32-7.36 (m, 2H), 7.26-7.38 (m, 1H), 5.72-6.02 (m, 1H), 3.93-3.96 (m, 4H), 3.72-3.76 (m, 1H), 3.69-3.70 (m, 1H), 3.27-3.29 (m, 1H), 3.08-3.11 (m, 1H), 2.56-2.58 (m, 1H), 2.13-2.15 (m, 1H), 2.02-2.11 (m, 2H), 1.97-1.99 (m, 2H), 1.62-1.65 (m, 1H), 1.23-1.29 (m, 3H), 0.98 (d, J=6.8 Hz, 3H), 0.86-0.88 (m, 1H).

Procedure for the Purification and Chiral Separation of Compounds 88-Ent1 and 88-Ent2:

The crude reaction was purified by prep-TLC (PE/EtOAc=2/1) to get a racemic compound, which was further purified by SFC (column: AD (250 mm*30 mm, 10 um), condition: Neu-MeOH) to give 88-Ent1 (48 mg, 56.8% in yield) and 88-Ent2 (48 mg, 56.8% in yield) as a white solid.

Spectra for 88-Ent1

¹HNMR: (400 MHz, CDCl₃) δ: 8.38 (s, 1H), 7.39-7.43 (m, 3H), 7.13-7.16 (m, 2H), 6.02-6.32 (m, 1H), 3.90-3.99 (m, 1H), 3.75-3.80 (m, 1H), 3.62-3.68 (m, 2H), 2.43-2.45 (m, 2H), 1.90-1.95 (m, 1H), 1.76-1.78 (m, 1H), 1.16 (d, J=6.4 Hz, 3H).

HPLC: (Purity: 100%)

SFC: (Column: Chiralpak AD-3 150×4.6 mm I.D., 3 um Mobile phase: A: CO₂ B: ethanol (0.05% DEA) Gradient: from 5% to 40% of B in 5 min and hold 40% for 2.5 min, then 5% of B for 2.5 min Flow rate: 2.5 mL/min Column temp.: 35° C. (ee: 99.58%)

LCMS: (M+H: 345.1).

Spectra for 88-Ent2

¹HNMR: (400 MHz, CDCl₃) δ: 8.34 (s, 1H), 7.41-7.43 (m, 3H), 7.13-7.16 (m, 2H), 6.02-6.32 (m, 1H), 3.99-4.02 (m, 1H), 3.70-3.77 (m, 1H), 3.62-3.68 (m, 2H), 2.43-2.45 (m, 2H), 1.90-1.95 (m, 1H), 1.74-1.79 (m, 1H), 1.16 (d, J=6.4 Hz, 3H).

HPLC: (Purity: 100%).

SFC: (Column: Chiralpak AD-3 150×4.6 mm I.D., 3 um Mobile phase: A: CO₂ B: ethanol (0.05% DEA) Gradient: from 5% to 40% of B in 5 min and hold 40% for 2.5 min, then 5% of B for 2.5 min Flow rate: 2.5 mL/min Column temp.: 35° C. (ee: 99.30%).

LCMS: (M+H: 345.1).

Example 72: Synthesis of 89-Ent1 and 89-Ent2

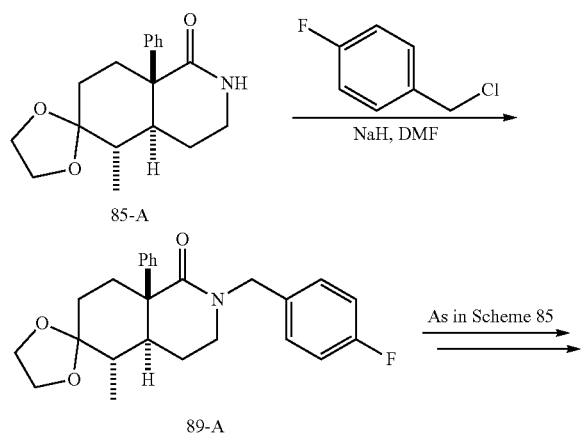

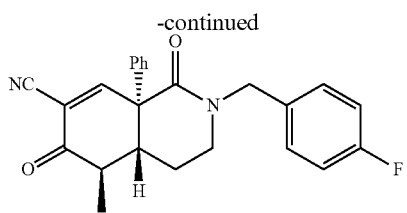

Compounds 89-Ent1 and 89-Ent2

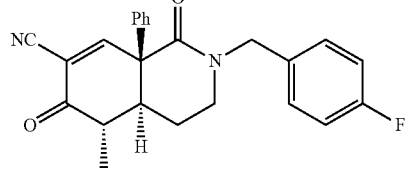

Compounds 89-Ent1 and 89-Ent2 can be made in a manner analogous to that described for 85-Ent1 and 85-Ent2.

Procedure for the Preparation of 89-A:

To a solution of compound 85-A (600 mg, 2 mmol, 1.0 eq) and 4-fluorobenzyl chloride (576 mg, 4 mmol, 1.0 eq) in DMF (10 mL) was added NaH (160 mg, 4 mmol, 2.0 eq) portionwise at 10-18° C. The reaction mixture was stirred at 10-18° C. for 6 h. LCMS showed the compound 85-A was consumed completely. The reaction mixture was quenched with saturated NH₄Cl (100 mL) and extracted with MTBE (50 mL×2). The combined organic layer was washed with brine (100 mL×2), dried over Na₂SO₄, filtered and concentrated to give compound 89-A (645 mg, yield: 71%) as a white solid, which was used for the next step without further purification.

¹H NMR: (400 MHz, CHLOROFORM-d) δ: 7.57 (d, J=7.4 Hz, 2H), 7.34-7.40 (m, 1H), 7.21-7.28 (m, 1H), 7.03-7.15 (m, 3H), 6.90-6.99 (m, 2H), 4.49-4.63 (m, 2H), 4.39 (d, J=14.8 Hz, 1H), 3.88-4.00 (m, 4H), 3.06-3.17 (m, 1H), 2.88 (td, J=8.2, 13.2 Hz, 1H), 2.49-2.61 (m, 1H), 1.87-2.22 (m, 5H), 1.64 (td, J=3.4, 13.6 Hz, 1H), 0.96 (d, J=6.6 Hz, 3H).

Procedure for the Purification and Chiral Separation of Compounds 89-Ent1 and 89-Ent2:

The final DDQ oxidation mixture was concentrated to give the crude and diluted with EtOAc (50 ml). The mixture was washed saturated NaHCO₃ (50 mL×3), dried over Na₂SO₄, filtered and concentrated to give the crude, which was purified by prep-TLC (EtOAc/PE=1:1) to give 220 mg, yield: 62% as a racemic mixture. The racemic mixture was further separated by SFC (column: AD (250 mm*30 mm, 5 um) condition: Neu-MeOH) to give 89-Ent1 (35 mg, yield: 16% Rt=3.355 min) and 89-Ent2 (36 mg, yield: 16%, Rt=3.694 min). Both were obtained as pale white solids.

Spectra for 89-Ent1

¹H NMR (400 MHz, CHLOROFORM-d) δ: 8.47 (s, 1H), 7.31-7.40 (m, 5H), 7.01-7.14 (m, 4H), 4.86 (d, J=14.2 Hz, 1H), 4.52 (d, J=14.4 Hz, 1H), 3.38-3.56 (m, 2H), 2.33-2.43 (m, 2H), 1.85 (br dd, J=7.4, 13.4 Hz, 1H), 1.60-1.69 (m, 1H), 1.12 (d, J=6.2 Hz, 3H).

SFC: (ee: 98.2%)

HPLC: (Purity: 100%)

LCMS: (M+H=389.1)

Spectra for 89-Ent2

¹H NMR (400 MHz, CHLOROFORM-d) δ: 8.47 (s, 1H), 7.31-7.40 (m, 5H), 7.01-7.14 (m, 4H), 4.86 (d, J=14.2 Hz,

1H), 4.52 (d, J=14.4 Hz, 1H), 3.38-3.56 (m, 2H), 2.33-2.43 (m, 2H), 1.85 (br dd, J=7.4, 13.4 Hz, 1H), 1.60-1.69 (m, 1H), 1.12 (d, J=6.2 Hz, 3H).

SFC: (ee: 97.2%)
HPLC: (Purity: 100%)
LCMS: (M+H=389.1)

Example 73: Synthesis of 90-Ent1 and 90-Ent2

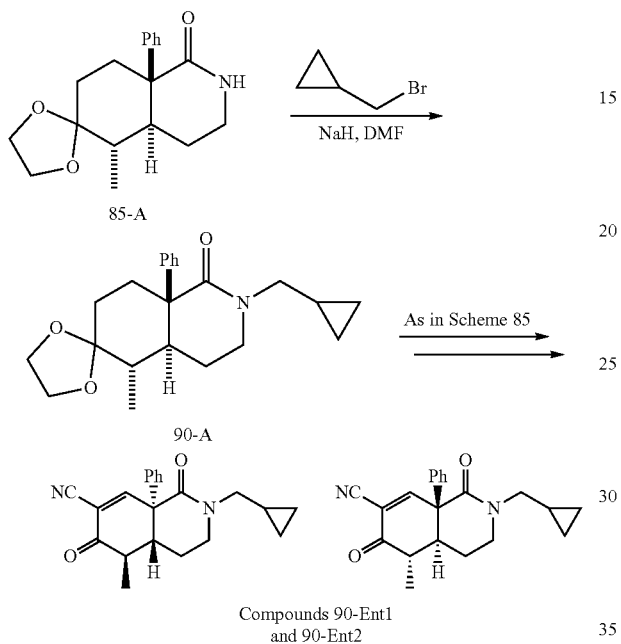

Compounds 90-Ent1 and 90-Ent2 can be made in a manner analogous to that described for 85-Ent1 and 85-Ent2.

Procedure for the Preparation of 90-A:

To a solution of compound 85-A (600 mg, 2 mmol, 1.0 eq) and NaH (160 mg, 4 mmol, 2.0 eq) in DMF (10 mL) was added (bromomethyl)cyclopropane (536 mg, 4 mmol, 1.0 eq) in one portion at 10-18° C. The reaction mixture was stirred at 10-18° C. for 18 hs. LCMS showed the compound 85-A was consumed completely. The reaction mixture was quenched with saturated NH$_4$Cl (100 mL) and extracted with MTBE (50 mL×2). The combined organic layer was washed with brine (100 mL×3), dried over Na$_2$SO$_4$, filtered and concentrated to give compound 90-A (620 mg, yield: 71%) as a white solid, which was used for the next step without further purification.

$^1$H NMR: (400 MHz, METHANOL-d4) δ: 7.37-7.50 (m, 2H), 7.14-7.20 (m, 2H), 7.06-7.12 (m, 1H), 3.67-3.87 (m, 4H), 3.16-3.22 (m, 1H), 3.10 (dd, J=2.2, 9.2 Hz, 1H), 2.82-2.96 (m, 2H), 2.39 (qd, J=6.4, 12.29 Hz, 1H), 2.02-2.12 (m, 1H), 1.91-2.00 (m, 2H), 1.72-1.85 (m, 2H), 1.47 (td, J=3.2, 13.6 Hz, 1H), 1.06-1.11 (m, 1H), 0.82 (d, J=6.4 Hz, 3H), 0.67-0.78 (m, 2H), 0.17-0.30 (m, 2H), −0.08-0.05 (m, 2H)

Procedure for the Purification and Chiral Separation of Compounds 90-Ent1 and 90-Ent2:

The final DDQ oxidation mixture was concentrated to give the crude and diluted with EtOAc (50 ml). The mixture was washed saturated NaHCO$_3$ (50 ml×3), dried over Na$_2$SO$_4$, filtered and concentrated to give the crude, which was purified by prep-TLC (EtOAc/PE=1:1) to give as a racemic mixture. The racemic mixture was further separated by SFC (column: AD (250 mm*30 mm, 5 um) condition: Neu-MeOH) to give 90-Ent1 (19425-102-1, 72 mg, yield: 34% Rt=3.336 min) and 90-Ent2 (19425-102-2, 65 mg, yield: 30.9%, Rt=3.934 min). Bath as pale white solid.

Spectra for 90-Ent1
$^1$H NMR (400 MHz, CHLOROFORM-d) δ: 8.45 (s, 1H), 7.32-7.44 (m, 3H), 7.19 (dd, J=1.6, 8.0 Hz, 2H), 3.67-3.77 (m, 1H), 3.53-3.65 (m, 2H), 3.27 (dd, J=6.8, 13.8 Hz, 1H), 2.36-2.49 (m, 2H), 1.90 (br dd, J=7.2, 13.8 Hz, 1H), 1.63-1.74 (m, 1H), 1.06-1.24 (m, 4H), 0.59-0.71 (m, 2H), 0.31-0.42 (m, 2H).

SFC: (ee: 99.1%)
HPLC: (Purity: 95.4%)
LCMS: (M+H=335.0)

Spectra for 90-Ent2
$^1$H NMR (400 MHz, METHANOL-d4) δ: 8.45 (s, 1H), 7.32-7.44 (m, 3H), 7.19 (dd, J=1.6, 8.0 Hz, 2H), 3.67-3.77 (m, 1H), 3.53-3.65 (m, 2H), 3.27 (dd, J=6.8, 13.8 Hz, 1H), 2.36-2.49 (m, 2H), 1.90 (br dd, J=7.2, 13.8 Hz, 1H), 1.63-1.74 (m, 1H), 1.06-1.24 (m, 4H), 0.59-0.71 (m, 2H), 0.31-0.42 (m, 2H).

SFC: (ee: 99.5%)
HPLC: (Purity: 98.4%)
LCMS: (M+H=335.0)

Example 74: Synthesis of 91-Ent1 and 91-Ent2

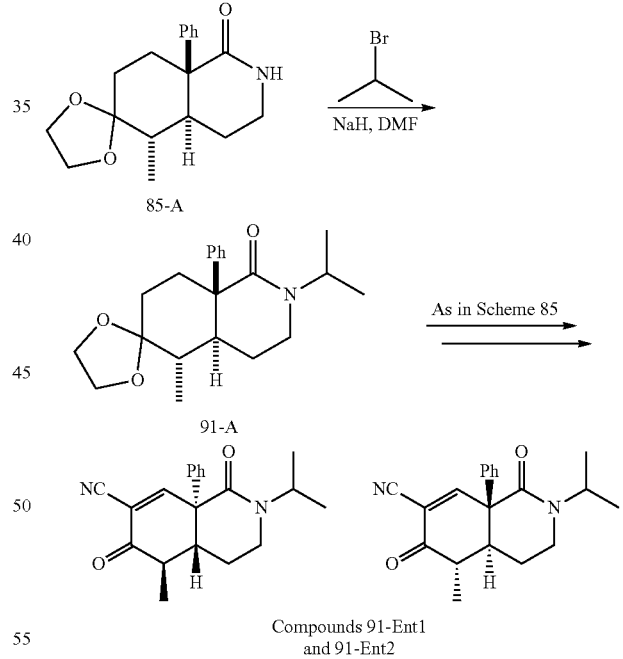

Compounds 91-Ent1 and 91-Ent2 can be made in a manner analogous to that described for 85-Ent1 and 85-Ent2.

Procedure for the Preparation of 91-A:

To a suspension of compound 85-A (800 mg, 2.65 mmol, 1.0 eq.) in anhydrous DMF (10 mL) was added 60% NaH (530 mg, 13.25 mmol, 5.0 eq.) under N$_2$ protection. The reaction mixture was stirred for 20 minutes, then isopropyl bromide (1.6 g, 13.25 mmol, 5.0 eq) was added. The resulting mixture was stirred for 40 hours at 9-15° C. TLC (petroleum ether/EtOAc=1/1) showed that a new spot was detected. The reaction mixture was quenched with saturated aqueous NH₄Cl (100 mL) extracted with EtOAc (80 mL×2). The combined organic layers were washed with brine (100 mL), dried over anhydrous sodium sulfate, filtered and concentrated under reduced pressure. The crude was purified by combi flash (5% to 30% EtOAc in PE) to give the compound 91-A (500 mg, 55% yield) as a white solid.

LCMS: (M+H: 344.2)

¹HNMR: (400 MHz, CDCl₃) δ 7.53-7.55 (m, 2H), 7.25-7.29 (m, 2H), 7.18-7.22 (m, 1H), 4.78-4.85 (m, 1H), 3.91-3.98 (m, 4H), 3.02-3.08 (m, 1H), 2.53-2.63 (m, 2H), 1.78-2.26 (m, 5H), 1.57-1.62 (m, 1H), 1.20-1.31 (m, 1H), 1.05 (d, J=6.8 Hz, 3H), 0.97 (d, J=6.8 Hz, 3H), 0.84 (d, J=6.8 Hz, 3H).

Procedure for the Purification and Chiral Separation of Compounds 91-Ent1 and 91-Ent2:

The crude DDQ reaction mixture was concentrated under reduced pressure, the residue was diluted with H₂O (15 mL) and saturated aqueous NaHCO₃ (20 mL), extracted with EtOAc (40 mL×3). The combined organic layers were washed with brine (50 mL), dried over anhydrous sodium sulfate, filtered and concentrated under reduced pressure. The crude was purified by combi flash (5% to 40% EtOAc in PE) to give the desired compound 200 mg, which was further purified by prep-SFC (Column: AD (250 mm*30 mm; 10 um); Condition: Neu-EtOH; 30%) and re-purified by prep-HPLC (Column: Xtimate C18 150 mm*25 mm; 5 um); Condition: Water (10 mM NH₄HCO₃)-ACN; 35%-65%) to give the desired compound 91-Ent1 (38 mg, 28% yield) and 91-Ent2 (36 mg, 28% yield) as a white solid.

Spectra of 91-Ent1:

¹HNMR: (400 MHz, CDCl₃) δ 8.45 (s, 1H), 7.37-7.40 (m, 3H), 7.12-7.14 (m, 2H), 4.95-5.04 (m, 1H), 3.35-3.50 (m, 2H), 2.30-2.48 (m, 2H), 1.90-1.95 (m, 1H), 1.62-1.71 (m, 1H), 1.32 (d, J=6.8 Hz, 3H), 1.24 (d, J=6.8 Hz, 3H), 1.15 (d, J=6.4 Hz, 3H).

HPLC: (Purity: 100%)

SFC: (Rt=3.337 min, ee: 99.86%)

LCMS: (M+H: 323.0)

Spectra of 91-Ent2:

¹H NMR: (400 MHz, CDCl₃) δ 8.45 (s, 1H), 7.37-7.40 (m, 3H), 7.12-7.14 (m, 2H), 4.93-5.02 (m, 1H), 3.35-3.50 (m, 2H), 2.30-2.48 (m, 2H), 1.90-1.95 (m, 1H), 1.60-1.71 (m, 1H), 1.32 (d, J=6.8 Hz, 3H), 1.24 (d, J=7.2 Hz, 3H), 1.15 (d, J=6.8 Hz, 3H).

HPLC: (Purity: 100%)

SFC: (Rt=4.232 min, ee: 99.80%)

LCMS: (M+Na: 345.1)

Example 75: Synthesis of Compounds 92-Ent1 and 92-Ent2

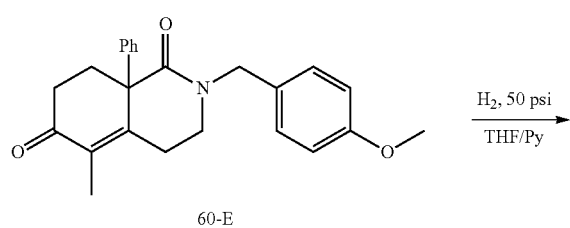

60-E

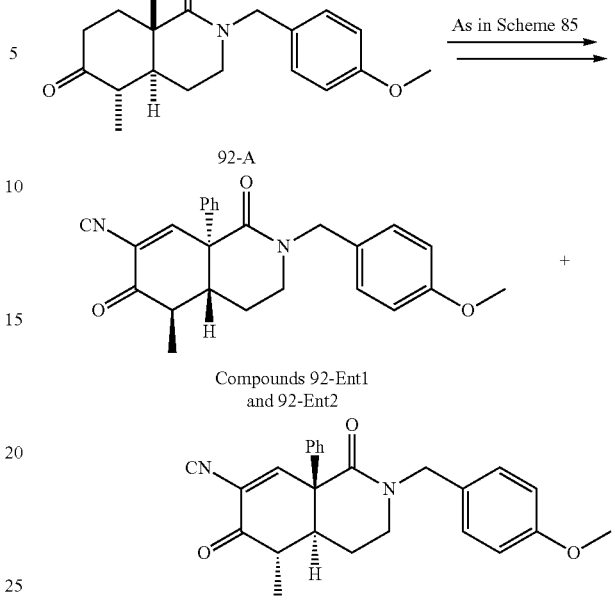

Compounds 92-Ent1 and 92-Ent2 can be made in a manner analogous to that described for 85-Ent1 and 85-Ent2.

Procedure for the Preparation of 92-A:

A mixture of compound 60-E (500 mg) in Py/THF (1 mL/5 mL) was added Pd/C (0.13 g, 10%) under N₂ atmosphere. The mixture was stirred at 35° C. for 20 hours under H₂ atmosphere. LCMS showed the starting material was almost consumed and the desired product was observed. The mixture was filtered and the filtrated was diluted with H₂O (10 mL) and extracted with EtOAc (20 mL×3). The combined organic layer was dried over Na₂SO₄ and filtered. The filtrated was concentrated to give the compound 92-A (380 mg, 77% yield) as a yellow solid.

¹HNMR: (400 MHz, CDCl₃) δ=7.61-7.69 (m, 2H), 7.32-7.40 (m, 3H), 7.07 (d, J=8.8 Hz, 2H), 6.81 (d, J=8.2 Hz, 2H), 4.45-4.57 (m, 2H), 3.80 (s, 3H), 3.00-3.19 (m, 2H), 2.74-2.94 (m, 2H), 2.25-2.41 (m, 3H), 2.08-2.20 (m, 2H), 1.98-2.05 (m, 1H), 1.16 (d, J=6.8 Hz, 3H).

Procedure for the Purification and Chiral Separation of Compounds 92-Ent1 and 92-Ent2:

The mixture was diluted with H₂O (20 mL) and extracted with EtOAc (25 mL×3). The combined organic layer was dried over Na₂SO₄ and filtered. The filtrate was concentrated to give the residue, which was purified by prep-TLC (PE: EtOAc=5:1) to give racemic product (40 mg, 66.7% yield) as a solid. The racemate was separated by SFC (Column: AD (250 mm*30 mm, 5 um) Mobile phase: Neu-MeOH; Flow Rate: 60 mL/min) to supply 92-Ent1 (5 mg, 12.5% yield, Rt=3.754 min) and 92-Ent2 (5 mg, 12.5% yield, Rt=5.122 min) as white solid.

Spectra of 92-Ent1:

¹HNMR: (400 MHz, CDCl₃) δ=8.52 (s, 1H), 7.31-7.41 (m, 5H), 7.06-7.14 (m, 2H), 6.95-6.97 (m, 1H), 6.91-6.95 (m, 1H), 4.88 (d, J=14.2 Hz, 1H), 4.50 (d, J=14.2 Hz, 1H), 3.83-3.90 (m, 3H), 3.40-3.60 (m, 2H), 2.27-2.50 (m, 2H), 1.85 (m, 1H), 1.63-1.70 (m, 1H), 1.13 (d, J=6.4 Hz, 3H)

HPLC: (Purity: 99.1%)

SFC: (ee: 100%)

LCMS: (M+H: 401.0)

Spectra of 92-Ent1:

$^1$HNMR: (400 MHz, CDCl$_3$) δ=8.52 (s, 1H), 7.30-7.41 (m, 5H), 7.10 (d, J=4.4 Hz, 2H), 6.95 (d, J=7.8 Hz, 2H), 4.88 (d, J=13.6 Hz, 1H), 4.50 (d, J=14.2 Hz, 1H), 3.86 (s, 3H), 3.40-3.59 (m, 2H), 2.40 (d, J=6.8 Hz, 2H), 1.79-1.93 (m, 1H), 1.60-1.71 (m, 1H), 1.14 (d, J=4.4 Hz, 3H)

HPLC: (Purity: 100%)
SFC: (ee: 99.3%)
LCMS: (M+H: 401.0)

Example 76: Synthesis of 93-Ent1 and 93-Ent2

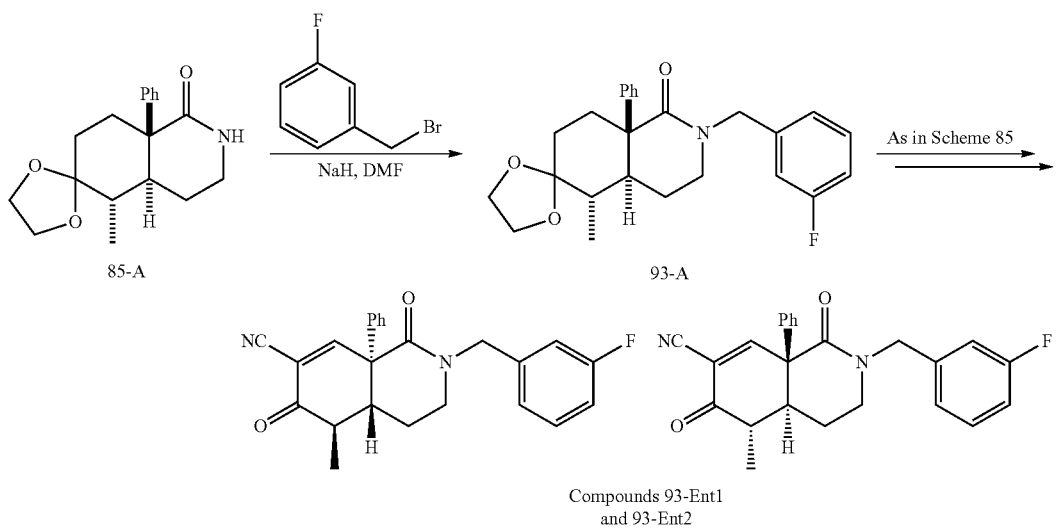

Compounds 93-Ent1 and 93-Ent2 can be made in a manner analogous to that described for 85-Ent1 and 85-Ent2.

Procedure for the Preparation of 93-A:

To a suspension of NaH (60%, 150 mg, 3.75 mmol, 1.5 eq.) in DMF (5 mL) was added compound 85-A (750 mg, 2.5 mmol, 1.0 eq.) at 16° C. and stirred at 16° C. for 1 hour. Then 3-fluorobenzyl bromide (570 mg, 3.0 mol, 1.2 eq.) was added at 16° C. and stirred at 16° C. for 16 hours. Then the reaction solution was quenched by water (50 mL) and extracted by EA (50 mL×3), the combined organic layer was washed by water and brine, dried over Na$_2$SO$_4$. Evaporation of solvents afforded a white solid 93-A (800 mg, crude).

LCMS: ([M+H]: 410.2)

Procedure for the Purification and Chiral Separation of Compounds 93-Ent1 and 93-Ent2:

Then completed DDQ reaction was diluted with EA (30 mL) and washed by saturated NaHCO$_3$ solution (15 mL), water (15 mL×3) and brine (10 mL), and dried over sodium sulphate. The solution was concentrated under reduced pressure to afford a black oil, which was purified by prep-TLC (PE/EA=2/1) to afford yellow solid (170 mg). The product (racemate, 170 mg) was separated by SFC (Column: AD 250 mm*30 mm, 10 um; Condition: MeOH—CO$_2$, 40%) to afford 93-Ent1 as a white solid (36 mg, yield=16%) and 93-Ent2 as a white solid (30 mg, yield=13.6%).

Spectra for 93-Ent1

$^1$H NMR: (METHANOL-d$_4$, 400 MHz): δ=8.34 (s, 1H), 7.34-7.50 (m, 4H), 7.23 (d, J=7.7 Hz, 1H), 7.14-7.20 (m, 3H), 7.05-7.12 (m, 1H), 4.82 (d, J=14.3 Hz, 1H), 4.64 (d, J=14.6 Hz, 1H), 3.48-3.64 (m, 2H), 2.57 (td, J=13.1, 2.8 Hz, 1H), 2.33-2.43 (m, 1H), 1.86-1.96 (m, 1H), 1.53-1.68 (m, 1H), 1.08 (d, J=6.6 Hz, 3H).

LCMS: ([M+H]: 389.0).
HPLC: (purity: 95.97%).
SFC: (ee: 100%).

Spectra for 93-Ent2

$^1$H NMR: (METHANOL-d$_4$, 400 MHz): δ=8.34 (s, 1H), 7.34-7.50 (m, 4H), 7.23 (d, J=7.7 Hz, 1H), 7.14-7.20 (m, 3H), 7.05-7.12 (m, 1H), 4.82 (d, J=14.3 Hz, 1H), 4.64 (d, J=14.6 Hz, 1H), 3.48-3.64 (m, 2H), 2.57 (td, J=13.1, 2.8 Hz, 1H), 2.33-2.43 (m, 1H), 1.86-1.96 (m, 1H), 1.53-1.68 (m, 1H), 1.08 (d, J=6.6 Hz, 3H).

LCMS: ([M+Na]: 411.0).
HPLC: (purity: 100%).
SFC: (ee: 98.88%).

Example 77: Synthesis of 94-Ent1 and 94-Ent2

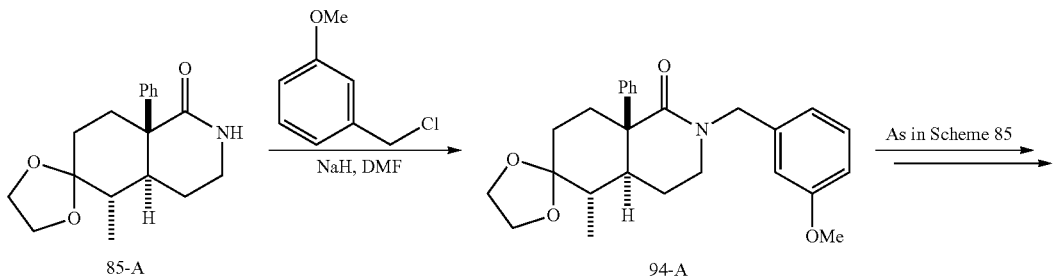

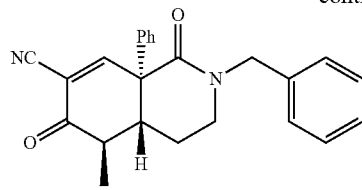
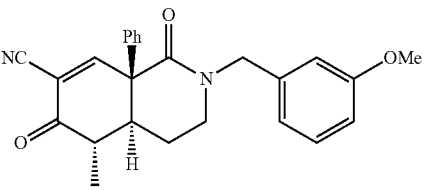

Compounds 94-Ent1
and 94-Ent2

Compounds 94-Ent1 and 94-Ent2 can be made in a manner analogous to that described for 85-Ent1 and 85-Ent2.
Procedure for the Preparation of 94-A:
NaH (79 mg, 1.98 mmol, 2.0 eq) was added to a solution of compound 85-A (300 mg, 0.99 mmol, 1.0 eq) in DMF 4 mL at 0° C. The mixture was stirred at 0° C. for 1 hour. Subsequently, 3-methoxybenzylchloride (232 mg, 1.49 mmol, 1.5 eq) was added to the mixture. The resulting mixture was stirred at 20° C. for 14 hours. LCMS (19441-143-1A) showed compound 85-A was consumed completely. The mixture was poured into water 50 mL, and filtered. The cake was dried to get compound 94-A (410 mg, 97.7% in yield) as yellow solid, which was used in the next step directly.
Procedure for the Purification and Chiral Separation of Compounds 94-Ent1 and 94-Ent2:
The DDQ reaction mixture was concentrated to get a residue, and the residue was purified by prep-TLC PE/EtOAc=2/1 to get a racemic compound, which was further purified by SFC (column: AD (250 mm*30 mm, 10 um), condition: Neu-MeOH) to give 94-Ent1 (51 mg, 32.0% in yield) and 94-Ent2 (77 mg, 35.8% in yield) as a white solid.

Spectra for 94-Ent1
$^1$HNMR: (400 MHz, CDCl$_3$) δ: 8.50 (s, 1H), 7.32-7.36 (m, 4H), 7.10-7.12 (m, 2H), 6.92-6.94 (m, 2H), 4.92 (d, J=14.0 Hz, 1H), 4.49 (d, J=14.0 Hz, 1H), 3.83 (s, 3H), 3.44-3.54 (m, 2H), 2.39-2.41 (m, 2H), 1.82-1.84 (m, 1H), 1.60-1.66 (m, 1H), 1.12 (d, J=6.4 Hz, 3H).
SFC: (Column: ChiralCel OJ-H 150×4.6 mm I.D., 3 um Mobile phase: A: CO$_2$ B: ethanol (0.05% DEA) Gradient: from 5% to 40% of B in 5 min and hold 40% for 2.5 min, then 5% of B for 2.5 min Flow rate: 2.5 mL/min Column temp.: 40° C. (ee: 95.46%)
LCMS: (M+H: 401.1).

Spectra for 94-Ent2
$^1$HNMR: (400 MHz, CDCl$_3$) δ: 8.50 (s, 1H), 7.32-7.36 (m, 4H), 7.11-7.12 (m, 2H), 6.92-6.94 (m, 2H), 4.92 (d, J=14.0 Hz, 1H), 4.49 (d, J=14.0 Hz, 1H), 3.83 (s, 3H), 3.44-3.56 (m, 2H), 2.39-2.41 (m, 2H), 1.82-1.87 (m, 1H), 1.63-1.65 (m, 1H), 1.12 (d, J=6.4 Hz, 3H).
HPLC: (Purity: 98.57%).
SFC: (Column: ChiraCel OJ-H 150×4.6 mm I.D., 3 um Mobile phase: A: CO$_2$ B: ethanol (0.05% DEA) Gradient: from 5% to 40% of B in 5 min and hold 40% for 2.5 min, then 5% of B for 2.5 min Flow rate: 2.5 mL/min Column temp.: 40° C. (ee: 96.25%).
LCMS: (M+H: 401.1).

Example 78: Synthesis of 95-Ent1 and 95-Ent2

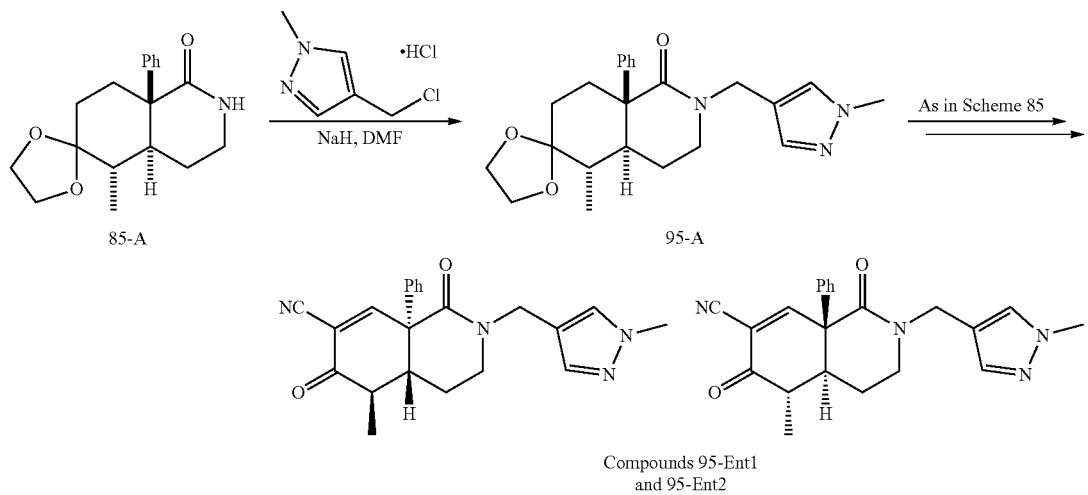

Compounds 95-Ent1
and 95-Ent2

Compounds 95-Ent1 and 95-Ent2 can be made in a manner analogous to that described for 85-Ent1 and 85-Ent2.
Procedure for the Preparation of 95-A:
To a suspension of compound 85-A (300 mg, 0.995 mmol, 1.0 eq.) in anhydrous DMF (8 mL) was added 60% NaH (119.4 mg, 2.985 mmol, 3.0 eq.) and stirred for 30 minutes at 15-23° C. under N$_2$ protection. Then 4-(chloromethyl)-1-methyl-1H-pyrazole hydrogen chloride (216 mg, 1.294 mmol, 1.3 eq) was added and the resulting mixture was stirred for 3 hours at 50° C. TLC (petroleum ether/EtOAc=1/1) showed that the starting material was consumed completely and a new spot was detected. The reaction mixture was quenched with saturated aqueous NH$_4$Cl (50 mL)

extracted with EtOAc (50 mL×3) (combined work up with 19146-85-1). The combined organic layers were washed with brine (50 mL), dried over anhydrous sodium sulfate, filtered and concentrated under reduced pressure. The crude was purified by combi flash (30% to 100% EtOAc in PE) to give the compound 95-A (430 mg, 81.9% yield) as a light yellow solid.

LCMS: (M+H: 396.1)

$^1$HNMR: (400 MHz, CDCl$_3$) δ 7.58-7.60 (m, 2H), 7.27-7.30 (m, 3H), 7.20-7.23 (m, 2H), 4.25-4.39 (m, 2H), 3.92-3.97 (m, 4H), 3.82 (s, 3H), 3.09-3.15 (m, 1H), 2.89-2.99 (m, 1H), 2.51-2.59 (m, 1H), 2.29-2.35 (m, 1H), 1.91-2.21 (m, 4H), 1.60-1.64 (m, 1H), 1.25-1.32 (m, 1H), 0.96 (d, J=6.4 Hz, 3H).

Procedure for the Purification and Chiral Separation of Compounds 95-Ent1 and 95-Ent2:

The DDQ reaction mixture was cooled to room temperature and quenched with water (80 mL) and saturated aqueous NaHCO$_3$ (50 mL), extracted with EtOAc (50 mL×3). The combined organic layers were washed with brine (50 mL), dried over anhydrous sodium sulfate, filtered and concentrated under reduced pressure. The crude was purified by combi flash (10% to 60% EtOAc in PE) to give the desired compound, which was further purified by prep-HPLC (Column: Xtimate C18 150 mm*25 mm; 5 um); Condition: Water (10 mM NH$_4$HCO$_3$)-ACN; 30%-60%) and prep-SFC (Column: AD (250 mm*30 mm; 10 um); Condition: Neu-EtOH; 40%) to give the desired compounds 95-Ent1 (77 mg, 50% yield) and 95-Ent2 (73 mg, 50% yield) as white solids.

Spectra of 95-Ent1:

$^1$HNMR: (400 MHz, CDCl$_3$) δ 8.44 (s, 1H), 752 (s, 1H), 7.47 (s, 1H), 7.32-7.34 (m, 3H), 7.01-7.03 (m, 2H), 4.66-4.70 (m, 1H), 4.34-4.37 (m, 1H), 3.91 (s, 3H), 3.48-3.62 (m, 2H), 2.31-2.41 (m, 2H), 1.83-1.88 (m, 1H), 1.60-1.67 (m, 1H), 1.12 (d, J=6.4 Hz, 3H).

HPLC: (Purity: 100%)

SFC: (Rt=3.593 min, ee: 100%)

LCMS: (M+H: 375.0)

Spectra of 95-Ent2:

$^1$HNMR: (400 MHz, CDCl$_3$) δ 8.44 (s, 1H), 752 (s, 1H), 7.47 (s, 1H), 7.30-7.34 (m, 3H), 7.01-7.03 (m, 2H), 4.66-4.70 (m, 1H), 4.34-4.37 (m, 1H), 3.91 (s, 3H), 3.48-3.62 (m, 2H), 2.31-2.42 (m, 2H), 1.83-1.88 (m, 1H), 1.61-1.67 (m, 1H), 1.12 (d, J=6.4 Hz, 3H).

HPLC: (Purity: 99.48%)

SFC: (Rt=4.751 min, ee: 100%)

LCMS: (M+H: 375.0)

Example 79: Synthesis of 96-Ent1 and 96-Ent2

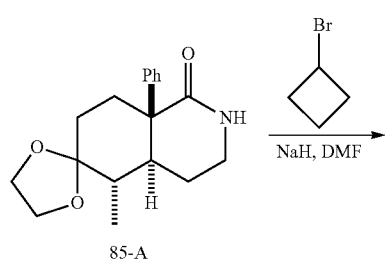

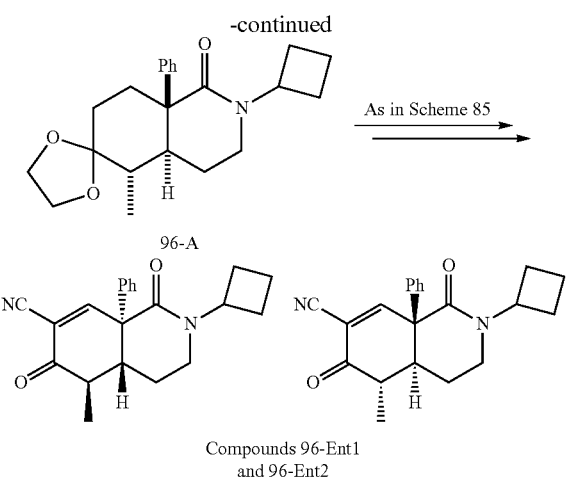

Compounds 96-Ent1 and 96-Ent2

Compounds 96-Ent1 and 96-Ent2 can be made in a manner analogous to that described for 85-Ent1 and 85-Ent2.

Procedure for the Preparation of 96-A:

To a solution of compound 85-A (500 mg, 1.66 mmol, 1.0 eq) in DMF 10 mL was added NaH (664 mg, 16.6 mmol, 10.0 eq) at 0° C. The mixture was stirred at 0° C. for 1 hour. Bromocyclobutane (2.3 g, 16.6 mmol, 10.0 eq) was added to the mixture. The resulting mixture was stirred at 20° C. for 14 hours. LCMS showed compound 85-A was consumed completely. The mixture was poured into water 50 mL, and filtered. The cake was dried to get compound 96-A (220 mg, 37.3% in yield) as yellow solid.

$^1$HNMR: (400 MHz, CDCl$_3$) δ: 7.56-7.61 (m, 2H), 7.23-7.31 (m, 3H), 4.85-4.91 (m, 1H), 3.96-3.99 (m, 4H), 3.26-3.30 (m, 1H), 2.78-2.80 (m, 1H), 2.58-2.60 (m, 1H), 2.22-2.24 (m, 4H), 2.02-2.04 (m, 3H), 1.97-1.99 (m, 1H), 1.59-1.63 (m, 1H), 1.26-1.30 (m, 1H), 0.99-1.01 (m, 3H).

Procedure for the Purification and Chiral Separation of Compounds 96-Ent1 and 96-Ent2:

The DDQ reaction mixture was concentrated to get a residue, and the residue was purified by prep-TLC PE/EtOAc=3/1 to get a racemic compound, which was further purified by SFC (column: AD (250 mm*30 mm, 10 um), condition: Neu-MeOH) to 96-Ent1 (15 mg, 37.7% in yield) as a white solid and 96-Ent2 (15 mg, 37.7% in yield) as a white solid.

Spectra for 96-Ent1

$^1$HNMR: (400 MHz, CDCl$_3$) δ: 8.43 (s, 1H), 7.36-7.40 (m, 3H), 7.10-7.12 (m, 2H), 4.93-5.02 (m, 1H), 3.60-3.65 (m, 1H), 3.49-3.50 (m, 1H), 2.42-2.46 (m, 1H), 2.32-2.36 (m, 1H), 2.25-2.30 (m, 4H), 1.81-1.82 (m, 1H), 1.80-1.82 (m, 2H), 1.63-1.65 (m 1H), 1.16 (d, J=6.4 Hz, 1H).

HPLC: (Purity: 100%).

SFC: (Column: ChiralPak AD-3 150×4.6 mm I.D., 3 um Mobile phase: A: CO$_2$ B: ethanol (0.05% DEA) Gradient: from 5% to 40% of B in 5 min and hold 40% for 2.5 min, then 5% of B for 2.5 min Flow rate: 2.5 mL/min Column temp.: 40° C. (ee: 91.4%).

LCMS: (M+H: 335.1).

Spectra for 96-Ent2

$^1$HNMR: (400 MHz, CDCl$_3$) δ: 8.43 (s, 1H), 7.36-7.40 (m, 3H), 7.10-7.12 (m, 2H), 4.93-5.02 (m, 1H), 3.60-3.63 (m, 1H), 3.49-3.50 (m, 1H), 2.42-2.46 (m, 1H), 2.30-2.32

(m, 1H), 2.25-2.28 (m, 4H), 1.81-1.82 (m, 1H), 1.79-1.80 (m, 2H), 1.64-1.66 (m 2H), 1.16 (d, J=6.4 Hz, 1H).

HPLC: (Purity: 100%).

SFC: (Column: ChiralPak AD-3 150×4.6 mm I.D., 3 um Mobile phase: A: CO$_2$ B: ethanol (0.05% DEA) Gradient: from 5% to 40% of B in 5 min and hold 40% for 2.5 min, then 5% of B for 2.5 min Flow rate: 2.5 mL/min Column temp.: 40° C. (ee: 92.3%).

LCMS: (M+H: 335.1).

Example 80: Synthesis of 97-Ent1 and 97-Ent2

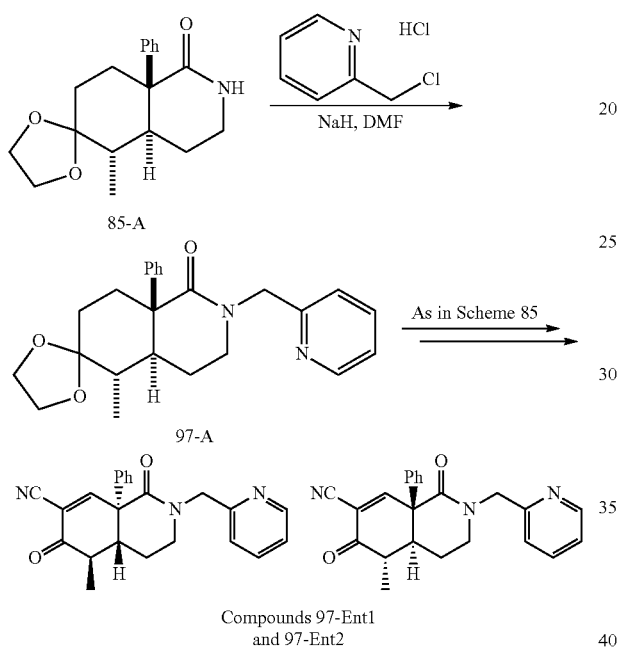

Compounds 97-Ent1 and 97-Ent2

Compounds 97-Ent1 and 97-Ent2 can be made in a manner analogous to that described for 85-Ent1 and 85-Ent2.

Procedure for the Preparation of 97-A:

To a suspension of compound 85-A (500 mg, 1.66 mmol, 1.0 eq.) in anhydrous DMF (12 mL) was added 60% NaH (266 mg, 6.64 mmol, 4.0 eq.) and stirred for 30 minutes at 22-34° C. under N$_2$ protection. Then 2-(chloromethyl)pyridine hydrochloride (354 mg, 2.16 mmol, 1.3 eq) was added and the resulting mixture was stirred for 2 hours at 50° C. TLC (EtOAc) showed that the starting material was consumed completely and a new spot was detected. The reaction mixture was poured into saturated aqueous NH$_4$Cl (80 mL), extracted with EtOAc (50 mL×3). The combined organic layers were washed with brine (80 mL), dried over anhydrous sodium sulfate, filtered and concentrated under reduced pressure to give the crude compound 97-A (786 mg, crude) as an off-white solid, which was used directly for next step without further purification.

$^1$HNMR: (400 MHz, CDCl$_3$) δ 8.45 (d, J=4.4 Hz, 1H), 7.53-7.62 (m, 3H), 7.27-7.31 (m, 2H), 7.21-7.24 (m, 1H), 7.10-7.14 (m, 1H), 7.04 (d, J=7.6 Hz, 1H), 4.63 (s, 2H), 3.95-3.98 (m, 4H), 3.02-3.22 (m, 2H), 2.54-2.62 (m, 1H), 2.09-2.35 (m, 4H), 1.86-1.97 (m, 1H), 1.62-1.65 (m, 1H), 1.24-1.32 (m, 1H), 0.98 (d, J=6.4 Hz, 3H).

Procedure for the Purification and Chiral Separation of Compounds 97-Ent1 and 97-Ent2:

The DDQ reaction mixture was poured into water (50 mL) and extracted with EtOAc (40 mL×4). The combined organic layers were washed with brine (50 mL), dried over anhydrous sodium sulfate, filtered and concentrated under reduced pressure. The crude was purified by combi flash (20% to 100% EtOAc in PE) to give the desired compound, which was further purified by prep-SFC (Column: Chiralcel OD (250 mm*30 mm; 5 um); Condition: 0.1% NH$_3$H$_2$O-EtOH; 30%) to give the desired compounds 97-Ent1 (28 mg, 40.9% yield) and 97-Ent2 (29 mg, 40.9% yield) as white solids.

Spectra of 97-Ent1:

$^1$HNMR: (400 MHz, CDCl$_3$) δ 8.63 (d, J=4.4 Hz, 1H), 8.45 (s, 1H), 7.69-7.73 (m, 1H), 7.33-7.40 (m, 4H), 7.26-7.28 (m, 1H), 7.21-7.25 (m, 2H), 4.96-5.00 (m, 1H), 4.61-4.65 (m, 1H), 3.82-3.87 (m, 1H), 3.62-3.69 (m, 1H), 2.39-2.50 (m, 2H), 1.85-1.90 (m, 1H), 1.68-1.76 (m, 1H), 1.14 (d, J=6.4 Hz, 3H).

HPLC: (Purity: 100%)

SFC: (Rt=3.518 min, ee: 97.30%)

LCMS: (M+H: 372.1)

Spectra of 97-Ent2:

$^1$HNMR: (400 MHz, CDCl$_3$) δ 8.63 (d, J=4.0 Hz, 1H), 8.45 (s, 1H), 7.69-7.73 (m, 1H), 7.33-7.40 (m, 4H), 7.26-7.28 (m, 1H), 7.22-7.25 (m, 2H), 4.96-5.00 (m, 1H), 4.61-4.65 (m, 1H), 3.82-3.87 (m, 1H), 3.62-3.69 (m, 1H), 2.37-2.50 (m, 2H), 1.85-1.90 (m, 1H), 1.68-1.76 (m, 1H), 1.14 (d, J=6.4 Hz, 3H).

HPLC: (Purity: 99.30%)

SFC: (Rt=3.706 min, ee: 94.42%)

LCMS: (M+H: 372.1)

Example 81: Synthesis of 98-Ent1 and 98-Ent2

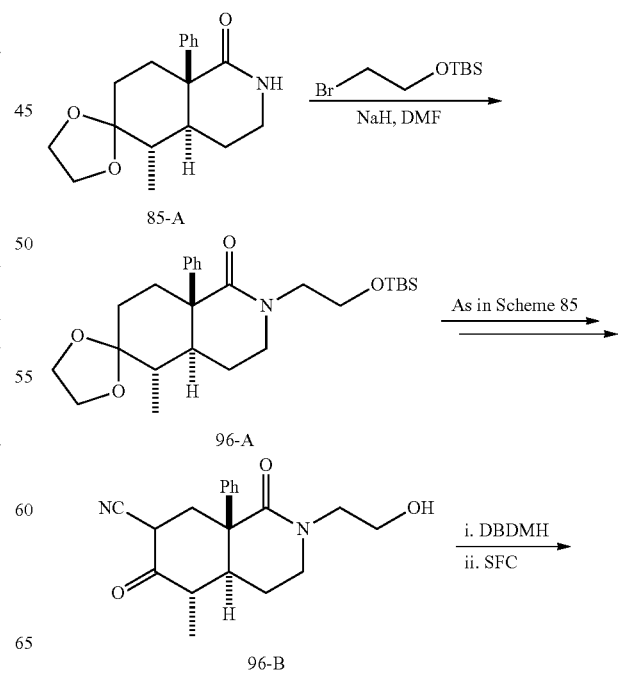

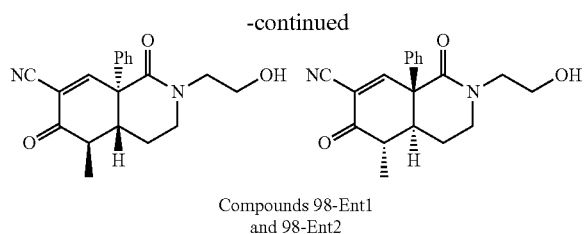

Compounds 98-Ent1 and 98-Ent2

Compounds 98-Ent1 and 98-Ent2 can be made in a manner analogous to that described for 85-Ent1 and 85-Ent2, noting that the TBS group is removed upon treatment with NH$_2$OH*HCl and that an alternative oxidation procedure is used in the final step, described below.

Procedure for the Preparation of 98-A:

To a suspension of compound 85-A (500 mg, 1.66 mmol, 1.0 eq.) in anhydrous DMF (12 mL) was added 60% NaH (265.6 mg, 6.64 mmol, 4.0 eq.) and stirred for 30 minutes at 21-30° C. under N$_2$ protection. Then compound 85-A (516 mg, 2.16 mmol, 1.3 eq) was added and the resulting mixture was stirred for 6 hours at 21-30° C. TLC (PE/EtOAc=3/1) showed that the starting material was consumed completely and a new spot was detected. The reaction mixture was poured into saturated aqueous NH$_4$Cl (80 mL), extracted with EtOAc (50 mL×2). The combined organic layers were washed with brine (50 mL), dried over anhydrous sodium sulfate, filtered and concentrated under reduced pressure to give the crude compound 98-A (890 mg, 1.66 mmol, crude) as a light brown oil, which was used directly for next step without further purification.

LCMS: (M+H: 460.3).

Procedure for the Preparation of 98-B:

Compound 98-B can be made from 98-A in a manner analogous to that described for the synthesis of 85-F from 85-B.

Procedure for the Preparation of 98-Ent1 and 98-Ent2 (Alternative Oxidation Protocol):

To a solution of compound 98-B (240 mg, 0.735 mmol, 1.0 eq.) in anhydrous DMF (8 mL) cooled to 0° C. in an ice water bath was added 1,3-Dibromo-5,5-Dimethylhydantoin [DBDMH] (105.2 mg, 0.368 mmol, 0.5 eq.) under N$_2$ protection. The resulting mixture was stirred at 0° C. for 1 hour, pyridine (581.4 mg, 7.35 mg, 10 eq) was added, and the reaction mixture was heated at 55° C. for 16 hours. LCMS (19146-136-1A) showed that the desired compound MS value was detected. Then the reaction mixture was poured into water (80 mL), extracted with EtOAc (40 mL×3). The combined organic layers were washed with brine (40 mL), dried over anhydrous sodium sulfate, filtered and concentrated under reduced pressure. The crude was purified by combi flash (20% to 80% EtOAc in PE) to give the desired compound, which was further separated by prep-SFC (Column: AD (250 mm*30 mm; 5 um); Condition: Neu-IPA; 30%) to give the desired compound 98-Ent1 (56 mg, 46.9% yield) and 98-Ent2 (56 mg, 46.9% yield) as white solid.

Spectra of 98-Ent1:

$^1$HNMR: (400 MHz, CDCl$_3$) δ 8.41 (s, 1H), 7.35-7.43 (m, 3H), 7.19-7.22 (m, 2H), 3.91-4.02 (m, 3H), 3.72-3.77 (m, 1H), 3.57-3.65 (m, 1H), 3.46-3.52 (m, 1H), 2.39-2.48 (m, 3H), 1.87-1.92 (m, 1H), 1.67-1.77 (m, 1H), 1.15 (d, J=6.4 Hz, 3H).

HPLC: (Purity: 100%)
SFC: (Rt=3.981 min, ee: 99.90%)
MS: (M+H: 325.1)

Spectra of 98-Ent2:

$^1$HNMR: (400 MHz, CDCl$_3$) δ 8.40 (s, 1H), 7.35-7.43 (m, 3H), 7.19-7.22 (m, 2H), 3.90-4.00 (m, 3H), 3.72-3.77 (m, 1H), 3.57-3.65 (m, 1H), 3.46-3.52 (m, 1H), 2.40-2.48 (m, 3H), 1.87-1.92 (m, 1H), 1.68-1.77 (m, 1H), 1.15 (d, J=6.4 Hz, 3H).

HPLC: (Purity: 98.19%)
SFC: (Rt=4.671 min, ee: 99.94%)
MS: (M+H: 325.1)

Example 82: Synthesis of 99-Ent1 and 99-Ent2

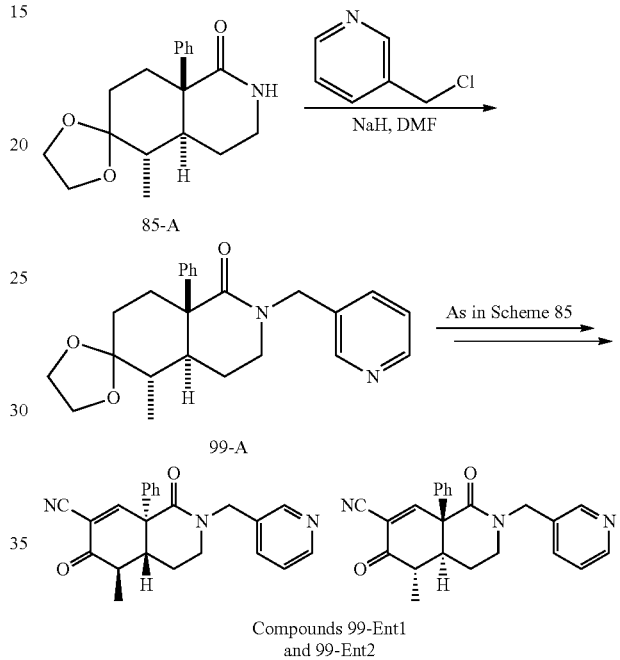

Compounds 99-Ent1 and 99-Ent2

Compounds 99-Ent1 and 99-Ent2 can be made in a manner analogous to that described for 85-Ent1 and 85-Ent2. The alternative DBMDH oxidation procedure described in Scheme 98 was used in the final step.

Procedure for the Preparation of 99-A:

To a solution of compound 85-A (600 mg, 2 mmol, 1.0 eq) and NaH (240 mg, 6 mmol, 3.0 eq) in DMF (10 mL) was added 3-(chloromethyl)pyridine (978 mg, 6 mmol, 3.0 eq) in one portion at 10-22° C. The reaction mixture was stirred at 10-22° C. for 18 h. LCMS showed the compound 85-A was consumed completely. The reaction mixture was quenched with saturated NH$_4$Cl (30 mL) and extracted with EA (50 mL×2). The combined organic layer was washed with brine (50 mL×2), dried over Na$_2$SO$_4$, filtered and concentrated to give compound 99-A (800 mg, crude) as yellow oil, which was used for the next step without further purification.

LCMS: (M+H: 393.2)

Procedure for the Purification and Chiral Separation of Compounds 99-Ent1 and 99-Ent2:

Upon completion, the crude DBMDH oxidation mixture was diluted with water (20 mL), extracted with EtOAc (15 mL×4). The combined organic layers were washed with brine (20 mL), dried over anhydrous Na$_2$SO$_4$, filtered, concentrated and purified by prep-TLC (DCM:EtOAc=2:1) to supply racemate (~90 mg) which was separated by SFC (condition: Neu-EtOH, column: C2 250 mm*30 mm, 10 um)

to supply 99-Ent1 (~30 mg, purity: 92.03% detected with HPLC) as white solid and 99-Ent2 (~30 mg, purity: 85.88% detected with HPLC) as white solid. 99-Ent1 (30 mg, purity: 92.03%) was re-purified by prep-HPLC (condition: water (0.225% FA-ACN), column: Phenomenex Synergi C18 150*30 mm*4 um) to supply impure product (~15 mg, purity: 91.571% detected by SFC), for which was further separated by SFC (condition: Neu-MeOH, column: AD 250 mm*30 mm, 5 um) to supply 99-Ent1 (11 mg, 9.26% yield, Rt=3.188 min) as a white solid.

99-Ent2 (~30 mg, purity: 85.88%) was re-purified by prep-HPLC (condition: water (0.225% FA-ACN), column: Phenomenex Synergi C18 150*30 mm*4 um) to supply impure product (~15 mg, putity: 93.83% detected with SFC) for which was further separated by SFC (condition: Neu-MeOH, column: Chiral park AS-H 250 mm*30 mm, 5 um) to supply 99-Ent2 (11 mg, 9.26% yield, Rt=5.216 min) as a white solid Spectra of Compound 99-Ent1:

$^1$HNMR: (400 MHz, CDCl$_3$) δ: 8.64 (br s, 2H), 8.46 (s, 1H), 7.80 (br d, J=8.0 Hz, 1H), 7.32-7.40 (m, 4H), 7.02-7.08 (m, 2H), 4.85 (d, J=14.0 Hz, 1H), 4.64 (d, J=14.4 Hz, 1H), 3.45-3.62 (m, 2H), 2.35-2.45 (m, 2H), 1.88 (m, 1H), 1.67 (m, 1H), 1.13 (d, J=6.4 Hz, 3H)

HPLC: (purity: 98.03%)

SFC: (purity: 98.491%)

LCMS: (M+H: 372.0)

Spectra of Compound 99-Ent2:

$^1$HNMR: (400 MHz, CDCl$_3$) δ: 8.65 (br s, 2H), 8.46 (s, 1H), 7.80 (br d, J=8.0 Hz, 1H), 7.32-7.39 (m, 4H), 7.02-7.09 (m, 2H), 4.85 (d, J=14.4 Hz, 1H), 4.64 (d, J=14. Hz, 1H), 3.45-3.62 (m, 2H), 2.35-2.45 (m, 2H), 1.88 (m, 1H), 1.69 (m, 1H), 1.13 (d, J=6.0 Hz, 3H)

HPLC: (Purity: 93.35%)

SFC: (purity: 97.833%)

LCMS: (M+H: 372.0)

Example 83R: Synthesis of 100-Ent1 and 100-Ent2

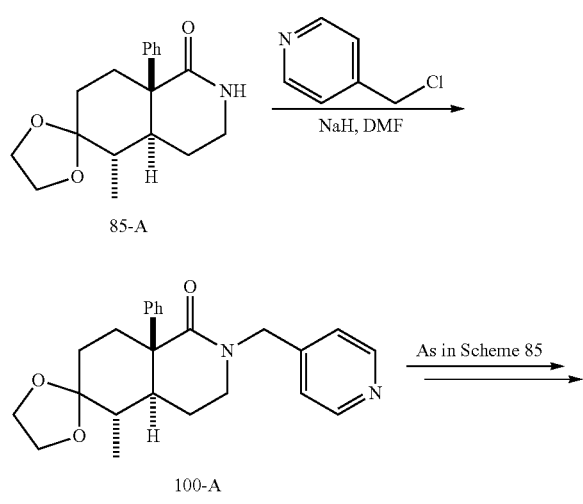

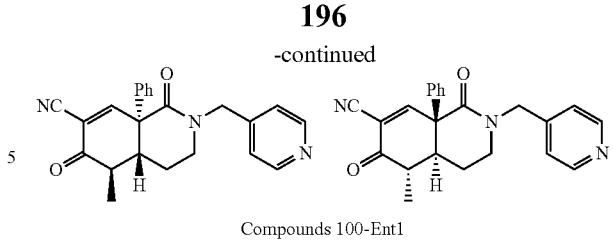

Compounds 100-Ent1 and 100-Ent2

Compounds 100-Ent1 and 100-Ent2 can be made in a manner analogous to that described for 85-Ent1 and 85-Ent2. The alternative DBMDH oxidation procedure described in Scheme 98 was used in the final step.

Procedure for the Preparation of 100-A:

To a solution of compound 85-A (600 mg, 2 mmol, 1.0 eq) in 15 mL of DMF was added NaH (240 mg, 6 mmol, 3.0 eq) at 0° C. by dropwise. After 15 minute, 4-(chloromethyl) pyridine was added and the reaction mixture was stirred at 22-26° C. for 18 hs. LCMS showed that the desired mass response was observed. The mixture was diluted with saturated water (60 mL) and extracted with EA (40 mL×3). The combined organic layer was washed with brine (30 mL*2), dried over Na$_2$SO$_4$, filtered and concentrated in vacuo to supply crude compound 100-A (800 mg, crude) as yellow oil, which was used for the next step without further purification.

LCMS: ([M+H]: 393.2)

Procedure for the Purification and Chiral Separation of Compounds 100-Ent1 and 100-Ent2:

Upon completion, the crude DBMDH oxidation mixture was diluted with water (30 mL), extracted with EtOAc (35 mL×3). The combined organic layers was washed with brine (20 mL×2), dried over Na$_2$SO$_4$, filtered and concentrated in vacuum to get the residue which was purified by prep-TLC (EtOAc, Rf=0.4) to supply the racemate (50 mg, yield=74%) as yellow oil.

The racemate was further separated by SFC (condition: Neu-EtOH, column: AD (250 mm*30 mm, 5 um)) to supply 100-Ent1 (7 mg, Rt=1.314 min, yield=28%) as white solid and 100-Ent2 (7 mg, Rt=2.667 min, yield=28%) as white solid.

Spectra for 100-Ent1

$^1$HNMR: (400 MHz, CDCl$_3$) δ: 8.68-8.63 (m, 2H), 8.46 (s, 1H), 7.40-7.35 (m, 3H), 7.29-7.27 (m, 2H), 7.11-7.07 (m, 2H), 4.73 (q, J=14.40 Hz, 2H), 3.59-3.42 (m, 2H), 2.46-2.39 (m, 2H), 1.92-1.85 (m, 1H), 1.80-1.69 (m, 1H), 1.14 (d, J=6.0 Hz, 3H)

HPLC: (purity: 98.22%)

SFC: (purity: 99.25%)

LCMS: ([M+H]: 372.1)

Spectra for 100-Ent2

$^1$HNMR: (400 MHz, CDCl$_3$) δ: 8.67-8.62 (m, 2H), 8.46 (s, 1H), 7.41-7.36 (m, 3H), 7.29-7.27 (m, 2H), 7.11-7.07 (m, 2H), 4.73 (q, J=14.8 Hz, 2H), 3.57-3.41 (m, 2H), 2.46-2.37 (m, 2H), 1.94-1.85 (m, 1H), 1.70-1.63 (m, 1H), 1.14 (d, m, J=6.0 Hz, 3H)

HPLC: (Purity: 96%)

SFC: (purity: 97.42%)

LCMS: ([M+H]: 372.1)

Example 84: Synthesis of 101-Ent1 and 101-Ent2

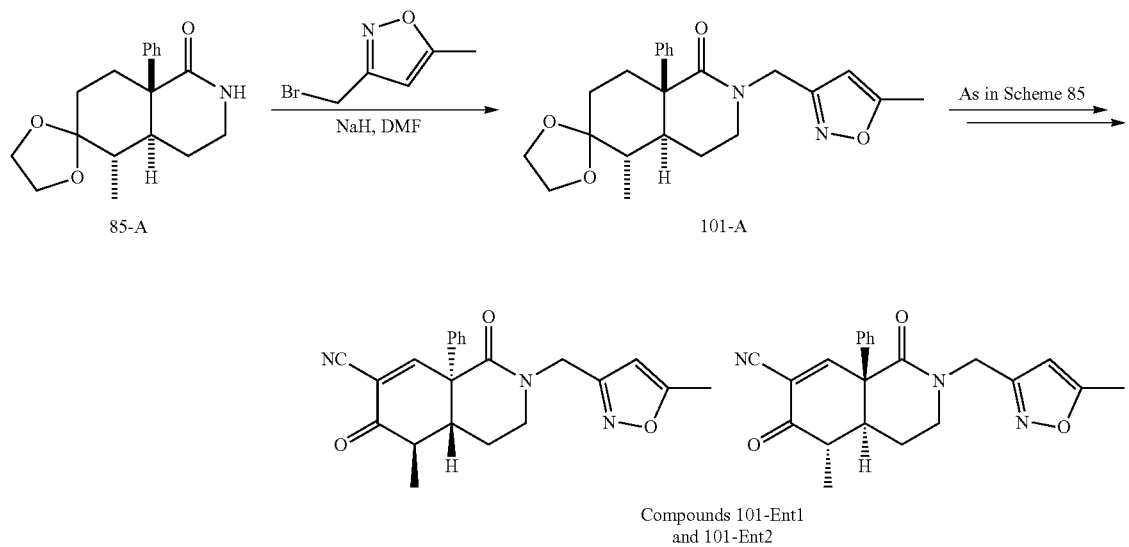

Compounds 101-Ent1 and 101-Ent2

Compounds 101-Ent1 and 101-Ent2 can be made in a manner analogous to that described for 85-Ent1 and 85-Ent2. The alternative DBMDH oxidation procedure described in Scheme 98 was used in the final step.
Procedure for the Preparation of 101-A:
To a solution of compound 85-A (500 mg, 1.7 mmol, 1 eq.) in 10 mL of DMF was added NaH (136 mg, 3.4 mmol, 2.0 eq), the mixture was stirred at 26° C. for 1.5 h. Subsequently, 3-(bromomethyl)-5-methylisoxazole (438 mg, 2.49 mmol, 1.5 eq) was added and the resulting mixture was stirred at 23-28° C. for 18 h. TLC (PE:EtOAc=2:1) showed one new spot was observed. The mixture was poured into 30 mL of ice-water, extracted with EtOAc (20 mL×3). The combined organic layers were washed with brine (20 mL), dried over anhydrous Na$_2$SO$_4$, filtered and concentrated. The residue was purified by flash column (PE:EtOAc=90:10-80:20-70:30) to supply compound 101-A (540 mg, 62.8% yield, purity: 78.3%) as colorless gum.
LCMS: (M+H: 397.2)
Procedure for the Purification and Chiral Separation of Compounds 101-Ent1 and 101-Ent2:
Upon completion, the crude DBMDH oxidation mixture was diluted with EtOAc (30 m), washed with 1M HCl aq. (10 mL×2), brine (10 mL×2), dried over anhydrous Na$_2$SO$_4$, filtered, concentrated and purified by prep-TLC (PE:E-tOAc=1:1) to supply racemate (~40 mg) which was separated by SFC (condition: Neu-IPA, column: AD 250 mm*30 mm; 5 um) to supply 101-Ent1 (13 mg, 21.8% yield, Rt=4.152 min) as white solid and 101-Ent2 (15 mg, 25.1% yield, Rt=4.827 min) as white solid.
Spectra of 101-Ent1:
$^1$HNMR: (400 MHz, CDCl$_3$) δ: 8.42 (s, 1H), 7.34-7.41 (m, 3H), 7.12 (m, 2H), 6.06 (d, J=0.8 Hz, 1H), 4.82 (d, J=14.8 Hz, 1H), 4.59 (d, J=14.8 Hz, 1H), 3.68-3.76 (m, 1H), 3.58 (m, 1H), 2.46 (d, J=0.8 Hz, 3H), 2.38-2.43 (m, 2H), 1.89 (m, 1H), 1.66-1.76 (m, 1H), 1.14 (d, J=6 Hz, 3H).
HPLC: (purity: 99.34%).
SFC: (purity: 99.78%).
LCMS: (M+H: 376.0).
Spectra of 101-Ent2:
$^1$HNMR: (400 MHz, CDCl$_3$) δ: 8.42 (s, 1H), 7.35-7.40 (m, 3H), 7.12 (m, 2H), 6.06 (s, 1H), 4.82 (d, J=14.8 Hz, 1H), 4.59 (d, J=15.2 Hz, 1H), 3.68-3.75 (m, 1H), 3.58 (m, 1H), 2.46 (s, 3H), 2.38-2.43 (m, 2H), 1.89 (m Hz, 1H), 1.71 (m, 1H), 1.14 (d, J=6.0 Hz, 3H).
HPLC: (Purity: 98.51%).
SFC: (purity: 99.91%).
LCMS: (M+H: 376.0).

Example 85: Synthesis of 102-Ent1 and 102-Ent2

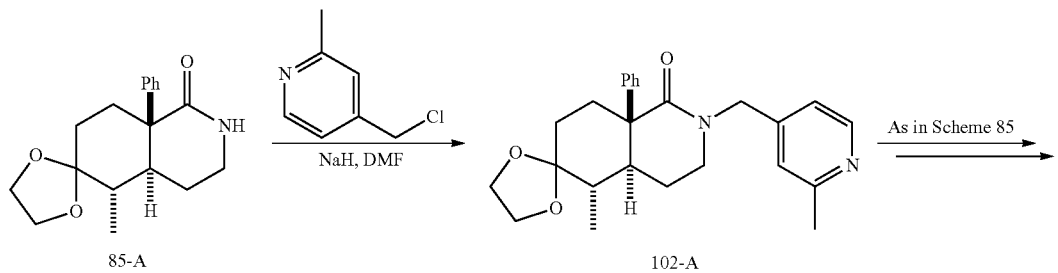

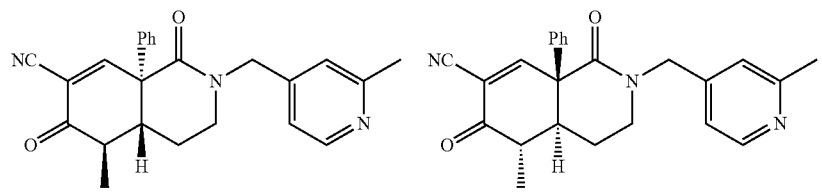

Compounds 102-Ent1
and 102-Ent2

Compounds 102-Ent1 and 102-Ent2 can be made in a manner analogous to that described for 85-Ent1 and 85-Ent2. The alternative DBMDH oxidation procedure described in Scheme 98 was used in the final step.

To a suspension of compound 85-A (600 mg, 2.0 mmol, 1.0 eq.) in DMF (15 mL) was added NaH (240 mg, 6.0 mmol, 3.0 eq.) at 26° C. and stirred at 26° C. for 1 hour. Then 4-(chloromethyl)-2-methylpyridine (352 mg, 2.5 mmol, 1.25 eq.) was added at 26° C. and the reaction suspension was stirred at 26° C. for 16 hours. The reaction solution was quenched by water (30 mL) extracted by EA (30 mL×3). The combined organic layer was washed by water (20 mL) and brine (20 mL), dried over sodium sulphate and filtered. The filtrate was evaporated under reduced pressure to afford yellow solid (570 mg, yield=70%).

LCMS: ([M+H]: 407.2)

Procedure for the Purification and Chiral Separation of Compounds 102-Ent1 and 102-Ent2:

Upon completion, the crude DBMDH oxidation mixture was diluted by water (15 mL) and extracted by EA (30 mL×3). The combined organic layer was washed by water (40 mL) and brine (20 mL), dried over sodium sulphate and filtered. The filtrate was evaporated under reduced pressure and the residue was purified by prep-TLC (EA) to afford white solid (28 mg, yield=91%). The racemic compound (28 mg, 0.08 mmol) was separated by SFC (Column: AD 250 mm*30 mm, 5 um; Condition: EtOH—CO$_2$, 40%) to afford 102-Ent1 as a white solid (12 mg, yield=42.9%) and 102-Ent2 as a white solid (9 mg, yield=32.1%).

Spectra for 102-Ent1

$^1$H NMR: (CHLOROFORM-d, 400 MHz): δ=8.46 (d, J=5.2 Hz, 1H), 8.40 (s, 1H), 7.28-7.33 (m, 3H), 7.08 (s, 1H), 6.99-7.06 (m, 3H), 4.72 (d, J=14.6 Hz, 1H), 4.51 (d, J=14.6 Hz, 1H), 3.36-3.49 (m, 2H), 2.52 (s, 3H), 2.32-2.40 (m, 2H), 1.76-1.86 (m, 1H), 1.57-1.61 (m, 1H), 1.07 ppm (d, J=6.4 Hz, 3H)

HPLC: (purity: 100%)

SFC: (ee: 99.08%)

LCMS: ([M+H]: 386.1)

Spectra for 102-Ent2

$^1$H NMR: (CHLOROFORM-d, 400 MHz): δ=8.46 (d, J=5.2 Hz, 1H), 8.40 (s, 1H), 7.28-7.33 (m, 3H), 7.08 (s, 1H), 6.99-7.06 (m, 3H), 4.72 (d, J=14.6 Hz, 1H), 4.51 (d, J=14.6 Hz, 1H), 3.36-3.49 (m, 2H), 2.52 (s, 3H), 2.32-2.40 (m, 2H), 1.76-1.86 (m, 1H), 1.57-1.61 (m, 1H), 1.07 ppm (d, J=6.4 Hz, 3H)

HPLC: (purity: 100%)

Example 86: Synthesis of Compounds 103-Ent1 and 103-Ent2

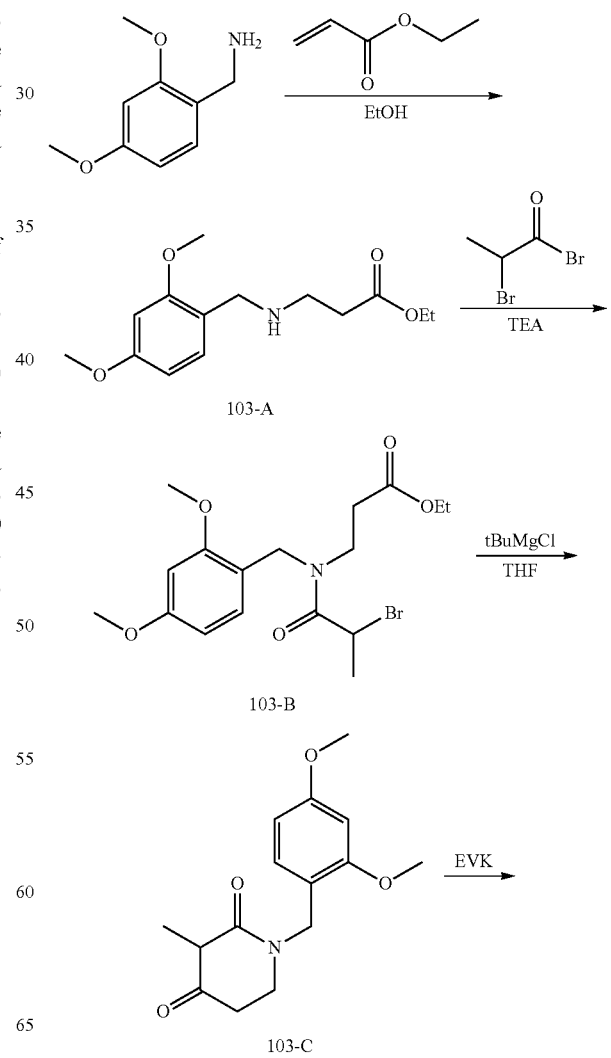

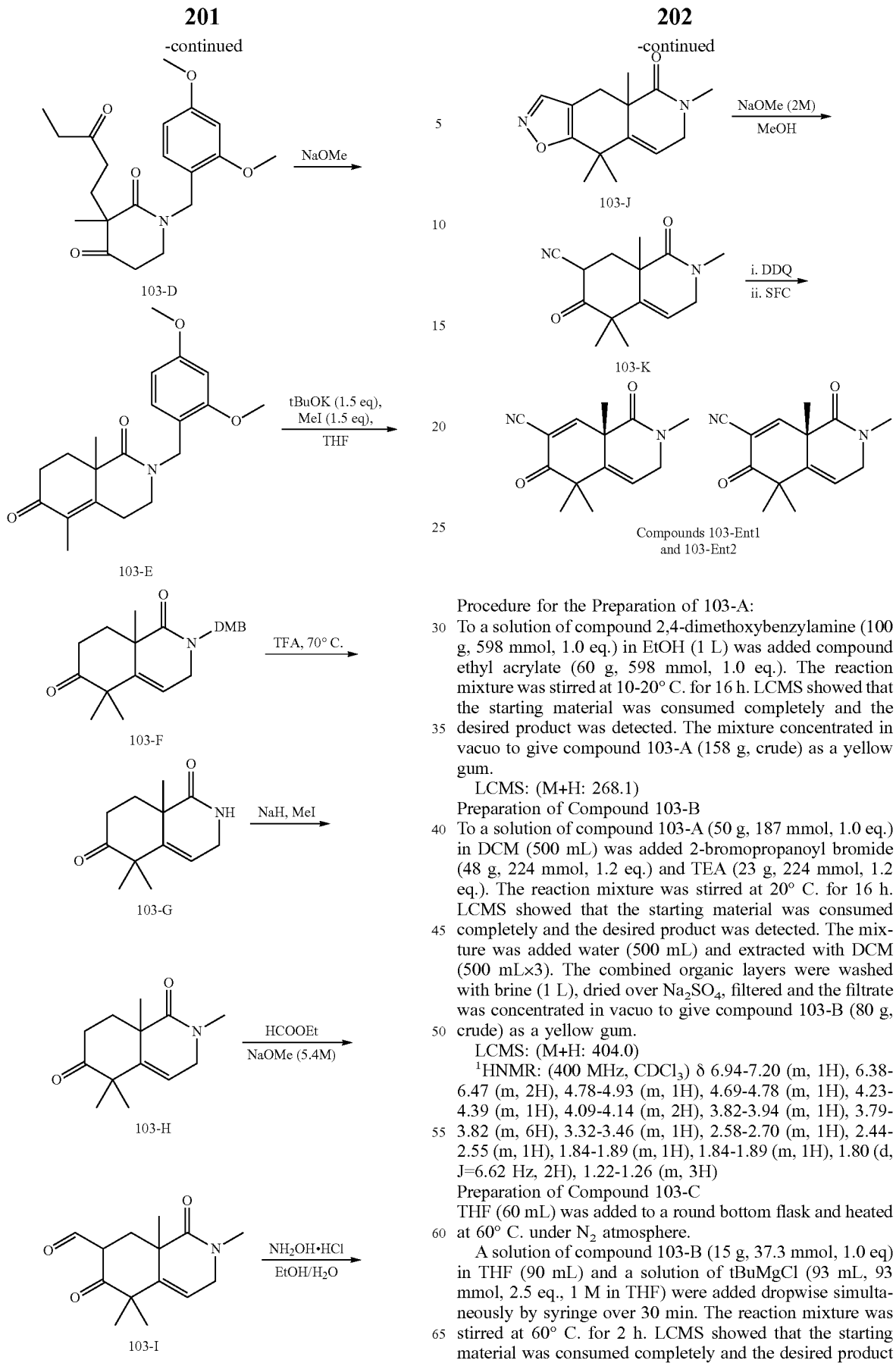

Procedure for the Preparation of 103-A:
To a solution of compound 2,4-dimethoxybenzylamine (100 g, 598 mmol, 1.0 eq.) in EtOH (1 L) was added compound ethyl acrylate (60 g, 598 mmol, 1.0 eq.). The reaction mixture was stirred at 10-20° C. for 16 h. LCMS showed that the starting material was consumed completely and the desired product was detected. The mixture concentrated in vacuo to give compound 103-A (158 g, crude) as a yellow gum.

LCMS: (M+H: 268.1)

Preparation of Compound 103-B

To a solution of compound 103-A (50 g, 187 mmol, 1.0 eq.) in DCM (500 mL) was added 2-bromopropanoyl bromide (48 g, 224 mmol, 1.2 eq.) and TEA (23 g, 224 mmol, 1.2 eq.). The reaction mixture was stirred at 20° C. for 16 h. LCMS showed that the starting material was consumed completely and the desired product was detected. The mixture was added water (500 mL) and extracted with DCM (500 mL×3). The combined organic layers were washed with brine (1 L), dried over $Na_2SO_4$, filtered and the filtrate was concentrated in vacuo to give compound 103-B (80 g, crude) as a yellow gum.

LCMS: (M+H: 404.0)

$^1$HNMR: (400 MHz, $CDCl_3$) δ 6.94-7.20 (m, 1H), 6.38-6.47 (m, 2H), 4.78-4.93 (m, 1H), 4.69-4.78 (m, 1H), 4.23-4.39 (m, 1H), 4.09-4.14 (m, 2H), 3.82-3.94 (m, 1H), 3.79-3.82 (m, 6H), 3.32-3.46 (m, 1H), 2.58-2.70 (m, 1H), 2.44-2.55 (m, 1H), 1.84-1.89 (m, 1H), 1.84-1.89 (m, 1H), 1.80 (d, J=6.62 Hz, 2H), 1.22-1.26 (m, 3H)

Preparation of Compound 103-C

THF (60 mL) was added to a round bottom flask and heated at 60° C. under $N_2$ atmosphere.

A solution of compound 103-B (15 g, 37.3 mmol, 1.0 eq) in THF (90 mL) and a solution of tBuMgCl (93 mL, 93 mmol, 2.5 eq., 1 M in THF) were added dropwise simultaneously by syringe over 30 min. The reaction mixture was stirred at 60° C. for 2 h. LCMS showed that the starting material was consumed completely and the desired product was detected. The mixture was added Sat. $NH_4Cl$ (150 mL)

and extracted with EtOAc (150 mL×3). The combined organic layers were washed with brine (1 L), dried over Na$_2$SO$_4$, filtered and the filtrate was concentrated in vacuo to give the crude. The crude was purified by column chromatography on silica gel (PE:EtOAc=20:1 to 2:1) to supply compound 103-C (7.5 g, 73% yield) as a yellow gum.

LCMS: (M+H: 278.1)

$^1$HNMR: (400 MHz, CDCl$_3$) δ 7.18-7.23 (m, 1H), 6.44-6.47 (m, 2H), 4.64-4.71 (m, 1H), 4.53-4.60 (m, 1H), 3.81 (d, J=2.18 Hz, 6H), 3.61-3.70 (m, 1H), 3.49-3.56 (m, 1H), 3.35 (q, J=6.86 Hz, 1H), 2.51-2.60 (m, 1H), 2.38-2.49 (m, 1H), 1.35 (d, J=7.02 Hz, 3H).

Preparation of Compound 103-D

To a solution of compound 103-C (30 g, 108.2 mmol, 1.0 eq.) in MeCN (300 mL) was added TEA (21.9 g, 21.64 mmol, 2.0 eq.) and EVK (10.9 g, 129.8 mmol, 1.2 eq.). The mixture was stirred at 70° C. for 16 hours. LCMS showed the starting materials were consumed completely and the desired product was detected. The mixture concentrated in vacuo and added Sat. NH$_4$Cl (300 mL) and extracted with EtOAc (400 mL×3). The combined organic layers were dried over Na$_2$SO$_4$, filtered and the filtrate was concentrated in vacuo to give compound 103-D (33 g, 84% yield) as a yellow gum.

LCMS: (M+H: 361.1).

Preparation of Compound 103-E

To a solution of compound 103-D (30 g, 83.0 mmol, 1.0 eq.) in MeOH (300 mL) was added NaOMe (5.4 g, 99.6 mmol, 1.2 eq.). The reaction mixture was stirred at 50° C. for 2 hours.

LCMS showed the starting materials were consumed completely and the desired product was detected. The mixture quenched by Sat. NH$_4$Cl (300 mL) and extracted with EtOAc (300 mL×3). The combined organic layer was dried over anhydrous Na$_2$SO$_4$, filtered, concentrated under reduced pressure to give the crude, which was triturated with EtOH (50 mL) and filtered to give the compound 103-E (27 g, 94.7% yield) as a yellow solid.

LCMS: (M+H: 344.1).

$^1$H NMR: (400 MHz, CDCl$_3$) δ 7.16 (d, J=9.04 Hz, 1H), 6.45-6.48 (m, 2H), 4.61-4.67 (m, 1H), 4.52-4.58 (m, 1H), 3.81 (s, 6H), 3.39-3.45 (m, 1H), 3.19-3.25 (m, 1H), 2.77-2.83 (m, 1H), 2.49-2.61 (m, 3H), 2.35-2.43 (m, 1H), 1.99-2.08 (m, 1H), 1.76 (s, 3H), 1.49 (s, 3H)

Preparation of Compound 103-F

To a solution of compound 103-E (6.0 g, 17.49 mmol, 1 eq.) in 200 mL of THF was added potassium tert-Butoxide (3.53 g, 31.48 mmol, 1.8 eq) under ice-bath (0-5° C.) cooling by portion wise, then the mixture was stirred at 0-5° C. for 1.5 h. Compound methyl iodide (3.73 g, 26.24 mmol, 1.5 eq) was added by drop wise. The resulting mixture was stirred at 13° C.~23° C. for 18 h. TLC (PE:EA=2:1) showed compound 103-E remained little, several spots were observed. The mixture was poured into 300 mL of water and 50 mL of brine, extracted with EtOAc (150 mL×3). The combined organic layers were dried over anhydrous Na$_2$SO$_4$, filtered and concentrated. The residue was purified by flash column (PE:EtOAc=90:10-50:50) to give compound 103-F (2.5 g, 40.06% yield) as pale-yellow gum.

$^1$HNMR: (400 MHz, CDCl$_3$) δ: 7.09-7.15 (m, 1H), 6.41-6.49 (m, 2H), 5.72 (dd, J=1.97, 5.92 Hz, 1H), 4.82 (d, J=14.91 Hz, 1H), 4.42 (d, J=14.47 Hz, 1H), 3.83-3.91 (m, 1H), 3.80 (d, J=1.75 Hz, 6H), 3.67-3.76 (m, 1H), 2.61-2.70 (m, 1H), 2.49-2.59 (m, 1H), 2.34-2.44 (m, 1H), 2.17 (m, 1H), 1.32 (s, 3H), 1.27 (d, J=2.63 Hz, 6H).

Preparation of Compound 103-G

Compound 103-F (2.5 g, 7.0 mmol, 1.0 eq.) was added into 30 mL of TFA. The resulting mixture was stirred at 70° C. for 1.5 h. TLC (PE:EA=2:1) showed compound 103-F was consumed completely. The mixture was concentrated, the residue was diluted with EtOAc (150 mL) and water (100 mL), adjusted pH to 7-8 by adding saturated aqueous NaHCO$_3$, extracted with EtOAc (100 mL×3). The combined organic layers were dried over anhydrous Na$_2$SO$_4$, filtered and concentrated. The residue was purified by flash column (PE:EtOAc=80:20-50:50) to give compound 103-G (900 mg, 62% yield) as pale-yellow solid.

$^1$HNMR: (400 MHz, CDCl$_3$) δ: 6.09 (br s, 1H), 5.81 (br d, J=5.51 Hz, 1H), 4.00-4.09 (m, 1H), 3.81-3.91 (m, 1H), 2.35-2.61 (m, 3H), 2.06-2.20 (m, 1H), 1.35 (s, 3H), 1.32 (s, 3H), 1.30 (s, 3H).

Preparation of Compound 103-H

To a solution of compound 103-G (400 mg, 1.93 mmol, 1 eq.) in 10 mL of THF was added NaH (108 mg, 2.71 mmol, 1.4 eq), then the mixture was stirred at 20° C. for 1.5 h. Methyl iodide (411 mg, 2.89 mmol, 1.5 eq, 0.18 mL) was added and the resulting mixture was stirred at 20° C. for 2 h. TLC (PE:EA=1:2) showed compound 103-G was consumed completely. The mixture was poured into 30 mL of water and 5 mL of brine, extracted with EtOAc (20 mL×3). The combined organic layers were dried over anhydrous Na$_2$SO$_4$, filtered and concentrated. The residue was purified by flash column (PE:EtOAc=80:20-50:50) to give compound 103-H (180 mg, 42.3% yield) as pale-yellow solid.

$^1$HNMR: (400 MHz, CDCl$_3$) δ: 5.74 (dd, J=2.01, 5.77 Hz, 1H), 4.06 (dd, J=2.01, 17.57 Hz, 1H), 3.77 (dd, J=5.52, 17.57 Hz, 1H), 3.03 (s, 3H), 2.48-2.60 (m, 2H), 2.36-2.47 (m, 1H), 2.16-2.23 (m, 1H), 1.34 (s, 3H), 1.29 (s, 3H), 1.26 (s, 3H).

Preparation of Compound 103-I

To a solution of compound 103-H (230 mg, 1.04 mmol, 1 eq.) in 4 mL of ethyl formate was added NaOMe (0.66 mL, 3.54 mmol, 3.4 eq. 5.4 M in methanol). The mixture was stirred at 26° C. under N$_2$ for 1 h. TLC (PE:EA=1:1) showed compound 103-H was consumed completely. The mixture was poured into 30 mL of water slowly, adjusted pH to 6-7 by adding 1M HCl aq., extracted with EtOAc (20 mL×3). The combined organic layers were washed with brine (20 mL), dried over anhydrous Na$_2$SO$_4$, filtered and concentrated to give crude compound 103-I (230 mg) as pale-yellow gum.

Preparation of Compound 103-J

To a solution of compound 103-I (230 mg, 0.92 mmol, 1.0 eq.) in EtOH (5 mL) and H$_2$O (1 mL) was added hydrochloride hydroxylamine (78 mg, 1.11 mmol, 1.2 eq.). After addition the mixture was stirred at 70° C. for 12 h. TLC (PE:EA=1:1) showed the starting materials were consumed completely. The mixture was concentrated, the residue was diluted with water (25 mL), extracted with EtOAc (15 mL×3). The combined organic layers were washed with brine (15 mL), dried over anhydrous Na$_2$SO$_4$, filtered and concentrated to supply compound 103-J (220 mg) as a pale-yellow solid.

$^1$HNMR: (400 MHz, CDCl$_3$) δ: 8.12 (s, 1H), 5.84 (dd, J=2.45, 4.28 Hz, 1H), 4.03-4.10 (m, 1H), 3.87-3.95 (m, 1H), 3.04 (s, 3H), 3.01 (d, J=15.89 Hz, 1H), 2.59 (d, J=15.77 Hz, 1H), 1.56 (s, 3H), 1.49 (s, 3H), 1.32 (s, 3H).

Preparation of Compound 103-K

To a solution of compound 103-J (220 mg, 0.89 mmol, 1 eq.) in 4 mL of methanol was added NaOMe (1.78 mL, 3.58 mmol, 4.0 eq. 2 M in methanol). After addition the mixture was stirred at 24° C. for 5 h. TLC (PE:EA=1:2) showed compound 103-J was consumed completely. The mixture was concentrated and the residue was diluted with water (30 mL), adjusted pH to ~6 by adding 1M HCl aq., extracted with EtOAc (15 mL×3). The combined organic layers were dried over anhydrous Na$_2$SO$_4$, filtered and concentrated to supply crude compound 103-K (220 mg) as pale-yellow gum.

Preparation of 103-Ent1 and 103-Ent2

To a solution of compound 103-K (220 mg, 0.89 mmol, 1.0 eq.) in toluene/MeCN (2 mL/2 mL) was added DDQ (242 mg, 1.1 mmol, 1.2 eq.). The mixture was stirred at 90° C. for 3 h. TLC (PE:EA=1:2) showed compound 103-K was consumed completely. The mixture was concentrated and the residue was purified by flash column (PE:EtOAc=80:20-50: 50) and prep-TLC (PE:EA=1:3) to supply racemate (85 mg), which was separated by SFC (Condition: Neu-IPA, Column: IC 250 mm*30 mm; 10 um) to supply peak 1 (25 mg) with purity of 92% and peak 2 (28 mg) with purity of 83.8%. Peak 1 (25 mg) was re-purified by prep-HPLC (condition: water (0.225% FA-CAN, column: Agela ASB 150*25 mm*5 um) to supply compound 103-Ent1 (6 mg, 2.7% yield, Rt=6.972 min) as pale-yellow solid. Peak 2 (28 mg) was re-purified by prep-HPLC (condition: water (0.225% FA-CAN, column: Agela ASB 150*25 mm*5 um) to supply compound 103-Ent2 (5 mg, 2.3% yield. Rt=8.046 min) as pale-yellow solid.

Spectra of Compound 103-Ent1:

$^1$HNMR: (400 MHz, CDCl$_3$) δ: 8.24 (br s, 1H), 5.90 (br d, J=4.19 Hz, 1H), 4.11 (br d, J=17.86 Hz, 1H), 3.81 (br dd, J=5.18, 17.97 Hz, 1H), 3.03 (br s, 3H), 1.63 (br s, 3H), 1.42 (br s, 6H).

HPLC: (purity: 98.73%)

SFC: (purity: 99.799%)

LCMS: (M+H: 245.0)

Spectra of Compound 103-Ent2:

$^1$HNMR: (400 MHz, CDCl$_3$) δ: 8.24 (s, 1H), 5.90 (br d, J=4.85 Hz, 1H), 4.11 (br d, J=17.86 Hz, 1H), 3.81 (br dd, J=5.62, 17.97 Hz, 1H), 3.03 (s, 3H), 1.63 (s, 3H), 1.42 (s, 6H).

HPLC: (Purity: 98.34%)

SFC: (purity: 99.322%)

LCMS: (M+H: 245.0)

Example 87: Synthesis of Compounds 104-Ent1 and 104-Ent2

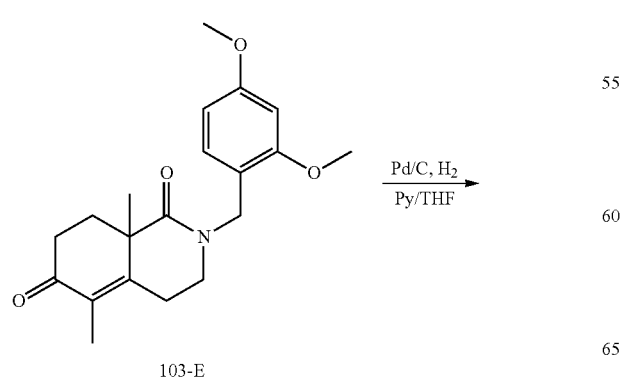

103-E

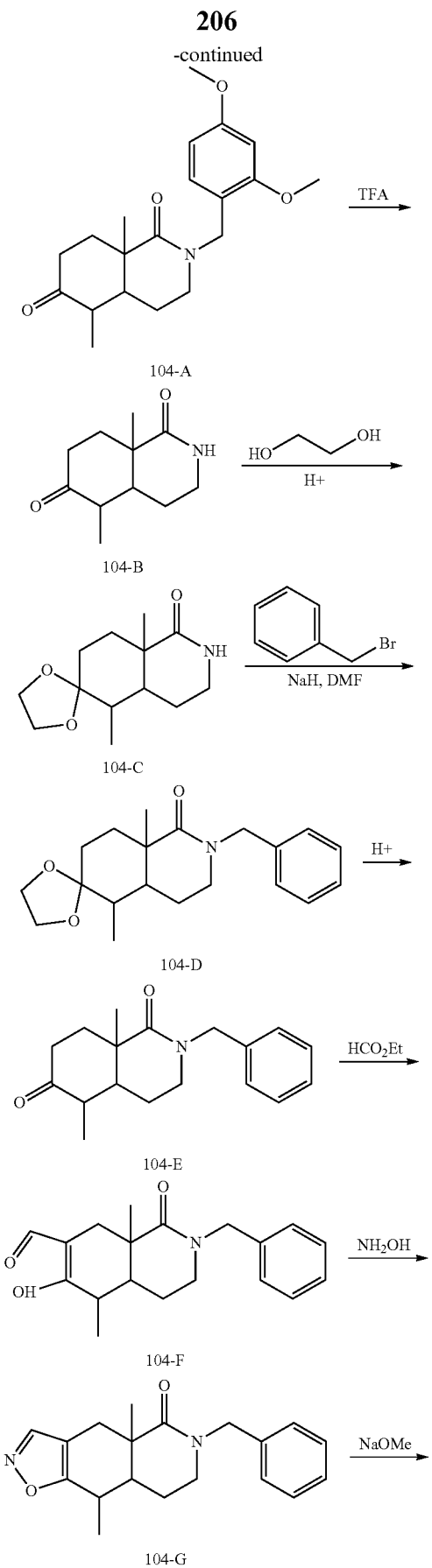

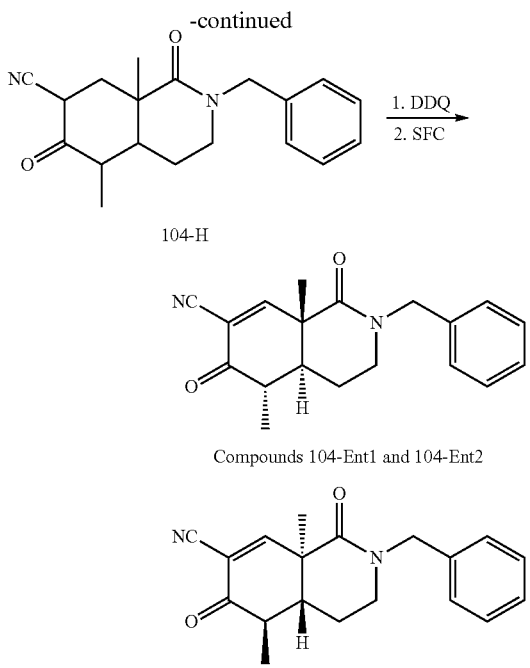

Preparation of 104-A:
To a solution of compound 103-E (5 g, 14.6 mmol, 1 eq.) in Py. (5 mL) and THF (50 mL) was added Pd/C (500 mg, 10%, dry) at 10° C. under N₂. The mixture was stirred at 25° C. for 48 hours under H₂ (50 psi). LCMS showed that the starting material was consumed completely and the desired product was detected. The suspension was filtered through a pad of celite and washed with DCM (30 mL×2) and EtOH (30 mL), the filtrate was concentrated under reduce pressure to give a crude product, which was purified by prep-HPLC (Column: Waters XSELECT C18 150*30 mm*5 um; Condition: water (0.1% TFA)-CAN; FlowRate: 25 mL/min) t to give compound 104-A (2.6 g, 52% yield) as a colorless oil.

¹H NMR: (400 MHz, CDCl₃) δ 7.05-7.13 (m, 1H), 6.40-6.45 (m, 2H), 4.56-4.63 (m, 1H), 4.40-4.49 (m, 1H), 3.78-3.80 (m, 6H), 3.21-3.27 (m, 1H), 3.09-3.20 (m, 1H), 2.91 (quin, J=6.34 Hz, 1H), 2.47-2.57 (m, 1H), 2.11-2.30 (m, 4H), 1.77 (d, J=13.68 Hz, 1H), 1.63 (s, 3H), 1.31-1.36 (m, 1H), 1.00 (d, J=6.62 Hz, 3H)

Preparation of Compound 104-B
A solution of compound 104-A (2.6 g, 7.5 mmol, 1 eq.) in TFA (40 mL) was stirred at 60° C. for 1 h. TLC (EtOAc, Rf=0.2, DNPH as coloration) the starting material was consumed completely and several new spots were observed. The reaction mixture was poured into Sat. NaHCO₃ (200 mL) and washed with EtOAc (30 mL×1). The aqueous layer was extracted with CH2Cl2 (50 mL×8). The combined organic layers was dried over Na2SO4, filtered and concentrated to get 104-B (1.04 g, yield=71.1%) as a white solid.

¹H NMR: (400 MHz, CDCl₃) δ 5.65-5.79 (m, 1H), 3.33-3.50 (m, 2H), 2.41-2.49 (m, 4H), 1.76-1.83 (m, 3H), 1.44 (s, 1H), 1.04-1.10 (m, 3H).

Preparation of Compound 104-C
To a solution of compound 104-B (1.03 g, 5.3 mmol, 1 eq.) and ethane-1,2-diol (4.9 g, 79 mmol, 15 eq.) in THF (20 mL) was added dropwise BF₃.Et₂O (752 mg, 5.3 mmol, 1 eq.) at 20° C., and the reaction mixture was stirred at 20° C. for 16 h. LCMS showed that the desired mass response was observed and TLC (EtOAc=100%, Rf=0.3) showed no new spot was observed. The reaction mixture was concentrated to get the residue which was purified by flash chromatography (CH₂Cl₂/MeOH=30/1-20/1) to obtain the title product 104-C as a white solid. (Yield=78.7%, 1.0 g).

LCMS: (M+H: 240.0)
¹H NMR: (400 MHz, CDCl₃) δ 5.39-5.60 (m, 1H), 3.90-4.04 (m, 4H), 3.23-3.41 (m, 2H), 2.34-2.50 (m, 1H), 1.99-2.07 (m, 1H), 1.74-1.88 (m, 3H), 1.57-1.72 (m, 3H), 1.21-1.28 (m, 3H), 0.87-0.94 (m, 3H).

Preparation of Compound 104-D
To a solution of compound 104-C (300 mg, 1.3 mmol, 1.0 eq) and NaH (80 mg, 2 mmol, 2.0 eq) in DMF (3 mL) was added compound benzyl bromide (340 mg, 2 mmol, 1.5 eq) in one portion at 10-25° C. The reaction mixture was stirred at 10-25° C. for 18 hs. LCMS showed the compound 104-C was consumed completely. The reaction mixture was quenched with saturated NH₄Cl (100 mL) and extracted with EA (60 mL×4). The combined organic layers were washed with brine (100 mL×3), dried over Na₂SO₄, filtered and concentrated to give compound 104-D (320 mg, yield: 71%) as a white solid, which was used for the next step without further purification.

LCMS: (M+H: 330.1)
Preparation of Compound 104-E
To a solution of compound 104-D (320 mg, crude) in THF (8 mL) was added HCl(1 mL, 1M) dropwise at 10-23° C. The reaction mixture was stirred at 10-23° C. for 1.8 hours. LCMS showed the compound 104-D was consumed completely. The mixture was adjust to PH=9 with solid NaHCO₃. The mixture was extracted with EA (10 mL×2), dried over Na₂SO₄, filtered and concentrated to give the crude, which was purified by column chromatography on silica gel (PE/EA=10:1-5:1-1:1) to give compound 104-E (150 mg, yield: 42%) as yellow oil.

LCMS: (M+H: 286.1)
Preparation of Compound 104-F
To a solution of compound 104-E (150 mg, 0.52 mmol, 1.0 eq) in ethyl formate (5 ml) was added a solution of NaOMe/MeOH (0.49 ml 2.6 mmoL, 5.0 eq, 5.4M) at 10-30° C. dropwise. The mixture was stirred at 10-18° C. for 18 hours. LCMS showed the compound 104-E was consumed completely. The mixture was poured into water (30 mL) and acidified with HCl (1M) to make PH=4-5. The mixture was extracted with EtOAc (30 mL×2). The combined organic phase was washed with brine (50 mL×l), dried over Na₂SO₄, and filtered. The filtrate was concentrated in vacuo to give compound 104-F (200 mg), which was used directly in the next step without purification.

LCMS: (M+H: 237.1)
Preparation of Compound 104-G
A mixture of compound 104-F (200 mg, 0.64 mmol, 1.0 eq) and hydrochloride hydroxylamine (44 mg, 0.64 mmol, 1.0 eq) in EtOH/H₂O (5 mL, V=5:1) were stirred at 80° C. for 18 hours. LCMS showed desired product was detected. The mixture was concentrated to remove EtOH and diluted with water (30 ml). The mixture was extracted with EA (30 mL×2), dried over Na₂SO₄, filtered and concentrated to give the crude 104-G (220 mg), which was used directly in the next step without purification.

LCMS: (M+H: 311.1)
Preparation of Compound 104-H
To a solution of compound 104-G (220 mg, 0.7 mmol, 1.0 eq) in MeOH (3 mL) was added a solution of NaOMe/MeOH (1.4 mL, 2M, 4.0). The mixture was stirred at 10-21° C. for 18 hours. TLC (PE:EA=1:3) showed most of the starting material was almost consumed and a new spot was detected. The mixture was acidified with HCl(M) to make PH=4-5 and diluted with water (20 ml). The mixture was extracted with EtOAc (30 mL×2), dried over Na₂SO₄, filtered and concentrated to give compound 104-H (180 mg, yield: 81%) as yellow oil, which was used for the next step without further purification.

Preparation of Compounds 104-Ent1 and 104-Ent2

To a solution of compound 104-H (180 mg, 0.58 mmol, 1.0 eq) in toluene (5 mL) was added DDQ (132 mg, 0.58 mmol, 1.0 eq) in one portion at 10-25° C. The mixture was stirred at 85° C. for 2 hours. TLC (PE:EA=1:2) showed most of the starting material was consumed and a new spot was detected. The mixture was concentrated to give the crude and diluted with EtOAc (30 ml). The mixture was washed saturated NaHCO₃ (30 ml×3), dried over Na₂SO₄, filtered and concentrated to give the crude, which was purified by pre-TLC (EtOAc/PE=1:1) to give 80 mg, (yield: 45%) of a racemate. The racemic mixture was further separated by SFC (column: AD (250 mm*30 mm, 10 um) condition: Neu-IPA) to give 104-Ent1 (19425-126-1, 9 mg, yield: 11.5%, Rt=4.787 min) and 104-Ent2 (19425-126-2, 10 mg, yield: 12.5%, Rt=5.240 min), both as pale white solids.

Spectra of 104-Ent1

¹H NMR (400 MHz, CHLOROFORM-d) δ: 8.52 (s, 1H), 7.28-7.38 (m, 3H), 7.22 (br d, J=6.6 Hz, 2H), 4.72 (d, J=14.4 Hz, 1H), 4.41 (d, J=14.8 Hz, 1H), 3.20-3.41 (m, 2H), 2.46 (qd, J=6.6, 12.8 Hz, 1H), 2.19 (dt, J=3.2, 12.6 Hz, 1H), 1.95-2.04 (m, 1H), 1.81-1.93 (m, 1H), 1.48 (s, 3H), 1.22 (d, J=6.6 Hz, 3H).

SFC: (ee: 95.1%)

HPLC: (Purity: 100%)

LCMS: (M+H=309.0)

Spectra of 104-Ent2

¹H NMR (400 MHz, METHANOL-d4) δ: 8.52 (s, 1H), 7.28-7.38 (m, 3H), 7.22 (br d, J=6.6 Hz, 2H), 4.72 (d, J=14.4 Hz, 1H), 4.41 (d, J=14.8 Hz, 1H), 3.20-3.41 (m, 2H), 2.46 (qd, J=6.6, 12.8 Hz, 1H), 2.19 (dt, J=3.2, 12.6 Hz, 1H), 1.95-2.04 (m, 1H), 1.81-1.93 (m, 1H), 1.48 (s, 3H), 1.22 (d, J=6.6 Hz, 3H).

SFC: (ee: 97.0%)

HPLC: (Purity: 100%)

LCMS: (M+H=309.0)

Example 88: Synthesis of 105-Ent1 and 105-Ent2

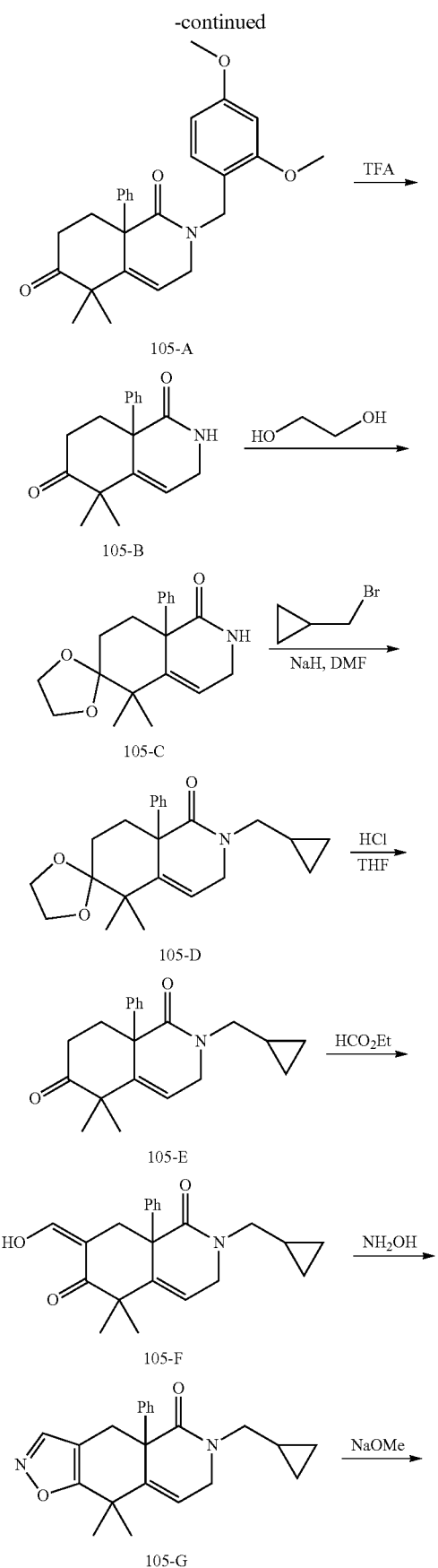

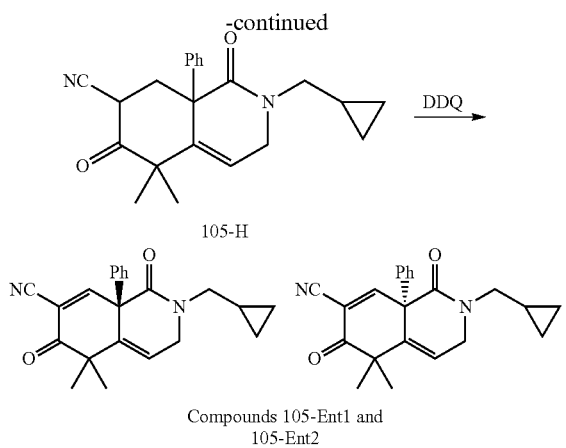

Compounds 105-Ent1 and 105-Ent2

Procedure for the Preparation of 105-A

MeI (5.9 g, 0.041 mol, 1.2 eq) was added to a mixture of Potassium tert-Butoxide (5.7 g, 0.051 mol, 1.5 eq) and compound 84-A (14.0 g, 0.04 mol, 1.0 eq) in 150 mL of THF by portionwise at 0° C., then the mixture was stirred at 20° C. for 14 hours. TLC (PE/EtOAc=3:1, Rf=0.5) showed compound 84-A was consumed completely and the desired product was observed. 50 mL of water was added and the mixture was extracted with EtOAc (200 mL). The organic layers was combined and washed with brine 100 mL, dried over anhydrous $Na_2SO_4$, filtered and concentrated. The residue was purified by column chromatography on silica gel (PE/EtOAc from 10/1 to 3:1) to give compound 105-A (6.0 g, 38.7% yield) as yellow solid.

$^1$HNMR: (400 MHz, $CDCl_3$) δ: 7.39 (d, Jd=7.2 Hz, 2H), 7.28-7.32 (m, 2H), 7.24-7.26 (m, 1H), 6.69 (d, J=8.0 Hz, 2H), 6.28 (s, 1H), 6.26 (d, J=6.0 Hz, 1H), 6.25-6.17 (m, 1H), 4.72 (d, J=14.8 Hz, 1H), 4.38 (d, J=15.2 Hz, 1H), 3.67 (s, 3H), 3.65-3.66 (m, 2H), 3.60 (s, 3H), 3.02-3.04 (m, 1H), 2.73-2.74 (m, 1H), 2.37-2.43 (m, 2H), 1.37 (s, 3H), 1.23 (s, 3H).

Preparation of Compound 105-B

Compound 105-A (5.0 g, 11.9 mmol, 1.0 eq) was added to TFA 50 mL, which was stirred at 70° C. for 1 hour. LCMS showed compound 105-A was consumed completely. The mixture was concentrated to get a residue. The residue was purified by column chromatography on silica gel (PE/EtOAc from 10/1 to 1:1) to give compound 105-B (2.9 g, 90.3% yield) as yellow solid

LCMS: (M+H: 270.0).

$^1$HNMR: (400 MHz, $CDCl_3$) δ: 7.39-7.42 (m, 2H), 7.30-7.34 (m, 2H), 7.24-7.27 (m, 1H), 6.26 (t, J=3.6 Hz, 1H), 5.93 (s, 1H), 3.83-3.85 (m, 2H), 2.90-2.95 (m, 1H), 2.70-2.71 (m, 1H), 2.35-2.44 (m, 2H), 1.40 (s, 3H), 1.26 (s, 3H).

Preparation of Compound 105-C $BF_3.Et_2O$ (1.37 g, 9.65 mmol, 1.0 eq) was added to a solution of compound 105-B (2.6 g, 9.65 mmol, 1.0 eq) and ethane-1,2-diol (6.0 g, 96.5 mmol, 10.0 eq) in THF 40 mL at 0° C. The mixture was stirred at 20° C. for 14 hours. LCMS (19441-148-1A) showed compound 105-B was consumed completely. The mixture was concentrated to get a residue. The residue was poured into MTBE (20 mL) and filtered. The filter cake was dried to give compound 105-C (1.9 g, 63.3% yield) as a pale solid, which was confirmed by HNMR (19441-148-1C).

LCMS: (M+H: 314.0).

$^1$HNMR: (400 MHz, $CDCl_3$) δ: 7.43-7.45 (m, 2H), 7.30-7.34 (m, 2H), 7.23-7.24 (m, 1H), 6.01 (d, J=1.6 Hz, 1H), 5.78 (s, 1H), 4.21-4.24 (m, 1H), 4.16-4.18 (m, 1H), 3.93-4.00 (m, 4H), 3.09-3.14 (m, 1H), 2.00-2.09 (m, 2H), 1.71-1.75 (m, 1H), 1.13 (s, 3H), 0.57 (s, 3H).

Preparation of Compound 105-D

To a solution of compound 105-C (500 mg, 1.60 mmol, 1.0 eq) in DMF 4 mL was added NaH (200 mg, 4.80 mmol, 3.0 eq) at 0° C. The mixture was stirred at 0° C. for 1 hour. (bromomethyl)cyclopropane (430 mg, 3.20 mmol, 2.0 eq) was added to the mixture. The resulting mixture was stirred at 20° C. for 14 hours. LCMS (19165-4-1A) showed compound 105-C was consumed completely. The mixture was poured into water 50 mL and filtered. The filter cake was dried to get compound 105-D (300 mg, 51.4% in yield) as yellow solid.

LCMS: (M+H: 368.1).

$^1$HNMR: (400 MHz, $CDCl_3$) δ: 7.39-7.44 (m, 2H), 7.28-7.32 (m, 2H), 7.20-7.22 (m, 1H), 5.97-6.01 (m, 1H), 4.26-4.32 (m, 1H), 4.12-4.14 (m, 1H), 3.96-3.99 (m, 4H), 3.33-3.35 (m, 1H), 3.13-3.15 (m, 1H), 3.02-3.07 (m, 1H), 2.00-2.03 (m, 2H), 1.25-1.29 (m, 1H), 1.11 (s, 3H), 0.78-0.80 (m, 1H), 0.56 (s, 3H), 0.41-0.43 (m, 2H), 0.20-0.21 (m, 1H), 0.06-0.08 (m, 1H).

Preparation of Compound 105-E

To a solution of compound 105-D (300 mg, 0.82 mmol, 1.0 eq) in THF 5 mL was added HCl (1 mL, 12M). The mixture was stirred at 20° C. for 14 hours. LCMS (19165-7-1A) showed compound 105-D was consumed completely. The mixture was poured into water 20 mL, and adjusted to pH=8 with Sat. $NaHCO_3$. The mixture was extracted with EtOAc (40 mL), washed with brine 20 mL. The organic layer was dried over anhydrous $Na_2SO_4$, filtered, and the filtrate was concentrated to get compound 105-E (250 mg, 94.7% yield) as yellow oil, which was confirmed by HNMR.

LCMS: (M+H: 324.0).

$^1$HNMR: (400 MHz, $CDCl_3$) δ: 7.39-7.41 (m, 2H), 7.29-7.33 (m, 2H), 7.23-7.26 (m, 1H), 6.21-6.25 (m, 1H), 3.85-3.88 (m, 1H), 3.39-3.45 (m, 1H), 3.00-3.01 (m, 1H), 2.94-2.98 (m, 1H), 2.68-2.72 (m, 1H), 2.35-2.46 (m, 2H), 1.87-1.93 (m, 2H), 1.71-1.77 (m, 2H), 1.40 (s, 3H), 1.28 (s, 3H), 0.78-0.82 (m, 1H), 0.34-0.44 (m, 2H), 0.16-0.18 (m, 1H), 0.07-0.08 (m, 1H).

Preparation of Compound 105-F

To a solution of compound 105-E (250 mg, 0.78 mmol, 1.0 eq) in $HCO_2Et$ 5 mL was added NaOMe (0.4 mL, 5.4M in MeOH) at 20° C. The mixture was stirred at 20° C. for 14 hours. LCMS (19165-10-1A) showed compound 105-E was consumed completely. The mixture was poured into water 20 mL, and adjusted to pH=5 with 1N HCl. The mixture was extracted with EtOAc (40 mL), washed with brine 20 mL. The organic layer was dried over anhydrous $Na_2SO_4$, filtered, and the filtrate was concentrated to get compound 105-F (250 mg, 92.3% yield) as yellow solid, which was used to next step directly.

LCMS: (M+H: 352.1).

Preparation of Compound 105-G

To a solution of compound 105-F (250 mg, 0.71 mmol, 1.0 eq) in 5 mL of $EtOH/H2O$ (V:V=5:1) was added hydrochloride hydroxylamine (74 mg, 1.07 mmol, 1.5 eq). The resulting mixture was stirred at 50° C. for 14 hours. LCMS (19165-16-1A) showed compound 105-F was consumed completely. The mixture was concentrated, and the residue was purified by pre-HPLC (Mobile phase A: water (10 mM NH4HCO3)-ACN, Mobile phase B: acetonitrile; Column: Xtimate C18 150*25 mm*5 um, Detection wavelength: 220 nm) to get compound 105-G (100 mg, 40.3% yield) as white solid, which was confirmed by HNMR (19165-16-1C).

LCMS: (M+H: 349.1).

¹HNMR: (400 MHz, CDCl₃) δ: 8.20 (d, J=2.4 Hz, 1H), 7.14-7.21 (m, 5H), 6.08-6.13 (m, 1H), 4.38-4.23 (m, 1H), 4.17-4.22 (m, 1H), 3.87-3.91 (m, 1H), 3.53-3.56 (m, 1H), 3.19-3.22 (m, 1H), 2.81-2.85 (m, 1H), 1.52 (s, 3H), 1.00-1.01 (m, 1H), 0.88 (s, 3H), 0.48-0.50 (m, 2H), 0.20-0.29 (m, 2H).

Preparation of Compound 105-H

To a solution of compound 105-G (100 mg, 0.29 mmol, 1.0 eq) in MeOH 2 mL was added NaOMe/MeOH (0.2 mL, 3.0 eq, 0.86 mmol, 5.4M). The resulting mixture was stirred at 20° C. for 14 hours. LCMS (19165-25-1A) showed compound 15-G was consumed completely. The mixture was adjusted to pH=5 with 1N HCl, and extracted with EtOAc (20 mL). The organic layer was washed with brine (20 mL), dried over anhydrous Na₂SO₄, filtered, and the filtrate was concentrated to get compound 105-H (90 mg, 90.0% yield) as a yellow solid, which was used to next step directly.

LCMS: (M+H: 349.1).

Preparation of 105-Ent1 and 105-Ent2

To a solution of compound 15-H (90 mg, 0.26 mmol, 1.0 eq) in toluene 2 mL was added DDQ (88 mg, 0.39 mmol, 1.5 eq). The mixture was stirred at 110° C. for 1 hour. TLC (PE/EtOAc=2/1, Rf=0.5) showed compound 9 was consumed completely. The mixture was concentrated to get a residue, and the residue was purified by pre-TLC PE/EtOAc=2/1 to get a racemic compound, which was further purified by SFC (column: AD (250 mm*30 mm, 10 um), condition: Neu-MeOH) to give 105-Ent1 (17 mg, 38.0% in yield) and 105-Ent2 (17 mg, 38.0% in yield) as a white solids.

Spectra for 105-Ent1

¹HNMR: (400 MHz, CDCl₃) δ: 8.83 (s, 1H), 7.31-7.39 (m, 5H), 6.20-6.22 (m, 1H), 4.25-4.30 (m, 1H), 4.03-4.09 (m, 1H), 3.35-3.38 (m, 1H), 3.13-3.18 (m, 1H), 1.45 (s, 3H), 0.88-0.89 (m, 4H), 0.44-0.52 (m, 2H), 0.22-0.24 (m, 1H), 0.10-0.13 (m, 1H).

HPLC: (Purity: 98.48%)

SFC: (Column: ChiralPak AD-3 150×4.6 mm I.D., 3 um Mobile phase: A: CO₂ B: ethanol (0.05% DEA) Gradient: from 5% to 40% of B in 5 min and hold 40% for 2.5 min, then 5% of B for 2.5 min Flow rate: 2.5 mL/min Column temp.: 40° C. (ee: 99.6%)

LCMS: (M+H: 347.1).

Spectra for 105-Ent2

¹HNMR: (400 MHz, CDCl₃) δ: 8.82 (s, 1H), 7.31-7.39 (m, 5H), 6.20-6.22 (m, 1H), 4.25-4.30 (m, 1H), 4.03-4.09 (m, 1H), 3.36-3.41 (m, 1H), 3.13-3.18 (m, 1H), 1.45 (s, 3H), 0.88-0.89 (m, 4H), 0.43-0.51 (m, 2H), 0.22-0.24 (m, 1H), 0.11-0.13 (m, 1H).

HPLC: (Purity: 100%).

SFC: (Column: ChiraPak AD-3 150×4.6 mm I.D., 3 um Mobile phase: A: CO₂ B: ethanol (0.05% DEA) Gradient: from 5% to 40% of B in 5 min and hold 40% for 2.5 min, then 5% of B for 2.5 min Flow rate: 2.5 mL/min Column temp.: 40° C. (ee: 100%).

LCMS: (M+H: 347.0).

Example 89: Synthesis of Compounds 106-Ent1 and 106-Ent2

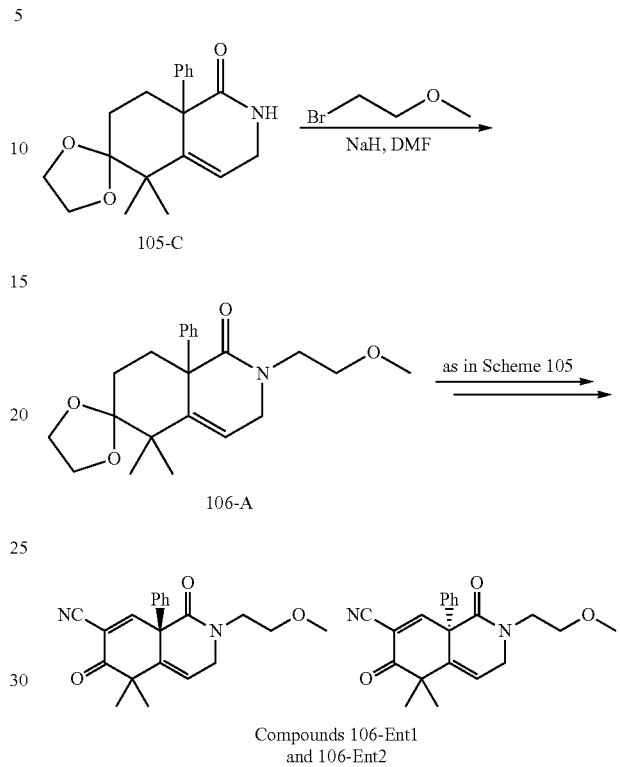

Compounds 106-Ent1 and 106-Ent2 can be made in a manner analogous to that described for 105-Ent1 and 105-Ent2.

Procedure for the Synthesis of Compound 106-A:

To a solution of compound 105-C (400 mg, 1.28 mmol, 1.0 eq) in DMF 4 mL was added NaH (102 mg, 2.56 mmol, 2.0 eq) at 0° C. The mixture was stirred at 0° C. for 1 hour. 1-bromo-2-methoxyethane (355 mg, 2.56 mmol, 2.0 eq) was added to the mixture. The resulting mixture was stirred at 20° C. for 14 hours. LCMS showed compound 105-C was consumed completely. The mixture was poured into water 50 mL, and filtered. The cake was dried to get compound 106-A (300 mg, 69.3% in yield) as yellow solid.

LCMS: (M+H: 372.1).

¹HNMR: (400 MHz, CDCl₃) δ: 7.41-7.43 (m, 2H), 7.28-7.33 (m, 2H), 7.20-7.23 (m, 1H), 5.95-5.96 (m, 1H), 4.33-4.38 (m, 1H), 4.14-4.16 (m, 1H), 3.93-3.99 (m, 4H), 3.64-3.69 (m, 1H), 3.43-3.47 (m, 1H), 3.33-3.37 (m, 1H), 3.23-3.28 (m, 1H), 3.22 (s, 3H), 3.11-3.15 (m, 1H), 2.00-2.05 (m, 2H), 1.71-1.74 (m, 1H), 1.11 (s, 3H), 0.55 (s, 3H).

Procedure for the Purification and Chiral Separation of Compounds 106-Ent1 and 106-Ent2:

The crude DDQ oxidation mixture was concentrated to get a residue, and the residue was purified by prep-TLC PE/EtOAc=2/1 to get a racemic compound, which was further purified by SFC (column: AD (250 mm*30 mm, 10 um), condition: Neu-MeOH) to give 106-Ent1 (10 mg, 18.3% in yield) and 106-Ent2 (10 mg, 18.3% in yield) as a white solid.

Spectra for 106-Ent1

¹HNMR: (400 MHz, CDCl₃) δ: 8.80 (s, 1H), 7.31-7.38 (m, 5H), 6.15-6.16 (m, 1H), 4.33-4.38 (m, 1H), 4.14-4.15 (m, 1H), 3.64-3.66 (m, 1H), 3.49-3.50 (s, 1H), 3.37-3.40 (m, 2H), 3.22 (s, 3H), 1.44 (s, 3H), 0.86 (s, 3H).

HPLC: (Purity: 99.12%)

SFC: (Column: ChiralPak AD-3 150×4.6 mm I.D., 3 um Mobile phase: A: CO₂ B: ethanol (0.05% DEA) Gradient: from 5% to 40% of B in 5 min and hold 40% for 2.5 min, then 5% of B for 2.5 min Flow rate: 2.5 mL/min Column temp.: 40° C. (ee: 99.48%)

LCMS: (M+H: 351.1).

Spectra for 106-Ent2

¹HNMR: (400 MHz, CDCl₃) δ: 8.79 (s, 1H), 7.31-7.38 (m, 5H), 6.15-6.16 (m, 1H), 4.33-4.37 (m, 1H), 4.14-4.15 (m, 1H), 3.64-3.66 (m, 1H), 3.49-3.51 (s, 1H), 3.36-3.40 (m, 2H), 3.22 (s, 3H), 1.44 (s, 3H), 0.86 (s, 3H).

HPLC: (Purity: 100%).

SFC: (Column: ChiraPak AD-3 150×4.6 mm I.D., 3 um Mobile phase: A: CO₂ B: ethanol (0.05% DEA) Gradient: from 5% to 40% of B in 5 min and hold 40% for 2.5 min, then 5% of B for 2.5 min Flow rate: 2.5 mL/min Column temp.: 40° C. (ee: 100%).

LCMS: (M+H: 351.0).

Example 90: Synthesis of Compounds 107-Ent1 and 107-Ent2

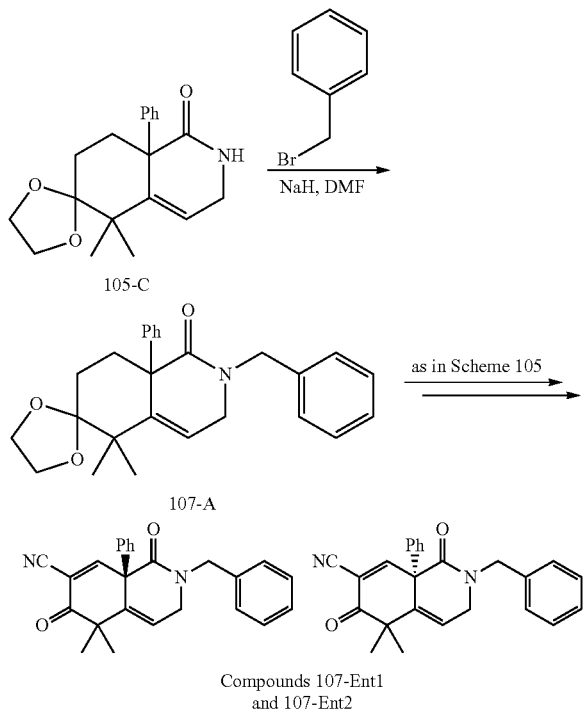

Compounds 107-Ent1 and 107-Ent2 can be made in a manner analogous to that described for 105-Ent1 and 105-Ent2.

Procedure for the Synthesis of Compound 107-A:

To a solution of compound 105-C (300 mg, 0.96 mmol, 1.0 eq) in DMF 10 mL was added NaH (115 mg, 2.88 mmol, 3.0 eq) at 0° C. The mixture was stirred at 0° C. for 1 hour. (bromomethyl)benzene (328 mg, 1.92 mmol, 2.0 eq) was added to the mixture. The resulting mixture was stirred at 20° C. for 14 hours. LCMS showed compound 105-A was consumed completely. The mixture was poured into water 50 mL, and filtered. The cake was dried to get compound 107-A (320 mg, 82.9% in yield) as yellow solid, which was used to next step directly.

LCMS: (M+H: 404.1).

Procedure for the purification and chiral separation of compounds 107-Ent1 and 107-Ent2:

The DDQ oxidation mixture was concentrated to get a residue, and the residue was purified by prep-TLC PE/EtOAc=2/1 to get a racemic compound, which was further purified by SFC (column: AD (250 mm*30 mm, 10 um), condition: Neu-MeOH) to give 107-Ent1 (23 mg, 42.0% in yield) and 107-Ent2 (24 mg, 43.9% in yield) as white solids.

Spectra for 107-Ent1

¹HNMR: (400 MHz, CDCl₃) δ: 8.89 (s, 1H), 7.34-7.39 (m, 5H), 7.25-7.27 (m, 3H), 7.01-7.02 (m, 2H), 6.13-6.14 (m, 1H), 4.73 (d, J=14.4 Hz, 1H), 4.40 (d, J=14.4 Hz, 1H), 3.97-4.03 (m, 1H), 3.83-3.87 (m, 1H), 1.42 (s, 3H), 0.88 (s, 3H).

HPLC: (Purity: 99.29%).

SFC: (Column: ChiralCel OJ-H 150×4.6 mm I.D., 3 um Mobile phase: A: CO₂ B: ethanol (0.05% DEA) Gradient: from 5% to 40% of B in 5 min and hold 40% for 2.5 min, then 5% of B for 2.5 min Flow rate: 2.5 mL/min Column temp.: 40° C. (ee: 100%)

LCMS: (M+H: 383.0).

Spectra for 107-Ent2 ¹HNMR: (400 MHz, CDCl₃) δ: 8.89 (s, 1H), 7.35-7.39 (m, 5H), 7.25-7.27 (m, 3H), 7.01-7.02 (m, 2H), 6.13-6.14 (m, 1H), 4.73 (d, J=14.4 Hz, 1H), 4.40 (d, J=14.4 Hz, 1H), 3.98-4.03 (m, 1H), 3.83-3.87 (m, 1H), 1.42 (s, 3H), 0.88 (s, 3H).

HPLC: (Purity: 100%).

SFC: (Column: ChiraCel OJ-H 150×4.6 mm I.D., 3 um Mobile phase: A: CO₂ B: ethanol (0.05% DEA) Gradient: from 5% to 40% of B in 5 min and hold 40% for 2.5 min, then 5% of B for 2.5 min Flow rate: 2.5 mL/min Column temp.: 40° C. (ee: 99.10%).

LCMS: (M+H: 383.0).

Example 91: Synthesis of Compounds 108-Ent1 and 108-Ent2

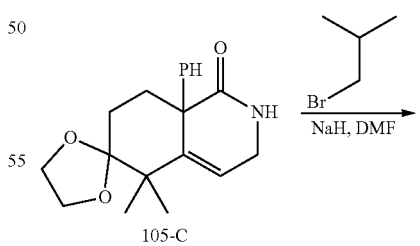

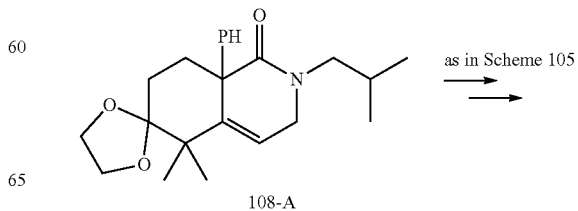

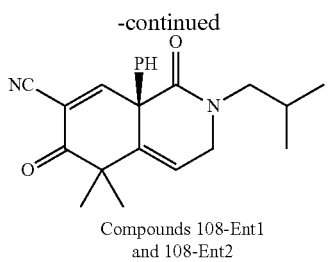

Compounds 108-Ent1 and 108-Ent2

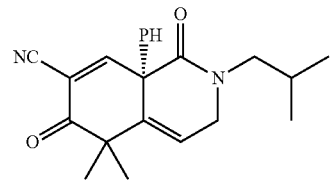

Compounds 108-Ent1 and 108-Ent2 can be made in a manner analogous to that described for 105-Ent1 and 105-Ent2. The alternative DBMDH oxidation procedure described in Scheme 98 was used in the final step.

Procedure for the Synthesis of Compound 108-A:

To a solution of compound 105-C (400 mg, 1.28 mmol, 1 eq.) in 10 mL of DMF was added NaH (102 mg, 2.55 mmol, 2.0 eq) under ice-bath (0-5° C.), then the mixture was stirred at 0-5° C. ° C. for 1 h. Subsequently, 1-Bromo-2-methyl-propane (349 mg, 2.55 mmol, 2.0 eq) was added and the resulting mixture was stirred at 20° C. for 18 h. TLC (PE:EA=1:1) showed one new spot was observed. The mixture was poured into 60 mL of ice-water and 10 mL of brine, extracted with EtOAc (30 mL×3). The combined organic layers were washed with brine (30 mL), dried over anhydrous $Na_2SO_4$, filtered and concentrated. The residue was purified by flash column (PE:EtOAc=90:10-80:20-60:40) to supply compound 108-A (400 mg, 84.7% yield) as white solid.

$^1$HNMR: (400 MHz, $CDCl_3$) δ: 7.40-7.45 (m, 2H), 7.30 (m, 2H), 7.17-7.22 (m, 1H), 5.99 (dd, J=2.14, 4.58 Hz, 1H), 4.21 (dd, J=2.08, 17.85 Hz, 1H), 3.89-4.01 (m, 5H), 3.54 (m, 1H), 3.11-3.19 (m, 1H), 2.71 (m, 1H), 1.85-2.03 (m, 3H), 1.68-1.74 (m, 1H), 1.12 (s, 3H), 0.82 (d, J=6.72 Hz, 3H), 0.63 (d, J=6.60 Hz, 3H), 0.58 (s, 3H).

Procedure for the Purification and Chiral Separation of Compounds 108-Ent1 and 108-Ent2:

Upon reaction completion, the DBMDH reaction mixture was diluted with water (30 mL), extracted with EtOAc (20 mL×3). The combined organic layers were washed with brine (20 mL), dried over anhydrous $Na_2SO_4$, filtered, concentrated and purified by prep-TLC (PE:EtOAc=2:1) to supply racemate (~45 mg) which was separated by SFC (condition: Neu-EtOH, column: AD 250 mm*30 mm; 10 um) to supply 108-Ent1 (9 mg, 12.8% yield, Rt=3.152 min) as white solid and 108-Ent2 (8 mg, 11.4% yield, Rt=4.179 min) as white solid Spectra of 108-Ent1:

$^1$HNMR: (400 MHz, $CDCl_3$) δ: 8.82 (s, 1H), 7.29-7.39 (m, 4H), 6.22 (dd, J=1.83, 5.38 Hz, 1H), 4.14 (dd, J=1.96, 18.22 Hz, 1H), 3.87 (dd, J=5.50, 18.22 Hz, 1H), 3.48 (dd, J=8.62, 13.39 Hz, 1H), 2.88 (dd, J=6.66, 13.39 Hz, 1H), 1.84-1.97 (m, 1H), 1.46 (s, 3H), 0.93 (s, 3H), 0.81 (d, J=6.72 Hz, 3H), 0.63 (d, J=6.60 Hz, 3H)

HPLC: (purity: 97.57%)
SFC: (purity: 100%)
LCMS: (M+H: 349.1)

Spectra of 108-Ent2:

$^1$HNMR: (400 MHz, $CDCl_3$) δ: 8.82 (s, 1H), 7.29-7.39 (m, 4H), 6.22 (dd, J=1.83, 5.38 Hz, 1H), 4.14 (dd, J=1.96, 18.22 Hz, 1H), 3.87 (dd, J=5.50, 18.22 Hz, 1H), 3.48 (dd, J=8.56, 13.45 Hz, 1H), 2.88 (dd, J=6.60, 13.45 Hz, 1H), 1.85-1.96 (m, 1H), 1.46 (s, 3H), 0.91-0.94 (m, 3H), 0.81 (d, J=6.72 Hz, 3H), 0.63 (d, J=6.60 Hz, 3H)

HPLC: (Purity: 98.05%)
SFC: (purity: 99.894%)
LCMS: (M+H: 349.1)

Example 92: Synthesis of Compounds 109-Ent1 and 109-Ent2

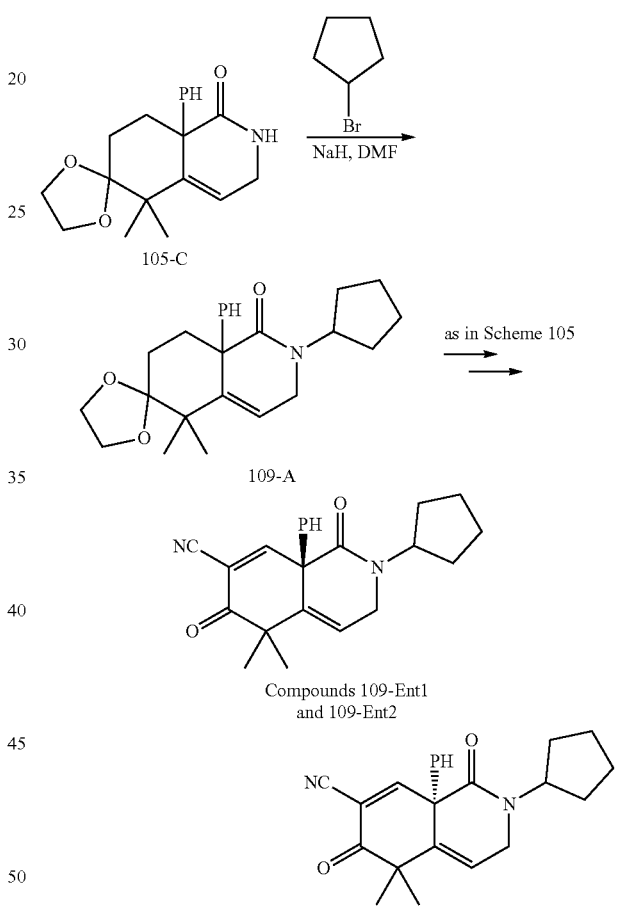

Compounds 109-Ent1 and 109-Ent2

Compounds 109-Ent1 and 109-Ent2 can be made in a manner analogous to that described for 105-Ent1 and 105-Ent2. The alternative DBMDH oxidation procedure described in Scheme 98 was used in the final step.

Procedure for the Synthesis of Compound 109-A:

To a solution of compound 105-C (400 mg, 1.28 mmol, 1.0 eq) in DMF 10 mL was added NaH (102 mg, 2.56 mmol, 2.0 eq) at 0° C. The mixture was stirred at 0° C. for 1 hour. bromocyclopentane (286 mg, 1.92 mmol, 2.0 eq) was added to the mixture. The resulting mixture was stirred at 20° C. for 14 hours. LCMS showed compound 105-C was consumed completely. The mixture was poured into water 20 mL, and filtered. The cake was purified by silica gel PE/EtOAc from 10/1 to 3/1 to get compound 5 (170 mg, 50.0% in yield) as yellow solid, which was used to next step directly.

LCMS: (M+H: 382.2).

Procedure for the Purification and Chiral Separation of Compounds 109-Ent1 and 109-Ent2:

Upon completion, the DBMDH reaction mixture was concentrated to get a residue, which was purified by pre-HPLC (Mobile phase A: water(0.05% HCl)-ACN, Mobile phase B: acetonitrile; Column: YMC-Actus Triart C18 100*30 mm*5 um, Detection wavelength: 220 nm) to get a racemic compound, which was further purified by SFC (column: AD (250 mm*30 mm, 10 um), condition: Neu-MeOH) to 109-Ent1 (15 mg, 43.1% in yield) as a white solid and 109-Ent2 (15 mg, 43.1% in yield) as a white solid.

Spectra for 109-Ent1

$^1$HNMR: (400 MHz, CDCl$_3$) δ: 8.82 (s, 1H), 7.31-7.37 (m, 5H), 6.22-6.24 (m, 1H), 4.65-4.73 (m, 1H), 3.85-4.01 (m, 2H), 1.86-1.87 (m, 1H), 1.61-1.70 (m, 5H), 1.45-1.48 (m, 5H), 0.90 (d, J=5.6 Hz, 3H).

HPLC: (Purity: 100%).

SFC: (Column: ChiralPak AD-3 150×4.6 mm I.D., 3 um Mobile phase: A: CO$_2$ B: ethanol (0.05% DEA) Gradient: from 5% to 40% of B in 5 min and hold 40% for 2.5 min, then 5% of B for 1.5 min Flow rate: 2.5 mL/min Column temp.: 40° C. (ee: 99.56%).

LCMS: (M+H: 361.1).

Spectra for 109-Ent2

$^1$HNMR: (400 MHz, CDCl$_3$) δ: 8.82 (s, 1H), 7.31-7.37 (m, 5H), 6.22-6.24 (m, 1H), 4.69-4.71 (m, 1H), 3.85-4.01 (m, 2H), 1.86-1.87 (m, 1H), 1.61-1.70 (m, 5H), 1.45-1.47 (m, 5H), 0.90 (d, J=5.6 Hz, 3H).

HPLC: (Purity: 100%).

SFC: (Column: ChiralPak AD-3 150×4.6 mm I.D., 3 um Mobile phase: A: CO$_2$ B: ethanol (0.05% DEA) Gradient: from 5% to 40% of B in 5 min and hold 40% for 2.5 min, then 5% of B for 1.5 min Flow rate: 2.5 mL/min Column temp.: 40° C. (ee: 99.10%).

LCMS: (M+H: 361.1).

Example 93: Synthesis of Compounds 110-Ent1 and 110-Ent2

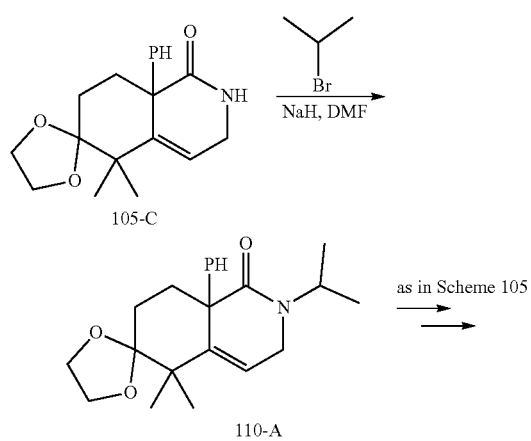

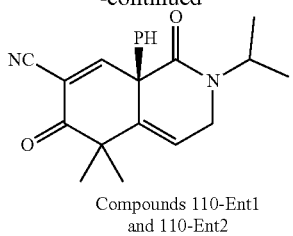

Compounds 110-Ent1 and 110-Ent2

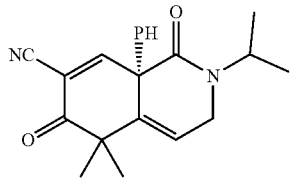

Compounds 110-Ent1 and 110-Ent2 can be made in a manner analogous to that described for 105-Ent1 and 105-Ent2. The alternative DBMDH oxidation procedure described in Scheme 98 was used in the final step.

Procedure for the Synthesis of Compound 110-A:

To a solution of compound 105-A (300 mg, 0.96 mmol, 1.0 eq) in DMF 10 mL was added NaH (76 mg, 1.91 mmol, 2.0 eq) at 0° C. The mixture was stirred at 0° C. for 1 hour. 2-bromopropane (235 mg, 1.91 mmol, 2.0 eq) was added to the mixture. The resulting mixture was stirred at 20° C. for 14 hours. LCMS showed compound 105-A was consumed completely. The mixture was poured into water 20 mL, and filtered. The cake was dried to get compound 110-A (170 mg, 50.0% in yield) as yellow solid.

LCMS: (M+H: 356.2).

$^1$HNMR: (400 MHz, CDCl$_3$) δ: 7.39-7.41 (m, 2H), 7.29-7.33 (m, 2H), 7.21-7.23 (m, 1H), 6.02-6.03 (m, 1H), 4.67-4.72 (m, 1H), 3.94-4.01 (m, 6H), 3.15-3.18 (m, 1H), 2.00-2.03 (m, 2H), 1.74-1.75 (m, 1H), 1.26-1.30 (m, 1H), 1.12-1.13 (m, 6H), 1.02 (d, J=6.8 Hz, 3H), 0.57 (s, 3H).

Procedure for the Purification and Chiral Separation of Compounds 110-Ent1 and 110-Ent2:

Upon completion, the DBMDH reaction mixture was concentrated to get a residue, which was purified by prep-HPLC (Mobile phase A: water(0.05% HCl)-ACN, Mobile phase B: acetonitrile; Column: YMC-Actus Triart C18 100*30 mm*5 um, Detection wavelength: 220 nm) to get a racemic compound, which was further purified by SFC (column: AD (250 mm*30 mm, 10 um), condition: Neu-MeOH) to 110-Ent1 (15 mg, 43.1% in yield) as a white solid and 110-Ent2 (15 mg, 43.1% in yield) as a white solid.

Spectra 110-Ent1

$^1$HNMR: (400 MHz, CDCl$_3$) δ: 8.82 (s, 1H), 7.29-7.39 (m, 5H), 6.22-6.26 (m, 1H), 4.63-4.70 (m, 1H), 3.91-3.93 (m, 2H), 1.45 (s, 3H), 1.14 (d, J=6.8 Hz, 3H), 1.04 (d, J=7.2 Hz, 3H), 0.89 (s, 3H).

HPLC: (Purity: 99.36%).

SFC: (Column: ChiralPak AD-3 150×4.6 mm I.D., 3 um Mobile phase: A: CO$_2$ B: ethanol (0.05% DEA) Gradient: from 5% to 40% of B in 5 min and hold 40% for 2.5 min, then 5% of B for 1.5 min Flow rate: 2.5 mL/min Column temp.: 40° C. (ee: 99.76%).

LCMS: (M+H: 335.1).

Spectra for 110-Ent2

$^1$HNMR: (400 MHz, CDCl$_3$) δ: 8.82 (s, 1H), 7.29-7.39 (m, 5H), 6.22-6.24 (m, 1H), 4.63-4.70 (m, 1H), 3.86-3.97

(m, 2H), 1.45 (s, 3H), 1.14 (d, J=6.8 Hz, 3H), 1.04 (d, J=7.2 Hz, 3H), 0.89 (s, 3H).

HPLC: (Purity: 100%).

SFC: (Column: ChiralPak AD-3 150×4.6 mm I.D., 3 um Mobile phase: A: $CO_2$ B: ethanol (0.05% DEA) Gradient: from 5% to 40% of B in 5 min and hold 40% for 2.5 min, then 5% of B for 1.5 min Flow rate: 2.5 mL/min Column temp.: 40° C. (ee: 99.67%).

LCMS: (M+H: 335.1).

Example 94: Synthesis of Compounds 111-Ent1 and 111-Ent2

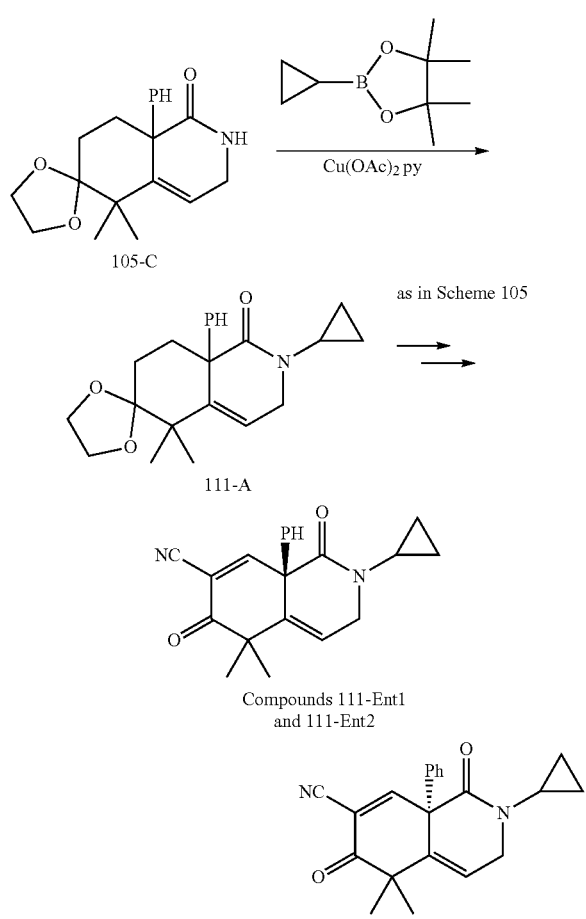

Compounds 111-Ent1 and 111-Ent2 can be made in a manner analogous to that described for 105-Ent1 and 105-Ent2. The alternative DBMDH oxidation procedure described in Scheme 98 was used in the final step.

Procedure for the Synthesis of Compound 111-A:

A mixture of compound 105-C (400 mg, 1.28 mmol, 1.0 eq), 2-cyclopropyl-4,4,5,5-tetramethyl-1,3,2-dioxaborolane (429 mg, 2.56 mmol, 2.0 eq), $Cs_2CO_3$ (208 mg, 0.64 mmol, 0.5 eq), pyridine (303 mg, 3.84 mmol, 3.0 eq) and $Cu(OAc)_2$ (231 mg, 1.28 mmol, 1.0 eq) in toluene 2 mL. The mixture was stirred at 110° C. for 14 hours. The mixture was concentrated to get a residue, which was purified by prep-HPLC (Mobile phase A: water (10 mM $NH_4HCO_3$)-ACN, Mobile phase B: acetonitrile; Column: Xtimate C18 150*25 mm*5 um, Detection wavelength: 220 nm) to get compound 111-A (250 mg, 55.4% in yield) as white solid.

LCMS: (M+H: 354.1).

$^1$HNMR: (400 MHz, $CDCl_3$) δ: 7.37-7.39 (m, 2H), 7.28-7.32 (m, 2H), 7.20-7.22 (m, 1H), 5.97-5.99 (m, 1H), 4.05-4.08 (m, 1H), 3.96-4.00 (m, 5H), 3.11-3.14 (m, 1H), 2.60-2.63 (m, 1H), 1.99-2.05 (m, 2H), 1.73-1.75 (m, 1H), 1.13 (s, 3H), 0.70-0.73 (m, 2H), 0.58-0.60 (m, 1H), 0.56 (s, 3H), 0.34-0.36 (m, 1H).

Procedure for the Purification and Chiral Separation of Compounds 111-Ent1 and 111-Ent2:

Upon completion, the DBMDH reaction mixture was concentrated to get a residue, which was purified by pre-HPLC (Mobile phase A: water(0.05% HCl)-ACN, Mobile phase B: acetonitrile; Column: YMC-Actus Triart C18 100*30 mm*5 um, Detection wavelength: 220 nm) to get a racemic compound, which was further purified by SFC (column: AD (250 mm*30 mm, 10 um), condition: Neu-MeOH) to 111-Ent1 (15 mg, 30.1% in yield) as a white solid and 111-Ent2 (15 mg, 30.1% in yield) as a white solid.

Spectra for 111-Ent1

$^1$HNMR: (400 MHz, $CDCl_3$) δ: 8.79 (s, 1H), 7.27-7.36 (m, 5H), 6.17-6.19 (m, 1H), 4.03-4.09 (m, 1H), 3.91-3.96 (m, 1H), 2.65-2.71 (m, 1H), 1.44 (s, 3H), 0.88 (s, 3H), 0.79-0.84 (m, 2H), 0.62-0.63 (m, 1H), 0.37-0.38 (m, 1H).

HPLC: (Purity: 99.29%).

SFC: (Column: ChiralPak AD-3 150×4.6 mm I.D., 3 um Mobile phase: A: $CO_2$ B: ethanol (0.05% DEA) Gradient: from 5% to 40% of B in 5 min and hold 40% for 2.5 min, then 5% of B for 1.5 min Flow rate: 2.5 mL/min Column temp.: 40° C. (ee: 99.26%).

LCMS: (M+H: 333.1).

Spectra for 111-Ent2

$^1$HNMR: (400 MHz, $CDCl_3$) δ: 8.78 (s, 1H), 7.27-7.36 (m, 5H), 6.17-6.19 (m, 1H), 4.03-4.08 (m, 1H), 3.91-3.96 (m, 1H), 2.65-2.71 (m, 1H), 1.44 (s, 3H), 0.88 (s, 3H), 0.78-0.82 (m, 2H), 0.62-0.63 (m, 1H), 0.37-0.38 (m, 1H).

HPLC: (Purity: 99.34%).

SFC: (Column: ChiralPak AD-3 150×4.6 mm I.D., 3 um Mobile phase: A: $CO_2$ B: ethanol (0.05% DEA) Gradient: from 5% to 40% of B in 5 min and hold 40% for 2.5 min, then 5% of B for 1.5 min Flow rate: 2.5 mL/min Column temp.: 40° C. (ee: 99.17%).

LCMS: (M+H: 333.0).

Example 95: Synthesis of Compounds 112-Ent1 and 112-Ent2

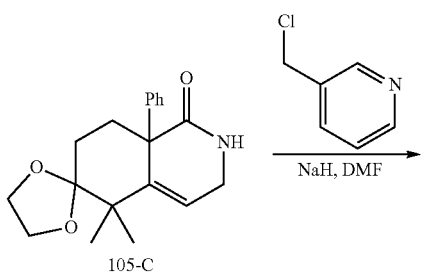

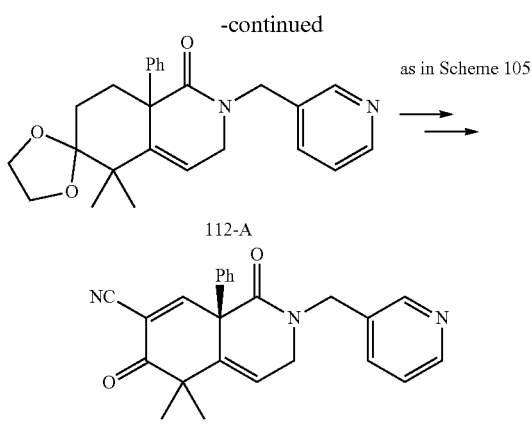

Compounds 112-Ent1 and 112-Ent2

Compounds 112-Ent1 and 112-Ent2 can be made in a manner analogous to that described for 105-Ent1 and 105-Ent2. The alternative DBMDH oxidation procedure described in Scheme 98 was used in the final step.

Procedure for the Synthesis of Compound 112-A:

To a solution of compound 105-C (300 mg, 0.96 mmol, 1.0 eq) in DMF 6 mL was added NaH (77 mg, 1.92 mmol, 2.0 eq) at 0° C. The mixture was stirred at 0° C. for 1 hour. Subsequently, 3-(chloromethyl) pyridine (182 mg, 1.44 mmol, 1.5 eq) was added to the mixture. The resulting mixture was stirred at 20° C. for 14 hours. LCMS showed compound 105-C was consumed completely. The mixture was poured into water 30 mL, and filtered. The cake was dried to get compound 112-A (350 mg, 90.4% in yield) as a yellow solid.

LCMS: (M+H: 405.2).

$^1$HNMR: (400 MHz, CDCl$_3$) δ: 8.47-8.48 (m, 1H), 8.37 (d, J=2.0 Hz, 1H), 7.39-7.41 (m, 2H), 7.30-7.34 (m, 3H), 7.12-7.14 (m, 1H), 5.93-5.94 (m, 1H), 4.79 (d, J=14.8 Hz, 1H), 4.23 (d, J=14.8 Hz, 1H), 3.89-4.03 (m, 6H), 3.17-3.23 (m, 1H), 2.00-2.01 (m, 1H), 1.72-1.75 (m, 1H), 1.09 (s, 3H), 0.83-0.88 (m, 2H), 0.56 (s, 3H).

Procedure for the Purification and Chiral Separation of Compounds 112-Ent1 and 112-Ent2:

Upon completion, the DBMDH reaction mixture was concentrated to get a residue, which was purified by pre-HPLC (Mobile phase A: water(0.05% HCl)-ACN, Mobile phase B: acetonitrile; Column: Phenomenex Synergi C18 150*30 mm*4 um, Detection wavelength: 220 nm) to get a racemic compound, which was further purified by SFC (column: AD (250 mm*30 mm, 10 um), condition: Neu-MeOH) to 112-Ent1 (12 mg, 30.0% in yield) as a yellow solid and 112-Ent2 (12 mg, 30.0% in yield) as a yellow solid.

Spectra for 112-Ent1

$^1$HNMR: (400 MHz, CDCl$_3$) δ: 8.84 (s, 1H), 8.52 (d, J=3.6 Hz, 1H), 8.36 (s, 1H), 7.32-7.39 (m, 6H), 7.18-7.19 (m, 1H), 6.15-6.17 (m, 1H), 4.74 (d, J=14.8 Hz, 1H), 4.40 (d, J=14.8 Hz, 1H), 4.03-4.08 (m, 1H), 3.86-3.90 (m, 1H), 1.43 (s, 3H), 0.89 (s, 3H).

HPLC: (Purity: 100%).

SFC: (Column: ChiralPak IC 100×4.6 mm I.D., 3 um Mobile phase: A: CO$_2$ B: Methanol (0.1% ethanolamine) Flow rate: 3 mL/min Column temp.: 40° C. (ee: 100%).

LCMS: (M+H: 384.1).

Spectra for 112-Ent2

$^1$HNMR: (400 MHz, CDCl$_3$) δ: 8.84 (s, 1H), 8.52 (d, J=3.6 Hz, 1H), 8.36 (s, 1H), 7.32-7.39 (m, 6H), 7.18-7.19 (m, 1H), 6.15-6.17 (m, 1H), 4.74 (d, J=14.8 Hz, 1H), 4.40 (d, J=14.8 Hz, 1H), 4.03-4.08 (m, 1H), 3.86-3.91 (m, 1H), 1.43 (s, 3H), 0.89 (s, 3H).

HPLC: (Purity: 100%).

SFC: (Column: ChiralPak IC 100×4.6 mm I.D., 3 um Mobile phase: A: CO$_2$ B: Methanol (0.1% ethanolamine) Flow rate: 3 mL/min Column temp.: 40° C. (ee: 95.26%).

LCMS: (M+H: 384.1).

Example 96: Synthesis of Compounds 113-Ent1 and 113-Ent2

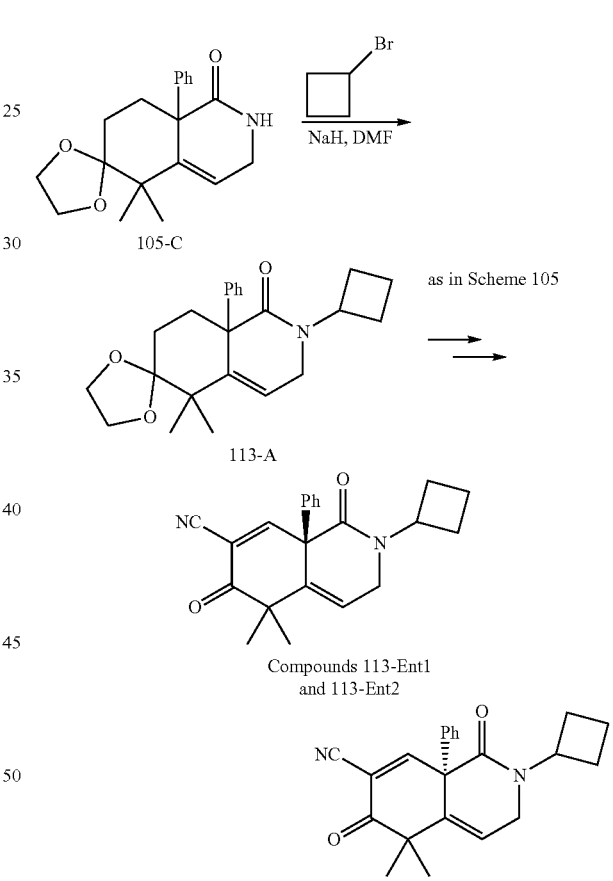

Compounds 113-Ent1 and 113-Ent2

Compounds 113-Ent1 and 113-Ent2 can be made in a manner analogous to that described for 105-Ent1 and 105-Ent2. The alternative DBMDH oxidation procedure described in Scheme 98 was used in the final step.

Procedure for the Synthesis of 113-A

To a solution of compound 105-C (500 mg, 1.60 mmol, 1.0 eq) in DMF 10 mL was added NaH (320 mg, 8.0 mmol, 5.0 eq) at 0° C. The mixture was stirred at 0° C. for 1 hour. Subsequently, bromocyclobutane (1.1 g, 8.0 mmol, 5.0 eq) was added to the mixture. The resulting mixture was stirred at 20° C. for 14 hours. TLC (PE/EtOAc=1/1, Rf=0.5) showed compound 105-C was consumed completely. The mixture was poured into water 20 mL, and filtered. The cake was purified by silica gel PE/EtOAc from 10/1 to 3/1 to get compound 113-A (150 mg, 25.6% yield) as yellow solid, which was used to next step directly.

$^1$HNMR: (400 MHz, CDCl$_3$) δ: 7.38-7.40 (m, 2H), 7.28-7.31 (m, 2H), 7.20-7.22 (m, 1H), 6.02-6.04 (m, 1H), 4.63-4.72 (m, 1H), 4.07-4.09 (m, 2H), 3.92-3.98 (m, 4H), 3.12-3.15 (m, 1H), 1.97-2.14 (m, 6H), 1.64-1.72 (m, 3H), 1.12 (s, 3H), 0.56 (s, 3H).

Procedure for the Purification and Chiral Separation of Compounds 113-Ent1 and 113-Ent2:

Upon completion, the DBMDH reaction mixture was concentrated to get a residue, which was purified by pre-HPLC (Mobile phase A: water(0.05% HCl)-ACN, Mobile phase B: acetonitrile; Column: YMC-Actus Triart C18 100*30 mm*5 um, Detection wavelength: 220 nm) to get a racemic compound, which was further purified by SFC (column: AD (250 mm*30 mm, 10 um), condition: Neu-MeOH) to 113-Ent1 (13 mg, 32.7% yield) as a white solid and 113-Ent2 (13 mg, 32.7% yield) as a white solid.

Spectra for 113-Ent1

$^1$HNMR: (400 MHz, CDCl$_3$) δ: 8.79 (s, 1H), 7.29-7.39 (m, 5H), 6.23-6.25 (m, 1H), 4.65-4.74 (m, 1H), 4.03-4.04 (m, 2H), 2.12-2.22 (m, 3H), 2.02-2.10 (m, 1H), 1.68-1.71 (m, 2H), 1.45 (s, 3H), 0.89 (s, 3H).

HPLC: (Purity: 100%).

SFC: (Column: ChiralPak AD-3 150×4.6 mm I.D., 3 um Mobile phase: A: CO$_2$ B: ethanol (0.05% DEA) Gradient: from 5% to 40% of B in 5 min and hold 40% for 2.5 min, then 5% of B for 1.5 min Flow rate: 2.5 mL/min Column temp.: 40° C. (ee: 100%).

LCMS: (M+H: 347.1).

Spectra for 113-Ent2

$^1$HNMR: (400 MHz, CDCl$_3$) δ: 8.79 (s, 1H), 7.31-7.39 (m, 5H), 6.23-6.25 (m, 1H), 4.65-4.74 (m, 1H), 4.03-4.04 (m, 2H), 2.12-2.15 (m, 3H), 2.02-2.10 (m, 1H), 1.68-1.71 (m, 2H), 0.90 (d, J=5.6 Hz, 3H), 1.45 (s, 3H), 0.89 (s, 3H).

HPLC: (Purity: 100%).

SFC: (Column: ChiralPak AD-3 150×4.6 mm I.D., 3 um Mobile phase: A: CO$_2$ B: ethanol (0.05% DEA) Gradient: from 5% to 40% of B in 5 min and hold 40% for 2.5 min, then 5% of B for 1.5 min Flow rate: 2.5 mL/min Column temp.: 40° C. (ee: 100%).

LCMS: (M+H: 347.1).

Example 97: Synthesis of Compounds 114-Ent1 and 114-Ent2

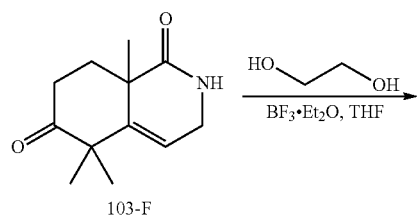

103-F

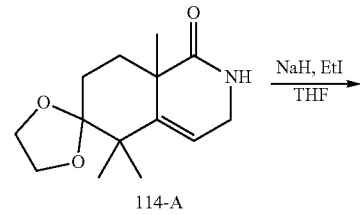

114-A

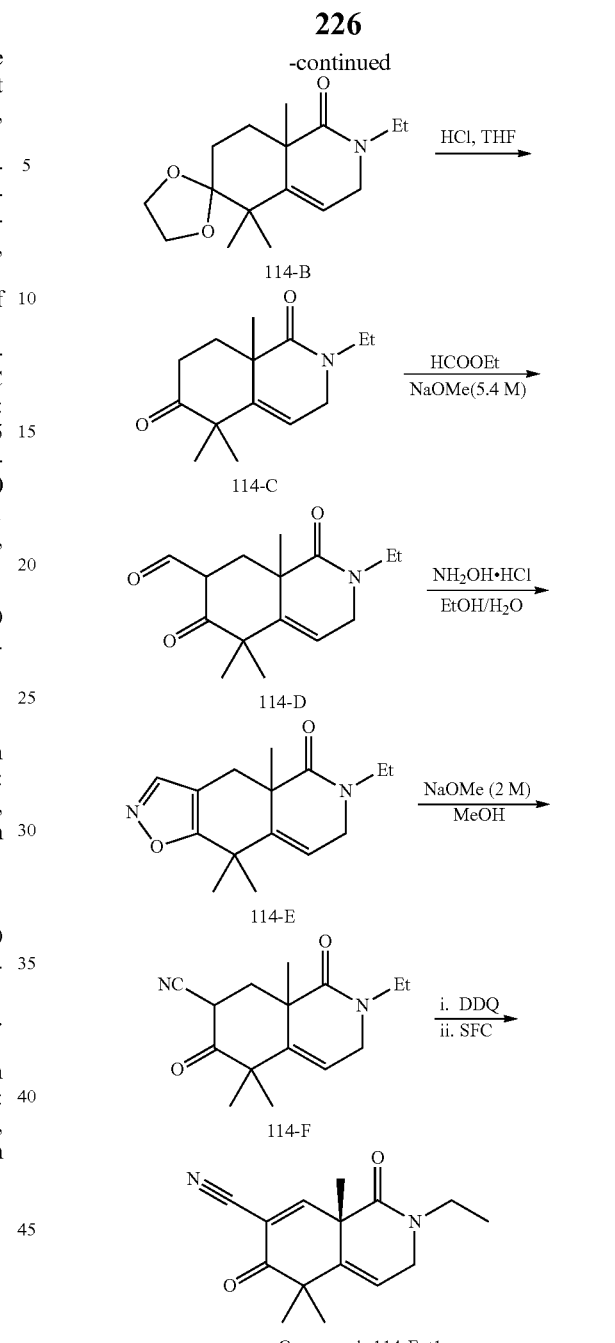

Preparation of Compound 114-A.

To a solution of compound 103-F (800 mg, 3.86 mmol, 1 eq.) in 10 mL of THF was added glycol (4.8 g, 77.2 mmol, 20 eq) and BF$_3$.Et$_2$O (274 mg, 1.93 mmol, 0.5 eq) then the mixture was stirred at 18-28° C. for 18 h. TLC (PE:EA=1:2) showed one new spot was observed. The mixture was stirred at 18-28° C. for 2 days. TLC (PE:EA=1:2) showed compound 103-F remained, 114-A product was detected by LCMS. The mixture was diluted with water (100 mL), extracted with EtOAc (50 mL×3). The combined organic layers were dried over anhydrous $Na_2SO_4$, filtered and concentrated. The residue was purified by flash column (PE:EtOAc=60:40-50:50-20:80) to give compound 114-A (540 mg, 55.8% yield) as pale-yellow solid.

$^1$HNMR: (400 MHz, $CDCl_3$) δ: 6.15 (br s, 1H), 5.71 (br d, J=4.85 Hz, 1H), 3.81-4.03 (m, 6H), 1.89-2.10 (m, 3H), 1.64-1.72 (m, 1H), 1.46 (s, 3H), 1.29 (s, 3H), 1.13 (s, 3H).

Preparation of Compound 114-B

To a solution of compound 114-A (300 mg, 1.2 mmol, 1 eq.) in 5 mL of DMF was added NaH (86 mg, 2.16 mmol, 1.8 eq), then the mixture was stirred at 18-28° C. for 1.5 h. Ethyl iodide (374 mg, 2.4 mmol, 2.0 eq, 0.19 mL) was added and the resulting mixture was stirred at 18~28° C. for 18 h. TLC (PE:EA=1:2) showed compound 114-A was consumed completely. The mixture was poured into 30 mL of ice-water and 10 mL of brine, extracted with EtOAc (20 mL×3). The combined organic layers were washed with brine (20 mL), dried over anhydrous $Na_2SO_4$, filtered and concentrated. The residue was purified by flash column (PE:EtOAc=70:30-50:50) to supply compound 114-B (200 mg, 59.5% yield) as pale-yellow solid.

$^1$HNMR: (400 MHz, $CDCl_3$) δ: 5.68 (dd, J=1.76, 5.27 Hz, 1H), 3.90-4.02 (m, 5H), 3.71-3.79 (m, 1H), 3.51-3.61 (m, 1H), 3.27 (qd, J=7.06, 13.71 Hz, 1H), 1.98-2.11 (m, 2H), 1.87-1.97 (m, 1H), 1.63-1.68 (m, 1H), 1.40 (s, 3H), 1.28 (s, 3H), 1.12 (s, 3H), 1.12 (t, J=8 Hz, 3H).

Preparation of Compound 114-C

To a solution of compound 114-B (360 mg, 1.28 mmol, 1 eq.) in 5 mL of THF was added HCl aq. (5 mL, 10%), then the mixture was stirred at 70° C. for 18 h. TLC (PE:EA=1:1) showed compound 114-B was consumed completely. The mixture was concentrated; the residue was diluted with EtOAc (20 mL) and water (25 mL) and separated. The aqueous phase was extracted with EtOAc (20 mL×2). The combined organic layers were dried over anhydrous $Na_2SO_4$, filtered and concentrated. The residue was purified by flash column (PE:EtOAc=60:40-50:50) to give compound 114-C (230 mg, 76.7% yield) as pale-yellow gum.

$^1$HNMR: (400 MHz, $CDCl_3$) δ: 5.78 (dd, J=1.76, 5.73 Hz, 1H), 4.04 (dd, J=1.87, 17.53 Hz, 1H), 3.75 (dd, J=5.73, 17.42 Hz, 1H), 3.62 (m, 1H), 3.36 (m, 1H), 2.55-2.65 (m, 1H), 2.47-2.65 (m, 1H), 2.47-2.54 (m, 1H), 2.32-2.44 (m, 1H), 1.34 (s, 3H), 1.29 (s, 3H), 1.25 (s, 3H), 1.16 (t, J=7.17 Hz, 3H).

Preparation of Compound 114-D

To a solution of compound 114-C (230 mg, 0.98 mmol, 1 eq.) in 5 mL of ethyl formate was added NaOMe (0.62 mL, 3.33 mmol, 3.4 eq. 5.4 M in methanol) under ice-bath The mixture was stirred at 28° C. under $N_2$ for 1 h. TLC (PE:EA=1:1) showed compound 114-C was consumed completely. The mixture was poured into 20 mL of ice-water slowly, adjusted pH to 4-5 by adding 1M HCl aq., extracted with EtOAc (15 mL×2). The combined organic layers were washed with brine (20 mL), dried over anhydrous $Na_2SO_4$, filtered and concentrated to give crude compound 114-D (240 mg) as pale-yellow gum.

Preparation of Compound 114-E

To a solution of compound 114-D (240 mg, 0.91 mmol, 1.0 eq.) in EtOH (5 mL) and $H_2O$ (1 mL) was added hydrochloride hydroxylamine (83 mg, 1.19 mmol, 1.3 eq.). After addition the mixture was stirred at 70° C. for 18 h. TLC (PE:EA=1:1) showed the starting materials were consumed completely. The mixture was concentrated, the residue was diluted with water (20 mL), extracted with EtOAc (15 mL×3). The combined organic layers were washed with brine (20 mL), dried over anhydrous $Na_2SO_4$, filtered and concentrated to supply crude compound 114-E (220 mg) as a pale-yellow solid.

$^1$HNMR: (400 MHz, $CDCl_3$) δ: 8.12 (s, 1H), 5.86 (dd, J=2.32, 4.30 Hz, 1H), 4.01-4.09 (m, 1H), 3.85-3.94 (m, 1H), 3.52-3.62 (m, 1H), 3.45 (m, 1H), 3.00 (d, J=15.66 Hz, 1H), 2.60 (d, J=15.66 Hz, 1H), 1.56 (s, 3H), 1.49 (s, 3H), 1.31 (s, 3H), 1.19 (t, J=7.17 Hz, 3H)

Preparation of Compound 114-F

To a solution of compound 114-E (220 mg, 0.84 mmol, 1 eq.) in 2 mL of methanol was added NaOMe (2.1 mL, 4.2 mmol, 5.0 eq. 2 M in methanol). After addition the mixture was stirred at 22-31° C. for 18 h. TLC (PE:EA=1:1) showed compound 114-E was consumed completely. The mixture was concentrated. The residue was diluted with water (20 mL), adjusted pH to 5-6 by adding 1M HCl aq., extracted with EtOAc (15 mL×3). The combined organic layers were dried over anhydrous $Na_2SO_4$, filtered and concentrated to supply crude compound 114-F (220 mg) as pale-yellow solid.

Preparation of Compounds 114-Ent1 and 114-Ent2

To a solution of compound 114-F (220 mg, 0.84 mmol, 1.0 eq.) in toluene/MeCN (3 mL/3 mL) was added DDQ (286 mg, 1.26 mmol, 1.5 eq.). The mixture was stirred at 90° C. for 1 h. TLC (PE:EA=1:2) showed compound 114-F remained. The mixture was stirred at 110° C. for 2 h. TLC (PE:EA=1:2) showed compound 114-F was consumed completely. The mixture was concentrated and the residue was diluted with EtOAc (60 mL), washed with saturated $NaHCO_3$ (40 mL×3), brine (30 mL). The organic phase was dried over anhydrous $Na_2SO_4$, filtered, concentrated and purified by prep-TLC (PE:EtOAc=1:1.5) to supply racemate (90 mg), which was separated by SFC (condition: Neu-EtOH, column: AY 250 mm*30 mm; 10 um) to supply 114-Ent1 (13 mg, 6.0% yield, Rt=3.399 min) as white solid and 114-Ent2 (20 mg, 9.3% yield, Rt=4.521 min) as pale-yellow solid Spectra of Compound 114-Ent1:

$^1$HNMR: (400 MHz, $CDCl_3$) δ: 8.23 (s, 1H), 5.92 (dd, J=1.47, 5.87 Hz, 1H), 4.07 (dd, J=1.90, 17.91 Hz, 1H), 3.81 (dd, J=5.93, 17.91 Hz, 1H), 3.36-3.58 (m, 2H), 1.62 (s, 3H), 1.42 (d, J=2.08 Hz, 6H), 1.17 (t, J=7.21 Hz, 3H)

HPLC: (purity: 100%)

SFC: (purity: 99.82%)

LCMS: (M+H: 259.1)

Spectra of Compound 114-Ent2:

$^1$HNMR: (400 MHz, $CDCl_3$) δ: 8.23 (s, 1H), 5.92 (dd, J=1.47, 5.87 Hz, 1H), 4.07 (dd, J=1.90, 17.91 Hz, 1H), 3.81 (dd, J=5.93, 17.91 Hz, 1H), 3.37-3.58 (m, 2H), 1.62 (s, 3H), 1.42 (d, J=2.20 Hz, 6H), 1.17 (t, J=7.15 Hz, 3H)

HPLC: (Purity: 98.69%)

SFC: (purity: 99.93%)

LCMS: (M+H: 259.1)

Example 98: Synthesis of Compounds 115-Ent1 and 115-Ent2

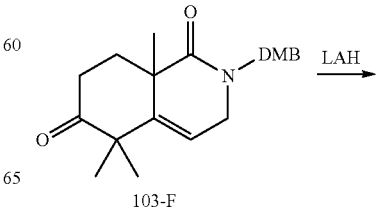

103-F

229
-continued

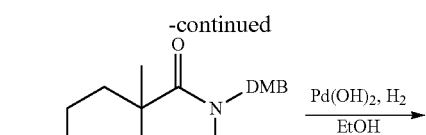
115-A
Pd(OH)₂, H₂ / EtOH →

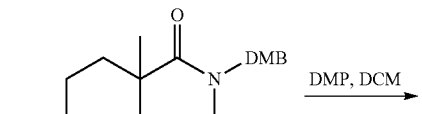
115-B mixture
DMP, DCM →

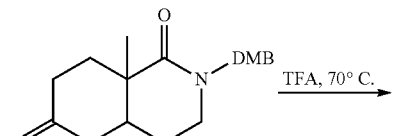
115-C mixture
TFA, 70° C. →

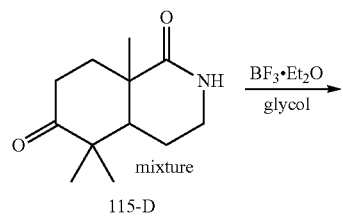
115-D mixture
BF₃·Et₂O / glycol →

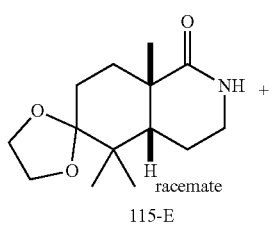
115-E racemate
+

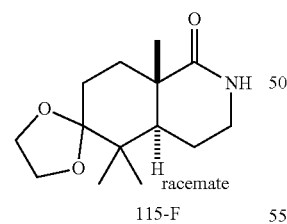
115-F racemate

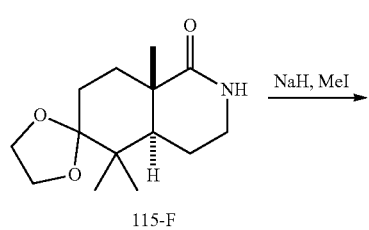
115-F
NaH, MeI →

230
-continued

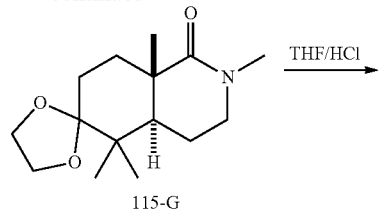
115-G
THF/HCl →

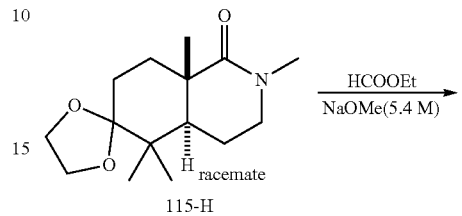
115-H racemate
HCOOEt / NaOMe(5.4 M) →

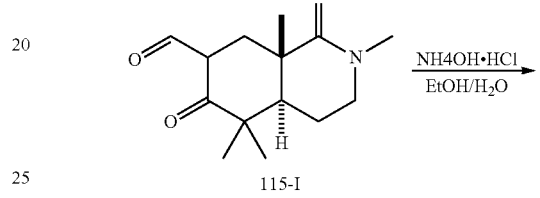
115-I
NH₄OH·HCl / EtOH/H₂O →

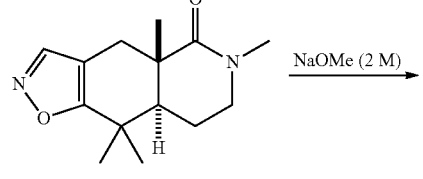
115-J
NaOMe (2 M) →

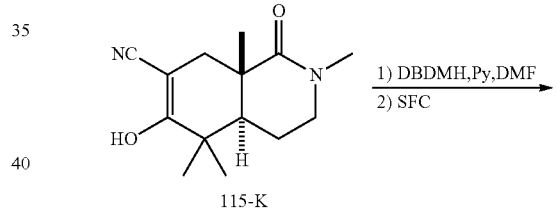
115-K
1) DBDMH, Py, DMF
2) SFC →

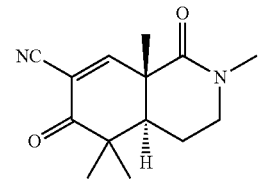
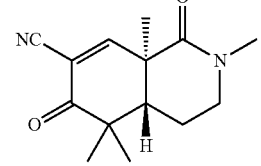
Compounds 115-Ent1 and 115-Ent2

Preparation of Compound 115-A

To the suspension of LAH (1.098 g, 28.9 mmol, 1.2 eq) in 250 mL of anhydrous THF was added compound 103-F (8.6 g, 24.09 mmol, 1.0 eq) in 50 mL of anhydrous THF by dropwise under ice-bath (0-5° C.). After addition the mixture was stirred at 0-20° C. for 1.5 h. TLC (PE:EtOAc=3:1) showed compound 103-F was consumed completely. 1.1 mL of water was added slowly (lots of gas formed), then 1.1 mL of 15% aqueous NaOH and 3.3 mL of water were added by turn. The mixture was diluted with THF (300 mL) and stirred with anhydrous Na$_2$SO$_4$ (10 g) for 30 min and filtered with a pad of celite. The solid was washed with EtOAc (300 mL×2) and filtered. The combined filtrates was concentrated under reduced pressure and purified by flash column (PE: EtOAc=80:20-50:50-40:60) to supply compound 115-A (4.5 g, 52.03% yield) as pale-yellow solid.

$^1$HNMR: (400 MHz, CDCl$_3$) δ: 7.09-7.19 (m, 1H), 6.45 (m, 2H), 5.66 (m, 1H), 4.77 (d, J=14.8 Hz, 1H), 4.40 (d, J=14.8 Hz, 1H), 3.80 (s, 6H), 3.72-3.80 (m, 1H), 366-3.74 (m, 1H), 3.31 (m, 1H), 2.20 (m, 1H), 1.82 (m, 2H), 1.63-1.72 (m, 1H), 1.37 (s, 3H), 1.20 (s, 3H), 1.11 (s, 3H).

Preparation of Compound 115-B

To a solution of compound 115-A (4.3 g, 11.98 mmol, 1.0 eq) in 80 mL of EtOH was added Pd/C (1.5 g, 10% w/w, water containing <1%) under Ar atmosphere. The suspension was degassed under vacuum with Ar and H$_2$ for 3 times each, and then stirred under H$_2$ (50 psi) at 40° C. for 16 h. LCMS showed compound 115-A was consumed completely. The mixture was filtered through a pad of celite, the pad was washed with EtOAc (80 mL×2) and filtered. The combined filtrates were concentrated under reduced pressure to give crude compound 115-B (3.7 g) as pale-yellow gum.

LCMS: (M+H: 362.2)

Preparation of Compound 115-C

To a solution of compound 115-B (3.5 g, 9.7 mmol, 1.0 eq) in 60 mL of DCM was added DMP (4.93 g, 11.6 mmol, 1.2 eq) under ice-bath. The mixture was stirred at 18-25° C. for 2.5 h. TLC (PE:EtOAc=1:1) showed compound 115-B was consumed completely. The mixture was diluted with saturated aqueous NaHCO$_3$ (200 mL), filtered through a pad of celite, the DCM phase was separated, the aqueous phase was extracted with EtOAc (100 mL×3), the combined organic layers were dried over anhydrous Na$_2$SO$_4$, filtered and concentrated. The residue was purified by flash column (PE:EtOAc=70:30-50:50) to give compound 115-C (2.7 g, 79.4% yield) as pale-yellow gum.

$^1$HNMR: (400 MHz, CDCl$_3$) δ: 7.09-7.21 (m, 1H), 6.43-6.48 (m, 2H), 4.65 (m, 1H), 4.74 (m, 1H), 3.78-3.83 (m, 6H), 3.16-3.38 (m, 2H), 2.60-2.72 (m, 1H), 2.29-2.53 (m, 2H), 1.68-1.96 (m, 4H), 1.30-1.38 (m, 3H), 1.01-1.10 (m, 6H).

Preparation of Compound 115-D

Compound 115-C (2.83 g, 7.88 mmol, 1.0 eq.) was added into 30 mL of TFA. The resulting mixture was stirred at 70° C. for 1.5 h. TLC (PE:EA=1:3) showed compound 115-C was consumed completely. The mixture was concentrated, the residue was diluted with water (150 mL) and EtOAc (50 mL), adjusted pH to 7-8 by adding 1M aqueous NaHCO$_3$, extracted with EtOAc (100 mL×6). The combined organic layers were dried over anhydrous Na$_2$SO$_4$, filtered and concentrated. The residue was purified by flash column (PE:EtOAc=60:40-50:50-40:60) to give compound 115-D (1.5 g, 90.9% yield) as white solid.

Preparation of Compound 115-E

Compound 115-D (1.45 g, 6.94 mmol, 1 eq.) and compound BF$_3$.Et$_2$O (493 mg, 3.47 mmol, 0.5 eq) were added into glycol (172 g, 278 mmol, 40 eq, ~17.2 mL). The mixture was stirred at 22-31° C. for 18 h. TLC (PE:EA=1:5) showed little compound 115-D remained, one new spot was observed. The mixture was diluted with water (100 mL), extracted with DCM/MeOH (60 mL×3, V:V=20:1). The combined organic layers were dried over anhydrous Na$_2$SO$_4$, filtered and concentrated. The residue was purified by flash column (PE:EtOAc=60:40-40:60) to give isomer 115-E (600 mg, 34.2% yield) as white solid and impure product (900 mg). The impure product (900 mg) was purified by prep-HPLC (condition: water (10 mM NH4HCO3)-ACN), column: Xtimate C18 150*25 mm*5 um) to supply isomer 115-F (340 mg, 19.4% yield) as a white solid.

Spectra of Compound 115-E $^1$HNMR: (400 MHz, CDCl$_3$) δ: 5.55 (br s, 1H), 3.87-3.99 (m, 4H), 3.40-3.54 (m, 2H), 2.42 (m, 1H), 2.10-2.25 (m, 1H), 1.90-2.02 (m, 2H), 1.80 (m, 1H), 1.49 (m, 1H), 1.39 (m, 1H), 1.28 (s, 3H), 1.06 (s, 3H), 0.96 (s, 3H)

Spectra of Compound 115-F $^1$HNMR: (400 MHz, CDCl$_3$) δ: 5.54-5.71 (m, 1H), 3.87-4.02 (m, 4H), 3.33-3.41 (m, 1H), 3.22-3.31 (m, 1H), 1.94-2.01 (m, 1H), 1.71-1.90 (m, 5H), 1.57-1.64 (m, 1H), 1.29 (s, 3H), 1.00 (s, 3H), 0.90 (s, 3H).

Preparation of Compound 115-G

To a solution of compound 115-F (340 mg, 1.34 mmol, 1 eq.) in 10 mL of THF was added NaH (80.4 mg, 2.01 mmol, 1.5 eq), then the mixture was stirred at 18-27° C. for 1.5 h. Methyl iodide (382 mg, 2.69 mmol, 2.0 eq, 170 uL) was added and the resulting mixture was stirred at 18-27° C. for 18 h. TLC (PE:EA=1:2) showed one new spot. LCMS indicated completion. The mixture was poured into 20 mL of water and 5 mL of brine, extracted with EtOAc (20 mL×4). The combined organic layers were washed with brine (20 mL), dried over anhydrous Na$_2$SO$_4$, filtered and concentrated to supply crude compound 115-G (350 mg) as pale-yellow solid.

$^1$HNMR: (400 MHz, CDCl$_3$) δ: 3.87-4.01 (m, 4H), 3.20-3.35 (m, 2H), 2.85 (s, 3H), 2.03 (m, 1H), 1.70-1.89 (m, 5H), 1.57-1.62 (m, 1H), 1.25 (s, 3H), 1.00 (s, 3H), 0.90 (s, 3H).

Preparation of Compound 115-H

To a solution of compound 115G (350 mg, 1.31 mmol, 1 eq.) in 5 mL of THF was added HCl aq. (2 mL, 10%), then the mixture was stirred at 80° C. for 18 h. TLC (PE:EA=1:3) showed compound 115-G was consumed completely. The mixture was diluted with water (30 mL), extracted with EtOAc (20 mL×4). The combined organic layers were washed with brine (30 mL), dried over anhydrous Na$_2$SO$_4$, filtered and concentrated. The residue was purified by prep-TLC (PE:EtOAc=1:2) to give compound 115-H (210 mg, 71.9% yield) as a pale-yellow solid.

$^1$HNMR: (400 MHz, CDCl$_3$) δ: 3.26-3.42 (m, 2H), 2.90 (s, 3H), 2.60-2.71 (m, 1H), 2.34-2.51 (m, 2H), 1.75-2.04 (m, 4H), 1.35 (s, 3H), 1.11 (d, J=12.4 Hz, 6H).

Preparation of Compound 115-I

To a solution of compound 115-H (210 mg, 0.94 mmol, 1 eq.) in 5 mL of ethyl formate was added NaOMe (0.60 mL, 3.2 mmol, 3.4 eq. 5.4 M in methanol). The mixture was stirred at 22-27° C. under N$_2$ for 3 h. LCMS indicated completion. The mixture was diluted with ice-water (20 mL), adjusted pH to ~5 by adding 1M HCl aq., extracted with EtOAc (20 mL×3). The combined organic layers were washed with brine (20 mL), dried over anhydrous Na$_2$SO$_4$, filtered and concentrated to give crude compound 115-I (230 mg) as pale-yellow oil.

Preparation of Compound 115-J

To the mixture of compound 115-I (230 mg, 0.92 mmol, 1.0 eq.) in EtOH (5 mL) and H$_2$O (1 mL) was added hydrochloride hydroxylamine (96 mg, 1.37 mmol, 1.5 eq.). After addition the mixture was stirred at 70° C. for 18 h. LCMS indicated completion. The mixture was concentrated, the residue was diluted with water (25 mL), extracted with EtOAc (15 mL×3). The combined organic layers were washed with brine (20 mL), dried over anhydrous Na$_2$SO$_4$, filtered, concentrated and purified by prep-TLC (PE:EtOAc=1:2) to supply compound 115-J (120 mg, 52.6% yield) as a white solid.

$^1$HNMR: (400 MHz, CDCl$_3$) δ: 8.09 (s, 1H), 3.30-3.44 (m, 2H), 2.95 (s, 3H), 2.91 (d, J=16 Hz, 1H), 2.48 (d, J=15.6 Hz, 1H), 1.87-1.99 (m, 3H), 1.36 (s, 3H), 1.27 (s, 3H) 1.18 (s, 3H).

Preparation of Compound 115-K

To a solution of compound 115-J (120 mg, 0.48 mmol, 1 eq.) in 2 mL of methanol was added NaOMe (1.2 mL, 2.42 mmol, 5.0 eq. 2 M in methanol). After addition the mixture was stirred at 22-26° C. for 18 h. TLC (PE:EA=1:2) showed compound 115-J was consumed completely. The mixture was concentrated. The residue was diluted with water (20 mL), adjusted pH to ~5 by adding 1M HCl aq., extracted with EtOAc (15 mL×4). The combined organic layers were washed with brine (20 mL), dried over anhydrous Na$_2$SO$_4$, filtered and concentrated to supply crude compound 115-K (120 mg) as white solid.

Preparation of 115-Ent1 and 115-Ent2

To a solution of compound 115-K (110 mg, 0.44 mmol, 1.0 eq.) in DMF (5 mL) was added DBDMH (76 mg, 0.27 mmol, 0.6 eq.). The mixture was stirred at 24° C. for 1 h. Pyridine (348 mg, 4.4 mmol, 10 eq.) was added and the mixture was stirred at 60° C. for 4 h. LCMS indicated completion. The mixture was diluted with water (20 mL), adjusted pH to ~5 by adding 1N HCl, extracted with EtOAc (15 mL×3). The combined organic layers were washed with brine (20 mL), dried over anhydrous Na$_2$SO$_4$, filtered, concentrated and purified by prep-TLC (PE:EtOAc=1:3) to supply racemate (~50 mg) which was separated by SFC (condition: Neu-IPA, column: IC 250 mm*30 mm; 10 um) to supply the first eluting compound (115-Ent1, 9 mg, 8.3% yield, Rt=4.478 min) as a white solid, and the second eluting compound (~20 mg) which was further purified by prep-HPLC (condition: water (0.05% HCl)-ACN), column: Phenomenex Synergi C18 150*30 mm*4 um) to supply isomer 115-Ent2 (9 mg, 8.3% yield, Rt=6.135 min) as a white solid.

Spectra of 115-Ent1

$^1$HNMR: (400 MHz, CDCl$_3$) δ: 8.46 (s, 1H), 3.43-3.51 (m, 1H), 3.33-3.42 (m, 1H), 2.94 (s, 3H), 2.25 (m, 1H), 2.02-2.16 (m, 1H), 1.94 (m, 1H), 1.48 (s, 3H), 1.26 (s, 3H), 1.18 (s, 3H).

HPLC: (purity: 99.72%)
SFC: (purity: 100%)
LCMS: (M+H: 247.0)

Spectra of Compound 115-Ent2:

$^1$HNMR: (400 MHz, CDCl$_3$) δ: 8.46 (s, 1H), 3.43-3.51 (m, 1H), 3.33-3.42 (m, 1H), 2.94 (s, 3H), 2.25 (m, 1H), 2.02-2.15 (m, 1H), 1.94 (m, 1H), 1.48 (s, 3H), 1.26 (s, 3H), 1.18 (s, 3H).

HPLC: (Purity: 98.42%)
SFC: (purity: 100%)
LCMS: (M+H: 247.1)

Example 99: Synthesis of Compounds 116-Ent1 and 116-Ent2

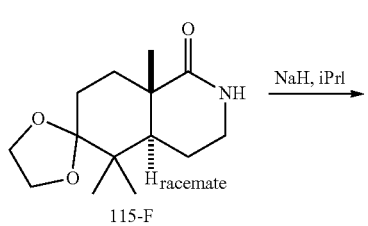

115-F

NaH, iPrI →

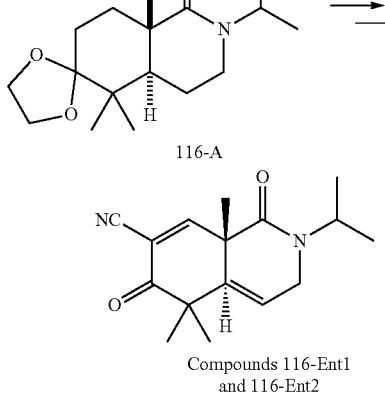

116-A as in Scheme 115 →

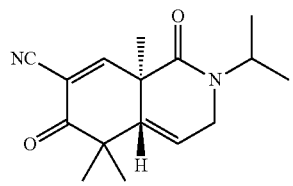

Compounds 116-Ent1 and 116-Ent2

Compounds 116-Ent1 and 116-Ent2 can be made in a manner analogous to that described for 115-Ent1 and 115-Ent2.

Procedure for the Synthesis of Compound 116-A:

To a solution of compound 115-F (500 mg, 1.98 mmol, 1.0 eq.) in 20 mL of DMF was added NaH (395 mg, 9.88 mmol, 5.0 eq), then the mixture was stirred at 30° C. for 1 h. Subsequently, 2-iodopropane (1.679 g, 9.88 mmol, 5.0 eq) was added and the resulting mixture was stirred at 50° C. for 40 h. TLC (PE:EA=1:4, 1:1) showed one new spot. The mixture was poured into 100 mL of ice-water slowly and 50 mL of brine, extracted with EtOAc (100 mL×3). The combined organic layers were washed with brine (100 mL), dried over anhydrous Na$_2$SO$_4$, filtered, concentrated and purified by flash column (PE:EtOAc=70:30-50:50-30:70) to supply compound 116-A (150 mg, 25.6% yield) as pale-yellow gum.

LCMS: (M+H: 296.2)

Procedure for the Purification and Chiral Separation of Compounds 116-Ent1 and 116-Ent2:

The final DBDMH oxidation mixture was diluted with EtOAc (30 mL), washed with aq. HCl (0.5 M) (15 mL), brine (15 mL×2), dried over anhydrous Na$_2$SO$_4$, filtered, concentrated and purified by prep-TLC (PE:EtOAc=1:1) to supply racemate (~26 mg) which was separated by SFC (condition: Neu-EtOH, column: OD 250 mm*30 mm; 5 um) to supply 116-Ent1 (9 mg, 13.6% yield, Rt=2.678 min) as grey solid and 116-Ent2 (9 mg, 13.6% yield, Rt=3.094 min) as grey solid.

Spectra of Compound 116-Ent1:

$^1$HNMR: (400 MHz, CDCl$_3$) δ: 8.47 (s, 1H), 4.70-4.84 (m, 1H), 3.36-3.45 (m, 1H), 3.18-3.29 (m, 1H), 2.13-2.22 (m, 1H), 1.93-2.07 (m, 2H), 1.46 (s, 3H), 1.26 (s, 3H), 1.17 (s, 3H), 1.14 (d, J=6.8 Hz, 6H).

HPLC: (purity: 96.49%)
SFC: (purity: 99.53%)
LCMS: (M+H: 275.0)

Spectra of Compound 116-Ent2:

$^1$HNMR: (400 MHz, CDCl$_3$) δ: 8.47 (s, 1H), 4.78 (m, 1H), 3.36-3.46 (m, 1H), 3.18-3.30 (m, 1H), 2.13-2.22 (m,

1H), 1.94-2.03 (m, 2H), 1.46 (s, 3H), 1.26 (s, 4H), 1.18 (s, 3H), 1.14 (d, J=6.8 Hz, 6H).
HPLC: (Purity: 97.89%)
SFC: (purity: 100%)
LCMS: (M+H: 275.1)

Example 100: Synthesis of Compounds 117-Ent1 and 117-Ent2 and concentrated to give the crude, which was purified by column chromatography on silica gel (PE/EA=10:1-1:2) to give compound 117-B (305 mg, yield of two steps: 42%) as red oil.
LCMS: (M+H: 224.1)
Preparation of Compound 117-C
To a solution of compound 117-B (300 mg, 1.44 mmol, 1.0 eq) in ethyl formate (10 mL) was added a solution of NaOMe/MeOH (1.59 mL, 5.4M) at 10-30° C. dropwise

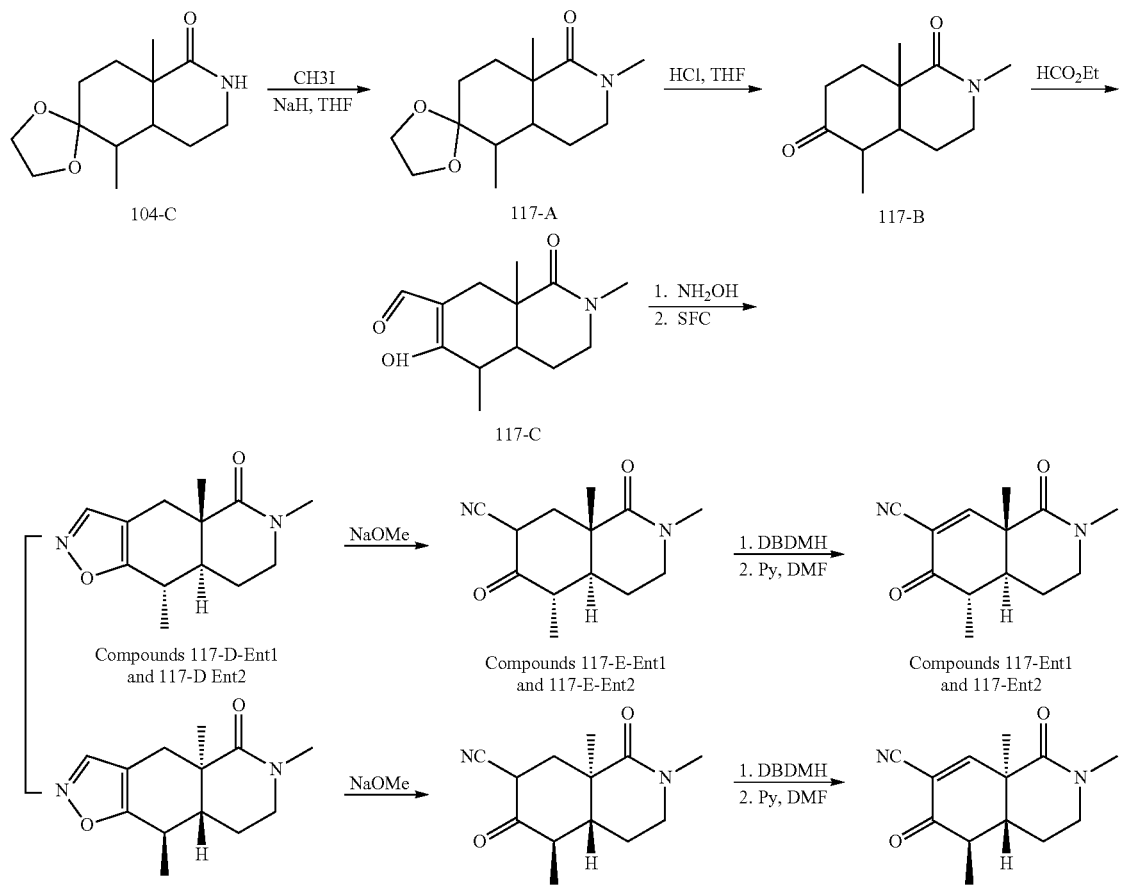

Preparation of 117-A
To a mixture of compound 104-C (500 mg, 2.1 mmol, 1.0 eq) and NaH (936 mg, 21 mmol, 10.0 eq) in DMF (10 mL) was added compound CH₃I (2.97 g, 21 mmol, 10.0 eq) in one portion at 10-25° C. The reaction mixture was stirred at 10-25° C. for 18 hs. TLC (PE/EA=1:2) showed the compound 1 was consumed completely. The reaction mixture was quenched with saturated NH₄Cl (50 mL) and extracted with EA (50 mL×2). The combined organic layers were washed with brine (50 mLx1), dried over Na₂SO₄, filtered and concentrated to give the crude (800 mg) as red oil, which was used for the next step without further purification.
LCMS: (M+H: 254.2)
Preparation of Compound 117-B
To a solution of compound 117-A (800 mg, crude) in THF (5 mL) was added HCl(1 mL, 1M) dropwise at 10-28° C. The reaction mixture was stirred at 10-28° C. for 18 hours. LCMS showed the compound 117-A was consumed completely. The mixture was poured into water (30 mL) and adjust to PH=9 with solid NaHCO₃. The mixture was extracted with EA (30 mL×3), dried over Na₂SO₄, filtered under N₂. The mixture was stirred at 10-27° C. for 18 hours. TLC (PE/EA=1:2) showed the compound 3 was consumed completely. The mixture was poured into water (30 mL) and acidified with HCl(M) to make PH=4-5. The mixture was extracted with EtOAc (30 mL×2). The combined organic phase was washed with brine (50 mL), dried over Na₂SO₄, and filtered. The filtrate was concentrated in vacuo to give compound crude (330 mg), which was used directly in the next step without purification.
LCMS: (M+H: 238.0)
Preparation of Compounds 117-D-Ent1 and 117-D-Ent2
A mixture of compound 117-C (300 mg, 1.19 mmol, 1.0 eq) and hydrochloride hydroxylamine (107 mg, 1.55 mmol, 1.0 eq) in EtOH/H₂O (5 mL, V=5:1) were stirred at 55° C. for 18 hours. LCMS showed desired product was detected. The mixture was concentrated to remove EtOH and diluted with water (30 mL). The mixture was extracted with EA (30 mL×2), dried over Na₂SO₄, filtered and concentrated to give the crude, which was purified by column chromatography on silica gel (PE/EA=5:1-2:1-1:3) to give racemic product (240 mg, yield: 76%) as yellow oil. The compound was further separated by SFC (column: AD (250 mm*30 mm, 5 um)) condition: 0.1% NH₃H₂O ETOH) to give enantiomer 117-D-Ent1 (40 mg, yield: 22.7%) and enantiomer 117-D-Ent2 (60 mg, yield: 22.7%), both as white solids.

¹H NMR (400 MHz, CHLOROFORM-d) δ 8.10 (s, 1H), 3.35-3.41 (m, 2H), 2.94-2.98 (m, 3H), 2.59-2.72 (m, 1H), 2.51 (dd, J=2.6, 16.22 Hz, 1H), 2.03-2.10 (m, 1H), 1.69-1.88 (m, 3H), 1.39 (d, J=6.6 Hz, 3H), 1.10 (s, 3H)

Preparation of Compound 117-E-Ent1

To a solution of compound 117-D-Ent1 (30 mg, 0.128 mmol, 1.0 eq) in MeOH (3 mL) was added a solution of NaOMe/MeOH (1 mL, 5.4M). The mixture was stirred at 10-38° C. for 18 hours. TLC (PE:EA=1:3) showed most of the starting material was almost consumed and a new spot was detected. The mixture was acidified with HCl(M) to make pH=4-5 and diluted with water (20 mL). The mixture was extracted with EtOAc (30 mL×2), dried over Na₂SO₄, filtered and concentrated to give compound 117-E-Ent1 (40 mg) as yellow oil, which was used for the next step without further purification.

Preparation of Compound 117-E-Ent2

To a solution of compound 117-D-Ent2 (50 mg, 0.26 mmol, 1.0 eq) in MeOH (3 mL) was added a solution of NaOMe/MeOH (0.22 mL, 5.4M, 6.0). The mixture was stirred at 10-38° C. for 18 hours. TLC (PE:EA=1:3) showed most of the starting material was almost consumed and a new spot was detected. The mixture was acidified with HCl(M) to make PH=4-5 and diluted with water (20 mL). The mixture was extracted with EtOAc (30 mL×2), dried over Na₂SO₄, filtered and concentrated to give compound 117-E-Ent2 (52 mg) as yellow oil, which was used for the next step without further purification.

Preparation of Compound 117-Ent1

A mixture of compound 117-E-Ent1 (40 mg, 0.128 mmol, 1.0 eq) and DBDMH (22 mg, 0.07 mmol, 0.6 eq) in DMF (6 mL) was stirred at 0° C. for 1 hour under N₂. Pyridine (101 mg, 1.28 mmol, 10.0 eq) was added to the above mixture in one portion at 0° C. The mixture was stirred at 60° C. for 18 hours under N₂. LCMS showed most of the starting material was consumed. The mixture was concentrated to give the crude, which was purified by pre-HPLC (Condition: water (0.05% HCl)-CAN, Column: Phenomenex Synergi C18 150*30 mm*4 um) to give 117-F-Ent1 (10 mg, purity: 80%) as a white solid. Further purification was separated by prep-TLC (PE/EA=1:3) to give the desired product (5 mg, yield: 12.5%, Rt=5.526 min) as a white solid.

¹H NMR (400 MHz, CHLOROFORM-d) δ: 8.46 (s, 1H), 3.32-3.50 (m, 2H), 2.95 (s, 3H), 2.46 (qd, J=6.6, 13.05 Hz, 1H), 2.14-2.22 (m, 1H), 2.00-2.13 (m, 1H), 1.87-2.00 (m, 1H), 1.39-1.47 (m, 3H), 1.25 (d, J=6.6 Hz, 3H).

SFC: (ee: 98.1%)
HPLC: (Purity: 98.01%)
LCMS: (M+H: 233.0)

Preparation of Compound 117-Ent2

A mixture of compound 117-E-Ent2 (52 mg, 0.2 mmol, 1.0 eq) and DBDMH (35 mg, 0.12 mmol, 0.6 eq) in DMF (5 mL) was stirred at 0° C. for 1 hour under N₂. Pyridine (158 mg, 2 mmol, 10.0 eq) was added to the above mixture in one portion at 0° C. The mixture was stirred at 55° C. for 18 hours under N₂. TLC (PE/EtOAc=1:3) showed most of the starting material was consumed. The mixture was diluted with EtOAc (50 mL), washed HCl (30 mL×2, 1M), brine (30 mL×1) dried over Na₂SO₄, filtered and concentrated to give the crude, which was purified by prep-TLC (PE/EA=1:3) to give the desired product (25 mg, not pure by ¹HNMR) as a white solid. Further purification was separated by prep-HPLC (Condition: water (0.05% HCl)-CAN, Column: Phenomenex Synergi C18 150*30 mm*4 um) to give 117-Ent2 (15 mg, yield: 38.6%, Rt=6.101 min) as a white solid.

¹H NMR (400 MHz, CHLOROFORM-d) δ: 8.46 (s, 1H), 3.32-3.50 (m, 2H), 2.95 (s, 3H), 2.46 (qd, J=6.6, 13.05 Hz, 1H), 2.14-2.22 (m, 1H), 2.00-2.13 (m, 1H), 1.87-2.00 (m, 1H), 1.39-1.47 (m, 3H), 1.25 (d, J=6.6 Hz, 3H).

SFC: (ee: 98.0%)
HPLC: (Purity: 99.39%)
LCMS: (M+H: 247.0)

Example 101: Synthesis of Compound 118-Ent1 and 118-Ent2

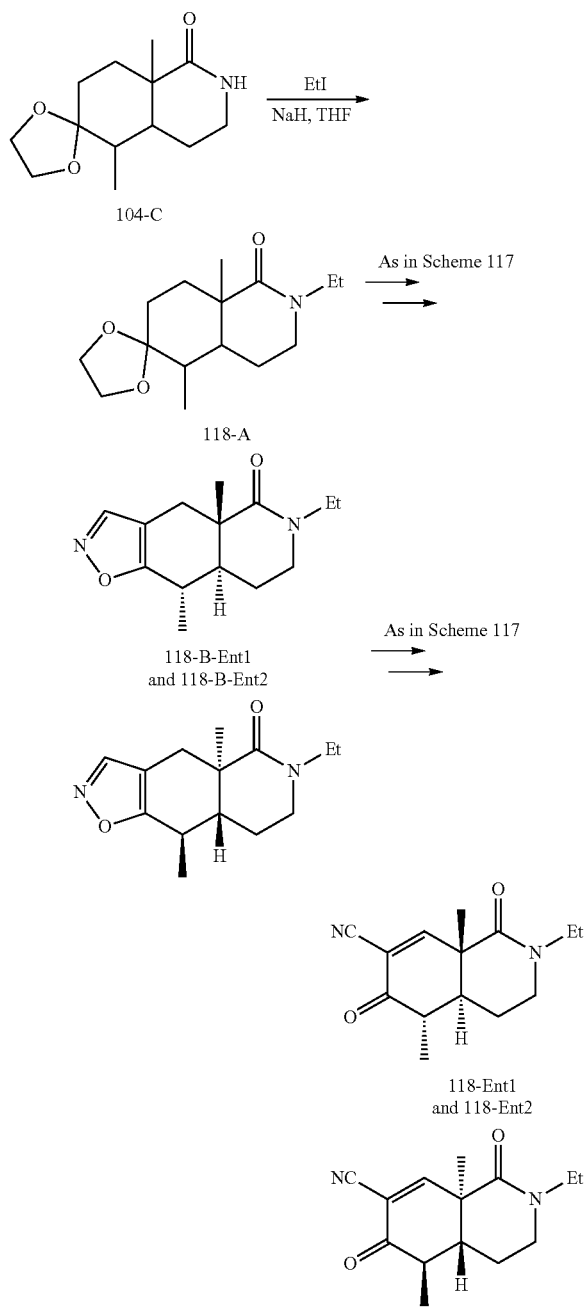

Compounds 118-Ent1 and 118-Ent2 can be made in a manner analogous to that described for 117-Ent1 and 117-Ent2.

Procedure for the Synthesis of 118-A

To a mixture of compound 104-C (800 mg, 3.34 mmol, 1.0 eq) and NaH (668 mg, 16.7 mmol, 5.0 eq) in DMF (10 mL) was added ethyl iodide (2.61 g, 16.7 mmol, 5.0 eq) in one portion at 10-25° C. The reaction mixture was stirred at 10-25° C. for 18 hs. LCMS showed the compound 104-C was consumed completely. The reaction mixture was quenched with saturated NH$_4$Cl (30 mL) and extracted with EA (30 mL×2). The combined organic layers were washed with brine (30 mL×2), dried over Na$_2$SO$_4$, filtered and concentrated to give compound 118-A (800 mg, yield: 85%) as red oil, which was used for the next step without further purification.

LCMS: (M+H: 268.3)

Procedure for the Purification and Chiral Separation of Compounds 118-B Ent1 and 118-B-Ent2:

After the isoxazole-forming reaction was complete (as described in the conversion of 117-C to 117-D-Ent1 and 117-D-Ent2), the mixture was extracted with EA (30 mL×2), dried over Na$_2$SO$_4$, filtered and concentrated to give the crude, which was purified by column chromatography on silica gel (PE/EA=1:3) to give racemic product (220 mg, yield: 75%) as a yellow oil. The product was further purified by SFC (column: OJ (250 mm*30 mm, 5 um) condition: 0.1% NH$_3$H$_2$O IPA) to give enantiomer 118-B-Ent1 (50 mg, yield: 22.7%) enantiomer and 118-B-Ent2 (50 mg, yield: 22.7%) both as white solid.

$^1$HNMR (400 MHz, CHLOROFORM-d) δ 8.10 (s, 1H), 3.34-3.43 (m, 4H), 2.88 (d, J=15.35 Hz, 1H), 2.56-2.65 (m, 1H), 2.42-2.55 (m, 1H), 2.07 (br d, J=4.39 Hz, 1H), 1.69-1.85 (m, 2H), 1.39 (d, J=7.02 Hz, 3H), 1.13 (t, J=7.24 Hz, 3H), 1.08 (s, 3H).

Purification and Spectral Data for 118-Ent1

After reaction completion, the crude DBDMH oxidation mixture was diluted with EtOAc (50 mL), washed HCl(30 mL×2, 1M), brine (30 mL×1) dried over Na$_2$SO$_4$, filtered and concentrated to give the crude, which was purified by prep-HPLC (Condition: water(0.05% HCl)-CAN, Column: Phenomenex Synergi C18 150*30 mm*4 um) to give 118-Ent1 (10 mg, yield: 20.4%, Rt=3.863 min) as a white solid.

Spectra of 118-Ent1

$^1$H NMR (400 MHz, METHANOL-d4) δ 8.33 (s, 1H), 3.33-3.53 (m, 4H), 2.61 (qd, J=6.6, 12.8 Hz, 1H), 2.27 (dt, J=3.2, 12.8 Hz, 1H), 2.02-2.11 (m, 1H), 1.90-2.00 (m, 1H), 1.41 (s, 3H), 1.20 (d, J=6.6 Hz, 3H), 1.12 (t, J=7.2 Hz, 3H).

SFC: (ee: 98.1%)
HPLC: (Purity: 94.87%)
LCMS: (M+H: 247.0)

Purification and Spectral Data for 118-Ent2

After reaction completion, the crude DBDMH oxidation mixture was diluted with EtOAc (50 mL), washed with HCl (30 mL×2, 1M), brine (30 mL×1) dried over Na$_2$SO$_4$, filtered and concentrated to give the crude, which was purified by pre-HPLC (Condition: water (0.05% HCl)-CAN, Column: Phenomenex Synergi C18 150*30 mm*4 um) to give 118-Ent2 (9 mg, yield: 20.1%, Rt=4.074 min) as a white solid.

$^1$H NMR (400 MHz, METHANOL-d$_4$) δ: 8.33 (s, 1H), 3.33-3.53 (m, 4H), 2.54-2.68 (m, 1H), 2.27 (dt, J=3.2, 12.8 Hz, 1H), 2.03-2.13 (m, 1H), 1.89-2.00 (m, 1H), 1.41 (s, 3H), 1.20 (d, J=6.6 Hz, 3H), 1.12 (t, J=7.2 Hz, 3H).

SFC: (ee: 98.0%)
HPLC: (Purity: 97.27%)
LCMS: (M+H: 247.0)

Example 102: General Method for the Synthesis of Compounds Via Cross-Coupling

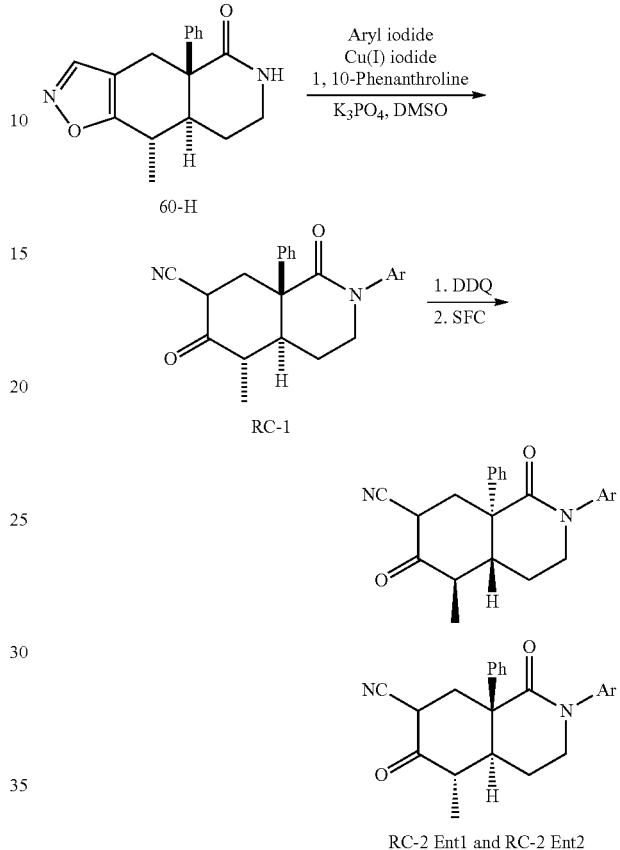

General Procedure for the Preparation of Compounds of Type RC-1

An oven-dried flask, which was equipped with a magnetic stir bar and fitted with a septum, was charged with 60-H (1.0 eq.), Aryl iodide (1.5 eq.), copper(I) iodide (0.3 eq.), 1,10-phenanthroline (0.3 eq.), K$_3$PO$_4$ (3.0 eq.) and DMSO (0.2 M). The reaction mixture solution was degassed with nitrogen for 5 min. The vessel was evacuated and backfilled with nitrogen (this process was repeated a total of 5 times) and was stirred at 100° C. for 24 hours. Analysis by LCMS revealed 60-H was consumed completely and new peak with a mass consistent with desired product RC-1. The reaction mixture was filtered through a short pad of Celite® to remove the catalyst, and DMSO was removed under high vacuum to provide the crude mixture of compound RC-1 which was used for next step without further purification.

General Procedure for the Preparation of Compounds of Type RC-2-Ent1 and RC2-Ent2

To a glass vial, which was charged crude Compound RC-1 (1.0 eq.) in Toluene (0.1 M), was added DDQ (1.3 eq.). The reaction mixture was heated at 120° C. for 2 hours. After cooling to room temperature, the reaction mixture was diluted with EtOAc and washed with saturated NaHCO$_3$ solution. The aqueous phase was extracted with EtOAc (3 times) and the combined organic layers were dried over MgSO$_4$. The solvent was removed in vacuo and the residue was purified by HPLC and separated by chiral SFC.

Example 103: Specific Example of Example 102, Synthesis of Compounds 120-Ent1 and 120-Ent2

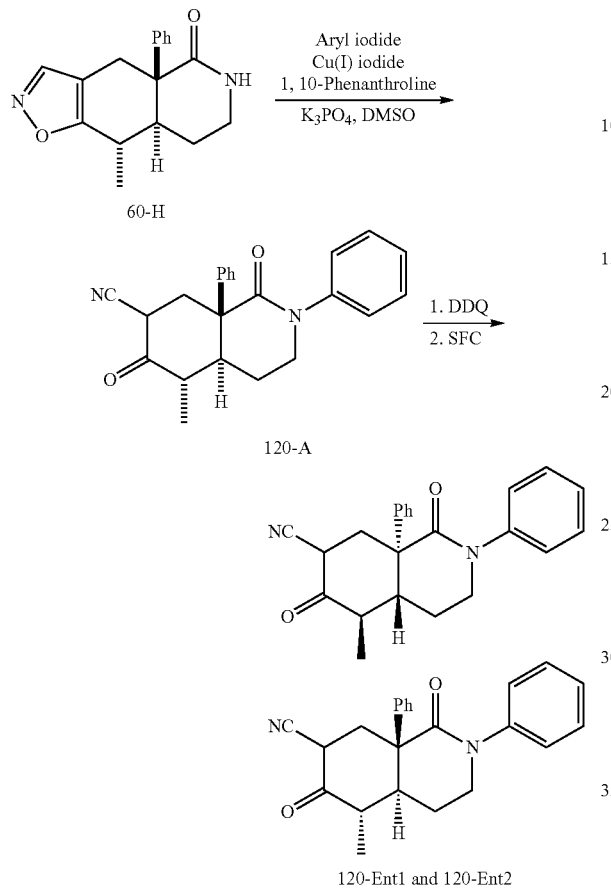

60-H

120-A

120-Ent1 and 120-Ent2

Preparation of Compound 120-A

An oven-dried flask, which was equipped with a magnetic stir bar and fitted with a septum, was charged with 60-H (96.0 mg, 338 µmol, 1.0 eq.), iodobenzene (103.2 mg, 506 µmol, 1.5 eq.), copper(I) iodide (19.2 mg, 102 µmol, 0.3 eq.), 1,10-phenanthroline (18.2 mg, 102 µmol, 0.3 eq.), $K_3PO_4$ (214.8 mg, 1012 µmol, 3.0 eq.) and DMSO (1.6 mL, 0.2 M). The reaction mixture solution was degassed with nitrogen for 5 min. The vessel was evacuated and backfilled with nitrogen (this process was repeated a total of 5 times) and was stirred at 100° C. for 24 hours. Analysis by LCMS revealed 60-H consumed completely and new peak with a mass consistent with desired product 120-A. The reaction mixture was filtered through a short pad of Celite® to remove the catalyst, and DMSO was removed under high vacuum to provide the crude mixture of compound 120-A which was used for next step without further purification.

Preparation of Compounds 120-Ent1 and 120-Ent2

To a glass vial, which was charged crude 120-A (100 mg, 212 µmol, 1.0 eq.) in Toluene (2.2 mL, 0.1 M), was added DDQ (62.6 mg, 276 µmol, 1.3 eq.). The reaction mixture was heated at 125° C. for 2 hours. After cooling to room temperature, the reaction mixture was diluted with EtOAc and washed with saturated $NaHCO_3$ solution. The aqueous phase was extracted with EtOAc (3 times) and the combined organic layers were dried over $MgSO_4$. The solvent was removed in vacuo and the residue was purified by HPLC and separated by SFC (Column: CHIRALPAK IA 30×250 mm, 5 um; Condition: 40% Methanol w/0.1% DEA in $CO_2$; Flow Rate: 100 mL/min; ABPR 120 bar; MBPR 40 psi) to give 120-Ent1 (15.3 mg, Rt=2.070 min) and 120-Ent2 (13.7 mg, Rt=3.250 min). The absolute stereochemistry was not determined.

Data for 120-Ent1
HPLC: (Purity: 98.7%)
LCMS: (M+H: 357.1)
SFC: (ee: 100%)
$^1$H NMR (500 MHz, CHLOROFORM-d) δ ppm 1.22 (d, J=6.1 Hz, 3H), 1.85-1.90 (m, 1H), 2.0-2.04 (m, 1H), 2.50-2.57 (m, 1H), 2.61-2.67 (m, 1H), 3.88-3.91 (m, 2H), 7.33-7.51 (m, 10H), 8.44 (s, 1H)

Data for 120-Ent2
HPLC: (Purity: 99.1%)
LCMS: (M+H: 357.1)
SFC: (ee: 100%)
$^1$H NMR (500 MHz, CHLOROFORM-d) δ ppm 1.22 (d, J=6.1 Hz, 3H), 1.86-1.89 (m, 1H), 2.0-2.03 (m, 1H), 2.50-2.57 (m, 1H), 2.61-2.67 (m, 1H), 3.88-3.91 (m, 2H), 7.33-7.51 (m, 10H), 8.44 (s, 1H)

Example 104: Synthesis of Compounds 121-Ent1 and 121-Ent2

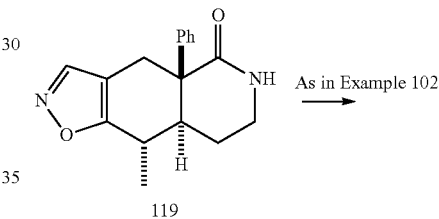

119

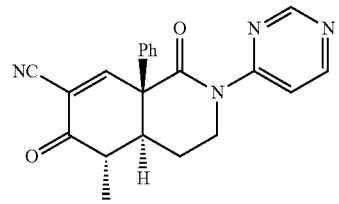

Compounds 121-Ent1 and 121-Ent2

Compounds 121-Ent1 and 121-Ent2 can be made according to Example 102.

SFC Purification: (Column: CHIRALPAK IA 30×250 mm, 5 um; Condition: 45% Ethanol w/0.1% DEA in $CO_2$; Flow Rate: 100 mL/min; ABPR 120 bar, MBPR 40 psi) to give 121-Ent1 (9.7 mg, Rt=2.926 min) and 121-Ent2 (9.9 mg, Rt=4.069). The absolute stereochemistry was not determined.

Data for 121-Ent1
HPLC: (Purity: 98.8%)
LCMS: (M: 358.1)
SFC: (ee: 100%)

$^1$H NMR (500 MHz, CHLOROFORM-d) δ ppm 1.26 (d, J=6.7 Hz, 3H), 1.87-1.94 (m, 1H), 2.20-2.23 (m, 1H), 2.54-2.60 (m, 1H), 2.63-2.69 (m, 1H), 4.16-4.20 (m, 1H), 4.35-4.38 (m, 1H), 7.23 (d, J=10.0, 2H), 7.43-7.47 (m, 3H), 8.37 (s, 1H), 8.40 (d, J=6.3 Hz, 1H), 8.75 (d, J=6.1 Hz, 1H), 9.17 (s, 1H)

Data for 121-Ent2
HPLC: (Purity: 99.7%)
LCMS: (M: 358.1)
SFC: (ee: 100%)
$^1$H NMR (500 MHz, CHLOROFORM-d) δ ppm 1.26 (d, J=6.7 Hz, 3H), 1.87-1.94 (m, 1H), 2.19-2.22 (m, 1H), 2.54-2.60 (m, 1H), 2.59-2.69 (m, 1H), 4.15-4.20 (m, 1H), 4.34-4.37 (m, 1H), 7.23 (d, J=10.0, 2H), 7.43-7.47 (m, 3H), 8.37 (s, 1H), 8.39 (d, J=6.3 Hz, 1H), 8.75 (d, J=6.1 Hz, 1H), 9.17 (s, 1H)

Example 105: Synthesis of Compounds 122-Ent1 and 122-Ent2

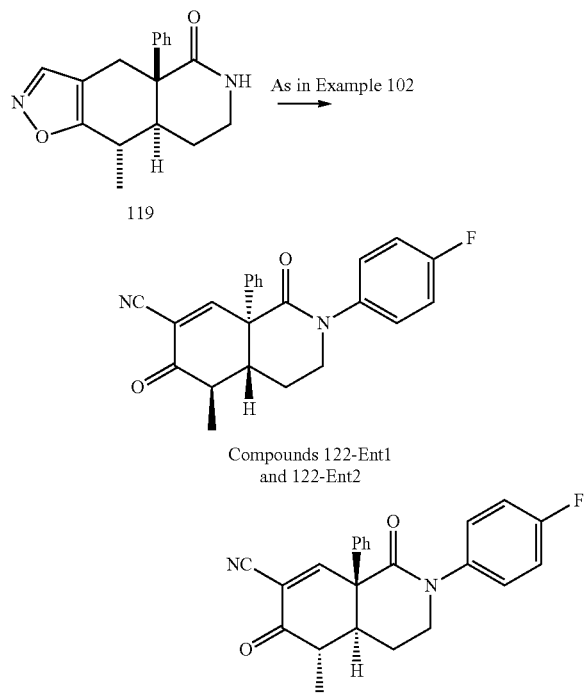

Compounds 122-Ent1 and 122-Ent2

Compounds 122-Ent1 and 122-Ent2 can be made according to Example 102.
SFC (Column: CHIRALPAK OX-H 30×250 mm, 5 um; Condition: 35% 2-Propanol w/0.1% DEA in $CO_2$; Flow Rate: 100 mL/min; ABPR 120 bar, MBPR 40 psi) to give 122-Ent1 (14.1 mg, Rt=2.324 min) and 122-Ent2 (14.8 mg, Rt=2.830). The absolute stereochemistry was not determined.
Data for 122-Ent1
HPLC: (Purity: 100%)
LCMS: (M: 374.1)
SFC: (ee: 98.02%)
$^1$H NMR (500 MHz, CHLOROFORM-d) δ ppm 1.21 (d, J=6.7 Hz, 3H), 1.83-1.90 (m, 1H), 2.0-2.04 (m, 1H), 2.49-2.56 (m, 1H), 2.60-2.65 (m, 1H) 3.85-3.88 (m, 2H) 7.15-7.19 (m, 2H) 7.30-7.34 (m, 4H), 7.41-7.49 (m, 3H), 8.42 (s, 1H)

Data for 122-Ent2
HPLC: (Purity: 99.3%)
LCMS: (M+H: 374.1)
SFC: (ee: 99.6%)
$^1$H NMR (500 MHz, CHLOROFORM-d) δ ppm 1.21 (d, J=6.7 Hz, 3H), 1.85-1.90 (m, 1H), 2.0-2.04 (m, 1H), 2.51-2.56 (m, 1H), 2.60-2.65 (m, 1H) 3.85-3.88 (m, 2H) 7.15-7.19 (m, 2H) 7.30-7.34 (m, 4H), 7.41-7.49 (m, 3H), 8.42 (s, 1H)

Example 106: Synthesis of Compounds 123-Ent1 and 123-Ent2

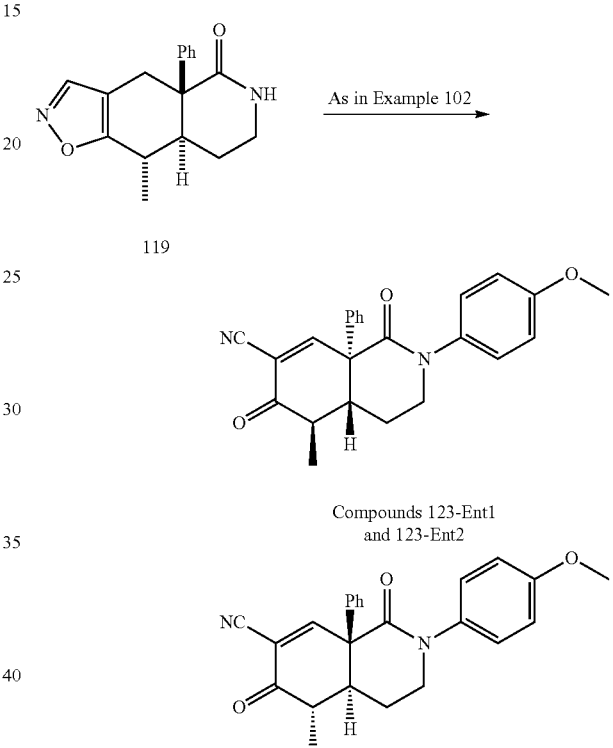

Compounds 123-Ent1 and 123-Ent2

Compounds 123-Ent1 and 123-Ent2 can be made according to Example 102. SFC (Column: CHIRALPAK IB 30×250 mm, 5 um; Condition: 25% Methanol w/0.1% DEA in $CO_2$; Flow Rate: 100 mL/min; ABPR 120 bar; MBPR 40 psi) to give 123-Ent1 (26.1 mg, Rt=2.354 min) and 123-Ent2 (25.4 mg, Rt=2.941 min). The absolute stereochemistry was not determined.
Data for 123-Ent1
HPLC: (Purity: 98.5%)
LCMS: (M+H: 387.2)
SFC: (ee: 100%)
$^1$H NMR (500 MHz, CHLOROFORM-d) δ ppm 1.21 (d, J=6.71 Hz, 3H), 1.85-1.88 (m, 1H), 1.98-2.02 (m, 1H), 2.50-2.55 (m, 1H), 2.59-2.65 (m, 1H), 3.84-3.87 (m, 2H), 3.84 (s, 3H), 6.97-7.0 (m, 2H), 7.25-7.26 (m, 1H), 7.31 (d, J=7.32 Hz, 2H), 7.40-7.48 (m, 3H) 8.44 (s, 1H)
Data for 123-Ent2
HPLC: (Purity: 100%)
LCMS: (M+H: 387.2)
SFC: (ee: 100%)
$^1$H NMR (500 MHz, CHLOROFORM-d) δ ppm 1.21 (d, J=6.71 Hz, 3H), 1.83-1.88 (m, 1H), 1.98-2.02 (m, 1H), 2.50-2.55 (m, 1H), 2.59-2.65 (m, 1H), 3.84-3.87 (m, 2H), 3.84 (s, 3H), 6.97-7.0 (m, 2H), 7.24-7.26 (m, 1H), 7.31 (d, J=7.32 Hz, 2H), 7.40-7.48 (m, 3H) 8.44 (s, 1H)

Example 107: Procedure for the Synthesis of 124-C

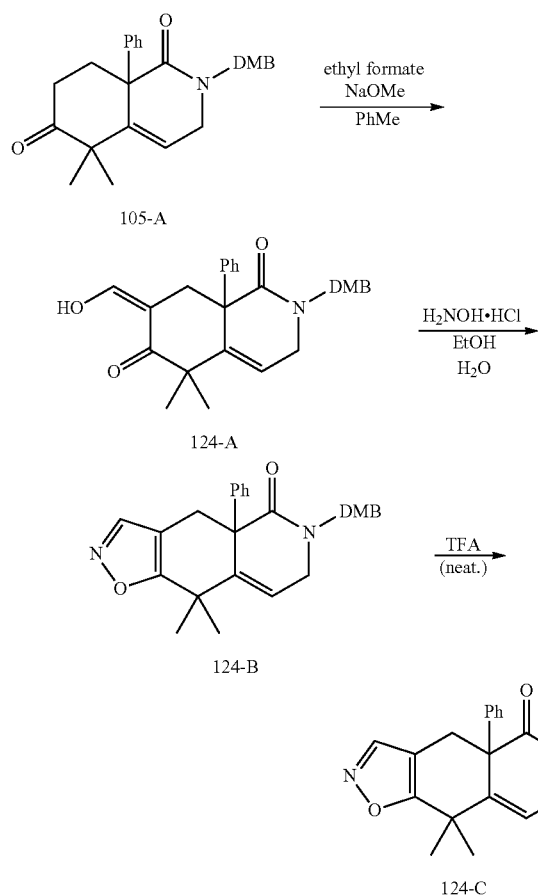

Procedure for the Synthesis of 124-A
An oven-dried flask, which was equipped with a magnetic stir bar and fitted with a septum, was charged with 105-A (2.6 g, 6.3 mmol, 1.0 eq.), ethyl formate (10.1 mL, 125.8 mmol, 20.0 eq.), sodium methoxide (4.4 M stock solution in MeOH, 5.7 mL, 25.2 mmol, 4.0 eq.) and toluene (50.0 mL, 0.12 M). The reaction mixture solution was stirred at room temperature for 16 hours. Analysis by LCMS revealed 105-A was consumed completely and new peak with a mass consistent with desired product 124-A The reaction mixture was quenched by water and acidified to pH~5 by HCl solution (1N). EtOAc was added into the aqueous solution and the layers were separated. The organic phase was washed with brine and was dried over MgSO$_4$. The solvent was removed in vacuo to provide the crude compound 124-B (2.5 g, 88.4% yield) which was used for next step without further purification.

LCMS: (M+1: 448.2)

Procedure for the Synthesis of 124-B
To a solution of crude 124-A (2.55 g, 5.7 mmol, 1.0 eq.) in ethanol/water (27 mL/1.4 mL, 95:5, 0.2 M) was added hydroxylamine hydrochloride (7.9 g, 113.4 mmol, 20.0 eq.). The solution was heated to reflux for 2 hours. Analysis by LCMS revealed 124-A consumed completely and new peak with a mass consistent with desired product 124-B. The solvent was removed, and the residue was then dissolved in NAHCO$_3$ solution (sat.). The aqueous solution was then extracted with EtOAc (30 mL, 3 times), and the combined organic layers were washed with water then dried over MgSO$_4$. The solvent was removed in vacuo to provide the crude compound 124-B (2.2 g, 87.3% yield) which was used for next step without further purification.

LCMS: (M+1: 445.2)

Procedure for the Synthesis of 124-C
Compound 124-B (2.5 g, 5.6 mmol, 1.0 eq.) was dissolved in TFA (21.3 mL, 277.7 mmol, 50.0 eq.), and the reaction mixture was heated to 85° C. for 16 hours. Analysis by LCMS revealed 124-B consumed completely and new peak with a mass consistent with desired product 124-C. The solvent was removed in vacuo, and the purple residue was taken up in minimum amount of chloroform and then subjected to column chromatography (35% to 55% to 90% EtOAc in Heptane) to provide 124-C (1.2 g, 75.4% yield) as a brown solid.

LCMS: (M: 294.1)

$^1$H NMR (500 MHz, METHANOL-d$_4$) δ ppm 0.86 (s, 3H), 1.54 (s, 3H), 2.80 (d, J=16.48 Hz, 1H), 3.88 (d, J=16.48, 2H), 4.16 (dd, J=18.62, 3.97 Hz, 1H), 4.32 (dd, J=18.92, 2.44 Hz, 1H), 6.29-6.31 (m, 1H), 7.19-7.22 (m, 1H), 7.23-7.30 (m, 4H), 8.40 (s, 1H)

Example 108: General Procedure for the Synthesis of Compounds Via Cross-Coupling

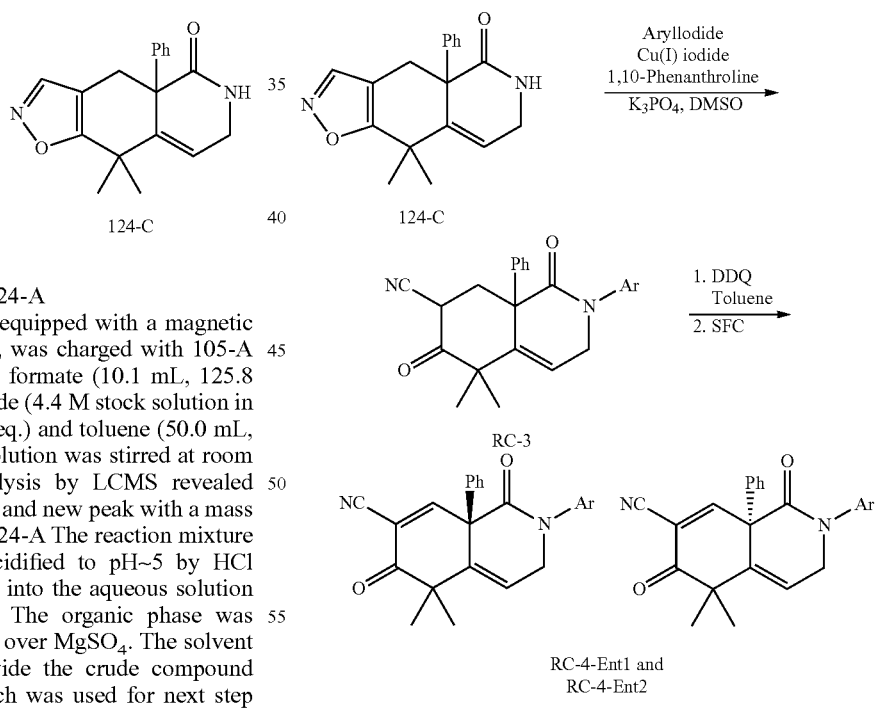

An oven-dried flask, which was equipped with a magnetic stir bar and fitted with a septum, was charged with 124-C (1.0 eq.), Aryl iodide (1.5 eq.), copper(I) iodide (0.3 eq.), 1,10-phenanthroline (0.3 eq.), K$_3$PO$_4$ (3.0 eq.) and DMSO (0.2 M). The reaction mixture solution was degassed with nitrogen for 5 min. The vessel was evacuated and backfilled with nitrogen (this process was repeated a total of 5 times) and was stirred at 100° C. for 24 hours. Analysis by LCMS revealed 124-C was consumed completely and new peak with a mass consistent with desired product RC-3. The reaction mixture was filtered through a short pad of Celite® to remove the catalyst, and DMSO was removed under high vacuum to provide the crude mixture of compound RC-3 which was used for next step without further purification.

To a glass vial, which was charged crude RC-3 (1.0 eq.) in Toluene (0.1 M), was added DDQ (1.3 eq.). The reaction mixture was heated at 125° C. for 2 hours. After cooling to room temperature, the reaction mixture was diluted with EtOAc and washed with saturated NaHCO$_3$ solution. The aqueous phase was extracted with EtOAc (3 times) and the combined organic layers were dried over MgSO$_4$. The solvent was removed in vacuo and the residue was purified by HPLC and separated by chiral SFC.

Example 109: Specific Example of Example 108; Synthesis of Compounds 124-Ent1 and 124-Ent2

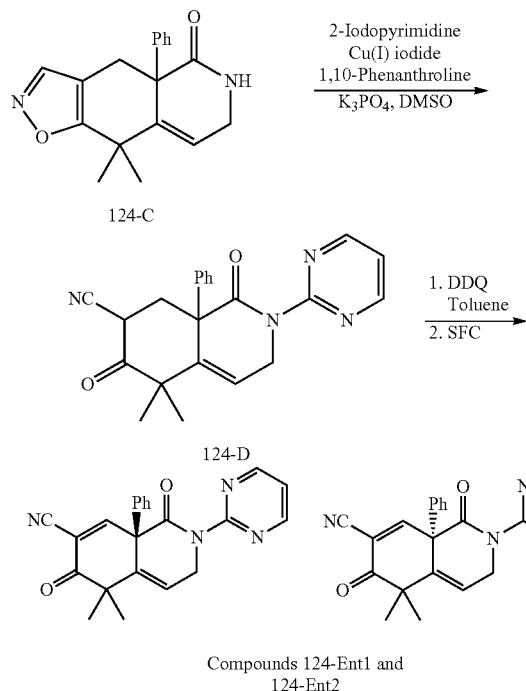

Procedure for the Synthesis of 124-D

An oven-dried flask, which was equipped with a magnetic stir bar and fitted with a septum, was charged with 124-C (100.0 mg, 340 μmol, 1.0 eq.), 2-iodopyrimidine (105.0 mg, 510 μmol, 1.5 eq.), copper(I) iodide (19.4 mg, 102 μmol, 0.3 eq.), 1,10-phenanthroline (18.4 mg, 102 μmol, 0.3 eq.), K$_3$PO$_4$ (216.4 mg, 1020 μmol, 3.0 eq.) and DMSO (1.7 mL, 0.2 M). The reaction mixture solution was degassed with nitrogen for 5 min. The vessel was evacuated and backfilled with nitrogen (this process was repeated a total of 5 times) and was stirred at 100° C. for 24 hours. Analysis by LCMS revealed 124-C consumed completely and new peak with a mass consistent with desired product 124-D. The reaction mixture was filtered through a short pad of Celite® to remove the catalyst, and DMSO was removed under high vacuum to provide the crude mixture of compound 124-D which was used for next step without further purification.

Preparation of Compound 124-Ent1 & 124-Ent2

To a glass vial, which was charged crude RC-1 (100 mg, 279 μmol, 1.0 eq.) in Toluene (2.8 mL, 0.1 M), was added DDQ (82.2 mg, 362 μmol, 1.3 eq.). The reaction mixture was heated at 125° C. for 2 hours. After cooling to room temperature, the reaction mixture was diluted with EtOAc and washed with saturated NaHCO$_3$ solution. The aqueous phase was extracted with EtOAc (3 times) and the combined organic layers were dried over MgSO$_4$. The solvent was removed in vacuo and the residue was purified by HPLC and separated by SFC (Column: CHIRALPAK IA 30×250 mm, 5 um; Condition: 40% Methanol w/0.1% DEA in CO$_2$; Flow Rate: 100 mL/min; ABPR 120 bar; MBPR 40 psi) to give 124-Ent1 (15.3 mg, Rt=2.070 min) and 124-Ent2 (13.7 mg, Rt=3.250 min). The absolute stereochemistry was not determined.

Data for 124-Ent1
HPLC: (Purity: 97.3%)
LCMS: (M+H: 371.1)
SFC: (ee: 100%)
$^1$H NMR (500 MHz, CHLOROFORM-d) δ ppm 1.06 (s, 3H), 1.51 (s, 3H), 4.44 (dd, J=18.01, 2.14 Hz, 1H), 4.79-4.84 (m, 1H), 6.40 (dd, J=6.10, 1.83 Hz, 1H), 7.17 (t, J=4.88 Hz, 1H), 7.33-7.37 (m, 1H), 7.38-7.42 (m, 2H), 7.45-7.47 (m, 2H), 8.71 (d, J=4.88 Hz, 2H), 8.74 (s, 1H)

Data for 124-Ent2
HPLC: (Purity: 98.4%)
LCMS: (M+H: 371.1)
SFC: (ee: 100%)
$^1$H NMR (500 MHz, CHLOROFORM-d) δ ppm 1.05 (s, 3H), 1.51 (s, 3H), 4.44 (dd, J=18.01, 2.14 Hz, 1H), 4.79-4.84 (m, 1H), 6.41 (dd, J=6.10, 1.83 Hz, 1H), 7.17 (t, J=4.88 Hz, 1H), 7.32-7.37 (m, 2H), 7.38-7.42 (m, 2H), 7.45-7.47 (m, 2H), 8.71 (d, J=4.88 Hz, 2H), 8.74 (s, 1H)

Example 110: Synthesis of Compounds 125-Ent1 and 125-Ent2

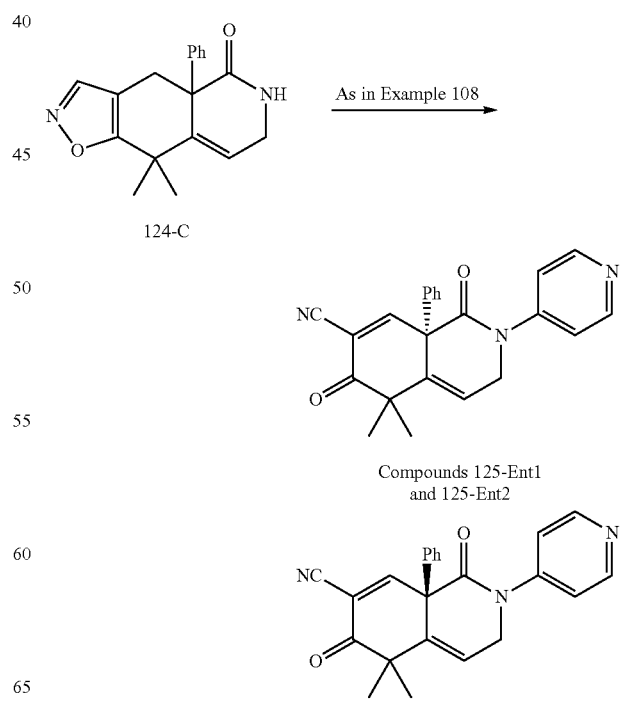

Compounds 125-Ent1 and 125-Ent2 can be made according to Example 108 SFC (Column: CHIRALPAK IA 30×250 mm, 5 um; Condition: 40% Ethanol w/0.1% DEA in CO$_2$; Flow Rate: 100 mL/min; ABPR 120 bar; MBPR 40 psi) to give 125-Ent1 (5.3 mg, Rt=2.109 min) and 125-Ent2 (5.0 mg, Rt=2.583 min). The absolute stereochemistry was not determined.

Data for 125-Ent
HPLC: (Purity: 96.4%)
LCMS: (M+H: 370.1)
SFC: (ee: 100%)
$^1$H NMR (500 MHz, CHLOROFORM-d) δ ppm 1.13 (s, 3H), 1.54 (s, 3H), 4.42-4.46 (m, 2H), 6.43-6.48 (m, 1H), 7.41-7.47 (m, 5H), 7.87 (d, J=6.1 Hz, 2H), 8.58 (s, 1H), 8.76 (d, J=6.71 Hz, 2H)

Data for 125-Ent2
HPLC: (Purity: 98.1%)
LCMS: (M+H: 370.1)
SFC: (ee: 100%)
$^1$H NMR (500 MHz, CHLOROFORM-d) δ ppm 1.13 (s, 3H), 1.54 (s, 3H), 4.44-4.46 (m, 2H), 6.43-6.48 (m, 1H), 7.39-7.47 (m, 5H), 7.87 (d, J=6.1 Hz, 2H), 8.58 (s, 1H), 8.76 (d, J=6.71 Hz, 2H)

Example 111: Synthesis of Compounds 126-Ent1 and 126-Ent2

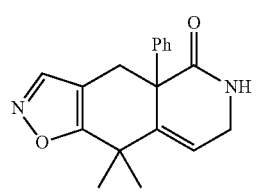

124-C

As in Example 108

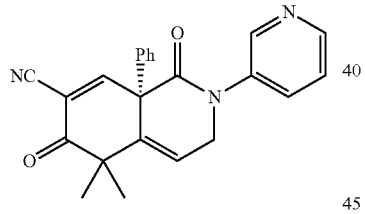

Compounds 126-Ent1 and 126-Ent2

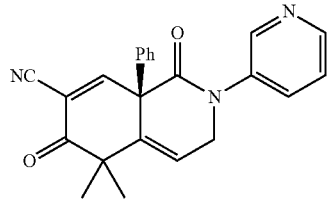

Compounds 126-Ent1 and 126-Ent2 can be made according to Example 108.
SFC (Column: CHIRALPAK IB 30×250 mm, 5 um; Condition: 30% Methanol w/0.1% DEA in CO$_2$; Flow Rate: 100 mL/min; ABPR 120 bar; MBPR 40 psi) to give 126-Ent (1.6 mg, Rt=2.617 min) and 126-Ent2 (1.3 mg, Rt=3.105 min). The absolute stereochemistry was not determined.

Data for 126-Ent1
HPLC: (Purity: 96.4%)
LCMS: (M+H: 370.1)
SFC: (ee: 100%)
$^1$H NMR (500 MHz, CHLOROFORM-d) δ ppm 1.04 (s, 3H), 1.53 (s, 3H), 4.33-4.37 (m, 1H), 4.58-4.62 (m, 1H), 6.40 (d, J=4.88 Hz, 1H), 7.33-7.49 (m, 5H), 7.70-7.73 (m, 1H), 8.19 (d, J=8.55 Hz, 1H), 8.6 (m, 1H), 8.67 (s, 1H), 8.79 (br s, 1H)

Data for 126-Ent2
HPLC: (Purity: 98.1%)
LCMS: (M+H: 370.1)
SFC: (ee: 100%)
$^1$H NMR (500 MHz, CHLOROFORM-d) δ ppm 1.04 (s, 3H), 1.53 (s, 3H), 4.32-4.36 (m, 1H), 4.57-4.61 (m, 1H), 6.41 (d, J=4.88 Hz, 1H), 7.33-7.49 (m, 5H), 7.70-7.73 (m, 1H), 8.19 (d, J=8.55 Hz, 1H), 8.6 (m, 1H), 8.67 (s, 1H), 8.79 (br s, 1H)

Example 112: Synthesis of Compounds 126-Ent1 and 126-Ent2

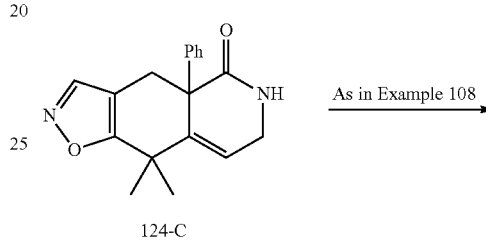

124-C

As in Example 108

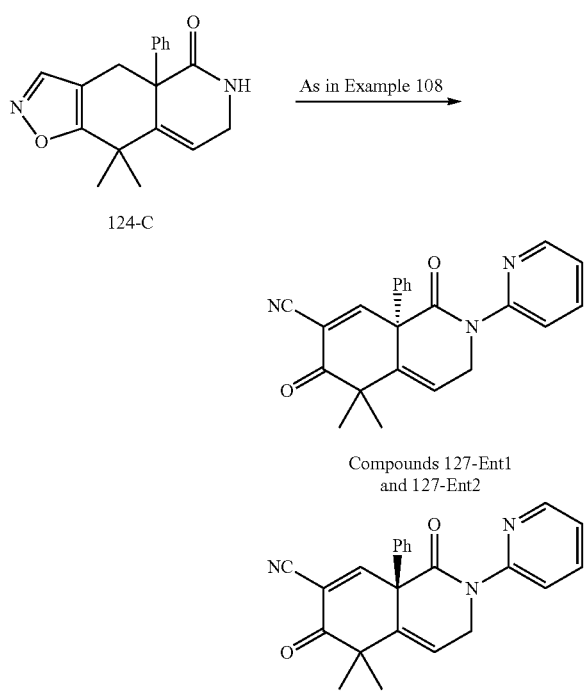

Compounds 127-Ent1 and 127-Ent2

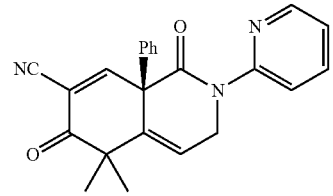

Compounds 127-Ent1 and 127-Ent2 can be made according to Example 108.
SFC (Column: CHIRALPAK IA 30×250 mm, 5 um; Condition: 40% Ethanol w/0.1% DEA in CO$_2$; Flow Rate: 100 mL/min; ABPR 120 bar; MBPR 40 psi) to give 127-Ent1 (11.5 mg, Rt=2.164 min) and 127-Ent2 (10.7 mg, Rt=3.485 min). The absolute stereochemistry was not determined.

Data for 127-Ent1
HPLC: (Purity: 97.1%)
LCMS: (M+H: 370.1)
SFC: (ee: 100%)
$^1$H NMR (500 MHz, CHLOROFORM-d) δ ppm 1.04 (s, 3H), 1.51 (s, 3H), 4.60 (d, J=3.66 Hz, 2H), 6.40 (t, J=3.97 Hz, 1H) 7.31-7.37 (m, 2H) 7.39-7.45 (m, 4H), 7.66 (d, J=7.94 Hz, 1H), 7.87-7.90 (m, 1H), 8.53 (dd, J=5.49, 1.22 Hz, 1H), 8.71 (s, 1H)

Data for 127-Ent2
HPLC: (Purity: 100%)
LCMS: (M+H: 370.1)
SFC: (ee: 100%)

¹H NMR (500 MHz, CHLOROFORM-d) δ ppm 1.04 (s, 3H), 1.51 (s, 3H), 4.60 (d, J=3.66 Hz, 2H), 6.40 (t, J=3.97 Hz, 1H) 7.31-7.37 (m, 2H) 7.39-7.46 (m, 4H), 7.66 (d, J=7.94 Hz, 1H), 7.87-7.90 (m, 1H), 8.53 (dd, J=5.49, 1.22 Hz, 1H), 8.71 (s, 1H)

Example 113: Synthesis of Compounds 128-Ent1 and 128-Ent2

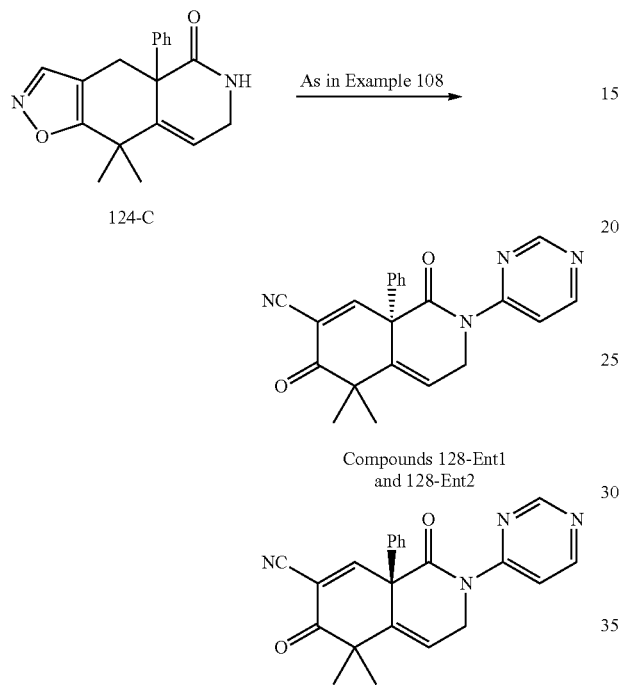

Compounds 128-Ent1 and 128-Ent2

Example 114: Synthesis of Compounds 129-Ent1 and 129-Ent2

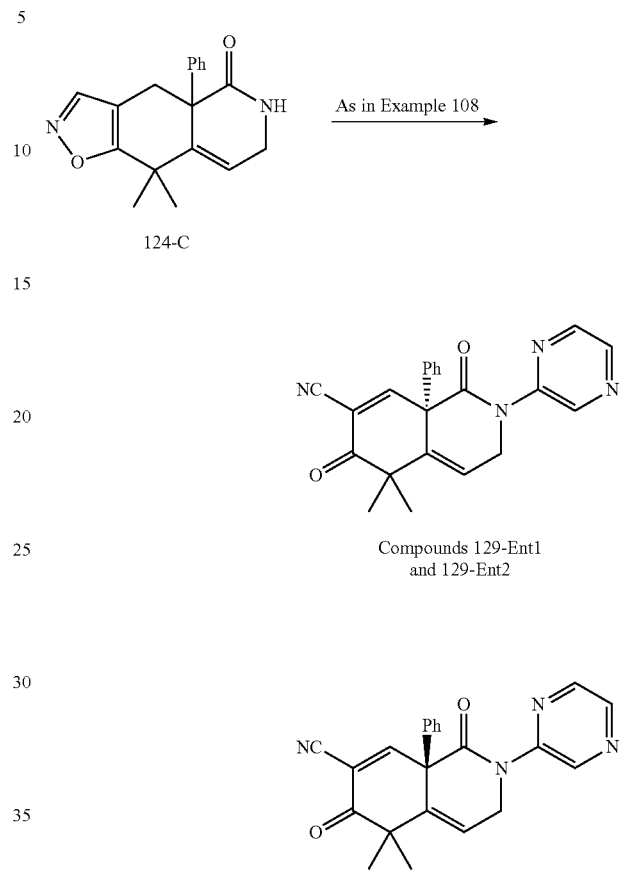

Compounds 129-Ent1 and 129-Ent2

Compounds 128-Ent1 and 128-Ent2 can be made according to Example 108.
SFC (Column: CHIRALPAK IG 30×250 mm, 5 um; Condition: 35% 2-Propanol w/0.1% DEA in CO₂; Flow Rate: 100 mL/min; ABPR 120 bar; MBPR 60 psi) to give 128-Ent1 (15.1 mg, Rt=3.152 min) and 128-Ent2 (5.3 mg, Rt=3.495 min). The absolute stereochemistry was not determined.

Data for 128-Ent1
HPLC: (Purity: 100%)
LCMS: (M+H: 370.1)
SFC: (ee: 98.3%)
¹H NMR (500 MHz, CHLOROFORM-d) δ ppm 1.10 (s, 3H), 1.53 (s, 3H), 4.29-4.33 (m, 1H), 5.01-5.06 (m, 1H), 6.45 (dd, J=6.10, 1.83 Hz, 1H), 7.36-7.47 (m, 5H), 8.24 (dd, J=6.10, 1.22 Hz, 1H), 8.63 (d, J=6.10 Hz, 1H), 8.65 (s, 1H), 9.02 (s, 1H)

Data for 128-Ent2
HPLC: (Purity: 98.1%)
LCMS: (M+H: 370.1)
SFC: (ee: 100%)
¹H NMR (500 MHz, CHLOROFORM-d) δ ppm 1.10 (s, 3H), 1.53 (s, 3H), 4.29-4.33 (m, 1H), 5.01-5.06 (m, 1H), 6.45 (dd, J=6.10, 1.83 Hz, 1H), 7.36-7.47 (m, 5H), 8.24 (dd, J=6.10, 1.22 Hz, 1H), 8.63 (d, J=6.10 Hz, 1H), 8.65 (s, 1H), 9.02 (s, 1H)

Compounds 129-Ent1 and 129-Ent2 can be made according to Example 108.
SFC (Column: CHIRALPAK IG 30×250 mm, 5 um; Condition: 40% 2-Propanol w/0.1% DEA in CO₂; Flow Rate: 100 mL/min; ABPR: 120 bar; MBPR: 60 psi) to give 129-Ent1 (2.2 mg, Rt=3.724 min) and 129-Ent2 (2.4 mg, Rt=4.555 min). The absolute stereochemistry was not determined.

Data for 129-Ent1
HPLC: (Purity: 99.6%)
LCMS: (M+H: 371.1)
SFC: (ee: 100%)
¹H NMR (500 MHz, CHLOROFORM-d) δ ppm 1.05 (s, 3H), 1.53 (s, 3H), 4.40-4.44 (m, 1H), 4.81-4.86 (m, 1H), 6.43 (dd, J=5.49, 1.83 Hz, 1H), 7.34-7.38 (m, 1H), 7.40-7.46 (m, 4H), 8.36-8.39 (m, 2H), 8.74 (s, 1H), 9.22 (s, 1H)

Data for 129-Ent2
HPLC: (Purity: 99.1%)
LCMS: (M+H: 371.1)
SFC: (ee: 99.2%)
¹H NMR (500 MHz, CHLOROFORM-d) δ ppm 1.06 (s, 3H), 1.54 (s, 3H), 4.41-4.44 (m, 1H), 4.81-4.86 (m, 1H), 6.43 (dd, J=5.49, 1.83 Hz, 1H), 7.34-7.38 (m, 1H), 7.40-7.46 (m, 4H), 8.36-8.39 (m, 2H), 8.74 (s, 1H), 9.22 (s, 1H)

Example 115: Synthesis of Compounds 130-Ent1 and 130-Ent2

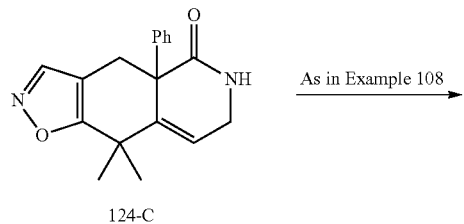

124-C

As in Example 108

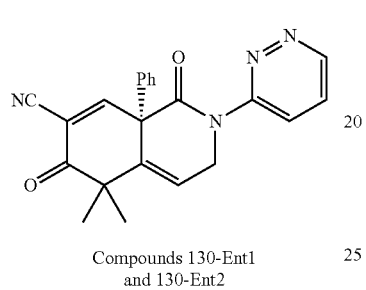

Compounds 130-Ent1 and 130-Ent2

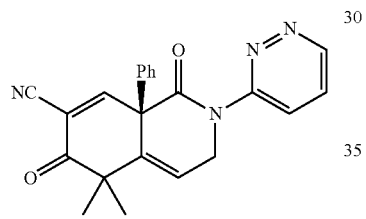

Compounds 130-Ent1 and 130-Ent2 can be made according to Example 108.

SFC (Column: CHIRALPAK IA 30×250 mm, 5 um; Condition: 40% 2-Propanol w/0.1% DEA in $CO_2$; Flow Rate: 100 mL/min; ABPR: 120 bar; MBPR: 60 psi) to give 130-Ent1 (2.3 mg, Rt=2.375 min) and 130-Ent2 (2.4 mg, Rt=3.193 min). The absolute stereochemistry was not determined.

Data for 130-Ent1

HPLC: (Purity: 94.6%)

LCMS: (M+H: 371.1)

SFC: (ee: 98.4%)

$^1$H NMR (500 MHz, CHLOROFORM-$d_3$) δ ppm 1.06 (s, 3H), 1.52 (s, 4H), 4.60-4.70 (m, 1H), 4.98-5.08 (m, 1H), 6.45-6.48 (m, 1H), 7.33-7.60 (m, 4H), 8.20-8.27 (m, 1H), 8.65-8.72 (m, 1H), 9.04 (s, 1H)

Data for 130-Ent2

HPLC: (Purity: 97.0%)

LCMS: (M+H: 371.1)

SFC: (ee: 100%)

$^1$H NMR (500 MHz, CHLOROFORM-d) δ ppm 1.06 (s, 3H), 1.52 (s, 4H), 4.60-4.70 (m, 1H), 4.98-5.08 (m, 1H), 6.45-6.48 (m, 1H), 7.33-7.60 (m, 4H), 8.20-8.27 (m, 1H), 8.65-8.72 (m, 1H), 9.04 (s, 1H)

Example 116: Synthesis of Compounds 131-Ent1 and 131-Ent2

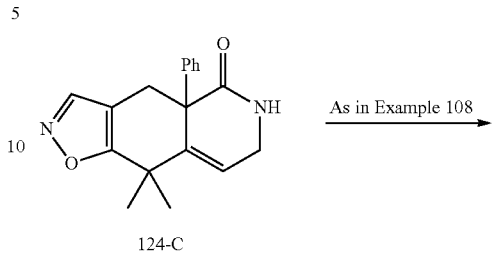

124-C

As in Example 108

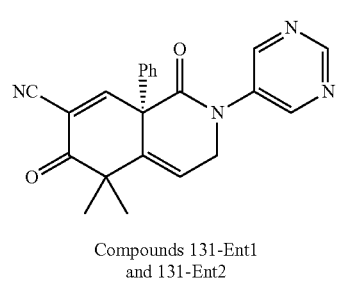

Compounds 131-Ent1 and 131-Ent2

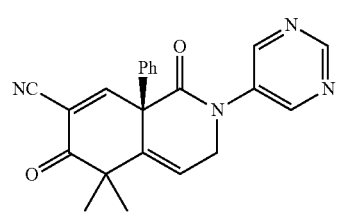

Compounds 131-Ent1 and 131-Ent2 can be made according to Example 108.

SFC (Column: CHIRALPAK IB 30×250 mm, 5 um; Condition: 15% Methanol w/0.1% DEA in $CO_2$; Flow Rate: 100 mL/min; ABPR: 120 bar; MBPR: 20 psi) to give 131-Ent1 (2.7 mg, Rt=2.228 min) and 131-Ent2 (2.6 mg, Rt=2.858 min). The absolute stereochemistry was not determined.

Data for 131-Ent1

HPLC: (Purity: 95.6%)

LCMS: (M+H: 371.1)

SFC: (ee: 98.5%)

$^1$H NMR (500 MHz, CHLOROFORM-d) δ ppm 1.03 (s, 3H), 1.52 (s, 3H), 4.28-4.32 (m, 1H), 4.54 (dd, J=17.09, 1.83 Hz, 1H), 6.39 (dd, J=5.49, 1.83 Hz, 1H), 7.38-7.42 (m, 1H), 7.43-7.46 (m, 4H), 8.69 (s, 2H), 8.70 (s, 1H), 9.10 (s, 1H)

Data for 131-Ent2

HPLC: (Purity: 98.4%)

LCMS: (M+H: 371.1)

SFC: (ee: 100%)

$^1$H NMR (500 MHz, CHLOROFORM-d) δ ppm 1.02 (s, 3H), 1.52 (s, 3H), 4.28-4.32 (m, 1H), 4.54 (dd, J=17.09, 1.83 Hz, 1H), 6.39 (dd, J=5.49, 1.83 Hz, 1H), 7.39-7.42 (m, 1H), 7.43-7.46 (m, 4H), 8.69 (s, 2H), 8.70 (s, 1H), 9.10 (s, 1H)

Example 117: Synthesis of Compounds 132-Ent1 and 132-Ent2

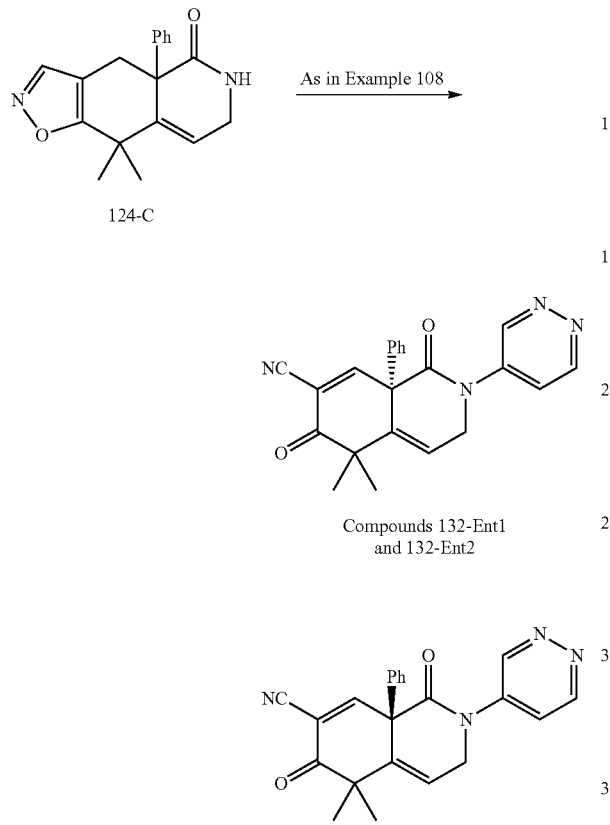

124-C

Compounds 132-Ent1 and 132-Ent2

Compounds 132-Ent1 and 132-Ent2 can be made according to Example 108.

SFC (Column: CHIRALPAK IB 30×250 mm, 5 um; Condition: 40% Ethanol w/0.1% DEA in $CO_2$; Flow Rate: 100 mL/min; ABPR: 120 bar; MBPR: 40 psi) to give 132-Ent1 (2.0 mg, Rt=2.515 min) and 132-Ent2 (2.3 mg, Rt=2.995 min). The absolute stereochemistry was not determined.

Data for 132-Ent1

HPLC: (Purity: 98.6%)

LCMS: (M: 370.1)

SFC: (ee: 100%)

$^1$H NMR (500 MHz, CHLOROFORM-d) δ ppm 1.10 (s, 3H), 1.54 (s, 3H), 4.37 (dd, J=16.48, 6.10 Hz, 1H), 4.47-4.51 (m, 1H), 6.43 (dd, J=6.10, 1.83 Hz, 1H), 7.39-7.47 (m, 5H), 7.71 (dd, J=6.10, 3.05 Hz, 1H), 8.64 (s, 1H), 9.19 (d, J=6.10 Hz 1H), 9.30 (s, 1H)

Data for 132-Ent2

HPLC: (Purity: 100%)

LCMS: (M: 370.1)

SFC: (ee: 100%)

$^1$H NMR (500 MHz, CHLOROFORM-d) δ ppm 1.10 (s, 3H), 1.54 (s, 3H), 4.37 (dd, J=16.48, 6.10 Hz, 1H), 4.47-4.51 (m, 1H), 6.43 (dd, J=6.10, 1.83 Hz, 1H), 7.39-7.47 (m, 5H), 7.72 (dd, J=6.10, 3.05 Hz, 1H), 8.64 (s, 1H), 9.19 (d, J=6.10 Hz 1H), 9.30 (s, 1H)

Example 118: Synthesis of Compounds 133-Ent1 and 133-Ent2

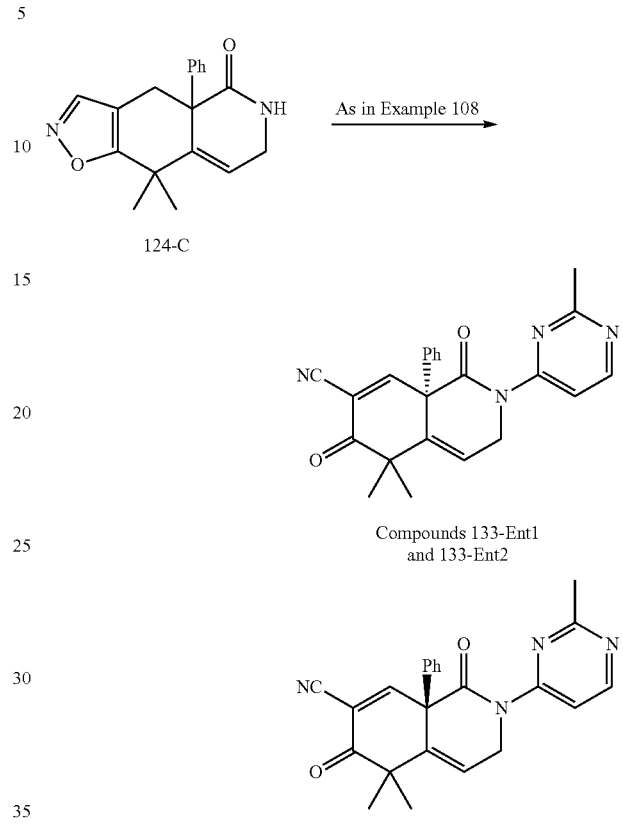

124-C

Compounds 133-Ent1 and 133-Ent2

Compounds 133-Ent1 and 133-Ent2 can be made according to Example 108.

SFC (Column: CHIRALCEL OD-H 30×250 mm, 5 um; Condition: 30% 2-Propanol w/0.1% DEA in $CO_2$; Flow Rate: 100 mL/min; ABPR: 120 bar; MBPR: 60 psi) to give 133-Ent1 (18.7 mg, Rt=2.810 min) and 133-Ent2 (17.9 mg, Rt=3.235 min). The absolute stereochemistry was not determined.

Data for 133-Ent1

HPLC: (Purity: 98.6%)

LCMS: (M+H: 385.2)

SFC: (ee: 100%)

$^1$H NMR (500 MHz, CHLOROFORM-d) δ ppm 1.14 (s, 3H), 1.54 (s, 3H), 2.79 (s, 3H), 4.28 (dd, J=18.31, 1.83 Hz, 1H), 5.06-5.11 (m, 1H), 6.46 (dd, J=6.10, 1.83 Hz, 1H), 7.37-7.46 (m, 5H), 8.32 (d, J=6.71 Hz, 1H), 8.57 (s, 1H), 8.66 (d, J=6.71 Hz, 1H)

Data for 133-Ent2

HPLC: (Purity: 100%)

LCMS: (M+H: 385.2)

SFC: (ee: 100%)

$^1$H NMR (500 MHz, CHLOROFORM-d) δ ppm 1.14 (s, 3H), 1.54 (s, 3H), 2.79 (s, 3H), 4.28 (dd, J=18.31, 1.83 Hz, 1H), 5.05-5.10 (m, 1H), 6.47 (dd, J=6.10, 1.83 Hz, 1H), 7.37-7.46 (m, 5H), 8.32 (d, J=6.71 Hz, 1H), 8.57 (s, 1H), 8.66 (d, J=6.71 Hz, 1H)

Example 119: Synthesis of Compounds 134-Ent1 and 134-Ent2

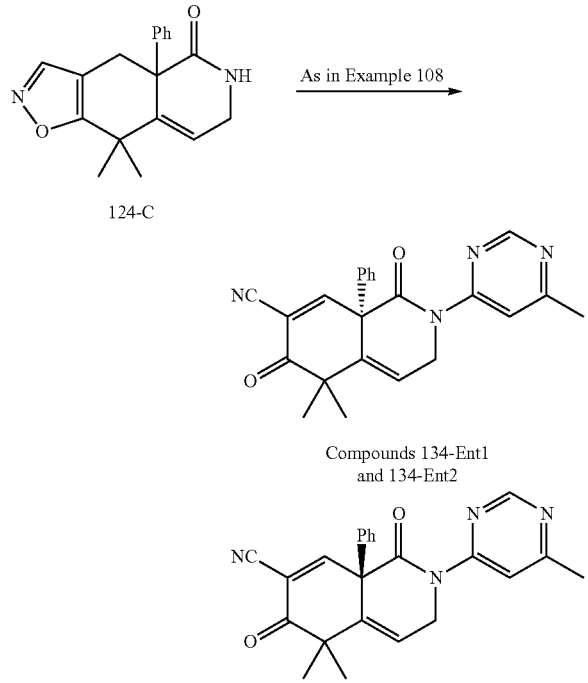

Compounds 134-Ent1 and 134-Ent2

Compounds 134-Ent1 and 134-Ent2 can be made according to Example 108.
SFC (Column: CHIRALPAK IA 30×250 mm, 5 um; Condition: 25% 2-Propanol w/0.1% DEA in $CO_2$; Flow Rate: 100 mL/min; ABPR: 120 bar; MBPR: 60 psi) to give 134-Ent1 (11.6 mg, Rt=1.642 min) and 134-Ent2 (13.6 mg, Rt=1.773 min). The absolute stereochemistry was not determined.

Data for 134-Ent1
HPLC: (Purity: 100%)
LCMS: (M+H: 385.2)
SFC: (ee: 97.2%)
$^1$H NMR (500 MHz, CHLOROFORM-d) δ ppm 1.11 (s, 3H), 1.53 (s, 3H), 2.62 (s, 3H), 4.31 (dd, J=18.31, 1.83 Hz, 1H), 5.04 (dd, J=18.92, 6.1 Hz, 1H), 6.45 (dd, J=6.1, 1.83 Hz, 1H), 7.36-7.44 (m, 5H), 8.23 (s, 1H), 8.61 (s, 1H), 9.01 (s, 1H)

Data for 134-Ent2
HPLC: (Purity: 95.6%)
LCMS: (M+H: 385.2)
SFC: (ee: 92.5%)

Example 120: Synthesis of Compounds 135-Ent1 and 135-Ent2

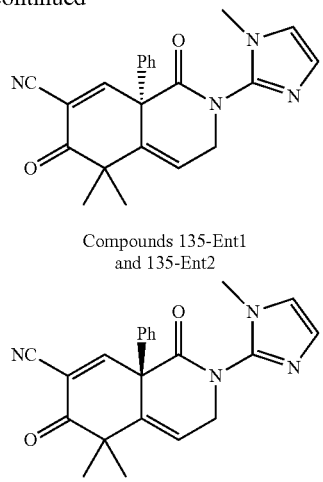

Compounds 135-Ent1 and 135-Ent2

Compounds 135-Ent1 and 135-Ent2 can be made according to Example 108.
$^1$H NMR (500 MHz, CHLOROFORM-d) δ ppm 1.12 (s, 3H), 1.53 (s, 3H), 2.62 (s, 3H), 4.31 (dd, J=18.31, 1.83 Hz, 1H), 5.04 (dd, J=18.92, 6.1 Hz, 1H), 6.45 (dd, J=6.1, 1.83 Hz, 1H), 7.36-7.44 (m, 5H), 8.23 (s, 1H), 8.61 (s, 1H), 9.01 (s, 1H) SFC (Column: CHIRALPAK IB 30×250 mm, 5 um; Condition: 40% Ethanol w/0.1% DEA in $CO_2$; Flow Rate: 100 mL/min; ABPR: 120 bar; MBPR: 40 psi) to give 135-Ent1 (3.3 mg, Rt=2.029 min) and 135-Ent2 (4.3 mg, Rt=2.450 min). The absolute stereochemistry was not determined.

Data for 135-Ent1
HPLC: (Purity: 97.7%)
LCMS: (M: 372.2)
SFC: (ee: 97.3%)
$^1$H NMR (500 MHz, CHLOROFORM-d) δ ppm 1.0 (s, 3H), 1.53 (s, 3H), 3.25 (s, 3H), 4.64-4.76 (m, 2H), 6.41 (br s, 1H), 7.0 (br s, 1H), 7.29-7.33 (m, 1H), 7.41-7.45 (m, 1H), 7.47-7.50 (m, 4H) 8.63 (s, 1H)

Data for 135-Ent2
HPLC: (Purity: 100%)
LCMS: (M: 372.2)
SFC: (ee: 92.5%)
$^1$H NMR (500 MHz, CHLOROFORM-d) δ ppm 1.0 (s, 3H), 1.53 (s, 3H), 3.25 (s, 3H), 4.64-4.76 (m, 2H), 6.41 (br s, 1H), 7.0 (br s, 1H), 7.29-7.33 (m, 1H), 7.41-7.45 (m, 1H), 7.46-7.50 (m, 4H) 8.63 (s, 1H)

Example 121: Synthesis of Compounds 136-Ent1 and 136-Ent2

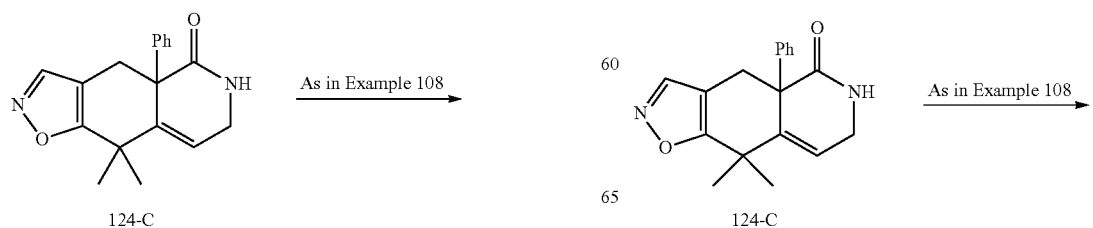

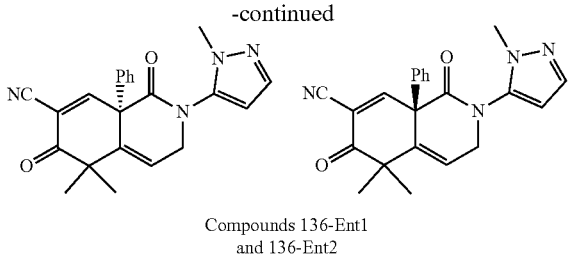

Compounds 136-Ent1
and 136-Ent2

Compounds 136-Ent1 and 136-Ent2 can be made according to Example 108.
SFC (Column: CHIRALPAK IA 30×250 mm, 5 um; Condition: 30% Ethanol w/0.1% DEA in $CO_2$; Flow Rate: 100 mL/min; ABPR: 120 bar; MBPR: 40 psi) to give 136-Ent1 (8.4 mg, Rt=1.896 min) and 136-Ent2 (8.3 mg, Rt=2.426 min). The absolute stereochemistry was not determined.
Data for 136-Ent1
  HPLC: (Purity: 95.4%)
  LCMS: (M: 372.2)
  SFC: (ee: 99.3%)
  $^1$H NMR (500 MHz, CHLOROFORM-d) δ ppm 1.0 (s, 3H), 1.52 (s, 3H), 3.20 (s, 3H), 4.27 (dd, J=18.01, 5.19 Hz, 1H), 4.38-4.42 (m, 1H), 6.14-6.17 (m, 1H), 6.35 (dd, J=5.49, 1.83 Hz, 1H), 7.37-7.42 (m, 1H), 7.44-7.49 (m, 4H), 7.53 (d, J=1.83 Hz, 1H), 8.73 (s, 1H)
Data for 136-Ent2
  HPLC: (Purity: 99.6%)
  LCMS: (M: 372.2)
  SFC: (ee: 98.9%)
  $^1$H NMR (500 MHz, CHLOROFORM-d) δ ppm 1.0 (s, 3H), 1.52 (s, 3H), 3.20 (s, 3H), 4.27 (dd, J=18.01, 5.19 Hz, 1H), 4.38-4.42 (m, 1H), 6.14-6.17 (m, 1H), 6.35 (dd, J=5.49, 1.83 Hz, 1H), 7.37-7.42 (m, 1H), 7.44-7.49 (m, 4H), 7.53 (d, J=1.83 Hz, 1H), 8.73 (s, 1H)

Example 122: Synthesis of Compounds 137-Ent1 and 137-Ent2

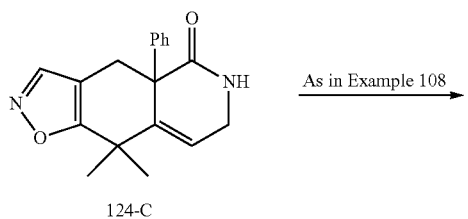

124-C

Compound 137-Ent1
and 137-Ent2

Compounds 137-Ent1 and 137-Ent2 can be made according to Example 108.
SFC (Column: CHIRALPAK IA 30×250 mm, 5 um; Condition: 40% Ethanol w/0.1% DEA in $CO_2$; Flow Rate: 100 mL/min; ABPR: 120 bar; MBPR: 40 psi) to give 137-Ent1 (13.0 mg, Rt=2.220 min) and 137-Ent2 (13.4 mg, Rt=2.669 min). The absolute stereochemistry was not determined.
Data for 137-Ent1
  HPLC: (Purity: 98.9%)
  LCMS: (M+H: 373.2)
  SFC: (ee: 100%)
  $^1$H NMR (500 MHz, CHLOROFORM-d) δ ppm 0.92 (s, 3H), 1.49 (s, 3H), 3.90 (s, 3H), 4.34 (dd, J=17.7, 5.49 Hz, 1H), 4.50 (dd, J=17.40, 2.14 Hz, 1H), 6.30 (dd, J=5.49, 1.83 Hz, 1H), 7.31-7.39 (m, 5H), 7.56 (s, 1H), 8.07 (s, 1H), 8.81 (s, 1H)
Data for 137-Ent2
  HPLC: (Purity: 100%)
  LCMS: (M+H: 373.2)
  SFC: (ee: 98.5%)
  $^1$H NMR (500 MHz, CHLOROFORM-d) δ ppm 0.93 (s, 3H), 1.49 (s, 3H), 3.90 (s, 3H), 4.34 (dd, J=17.7, 5.49 Hz, 1H), 4.50 (dd, J=17.40, 2.14 Hz, 1H), 6.30 (dd, J=5.49, 1.83 Hz, 1H), 7.32-7.37 (m, 5H), 7.56 (s, 1H), 8.07 (s, 1H), 8.81 (s, 1H)

Example 123: Synthesis of Compounds 138-Ent1 and 138-Ent2

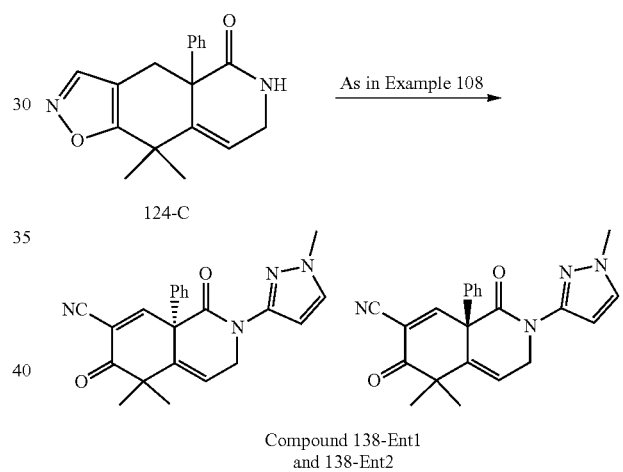

Compound 138-Ent1
and 138-Ent2

Compounds 138-Ent1 and 138-Ent2 can be made according to Example 108.
SFC (Column: CHIRALPAK IB 30×250 mm, 5 um; Condition: 25% Methanol w/0.1% DEA in $CO_2$; Flow Rate: 100 mL/min; ABPR: 120 bar; MBPR: 40 psi) to give 138-Ent1 (15.4 mg, Rt=2.046 min) and 138-Ent2 (14.8 mg, Rt=2.409 min). The absolute stereochemistry was not determined.
Data for 138-Ent1
  HPLC: (Purity: 95.2%)
  LCMS: (M: 372.2)
  SFC: (ee: 97.2%)
  $^1$H NMR (500 MHz, CHLOROFORM-d) δ ppm 0.96 (s, 3H), 1.49 (s, 3H), 3.83 (s, 3H), 4.51 (dd, J=18.62, 2.14 Hz, 1H), 4.63 (dd, J=18.62, 5.80 Hz, 1H), 6.32 (dd, J=5.49, 1.83 Hz, 1H), 6.65 (d, J=2.44 Hz, 1H), 7.27 (d, J=2.44 Hz, 1H), 7.29-7.33 (m, 1H), 7.35-7.41 (m, 4H), 8.80 (m, 1H)
Data for 138-Ent2
  HPLC: (Purity: 95.6%)
  LCMS: (M: 372.2)
  SFC: (ee: 95.4%)
  $^1$H NMR (500 MHz, CHLOROFORM-d) δ ppm 0.96 (s, 3H), 1.49 (s, 3H), 3.83 (s, 3H), 4.51 (dd, J=18.62, 2.14 Hz, 1H), 4.63 (dd, J=18.62, 5.80 Hz, 1H), 6.32 (dd, J=5.49, 1.83 Hz, 1H), 6.66 (d, J=2.44 Hz, 1H), 7.27 (d, J=2.44 Hz, 1H), 7.30-7.33 (m, 1H), 7.35-7.41 (m, 4H), 8.80 (m, 1H)

Example 124: Synthesis of Compound 166

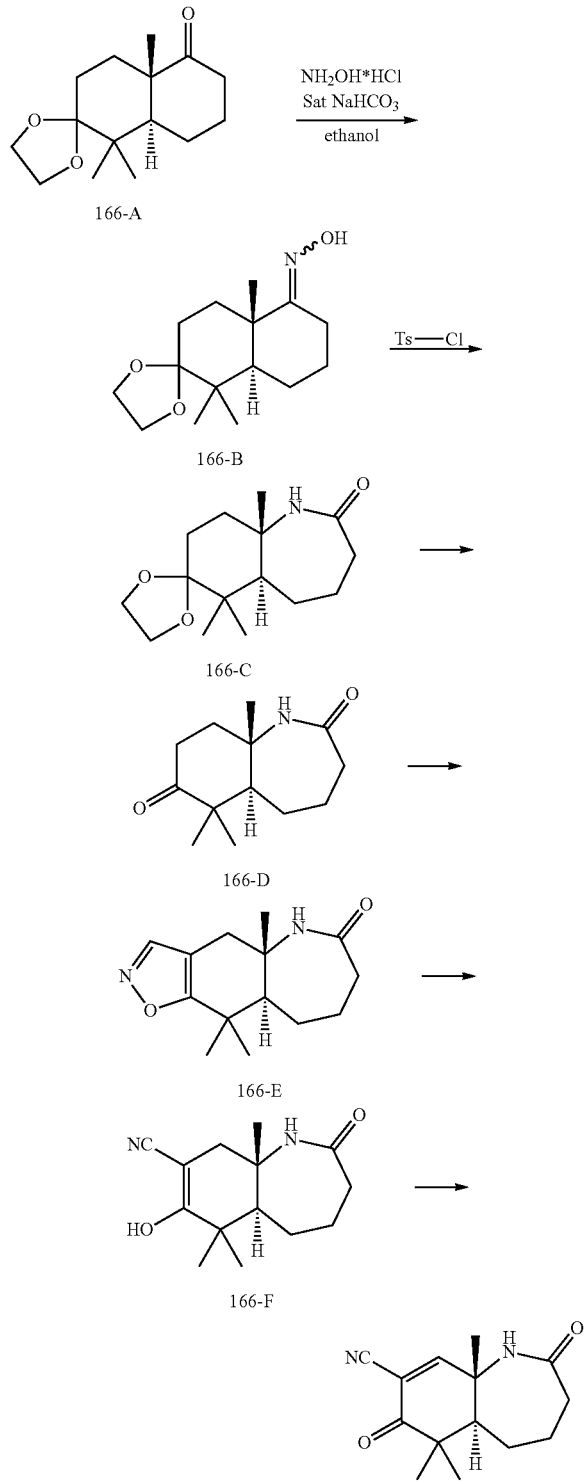

Preparation of 166-B

A solid portion of hydroxylamine hydrochloride (1.37 g, 19.72 mmol, 820.36 uL) was dissolved in ethanol (48.00 mL) and Sat NaHCO$_3$ (12.00 mL). The solution was stirred until no longer turbid. Compound 166-A (Yajima, A., Mori, K. Tetrahedron Letters, 2000, 41, p. 351-354) (1.17 g, 4.64 mmol) was added as a solid. The reaction was stirred at RT for 1.5 h then diluted with 50 mL of sat NaHCO$_3$ solution (caution: bubbling) and 200 mL of ethyl acetate. The reaction was further diluted with 50 mL brine and the layers were separated. The aq phase was extracted twice with 75 mL EtoAc and the combined organic phases were washed with brine, dried over MgSO$_4$, filtered, and concentrated to afford 1.36 g of crude 166-B which was used without further purification.

$^1$H NMR (500 MHz, DMSO-d$_6$) δ ppm 0.77 (s, 3H) 0.93 (s, 3H) 1.09 (s, 3H) 1.11-1.24 (m, 1H) 1.37 (dd, J=11.60, 3.05 Hz, 1H) 1.42-1.58 (m, 4H) 1.64-1.80 (m, 2H) 1.81-1.98 (m, 2H) 3.12 (br dd, J=14.35, 3.36 Hz, 1H) 3.32 (s, 1H) 3.73-3.84 (m, 1H) 3.84-3.95 (m, 3H) 10.16 (s, 1H)

Preparation of 166-C

A solid portion of sodium bicarbonate (3.42 g, 40.69 mmol) was added to 20 mL of water and stirred at RT for 10 min. Compound 166-B (1.36 g, 5.09 mmol) in 45 mL of acetone was added, followed by tosyl chloride (1.94 g, 10.17 mmol) in 4.5 mL of acetone. The reaction was heated to 65° C. and stirred for 2 h. An additional charge of tosyl chloride (1 eq) and sodium bicarbonate (4 eq) were added and the reaction was heated back to 65° C. After 2 h, the reaction was concentrated to remove acetone and diluted with ethyl acetate. The phases were separated and the ethyl acetate layer was washed with sat NaHCO$_3$ and brine, dried over MgSO$_4$, filtered, and concentrated. Purification on a 40 g silica gel cartridge eluted with 20-60% acetone in heptanes afforded 166-C (780.00 mg, 2.92 mmol, 57.32% yield) as the major product.

$^1$H NMR (500 MHz, CHLOROFORM-d) δ ppm 0.83-1.00 (m, 6H) 1.44-1.50 (m, 3H) 1.52-1.71 (m, 5H) 1.73-1.83 (m, 2H) 1.87-2.00 (m, 3H) 2.50-2.58 (m, 2H) 3.91-4.04 (m, 4H) 5.59 (br s, 1H).

Preparation of 166-D

Compound 166-C (230.00 mg, 860.26 umol) was dissolved in 4 mL THF and treated with 2 mL of 1N HCL and allowed to stir overnight. The reaction was diluted with 20 mL brine and 60 mL EtOAc. The layers were separated and the aq. layer was extracted with 20 mL EtOAc. The combined organic phases were washed with sat NaHCO$_3$ and brine, dried over MgSO$_4$, filtered, and concentrated to afford a white solid (180 mg).

$^1$H NMR (500 MHz, CHLOROFORM-d) δ ppm 1.06 (s, 3H) 1.17 (s, 3H) 1.60-1.66 (m, 4H) 1.77-2.09 (m, 6H) 2.39 (dt, J=15.26, 3.97 Hz, 1H) 2.56-2.65 (m, 2H) 2.70 (td, J=14.80, 5.19 Hz, 1H) 5.67 (br s, 1H)

Preparation of 166-E:

Compound 166-D (180.00 mg, 806.05 umol) and ethyl formate (1.19 g, 16.12 mmol, 1.30 mL) were combined and treated with sodium methoxide (4.3 M, 749.81 uL) and allowed to stir overnight. The reaction was quenched by the addition of 3.2 mL of 1N HCl and extracted with ethyl acetate. The organic phase was washed with brine, dried over MgSO$_4$, filtered, and concentrated to afford a waxy solid. The solid was dissolved in 4 mL ethanol and 1 mL water and treated with hydroxylamine hydrochloride (180.83 mg, 2.60 mmol, 108.28 uL) and stirred overnight. The reaction was concentrated to remove ethanol. The reaction was further diluted with ethyl acetate and washed with sat NaHCO$_3$ and brine, dried over MgSO$_4$, filtered, and concentrated to afford 166-E (215.00 mg, 865.82 umol, 99.82% yield) as a white solid.

$^1$H NMR (400 MHz, DMSO-$d_6$) δ ppm 8.40 (s, 1H) 7.07 (s, 1H) 2.54-2.69 (m, 2H) 2.27-2.48 (m, 2H) 1.96-2.07 (m, 1H) 1.79-1.95 (m, 2H) 1.63-1.76 (m, 1H) 1.37-1.52 (m, 2H) 1.30 (s, 3H) 1.20 (s, 3H) 1.14-1.17 (m, 3H).

Preparation of 166-F:

Compound 166-E (215.00 mg, 865.82 umol) was dissolved in 5 mL methanol and treated with sodium methoxide (4.3 M, 805.41 uL). The color of the reaction was noted to change from red then green, then yellow. After 3 days, the reaction was quenched by addition of 3.5 mL of 1N HCl and concentrated to remove methanol. The organic phase was partioned between ethyl acetate and brine. The layers were separated and the organic phase dried over MgSO$_4$, filtered, and concentrated. The crude material was carried onto the next step.

Preparation of 166:

Crude compound 166-F (215.00 mg, 865.82 umol) in 10 mL of benzene was heated to reflux with DDQ (216.20 mg, 952.40 umol). After 2 h, the reaction was cooled to RT, filtered through Celite™ and rinsed with 10 mL of benzene. The filtrate was concentrated and deposited on silica gel (1.2 g). Purified by column chromatography three times—twice using 30-50% acetone in heptane on 12 g column, the final purification using 90-100% ethyl acetate in heptane on a 4 g silica gel column. Isolated 166 (56.00 mg, 227.37 umol, 26.26% yield, 100% purity) as a yellow/orange solid.

HPLC purity: >99%
LCMS: (M+H) 247.1
ee: unknown $^1$H NMR (500 MHz, DMSO-d6) δ ppm 0.96-1.02 (m, 3H) 1.18 (s, 3H) 1.39-1.52 (m, 1H) 1.54-1.60 (m, 3H) 1.76-1.96 (m, 3H) 2.12-2.21 (m, 1H) 2.31 (br s, 1H) 2.57 (ddd, J=15.11, 12.97, 1.83 Hz, 1H) 7.74 (s, 1H) 7.80 (s, 1H).

Example 125: Synthesis of Compound 167

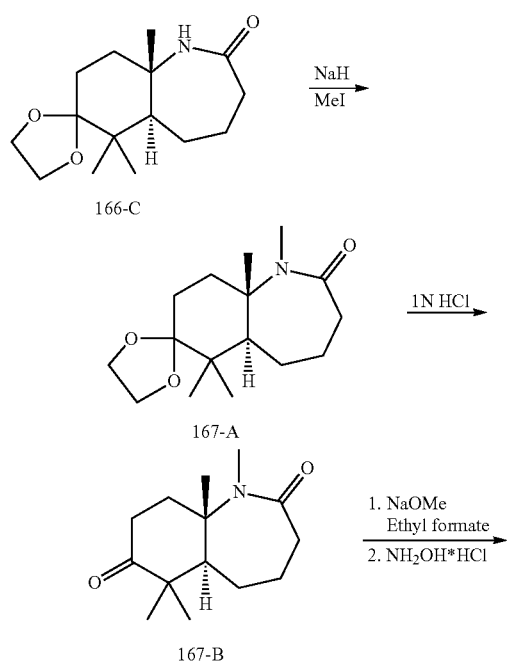

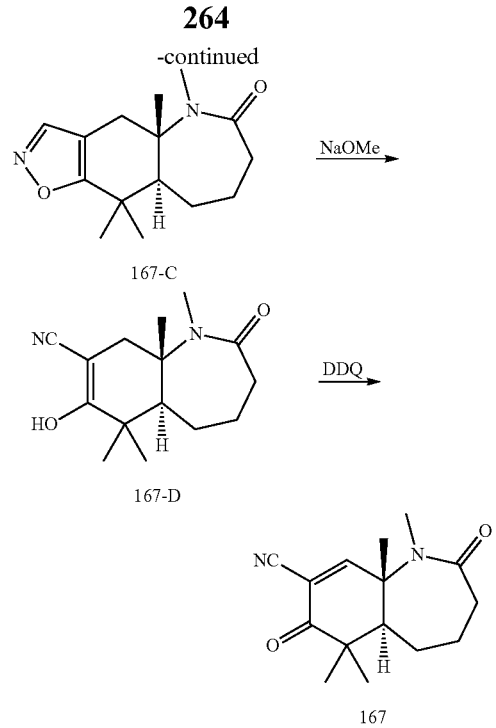

Preparation of 167-A

To a suspension of Sodium hydride, 60% dispersion in mineral oil (44.00 mg, 1.10 mmol) in THF (1.1 mL) was added 166-C (268.00 mg, 1.00 mmol) in 4 mL THF. The reaction was allowed to stir at RT for 1 h. Added iodomethane (177.43 mg, 1.25 mmol, 77.82 uL) was added and the reaction was allowed to stir overnight. The reaction was quenched by addition of sat NH$_4$Cl solution, extracted with ethyl acetate, and washed with brine. The organic phases were dried over MgSO$_4$, filtered, and concentrated. The crude reaction mixture was deposited on 1.5 g silica gel and eluted on 12 g silica gel column with 30-50% acetone in heptanes to afford 167-A as a white solid.

$^1$H NMR (500 MHz, CHLOROFORM-d) δ ppm 0.95 (s, 3H) 1.05 (s, 3H) 1.37 (s, 3H) 1.52 (dt, J=13.73, 4.12 Hz, 1H) 1.66-1.85 (m, 5H) 1.87-2.06 (m, 2H) 2.21-2.29 (m, 1H) 2.47-2.66 (m, 2H) 2.82 (s, 3H) 3.80-4.04 (m, 4H).

Preparation of 167-B

Compound 167-A (225.00 mg, 799.60 umol) was dissolved in 4 mL THF and treated with 2 mL of 1N HCL and allowed to stir overnight. The reaction was diluted with 20 mL brine and 60 mL EtOAc and the layers were separated. The aqueous layer was extracted with 20 mL EtOAc. The combined organic phases were washed with sat. NaHCO$_3$ and brine, dried over MgSO$_4$, filtered, and concentrated to afford a white crystalline solid called 167-B (190.00 mg, 800.54 umol, 100.12% yield).

$^1$H NMR (500 MHz, CHLOROFORM-d) δ ppm 2.92 (s, 3H) 2.69-2.78 (m, 1H) 2.58-2.65 (m, 1H) 2.47-2.57 (m, 1H) 2.33-2.44 (m, 1H) 2.08-2.28 (m, 3H) 1.73-1.94 (m, 4H) 1.54 (s, 3H) 1.19 (s, 3H) 1.14 (s, 3H).

Preparation of 167-C:

Compound 167-B (180.00 mg, 758.41 umol) and ethyl formate (1.12 g, 15.17 mmol, 1.22 mL) were combined and treated with sodium methoxide (4.3 M, 705.49 uL) and allowed to stir overnight. The reaction was quenched by the addition of 3.2 mL of 1N HCl and extracted with ethyl acetate. The organic phase was washed with brine, dried over MgSO$_4$, filtered, and concentrated to afford a yellow oil. The yellow oil (200.00 mg, 753.72 umol) was dissolved in 4 mL ethanol and 1 mL water. To this solution was added hydroxylamine hydrochloride (157.13 mg, 2.26 mmol, 94.09 uL) and stirred overnight. The reaction was concentrated to remove ethanol and then diluted with ethyl acetate. The organic phase was washed with sat NaHCO$_3$ and brine, then dried over MgSO$_4$, filtered, and concentrated to afford 167-C as a white solid.

LCMS (M+H)=263.1

Preparation of 167-D

Compound 167-C (200.00 mg, 762.34 umol) was dissolved in 5 mL methanol and treated with sodium methoxide (4.3 M, 709.15 uL) and allowed to stir at RT. After 3 days, the reaction was quenched by addition of 3.5 mL of 1N HCl and concentrated to remove methanol. The organic phase was partitioned between ethyl acetate and brine. The layers were separated and the organic phase dried over MgSO$_4$, filtered, and concentrated. The crude material (167-D) was carried onto the next step.

LCMS (M+H)=263.1

Preparation of 167

Crude compound 167-D (140.00 mg, 533.64 umol) was dissolved in 6 mL of anhydrous benzene and treated with DDQ and heated to reflux for 1 h. The reaction was concentrated and purified by two silica gel columns using 35% acetone in heptane to afford 167 (58.00 mg, 222.79 umol, 41.75% yield, 100% purity).

$^1$H NMR (500 MHz, DMSO-d6) δ ppm 0.97 (s, 3H) 1.17 (s, 3H) 1.31-1.47 (m, 1H) 1.71 (s, 3H) 1.82-2.00 (m, 3H) 2.13-2.23 (m, 1H) 2.42 (dd, J=15.57, 4.58 Hz, 1H) 2.78-2.97 (m, 4H) 8.17 (s, 1H).

LCMS (M+H)=261.1

Ee: unknown

HPLC Purity>99%

Examples 126 to 132 are intentionally deleted.

Example 133: Synthesis of Compound 149

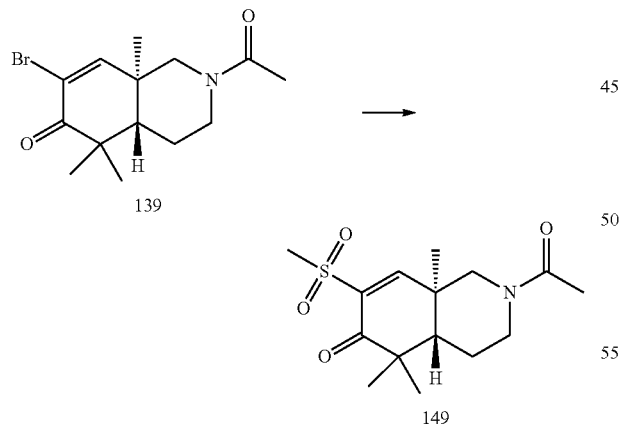

To a solution of compound 139 (107.90 mg, 343.39 umol) in DMF (936.42 mg, 12.81 mmol, 996.19 uL) was added sodium methanesulfinate (157.76 mg, 1.55 mmol) and Copper(I) iodide (98.10 mg, 515.09 umol, 17.46 uL). Reaction mixture was degassed under an atmosphere of nitrogen and stirred at 135° C. for overnight. Added EtOAc then washed with NaHCO$_{3(aq)}$, H$_2$O, and Brine. The organic layer was dried over sodium sulfate and solvent removed in vacuo. The residue was purified by reversed phase chromatography (C-18) to yield compound (149 (18.1 mg, 17% yld) as an off white solid powder.

LCMS: ESI-MS (M+H)+: 314.1

$^1$H NMR (500 MHz, CHLOROFORM-d) δ 7.74-7.81 (m, 1H), 4.89-4.95 (m, 0.36H), 4.70 (dd, J=1.83, 12.21 Hz, 0.52H), 4.06 (td, J=2.14, 13.43 Hz, 0.54H), 3.74 (dd, J=1.83, 12.82 Hz, 0.36H), 3.20 (d, J=3.66 Hz, 3H), 3.13-3.19 (m, 0.44H), 3.09-3.13 (m, 0.66H), 2.54 (d, J=12.21 Hz, 1H), 2.24 (s, 3H), 1.94 (br s, 1H), 1.64-1.82 (m, 2H), 1.25 (s, 4H), 1.20-1.22 (m, 2H), 1.14 (s, 3H)

Example 134: Procedure for the Synthesis of Compounds 150-Ent1 and 150-Ent2

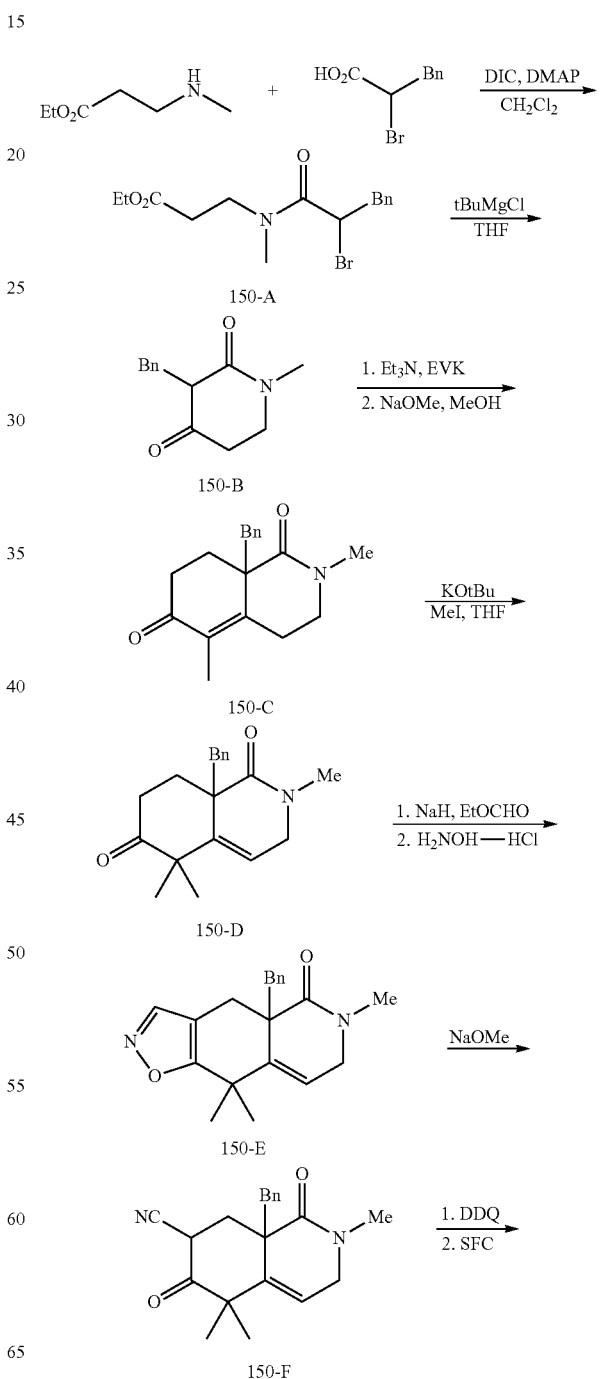

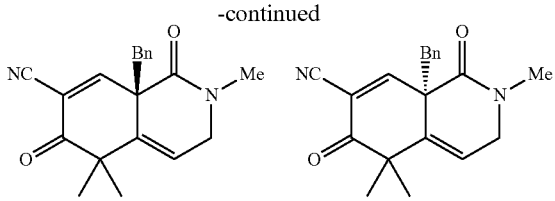

Compounds 150-Ent1
and 150-Ent2

Procedure for Preparation of Compound 150-A
To a solution of ethyl 3-(methylamino)propanoate (10.00 g, 76.24 mmol), 2-bromo-3-phenyl-propanoic acid (17.46 g, 76.24 mmol), and DMAP (931.39 mg, 7.62 mmol) in DCM (381.20 mL) was added DIC (10.58 g, 83.86 mmol, 12.90 mL) at 0° C. The reaction was warmed to room temperature and stirred for 24 hours. The mixture was then quenched upon addition of water. The layers were separated and the aqueous layer was extracted 2× with DCM. The combined organic layers were dried over sodium sulfate, filtered, and concentrated then purified by flash chromatography (5-40% EtOAc/heptane) to provide 7.14 g (27% yield) of 150-A as an apparent mixture of amide rotomers.

$^1$HNMR (500 MHz, CDCl$_3$) δ ppm 7.36-7.28 (m, 3H), 7.27-7.20 (m, 2H), 4.87-4.80 (m, 1H, minor rotamer), 4.56 (dd, J=6.7, 8.5 Hz, 1H, major rotamer), 4.15-4.06 (m, 2H), 3.76 (td, J=7.4, 15.1 Hz, 1H, minor rotamer), 3.64-3.53 (m, 2H), 3.36 (ddd, J=5.5, 7.3, 15.3 Hz, 1H, minor rotamer), 3.31-3.20 (m, 1H), 3.00 (s, 3H, major rotamer), 2.92 (s, 3H, minor rotamer), 2.59-2.49 (m, 2H), 2.43-2.32 (m, 1H, minor rotamer), 1.34-1.15 (m, 3H, major rotamer), 0.89 (t, J=7.0 Hz, 3H, minor rotamer).

Procedure for Preparation of Compound 150-B
THF (30.62 mL) was added to an oven dried flask under nitrogen. The solution was heated to 60° C. and a solution of 150-A (6.55 g, 19.14 mmol) in THF (45.94 mL) was added simultaneously with a 2M solution of tert-butyl (chloro)magnesium (23.93 mL) in ethyl ether. The mixture was then stirred at 60° C. for 2 h then cooled to room temperature. The mixture was diluted with saturated ammonium chloride solution and extracted with EtOAc (3×). The combined organic layers were washed with brine, dried over sodium sulfate, filtered, and concentrated. The residue was purified by flash chromatography (5-50% EtOAc/heptane) to obtain 1.96 g (47% yield) of 150-B as a white solid which appeared as a mixture of tautomers by $^1$H NMR.

$^1$HNMR (500 MHz, CDCl$_3$) δ ppm 7.31-7.18 (m, 5H), 3.74 (s, 1H, minor tautomer), 3.48-3.28 (m, 4H, major and minor tautomers), 3.02 (s, 3H, major tautomer), 2.99 (s, 3H, minor tautomer), 2.98-2.90 (m, 1H, major and minor tautomers), 2.78 (d, J=4.9 Hz, 1H, minor tautomer), 2.62-2.37 (m, 2H, major and minor tautomers).

Procedure for Preparation of Compound 150-C
To a solution of 150-B (1.96 g, 9.02 mmol) in acetonitrile (18.04 mL) was added triethylamine (2.50 mL, 18.04 mmol) and ethyl vinyl ketone (1.07 mL, 10.82 mmol). The mixture was heated to 75° C. overnight then concentrated. The residue was then dissolved in MeOH (45 mL) at room temperature under nitrogen and NaOMe (4.37 M, 2.48 mL) was added. The mixture was then stirred for 15 hours at which point a saturated, aqueous solution of ammonium chloride was added followed by EtOAc. The layers were separated and the aqueous layer was extracted with EtOAc (2×). The combined organic layers were dried over sodium sulfate, filtered, and concentrated. The residue was then purified by flash chromatography (5-60% EtOAc/Heptane) to provide 150-C as a red oil (750 mg, 29% yield).

$^1$HNMR (500 MHz, CDCl$_3$) δ ppm 7.26-7.22 (m, 3H), 7.10-7.03 (m, 2H), 3.45 (d, J=12.8 Hz, 1H), 3.19 (ddd, J=4.3, 11.0, 12.2 Hz, 1H), 3.01 (br d, J=13.4 Hz, 2H), 2.98 (s, 3H), 2.71-2.57 (m, 2H), 2.55-2.48 (m, 2H), 2.04 (dt, J=5.5, 13.4 Hz, 1H), 1.82 (s, 3H), 1.69-1.62 (m, 1H).

Procedure for Preparation of Compound 150-D
To a solution of 150-C (750.00 mg, 2.65 mmol) in THF (16.56 mL) was added potassium tert-butoxide (1 M in THF, 3.18 mL) slowly at 0° C. The resulting solution was stirred at 0° C. for 60 minutes. Iodomethane (376.14 mg, 2.65 mmol, 165 uL) was then added and the suspension was slowly warmed to room temperature and stirred at this temperature overnight. The mixture was quenched by addition of saturated aqueous ammonium chloride and diluted with EtOAc. The layers were separated and the aqueous layer was extracted with EtOAc (3×). The combined organic layers were washed with brine then dried over sodium sulfate, filtered, and concentrated. The material was then purified by flash chromatography (5-50% EtOAc/heptanes) to obtain 441.5 mg (56% yield) of 150-D.

$^1$HNMR (500 MHz, CDCl$_3$) δ ppm 7.23-7.19 (m, 3H), 7.06-7.01 (m, 2H), 5.69 (dd, J=1.8, 5.5 Hz, 1H), 3.18 (dd, J=5.5, 17.1 Hz, 1H), 3.00 (d, J=12.8 Hz, 1H), 2.72-2.68 (m, 4H), 2.66-2.48 (m, 4H), 2.24 (dd, J=1.5, 17.4 Hz, 1H), 1.51 (s, 3H), 1.34 (s, 3H).

Procedure for Preparation of Compound 150-E
150-D (440.14 mg, 1.48 mmol) was dissolved in ethyl formate (2.38 mL, 29.60 mmol) and treated with sodium methoxide (4.37 M in methanol, 1.35 mL). The mixture was diluted with toluene (21.14 mL) and stirred for 16 hrs. Water was then added followed by 1M HCl to adjust the pH to ~5. The mixture was then concentrated to remove methanol before ethyl acetate was then added and the layers were separated. The organic phase was washed with brine then dried over sodium sulfate, filtered, and concentrated. The crude residue was then used in the next step without further purification. LCMS: (M+H=326.1). To a solution of 8a-benzyl-2,5,5-trimethyl-1,6-dioxo-1,2,3,5,6,7,8,8a-octahydroisoquinoline-7-carbaldehyde (482 mg, 1.48 mmol) in ethanol (6.87 mL) and water (0.53 mL) was added hydroxylamine hydrochloride (1.03 g, 14.80 mmol). The solution was stirred under reflux for 2 hours. The solvent was removed to provide a solid. The solid was then dissolved in saturated aqueous sodium bicarbonate and ethyl acetate. The layers were then separated and the organic layer was washed with water then dried over sodium sulfate, filtered, and concentrated. The crude 150-E was then used in the next step without further purification.

LCMS: (M+H=323.2)

Procedure for Preparation of Compound 150-F
To a solution of 150-E (477 mg, 1.48 mmol) in ether (14.8 mL) under nitrogen was added sodium methoxide (4.37 M in methanol, 1.69 mL) at room temperature. The mixture was stirred at this temperature for 4 hrs then diluted with EtOAc then washed with 5% HCl solution (2×) then washed with water and brine before being dried over sodium sulfate then filtered and concentrated. The crude 150-F obtained was used in the next step in the sequence without further purification.

LCMS: (M+H=323.1)

Procedure for Preparation of Compounds 150-Ent1 and 150-Ent2
Compound 150-F (477 mg, 1.48 mmol) was dissolved in DMF (12.9 mL) and cooled to 0° C. 1,3-dibromo-5,5-dimethyl-imidazolidine-2,4-dione (254 mg, 888 umol) was added and the mixture was stirred for 1.5 hours at this temperature. Pyridine (2.00 mL) was then added and the mixture was heated to 60° C. for 4 hours. The mixture was then cooled to room temperature and concentrated. The material was then purified by column chromatography to obtain 254.6 mg (53% yield) of the desired product. The racemate was then separated by SFC (Column: CHIRALPAK IA 30×250 mm, 5 um; method: 25% Methanol in $CO_2$ (flow rate: 100 mL/min), ABPR 120 bar, MBPR 20 psi) to obtain 150-Ent1 (46 mg, Rt=1.83 min) and 150-Ent2 (61.4 mg, Rt=2.18 min) as off-white solids.

Data for 150-Ent1

HPLC: (Purity: 98%)

LCMS: (M+H=321.1)

SFC: (ee: 100%)

$^1$HNMR (500 MHz, $CDCl_3$) δ ppm 8.39 (s, 1H), 7.30-7.35 (m, 1H), 7.27-7.30 (m, 2H), 7.10-7.17 (m, 2H), 5.85 (dd, J=5.80, 1.53 Hz, 1H), 3.34 (d, J=12.82 Hz, 1H), 3.21 (dd, J=17.70, 6.10 Hz, 1H), 2.97 (d, J=12.82 Hz, 1H), 2.70 (s, 3H), 2.23 (dd, J=17.70, 1.83 Hz, 1H), 1.65 (s, 3H), 1.45 (s, 3H).

Data for 150-Ent2

HPLC: (Purity: 98%)

LCMS: (M+H=321.1)

SFC: (ee: 100%)

$^1$HNMR (500 MHz, $CDCl_3$) δ ppm 8.39 (s, 1H), 7.27-7.35 (m, 2H), 7.26 (s, 1H), 7.12-7.16 (m, 2H), 5.85 (dd, J=6.10, 1.83 Hz, 1H), 3.34 (d, J=12.82 Hz, 1H), 3.22 (dd, J=17.70, 6.10 Hz, 1H), 2.97 (d, J=12.82 Hz, 1H), 2.70 (s, 3H), 2.23 (dd, J=18.01, 1.53 Hz, 1H), 1.65 (s, 3H), 1.45 (s, 3H).

Example 135: Synthesis of Compound 151-Ent1 and 151-Ent2

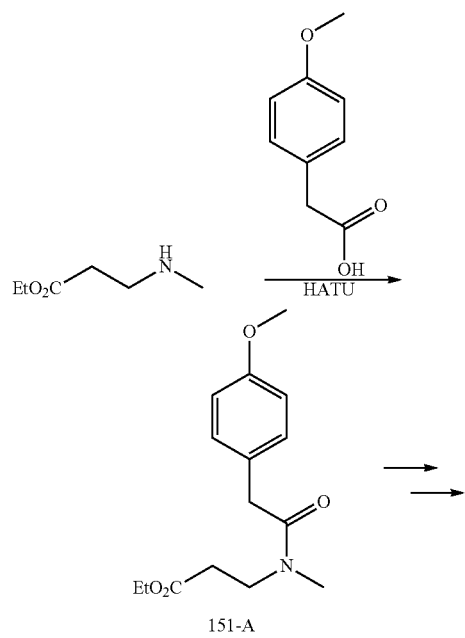

151-A

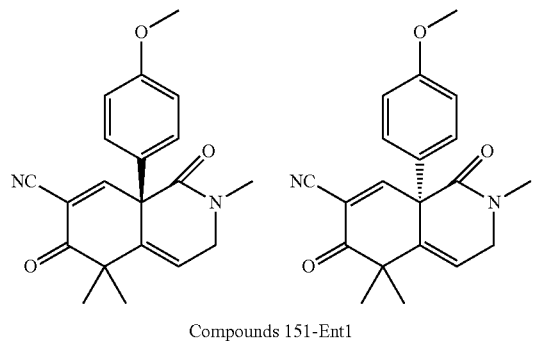

Compounds 151-Ent1 and 151-Ent2

Compounds 151-Ent1 and 151-Ent2 can be synthesized in a manner analogous to that described for compounds 70-Ent1 and 70-Ent2.

Procedure for the Synthesis of 151-A:

To a solution of ethyl 3-(methylamino)propanoate (5.1 g, 39 mmol), 2-(4-methoxyphenyl)acetic acid (7.1 g, 43 mmol) and HATU (17.4 g, 46 mmol) in DCM (50 mL) was added TEA (7.8 g, 76 mmol). The mixture was stirred at rt for 3 h. The mixture was poured into water (50 mL), extracted with DCM (50 mL×3). The combined organic layer was dried and concentrated. The residue was purified by silica gel column (PE:EA=5:1) to give 151-A (9.5 g, Y: 87%) as a brown oil.

LCMS: (M+H=280.1)

Procedure for the Purification and Chiral Separation of Compounds 151-Ent1 and 151-Ent2

Following DDQ oxidation, the reaction was concentrated and the residue was then purified by column chromatography (10-75% EtOAc/Heptane). The product (79.9 mg, 30% yield) was isolated as an oil which was then separated by SFC (Column: CHIRALPAK IC 30×250 mm, 5 um; Method: 40% Methanol in $CO_2$ [flow rate: 100 mL/min], ABPR 120 bar, MBPR 40 psi) to provide 151-Ent1 (13.3 mg, Rt=2.74 min) and 151-Ent2 (15.9 mg, Rt=3.55 min) as off-white solids.

Data for 151-Ent1

HPLC: (Purity: 95%)

LCMS: (M+H=337.1)

SFC: (ee: 100%)

$^1$HNMR (500 MHz, $CDCl_3$)$_6$ ppm 8.80 (s, 1H), 7.25-7.22 (m, 2H), 6.91-6.86 (m, 2H), 6.15 (dd, J=5.5, 1.8 Hz, 1H), 4.19 (dd, J=18.3, 1.8 Hz, 1H), 3.92 (dd, J=18.3, 5.5 Hz, 1H), 3.80 (s, 3H), 2.97 (s, 3H), 1.44 (s, 3H), 0.89 (s, 3H).

Data for 151-Ent2

HPLC: (Purity: 99%)

LCMS: (M+H=337.1)

SFC: (ee: 100%)

$^1$HNMR (500 MHz, $CDCl_3$)$_6$ ppm 8.80 (s, 1H) 7.22-7.25 (m, 2H) 6.85-6.91 (m, 2H) 6.15 (dd, J=5.49, 1.83 Hz, 1H) 4.19 (dd, J=18.31, 1.83 Hz, 1H) 3.92 (dd, J=18.31, 5.49 Hz, 1H) 3.80 (s, 3H) 2.97 (s, 3H) 1.44 (s, 3H) 0.89 (s, 3H).

Example 136: Synthesis of Compounds 151-Ent1 and 151-Ent2

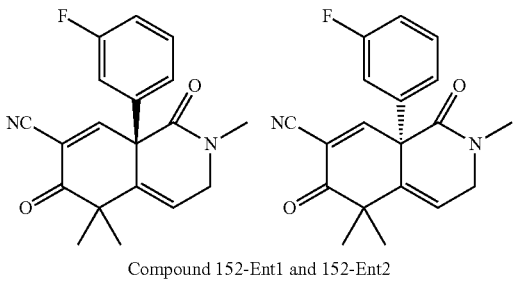

Compound 152-Ent1 and 152-Ent2

Compounds 152-Ent2 and 152-Ent2 can be synthesized in a manner analogous to that described for compounds 151-Ent1 and 151-Ent2, starting with 3-fluorophenylacetic acid. Purification and Chiral Separation of Compounds 152-Ent1 and 152-Ent2:

After reaction completion, the final DDQ oxidation reaction was filtered and concentrated. The residue was then purified by column chromatography (10-75% EtOAc/Heptane, 12 g column). The product was isolated as an oil (126 mg, 20% yield) which was then separated by SFC (Column: CHIRALPAK IA 30×250 mm, 5 um; method: 15% Methanol in $CO_2$ (flow rate: 100 mL/min), ABPR 120 bar, MBPR 20 psi) to provide 152-Ent1 (18.1 mg, Rt=2.24 min) and 152-Ent2 (19.5 mg, Rt=2.79 min) as pale yellow solids.

Data for 152-Ent1
  HPLC: (Purity: 97%)
  LCMS: (M+H=325.2)
  SFC: (ee: 100%)
  $^1$HNMR (500 MHz, $CDCl_3$) δ ppm 8.76 (s, 1H), 7.37 (dt, J=5.8, 8.4 Hz, 1H), 7.15 (dd, J=1.8, 7.9 Hz, 1H), 7.06-7.01 (m, 2H), 6.20 (dd, J=2.1, 5.2 Hz, 1H), 4.24 (dd, J=1.8, 18.9 Hz, 1H), 3.96 (dd, J=4.9, 18.3 Hz, 1H), 2.98 (s, 3H), 1.45 (s, 3H), 0.87 (s, 3H).

Data for 152-Ent2
  HPLC: (Purity: 98%)
  LCMS: (M+H=325.2)
  SFC: (ee: 100%)
  $^1$HNMR (500 MHz, $CDCl_3$) δ ppm 8.76 (s, 1H), 7.40-7.34 (m, 1H), 7.15 (dd, J=1.8, 7.9 Hz, 1H), 7.06-7.01 (m, 2H), 6.20 (dd, J=2.1, 5.2 Hz, 1H), 4.24 (dd, J=1.8, 18.9 Hz, 1H), 3.96 (dd, J=4.3, 18.9 Hz, 1H), 2.98 (s, 3H), 1.45 (s, 3H), 0.87 (s, 3H).

Example 137: Synthesis of Compounds 153-Ent1 and 153-Ent2

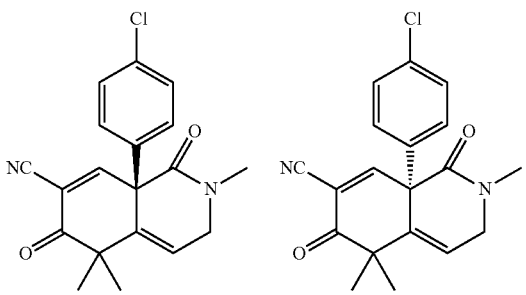

Compounds 153-Ent1 and 153-Ent2

Compounds 153-Ent2 and 153-Ent2 can be synthesized in a manner analogous to that described for compounds 151-Ent1 and 151-Ent2, starting with 4-chlorophenylacetic acid. Purification and Chiral Separation of Compounds 153-Ent1 and 153-Ent2:

After reaction completion, the final DDQ oxidation reaction was filtered and concentrated. The residue was then purified by column chromatography. The product (331 mg, 59% yield) was isolated as an oil which was then separated by SFC (Column: CHIRALPAK IA 30×250 mm, 5 um; Method: 40% Methanol in $CO_2$ (flow rate: 100 mL/min), ABPR 120 bar, MBPR 40 psi) to provide 153-Ent1 (69.1 mg, Rt=1.76 min) and 153-Ent2 (65.3 mg, Rt=2.18 min) at white solids.

Data for 153-Ent1
  HPLC: (Purity: 100%)
  LCMS: (M+H=341.1)
  SFC: (ee: 100%)
  $^1$HNMR (400 MHz, $CDCl_3$) δ ppm 8.76 (s, 1H), 7.33-7.38 (m, 2H), 7.27-7.30 (m, 2H), 6.19 (dd, J=5.27, 2.01 Hz, 1H), 4.20 (dd, J=18.57, 2.01 Hz, 1H), 3.95 (dd, J=18.45, 5.15 Hz, 1H), 2.97 (s, 3H), 1.44 (s, 3H), 0.87 (s, 3H).

Data for 153-Ent2
  HPLC: (Purity: 100%)
  LCMS: (M+H=341.1)
  SFC: (ee: 100%)
  $^1$HNMR (400 MHz, $CDCl_3$) δ ppm 8.76 (s, 1H), 7.33-7.39 (m, 2H), 7.27-7.30 (m, 2H), 6.19 (dd, J=5.27, 2.01 Hz, 1H), 4.20 (dd, J=18.57, 2.01 Hz, 1H), 3.95 (dd, J=18.45, 5.15 Hz, 1H), 2.97 (s, 3H), 1.44 (s, 3H), 0.87 (s, 3H).

Example 138: Synthesis of Compounds 154-Ent1 and 154-Ent2

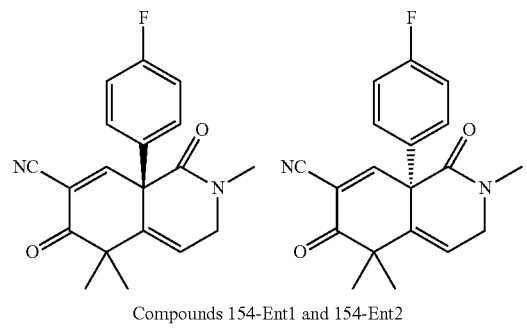

Compounds 154-Ent1 and 154-Ent2

Compounds 154-Ent2 and 154-Ent2 can be synthesized in a manner analgous to that described for compounds 151-Ent1 and 151-Ent2, starting with 4-fluorophenylacetic acid. Purification and Chiral Separation of Compounds 154-Ent1 and 154-Ent2:

After reaction completion, the final DDQ oxidation reaction was filtered and concentrated. The residue was then purified by column chromatography to obtain 232 mg (41% yield) of the desired product as an oil which was then separated by SFC (Column: CHIRALPAK IC 30×250 mm, 5 um; Method: 30% Methanol in $CO_2$ (flow rate: 100 mL/min), ABPR 120 bar, MBPR 40 psi) to obtain 154-Ent1 (35.2 mg, Rt=2.47 min) and 154-Ent2 (36.1 mg, Rt=3.00 min) as off-white solids.

Data for 154-Ent1
  HPLC: (Purity: 100%)
  LCMS: (M+H=325.1)
  SFC: (ee: 100%)

¹HNMR (500 MHz, CDCl₃) δ ppm 8.78 (s, 1H), 7.28-7.36 (m, 2H), 7.04-7.10 (m, 2H), 6.15-6.23 (m, 1H), 4.20 (dd, J=18.92, 2.44 Hz, 1H), 3.95 (dd, J=18.31, 5.49 Hz, 1H), 2.98 (s, 3H), 1.45 (s, 3H), 0.87 (s, 3H).

Data for 154-Ent2
  HPLC: (Purity: 100%)
  LCMS: (M+H=325.1)
  SFC: (ee: 100%)
  ¹HNMR (500 MHz, CDCl₃) δ ppm 8.78 (s, 1H), 7.30-7.34 (m, 2H), 7.05-7.10 (m, 2H), 6.18 (dd, J=5.19, 2.14 Hz, 1H), 4.20 (dd, J=18.31, 2.44 Hz, 1H), 3.95 (dd, J=18.31, 5.49 Hz, 1H), 2.98 (s, 3H), 1.45 (s, 3H), 0.87 (s, 3H).

Example 139: Synthesis of Compound 155-Ent1

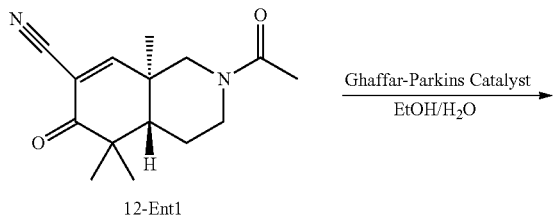

12-Ent1

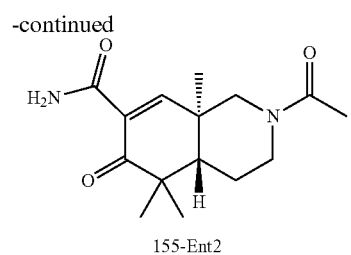

155-Ent1

Compound 12-Ent1 (80.00 mg, 307.30 umol) was dissolved in a solution of ethanol (2.00 mL) and water (500.00 uL) Hydrido(dimethylphosphinous acid-kP)[hydrogen bis(dimethylphosphinito-kP)]platinum(II) Ghaffar-Parkins catalyst (39.57 mg, 92.19 umol) was added and the reaction was heated to 80° C. for 18 hrs. The reaction was filtered and the filtrate washed with 10 ml of methanol. Solvent was removed in vacuo. Purification by column chromatography with 0-10% MeOH in CH2Cl2 afforded the desired compound 155-Ent1 in 65% yield.

LCMS: ESI-MS (M+H)⁺: 279.2.

¹H NMR (400 MHz, CHLOROFORM-d) δ 8.45 (br d, J=10.54 Hz, 1H), 7.95-8.14 (m, 1H), 5.71 (br s, 1H), 4.80-5.00 (m, 0.5H), 4.67 (dd, J=1.88, 12.67 Hz, 0.5H), 4.02 (td, J=2.20, 13.43 Hz, 0.5H), 3.68 (dd, J=1.76, 13.05 Hz, 0.5H), 2.96-3.15 (m, 1H), 2.45 (br d, J=12.55 Hz, 1H), 2.14 (d, J=15.31 Hz, 3H), 1.81-1.94 (m, 1H), 1.60-1.76 (m, 2H), 1.07-1.27 (m, 9H).

Example 140: Synthesis of Compound 155-Ent2

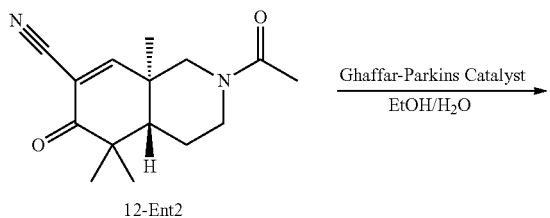

12-Ent2

155-Ent2

Compound 155-Ent2 was made in a manner analogous to that described for 155-Ent1.

LCMS: ESI-MS (M+H)+: 279.1

¹H NMR (400 MHz, CHLOROFORM-d) δ 8.44 (br d, J=8.78 Hz, 1H), 7.90-8.11 (m, 1H), 7.90-8.11 (m, 1H), 5.81 (br s, 1H), 4.81-4.97 (m, 0.5H), 4.67 (dd, J=1.76, 12.55 Hz, 0.5H), 4.02 (td, J=2.13, 13.30 Hz, 0.5H), 3.68 (dd, J=1.88, 12.93 Hz, 0.5H), 2.95-3.15 (m, 1H), 2.40-2.59 (m, 1H), 2.15 (d, J=15.31 Hz, 3H), 1.83-1.96 (m, 1H), 1.60-1.76 (m, 2H), 1.07-1.27 (m, 9H).

Example 141: Synthesis of Compound 156

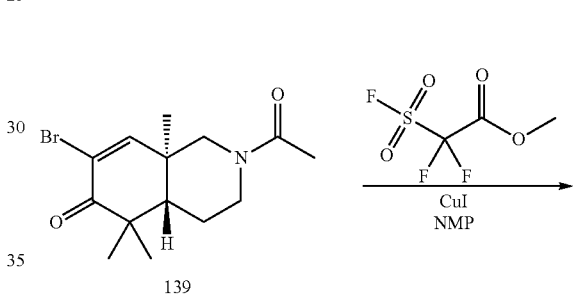

139

156

Compound 139 (55.00 mg, 175.04 umol) and Copper(I) iodide (40.00 mg, 210.04 umol) were dissolved in anhydrous NMP (1.00 mL) in an flame dried vial under a nitrogen atmosphere. Methyl 2,2-difluoro-2-(fluorosulfonyl)acetate (218.57 mg, 1.14 mmol, 144.75 uL) was added and the reaction heated to 80° C. for 6 hrs. Heating was turned down to 70° C. and the reaction stirred overnight. The crude reaction mixture was dilutes with EtOAc and filtered. Purification by reverse phase HPLC: 20% acetonitrile and linear gradient to 50% acetonitrile over 15 min in 0.1% TFA modifier (flow rate: 80 mL/min) afforded the desired compound 156 in 30% yield.

LCMS: ESI-MS (M+H)⁺: 304.0

¹H NMR (400 MHz, CHLOROFORM-d) δ 7.49 (d, J=11.04 Hz, 1H), 4.71-4.81 (m, 0.5H), 4.54 (dd, J=2.26, 12.55 Hz, 0.5H), 4.05-4.18 (m, 0.5H), 3.90 (dd, J=2.13, 13.18 Hz, 0.5H), 2.97-3.20 (m, 1H), 2.48-2.66 (m, 1H), 2.15 (d, J=16.56 Hz, 3H), 1.93-2.09 (m, 1H), 1.57-1.88 (m, 2H), 1.14-1.35 (m, 6H), 1.09 (d, J=1.51 Hz, 3H).

Examples 142 and 143 are intentionally deleted.

Example 144: Synthesis of Compounds 159 Ent1 and 159 Ent2

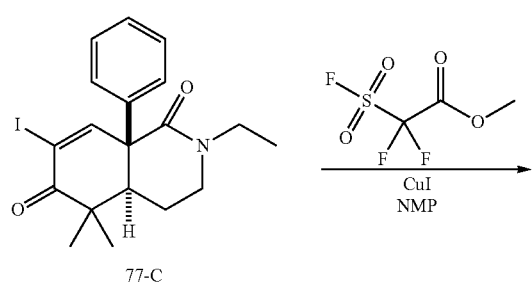

77-C

Compounds 159-Ent1 and 159-Ent2

Compound of 77-C was added to a flame dried vial. Copper (I) iodide (48.59 mg, 255.14 umol, 8.65 uL), anhydrous NMP (5.00 mL) and Methyl 2,2-difluoro-2-(fluorosulfonyl)acetate (265.50 mg, 1.38 mmol, 175.83 uL) were added. Nitrogen gas was bubbled through the reaction mixture for 5 minutes and the reaction was sealed and heated to 80° C. for 6 hrs. Heating was turned down to 70° C. and the reaction stirred overnight. The crude reaction mixture was diluted with EtOAc and filtered. Purification by reverse phase HPLC: 20% acetonitrile and linear gradient to 50% acetonitrile over 15 min in 0.1% TFA modifier (flow rate: 80 mL/min) separated the dimethyl and monomethyl products. Further purification of each set of isomers on a CHIRALPAK IG 30×250 mm, 5 um Column (15% Methanol (no modifier) in $CO_2$ (flow rate: 100 mL/min), ABPR 120 bar, MBPR 40 psi) afforded three clean products 159-Ent1 and 159-Ent2.

Compound 159-Ent1

LCMS: ESI-MS (M+H)+: 366.1.

$^1$H NMR (400 MHz, Methanol-d4) δ 8.20 (s, 1H), 7.25-7.47 (m, 3H), 7.08-7.25 (m, 2H), 3.72-3.86 (m, 1H), 3.56-3.73 (m, 2H), 3.34-3.52 (m, 1H), 2.58 (dd, J=2.51, 13.30 Hz, 1H), 2.09 (ddt, J=7.03, 12.05, 13.55 Hz, 1H), 1.90 (ddd, J=2.51, 6.46, 13.87 Hz, 1H), 1.26 (t, J=7.15 Hz, 3H), 1.15 (s, 3H), 0.49 (s, 3H).

Compound 159-Ent2

LCMS: ESI-MS (M+H)$^+$: 366.1.

$^1$H NMR (400 MHz, METHANOL-d$_4$) δ 8.20 (s, 1H), 7.29-7.45 (m, 3H), 7.10-7.26 (m, 2H), 3.73-3.83 (m, 1H), 3.55-3.70 (m, 2H), 3.32-3.49 (m, 1H), 2.58 (dd, J=2.51, 13.30 Hz, 1H), 2.09 (ddt, J=7.03, 12.05, 13.55 Hz, 1H), 1.90 (ddd, J=2.51, 6.53, 13.80 Hz, 1H), 1.26 (t, J=7.15 Hz, 3H), 1.15 (s, 3H), 0.49 (s, 3H)

Example 145: Synthesis of Compounds 161-Ent1 and 161-Ent2

69-D → (CeCl$_3$·7H$_2$O, NaBH$_4$)

161-A → (Bu$_2$PO$_4$H, Et$_2$Zn, CH$_2$I$_2$)

161-B → (Dess-Martin)

161-C → (NaOMe, Ethyl Formate)

161-D → (NH$_2$OH·HCl)

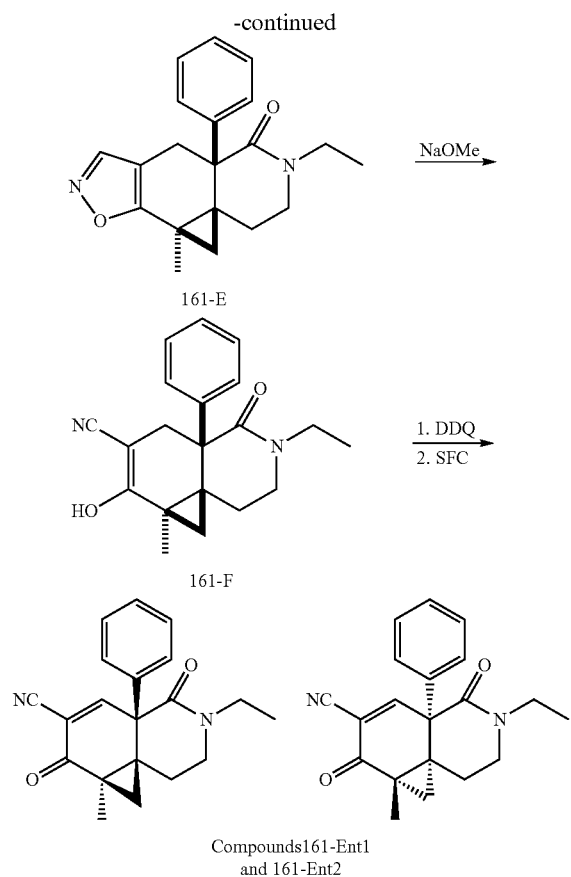

Compounds 161-Ent1 and 161-Ent2

Preparation of Compound 161-A
Compound 69-D (325.00 mg, 1.15 mmol) and Cerium(III) chloride heptahydrate (428.47 mg, 1.15 mmol, 2.88 mL) were combined in 11.5 mL of methanol and cooled to −10° C. using an ice/salt bath. To the reaction was added Sodium borohydride (87.01 mg, 2.30 mmol) and the reaction was allowed to stir at −10° C. Ultimately warmed to +10° C. over ~3 h, quenched by addition of water and stirred overnight. The solvent was removed in vacuo. The reaction was partioned between ethyl acetate and 0.1N HCl. The aqueous layer was extracted with ethyl acetate and the combined organic phases and dried over MgSO$_4$, filtered, and concentrated to a pale white solid. The material was taken on to the next step without further purification.

$^1$H NMR (500 MHz, CHLOROFORM-d) δ ppm 1.00-1.07 (m, 3H) 1.30-1.39 (m, 1H) 1.87 (s, 3H) 1.88-1.94 (m, 1H) 2.04 (ddd, J=13.89, 5.34, 2.75 Hz, 1H) 2.27 (td, J=13.73, 2.44 Hz, 1H) 2.39-2.48 (m, 1H) 2.54-2.66 (m, 1H) 2.80-2.90 (m, 1H) 2.97 (ddd, J=12.82, 6.71, 2.44 Hz, 1H) 3.21-3.33 (m, 1H) 3.53-3.65 (m, 1H) 4.08-4.15 (m, 1H) 7.23-7.27 (m, 1H) 7.30-7.37 (m, 4H).

Preparation of Compound 161-B
To a solution of Diiodomethane (183.01 mg, 683.29 umol, 54.96 uL) in 5 mL dichloromethane at 0° C. was added diethylzinc (562.62 mg, 683.29 umol, 614.89 uL, 15% purity) After 5 min, 161-A (150.00 mg, 525.61 umol) in 4.0 mL dichloromethane was added. The reaction was alowed to slowly warm to RT over 4 h. The desired product was noted by LC/MS. The reaction was allowed to stir overnight and then treated with 1N NaOH for 20 min and extracted with dichloromethane. The dichloromethane layers were washed with brine, dried over MgSO$_4$, filtered, and concentrated.

Silica gel purification using 40-70% ethyl acetate in heptane afforded product 161-B (66.00 mg, 220.43 umol, 41.94% yield)

LCMS (M+H) 300.1

$^1$H NMR (500 MHz, CHLOROFORM-d) δ ppm 0.42 (d, J=5.49 Hz, 1H) 1.17 (t, J=7.02 Hz, 3H) 1.33 (d, J=5.49 Hz, 1H) 1.35 (d, J=3.66 Hz, 1H) 1.37-1.40 (m, 3H) 1.41-1.53 (m, 2H) 1.56 (s, 2H) 1.57-1.71 (m, 2H) 2.18-2.36 (m, 2H) 3.12-3.29 (m, 1H) 3.37 (td, J=11.75, 5.19 Hz, 1H) 3.42-3.58 (m, 2H) 4.01-4.09 (m, 1H) 7.15-7.25 (m, 1H) 7.26-7.39 (m, 2H) 7.46-7.61 (m, 2H).

Preparation of Compound 161-C
To a solution of 161-B (132.49 mg, 442.50 umol) in 5 mL anhydrous DCM was added Dess-Martin periodinane (225.22 mg, 531.00 umol). After 2 h, water (9.57 mg, 531.00 umol, 9.57 uL) in 10 mL DCM was added dropwise. After 1 h, quenched by addition of 1:1 sat Sodium thiosulfate: sat NaHCO$_3$. Stirred for 1 h. Washed with 1:1 sat sodium thiosulfate:sat NaHCO$_3$, sat NaHCO$_3$, brine. The organic phase was dried over MgSO$_4$, filtered, and concentrated. Purification using 10-50% ethyl acetate in heptanes on 12 g silica gel column afforded 75 mg of 161-C.

$^1$H NMR (500 MHz, CHLOROFORM-d) δ ppm 1.14 (t, J=7.02 Hz, 4H) 1.43 (s, 3H) 1.60 (ddd, J=14.65, 6.71, 2.44 Hz, 1H) 1.74 (ddd, J=14.35, 12.21, 6.41 Hz, 1H) 2.10 (d, J=5.49 Hz, 1H) 2.26-2.47 (m, 3H) 2.60 (ddd, J=14.19, 7.17, 1.83 Hz, 1H) 3.14 (ddd, J=12.21, 7.33, 1.83 Hz, 1H) 3.30 (td, J=11.60, 6.71 Hz, 1H) 3.41 (dq, J=14.04, 6.84 Hz, 1H) 3.51 (dq, J=13.43, 7.33 Hz, 1H) 7.24-7.28 (m, 1H) 7.30-7.41 (m, 2H) 7.43-7.54 (m, 2H)

Preparation of Compound 161-D
Compound 161-C (75.00 mg, 252.19 umol) was dissolved in ethyl formate (1.87 g, 25.22 mmol, 2.03 mL) and treated with sodium methoxide (4.3 M, 234.60 uL). The reaction was allowed to stir overnight at RT. The reaction was quenched by addition of 1N HCl to pH of 3. The reaction was extracted with ethyl acetate. The organic phases were combined and washed with brine, dried over MgSO$_4$, filtered, and concentrated to afford 161-D (80 mg). The material was carried on crude to next step.

LCMS (M+H)=326.1

Preparation of Compound 161-E
Compound 161-D (80 mg, 0.245 mmol) in 4 mL ethanol/1 mL water was treated with hydroxylamine hydrochloride (42.71 mg, 614.63 umol) overnight. The reaction was concentrated to dryness and partioned between ethyl acetate and sodium bicarbonate solution. The layers were separated and the organic phase was washed with Sat NaHCO$_3$ solution and brine, dried over MgSO$_4$, filtered, and concentrated to afford a white solid, 161-E, 75 mg.

LCMS (M+H)=323.1

Preparation of Compound 161-F
Compound 161-E in 2 mL of anhydrous methanol was treated with sodium methoxide (4.3 M, 216.40 uL) and allowed to stir at RT for 24 h. The reaction was quenched by addition of ~1.1 1N HCl to a pH of 3 and concentrated to remove methanol. The reaction was partioned between ethyl acetate and brine, dried over MgSO4, filtered, and concentrated to afford 161-F.

LCMS (M+H)=323.1

Preparation of Compounds 161-Ent1 and 161-Ent2
Compound 161-F (80.00 mg, 248.14 umol) was taken up in 5 mL of benzene and treated with DDQ (61.96 mg, 272.95 umol). The reaction was heated to reflux for 4 h, then cooled to RT and concentrated. The reaction was deposited on silica gel and chromatographed twice using 20-60% ethyl acetate in heptanes. The first column was on 12 g silica gel, the second column used a 4 g silica gel cartridge. Isolated 20 mg of a white solid (racemic), submitted to chiral SFC.

The method used for the chiral separation was; Column: CHIRALPAK IA 30×250 mm, 5 um; Method: 30% Methanol w/0.1% diethyl amine in $CO_2$ (flow rate: 100 mL/min), ABPR 120 bar, MBPR 40 psi to yield the first eluting enantiomer 161-Ent1 (8.40 mg, 26.22 umol, 10.57% yield) and the second eluting enantiomer 161-Ent2 (7.90 mg, 24.66 umol, 9.94% yield).

Data for 161-Ent1

LCMS (M+H)=321.1

$^1$H NMR (500 MHz, CHLOROFORM-d) δ ppm 0.98 (d, J=5.49 Hz, 1H) 1.24 (t, J=7.33 Hz, 3H) 1.48-1.52 (m, 3H) 1.53-1.66 (m, 3H) 2.46 (ddd, J=14.96, 10.99, 7.63 Hz, 1H) 3.18-3.35 (m, 1H) 3.35-3.50 (m, 2H) 3.60-3.80 (m, 1H) 7.16-7.26 (m, 2H) 7.32-7.49 (m, 3H) 7.63 (s, 1H)

SFC: RT 1.67 min; ee=100%

Data for 161-Ent2

LCMS (M+H)=321.1

$^1$H NMR (500 MHz, CHLOROFORM-d) δ ppm 0.98 (d, J=5.49 Hz, 1H) 1.24 (t, J=7.33 Hz, 3H) 1.48-1.52 (m, 3H) 1.53-1.66 (m, 3H) 2.46 (ddd, J=14.96, 10.99, 7.63 Hz, 1H) 3.18-3.35 (m, 1H) 3.35-3.50 (m, 2H) 3.60-3.80 (m, 1H) 7.16-7.26 (m, 2H) 7.32-7.49 (m, 3H) 7.63 (s, 1H)

SFC: RT 2.35 min; ee=100%

Example 146 is Intentionally Deleted.

Example 147: Synthesis of Compounds 163-Ent1 and 163-Ent2

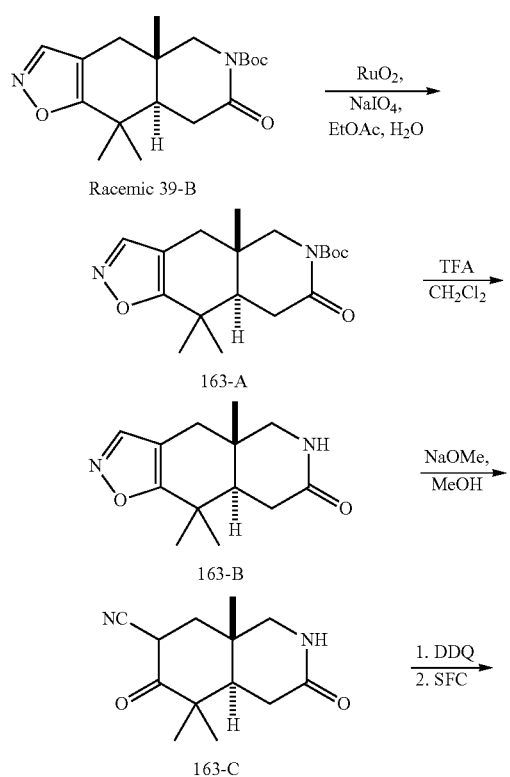

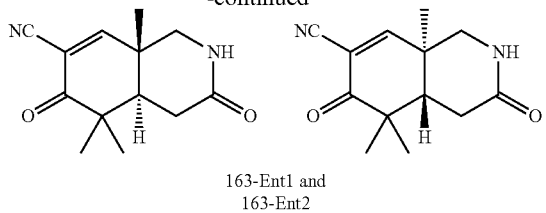

163-Ent1 and 163-Ent2

Procedure for Preparation of Compound 163-A

Sodium periodate (9.73 g, 45.49 mmol) was added to a solution of ruthenium(IV) oxide hydrate (654 mg, 4.33 mmol) in water (82 mL) and a yellow solution formed. A solution of racemic 39-B (6.94 g, 21.66 mmol) in ethyl acetate (135 mL) was then slowly added and the mixture was vigorously stirred at room temperature for 2 hours. The solution was filtered then the organic layer was then separated and the aqueous layer was extracted twice with EtOAc. The combined organic layers were the dried over sodium sulfate, filtered, and concentrated. The black residue was then purified by column chromatography (5-35% EtOAc/Heptane) to provide 483 mg (6.67% yield) of 163-A a white solid.

$^1$H NMR (400 MHz, CHLOROFORM-d) δ ppm 8.08 (s, 1H), 3.76 (d, J=12.5 Hz, 1H), 3.24 (d, J=12.6 Hz, 1H), 2.66 (d, J=9.3 Hz, 2H), 2.43 (d, J=15.2 Hz, 1H), 2.34 (d, J=15.2 Hz, 1H), 2.06 (t, J=9.8 Hz, 1H), 1.55 (s, 9H), 1.34 (s, 3H), 1.26 (s, 3H), 1.09 (s, 3H)

Procedure for Preparation of Compound 163-B

A solution of 163-A (483 mg, 1.44 mmol) in dichloromethane (4.80 mL) and TFA (221 uL, 2.89 mmol) was stirred at room temperature for 1.5 hours. At this point LCMS analysis indicated complete consumption of the starting material and the mixture was then concentrated. The residue was then diluted with DCM and sat. aq. $NaHCO_3$ and after separation of layers, the aqueous layer was extracted with DCM (2×). The combined organic layers were dried over sodium sulfate, filtered and concentrated. The white solid (163-B) was used in the next step without further purification.

LCMS: (M+H: 235.1)

Procedure for Preparation of Compound 163-C

To a solution of 163-B (150 mg, 640 umol) in ether (3.20 mL) under nitrogen was added sodium methoxide (732 uL, 3.20 mmol, 25% in MeOH) at room temperature. The mixture was stirred at this temperature for 1.5 hours then diluted with EtOAc then washed with 5% HCl solution (2×). The aqueous layers were combined and extracted with EtOAc (2×) and the combined organic layers were dried over sodium sulfate then filtered and concentrated. 163-C was obtained (104.5 mg) and was used in the next step in the sequence without further purification.

$^1$H NMR (400 MHz, CDCl$_3$) δ ppm 6.57 (br s, 1H), 4.04 (dd, J=14.18, 4.89 Hz, 1H), 3.10 (d, J=11.04 Hz, 1H), 3.01 (dd, J=12.05, 4.52 Hz, 1H), 2.44 (d, J=9.04 Hz, 2H), 2.31 (dd, J=13.18, 4.89 Hz, 1H), 1.93-1.98 (m, 1H), 1.39 (s, 3H), 1.14-1.18 (m, 6H).

Procedure for Preparation of Compounds 163-Ent and 163-Ent2

Compound 163-C (104.5 mg, 446.0 umol) was dissolved in toluene (4.46 mL) and DDQ (132 mg, 580 umol) was added. The mixture was heated to reflux for 60 minutes then cooled to room temperature. The reaction was filtered and concentrated and the residue was purified by column chromatography (50-100% EtOAc/Heptane). The red residue obtained was then diluted with sat. sodium bicarbonate and extracted with DCM (3×). The organic layers were dried, filtered, and concentrated to provide the product as an oil (18.5 mg, 17.9% yield). This material was then purified by chiral SFC (Column: Chiralcel OD-H 21×250 mm; Method: 20% methanol in $CO_2$ [flow rate: 80 g/min], ABPR 110 bar) to provide 163-Ent1 (6.0 mg, Rt=0.9 min) and 163-Ent2 (6.2 mg, Rt=1.1 min) as white solids.

Data for 163-Ent1
  HPLC: (Purity: 97.5%)
  LCMS: (M+H: 233.1)
  SFC: (ee: 99.5%)
  $^1$HNMR (400 MHz, $CDCl_3$) δ ppm 7.37 (s, 1H), 5.71 (s, 1H), 3.30 (d, J=12.3 Hz, 1H), 3.13 (dd, J=11.3, 4.5 Hz, 1H), 2.56 (dd, J=18.1, 5.8 Hz, 1H), 2.42-2.51 (m, 1H), 2.30 (dd, J=13.1, 5.3 Hz, 1H), 1.42 (d, J=0.8 Hz, 3H), 1.24 (s, 3H), 1.14 (s, 3H).

Data for 163-Ent2
  HPLC: (Purity: 97.3%)
  LCMS: (M+H: 233.1)
  SFC: (ee: 96.9%)
  $^1$HNMR (400 MHz, $CDCl_3$) δ ppm 7.37 (s, 1H), 5.72 (s, 1H), 3.30 (d, J=11.0 Hz, 1H), 3.13 (dd, J=11.3, 4.5 Hz, 1H), 2.56 (dd, J=17.8, 5.5 Hz, 1H), 2.42-2.50 (m, 1H), 2.30 (dd, J=12.8, 5.5 Hz, 1H), 1.42 (s, 3H), 1.24 (s, 3H), 1.14 (s, 3H).

Example 148: Synthesis of Compounds 164-Ent1 and 164-Ent2

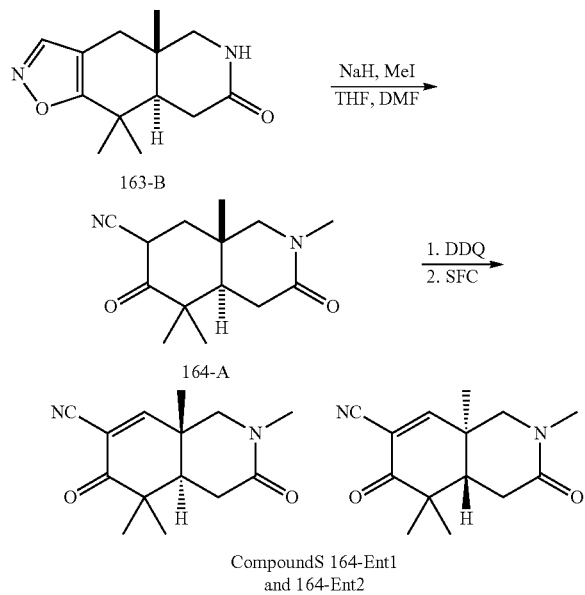

Procedure for Preparation of Compound 164-A

Compound 163-B (125 mg, 533 umol) was dissolved in THF (5.34 mL) and DMF (1.25 mL) and cooled to 0° C. then sodium hydride (44.8 mg, 1.12 mmol, 60% in mineral oil) was added. This solution was stirred for 30 minutes then methyl iodide (36.5 uL, 586.88 umol) was added and the mixture was warmed to room temperature overnight. The reaction was then quenched with saturated aqueous ammonium chloride and diluted with ethyl acetate. After separation of layers the organic layer was washed with brine and water then dried over sodium sulfate, filtered, and concentrated to provide 83 mg of 164-A which was used in the next step without further purification.

LCMS: (M+H: 249.1)

Procedure for Preparation of Compounds 164-Ent and 164-Ent2

Compound 164-A (83 mg, 334 umol) was dissolved in toluene (3.3 mL) and DDQ (99 mg, 434 umol) was added. The mixture was heated to reflux for 60 minutes then cooled to room temperature. The reaction was filtered and concentrated and the residue was then purified by column chromatography (50-100% EtOAc/Heptane, 12 g column). The red residue obtained was then diluted with sat. sodium bicarbonate and extracted with DCM (3×). The organic layers were dried, filtered, and concentrated to provide the product as an oil which was then purified by chiral SFC (Preparative method: Column: ChromegaChiral CCS 20×250 mm, Method: 20% methanol/isopropanol [1:1] in $CO_2$ [flow rate: 80 g/min], ABPR 120 bar; Analytical method: Column: Chiralpak AS-H 4.6×100 mm, Method: 10% methanol: isopropanol [1:1] in $CO_2$ [flow rate: 4 mL/min], ABPR 125 bar) to provide 164-Ent1 (6.2 mg, Rt=2.84 min) and 164-Ent2 (5.8 mg, Rt=2.46 min) as white solids.

Data for 164-Ent1
  HPLC: (Purity: 93%)
  LCMS: (M+H: 247.1)
  SFC: (ee: 99.3%)
  $^1$HNMR (400 MHz, $CDCl_3$) δ ppm 7.36 (s, 1H), 3.34 (d, J=11.5 Hz, 1H), 3.04 (d, J=11.8 Hz, 1H), 3.01 (s, 3H), 2.57 (dd, J=18.1, 5.8 Hz, 1H), 2.42-2.52 (m, 1H), 2.28 (dd, J=13.1, 5.5 Hz, 1H), 1.38 (s, 3H), 1.22 (s, 3H), 1.13 (s, 3H).

Data for 164-Ent2
  HPLC: (Purity: 91%)
  LCMS: (M+H: 247.1)
  SFC: (ee: 97.8%)
  $^1$HNMR (400 MHz, $CDCl_3$) δ ppm 7.36 (s, 1H), 3.35 (d, J=11.0 Hz, 1H), 3.04 (d, J=11.8 Hz, 1H), 3.01 (s, 3H), 2.36-2.60 (m, 2H), 2.29 (dd, J=14.1, 5.8 Hz, 1H), 1.38 (s, 3H), 1.22 (s, 3H), 1.13 (s, 3H).

Example 149: Synthesis of Compounds 165-Ent1 and 165-Ent2

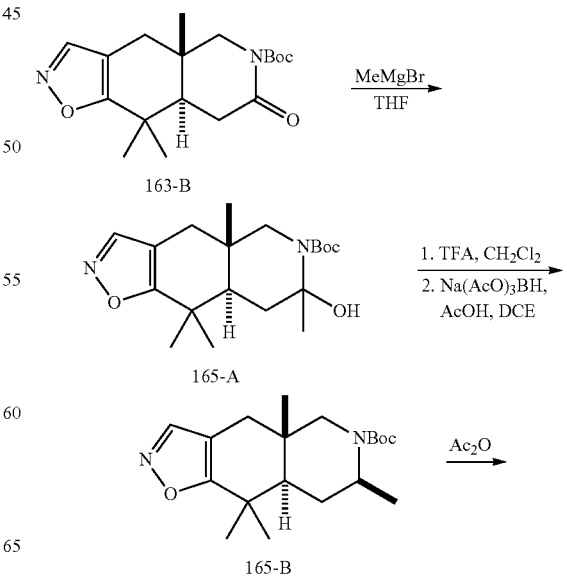

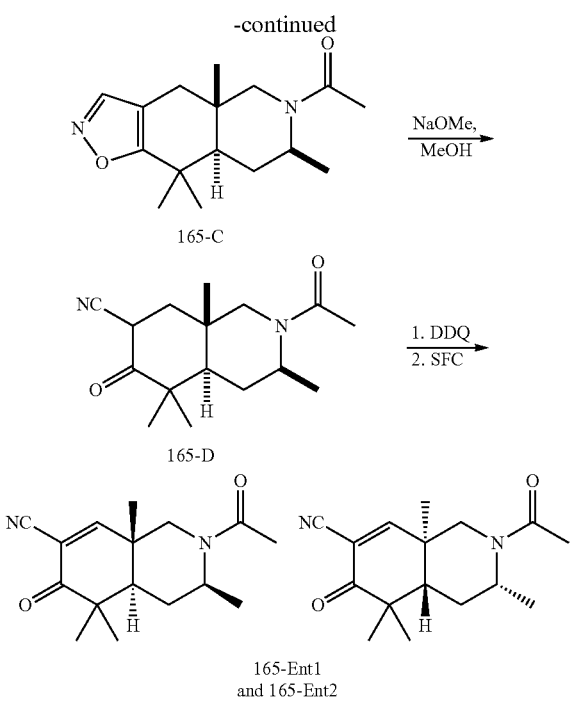

165-C

165-D

165-Ent1
and 165-Ent2

Procedure for Preparation of Compound 165-Ent and 165-Ent2

A solution of 163-B (231 mg, 0.691 mmol) in THF (3.45 mL) was cooled to −78° C. under nitrogen. To this solution was added methylmagnesium bromide (299 uL, 3.0 M in THF). The mixture was stirred for two hours then quenched upon addition of HCl (0.97 mL, 1 M in water). The mixture was extracted with ether and the combined organic layers were then dried over sodium sulfate, filtered, and concentrated to obtain crude 165-A. This material was then used in the next step in the sequence without further purification.

LCMS: (M-tBu+H: 295.1)

Procedure for Preparation of Compound 165-B

A solution of 165-A (242 mg, 0.691 mmol) in dichloromethane (1.73 mL) and TFA (1.73 mL) was stirred at room temperature for 1 hour then the mixture was concentrated. This residue was then dissolved in DCE (2.16 mL) and acetic acid (39.5 uL, 0.691 mmol) was added followed by sodium triacetoxyborohydride (205 mg, 0.967 mmol). The mixture was stirred for 1 hour then quenched upon addition of saturated, aqueous sodium bicarbonate (10 mL). The solution was extracted with dichloromethane (3×20 ml) then the combined organic layers were dried over sodium sulfate, filtered, and concentrated to provide 137.6 mg of crude 165-B. This material was then used in the next step in the sequence without further purification.

LCMS: (M+H: 235.2)

Procedure for Preparation of Compound 165-C

Compound 165-B (137.6 mg, 587 umol) was dissolved in THF (2.49 mL) and water (0.45 mL) then sodium bicarbonate (148 mg, 1.76 mmol) and acetic anhydride (83 uL, 881 umol) were added. The mixture was stirred at room temperature for 5 hours. The mixture was then diluted with EtOAc (20 mL) and water (20 mL). After separation of layers, the water layer was extracted with ethyl acetate (2×20 mL) and the combined organic layers were dried over sodium sulfate, filtered, and concentrated. The residue was then purified by column chromatography (10-100% EtOAc/Heptane) to provide 69.6 mg (43% yield) of 165-C as a colorless oil.

LCMS: (M+H: 277.1)

Procedure for Preparation of Compound 165-D

To a solution of 165-C (69.6 mg, 252 umol) in ether (2.52 mL) under nitrogen was added sodium methoxide (288 uL, 1.26 mmol, 25% in methanol). The mixture was stirred at room temperature for 2 hours then diluted with EtOAc (25 mL) then washed with 5% HCl solution (2×15 mL). The aqueous layers were combined and extracted with EtOAc (2×25 mL) and the combined organic layers were dried over sodium sulfate then filtered and concentrated to provide crude 165-D. This material was used in the next step in the sequence without further purification.

LCMS: (M+H: 277.2)

Procedure for Preparation of Compounds 165-Ent and 165-Ent2

Compound 165-D (69.6 mg, 252 umol) was dissolved in toluene (2.52 mL) and DDQ (74 mg, 327 umol) was added. The mixture was heated to reflux for 60 minutes then cooled to room temperature. The reaction was filtered and concentrated and the residue was then purified by column chromatography (50-100% EtOAc/Heptane). The red residue obtained was then diluted with saturated sodium bicarbonate (20 mL) and extracted with DCM (3×25 mL). The organic layers were dried over sodium sulfate, filtered, and concentrated to provide the product as a red oil (37 mg, 53%, 92% purity by HPLC). This material was then purified by chiral SFC (Column: Chiralcel AD-H 21×250 mm; Method: 20% methanol in $CO_2$ [flow rate: 80 g/min], ABPR 110 bar) to provide 165-Ent1 (12.1 mg, 1.82 min) and 165-Ent2 (10.4 mg, Rt=2.32 min) as off-white solids.

Data for 165-Ent1
HPLC: (Purity: 92%)
LCMS: (M+H: 275.1)
SFC: (ee: 82.32%)
$^1$HNMR (400 MHz, $CDCl_3$)$_δ$ ppm 7.72 (s, 1H), 3.81-3.96 (m, 2H), 3.13 (d, J=14.3 Hz, 1H), 2.11-2.15 (m, 3H), 1.79-1.91 (m, 2H), 1.36-1.47 (m, 4H), 1.25 (s, 3H), 1.22 (s, 3H), 1.16 (s, 3H).

Data for AGC-9012-Ent-2 (BIO-1472595-01)
HPLC: (Purity: 95%)
LCMS: (M+H: 275.2)
SFC: (ee: 94.70%)
$^1$HNMR (400 MHz, $CDCl_3$) δ ppm 7.72 (s, 1H), 3.82-3.97 (m, 2H), 3.13 (d, J=13.6 Hz, 1H), 2.12-2.15 (m, 3H), 1.80-1.91 (m, 2H), 1.38-1.47 (m, 4H), 1.25 (s, 3H), 1.22 (s, 3H), 1.16 (s, 3H).

Example 150. Cellular Assay

The assay was performed by DiscoverX Corporation, 42501 Albrae Street, Suite 100, Fremont, Calif. 94538. The PathHunter® Nuclear Translocation assay detects translocation of a target protein to, or from, the nucleus. In this system, ProLink™ (PK), a small enzyme fragment, is fused to the protein of interest and EA is localized in the nucleus. Activation of the signaling pathway induces the target protein to either transit into the nucleus, thus forcing complementation of the PK and EA fragments, or out of the nucleus, hindering complementation of the fragments.

$EC_{50}$ determinations were performed in duplicate at 10 concentrations with 3-fold serial dilutions at a 30 μM top concentration or an otherwise specified top concentration.

Cell Handling:

PathHunter Pathway cell lines were expanded from freezer stocks according to standard procedures. 5000 cells were seeded in Cell Plating Reagent 0 (containing 1% FBS) to a total volume of 20 uL into white walled, 384-well microplates and incubated for the overnight prior to testing.

Agonist Format:

For Agonist determination, cells were incubated with sample to induce response. Sample stocks were serially diluted in DMSO to generate 100× sample. Intermediate dilution of sample stocks was performed to generate 5× sample in assay buffer (Cell Plating Reagent 0 containing 1% FBS). 5 µL of 5× sample was added to cells and incubated at room temperature for 6 hours. Vehicle concentration was 1%.

Signal Detection:

Assay signal was generated through a single addition of 25 µL (100% v/v) of PathHunter Flash Detection reagent, followed by a one hour incubation at room temperature. Microplates were read following signal generation with a PerkinElmer Envision™ instrument for chemiluminescent signal detection.

Data Analysis:

Compound activity was analyzed using CBIS data analysis suite (ChemInnovation, CA). For agonist mode assays, percentage activity was calculated using the following formula: % Activity=100%×(mean RLU of test sample—mean RLU of vehicle control)/(mean MAX RLU control ligand–mean RLU of vehicle control). For EC50 determination, data was normalized to the maximal and minimal response observed in the presence of the control ligand and vehicle respectively. CDDO methyl ester was used as a control compound.

The compounds described herein were tested for in the above nuclear translocation assay. The results are provided below, wherein the compound number corresponds to the numbers set forth in the examples above, a "+" represents an $EC_{50}$ of greater than 10 µM, a "++" represents an $EC_{50}$ of less than or equal to 10 µM, a "+++" represents an $EC_{50}$ of less than or equal to 1 µM, a "++++" represents an $EC_{50}$ of less than or equal to 0.1 µM, and a "+++++" represents an $EC_{50}$ of less than or equal to 0.01 µM.

| COMPOUNDS | $EC_{50}$ (NRF2 TRANSLOCATION) |
|---|---|
| 122-Ent2 and 156 | xxxxx (<0.01 µM) |
| 28-Ent1, 46-Ent2, 69-Ent2, 70-Ent2, 71-Ent2, 72-Ent1, 73-Ent1, 77-Ent2, 78-Ent2, 79, 84-Ent2, 85-Ent2, 87-Ent2, 89-Ent2, 90-Ent2, 91-Ent2, 92-Ent2, 93-Ent2, 94-Ent2, 97-Ent1, 100-Ent2, 101-Ent2, 103-Ent2, 107-Ent2, 108-Ent2, 109-Ent2, 110-Ent2, 111-Ent2, 113-Ent2, 121-Ent2, 123-Ent2, 124-Ent1, 124-Ent2, 125-Ent2, 126-Ent1, 127-Ent2, 128-Ent2, 129-Ent2, 130-Ent2, 133-Ent2, 134-Ent1, 138-Ent1, 152-Ent2, 153-Ent2, 159-Ent1, and 159-Ent2 | xxxx (<0.1 µM) |
| 12-Ent1, 14-Ent1, 15-Ent1, 16-Ent1, 16-Ent2, 17-Ent1, 18-Ent1, 19-Ent1, 20-Ent2, 21-Ent1, 25-Ent1, 26-Ent1, 27-Ent1, 30-Ent1, 30-Ent2, 31-Ent1, 31-Ent2, 32-Ent1, 33-Ent1, 34-Ent1, 34-Ent2, 35-Ent1, 36-Ent1, 38-Ent1, 38-Ent2, 39-Ent2, 47-Ent1, 49-Ent1, 53-Ent1, 56-Ent1, 57-Ent1, 57-Ent2, 58-Ent1, 58-Ent2, 59, 60-Ent1, 62, 63, 64, 66, 67, 70-Ent1, 71-Ent1, 74-Ent1, 75-Ent1, 76-Ent1, 78-Ent1, 80, 83-Ent1, 86-Ent2, 88-Ent2, 92-Ent1, 93-Ent1, 95-Ent2, 96-Ent2, 97-Ent2, 98-Ent2, 104-Ent2, 105-Ent2, 106-Ent2, 108-Ent1, 111-Ent1, 112-Ent2, 114-Ent1, 114-Ent2, 116-Ent1, 116-Ent2, 120-Ent2, 122-Ent1, 125-Ent1, 126-Ent2, 127-Ent1, 128-Ent1, 129-Ent1, 131-Ent1, 134-Ent2, 136-Ent2, 137-Ent2, 149, 150-Ent2, 151-Ent2, 154-Ent2, 164-Ent1, 166, 167 and 168-Ent1 | xxx (<1 µM) |
| 12-Ent2, 12-Jent2, 13-Ent1, 13-Ent2, 14-Ent2, 15-Ent2, 17-Ent2, 18-Ent2, 19-Ent2, 20-Ent1, 21-Ent2, 22-Ent2, 22-Ent1, 23-Ent2, 24-Ent1, 25-Ent2, 26-Ent2, 27-Ent2, 28-Ent2, 29-Ent1, 29-Ent2, 32-Ent2, 33-Ent2, 35-Ent2, 36-Ent2, 39-Ent1, 46-Ent1, 48-Ent1, 48-Ent2, 51-Ent1, 52-Ent1, 53-Ent2 54, 55, 56-Ent2, 60-Ent2, 61-Ent1, 61-Ent2, 65-Ent1, 65-Ent2, 69-Ent1, 77-Ent1, 81-Ent1, 82-Ent1, 84-Ent1, 87-Ent1, 88-Ent1, 89-Ent1, 90-Ent1, 91-Ent1, 94-Ent1, 95-Ent1, 98-Ent1, 99-Ent2, 103-Ent1, 104-Ent1, 105-Ent1, 106-Ent1, 107-Ent1, 112-Ent1, 117-Ent1, 121-Ent1, 161-Ent2, 163-Ent1, 163-Ent2, 164-Ent2, and 165-Ent2 | xx (<10 µM) |
| 12-J-Ent1, 24-Ent1, 50-Ent1, 85-Ent1, 86-Ent1, 96-Ent1, 120-Ent1, 123-Ent1, 155-Ent1, 155-Ent2, 161-Ent1 and 165-Ent1 | x (>10 µM) |

Example 151. Testing Nrf2 Activator Compounds in Cultured Human Astrocytes

Cells

Human astrocytes from ScienCell (cat #1820) were grown in astrocyte medium per supplier's instructions. Cells cultured for no more than two passages were plated in poly-D-lysine coated 96-well plates at 40,000 cells per well for gene transcription experiments and 20,000 cell per well for glutathione and cytoprotection assays.

Gene Expression

Primary cultures of human spinal cord astrocytes were treated with test compounds for 20 hours. The cells were then rinsed in PBS, lysed, and processed for RNA using Ambion Taqman™ Cells-to-CT kit. The resulting cDNA was stored at −20° C. until analysis by real-time polymerase chain reaction (RT-PCR). The cDNA mixture from Cells-to-CT was diluted 5× before loading into PCR. This yields results similar to using 6 ng of purified cDNA. RT-PCR was performed on Life Technologies QuantStudio platform using OpenArray technique according to manufacturer's protocol using the following Taqman primers:

| Target | Taqman assay | |
|---|---|---|
| GCLC | Hs00155249_m1 | glutamate-cysteine ligase, catalytic subunit |
| GCLM | Hs00157694_m1 | glutamate-cysteine ligase, modifier subunit |
| OSGIN1 | Hs00203539_m1 | oxidative stress induced growth inhibitor 1 |
| TBP | Hs00427620_m1 | TATA box binding protein [Homo sapiens (human)] |
| PRDX1 | Hs00602020_mH | peroxiredoxin 6 |
| SRXN1 | Hs00607800_m1 | sulfiredoxin 1 |
| TXNRD1 | Hs00917067_m1 | thioredoxin reductase 1 |
| ACTB | Hs01060665_g1 | actin, beta [Homo sapiens(human)] |
| HMOX1 | Hs01110250_m1 | heme oxygenase 1 [Homo sapiens(human)] |

-continued

| Target | Taqman assay | |
|---|---|---|
| UBC | Hs01871556_s1 | ubiquitin C [Homo sapiens (human)] |
| NQO1 | Hs02512143_s1 | NAD(P)H dehydrogenase, quinone 1 |
| GAPDH | Hs02758991_g1 | glyceraldehyde-3-phosphate dehydrogenase [Homo sapiens (human)] |

The comparative CT method was used to calculate fold changes using ThermoFisher Cloud software for PCR analysis. Samples were compared to 0.03% DMSO vehicle control.

As shown in FIGS. 1A to 1D, Compound 12-Ent1 induces transcription of Nrf2 target genes, including GCLC, HMOX1, OSGIN1 and NQO1.

Glutathione Assay

Intracellular glutathione was measured after a 20-hr exposure to test compounds by a two-step process. First, cells were lysed and luciferin quantitatively generated from substrate, catalyzed by glutathione-S-transferase in the presence of analyte glutathione. Then luciferin was assayed using stabilized luciferase to produce a luminescent signal proportional to the concentration of glutathione (Promega GSH-Glo, cat #V6912).

Figure 2:
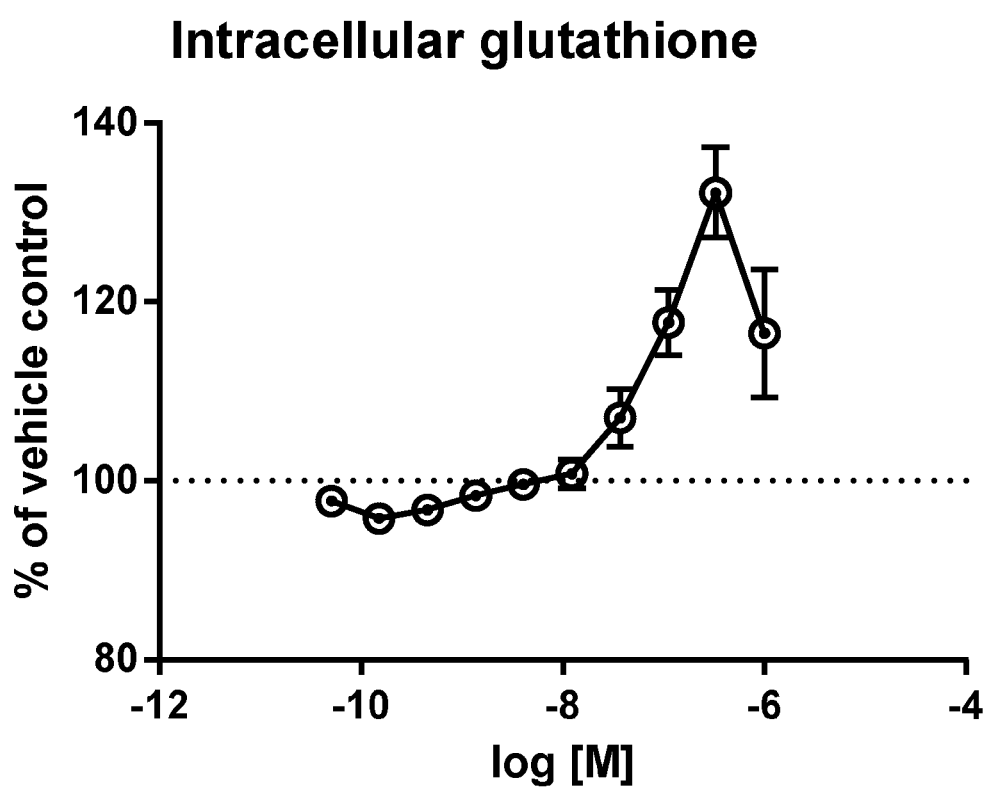
FIG. 2 shows levels of intracellular glutathione Compound 12-Ent1 in human astrocytes treated with increasing concentrations of Compound 12-Ent1 for 20 hours. The x-axis represents log (molar concentrations of compound 12-Ent1). Values shown are mean±S.E.M. n=5-6 experiments.

As shown in FIG. 2, Compound 12-Ent1 increases intracellular glutathione.

Cytoprotection

Astrocytes were treated for 20 hrs with test compounds, then the medium was removed and replaced with serum- and supplement-free growth medium with and without 25 µM sodium arsenite. After 22 hrs., cells were washed with PBS, fixed with 4% paraformaldehyde/4% sucrose in PBS, stained with 4',6-Diamidino-2-phenylindole dihydrochloride (DAPI) and counted by quantitative fluorescence microscopy.

Figure 3:
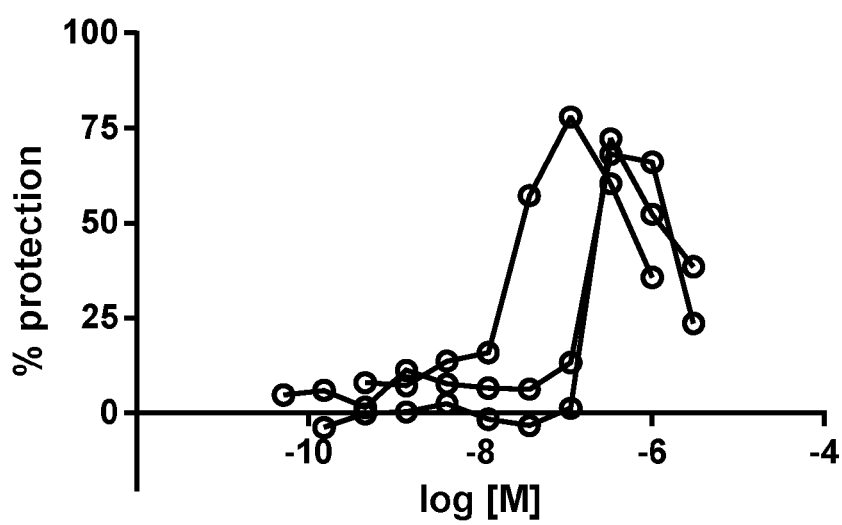
FIG. 3 shows levels of protection of astrocytes by increasing concentrations of Compound 12-Ent1 from oxidative stress-induced cell death caused by 25 µM sodium arsenite. The compound was added to human astrocytes 20 hrs prior to addition of arsenite and the astrocytes were further incubated for 22 hours after addition of arsenite. The x-axis represents log (molar concentrations of compound 12-Ent1). This figure shows results from 3 separate experiments.
Figure 5A:
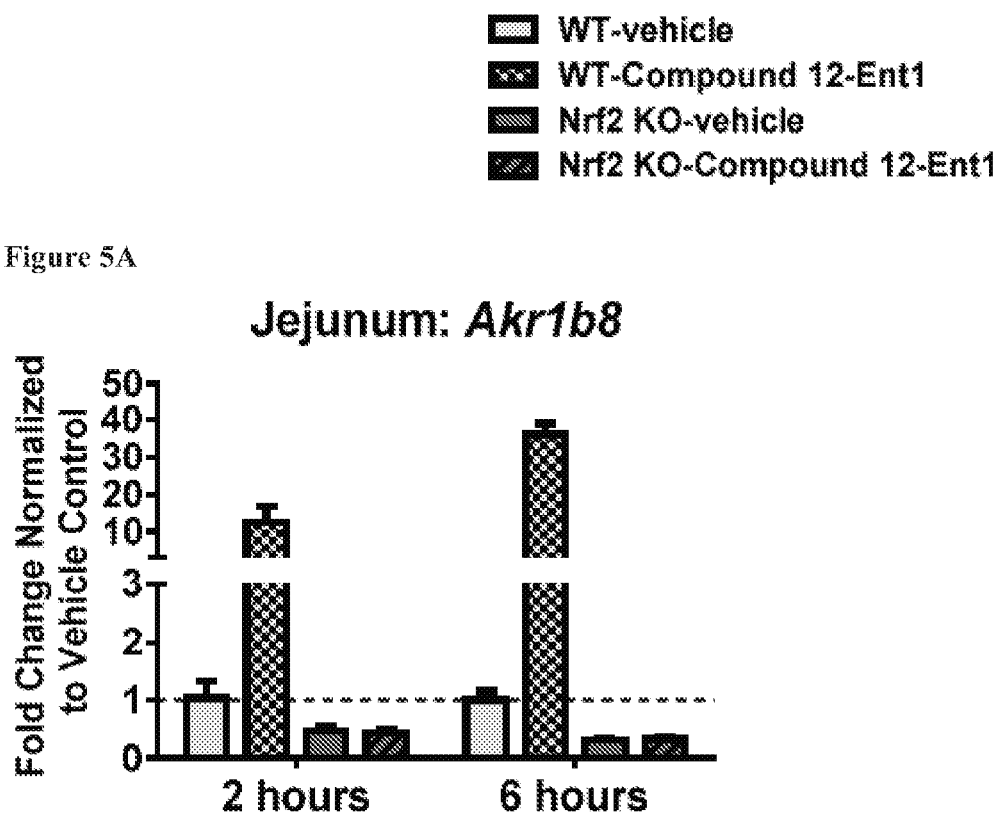
Figure 5B:
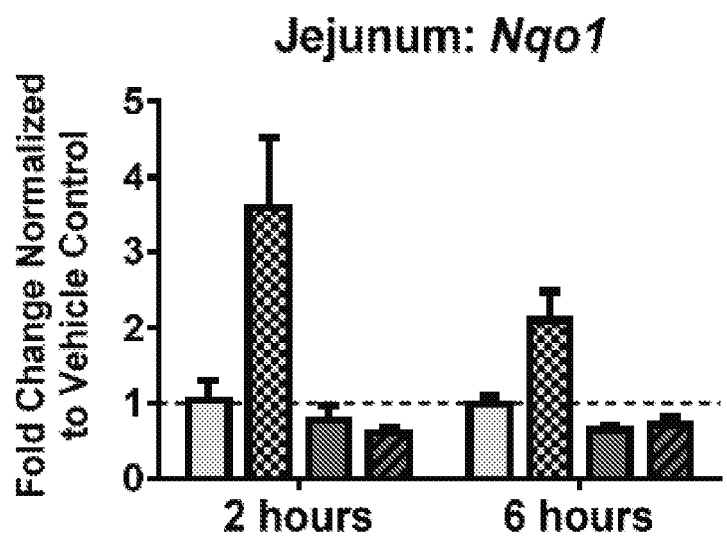

As shown in FIG. 3, Compound 12-Ent1 protects cells from oxidative stress-induced cell death caused by 25 µM sodium arsenite.

Example 152. Method for Testing Nrf2 Activator Compounds in Mice

Animals

All procedures involving animals were performed in accordance with standards established in the Guide for the Care and Use of Laboratory Animals as adopted by the U.S. National Institutes of Health. All animal protocols were approved by the Biogen Institutional Animal Care and Use Committee, which is accredited by the Association for Assessment and Accreditation of Laboratory Animal Care International. Female 6-10 week-old wild type C57BL/6 and Nrf2−/− mice (Itoh et al, 1997; maintained at Jackson Labs, Bar Harbor, Me.) were maintained on a 12-hour light/dark cycle and given access to food and water ad libitum.

Compound 12-Ent1 (25 mg/kg) was administered as a single, oral dose in a vehicle of Solutol HS-15/polyethylene glycol/ethanol/water (10/10/10/70) to C57BL/6 (wt) and Nrf2−/− mice. Brain, jejunum, kidney and spleen were collected at 2 or 6 hours after dosing and snap frozen for RNA analysis of Nrf2 target genes.

Tissue RNA Extraction

For RNA preparation, frozen tissues were placed in 2 mL RNAse-free 96-well blocks with 1.5 ml QIAzol Lysis Reagent (QIAgen) and a 3.2 mm stainless steel bead (BioSpec Products, Bartlesville, Okla.). Tissues were disrupted for four cycles of 45 seconds in a Mini-Beadbeater (Biospec Products). RNA was extracted in chloroform and the aqueous phase was mixed with an equal volume of 70% ethanol. Extracted RNA was applied to RNeasy 96 plates and purified by the spin method according to the manufacturer's protocol (RNeasy 96 Universal Tissue Protocol, QIAgen, Hilden Germany).

Quantitative Real-Time PCR (qRT-PCR)

qRT-PCR was performed from total mRNA isolated from tissues and reverse-transcribed into cDNA according to manufacturer protocols (Life Technologies, Carlsbad, Calif.). 20× Taqman target gene mouse primer/probe sets (see table below) were mixed with cDNA and 2× Taqman Universal Master Mix to a final volume of 20 uL. All final reactions contained 100 ng of cDNA, 900 nM of each primer, and 250 nM TaqMan® probes and were cycled on a QuantStudio™ 12K Flex system (Life Technologies). All samples were measured in triplicate using beta actin as a normalizing gene. Final analysis was performed using the comparative CT method to calculate fold changes and samples were normalized relative to wild type vehicle control at each time point.

Taqman Primer/Probe Assays (Life Technologies)

| Gene | Taqman Assay ID |
|---|---|
| HMOX1 | Mm00516005_m1 |
| OSGIN1 | Mm00660947_m1 |
| NQO1 | Mm01253561_m1 |
| AKR1B8 | Mm00484314_m1 |
| ACTB | Mm02619580_g1 |

As shown in FIGS. 4A to 4D, Compound 12-Ent1 increases the expression of Akr1b8, Nqo1, Hmox1 and Osgin1 in kidney at 2 hours and 6 hours after dosing and the increases are Nrf2-dependent. As shown in FIGS. 5A to 5D, Compound 12-Ent1 increases the expression of Akr1b8, Nqo1, Hmox1 and Osgin1 in Jejunum at 2 hours and 6 hours after dosing and the increases are Nrf2-dependent. As shown in FIGS. 6A to 6D, Compound 12-Ent1 increases the expression of Nqo1, Hmox1 and Osgin1 in spleen at 2 hours and 6 hours after dosing and the increases are Nrf2-dependent. As shown in FIGS. 7A to 7D, Compound 12-Ent1 increases the expression of Nqo1, Hmox1 and Osgin1 in brain at 2 hours and 6 hours after dosing and the increases are Nrf2-dependent.

References:

Itoh K, Chiba T, Takahashi S, Ishii T, Igarashi K, Katoh Y, Oyake T, Hayashi N, Satoh K, Hatayama I, Yamamoto M, Nabeshima Y. Biochem Biophys Res Commun. 1997 Jul. 18; 236(2):313-22.

Example 153. Method for Testing Nrf2 Activator Compounds in Cultured HUDEPS

Cells

Human Umbilical Derived Erythroid Cells (HUDEP; from Riken Institute, Japan) were cultured in Stemspan SFEM medium (Stemcell Technologies, Vancouver, Canada) supplemented with erythroid cytokines and growth factors. Compound incubations were performed in HUDEP cells cultured in differentiation media.

Gene Expression

Differentiating HUDEP cells were cultured with increasing concentrations of 12-Ent1 or equivalent DMSO concentrations for 72 hours and the levels of HbF protein was measured using a commercially available ELISA specific for human HbF (Bethyl Laboratories, TX) based on manufacturer's protocol.

Figure 8:
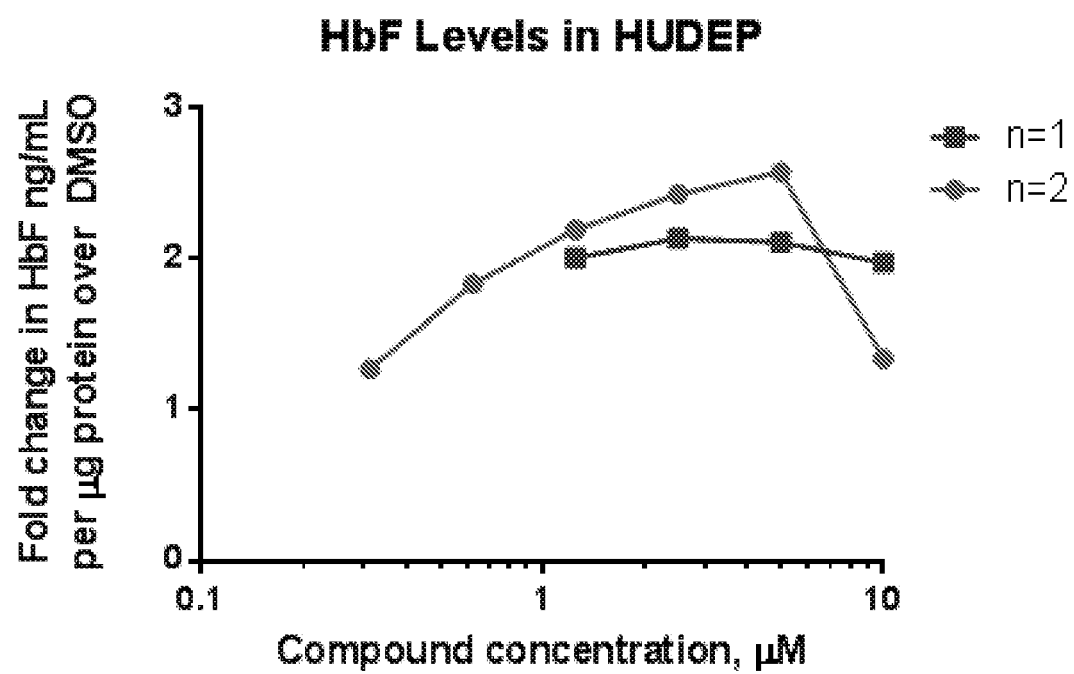
FIG. 8 shows the levels of HbF protein in cultured HUDEP cells treated with increasing concentrations of 12-Ent1, in the two separate experiments.
Figure 9A:
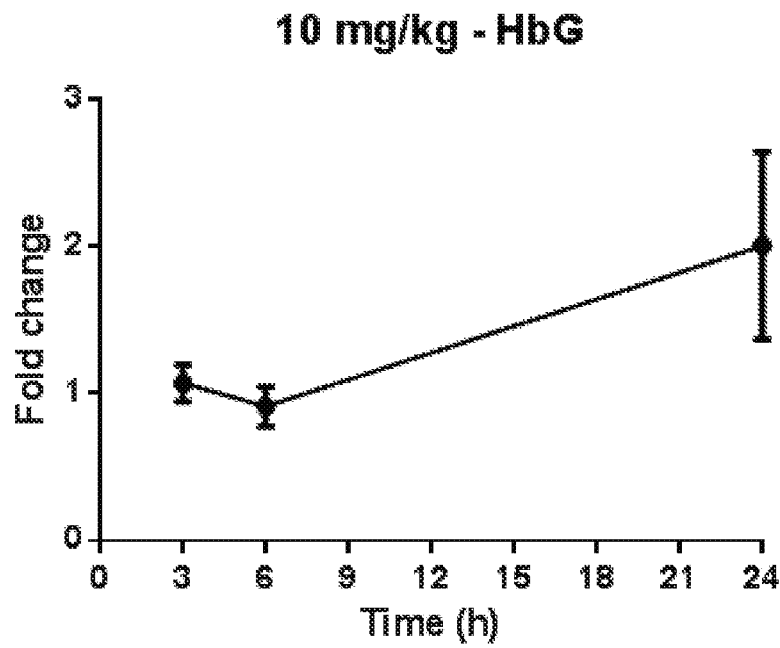
FIGS. 9A to 9D each show a time course and dose response of compound 12-Ent1 for induction of γ-globin gene in the spleen of townes mice, including a single dose and two doses of compound 12-Ent1, i.e., a single dose of 10 mg/kg (FIG. 9A), 25 mg/kg (FIG. 9B) or 50 mg/kg (FIG. 9D), and two doses of 25 mg/kg (FIG. 9C). The two doses were administered 12 hours apart.
Figure 9B:
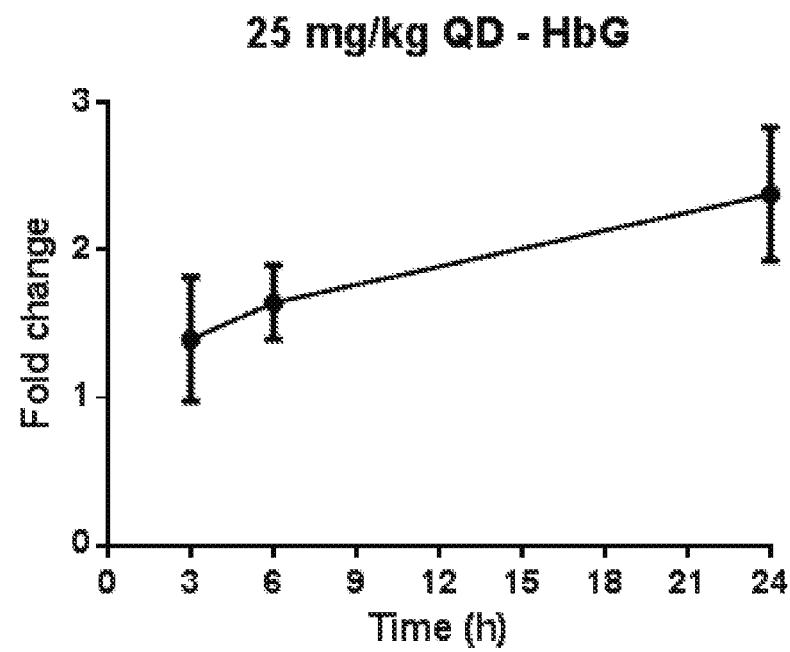
Figure 9C:
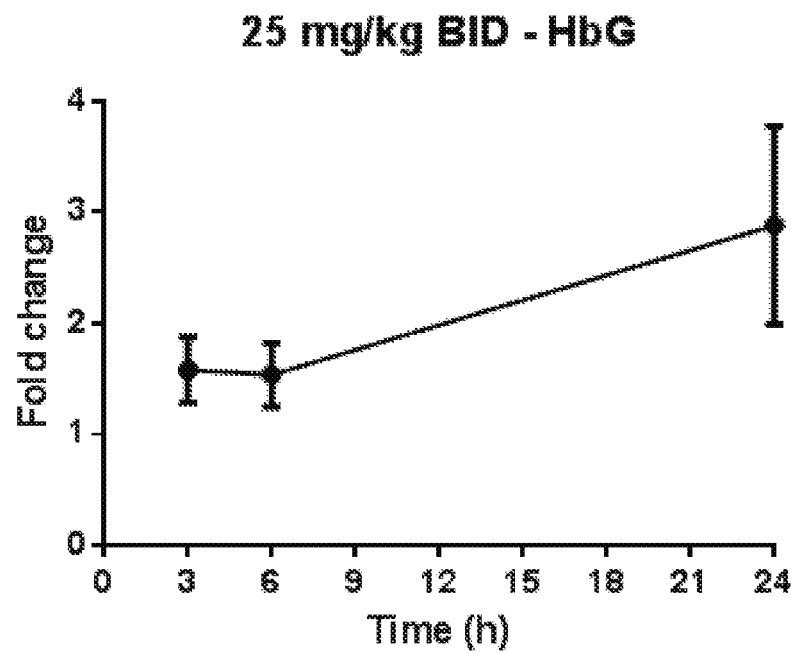
Figure 9D:
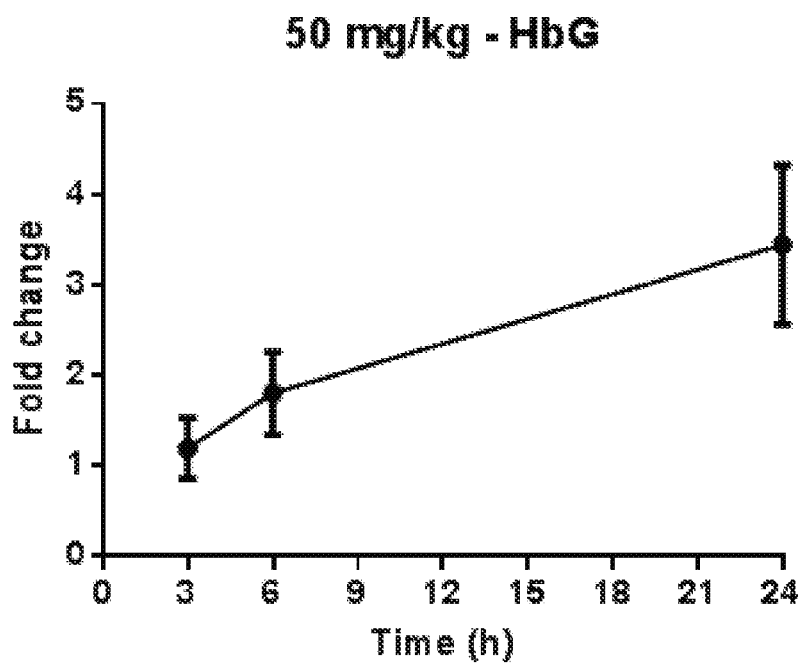
Figure 10A:
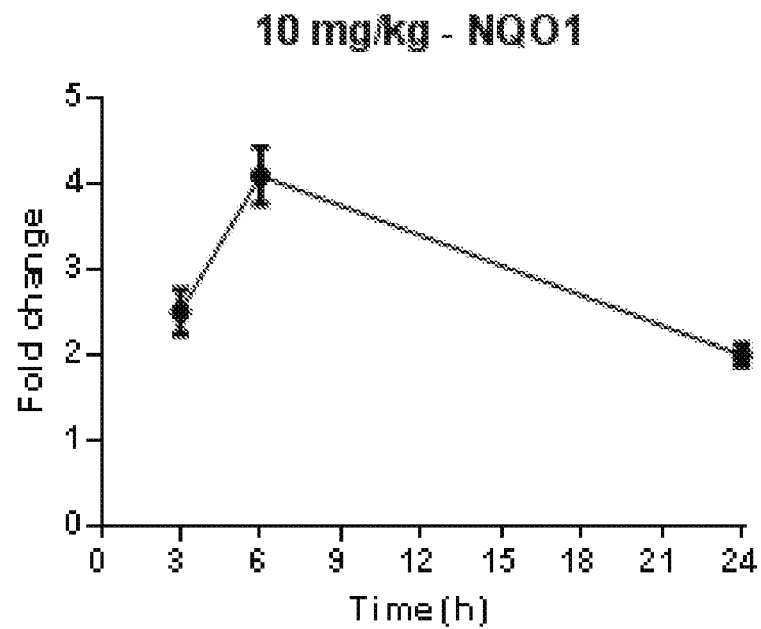
FIGS. 10A to 10C each show a time course and dose response of compound 12-Ent1 for induction of NQO1 in the spleen of townes mice, including a single dose and two doses of compound 12-Ent1, i.e., a single dose of 10 mg/kg (FIG. 10A) or 50 mg/kg (FIG. 10C), and two doses of 25 mg/kg (FIG. 10B). The two doses were administered 12 hours apart.
Figure 10B:
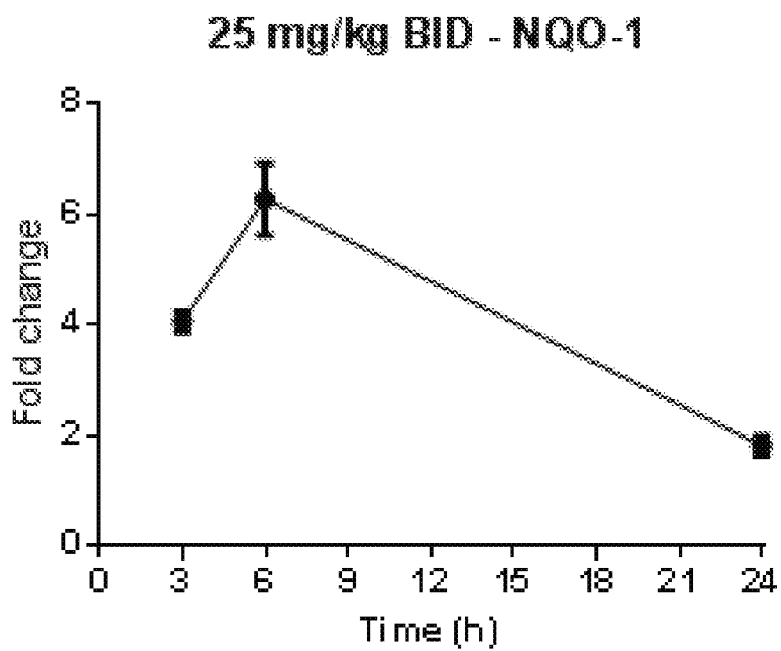
Figure 10C:
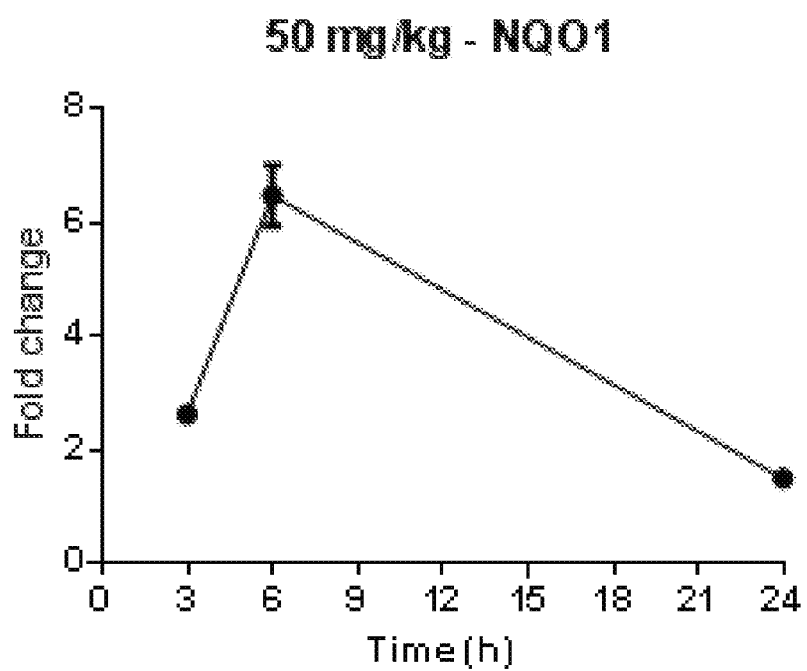
Figure 11:
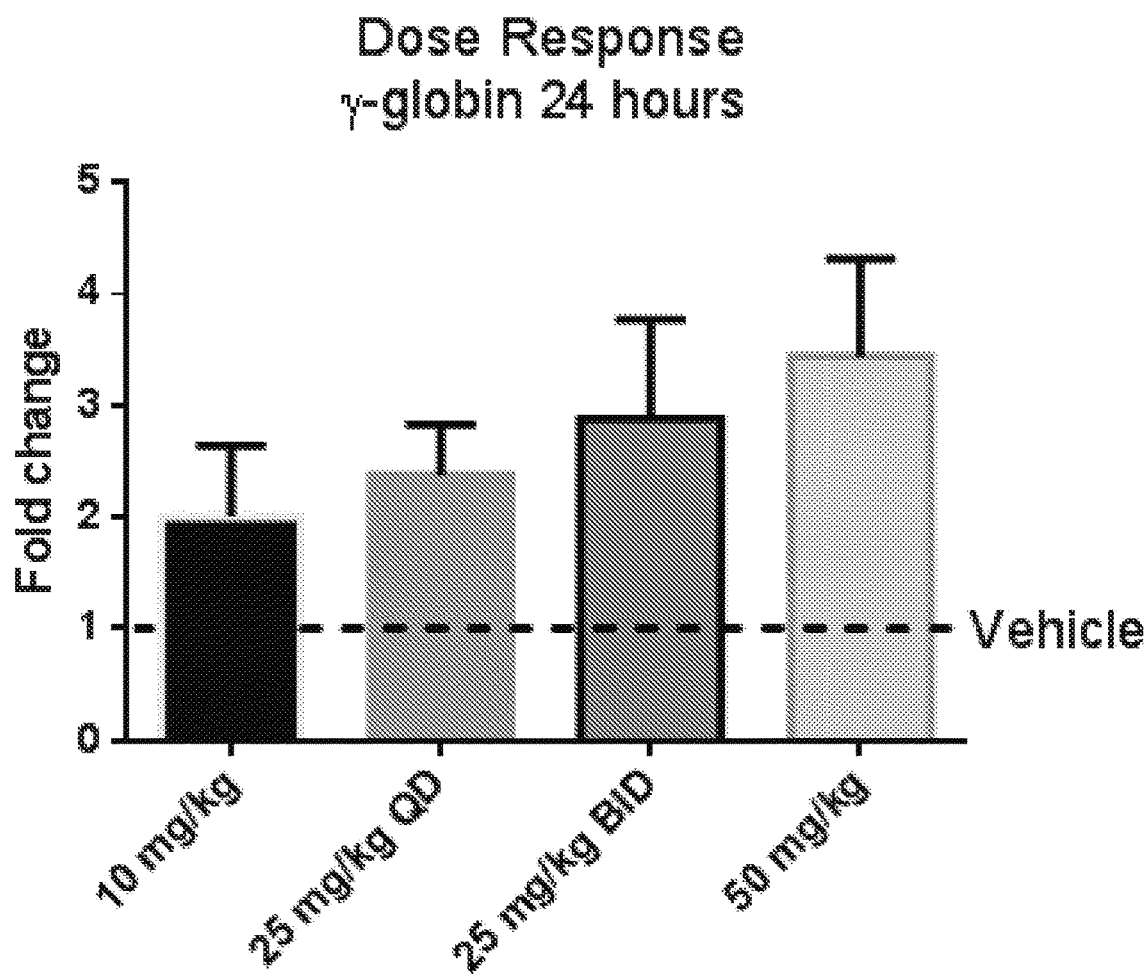
FIG. 11 is a bar graph showing dose responses of compound 12-Ent1 for induction of γ-globin gene in the spleen of townes mice at the 24 hour time point, including to a single dose and two doses of compound 12-Ent1, i.e., a single dose of 10 mg/kg, 25 mg/kg (as noted with QD) or 50 mg/kg, and two doses of 25 mg/kg (as noted with BID). The two doses were administered 12 hours apart.
Figure 12:
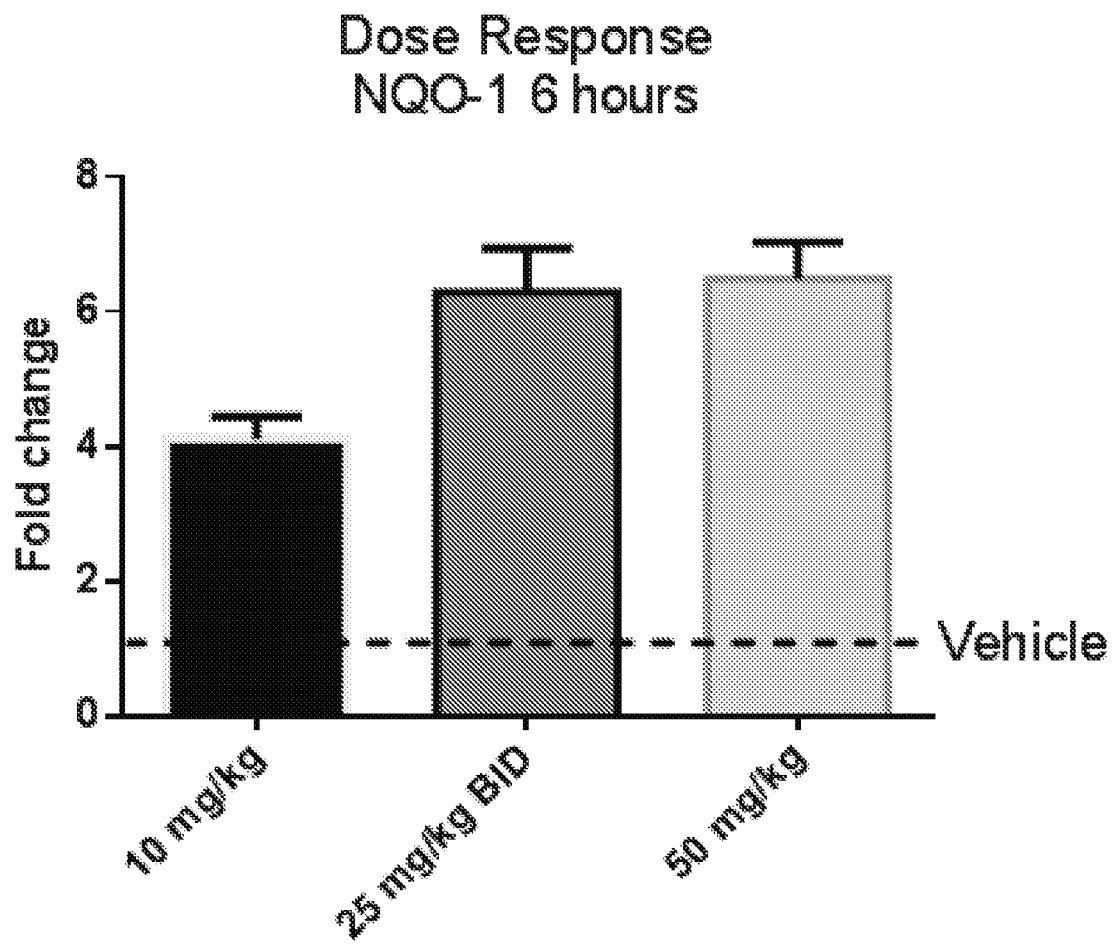
FIG. 12 is a bar graph showing dose responses of compound 12-Ent1 for induction of NQO1 in the spleen of townes mice at the 6 hour time point, including a single dose and two doses of compound 12-Ent1, i.e., a sing1 dose of 10 mg/kg or 50 mg/kg, and two doses of 25 mg/kg (as noted with BID). The two doses were administered 12 hours apart.

As shown in FIG. 8, Compound 12-Ent1 induces HbF protein in cultured HUDEP cells compared to HUDEP cells incubated with DMSO.

Example 154, Method for Testing γ-Globin Gene Induction in Townes Mice Using Nrf2 Activator Compounds Animals All animal experiments conformed to the guidance issued by the Biogen Institutional Animal Care and Use Committee and are described in approved protocols. The SCD mouse strain used in the in vivo studies is the Townes SCD mouse [Wu L C, Sun C W, Ryan™, Pawlik K M, Ren J, Townes™. Correction of sickle cell disease by homologous recombination in embryonic stem cells. Blood. 2006, 108(4):1183-8]. These mice are genetically modified with deletions of the endogenous murine hemoglobin genes and knock in of the human alpha, beta and gamma globin genes, of which the beta globin genes possess the sickle mutation. Of note, these mice have only the Aγ globin gene and do not carry the Gγ gene. These mice harboring the sickle cell mutations in the hemoglobin β-globins chain show the presence of sickle cell disease characterized by abnormally low hemoglobin, circulating sickle shaped erythrocytes, varying degrees of damage of internal organs such as spleen, liver, and kidney. Male and female Townes SS mice aged 8 to 12 weeks were used for studies described here.

Acute SCD study: Four SCD studies were performed with compound 12-Ent1. There were three studies in which a single dose of 10, 25, and 50 mg/kg of the compound was administered to the mice. In the fourth study, two doses of 25 mg/kg were administered 12 hours apart. For each study, 12 mice from the same age group were sorted randomly based on gender, weight, and date of birth into 3 groups of 4 each—time 3 hours, time 6 hours, and time 24 hours. One group of 4 mice was used as control which were administered with vehicle only equivalent. The compound was administered in SPEW (Solutol HS-15/polyethylene glycol/ethanol/water (10/10/10/70)) by oral gavage. At each corresponding time point after dosing, the group of mice was euthanized via asphyxiation in a CO2 chamber. Upon euthanasia, the mice were exsanguinated and blood was collected from the vena cava and immediately placed into EDTA tubes at room temperature. Whole blood was centrifuged at 5000 rpm for 10 mins for plasma isolation for PK analysis. After exsanguination, the spleen was harvested and snap frozen on dry ice for RNA extraction and analysis.

Spleen RNA Extraction, Conversion to cDNA, and Real Time PCR

Frozen spleens were placed at room temperature. Before complete thawing, RLT Plus buffer (Qiagen, Hilden, Germany) containing β-mercaptoethanol and reagent DX (Qiagen) was added to the spleen samples for tissue lysis. Spleen samples were then homogenized using a gentleMACS tissue disruptor (Miltenyi Biotec, Germany). An aliquot of 50 µl of the homogenate was then lysed further using a Tissuelyser LT instrument (Qiagen). RNA was extracted from the lysates using the RNeasy Plus Kit (Qiagen). Extracted RNA was then quantitated using a Nanodrop and 1 µg of total RNA was converted to cDNA using VILO Mastermix kit according to manufacturer's protocol.

cDNA prepared from RNA isolated from tissue samples was used to determine gene expression levels of using Taqman based real time PCR (Life Technologies, ThermoFisher Scientific). Primer-probe pairs for each gene of interest were purchased from Life Technologies. The reaction mix was prepared using 50 ng of cDNA, 2× Taqman reagent and primer-probe pairs and the reaction carried out based on manufacturer's recommendation in the ABI 7900 Fast Block real-time PCR machine (Applied Biosystems, Foster City, Calif.). Results were analyzed using the 7500 software version 2.0.5 and the relative levels of transcripts were measured with GAPDH as the endogenous housekeeping gene control using the $2^{-\Delta\Delta C_t}$ relative quantification method.

Results

As shown in FIGS. 9A-9D and 11, Compound 12-Ent1 induces human γ-globin gene in spleen, at least at the 24 hour time point. As shown in FIGS. 10A-10C and 12, Compound 12-Ent1 also induces NQO-1 gene in spleen, at least at the 6 hour time point.

Other embodiments are within the scope of the following claims.

What is claimed is:
1. A compound represented by Formula I:

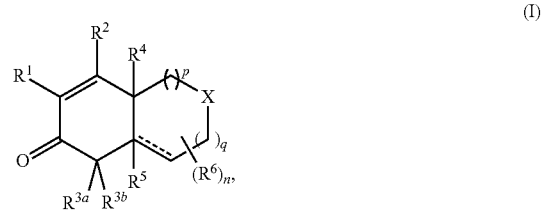

(I)

or a pharmaceutically acceptable salt thereof, wherein
$R^1$ is —CN, —C(O)$R^a$, $CH_3S(O)_2$— or $C_{1-8}$alkyl substituted with one or more fluorine atoms;
$R^a$ is H, $C_{1-12}$alkyl, $C_{2-12}$alkenyl, $C_{2-12}$alkynyl, a carbocyclyl, a heterocyclyl, —O$R^{11}$, —S$R^{14}$, —N($R^{12}$)$_2$, —N$R^{13}$O$R^{13}$, —N$R^{13}$S(O)$_2$$R^{13}$, —N$R^{13}$C(O)$R^{13}$, —N($R^{13}$)N($R^{13}$)$_2$, —N($R^{13}$)C(O)O$R^{13}$ or —N($R^{13}$)C(O)N($R^{13}$)$_2$, wherein the $C_{1-12}$alkyl, $C_{2-12}$alkenyl, $C_{2-12}$alkynyl, carbocyclyl, and heterocyclyl are each optionally substituted with one or more $R^{21}$;
$R^2$ is H, halo, —NO$_2$, —CN, —N$_3$, $C_{1-12}$alkyl, $C_{2-12}$alkenyl, $C_{2-12}$alkynyl, a carbocyclyl, a heterocyclyl, —C(O)$R^{13}$, —C(S)$R^{13}$, —C(O)O$R^{13}$, —C(S)S$R^{13}$, —C(O)S$R^{13}$, —C(S)O$R^{13}$, —SC(O)$R^{13}$, —OC(S)$R^{13}$, —SC(S)$R^{13}$, —C(O)N($R^{13}$)$_2$, —O$R^{11}$, —S$R^{14}$, —N($R^{12}$)$_2$, —N($R^{13}$)O$R^{13}$, —N($R^{13}$)S(O)$_2$$R^{13}$, —N($R^{13}$)C(O)$R^{13}$, —N($R^{13}$)N($R^{13}$)$_2$, —N($R^{13}$)C(O)O$R^{13}$, —N($R^{13}$)C(O)N($R^{13}$)$_2$, —S(O)$_2$$R^{13}$, —S(O)$R^{13}$, —S(O)N($R^{13}$)$_2$, —S(O)$_2$N($R^{13}$)$_2$, —N$^+$($R^{13}$)$_3$, —S$^+$($R^{13}$)$_2$ or —Si($R^{13}$)$_3$, wherein the $C_{1-12}$alkyl, $C_{2-12}$alkenyl, $C_{2-12}$alkynyl, carbocyclyl and heterocyclyl are each optionally substituted with one or more $R^{21}$;
$R^{3a}$ is H, $C_{1-2}$alkyl, $C_{2-12}$alkenyl, $C_{2-12}$alkynyl, a carbocyclyl, a heterocyclyl, —C(O)$R^{13}$, —C(O)O$R^{13}$, —C(O)N($R^{13}$)$_2$, —O$R^{11}$, —N($R^{12}$)$_2$, —N($R^{13}$)O$R^{13}$, —N($R^{13}$)S(O)$_2$$R^{13}$, —N($R^{13}$)C(O)$R^{13}$, —N($R^{13}$)N($R^{13}$)$_2$, —N($R^{13}$)C(O)O$R^{13}$, —N($R^{13}$)C(O)N($R^{13}$)$_2$, —S(O)$R^{13}$, —S(O)N($R^{13}$)$_2$ or —S(O)$_2$N($R^{13}$)$_2$, wherein the $C_{1-12}$alkyl, $C_{2-12}$alkenyl, $C_{2-12}$alkynyl, carbocyclyl and heterocyclyl are each optionally substituted with one or more $R^{21}$; and $R^{3b}$ is $C_{1-12}$alkyl, $C_{2-12}$alkenyl, $C_{2-12}$alkynyl, a carbocyclyl, a heterocyclyl, —C(O)$R^{13}$, —C(O)O$R^{13}$, —C(O)N($R^{13}$)$_2$, —O$R^{11}$, —N($R^{12}$)$_2$, —N($R^{13}$)O$R^{13}$, —N($R^{13}$)S(O)$_2R^{13}$, —N($R^{13}$)C(O)$R^{13}$, —N($R^{13}$)N($R^{13}$)$_2$, —N($R^{13}$)C(O)O$R^{13}$, —N($R^{13}$)C(O)N($R^{13}$)$_2$, —S(O)$R^{13}$, —S(O)N($R^{13}$)$_2$ or —S(O)$_2$N($R^{13}$)$_2$, wherein the $C_{1-12}$alkyl, $C_{2-12}$alkenyl, $C_{2-12}$alkynyl, carbocyclyl and heterocyclyl are each optionally substituted with one or more $R^{21}$; or $R^{3a}$ and $R^{3b}$ are taken together and are $C_{2-12}$alkylene, $C_{2-12}$alkenylene or $C_{2-12}$alkynylene; wherein the $C_{2-12}$alkylene, $C_{2-12}$alkenylene, $C_{2-12}$alkynylene and 3-6-membered carbocyclyl are each optionally substituted with one or more $R^{21}$;

$R^4$ is H, halo, —NO$_2$, —CN, —N$_3$, $C_{1-12}$alkyl, $C_{2-12}$alkenyl, $C_{2-12}$alkynyl, a membered carbocyclyl, a heterocyclyl, —C(O)$R^{13}$, —C(S)$R^{13}$, —C(O)O$R^{13}$, —C(S)S$R^{13}$, —C(O)S$R^{13}$, —C(S)O$R^{13}$, —SC(O)$R^{13}$, —OC(S)$R^{13}$, —SC(S)$R^{13}$, —C(O)N($R^{13}$)$_2$, —O$R^{11}$, —S$R^{14}$, —N($R^{12}$)$_2$, —N($R^{13}$)O$R^{13}$, —N($R^{13}$)S(O)$_2R^{13}$, —N($R^{13}$)C(O)$R^{13}$, —N($R^{13}$)N($R^{13}$)$_2$, —N($R^{13}$)C(O)O$R^{13}$, —N($R^{13}$)C(O)N($R^{13}$)$_2$, —S(O)$_2R^{13}$, —S(O)$R^{13}$, —S(O)N($R^{13}$)$_2$, —S(O)$_2$N($R^{13}$)$_2$, —N$^+$($R^{13}$)$_3$, —S$^+$($R^{13}$)$_2$ or —Si($R^{13}$)$_3$, wherein the $C_{1-12}$alkyl, $C_{2-12}$alkenyl, $C_{2-12}$alkynyl, carbocyclyl and heterocyclyl are each optionally substituted with one or more $R^{21}$;

" ----- " is either a single bond or a double bond, wherein when " ----- " is a double bond, then $R^5$ is absent; and when " ----- " is a single bond, then $R^5$ is H, halo, —NO$_2$, —CN, —N$_3$, $C_{1-12}$alkyl, $C_{2-12}$alkenyl, $C_{2-12}$alkynyl, a carbocyclyl, a heterocyclyl, —C(O)$R^{13}$, —C(S)$R^{13}$, —C(O)O$R^{13}$, —C(S)S$R^{13}$, —C(O)S$R^{13}$, —C(S)O$R^{13}$, —SC(O)$R^{13}$, —OC(S)$R^{13}$, —SC(S)$R^{13}$, —C(O)N($R^{13}$)$_2$, —O$R^{11}$, —S$R^{14}$, —N($R^{12}$)$_2$, —N($R^{13}$)O$R^{13}$, —N($R^{13}$)S(O)$_2R^{13}$, —N($R^{13}$)C(O)$R^{13}$, —N($R^{13}$)N($R^{13}$)$_2$, —N($R^{13}$)C(O)O$R^{13}$, —N($R^{13}$)C(O)N($R^{13}$)$_2$, —S(O)$_2R^{13}$, —S(O)$R^{13}$, —S(O)N($R^{13}$)$_2$, —S(O)$_2$N($R^{13}$)$_2$, —N$^+$($R^{13}$)$_3$, —S$^+$($R^{13}$)$_2$ or —Si($R^{13}$)$_3$, wherein the $C_{1-12}$alkyl, $C_{2-12}$alkenyl, $C_{2-12}$alkynyl, carbocyclyl and heterocyclyl are each optionally substituted with one or more $R^{21}$; or $R^5$ and $R^{3b}$ are taken together with the carbons to which they each are attached form a 3-6-membered carbocyclyl, wherein the 3-6-membered carbocyclyl is optionally substituted with one or more $R^{21}$;

$R^6$, in each occurrence, is independently halo, —NO$_2$, —CN, —N$_3$, $C_{1-12}$alkyl, $C_{2-12}$alkenyl, $C_{2-12}$alkynyl, a carbocyclyl, a heterocyclyl, —C(O)$R^{13}$, —C(S)$R^{13}$, —C(O)O$R^{13}$, —C(S)S$R^{13}$, —C(O)S$R^{13}$, —C(S)O$R^{13}$, —SC(O)$R^{13}$, —OC(S)$R^{13}$, —SC(S)$R^{13}$, —C(O)N($R^{13}$)$_2$, —O$R^{11}$, —S$R^{14}$, —N($R^{12}$)$_2$, —N($R^{13}$)O$R^{13}$, —N($R^{13}$)S(O)$_2R^{13}$, —N($R^{13}$)C(O)$R^{13}$, —N($R^{13}$)N($R^{13}$)$_2$, —N($R^{13}$)C(O)O$R^{13}$, —N($R^{13}$)C(O)N($R^{13}$)$_2$, —S(O)$_2R^{13}$, —S(O)$R^{13}$, —S(O)N($R^{13}$)$_2$, —S(O)$_2$N($R^{13}$)$_2$, —N$^+$($R^{13}$)$_3$, —S($R^{13}$)$_2$ or —Si($R^{13}$)$_3$; or two $R^6$ attached to the same ring carbon to form an oxo, =N$R^{14}$ or $C_{1-12}$alkylidene, wherein the $C_{1-12}$alkyl, $C_{2-12}$alkenyl, $C_{2-12}$alkynyl, carbocyclyl heterocyclyl and $C_{1-12}$alkylidene are each optionally substituted with one or more $R^{21}$;

X is N$R^b$ or O;

$R^b$ is H, $C_{1-12}$alkyl, $C_{2-12}$alkenyl, $C_{2-12}$alkynyl, a carbocyclyl, a heterocyclyl, —C(O)$R^c$, —C(O)O$R^c$, —C(O)N$R^cR^c$, —S(O)$_2R^c$, —S(O)$_2$O$R^c$ or —S(O)$_2$N$R^cR^c$, wherein the $C_{1-12}$alkyl, $C_{2-12}$alkenyl, $C_{2-12}$alkynyl, carbocyclyl and heterocyclyl are each optionally substituted with one or more $R^{21}$;

$R^c$, in each occurrence, is independently selected from H, $C_{1-12}$alkyl, $C_{2-12}$alkenyl, $C_{2-12}$alkynyl, a carbocyclyl and a heterocyclyl, wherein the $C_{1-12}$alkyl, $C_{2-12}$alkenyl, $C_{2-12}$alkynyl, carbocyclyl and heterocyclyl are each optionally substituted with one or more $R^{21}$;

$R^{11}$, in each occurrence, is independently selected from H, $C_{1-12}$alkyl, $C_{2-12}$alkenyl, $C_{2-12}$alkynyl, a carbocyclyl, a heterocyclyl, $C_{1-12}$acyl and —Si($R^{13}$)$_3$, wherein the $C_{1-12}$alkyl, $C_{2-12}$alkenyl, $C_{2-12}$alkynyl, carbocyclyl, heterocyclyl, and $C_{1-12}$acyl are each optionally substituted with one or more $R^{21}$;

$R^{12}$, in each occurrence, is independently selected from H, $C_{1-12}$alkyl, $C_{1-12}$alkoxy, $C_{2-12}$alkenyl, $C_{2-12}$alkynyl, a carbocyclyl, a heterocyclyl and —Si($R^{13}$)$_3$, wherein the $C_{1-12}$alkyl, $C_{1-12}$alkoxy, $C_{2-12}$alkenyl, $C_{2-12}$alkynyl, carbocyclyl and heterocyclyl are each optionally substituted with one or more $R^{21}$;

$R^{13}$, in each occurrence, is independently selected from H, $C_{1-12}$alkyl, $C_{2-12}$alkenyl, $C_{2-12}$alkynyl, a carbocyclyl, and a heterocyclyl, wherein the $C_{1-12}$alkyl, $C_{2-12}$alkenyl, $C_{2-12}$alkynyl, carbocyclyl and heterocyclyl are optionally substituted with one or more $R^{21}$;

$R^{14}$, in each occurrence, is independently selected from H, $C_{1-12}$alkyl, $C_{2-12}$alkenyl, $C_{2-12}$alkynyl, a carbocyclyl, a heterocyclyl and $C_{1-12}$acyl, wherein the $C_{1-12}$alkyl, $C_{2-12}$alkenyl, $C_{2-12}$alkynyl, carbocyclyl, heterocyclyl and $C_{1-12}$acyl are each optionally substituted with one or more $R^{21}$;

$R^{21}$, in each occurrence, is independently selected from halo, —OH, —S(O)$_2R^{16}$, $C_{1-12}$alkyl, $C_{2-12}$alkenyl, $C_{2-12}$alkynyl, $C_{1-12}$alkoxy, a carbocyclyl and a heterocyclyl, wherein the $C_{1-12}$alkyl, $C_{2-12}$alkenyl, $C_{2-12}$alkynyl, $C_{1-12}$alkoxy, carbocyclyl and heterocyclyl are each optionally substituted with 1 to 3 groups selected from halo, —OH, $C_{1-4}$alkyl and $C_{1-4}$alkoxy;

$R^{16}$, in each occurrence, is independently selected from H or $C_{1-12}$alkyl;

n is 0 or an integer from 1 to 8;

p is 0, 1 or 2; and q is 1, 2 or 3, provided that the sum of p and q is not 4 or 5;

wherein the carbocyclyl is a 3 to 6-membered monocyclic cycloalkyl or phenyl and wherein the heterocyclyl is a 3 to 7-membered saturated monocyclic ring having 1 to 4 heteroatoms independently selected from O, S and N, or a 5- to 7-membered monocyclic heteroaryl having 1 to 4 heteroatoms independently selected from O, S and N.

2. The compound of claim 1, wherein the compound is represented by Formula II:

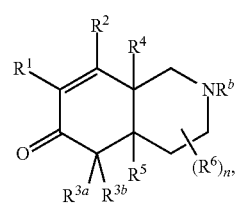

or Formula III:

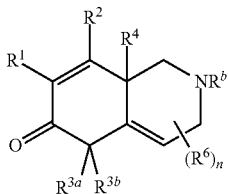

or Formula IV:

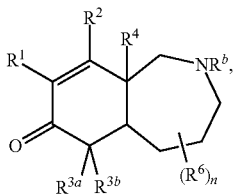

or Formula V:

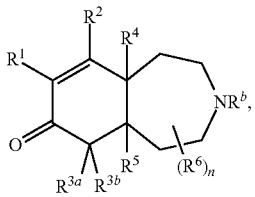

or a pharmaceutically acceptable salt thereof.

3. The compound of claim 1, or a pharmaceutically acceptable salt thereof, wherein $R^b$ is H, $C_{1-12}$alkyl, phenyl, a heterocyclyl, —C(O)$R^c$, —C(O)O$R^c$, —C(O)N$R^cR^c$, —S(O)$_2R_c$, —S(O)$_2$O$R^c$ or —S(O)$_2$N$R^cR^c$, wherein $R^c$, in each occurrence, is independently H, $C_{1-6}$alkyl, a cycloalkyl, a heterocyclyl or phenyl, wherein the alkyl, cycloalkyl, heterocyclyl and phenyl, in each occurrence, in $R^b$ or $R^c$ are optionally substituted with 1 to 3 groups selected from halo, —OH, $C_{1-4}$alkoxy, phenyl and a heteroaryl, wherein the heterocyclyl and heteroaryl each comprise 1 to 3 heteroatoms, wherein the heteroatoms are selected from the group consisting of N, S and O.

4. The compound of claim 1, wherein the compound is represented by Formula VI:

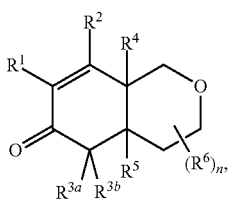

or Formula VII:

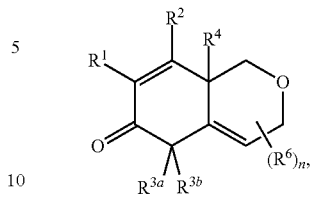

or a pharmaceutically acceptable salt thereof.

5. The compound of claim 1, or a pharmaceutically acceptable salt thereof, wherein $R^1$ is —CN, —CF$_3$ or —C(O)$R^a$.

6. The compound of claim 1, or a pharmaceutically acceptable salt thereof, wherein $R^2$ is H, —OH, halo, $C_{1-12}$alkyl or $C_{1-12}$alkoxy, wherein the alkyl and alkoxy are each optionally substituted with 1 to 3 groups selected from halo, —OH, $C_{1-4}$alkoxy, phenyl and a heteroaryl.

7. The compound of claim 1, or a pharmaceutically acceptable salt thereof, wherein $R^{3a}$ is H; and $R^{3b}$ is $C_{1-12}$alkyl, $C_{2-12}$alkenyl, $C_{2-12}$alkynyl, phenyl, a heteroaryl, —C(O)$R^{13}$, —O$R^{11}$, —N($R^{12}$)$_2$ or —N($R^{13}$)C(O)$R^{13}$, wherein $R^{11}$ is independently H, $C_{1-12}$alkyl, $C_{1-12}$acyl, phenyl, or a heteroaryl; and $R^{12}$ and $R^{13}$, in each occurrence, are independently H, $C_{1-12}$alkyl, phenyl or a heteroaryl, wherein the alkyl, alkenyl, alkynyl, phenyl, heteroaryl and acyl, in each occurrence, in $R^{11}$, $R^{12}$ and $R^{13}$ are optionally substituted with 1 to 3 groups selected from halo, —OH, $C_{1-4}$alkoxy, phenyl and a heteroaryl.

8. The compound of claim 1, or a pharmaceutically acceptable salt thereof, wherein $R^{3a}$ is $C_{1-12}$alkyl, $C_{2-12}$alkenyl, $C_{2-12}$alkynyl, a carbocyclyl, a heterocyclyl, —C(O)$R^{13}$, —C(O)O$R^{13}$, —C(O)N($R^{13}$)$_2$, —O$R^{11}$, —N($R^{12}$)$_2$, —N($R^{13}$)O$R^{13}$, —N($R^{13}$)S(O)$_2R^{13}$, —N($R^{13}$)C(O)$R^{13}$, —N($R^{13}$)N($R^{13}$)$_2$, —N($R^{13}$)C(O)O$R^{13}$, —N($R^{13}$)C(O)N($R^{13}$)$_2$, —S(O)$R^{13}$, —S(O)N($R^{13}$)$_2$ or —S(O)$_2$N($R^{13}$)$_2$, wherein the $C_{1-12}$alkyl, $C_{2-12}$alkenyl, $C_{2-12}$alkynyl, carbocyclyl and heterocyclyl are each optionally substituted with one or more $R^{21}$.

9. The compound of claim 1, or a pharmaceutically acceptable salt thereof, wherein $R^{3a}$ and $R^{3b}$ are taken together and are $C_{2-12}$alkylene, $C_{2-12}$alkenylene or $C_{2-12}$alkynylene.

10. The compound of claim 1, or a pharmaceutically acceptable salt thereof, wherein $R^4$ is H, —OH, halo, $C_{1-12}$alkyl, $C_{1-12}$alkoxy or phenyl, wherein the alkyl, alkoxy and phenyl are each optionally substituted with 1 to 3 groups selected from halo, —OH, $C_{1-4}$alkoxy, phenyl and a heteroaryl.

11. The compound of claim 1, or a pharmaceutically acceptable salt thereof, wherein $R^5$ is H, —OH, halo, $C_{1-12}$alkyl or $C_{1-12}$alkoxy, wherein the alkyl and alkoxy are each optionally substituted with 1 to 3 groups selected from halo, —OH, $C_{1-4}$alkoxy, phenyl and a heteroaryl.

12. The compound of claim 1, or a pharmaceutically acceptable salt thereof, wherein $R^6$ is —OH, halo, $C_{1-12}$alkyl or $C_{1-12}$alkoxy, wherein the alkyl and alkoxy are each optionally substituted with 1 to 3 groups selected from halo, —OH, $C_{1-4}$alkoxy, phenyl and a heteroaryl.

13. The compound of claim 1, or a pharmaceutically acceptable salt thereof, wherein n is 1 or 2.

14. The compound of claim 1, or a pharmaceutically acceptable salt thereof, wherein n is 2; and two $R^6$ are attached to the same ring carbon to form an oxo, =N$R^{14}$ or $C_{1-12}$alkylidene.

15. The compound of claim 14, or a pharmaceutically acceptable salt thereof, wherein the compound is represented by Formula VIII(A):

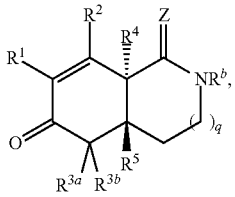

or Formula VIII(B):

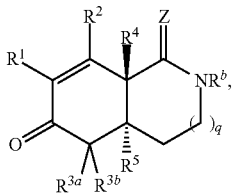

or Formula IX(A):

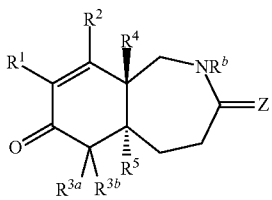

or Formula IX(B):

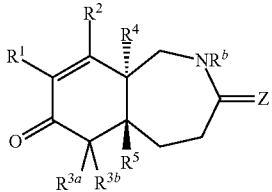

or Formula X(A):

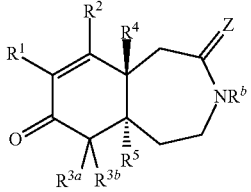

or Formula X(B):

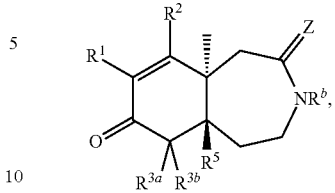

or a pharmaceutically acceptable salt thereof, wherein Z is O, $NR^{22}$ or $C(R^{22})_2$, wherein $R^{22}$, in each occurrence, is independently H or a $C_{1-4}$alkyl optionally substituted with 1 to 3 groups selected from halo, —OH and $C_{1-4}$alkoxy.

16. The compound of claim 15, or a pharmaceutically acceptable salt thereof, wherein Z is O.

17. The compound of claim 1, or a pharmaceutically acceptable salt thereof, wherein n is 0.

18. The compound of claim 1, or a pharmaceutically acceptable salt thereof, wherein
$R^1$ is CN, —$CF_3$ or —$C(O)R^a$;
$R^2$ is H, —OH, halo, $C_{1-12}$alkyl or $C_{1-12}$alkoxy, wherein the alkyl and alkoxy are each optionally substituted with 1 to 3 groups selected from halo, —OH, $C_{1-4}$alkoxy, phenyl and a heteroaryl;
$R^{3a}$ is H, $C_{1-12}$alkyl, $C_{2-12}$alkenyl, $C_{2-12}$alkynyl, —C(O)$R^{13}$, —$OR^{11}$, —$N(R^{12})_2$ or —$N(R^{13})C(O)R^{13}$; and $R^{3b}$ is $C_{1-12}$alkyl, $C_{2-12}$alkenyl, $C_{2-12}$alkynyl, —C(O)$R^{13}$, —$OR^{11}$, —$N(R^{12})_2$ or —$N(R^{13})C(O)R^{13}$, wherein $R^{11}$ to $R^{13}$ are each independently H or $C_{1-4}$alkyl; or $R^{3a}$ and $R^{3b}$ taken together with the carbon, to which they are both attached to, form a $C_{3-8}$ membered non-aromatic ring;
$R^4$ is H, —OH, halo, $C_{1-12}$alkyl, $C_{1-12}$alkoxy or phenyl, wherein the alkyl, alkoxy and phenyl are each optionally substituted with 1 to 3 groups selected from halo, —OH, $C_{1-4}$alkoxy, phenyl and a heteroaryl;
" ------ " is a single bond;
$R^5$ is H, —OH, halo, $C_{1-12}$alkyl or $C_{1-12}$alkoxy, wherein the alkyl and alkoxy are each optionally substituted with 1 to 3 groups selected from halo, —OH, $C_{1-4}$alkoxy, phenyl and a heteroaryl;
$R^b$ is H, phenyl, a heterocyclyl, —C(O)$R^c$, —C(O)O$R^c$, —C(O)N$R^cR^c$, —S(O)$_2R^c$, —S(O)$_2$O$R^c$ or —S(O)$_2$N$R^cR^c$, wherein $R^c$, in each occurrence, is independently H, $C_{1-6}$alkyl, a cycloalkyl, a heterocyclyl or phenyl, wherein the alkyl, cycloalkyl, heterocyclyl and phenyl in each occurrence, in $R^b$ or $R^c$ are optionally substituted with 1 to 3 groups selected from halo, —OH, $C_{1-4}$alkoxy, phenyl and a heteroaryl, wherein the heterocyclyl comprises 1 to 3 heteroatoms, wherein the heteroatoms are selected from the group consisting of N, S and O; and
n is 0 or 2, wherein, when n is 2, two $R^6$ are attached to the same ring carbon to form an oxo, =$NR^{14}$ or $C_{1-12}$alkylidene.

19. The compound of claim 1, or a pharmaceutically acceptable salt thereof, wherein
$R^1$ is —CN, —$CF_3$ or —$C(O)R^a$;
$R^2$ is H, —OH, halo, $C_{1-12}$alkyl or $C_{1-12}$alkoxy, wherein the alkyl and alkoxy are each optionally substituted with 1 to 3 groups selected from halo, —OH, $C_{1-4}$alkoxy, phenyl and a heteroaryl;

R³ᵃ is H, C₁₋₁₂alkyl, C₂₋₁₂alkenyl, C₂₋₁₂alkynyl, —C(O)R¹³, —OR¹¹, —N(R¹²)₂ or —N(R¹³)C(O)R¹³; and R³ᵇ is C₁₋₁₂alkyl, C₂₋₁₂alkenyl, C₂₋₁₂alkynyl, —C(O)R¹³, —OR¹¹, —N(R¹²)₂ or —N(R¹³)C(O)R¹³, wherein R¹¹ to R¹³ are each independently H or C₁₋₄alkyl; or R³ᵃ and R³ᵇ taken together with the carbon, to which they are both attached to, form a C₃₋₈ membered non-aromatic ring;

R⁴ is H, —OH, halo, C₁₋₁₂alkyl, C₁₋₁₂alkoxy or phenyl, wherein the alkyl, alkoxy and phenyl are each optionally substituted with 1 to 3 groups selected from halo, —OH, C₁₋₄alkoxy, phenyl and a heteroaryl;

" ===== " is a double bond;

Rᵇ is H, C₁₋₁₂alkyl, phenyl, a heterocyclyl, —C(O)Rᶜ, —C(O)ORᶜ, —C(O)NRᶜRᶜ, —S(O)₂Rᶜ, —S(O)₂ORᶜ or —S(O)₂NRᶜRᶜ, wherein Rᶜ, in each occurrence, is independently H, C₁₋₆alkyl, a cycloalkyl, a heterocyclyl or phenyl, wherein the alkyl, cycloalkyl, heterocyclyl and phenyl, in each occurrence, in Rᵇ or Rᶜ are optionally substituted with 1 to 3 groups selected from halo, —OH, C₁₋₄alkoxy, phenyl and a heteroaryl, wherein the heterocyclyl and heteroaryl each comprise 1 to 3 heteroatoms, wherein the heteroatoms are selected from the group consisting of N, S and O; and n is 0.

20. The compound of claim 1 selected from the group consisting of:

(4aS,5S,8aR)-2-benzyl-5-methyl-1,6-dioxo-8a-phenyl-1,2,3,4,4a,5,6,8a-octahydroisoquinoline-7-carbonitrile;
(4aR,5R,8aS)-2-benzyl-5-methyl-1,6-dioxo-8a-phenyl-1,2,3,4,4a,5,6,8a-octahydroisoquinoline-7-carbonitrile;
(4aR,5R,8aS)-5-methyl-1,6-dioxo-8a-phenyl-2-(3-pyridylmethyl)-3,4,4a,5-tetrahydroisoquinoline-7-carbonitrile;
(4aS,5S,8aR)-5-methyl-1,6-dioxo-8a-phenyl-2-(3-pyridylmethyl)-3,4,4a,5-tetrahydroisoquinoline-7-carbonitrile;
(4aR,5R,8aR)-2-(2-hydroxyethyl)-5-methyl-1,6-dioxo-8a-phenyl-3,4,4a,5-tetrahydroisoquinoline-7-carbonitrile;
(4aS,5S,8aS)-2-(2-hydroxyethyl)-5-methyl-1,6-dioxo-8a-phenyl-3,4,4a,5-tetrahydroisoquinoline-7-carbonitrile;
(4aS,5R,8aR)-5-methyl-1,6-dioxo-8a-phenyl-2-(2-pyridylmethyl)-3,4,4a,5-tetrahydroisoquinoline-7-carbonitrile;
(4aR,5S,8aS)-5-methyl-1,6-dioxo-8a-phenyl-2-(2-pyridylmethyl)-3,4,4a,5-tetrahydroisoquinoline-7-carbonitrile;
(4aR,5R,8aS)-2-cyclobutyl-5-methyl-1,6-dioxo-8a-phenyl-3,4,4a,5-tetrahydroisoquinoline-7-carbonitrile;
(4aS,5S,8aR)-2-cyclobutyl-5-methyl-1,6-dioxo-8a-phenyl-3,4,4a,5-tetrahydroisoquinoline-7-carbonitrile;
(4aR,5R,8aR)-5-methyl-2-[(1-methylpyrazol-4-yl)methyl]-1,6-dioxo-8a-phenyl-3,4,4a,5-tetrahydroisoquinoline-7-carbonitrile;
(4aS,5S,8aS)-5-methyl-2-[(1-methylpyrazol-4-yl)methyl]-1,6-dioxo-8a-phenyl-3,4,4a,5-tetrahydroisoquinoline-7-carbonitrile;
(4aR,5R,8aS)-2-[(3-methoxyphenyl)methyl]-5-methyl-1,6-dioxo-8a-phenyl-3,4,4a,5-tetrahydroisoquinoline-7-carbonitrile;
(4aS,5S,8aR)-2-[(3-methoxyphenyl)methyl]-5-methyl-1,6-dioxo-8a-phenyl-3,4,4a,5-tetrahydroisoquinoline-7-carbonitrile;
(4aS,5S,8aR)-2-[(3-fluorophenyl)methyl]-5-methyl-1,6-dioxo-8a-phenyl-3,4,4a,5-tetrahydroisoquinoline-7-carbonitrile;
(4aR,5R,8aS)-2-[(3-fluorophenyl)methyl]-5-methyl-1,6-dioxo-8a-phenyl-3,4,4a,5-tetrahydroisoquinoline-7-carbonitrile;
(4aS,5S,8aR)-2-[(4-methoxyphenyl)methyl]-5-methyl-1,6-dioxo-8a-phenyl-3,4,4a,5-tetrahydroisoquinoline-7-carbonitrile;
(4aR,5R,8aS)-2-[(4-methoxyphenyl)methyl]-5-methyl-1,6-dioxo-8a-phenyl-3,4,4a,5-tetrahydroisoquinoline-7-carbonitrile;
(4aS,5S,8aS)-2-isopropyl-5-methyl-1,6-dioxo-8a-phenyl-3,4,4a,5-tetrahydroisoquinoline-7-carbonitrile;
(4aR,5R,8aR)-2-isopropyl-5-methyl-1,6-dioxo-8a-phenyl-3,4,4a,5-tetrahydroisoquinoline-7-carbonitrile;
(4aS,5S,8aR)-2-(cyclopropylmethyl)-5-methyl-1,6-dioxo-8a-phenyl-3,4,4a,5-tetrahydroisoquinoline-7-carbonitrile;
(4aR,5R,8aS)-2-(cyclopropylmethyl)-5-methyl-1,6-dioxo-8a-phenyl-3,4,4a,5-tetrahydroisoquinoline-7-carbonitrile;
(4aS,5S,8aR)-2-[(4-fluorophenyl)methyl]-5-methyl-1,6-dioxo-8a-phenyl-3,4,4a,5-tetrahydroisoquinoline-7-carbonitrile;
(4aR,5R,8aS)-2-[(4-fluorophenyl)methyl]-5-methyl-1,6-dioxo-8a-phenyl-3,4,4a,5-tetrahydroisoquinoline-7-carbonitrile;
(4aS,5S,8aR)-2-(2,2-difluoroethyl)-5-methyl-1,6-dioxo-8a-phenyl-3,4,4a,5-tetrahydroisoquinoline-7-carbonitrile;
(4aR,5R,8aS)-2-(2,2-difluoroethyl)-5-methyl-1,6-dioxo-8a-phenyl-3,4,4a,5-tetrahydroisoquinoline-7-carbonitrile;
(4aS,5S,8aR)-2-[(2-fluorophenyl)methyl]-5-methyl-1,6-dioxo-8a-phenyl-3,4,4a,5-tetrahydroisoquinoline-7-carbonitrile;
(4aR,5R,8aS)-2-[(2-fluorophenyl)methyl]-5-methyl-1,6-dioxo-8a-phenyl-3,4,4a,5-tetrahydroisoquinoline-7-carbonitrile;
(4aS,8aR)-2-(2-methoxyethyl)-5,5-dimethyl-1,6-dioxo-8a-phenyl-4,4a-dihydro-3H-isoquinoline-7-carbonitrile;
(4aR,8aR)-2-(2-methoxyethyl)-5,5-dimethyl-1,6-dioxo-8a-phenyl-4,4a-dihydro-3H-isoquinoline-7-carbonitrile;
(4aS,5S,8aR)-2-(2-methoxyethyl)-5-methyl-1,6-dioxo-8a-phenyl-3,4,4a,5-tetrahydroisoquinoline-7-carbonitrile;
(4aR,5R,8aS)-2-(2-methoxyethyl)-5-methyl-1,6-dioxo-8a-phenyl-3,4,4a,5-tetrahydroisoquinoline-7-carbonitrile;
(4aS,8aS)-2,5,5-trimethyl-1,6-dioxo-8a-phenyl-4,4a-dihydro-3H-isoquinoline-7-carbonitrile;
(4aR,8aR)-2,5,5-trimethyl-1,6-dioxo-8a-phenyl-4,4a-dihydro-3H-isoquinoline-7-carbonitrile;
(4aR,8aR)-5,5,8a-trimethyl-2-(2-methylpyrimidin-4-yl)-6-oxo-1,3,4,4a-tetrahydroisoquinoline-7-carbonitrile;
(5aR,9aS)-3-acetyl-5a,9,9-trimethyl-8-oxo-2,4,5,9a-tetrahydro-1H-3-benzazepine-7-carbonitrile;
(4aR,8aR)-5,5,8a-trimethyl-2-(6-methylpyrimidin-4-yl)-6-oxo-1,3,4,4a-tetrahydroisoquinoline-7-carbonitrile hydrochloride;
(5aS,9aR)-2-(2,2-difluoroethyl)-6,6,9a-trimethyl-7-oxo-3,4,5,5a-tetrahydro-1H-2-benzazepine-8-carbonitrile;
(4aS,8aR)-5,5,8a-trimethyl-2-(2-methylpyrimidin-5-yl)-6-oxo-1,3,4,4a-tetrahydroisoquinoline-7-carbonitrile;
(4aS,8aR)-5,5,8a-trimethyl-6-oxo-2-(2,2,2-trifluoroacetyl)-1,3,4,4a-tetrahydroisoquinoline-7-carbonitrile;

(8aR)-2-ethyl-5,5-dimethyl-1,6-dioxo-8a-phenyl-3H-isoquinoline-7-carbonitrile;
(8aS)-2-ethyl-5,5-dimethyl-1,6-dioxo-8a-phenyl-3H-isoquinoline-7-carbonitrile;
(4aR,8aS)-2-ethyl-5,5-dimethyl-1,6-dioxo-8a-phenyl-4,4a-dihydro-3H-isoquinoline-7-carbonitrile;
(4aS,8aR)-2-ethyl-5,5-dimethyl-1,6-dioxo-8a-phenyl-4,4a-dihydro-3H-isoquinoline-7-carbonitrile;
(4aR,5S,8aR)-2-acetyl-5-ethyl-5,8a-dimethyl-6-oxo-1,3,4,4a-tetrahydroisoquinoline-7-carbonitrile;
(5R,8aR)-2-acetyl-5-benzyl-5,8a-dimethyl-6-oxo-1,3-dihydroisoquinoline-7-carbonitrile;
(5S,8aR)-2-acetyl-5-benzyl-5,8a-dimethyl-6-oxo-1,3-dihydroisoquinoline-7-carbonitrile;
(5R,8aR)-2-acetyl-5-ethyl-5,8a-dimethyl-6-oxo-1,3-dihydroisoquinoline-7-carbonitrile;
(5S,8aR)-2-acetyl-5-ethyl-5,8a-dimethyl-6-oxo-1,3-dihydroisoquinoline-7-carbonitrile;
(4aS,5R,8aR)-2,5-dimethyl-1,6-dioxo-8a-phenyl-3,4,4a,5-tetrahydroisoquinoline-7-carbonitrile;
(4aR,5S,8aS)-2,5-dimethyl-1,6-dioxo-8a-phenyl-3,4,4a,5-tetrahydroisoquinoline-7-carbonitrile;
(8aR)-2,5,5-trimethyl-1,6-dioxo-8a-phenyl-3H-isoquinoline-7-carbonitrile;
(8aS)-2,5,5-trimethyl-1,6-dioxo-8a-phenyl-3H-isoquinoline-7-carbonitrile;
(4aS,5R,8aR)-2-ethyl-5-methyl-1,6-dioxo-8a-phenyl-3,4,4a,5-tetrahydroisoquinoline-7-carbonitrile;
(4aR,5S,8aS)-2-ethyl-5-methyl-1,6-dioxo-8a-phenyl-3,4,4a,5-tetrahydroisoquinoline-7-carbonitrile;
(4aS,8aR)-2-[(2S)-2-fluoropropanoyl]-5,5,8a-trimethyl-6-oxo-1,3,4,4a-tetrahydroisoquinoline-7-carbonitrile;
(4aS,8aR)-2-[(2R)-2-fluoropropanoyl]-5,5,8a-trimethyl-6-oxo-1,3,4,4a-tetrahydroisoquinoline-7-carbonitrile;
(4aS,8aR)-2-(2,2-difluoroethyl)-5,5-dimethyl-6-oxo-8a-phenyl-1,3,4,4a-tetrahydroisoquinoline-7-carbonitrile;
(4aR,8aS)-2-(2,2-difluoroethyl)-5,5-dimethyl-6-oxo-8a-phenyl-1,3,4,4a-tetrahydroisoquinoline-7-carbonitrile;
methyl (4aS,8aR)-7-cyano-5,5,8a-trimethyl-6-oxo-1,3,4,4a-tetrahydroisoquinoline-2-carboxylate;
(4aS,8aR)-2-acetyl-5,5,8a-trimethyl-6-oxo-1,3,4,4a-tetrahydroisoquinoline-7-carbonitrile;
tert-butyl (4aR,8aR)-7-cyano-5,5,8a-trimethyl-6-oxo-1,3,4,4a-tetrahydroisoquinoline-2-carboxylate;
(4aS,8aR)-2-acetyl-5,5-dimethyl-6-oxo-8a-phenyl-1,3,4,4a-tetrahydroisoquinoline-7-carbonitrile;
(4aR,8aS)-2-acetyl-5,5-dimethyl-6-oxo-8a-phenyl-1,3,4,4a-tetrahydroisoquinoline-7-carbonitrile;
(4aR,5R,8aS)-5-methyl-1,6-dioxo-8a-phenyl-3,4,4a,5-tetrahydro-2H-isoquinoline-7-carbonitrile;
(4aS,5S,8aR)-5-methyl-1,6-dioxo-8a-phenyl-3,4,4a,5-tetrahydro-2H-isoquinoline-7-carbonitrile;
(4aS,8aR)-5,5,8a-trimethyl-6-oxo-2-pyrazin-2-yl-1,3,4,4a-tetrahydroisoquinoline-7-carbonitrile;
(4aS,8aR)-2-(2,2-difluoroethyl)-8a-ethyl-5,5-dimethyl-6-oxo-1,3,4,4a-tetrahydroisoquinoline-7-carbonitrile;
(4aR,8aS)-2-(2,2-difluoroethyl)-8a-ethyl-5,5-dimethyl-6-oxo-1,3,4,4a-tetrahydroisoquinoline-7-carbonitrile;
(4aS,8aR)-8a-ethyl-5,5-dimethyl-6-oxo-2-pyrimidin-2-yl-1,3,4,4a-tetrahydroisoquinoline-7-carbonitrile;
(4aR,8aS)-8a-ethyl-5,5-dimethyl-6-oxo-2-pyrimidin-2-yl-1,3,4,4a-tetrahydroisoquinoline-7-carbonitrile;
(4aS,8aR)-2-acetyl-8a-ethyl-5,5-dimethyl-6-oxo-1,3,4,4a-tetrahydroisoquinoline-7-carbonitrile;
(4aR,8aS)-2-acetyl-8a-ethyl-5,5-dimethyl-6-oxo-1,3,4,4a-tetrahydroisoquinoline-7-carbonitrile;
(4aR,8aR)-2-(2-methoxyethyl)-5,5,8a-trimethyl-6-oxo-1,3,4,4a-tetrahydroisoquinoline-7-carbonitrile;
(4aR,8aR)-5,5,8a-trimethyl-2-(2-methylsulfonylethyl)-6-oxo-1,3,4,4a-tetrahydroisoquinoline-7-carbonitrile;
(5aS,9aR)-2-acetyl-6,6,9a-trimethyl-7-oxo-3,4,5,5a-tetrahydro-1H-2-benzazepine-8-carbonitrile;
(5aS,9aR)-6,6,9a-trimethyl-3,7-dioxo-2,4,5,5a-tetrahydro-1H-2-benzazepine-8-carbonitrile;
(5aR,9aS)-5a,9,9-trimethyl-4,8-dioxo-2,3,5,9a-tetrahydro-1H-3-benzazepine-7-carbonitrile;
(5aS,9aS)-1,6,6,9a-tetramethyl-2,7-dioxo-3,4,5,5a-tetrahydro-1-benzazepine-8-carbonitrile;
(5aS,9aS)-6,6,9a-trimethyl-2,7-dioxo-3,4,5,5a-tetrahydro-1H-1-benzazepine-8-carbonitrile;
(3R,4aS,8aR)-2-acetyl-3,5,5,8a-tetramethyl-6-oxo-1,3,4,4a-tetrahydroisoquinoline-7-carbonitrile;
(3 S,4aR,8aS)-2-acetyl-3,5,5,8a-tetramethyl-6-oxo-1,3,4,4a-tetrahydroisoquinoline-7-carbonitrile;
(4aR,8aS)-2,5,5,8a-tetramethyl-3,6-dioxo-4,4a-dihydro-1H-isoquinoline-7-carbonitrile;
(4aS,8aR)-2,5,5,8a-tetramethyl-3,6-dioxo-4,4a-dihydro-1H-isoquinoline-7-carbonitrile;
(4aR,8aS)-5,5,8a-trimethyl-3,6-dioxo-1,2,4,4a-tetrahydroisoquinoline-7-carbonitrile;
(4aS,8aR)-5,5,8a-trimethyl-3,6-dioxo-1,2,4,4a-tetrahydroisoquinoline-7-carbonitrile;
(4aR,7aR,8aR)-3-ethyl-7a-methyl-4,7-dioxo-4a-phenyl-2,8-dihydro-1H-cyclopropa[e]isoquinoline-6-carbonitrile;
(4aS,7aS,8aS)-3-ethyl-7a-methyl-4,7-dioxo-4a-phenyl-2,8-dihydro-1H-cyclopropa[e]isoquinoline-6-carbonitrile;
(4aR,8aR)-2-ethyl-5,5-dimethyl-8a-phenyl-7-(trifluoromethyl)-4,4a-dihydro-3H-isoquinoline-1,6-dione;
(4aS,8aS)-2-ethyl-5,5-dimethyl-8a-phenyl-7-(trifluoromethyl)-4,4a-dihydro-3H-isoquinoline-1,6-dione;
(4aS,8aR)-2-acetyl-5,5,8a-trimethyl-7-(trifluoromethyl)-1,3,4,4a-tetrahydroisoquinolin-6-one;
(4aR,8aS)-2-acetyl-5,5,8a-trimethyl-6-oxo-1,3,4,4a-tetrahydroisoquinoline-7-carboxamide;
(4aS,8aR)-2-acetyl-5,5,8a-trimethyl-6-oxo-1,3,4,4a-tetrahydroisoquinoline-7-carboxamide;
(8aR)-8a-(4-fluorophenyl)-2,5,5-trimethyl-1,6-dioxo-3H-isoquinoline-7-carbonitrile;
(8aS)-8a-(4-fluorophenyl)-2,5,5-trimethyl-1,6-dioxo-3H-isoquinoline-7-carbonitrile;
(8aR)-8a-(4-chlorophenyl)-2,5,5-trimethyl-1,6-dioxo-3H-isoquinoline-7-carbonitrile;
(8aR)-8a-(4-chlorophenyl)-2,5,5-trimethyl-1,6-dioxo-3H-isoquinoline-7-carbonitrile;
(8aS)-8a-(3-fluorophenyl)-2,5,5-trimethyl-1,6-dioxo-3H-isoquinoline-7-carbonitrile;
(8aR)-8a-(3-fluorophenyl)-2,5,5-trimethyl-1,6-dioxo-3H-isoquinoline-7-carbonitrile;
(8aR)-8a-(4-methoxyphenyl)-2,5,5-trimethyl-1,6-dioxo-3H-isoquinoline-7-carbonitrile;
(8aR)-8a-(4-methoxyphenyl)-2,5,5-trimethyl-1,6-dioxo-3H-isoquinoline-7-carbonitrile;
(8aR)-8a-benzyl-2,5,5-trimethyl-1,6-dioxo-3H-isoquinoline-7-carbonitrile;
(8aS)-8a-benzyl-2,5,5-trimethyl-1,6-dioxo-3H-isoquinoline-7-carbonitrile;
(4aS,8aS)-2-acetyl-5,5,8a-trimethyl-7-methylsulfonyl-1,3,4,4a-tetrahydroisoquinolin-6-one;
(8aS)-5,5-dimethyl-2-(1-methylpyrazol-3-yl)-1,6-dioxo-8a-phenyl-3H-isoquinoline-7-carbonitrile;

(8aR)-5,5-dimethyl-2-(1-methylpyrazol-3-yl)-1,6-dioxo-8a-phenyl-3H-isoquinoline-7-carbonitrile;
(8aS)-5,5-dimethyl-2-(1-methylpyrazol-4-yl)-1,6-dioxo-8a-phenyl-3H-isoquinoline-7-carbonitrile;
(8aR)-5,5-dimethyl-2-(1-methylpyrazol-4-yl)-1,6-dioxo-8a-phenyl-3H-isoquinoline-7-carbonitrile;
(8aS)-5,5-dimethyl-2-(2-methylpyrazol-3-yl)-1,6-dioxo-8a-phenyl-3H-isoquinoline-7-carbonitrile;
(8aR)-5,5-dimethyl-2-(2-methylpyrazol-3-yl)-1,6-dioxo-8a-phenyl-3H-isoquinoline-7-carbonitrile;
(8aS)-5,5-dimethyl-2-(1-methylimidazol-2-yl)-1,6-dioxo-8a-phenyl-3H-isoquinoline-7-carbonitrile;
(8aR)-5,5-dimethyl-2-(1-methylimidazol-2-yl)-1,6-dioxo-8a-phenyl-3H-isoquinoline-7-carbonitrile;
(8aS)-5,5-dimethyl-2-(6-methylpyrimidin-4-yl)-1,6-dioxo-8a-phenyl-3H-isoquinoline-7-carbonitrile;
(8aR)-5,5-dimethyl-2-(6-methylpyrimidin-4-yl)-1,6-dioxo-8a-phenyl-3H-isoquinoline-7-carbonitrile;
(8aS)-5,5-dimethyl-2-(2-methylpyrimidin-4-yl)-1,6-dioxo-8a-phenyl-3H-isoquinoline-7-carbonitrile;
(8aR)-5,5-dimethyl-2-(2-methylpyrimidin-4-yl)-1,6-dioxo-8a-phenyl-3H-isoquinoline-7-carbonitrile;
(8aS)-5,5-dimethyl-1,6-dioxo-8a-phenyl-2-pyridazin-4-yl-3H-isoquinoline-7-carbonitrile;
(8aR)-5,5-dimethyl-1,6-dioxo-8a-phenyl-2-pyridazin-4-yl-3H-isoquinoline-7-carbonitrile;
(8aS)-5,5-dimethyl-1,6-dioxo-8a-phenyl-2-pyrimidin-5-yl-3H-isoquinoline-7-carbonitrile;
(8aR)-5,5-dimethyl-1,6-dioxo-8a-phenyl-2-pyrimidin-5-yl-3H-isoquinoline-7-carbonitrile;
(8aS)-5,5-dimethyl-1,6-dioxo-8a-phenyl-2-pyridazin-3-yl-3H-isoquinoline-7-carbonitrile;
(8aR)-5,5-dimethyl-1,6-dioxo-8a-phenyl-2-pyridazin-3-yl-3H-isoquinoline-7-carbonitrile;
(8aS)-5,5-dimethyl-1,6-dioxo-8a-phenyl-2-pyrazin-2-yl-3H-isoquinoline-7-carbonitrile;
(8aR)-5,5-dimethyl-1,6-dioxo-8a-phenyl-2-pyrazin-2-yl-3H-isoquinoline-7-carbonitrile;
(8aS)-5,5-dimethyl-1,6-dioxo-8a-phenyl-2-pyrimidin-4-yl-3H-isoquinoline-7-carbonitrile;
(8aR)-5,5-dimethyl-1,6-dioxo-8a-phenyl-2-pyrimidin-4-yl-3H-isoquinoline-7-carbonitrile;
(8aS)-5,5-dimethyl-1,6-dioxo-8a-phenyl-2-(2-pyridyl)-3H-isoquinoline-7-carbonitrile;
(8aR)-5,5-dimethyl-1,6-dioxo-8a-phenyl-2-(2-pyridyl)-3H-isoquinoline-7-carbonitrile;
(8aS)-5,5-dimethyl-1,6-dioxo-8a-phenyl-2-(3-pyridyl)-3H-isoquinoline-7-carbonitrile;
(8aR)-5,5-dimethyl-1,6-dioxo-8a-phenyl-2-(3-pyridyl)-3H-isoquinoline-7-carbonitrile;
(8aS)-5,5-dimethyl-1,6-dioxo-8a-phenyl-2-(4-pyridyl)-3H-isoquinoline-7-carbonitrile;
(8aR)-5,5-dimethyl-1,6-dioxo-8a-phenyl-2-(4-pyridyl)-3H-isoquinoline-7-carbonitrile;
(8aS)-5,5-dimethyl-1,6-dioxo-8a-phenyl-2-pyrimidin-2-yl-3H-isoquinoline-7-carbonitrile;
(8aR)-5,5-dimethyl-1,6-dioxo-8a-phenyl-2-pyrimidin-2-yl-3H-isoquinoline-7-carbonitrile;
(4aS,5S,8aR)-2-(4-methoxyphenyl)-5-methyl-1,6-dioxo-8a-phenyl-3,4,4a,5-tetrahydroisoquinoline-7-carbonitrile;
(4aR,5R,8aS)-2-(4-methoxyphenyl)-5-methyl-1,6-dioxo-8a-phenyl-3,4,4a,5-tetrahydroisoquinoline-7-carbonitrile;
(4aS,5S,8aR)-2-(4-fluorophenyl)-5-methyl-1,6-dioxo-8a-phenyl-3,4,4a,5-tetrahydroisoquinoline-7-carbonitrile;
(4aR,5R,8aS)-2-(4-fluorophenyl)-5-methyl-1,6-dioxo-8a-phenyl-3,4,4a,5-tetrahydroisoquinoline-7-carbonitrile;
(4aS,5S,8aR)-5-methyl-1,6-dioxo-8a-phenyl-2-pyrimidin-4-yl-3,4,4a,5-tetrahydroisoquinoline-7-carbonitrile;
(4aR,5R,8aS)-5-methyl-1,6-dioxo-8a-phenyl-2-pyrimidin-4-yl-3,4,4a,5-tetrahydroisoquinoline-7-carbonitrile;
(4aS,5R,8aR)-5-methyl-1,6-dioxo-2,8a-diphenyl-3,4,4a,5-tetrahydroisoquinoline-7-carbonitrile;
(4aR,5S,8aS)-5-methyl-1,6-dioxo-2,8a-diphenyl-3,4,4a,5-tetrahydroisoquinoline-7-carbonitrile;
(4aR,5R,8aS)-2-ethyl-5,8a-dimethyl-1,6-dioxo-3,4,4a,5-tetrahydroisoquinoline-7-carbonitrile;
(4aS,5S,8aR)-2-ethyl-5,8a-dimethyl-1,6-dioxo-3,4,4a,5-tetrahydroisoquinoline-7-carbonitrile;
(4aR,5R,8aS)-2,5,8a-trimethyl-1,6-dioxo-3,4,4a,5-tetrahydroisoquinoline-7-carbonitrile;
(4aS,5S,8aR)-2,5,8a-trimethyl-1,6-dioxo-3,4,4a,5-tetrahydroisoquinoline-7-carbonitrile;
(4aR,8aR)-2-isopropyl-5,5,8a-trimethyl-1,6-dioxo-4,4a-dihydro-3H-isoquinoline-7-carbonitrile;
(4aS,8aS)-2-isopropyl-5,5,8a-trimethyl-1,6-dioxo-4,4a-dihydro-3H-isoquinoline-7-carbonitrile;
(4aS,8aS)-2,5,5,8a-tetramethyl-1,6-dioxo-4,4a-dihydro-3H-isoquinoline-7-carbonitrile;
(4aR,8aR)-2,5,5,8a-tetramethyl-1,6-dioxo-4,4a-dihydro-3H-isoquinoline-7-carbonitrile;
(8aR)-2-ethyl-5,5,8a-trimethyl-1,6-dioxo-3H-isoquinoline-7-carbonitrile;
(8aS)-2-ethyl-5,5,8a-trimethyl-1,6-dioxo-3H-isoquinoline-7-carbonitrile;
(8aR)-2-cyclobutyl-5,5-dimethyl-1,6-dioxo-8a-phenyl-3H-isoquinoline-7-carbonitrile;
(8aS)-2-cyclobutyl-5,5-dimethyl-1,6-dioxo-8a-phenyl-3H-isoquinoline-7-carbonitrile;
(8aR)-5,5-dimethyl-1,6-dioxo-8a-phenyl-2-(3-pyridylmethyl)-3H-isoquinoline-7-carbonitrile;
(8aS)-5,5-dimethyl-1,6-dioxo-8a-phenyl-2-(3-pyridylmethyl)-3H-isoquinoline-7-carbonitrile;
(8aR)-2-cyclopropyl-5,5-dimethyl-1,6-dioxo-8a-phenyl-3H-isoquinoline-7-carbonitrile;
(8aS)-2-cyclopropyl-5,5-dimethyl-1,6-dioxo-8a-phenyl-3H-isoquinoline-7-carbonitrile;
(8aR)-2-isopropyl-5,5-dimethyl-1,6-dioxo-8a-phenyl-3H-isoquinoline-7-carbonitrile;
(8aS)-2-isopropyl-5,5-dimethyl-1,6-dioxo-8a-phenyl-3H-isoquinoline-7-carbonitrile;
(8aR)-2-cyclopentyl-5,5-dimethyl-1,6-dioxo-8a-phenyl-3H-isoquinoline-7-carbonitrile;
(8aS)-2-cyclopentyl-5,5-dimethyl-1,6-dioxo-8a-phenyl-3H-isoquinoline-7-carbonitrile;
(8aR)-2-isobutyl-5,5-dimethyl-1,6-dioxo-8a-phenyl-3H-isoquinoline-7-carbonitrile;
(8aS)-2-isobutyl-5,5-dimethyl-1,6-dioxo-8a-phenyl-3H-isoquinoline-7-carbonitrile;
(8aR)-2-benzyl-5,5-dimethyl-1,6-dioxo-8a-phenyl-3H-isoquinoline-7-carbonitrile;
(8aS)-2-benzyl-5,5-dimethyl-1,6-dioxo-8a-phenyl-3H-isoquinoline-7-carbonitrile;
(8aR)-2-(2-methoxyethyl)-5,5-dimethyl-1,6-dioxo-8a-phenyl-3H-isoquinoline-7-carbonitrile;
(8aS)-2-(2-methoxyethyl)-5,5-dimethyl-1,6-dioxo-8a-phenyl-3H-isoquinoline-7-carbonitrile;
(8aR)-2-(cyclopropylmethyl)-5,5-dimethyl-1,6-dioxo-8a-phenyl-3H-isoquinoline-7-carbonitrile;

(8aS)-2-(cyclopropylmethyl)-5,5-dimethyl-1,6-dioxo-8a-phenyl-3H-isoquinoline-7-carbonitrile;

(4aR,5R,8aS)-2-benzyl-5,8a-dimethyl-1,6-dioxo-3,4,4a,5-tetrahydroisoquinoline-7-carbonitrile;

(4aS,5S,8aR)-2-benzyl-5,8a-dimethyl-1,6-dioxo-3,4,4a,5-tetrahydroisoquinoline-7-carbonitrile;

(8aR)-2,5,5,8a-tetramethyl-1,6-dioxo-3H-isoquinoline-7-carbonitrile;

(8aS)-2,5,5,8a-tetramethyl-1,6-dioxo-3H-isoquinoline-7-carbonitrile;

(4aR,5R,8aS)-5-methyl-2-[(2-methyl-4-pyridyl)methyl]-1,6-dioxo-8a-phenyl-3,4,4a,5-tetrahydroisoquinoline-7-carbonitrile;

(4aS,5S,8aR)-5-methyl-2-[(2-methyl-4-pyridyl)methyl]-1,6-dioxo-8a-phenyl-3,4,4a,5-tetrahydroisoquinoline-7-carbonitrile;

(4aR,5R,8aS)-5-methyl-2-[(5-methylisoxazol-3-yl)methyl]-1,6-dioxo-8a-phenyl-3,4,4a,5-tetrahydroisoquinoline-7-carbonitrile;

(4aS,5S,8aR)-5-methyl-2-[(5-methylisoxazol-3-yl)methyl]-1,6-dioxo-8a-phenyl-3,4,4a,5-tetrahydroisoquinoline-7-carbonitrile;

(4aR,5R,8aS)-5-methyl-1,6-dioxo-8a-phenyl-2-(4-pyridylmethyl)-3,4,4a,5-tetrahydroisoquinoline-7-carbonitrile;

(4aS,5S,8aR)-5-methyl-1,6-dioxo-8a-phenyl-2-(4-pyridylmethyl)-3,4,4a,5-tetrahydroisoquinoline-7-carbonitrile;

(5aS,9aR)-5a,9,9-trimethyl-4,8-dioxo-2,3,4,5,5a,8,9,9a-octahydro-1H-benzo[d]azepine-7-carbonitrile;

(5aR,9aS)-6,6,9a-trimethyl-3,7-dioxo-2,3,4,5,5a,6,7,9a-octahydro-1H-benzo[c]azepine-8-carbonitrile;

(5aR,9aS)-2-acetyl-6,6,9a-trimethyl-7-oxo-2,3,4,5,5a,6,7,9a-octahydro-1H-benzo[c]azepine-8-carbonitrile;

(4aS,8aR)-2-(2-fluoroethyl)-5,5,8a-trimethyl-6-oxo-1,3,4,4a-tetrahydroisoquinoline-7-carbonitrile;

(8aR)-2,5,5,8a-tetramethyl-6-oxo-1,3-dihydroisoquinoline-7-carbonitrile hydrochloride;

(8aS)-2,5,5,8a-tetramethyl-6-oxo-1,3-dihydroisoquinoline-7-carbonitrile hydrochloride;

(4aS,8aR)-5,5,8a-trimethyl-2-(oxetan-3-yl)-6-oxo-1,3,4,4a-tetrahydroisoquinoline-7-carbonitrile;

(4aR,8aS)-5,5,8a-trimethyl-2-(oxetan-3-yl)-6-oxo-1,3,4,4a-tetrahydroisoquinoline-7-carbonitrile;

(8aR)-5,5,8a-trimethyl-6-oxo-2-pyrimidin-2-yl-1,3-dihydroisoquinoline-7-carbonitrile hydrochloride;

(8aS)-5,5,8a-trimethyl-6-oxo-2-pyrimidin-2-yl-1,3-dihydroisoquinoline-7-carbonitrile hydrochloride;

(4aR,5R,8aS)-2-benzyl-5-methyl-1,6-dioxo-8a-phenyl-3,4,4a,5-tetrahydroisoquinoline-7-carbonitrile;

(4aS,5S,8aR)-2-benzyl-5-methyl-1,6-dioxo-8a-phenyl-3,4,4a,5-tetrahydroisoquinoline-7-carbonitrile;

(8aR)-2-(2,2-dimethylpropanoyl)-5,5,8a-trimethyl-6-oxo-1,3-dihydroisoquinoline-7-carbonitrile;

(8aS)-2-(2,2-dimethylpropanoyl)-5,5,8a-trimethyl-6-oxo-1,3-dihydroisoquinoline-7-carbonitrile;

(4aS,8aR)-2-formyl-5,5,8a-trimethyl-6-oxo-1,3,4,4a-tetrahydroisoquinoline-7-carbonitrile;

(4aR,8aS)-2-formyl-5,5,8a-trimethyl-6-oxo-1,3,4,4a-tetrahydroisoquinoline-7-carbonitrile;

(4aS,8aR)-2-(2,2-difluoroethyl)-5,5,8a-trimethyl-6-oxo-1,3,4,4a-tetrahydroisoquinoline-7-carbonitrile;

(4aR,8aS)-2-(2,2-difluoroethyl)-5,5,8a-trimethyl-6-oxo-1,3,4,4a-tetrahydroisoquinoline-7-carbonitrile;

(4aS,8aR)-7-cyano-N,5,5,8a-tetramethyl-6-oxo-1,3,4,4a-tetrahydroisoquinoline-2-carboxamide;

(4aR,8aS)-7-cyano-N,5,5,8a-tetramethyl-6-oxo-1,3,4,4a-tetrahydroisoquinoline-2-carboxamide;

(4aS,8aR)-5,5,8a-trimethyl-6-oxo-2-(2,2,2-trifluoroethyl)-1,3,4,4a-tetrahydroisoquinoline-7-carbonitrile;

(4aR,8aS)-5,5,8a-trimethyl-6-oxo-2-(2,2,2-trifluoroethyl)-1,3,4,4a-tetrahydroisoquinoline-7-carbonitrile;

(4aS,8aR)-5,5,8a-trimethyl-6-oxo-2-pyrimidin-2-yl-1,3,4,4a-tetrahydroisoquinoline-7-carbonitrile;

(4aR,8aS)-5,5,8a-trimethyl-6-oxo-2-pyrimidin-2-yl-1,3,4,4a-tetrahydroisoquinoline-7-carbonitrile;

(4aS,8aR)-2-(2,2-dimethylpropanoyl)-5,5,8a-trimethyl-6-oxo-1,3,4,4a-tetrahydroisoquinoline-7-carbonitrile;

(4aR,8aS)-2-(2,2-dimethylpropanoyl)-5,5,8a-trimethyl-6-oxo-1,3,4,4a-tetrahydroisoquinoline-7-carbonitrile;

(4aS,8aR)-5,5,8a-trimethyl-2-(2-methylpropanoyl)-6-oxo-1,3,4,4a-tetrahydroisoquinoline-7-carbonitrile;

(4aR,8aS)-5,5,8a-trimethyl-2-(2-methylpropanoyl)-6-oxo-1,3,4,4a-tetrahydroisoquinoline-7-carbonitrile;

(4aS,8aR)-5,5,8a-trimethyl-6-oxo-2-propanoyl-1,3,4,4a-tetrahydroisoquinoline-7-carbonitrile;

(4aR,8aS)-5,5,8a-trimethyl-6-oxo-2-propanoyl-1,3,4,4a-tetrahydroisoquinoline-7-carbonitrile;

(4aS,5S,8aR)-2-acetyl-5,8a-dimethyl-6-oxo-3,4,4a,5-tetrahydro-1H-isoquinoline-7-carbonitrile;

(4aR,5R,8aS)-2-acetyl-5,8a-dimethyl-6-oxo-3,4,4a,5-tetrahydro-1H-isoquinoline-7-carbonitrile;

(8aR)-2-acetyl-5,5,8a-trimethyl-6-oxo-1,3-dihydroisoquinoline-7-carbonitrile;

(8aS)-2-acetyl-5,5,8a-trimethyl-6-oxo-1,3-dihydroisoquinoline-7-carbonitrile;

(4aR,8aS)-5,5,8a-trimethyl-2-(1-methylpyrazole-4-carbonyl)-6-oxo-1,3,4,4a-tetrahydroisoquinoline-7-carbonitrile;

(4aS,8aR)-5,5,8a-trimethyl-2-(1-methylpyrazole-4-carbonyl)-6-oxo-1,3,4,4a-tetrahydroisoquinoline-7-carbonitrile;

(4aR,8aS)-5,5,8a-trimethyl-6-oxo-2-(pyrimidine-5-carbonyl)-1,3,4,4a-tetrahydroisoquinoline-7-carbonitrile;

(4aS,8aR)-5,5,8a-trimethyl-6-oxo-2-(pyrimidine-5-carbonyl)-1,3,4,4a-tetrahydroisoquinoline-7-carbonitrile;

(4aR,8aS)-5,5,8a-trimethyl-6-oxo-2-(pyridine-3-carbonyl)-1,3,4,4a-tetrahydroisoquinoline-7-carbonitrile;

(4aS,8aR)-5,5,8a-trimethyl-6-oxo-2-(pyridine-3-carbonyl)-1,3,4,4a-tetrahydroisoquinoline-7-carbonitrile;

(4aR,8aS)-2-(2-methoxyacetyl)-5,5,8a-trimethyl-6-oxo-1,3,4,4a-tetrahydroisoquinoline-7-carbonitrile;

(4aS,8aR)-2-(2-methoxyacetyl)-5,5,8a-trimethyl-6-oxo-1,3,4,4a-tetrahydroisoquinoline-7-carbonitrile;

(4aR,8aS)-5,5,8a-trimethyl-2-(oxetane-3-carbonyl)-6-oxo-1,3,4,4a-tetrahydroisoquinoline-7-carbonitrile;

(4aS,8aR)-5,5,8a-trimethyl-2-(oxetane-3-carbonyl)-6-oxo-1,3,4,4a-tetrahydroisoquinoline-7-carbonitrile;

(4aR,8aS)-2-(cyclopropanecarbonyl)-5,5,8a-trimethyl-6-oxo-1,3,4,4a-tetrahydroisoquinoline-7-carbonitrile;

(4aS,8aR)-2-(cyclopropanecarbonyl)-5,5,8a-trimethyl-6-oxo-1,3,4,4a-tetrahydroisoquinoline-7-carbonitrile;

(4aS,8aR)-2-butanoyl-5,5,8a-trimethyl-6-oxo-1,3,4,4a-tetrahydroisoquinoline-7-carbonitrile;

(4aR,8aS)-2-butanoyl-5,5,8a-trimethyl-6-oxo-1,3,4,4a-tetrahydroisoquinoline-7-carbonitrile;

(4aS,8aR)-2-(cyclohexanecarbonyl)-5,5,8a-trimethyl-6-oxo-1,3,4,4a-tetrahydroisoquinoline-7-carbonitrile;

(4aR,8aS)-2-(cyclohexanecarbonyl)-5,5,8a-trimethyl-6-oxo-1,3,4,4a-tetrahydroisoquinoline-7-carbonitrile;

(4aS,8aR)-2-benzyl-5,5,8a-trimethyl-6-oxo-1,3,4,4a-tetrahydroisoquinoline-7-carbonitrile;

(4aR,8aS)-2-benzyl-5,5,8a-trimethyl-6-oxo-1,3,4,4a-tetrahydroisoquinoline-7-carbonitrile;

(4aS,8aR)-2-(benzenesulfonyl)-5,5,8a-trimethyl-6-oxo-1,3,4,4a-tetrahydroisoquinoline-7-carbonitrile;

(4aR,8aS)-2-(benzenesulfonyl)-5,5,8a-trimethyl-6-oxo-1,3,4,4a-tetrahydroisoquinoline-7-carbonitrile;

(4aS,8aR)-5,5,8a-trimethyl-2-methylsulfonyl-6-oxo-1,3,4,4a-tetrahydroisoquinoline-7-carbonitrile;

(4aR,8aS)-5,5,8a-trimethyl-2-methylsulfonyl-6-oxo-1,3,4,4a-tetrahydroisoquinoline-7-carbonitrile;

(4aS,8aR)-2-benzoyl-5,5,8a-trimethyl-6-oxo-1,3,4,4a-tetrahydroisoquinoline-7-carbonitrile;

(4aR,8aS)-2-benzoyl-5,5,8a-trimethyl-6-oxo-1,3,4,4a-tetrahydroisoquinoline-7-carbonitrile;

(4aS,8aR)-2,5,5,8a-tetramethyl-6-oxo-1,3,4,4a-tetrahydroisoquinoline-7-carbonitrile;

(4aR,8aS)-2,5,5,8a-tetramethyl-6-oxo-1,3,4,4a-tetrahydroisoquinoline-7-carbonitrile;

(4aS,8aR)-5,5,8a-trimethyl-6-oxo-2,3,4,4a-tetrahydro-1H-isoquinoline-7-carbonitrile hydrochloride;

(4aR,8aS)-5,5,8a-trimethyl-6-oxo-2,3,4,4a-tetrahydro-1H-isoquinoline-7-carbonitrile hydrochloride;

(4aR,8aS)-2-acetyl-5,5,8a-trimethyl-6-oxo-1,3,4,4a-tetrahydroisoquinoline-7-carbonitrile;

(4aS,8aR)-2-acetyl-5,5,8a-trimethyl-6-oxo-1,3,4,4a-tetrahydroisoquinoline-7-carbonitrile;

(8aS)-5,5,8a-trimethyl-6-oxo-1,3-dihydroisochromene-7-carbonitrile and (8aS)-5,5,8a-trimethyl-6-oxo-1,3,4,4a-tetrahydroisochromene-7-carbonitrile, and pharmaceutically acceptable salts thereof.

21. The compound of claim 1, wherein the compound is represented by Formula XI:

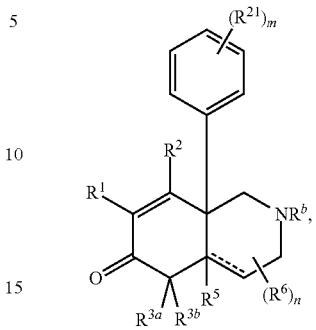

or a pharmaceutically acceptable salt thereof.

22. The compound of claim 21, or a pharmaceutically acceptable salt thereof, wherein $R^1$ is —$CF_3$.

23. The compound of claim 21, wherein the compound is represented by Formula XIII:

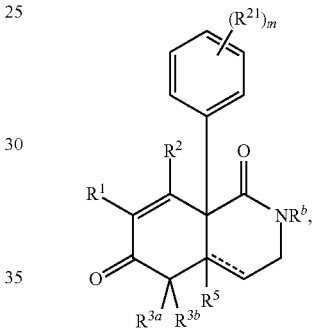

or a pharmaceutically acceptable salt thereof.

24. A pharmaceutical composition comprising at least one compound of claim 1, or a pharmaceutically acceptable salt thereof, and at least one pharmaceutically acceptable excipient.

* * * * *